US008546421B1

(12) United States Patent
Stockwell et al.

(10) Patent No.: US 8,546,421 B1

(45) Date of Patent: Oct. 1, 2013

(54) ONCOGENIC-RAS-SIGNAL DEPENDENT LETHAL COMPOUNDS

(75) Inventors: Brent R. Stockwell, New York, NY (US); Wan Seok Yang, New York, NY (US); Rohitha Sriramaratnam, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 737 days.

(21) Appl. No.: 12/583,579

(22) Filed: Aug. 21, 2009

Related U.S. Application Data

(63) Continuation-in-part of application No. PCT/US2008/002390, filed on Feb. 21, 2008.

(60) Provisional application No. 60/902,575, filed on Feb. 21, 2007.

(51) Int. Cl.
*A61K 31/437* (2006.01)
*C07D 471/04* (2006.01)
*C07D 495/04* (2006.01)

(52) U.S. Cl.
USPC ................ 514/292; 546/80; 546/81; 514/290

(58) Field of Classification Search
USPC ........................................... 546/80; 514/290
See application file for complete search history.

(56) References Cited

U.S. PATENT DOCUMENTS

| | | | |
|---|---|---|---|
| 3,644,384 | A | 2/1972 | Schulenbert et al. |
| 6,048,868 | A | 4/2000 | Fourtillan et al. |
| 6,143,746 | A | 11/2000 | Daugan et al. |
| 6,784,179 | B2 | 8/2004 | Daugan |
| 6,890,933 | B1 | 5/2005 | Feng et al. |
| 7,601,840 | B2 | 10/2009 | Moon et al. |
| 2005/0272759 | A1 | 12/2005 | Moon et al. |
| 2005/0282849 | A1 | 12/2005 | Moon et al. |

FOREIGN PATENT DOCUMENTS

| | | |
|---|---|---|
| AU | 636232 | 2/1992 |
| CA | 982132 | 1/1976 |
| WO | WO 96/08490 | 3/1996 |
| WO | WO 03/099821 | 5/2003 |
| WO | WO 2005/070930 | 1/2005 |
| WO | WO 2005/089764 | 3/2005 |

OTHER PUBLICATIONS

Dorwald F. A. Side Reactions in Organic Synthesis, 2005, Wiley: VCH, Weinheim p. IX of Preface.*

Alain Daugan et al, The discovery of Tadalafil. 20o3, J. Med. Chem, Issue 46, pp. 4533-4542.*

Abeliovich, et al. "Chemical genetic analysis of Apg1 reveals a non-kinase role in the induction of autophagy," Mol Bioi Cell 14, 477-90 (2003).

Alexandre, et al. "Accumulation of hydrogen peroxide is an early and crucial step for paclitaxel-induced . . . ," International journal of cancer 119, 41-48 (2006).

Andoh, et al. Characterization of a mammalian mutant with a camptothecin-resistant DNA topoisomerase I, Proc Natl Acad Sci USA 84, 5565-9. (1987).

Anflous, et al. "Altered mitochondrial sensitivity for ADP and maintenance of creatine-stimulated respiration . . . ," J Biol Chem 276, 1954-60 (2001).

Arbiser, et al. "Oncogenic H-ras stimulates tumor angiogenesis by two distinct pathways," Proc Natl Acad Sci USA 94, 861-866 (1997).

Arbiser, et al. "Reactive oxygen generated by Nox1 triggers . . . ," Proceedings of the National Academy of Sciences of the United States of America 99, 715-720 (2002).

Averet, et al. "NADH is specifically channeled through the mitochondrial porin channel in *Saccharomyces cerevisiae*," J Bioenerg Biomembr 34, 499-506 (2002).

Baehrecke, "Autophagic programmed cell death in *Drosophila*," Cell Death Differ 10, 940-5 (2003).

Bahamonde, et al. "Voltage-dependent anion channel localises to the plasma membrane and peripheral but not perinuclear mitochondria," Pflugers Arch 446, 309-13 (2003).

Bahamonde, et al. "Plasma membrane voltage-dependent anion channel mediates antiestrogen-activated maxi Cl- currents in C1300 . . . ," J Biol Chem 278, 33284-9 (2003).

Bailey, et al. "Microarrays of Small Molecules Embedded in Biodegradable Polymers for Use in Mammalian Cell-Based Screens," Proc Natl Acad Sci 101, 16144-16149 (2004).

Baker, et al. "VDAC1 is a transplasma membrane NADH-ferricyanide reductase," J Biol Chem 279, 4811-9 (2004).

Banerjee, et al. "Role of E2F-1 in chemosensitivity," Cancer Res. 58, 4292-4296 (1998).

Barbacid, M. "ras genes," Annu Rev Biochem 56, 779-827 (1987).

Barbour, et al. "Synthetic lethal screen," Methods Mol Biol 313, 161-169 (2006).

Beck, et al. "Mechanisms of resistance to drugs that inhibit DNA topoisomerases," Semin Cancer Biol 2, 235-44 (1991).

Berge et al, "Pharmaceutical Salts," J. Pharm. Sci., 66, 1-19 (1977).

Bernards, "Ras superfamily and interacting proteins database," Methods Enzymol. 407, 1-9 (2005).

Bjornsti, et al. "Expression of human DNA topoisomerase I in yeast cells lacking yeast DNA topoisomerase I: restoration of sensitivity of the . . . ," Cancer Res 49,6318-23 (1989).

Blanchard, et al. "Efficient reversal of Alzheimer's disease fibril formation and elimination of neurotoxicity by a small molecule," Proc Natl Acad Sci 101, 14326-32 (2004).

Blanchard, et al. Eliminating membrane depolarization caused by the Alzheimer peptide Abeta(1-42, aggr.), Biochem Biophys Res Commun 293, 1204-8 (2002).

Blankenberg, "Recent advances in the imaging of programmed cell death," Curr Pharm Des 10, 1457-67 (2004).

Block, et al. "Early clinical studies with lapachol (NSC-11905)," Cancer Chemother Rep 2 4, 27-28 (1974).

(Continued)

*Primary Examiner* — Rita Desai

(74) *Attorney, Agent, or Firm* — Bryan Cave LLP

(57) ABSTRACT

Compounds with cancer cell specific lethality are provided. In particular, RAS-selective lethal compounds and compositions are provided. Also provided are methods of screening for such compounds and methods of treating a condition in a mammal, by administering to the mammal a therapeutically effective amount of such compounds or compositions.

4 Claims, 133 Drawing Sheets
(121 of 133 Drawing Sheet(s) Filed in Color)

(56) References Cited

OTHER PUBLICATIONS

Borst, et al. "A family of drug transporters: the multidrug resistance-associated proteins," J Natl Cancer Inst 92, 1295-1302 (2000).
Bos, "ras oncogenes in human cancer: a review," Cancer Res 49, 4682-9 (1989).
Bosch, et al. "Prevalence of human papillomavirus in cervical cancer: a worldwide perspective. International biological study . . . ," J Natl Cancer Inst 87, 796-802 (1995).
Boyce, et al. "Caspases: an ancient cellular sword of Damocles," Cell Death Differ 11, 29-37 (2004).
Brdiczka, "Contact sites between mitochondrial envelope membranes. Structure and function in energy- and protein-transfer," Biochim Biophys Acta 1071, 291-312 (1991).
Brown, et al. "A mammalian protein targeted by G1-arresting rapamycin-receptor complex," Nature 369, 756-758 (1994).
Bryant, et al. "Specific killing of BRCA2-deficient tumours with inhibitors of poly (ADP-ribose) polymerase," Nature 434, 913-917 (2005).
Buettner, et al. "Evidence for secretory pathway localization of a voltage-dependent anion channel isoform," Proc Natl Acad Sci 97, 3201-6 (2000).
Capdeville, et al. "Glivec (STI571, imatinib), a rationally developed, targeted anticancer drug," Nat Rev Drug Discov 1, 493-502 (2002).
Casadio, et al. "A 3D model of the voltage-dependent anion channel (VDAC)," FEBS Lett 520, 1-7 (2002).
Casey, et al. "The promoter region of the human transferrin receptor gene," Ann NY Acad Sci 526, 54-64 (1988).
Cazzola, et al. "Manipulations of cellular iron metabolism for modulating normal and malignant cell proliferation: achievements and prospects," Blood 75, 1903-1919 (1990).
Champoux, "Structure-based analysis of the effects of camptothecin on the activities of human topoisomerase," Ann NY Acad Sci 922, 56-64. (2000).
Chan, et al. "Caspase inhibitors promote the survival of avulsed spinal motoneurons in neonatal rats," Neuroreport 12, 541-545 (2001).
Chandra, et al. "Bax-dependent regulation of Bak by voltage-dependent anion channel 2," J Biol Chem 280, 19051-61 (2005).
Cheng, et al. Structure of the human transferrin receptor-transferrin complex, Cell 116, 565-576 (2004).
Chou, et al. "Role of NADPH oxidase in arsenic-induced reactive oxygen species formation and cytotoxicity in myeloid . . . ," Proc Natl Acad Sci USA 101, 4578-4583 (2004).
Cliff, et al. "A survey of the year 2003 literature on applications of isothermal titration calorimetry," J Mol Recognit 17, 513-23 (2004).
Coleman, et al. "RAS and RHO GTPases in G1-phase cell-cycle regulation," Nat Rev Mol Cell Bioi 5, 355-66 (2004).
Colicelli, "Human RAS superfamily proteins and related GTPases," Sci STKE 2004, RE13 (2004).
Cover, et al. "Characterization of HeLa cell vacuoles induced by Helicobacter pylori broth culture supematant," Hum Pathol 23, 1004-10 (1992).
Crompton, "The mitochondrial permeability transition pore and its role in cell death," Biochem J 341 (Pt 2), 233-49 (1999).
Cross, et al. "The NADPH oxidase of professional phagocytes—prototype of the NOX electron transport chain systems," Biochimica et biophysics acts 1657, 1-22 (2004).
da Consolacao, et al. "A lapachol derivative active against mouse lymphocytic leukemia P-388," J Med Chem 18, 1159-1161 (1975).
Danial, et al. "Cell death: critical control points," Cell 116, 205-19 (2004).
D'Arpa, et al. "Involvement of nucleic acid synthesis in cell killing mechanisms of topoisomerase poisons," Cancer Res 50, 6919-24. (1990).
Daugan,et al. "The discovery of tadalafil: a novel and highly selective PDE5 inhibitor . . . ," Journal of Medicinal Chemistry 46:4533-4542 (2003).
Davies, et at. "Mutations of the BRAF gene in human cancer," Nature 417, 949-54 (2002).
Dermietzel, et al. "Cloning and in situ localization of a brain-derived porin that constitutes a large-conductance anion channel..," Proc Natl Acad Sci USA 91, 499-503 (1994).
Dolma, et al. "Identification of genotype-selective antitumor agents using synthetic lethal chemical screening in engineered human tumor cells," Cancer Cell 3, 285-296 (2003).
Dorman, et al. "Benzophenone photophores in biochemistry," Biochemistry 33,5661-73 (1994).
Dorman, et al. "Using photolabile ligands in drug discovery and development," Trends Biotechnol 18, 64-77 (2000).
Dorr, "Bleomycin pharmacology: mechanism of action and resistance, and clinical pharmacokinetics," Seminars in oncology 19, 3-8 (1992).
Downward, "Targeting RAS signalling pathways in cancer therapy," Nat Rev Cancer 3, 11-22 (2003).
Druker, et al. "Effects of a selective inhibitor of the Abl tyrosine kinase on the growth of Bcr-Abl positive cells," Nat Med 2, 561-6. (1996).
Duncia, et al. "MEK inhibitors: the chemistry and biological activity of U0126, its analogs, and cyclization products," Bioorg Med Chem Lett 8, 2839-44 (1998).
Elenbaas, et al. "Human breast cancer cells generated by oncogenic transformation of primary mammary epithelial cells," Genes Dev 15, 50-65. (2001).
Eng, et al. "Evidence that DNA topoisomerase I is necessary for the cytotoxic effects of camptothecin," Mol Pharmacol 34, 755-60. (1988).
Fantin, et al. "A novel mitochondriotoxic small molecule that selectively inhibits tumor cell growth," Cancer Cell 2, 29-42 (2002).
Fiek, et al. Evidence for identity between the hexokinase-binding protein and the mitochondrial porin in the outer membrane of rat . . . ,Biochim Biophys Acta 688, 429-40 (1982).
Finch, et al. "Triapine (3-aminopyridine-2-carboxaldehyde-thiosemicarbazone): A potent inhibitor of ribonucleotide reductase . . . ," Biochem Pharmacol 59, 983-991 (2000).
Forte, et al. "A Molecular genetics of the VDAC ion channel: structural model and sequence analysis," J Bioenerg Biomembr 19,341-50 (1987).
Foster, et al. "Pharmacological rescue of mutant p53 conformation and function," Science 286, 2507-2510 (1999).
Fry, et al. "Targeting protein-protein interactions for cancer therapy," Journal of molecular medicine (Berlin, Germany) 83, 955-963 (2005).
G. Von Jagow et al. "Inhibition of electron transfer from ferrocytochrome b to ubiquinone, cytochrome c1 and duroquinone by antimycin," Biochim Biophys Acta 387, 409-24 (1975).
Gilad, et al. "Melatonin is a scavenger of peroxynitrite," Life Sci 60, PL169-74 (1997).
Gonzalez-Gronow, et al. "The voltage-dependent anion channel is a receptor for plasminogen kringle 5 on human endothelial cells," J Biol Chem 278, 27312-8 (2003).
Graham, et al. "Genetic approaches to analyzing mitochondrial outer membrane permeability," Currr Top Dev Biol 59, 87-118 (2004).
Green, et al. "Inhibition of malignant cell growth by 311, a novel iron chelator of the pyridoxal . . . ," Clin Cancer Res 7, 3574-3579 (2001).
Guerra, et al. "Tumor induction by an endogenous K-ras oncogene is highly dependent on cellular context," Cancer Cell 4, 111-20 (2003).
Hahn, "Immortalization and transformation of human cells," Mol Cells 13, 351-61. (2002).
Hahn, et al. "Creation of human tumour cells with defined genetic elements,". Nature 400, 464-468 (1999).
Hahn, et al. "Enumeration of the simian virus 40 early region elements necessary for human cell transformation," Mol Cell Biol 22, 2111-2123 (2002).
Hahn, et al. "Modelling the molecular circuitry of cancer," Nat Rev Cancer 2, 331-41 (2002).
Hahn, et al. "Rules for making human tumor cells," N Engl J Med 347, 1593-603 (2002).
Halliwell, et al. "Role of free radicals and catalytic metal ions in human disease: an overview," Methods Enzymol 186, 1-85 (1990).
Hanahan, et al. "The hallmarks of cancer," Cell 100, 57-70 (2000).

Harrison, et al. "The ferritins: molecular properties, iron storage function and cellular regulation," Biochim. Biophys. Acta. 1275, 161-203 (1996).
Hartwell, et al. "Integrating genetic approaches into the discovery of anticancer drugs," Science 278, 1064-1068 (1997).
Harvey, "An Unidentified Virus Which Causes the Rapid Production of Tumours in Mice," Nature 204, 1104-5 (1.964).
Ho, et al. "Detection of antimycin-binding subunits of complex III by photoaffinity-labeling with an azido derivative of antimycin," J Bioenerg Biomembr 17, 269-82 (1985).
Hsiang, et al. "Arrest of replication forks by drug-stabilized topoisomerase I-DNA cleavable complexes as a mechanism of cell killing . . . ," Cancer Res 49,5077-82. (1989).
Hsiang, et al. "Identification of mammalian DNA topoisomerase I as an intracellular target of the anticancer drug camptothecin," Cancer Res 48, 1722-6. (1988).
Huang, et al. "Superoxide dismutase as a target for the selective killing of cancer cells," Nature 407, 390-5 (2000).
Jackson, et al. "Analysis of lung tumor initiation and progression using conditional expression of oncogenic K-ras," Genes Dev 15, 3243-8 (2001).
Jagtap, et al. "Poly(ADP-ribose) polymerase and the therapeutic effects of its inhibitors," Nat Rev Drug Discov 4, 421-40 (2005).
Johnson, et al. "Somatic activation of the K-ras oncogene causes early onset lung cancer in mice," Nature 410, 1111-6 (2001).
Kaelin, "The concept of synthetic lethality in the context of anticancer therapy," Nat Rev Cancer 5, 689-98 (2005).
Kalinowski, et al. "The evolution of iron chelators for the treatment of iron overload disease and cancer," Pharmacol Rev 57, 547-583 (2005).
Kartalou, et al. "Mechanisms of resistance to cisplatin," Mutat Res 478, 23-43 (2001).
Kau, et al. "A chemical genetic screen identifies inhibitors of regulated nuclear export of a Forkhead transcription factor in PTEN-deficient . . . ," Cancer Cell 4, 463-76 (2003).
Kelley, et al. "A Flexible Data Analysis Tool for Chemical Genetic Screens," Chemistry & Biology 11, 1495-1503 (2004).
Kelley, et al. "Conserved pathways within bacteria and yeast as revealed by global protein network alignment," Proc Natl Acad Sci USA 100, 11394-9 (2003).
Kelley, et al. "PathBLAST: a tool for alignment of pretein interaction networks," Nucleic Acids Res 32, W83-8 (2004).
Kerr, et al. "Apoptosis: a basic biological phenomenon with wide-ranging implications in tissue kinetics," Br J Cancer 26, 239-57 (1972).
Khersonsky, et al. "Facilitated forward chemical genetics using a tagged triazine library and zebrafish embryo screening," J Am Chem Soc 125,11804-5 (2003).
Kim, et al. "Sequential cleavage of poly(ADP-ribose)polymerase and appearance of a small Baximmunoreactive . . . ," J Neurochem 72, 2456-63 (1999).
Kirsten, et al. "Morphological responses to a murine erythroblastosis virus," J. Natl. Cancer Inst. 39, 311-335 (1967).
Kmita, et al. "Modulation of the voltage-dependent anion-selective channel by cytoplasmic proteins from wild type and the channel . . . ," Acta Biochim Pol 50, 415-24 (2003).
Kohl, et al. "Inhibition of farnesyltransferase induces regression of mammary and salivary carcinomas in ras transgenic mice," Nat Med 1, 792-797 (1995).
Kondagunta, et al. "Chemotherapy for advanced germ cell tumors," J Clin Oncol 24, 5493-5502 (2006).
Koppel, et al. "Bacterial expression and characterization of the mitochondrial outer membrane channel. Effects of n-terminal modifications," J Biol Chem 273, 13794-800 (1998).
Krimmer, et al. "Biogenesis of porin of the outer mitochondrial membrane involves an import pathway via receptors and the general import . . . ," J Cell Biol 152, 289-300 (2001).
Kwok, et al. "Anthracyclines induce accumulation of iron in ferritin in myocardial and neoplastic cells: . . . ," Molecular pharmacology 63, 849-861 (2003).
Le, et al. "The role of iron in cell cycle progression and the proliferation of neoplastic cells," Biochim Biophys Acta 1603, 31-46 (2002).
Leavitt, et al. "Direct measurement of protein binding energetics by isothermal titration calorimetry," Curr Opin Struct Biol 11, 560-6 (2001).
Lebedev, et al. "Echinochrome, a naturally occurring iron chelator and free radical scavenger in artificial and natural membrane systems," Life Sci 76, 863-875 (2005).
Leist, et al. "Four deaths and a funeral: from caspases to alternative mechanisms," Nat Rev Mol Cell Biol 2, 589-98 (2001).
Lemasters, et al. "Voltage-dependent anion channel (VDAC) as mitochondrial governor—thinking outside the box," Biochim. Biophys. Acta. 1762, 181-190 (2006).
Lessnick, et al. "The Ewing's sarcoma oncoprotein EWS/FLI induces a p53-dependent growth arrest in primary human fibroblasts," Cancer Cell 1, 393-401 (2002).
Linden, et al. "Identification of porin as a binding site for MAP2," Biochem Biophys Res Commun 218, 833-6 (1996).
Liu, et al. "Chemical and biological properties of cytotoxic alpha-(N)-heterocyclic carboxaldehyde thiosemicarbazones," Prog Med Chem 32, 1-35 (1995).
Liu, et al. "Mechanism of action of camptothecin," Ann NY Acad Sci 922,1-10 (2000).
Low, et al. "Clinical trials referral resource. Current clinical trials investigating 3-AP," Oncology (Williston Park) 19, 354, 357-358 (2005).
Lunn, et al. "Indoprofen upregulates the survival motor neuron protein through a cyclooxygenase-independent mechanism," Chemistry & Biology 11, 1489-1493 (2004).
Madden, et al. "Overexpression of human topoisomerase I in baby hamster kidney cells: hypersensitivity of clonal isolates to camptothecin," Cancer Res 52, 525-32. (1992).
Madesh, et al. "VDAC-dependent permeabilization of the outer mitochondrial membrane . . . ," J Cell Biol 155, 1003-15 (2001).
Majno, et al. "Apoptosis, oncosis, and necrosis. An overview of cell death," Am J Pathol 146, 3-15. (1995).
Makin, "Targeting apoptosis in cancer chemotherapy," Expert Opin Ther Targets 6, 73-84. (2002).
Malumbres, et al. "RAS oncogenes: the first 30 years," Nat Rev Cancer 3, 459-465 (2003).
Mannella, "Minireview: on the structure and gating mechanism of the mitochondrial channel, VDAC," J Bioenerg Biomembr 29,525-31 (1997).
Marciano, et al. "Farnesyl derivatives of rigid carboxylic acids-inhibitors of ras-dependent cell growth," J Med Chem 38, 1267-1272 (1995).
Marom, et al. "Selective inhibition of Ras-dependent cell growth by farnesylthiosalisylic acid," J Biol Chem 270, 22263-22270 (1995).
Meuwissen, et al. "Mouse model for lung tumorigenesis through Cre/lox controlled sporadic activation of the K-Ras oncogene," Oncogene 20, 6551-8 (2001).
Moffat, et al. "A lentiviral RNAi library for human and mouse genes applied to an arrayed viral high-content screen," Cell 124, 1283-1298 (2006).
Moffat, et al. "Building mammalian signalling pathways with RNAi screens," Nat Rev Mol Cell Biol 7, 177-187 (2006).
Mokbel, et al. "From HER2 to herceptin," Curr Med Res Opin 17, 51-9. (2001).
Montal, et al. "Formation of bimolecular membranes from lipid monolayers and a study of their electrical properties," Proc Natl Acad Sci 69, 3561-6 (1972).
Nagasu, et al. "Inhibition of human tumor xenograft growth by treatment with the farnesyl transferase inhibitor B956," Cancer Res 55, 5310-5314 (1995).
Navratilova, et al. "Solubilization, stabilization, and purification of chemokine receptors using biosensor technology," Anal Biochem 339,271-81 (2005).
Neshat, et al. "Enhanced sensitivity of PTEN-deficient tumors to inhibition of FRAP/mTOR," Proc. Natl. Acad. Sci. USA 98, 10314-10319 (2001).
Nicolaou, et. al., "Studies toward Diazonamide a: Initial Synthetic Forays Directed toward the Originally Proposed Structure," JACS 126 (32) 10162-10173 (2004).

Nishibori, "Isolation of echinochrome a from the spines of the sea urchin, Stomopneustes variolaris (Lamarck)," Nature 192, 1293-1294 (1961).
Nociari et al. "A novel one-step, highly sensitive fluorometric assay to evaluate cell-mediated cytotoxicity," J. Immunol. Methods 213, 157-167 (1998).
Oda, et al. "Quantitative chemical proteomics for identifying candidate drug targets," Anal Chem 75, 2159-65 (2003).
Ohsumi, "Molecular dissection of autophagy: two ubiquitin-like systems," Nat Rev Mol Cell Biol 2, 211-6. (2001).
Olszewski, et al. "Tethered benzophenone reagents for the synthesis of photoactivatable ligands," Bioconjug Chem 6, 395-400 (1995).
Ouyang, et al. "A mitogen-responsive promoter region that is synergistically activated through multiple signalling pathways," Mol Cell Biol 13, 1796-1804 (1993).
Pardee, et al. "Cancer therapy with beta-lapachone," Curr Cancer Drug Targets 2, 227-242 (2002).
Parsons, et al. "Integration of chemical-genetic and genetic interaction data links bioactive compounds to cellular target pathways," Nat Biotechnol X, XX (2003).
Patel, et al. "Plasma membrane cholesterol modulates cellular vacuolation induced by the Helicobacter pylori vacuolating cytotoxin," Infect Immun 70, 4112-23 (2002).
Paull, et al. "Display and analysis of patterns of differential activity of drugs against human tumor cell lines: development . . . ," J Natl Cancer Inst 81, 1088-1092 (1989).
Perez-Stable, et al. "Prostate cancer progression, metastasis, and gene expression in transgenic mice," Cancer Res 57, 900-6. (1997).
Pestic-Dragovich, et al. "A myosin I isoform in the nucleus," Science 290,337-41 (2000).
Petrat, et al. "Determination of the chelatable iron pool of single intact cells by laser scanning microscopy," Arch Biochem Biophys 376, 74-81 (2000).
Plattner, at al. "Differential contribution of the ERK and JNK mitogen-activated protein kinase . . . ," Oncogene 18,1807-17 (1999).
Pollitt. et al. "A rapid cellular FRET assay of polyglutamine aggregation identifies a novel inhibitor," Neuron 40, 685-94 (2003).
Prestwich, et al. "Benzophenone photoprobes for phosphoinositides, peptides and drugs," Photochem Photobiol 65, 222-34 (1997).
Rahmani, et al. "Isolation of a novel human voltage-dependent anion channel gene," Eur J Hum Genet 6, 337-40 (1998).
Rahmani, et al. "Hepatitis B virus X protein colocalizes to mitochondria with a human voltage-dependent anion channel . . . ," J Virol 74,2840-6 (2000).
Rich, et at. "A genetically tractable model of human glioma formation," Cancer Res 61,3556-60. (2001).
Rodenhuis, "ras and human tumors," Semin Cancer Biol 3, 241-247 (1992).
Root, et al. "Detecting spatial patterns in biological array experiments," J Biomol Screen 8, 393-8 (2003).
Root, et al. "Global analysis of large-scale chemical and biological experiments," Curr Opin Drug Discov Devel 5, 355-60 (2002).
Root, et al. "Biological Mechanism Profiling Using an Annotated Compound Library," Chemistry & Biology, 10:881-92 (2003).
Rostovtseva, et al. "On the Role of VDAC in Apoptosis: Fact and Fiction," J Bioenerg Biomembr 37, 129-42 (2005).
Rostovtseva, et al. "VDAC channels mediate and gate the flow of ATP: implications for the regulation of mitochondrial function," Biophys J 72, 1954-62 (1997).
Rowell, et al. "Direct demonstration of geranylgeranylation and farnesylation of Ki-Ras in vivo," J Biol Chem 272, 14093-14097 (1997).
Sabatini, et al. "RAFT1: a mammalian protein that binds to FKBP12 in a rapamycin-dependent fashion and is homologous to yeast TORs," Cell 78, 35-43. (1994).
Sampson, et al. "Immotile sperm and infertility in mice lacking mitochondrial voltage-dependent anion channel type 3," J Biol Chem 276, 39206-12 (2001).
Saraste, et al. "Morphologic and biochemical hallmarks of apoptosis," Cardiovasc Res 45, 528-37 (2000).
Schafer, et al. "Enzymatic coupling of cholesterol intermediates to a mating pheromone precursor and to the ras protein," Science 249, 1133-1139 (1990).
Schafer, et al. "Genetic and pharmacological suppression of oncogenic mutations in ras genes of yeast and humans," Science 245, 379-385 (1989).
Schreiber, "Chemical genetics resulting from a passion for synthetic organic chemistry," Bioorg Med. Chem. 6,1127-1152 (1998).
Schreiber, "Target-oriented and diversity-oriented organic synthesis in drug discovery," Science 287, 1964-9. (2000).
Schreiber, "The small-molecule approach to biology: Chemical genetics and diversity-oriented organic synthesis . . . ," Chem. & Eng. News 81, 51-61 (2003).
Seong, et al. "HD CAG repeat implicates a dominant property of huntingtin in mitochondrial energy metabolism," Hum Mol Genet 14, 2871-80 (2005).
Sgonc, et al. "Apoptosis detection: an overview," Exp Gerontol 33, 525-33 (1998).
Shao, et al. "Circular dichroism studies of the mitochondrial channel, VDAC, from Neurospora crassa," Biophys J 71, 778-86 (1996).
Shaw, et al. Ras, PI(3)K and mTOR signalling controls tumour cell growth, Nature 441, 424-430 (2006).
Shawver, et al. "Smart drugs: tyrosine kinase inhibitors in cancer therapy," Cancer Cell 1, 117-23. (2002).
Shi, et al. "Enhanced sensitivity of multiple myeloma cells containing PTEN mutations to CCI-779," Cancer Res 62, 5027-34. (2002).
Shimizu, et al. "BH4 domain of antiapoptotic Bcl-2 family members closes voltage-dependent anion channel and inhibits apoptotic . . . ," Proc Natl Acad Sci 97,3100-5 (2000).
Shimizu, et al. "Bcl-2 family proteins regulate the release of apoptogenic cytochrome c by the mitochondrial channel VDAC," Nature 399, 483-7 (1999).
Shterman, et al. "Comparison of transferrin receptors, iron content and isoferritin profile in normal and malignant human breast cell lines," Pathobiology 59, 19-25 (1991).
Singh, et al. "Biological activity of the labdane diterpenes," Planta Med 65, 2-8 (1999).
Smith, et al. "Requirement for c-ras proteins during viral oncogene transformation," Nature 320, 540-543 (1986).
Smukste, et al. "Advances in chemical genetics," Annual Review of Genomics and Human Genetics, 6:261-86 (2005).
Smukste, et al. "Using small molecules to overcome drug resistance induced by a viral oncogene," Cancer Cell, 9, 133-146 (2006).
Stanley, et al. "Peptide-specific antibodies as probes of the topography of the voltage-gated channel in the mitochondrial outer membrane..," J Biol Chem 270, 16694-700 (1995).
Stegmaier,et al. "Gene expression-based high-throughput screening (GE-HTS) and application to leukemia differentiation," Nature Genetics, 36: 257-63 (2004).
Stenlund, et al. "Capture and reconstitution of G protein-coupled receptors on a biosensor surface," Anal Biochem 316, 243-50 (2003).
Stevens, et al. "Body iron stores and the risk of cancer," N Engl J Med 319, 1047-1052 (1988).
Stewart, et al. "Lentivirus-delivered stable gene silencing by RNAi in primary cells," Rna 9, 493-501 (2003).
Stockwell, "Chemical genetic: Screening Approaches to Neurobiology," Neuron 36, 559-62 (2002).
Stockwell, "Chemical genetics: ligand-based discovery of gene function," Nat. Rev. Genet. 1, 116-125 (2000).
Stockwell, "Exploring biology with small organic molecules," Nature 432: 846-54 (2004).
Stockwell, "Frontiers in chemical genetics," Trends Biotechnol 18, 449-55. (2000).
Stockwell, et al. "High-throughput screening of small molecules in miniaturized mammalian cell-based assays involving post-translational . . . ," Chem Biol 6, 71-83 (1999).
Syntichaki, et al. "The biochemistry of neuronal necrosis: rogue biology?" Nat Rev Neurosci 4, 672-84 (2003).
Szabo et al. "Evaluation of an automated instrument for viability and concentration measurements of cryopreserved hematopoietic cells," Lab Hematol 10, 109-11 (2004).
Testa, et al. "SV40 and cell cycle perturbations in malignant mesothelioma," Semin Cancer Biol 11, 31-8. (2001).
Thinnes, et al. "Studies on human porin XXI: gadolinium opens Up cell membrane standing porin . . . ," Mol Genet Metab 69, 240-51 (2000).

Thinnes, "Evidence for extra-mitochondrial localization of the VDAC/porin channel in eukaryotic cells," J Bioenerg Biomembr 24,71-5 (1992).
Thomas, et al. "Mapping of residues forming the voltage sensor of the voltage-dependent anion-selective channel," Proc Natl Acad Sci USA 90, 5446-9 (1993).
Tong, et al. "Systematic genetic analysis with ordered arrays of yeast deletion mutants," Science 294, 2364-2368 (2001).
Torrance, et al. "Use of isogenic human cancer cells for high-throughput screening and drug discovery," Nature biotechnology 19, 940-945 (2001).
Traganos, et al. "Induction of apoptosis by camptothecin and topotecan," Ann NY Acad Sci 803,101-10. (1996).
Tsao, et al. "Interaction between replication forks and topoisomerase I-DNA cleavable complexes: studies in a cell-free SV40 Dna . . . ," Cancer Res 53, 5908-14. (1993).
Tsuji, et al. "FER-1, an enhancer of the ferritin H gene and a target of E1A-mediated transcriptional repression," Mol Cell Biol 15, 5152-5164 (1995).
Tsujimoto, et al. "VDAC regulation by the Bcl-2 family of proteins," Cell Death Differ 7, 1174-81 (2000).
Vander Heiden, et al. "Outer mitochondrial membrane permeability can regulate coupled respiration and cell survival," Proc Natl Acad Sci USA 97, 4666-71 (2000).
Varma, et al. "Selective inhibitors of death in mutant huntingtin cells," Nature chemical biology 3, 99-100 (2007).
Verma, et at. "Ubistatins inhibit proteasome-dependent degradation by binding the ubiquitin chain," Science 306,117-20 (2004).
Vogelstein, et al. "Cancer genes and the pathways they control," Nat Med 10, 789-799 (2004).
Walker, et al. "Targeting Ras and Rho GTPases as opportunities for cancer therapeutics," Curr Opin Genet Dev 15, 62-8 (2005).
Walker, "Patterns of cell death," Methods Achiev Exp Pathol 13, 18-54 (1988).
Wan, et al. "Synthesis and target identification of hymenialdisine analogs," Chem Biol 11, 247-59 (2004).
Wang, et al. "Identification of an Agent Selectively Targeting DPC4 (Deleted in Pancreatic Cancer Locus 4)—Deficient Pancreatic Cancer Cells," Cancer Res 66, 9722-9730 (2006).
Wang, et al. "A new microcellular cytotoxicity test based on calcein AM release," Hum. Immunol. 37, 264-270 (1993).
Weber, "Comparison of the photochemical behavior of four different photoactivatable probes," J Pept Res 49, 375-83 (1997).
Whyte, et al. "K- and N-Ras are geranylgeranylated in cells treated with farnesyl protein transferase inhibitors," J Biol Chem 272, 14459-14464 (1997).
Wilhelm, et al. "Discovery and development of sorafenib: a multikinase inhibitor for treating cancer," Nat Rev Drug Discov 5, 835-844 (2006).
Williams, et al. "Identification of compounds that bind mitochondrial F1 FO ATPase by screening a triazine library for correction of albinism," Chem Biol 11, 1251-9 (2004).
Wood, L. et al. "Inhibition of superoxide dismutase by 2-methoxyoestradiol analogues and oestrogen derivatives: structure-activity . . . ," Anticancer Drug Des 16, 209-15 (2001).
Wu, et al. "Coordinated regulation of iron-controlling genes, H-ferritin and IRP2, by c-MYC," Science 283, 676-679 (1999).
Xu, et al. "Mouse VDAC isoforms expressed in yeast: channel properties and their roles in mitochondrial outer membrane permeability," J Membr Biol 170, 89-102 (1999).
Yagoda, et al. "RAS-RAF-MEK-dependent oxidative cell death involving voltage-dependent anion channels," Nature 447, 864-868 (2007).
Yu, et al. "Regulation of an ATG7-beclin 1 program of autophagic cell death by caspase-8," Science 304, 1500-2 (2004).
Zhivotovsky, "Apoptosis, necrosis and between," Cell Cycle 3, 64-6 (2004).
Sharma, et al. Diastereoselective Synthesis of 1,3-disubstituted 1,2,3,4 tetrahydro-beta-carbolines using.., Indian Journal of Chemistry, vol. 45B, Dec. 2006, pp. 2710-2715.

* cited by examiner

Compound 3

Group 1

Compound 6

Group 2

Compound 28

Compound 27

Group 3

Compound 36

Compound 37

Group 4

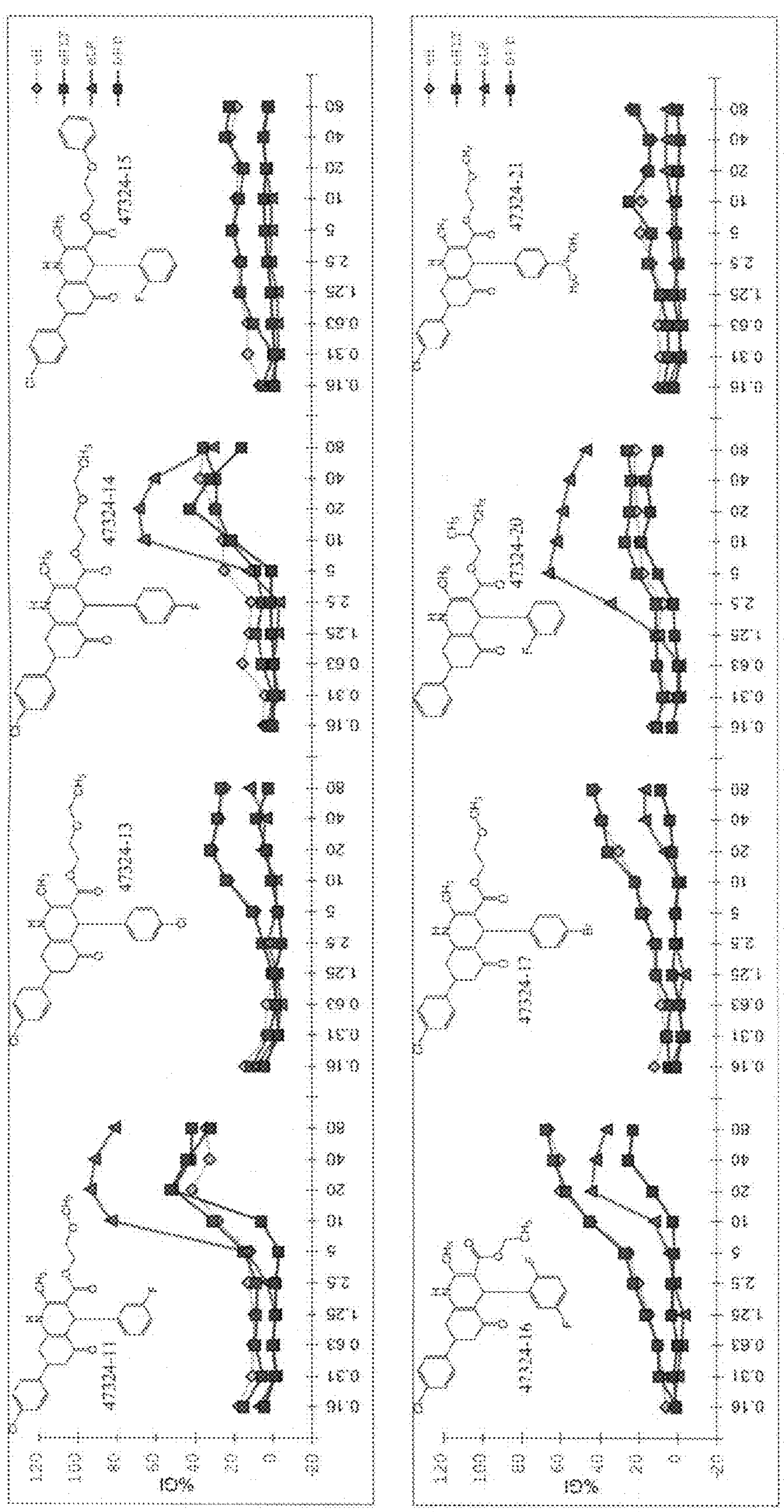
Figure 4 (con't)

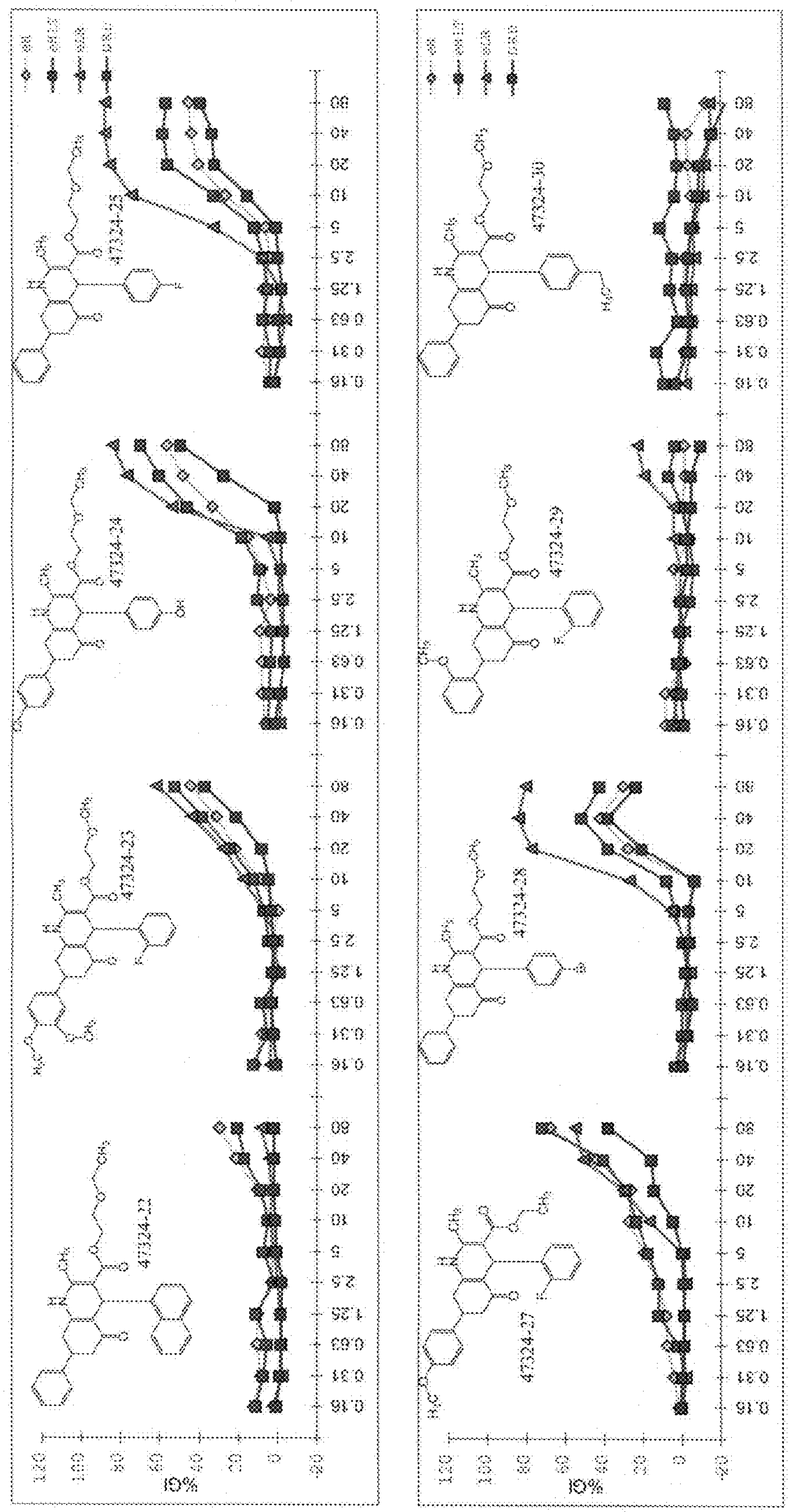
Figure 4 (con't)

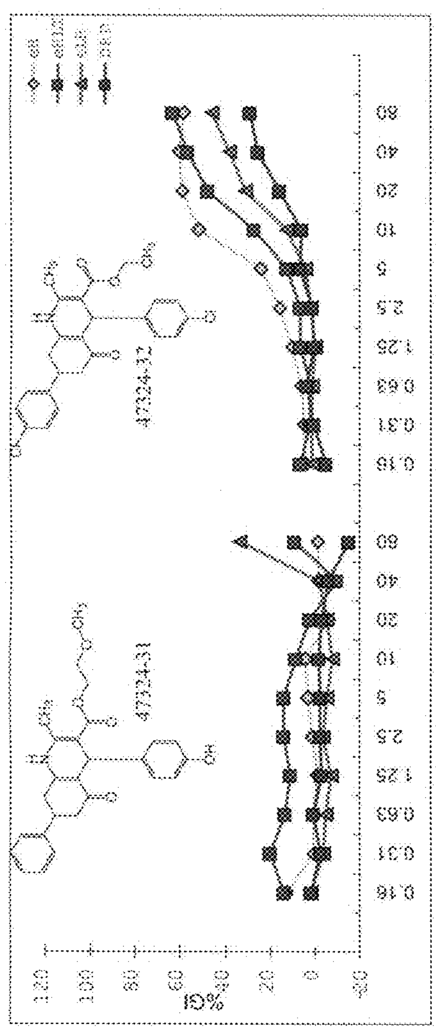
Figure 4 (con't)

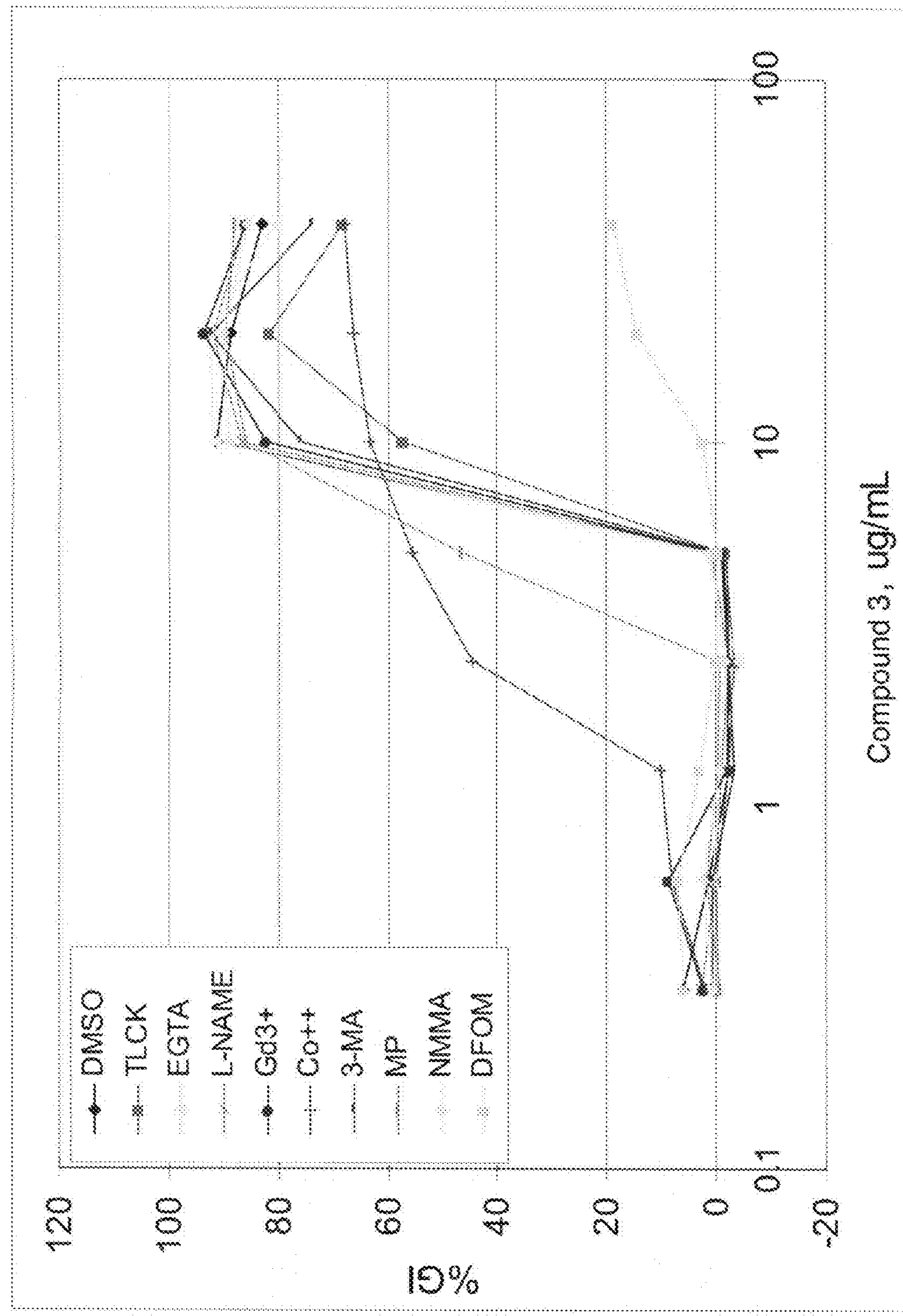
Figure 5 (con't)

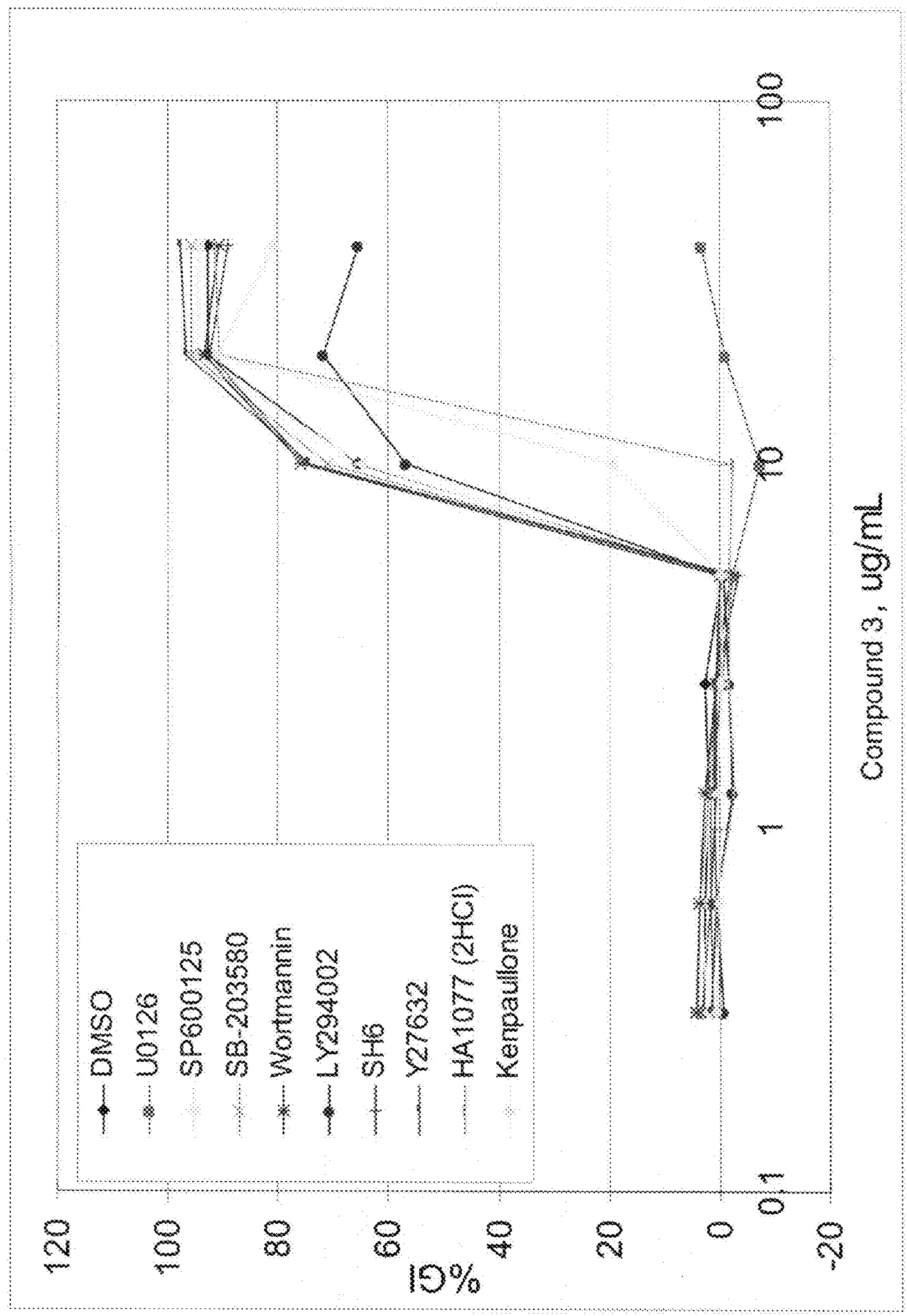
Figure 5 (con't)

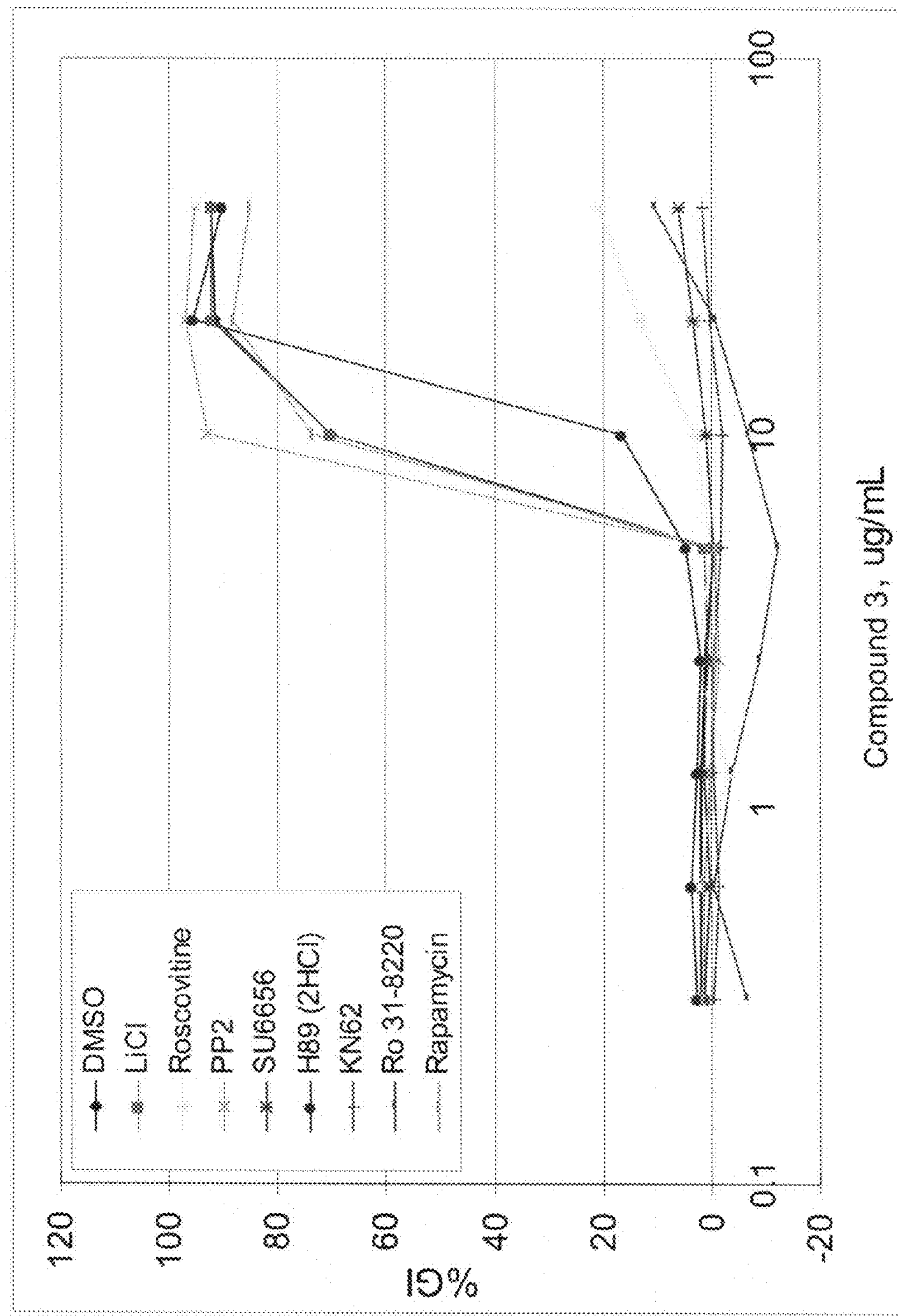
Figure 5 (con't)

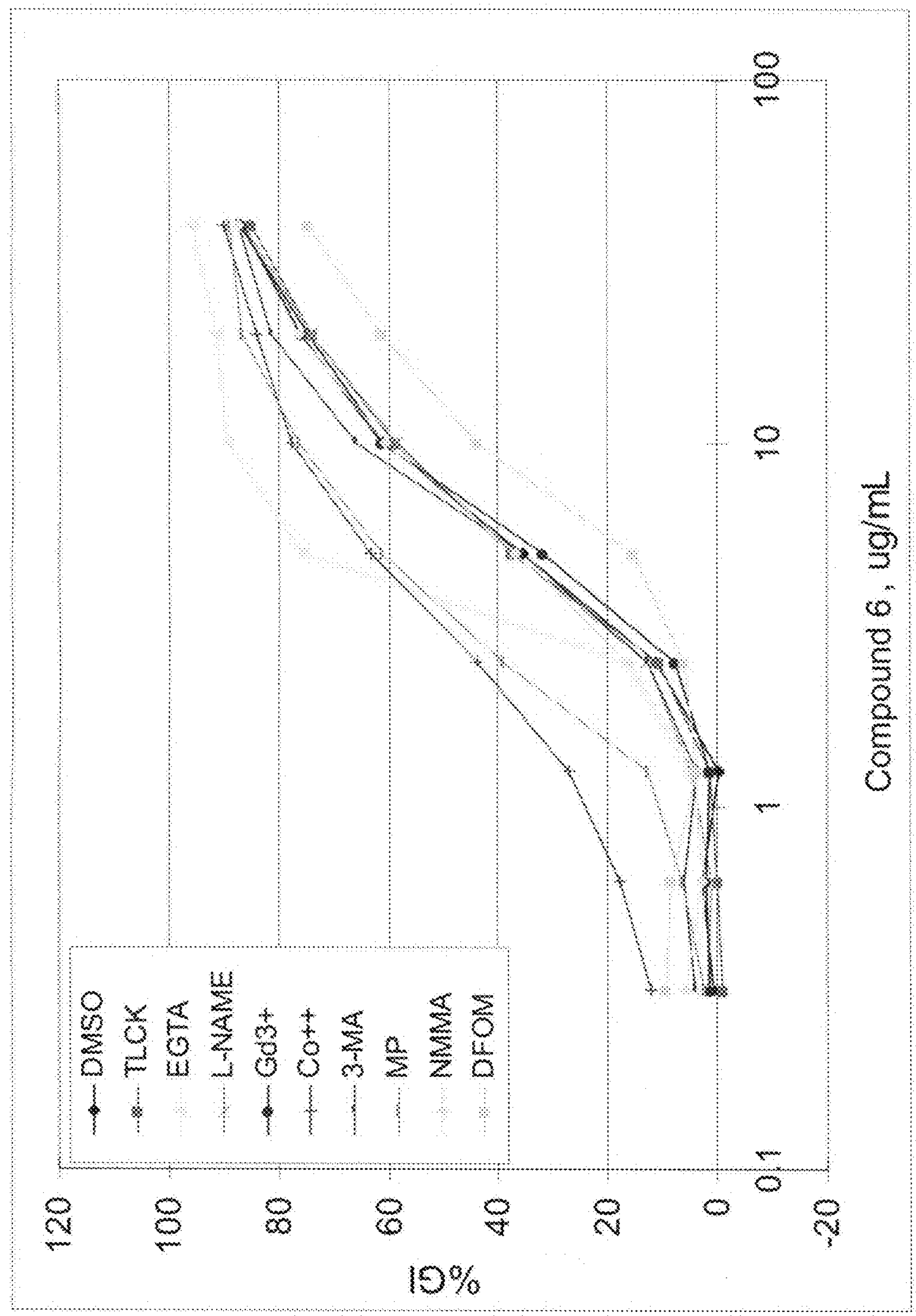
Figure 8 (con't)

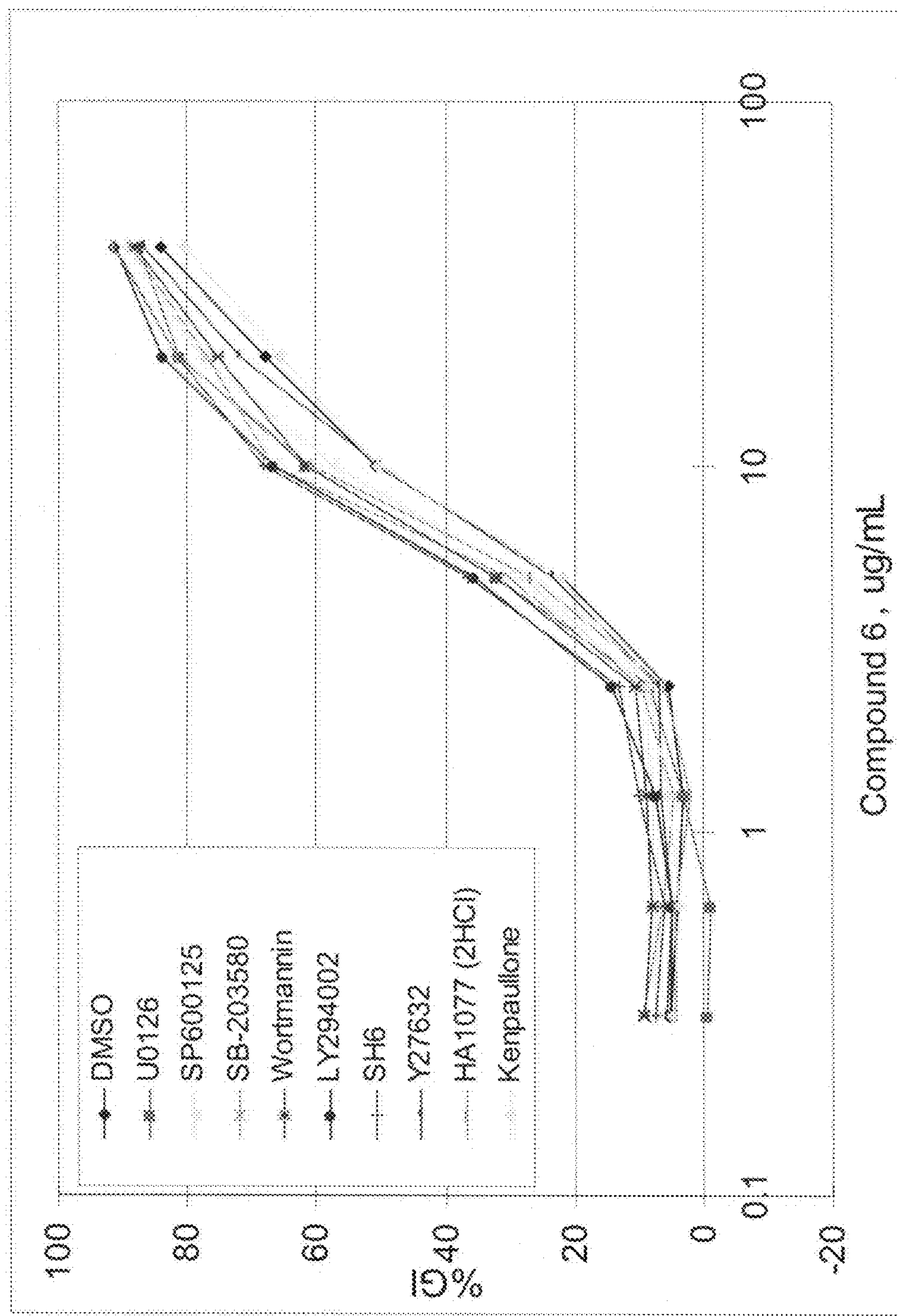
Figure 8 (con't)

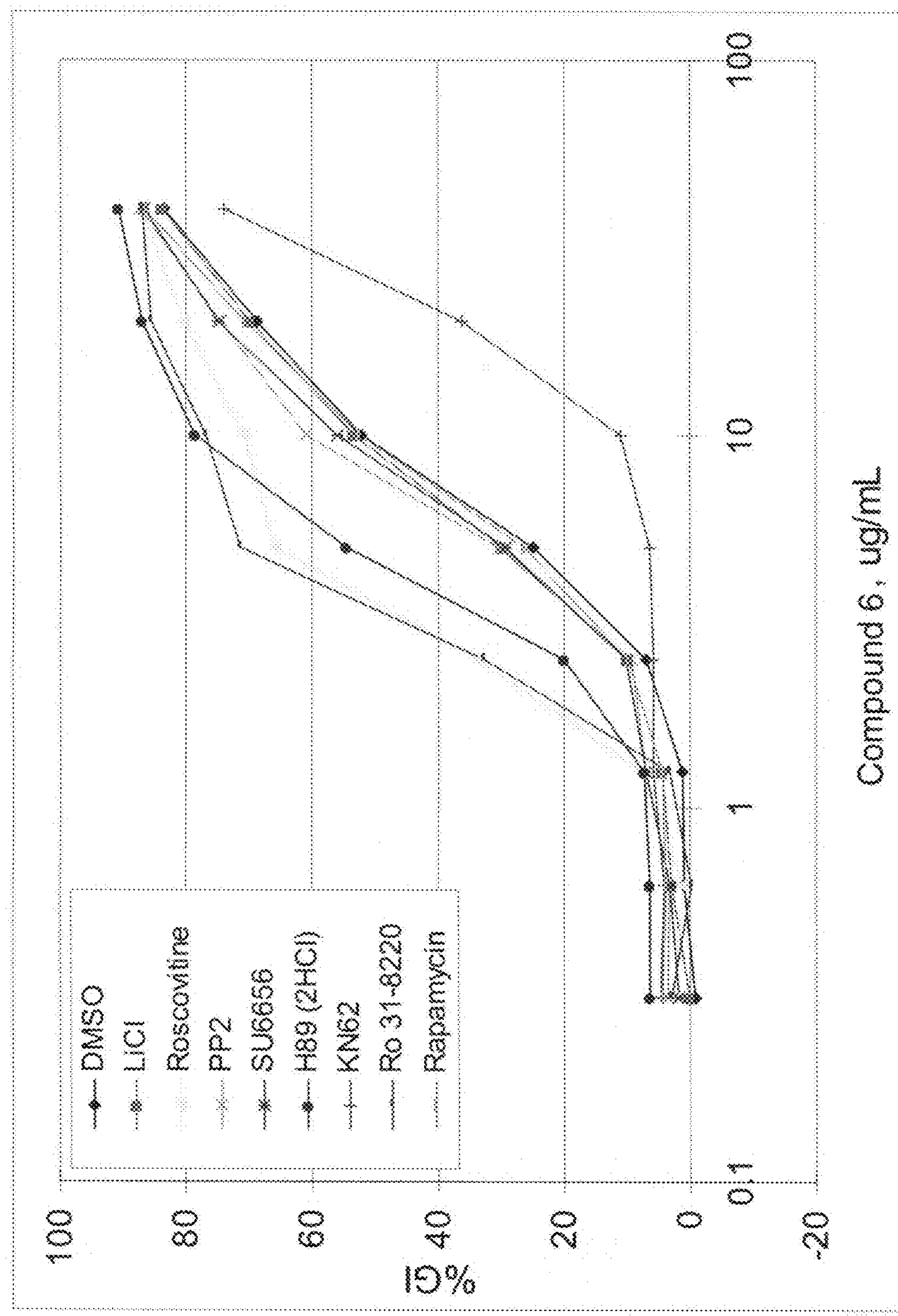
Figure 8 (con't)

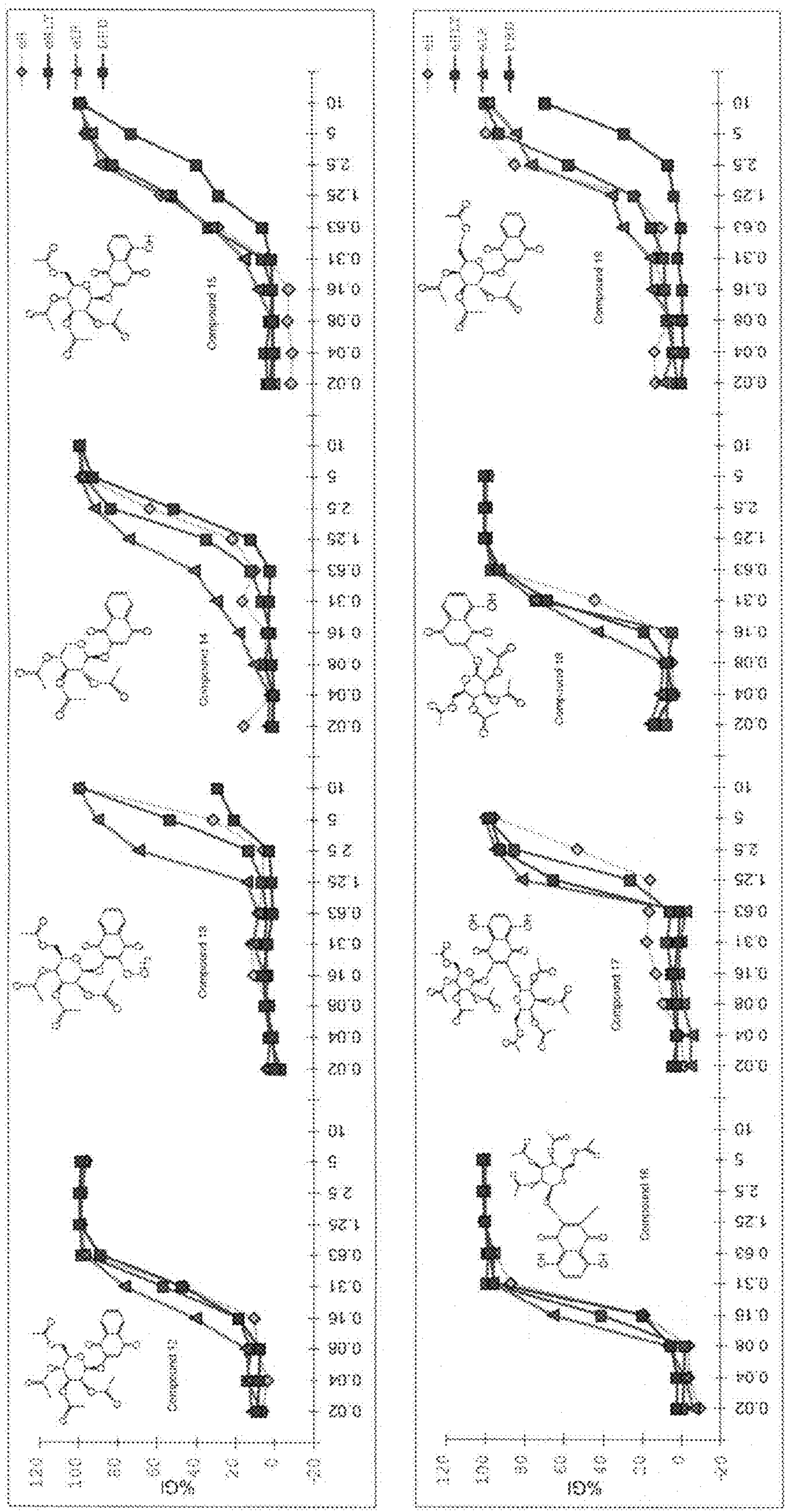
Figure 9 (con't)

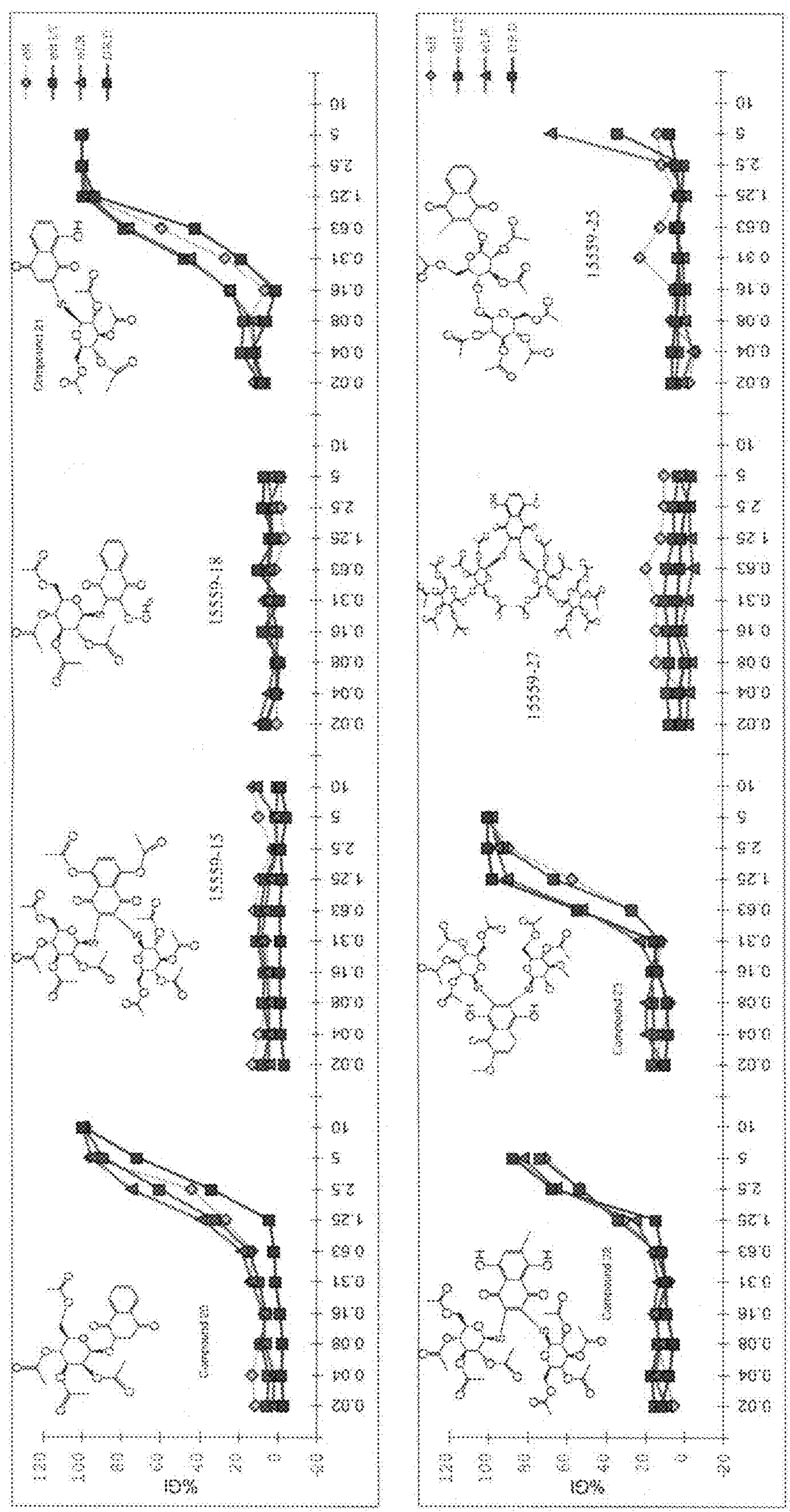
Figure 9 (con't)

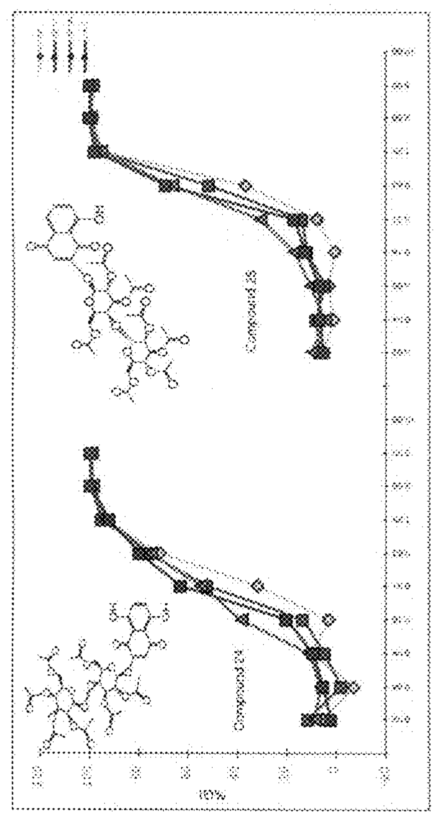
Figure 9 (con't)

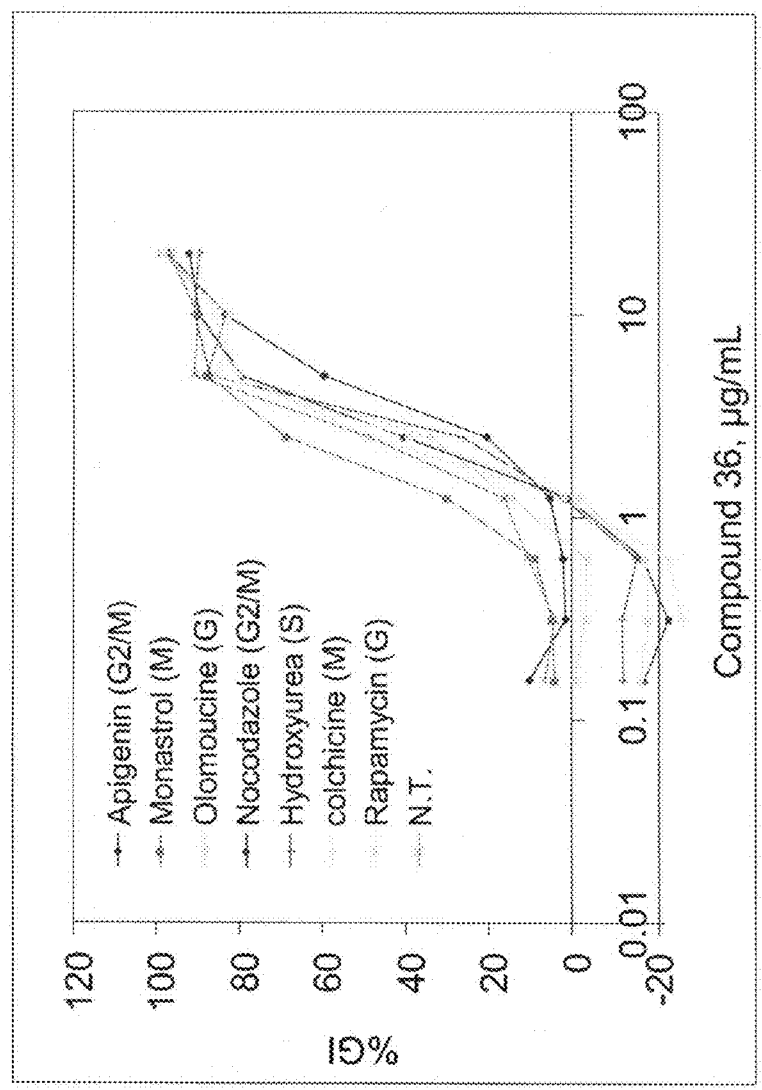
C
Figure 10 (con't)

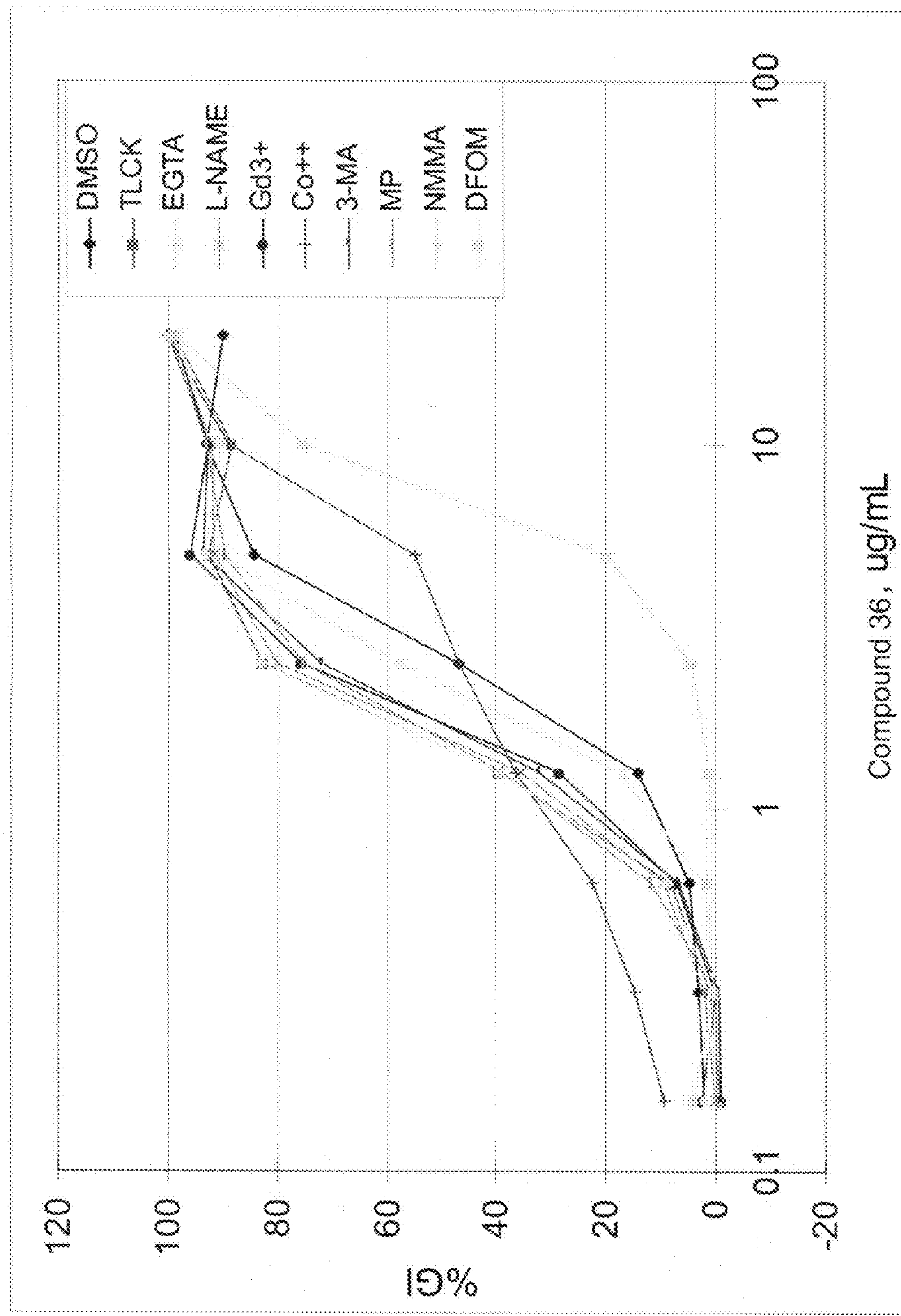
Figure 12 (con't)

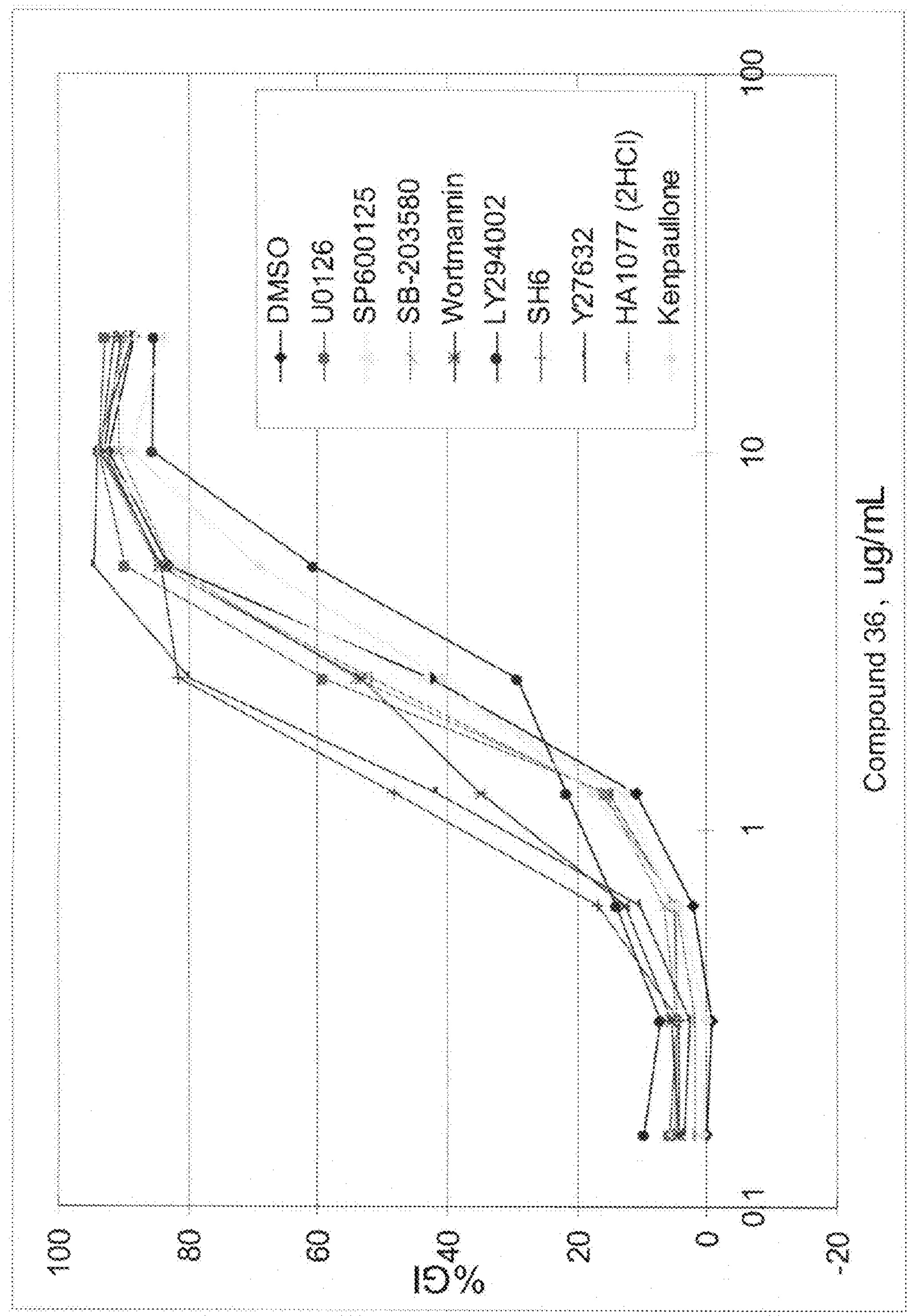
Figure 12 (con't)

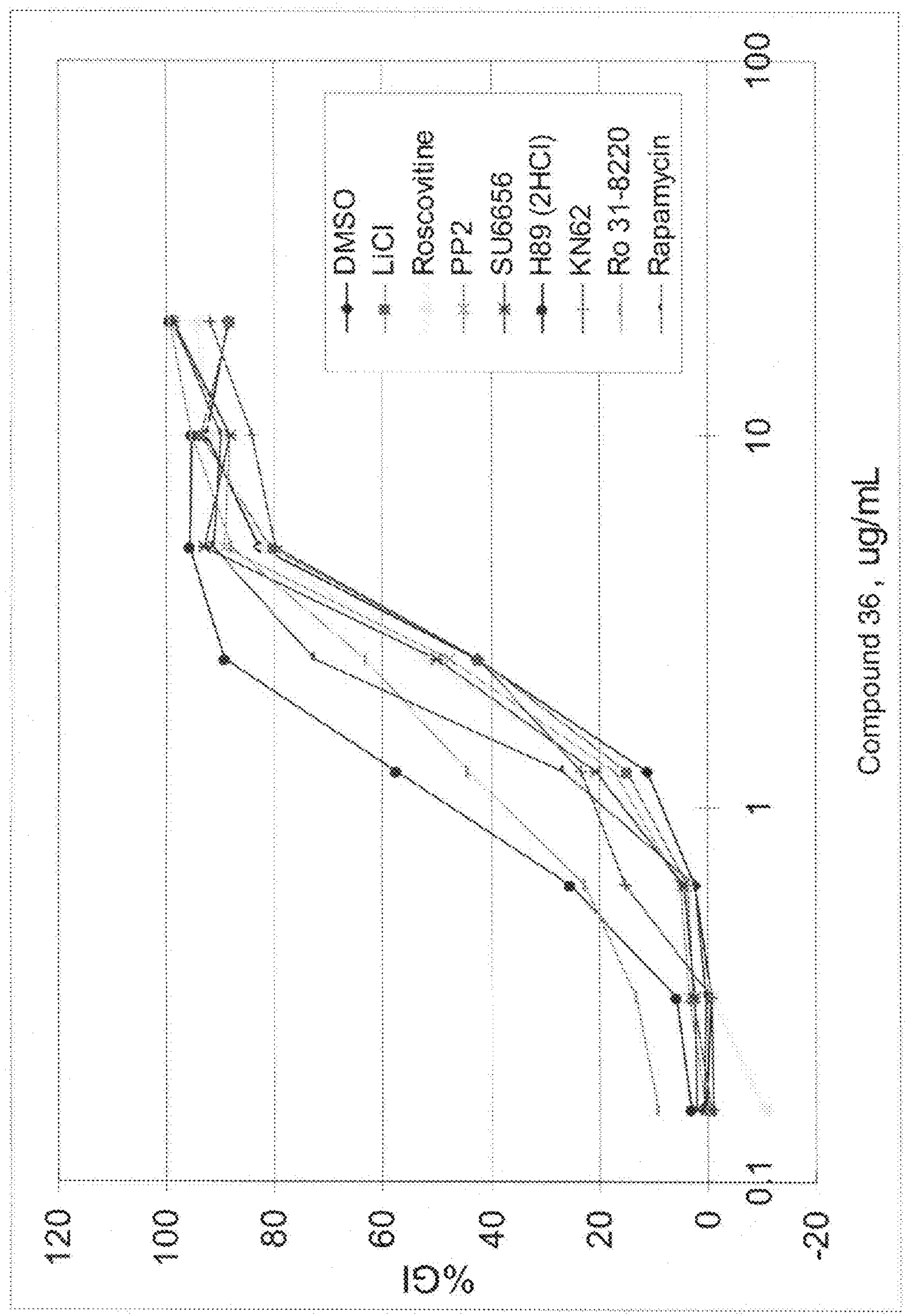
Figure 12 (con't)

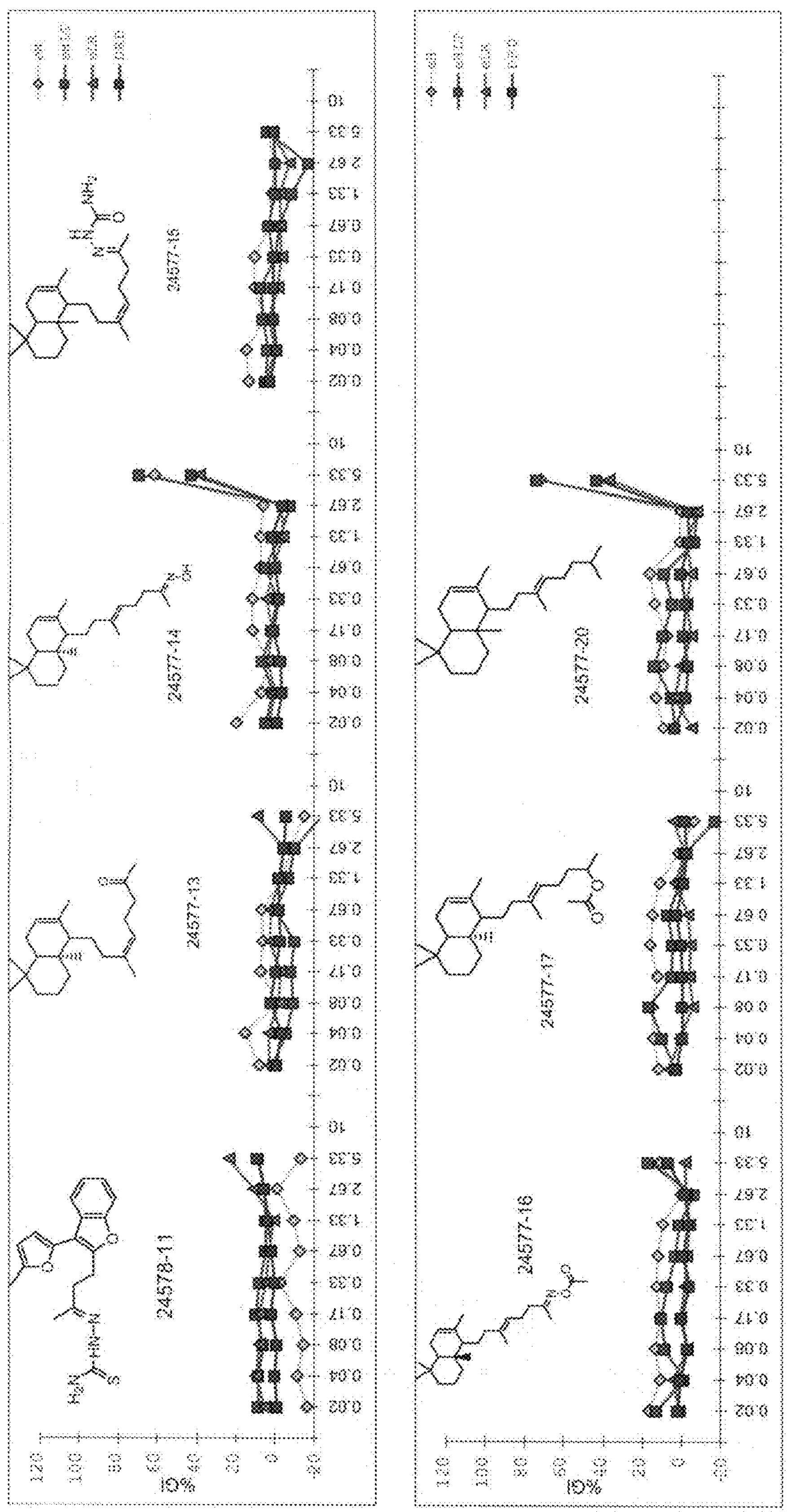
Figure 13 (con't)

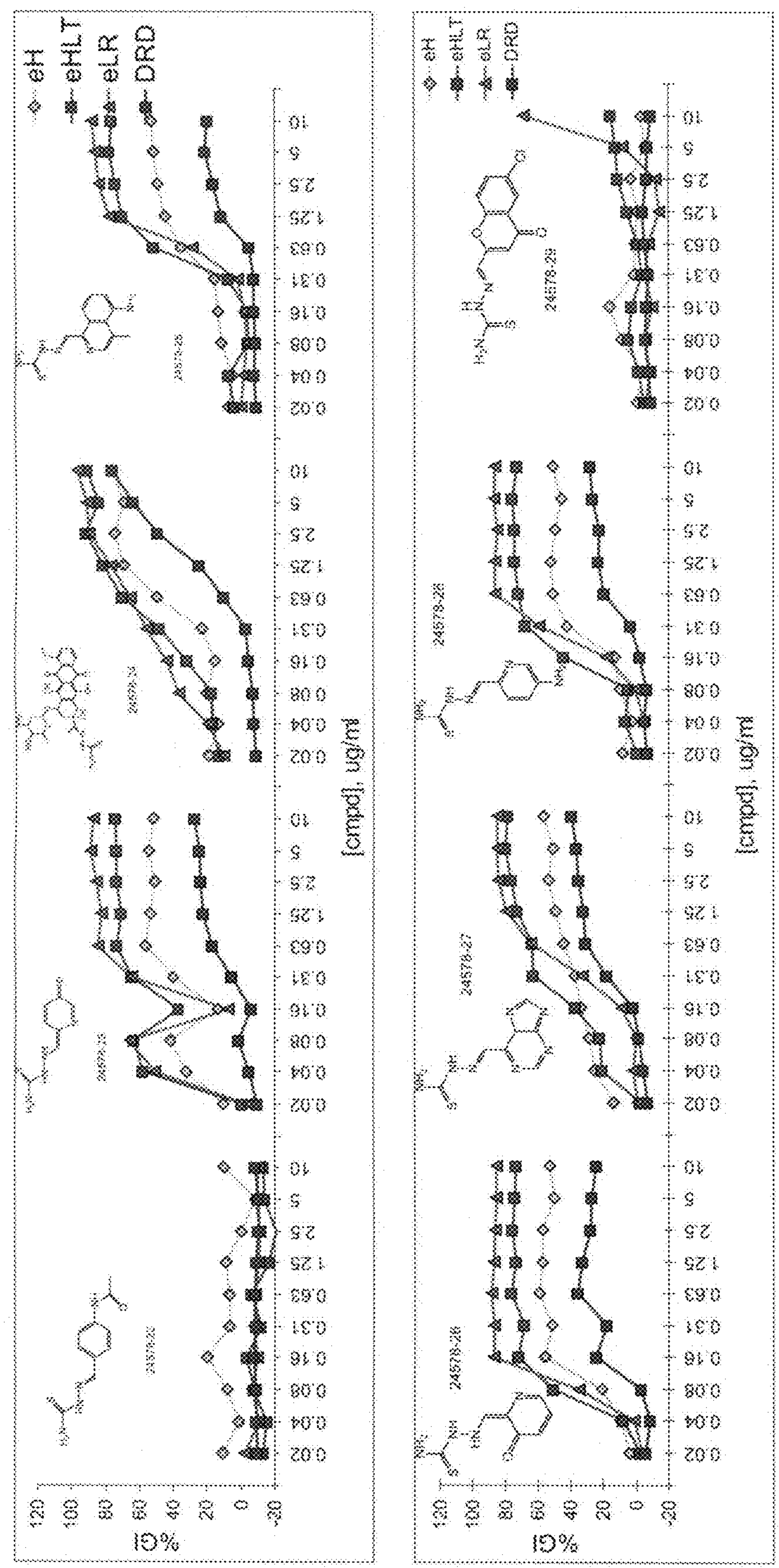
Figure 13 (con't)

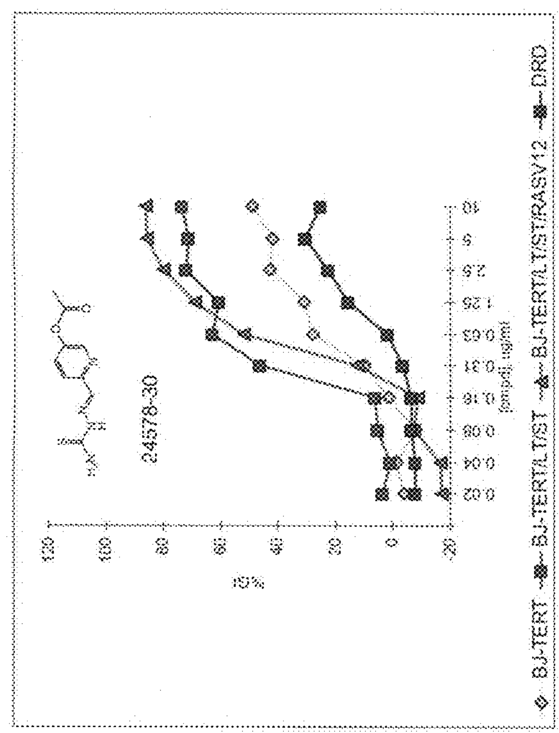
Figure 13 (con't)

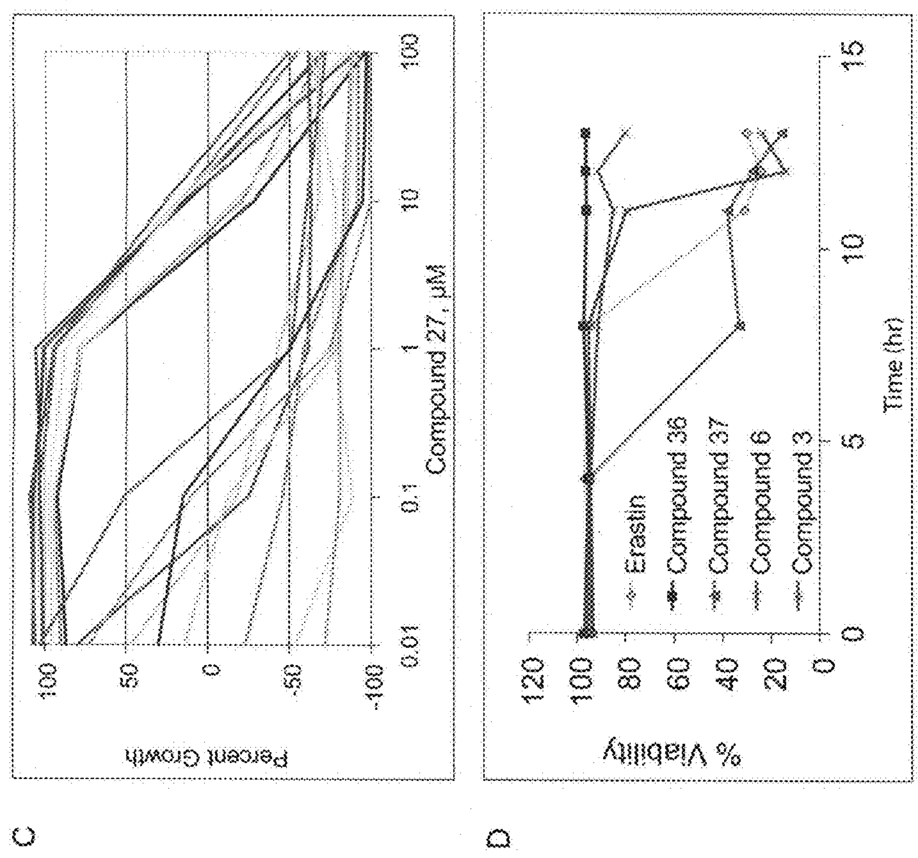
Figure 14 (con't)

E
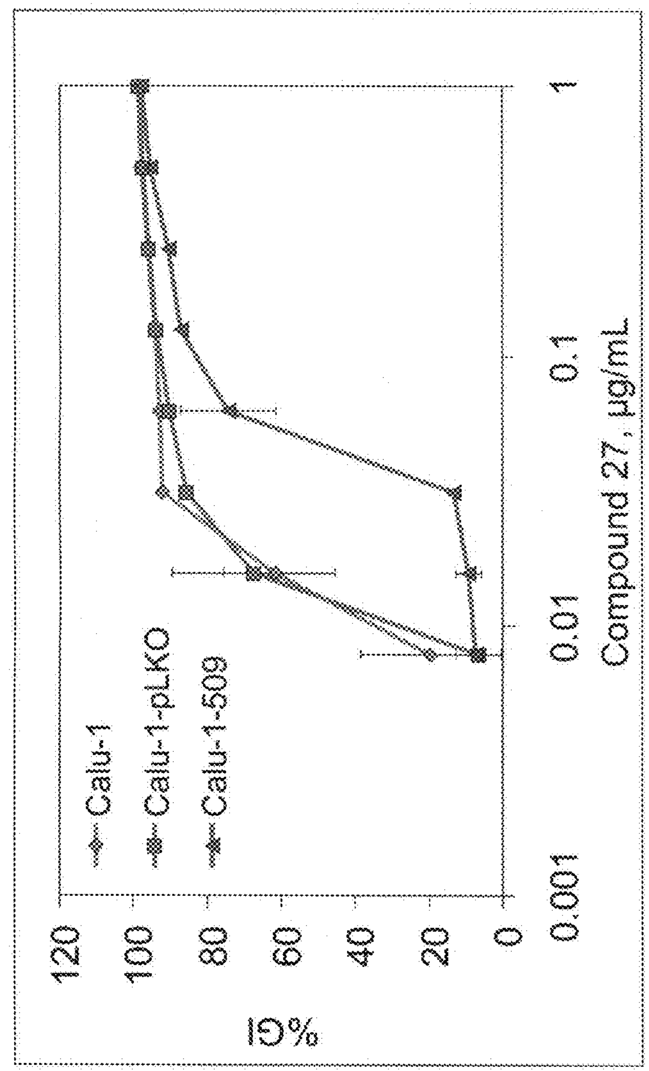
Figure 14 (con't)

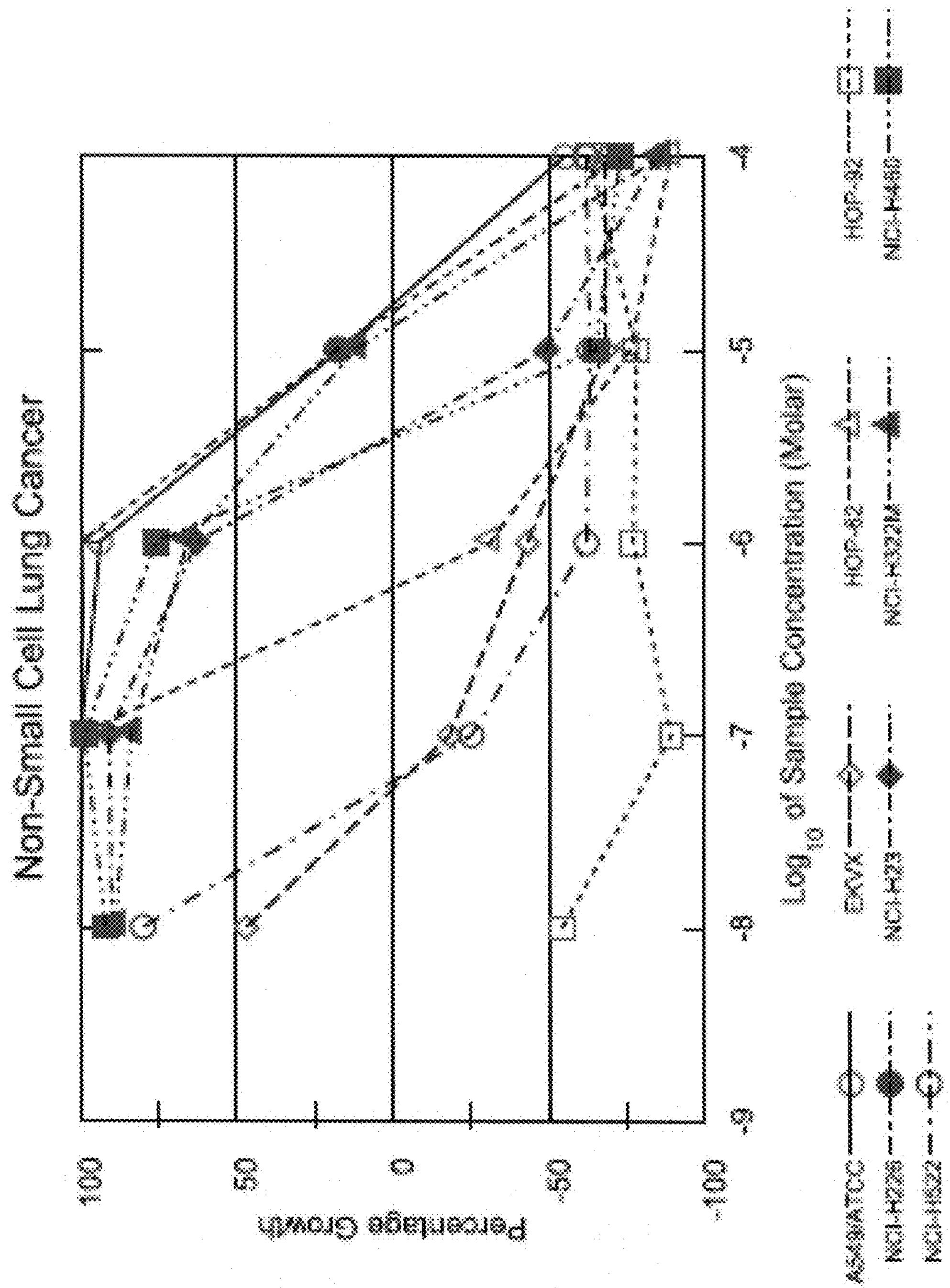
Figure 16 (con't)

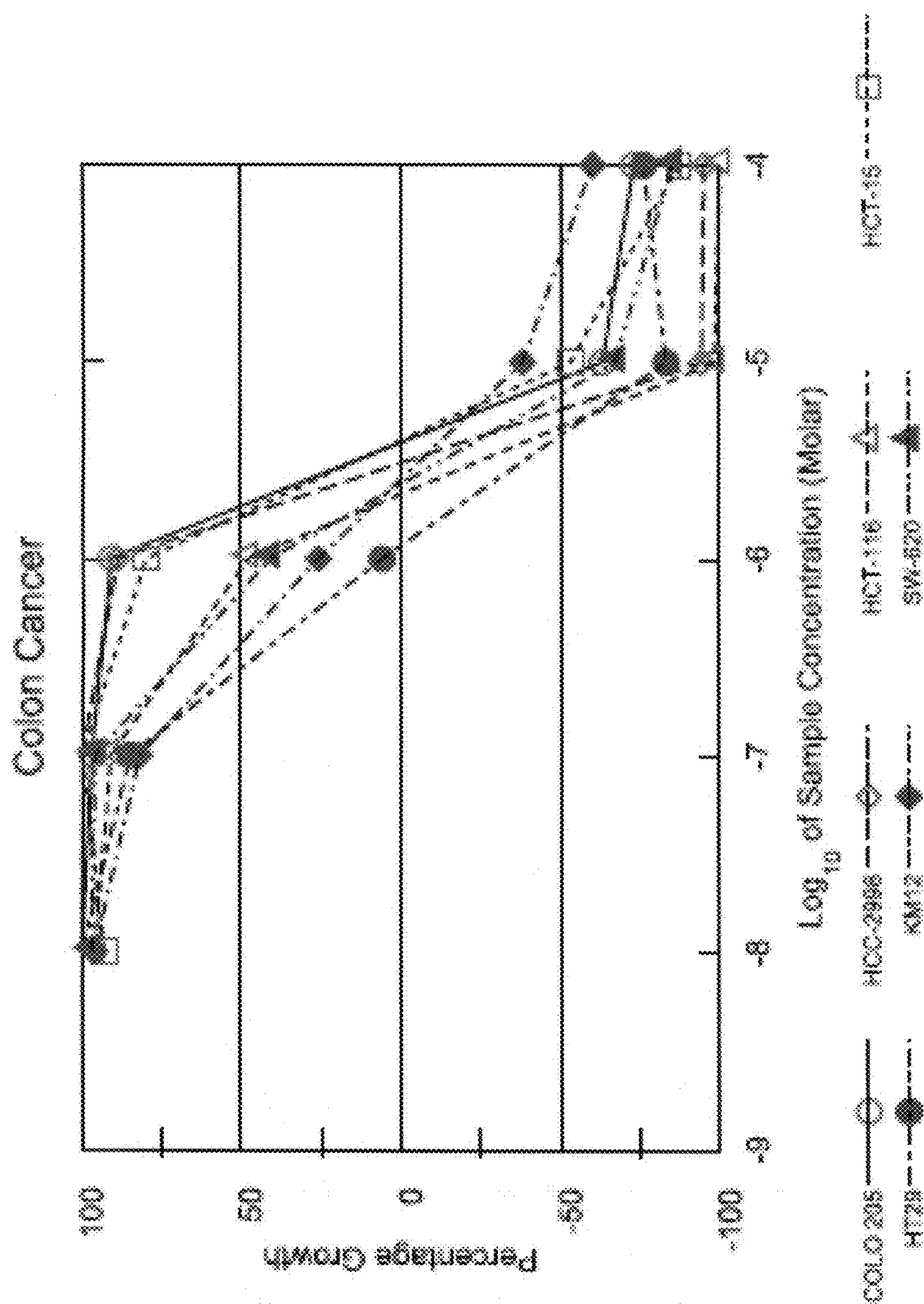
Figure 16 (con't)

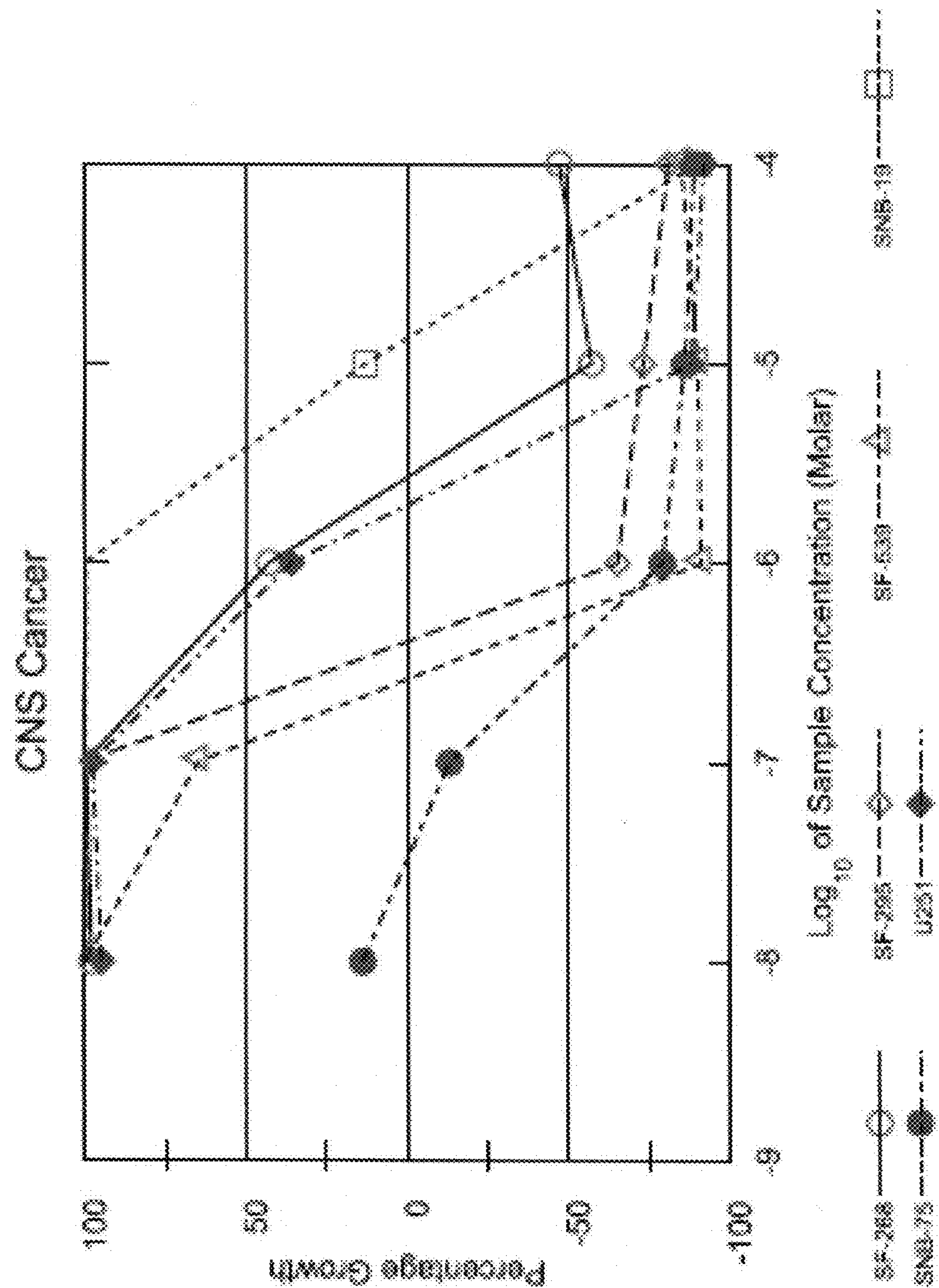
Figure 16 (con't)

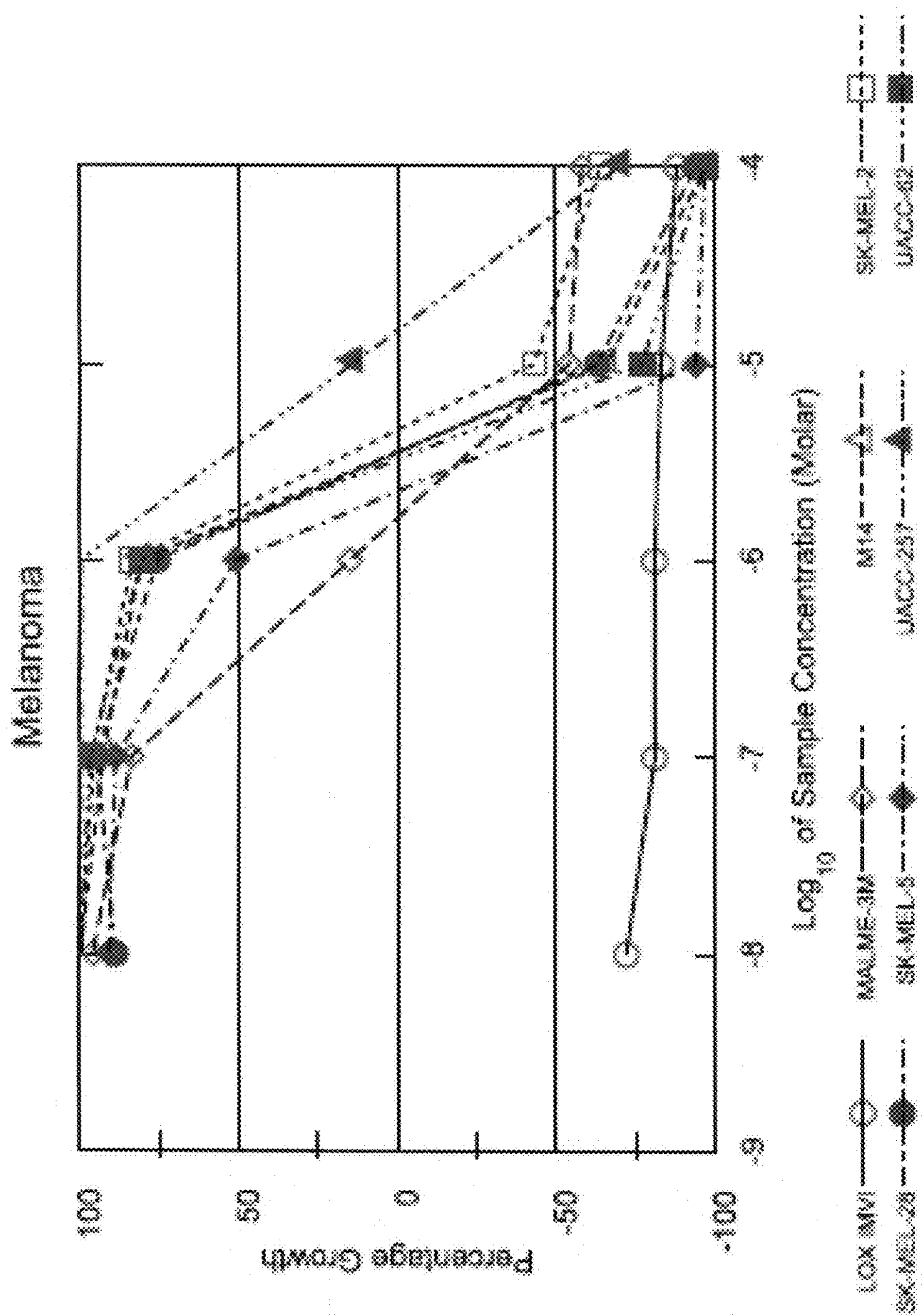
Figure 16 (con't)

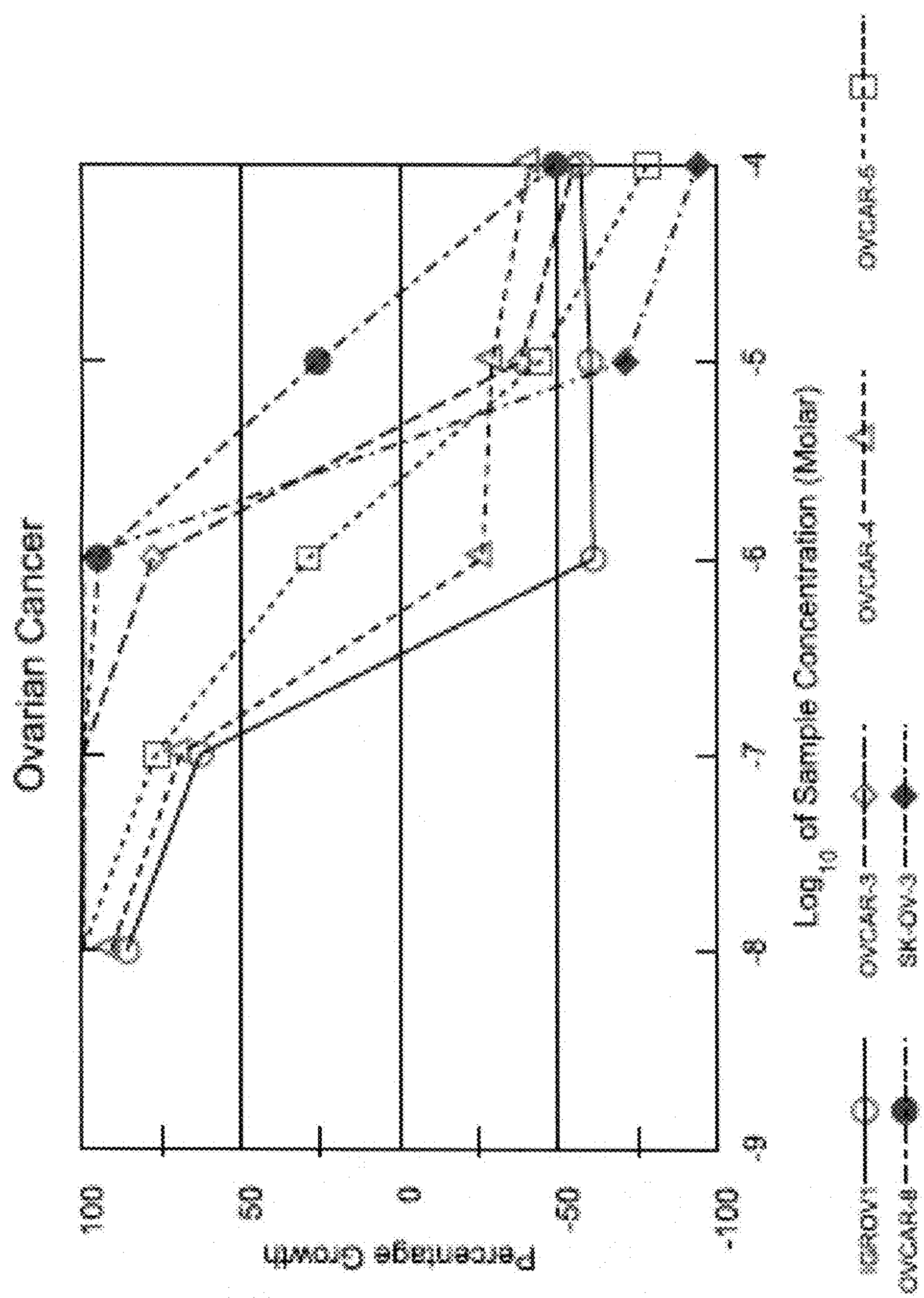
Figure 16 (con't)

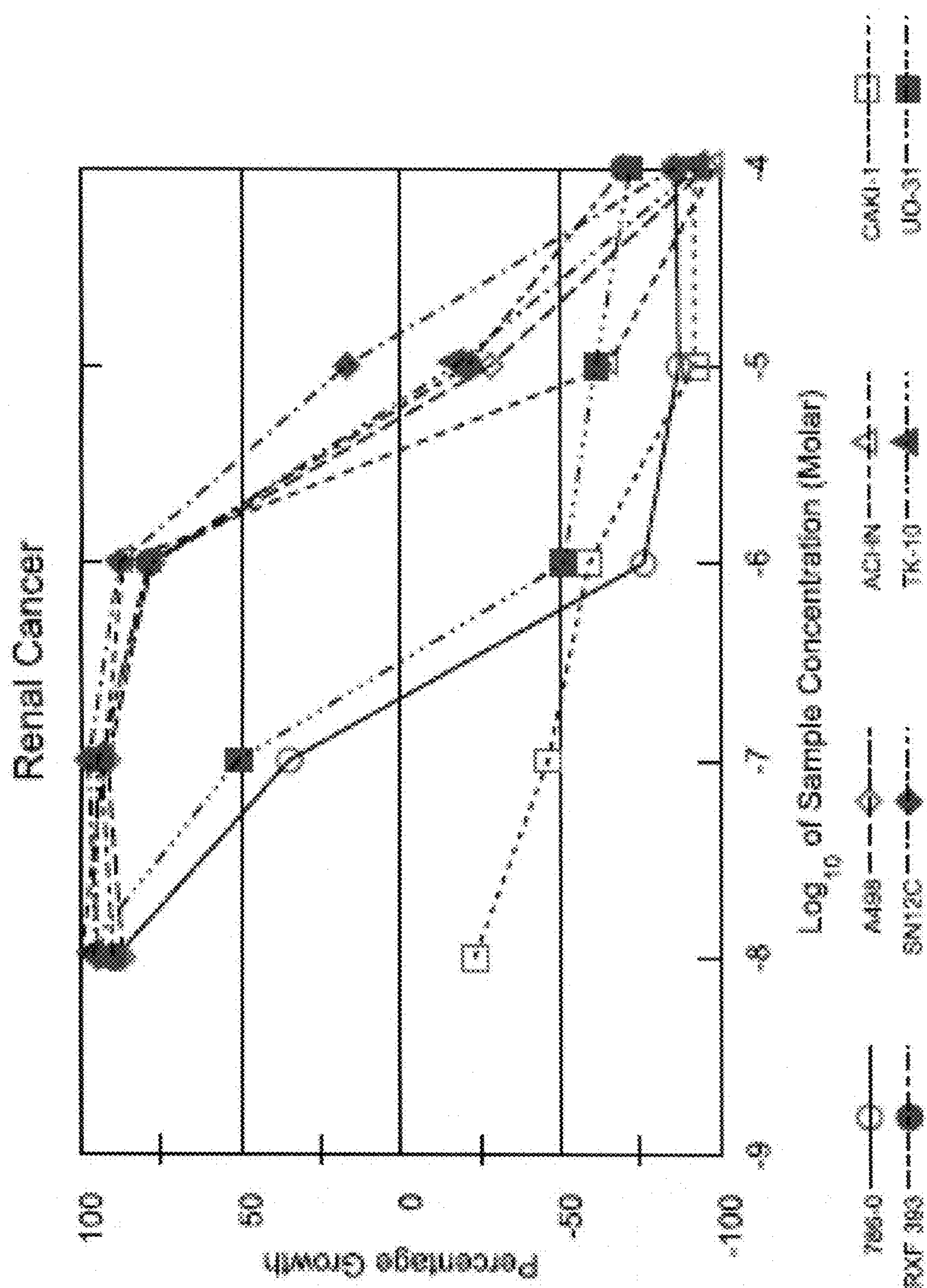
Figure 16 (con't)

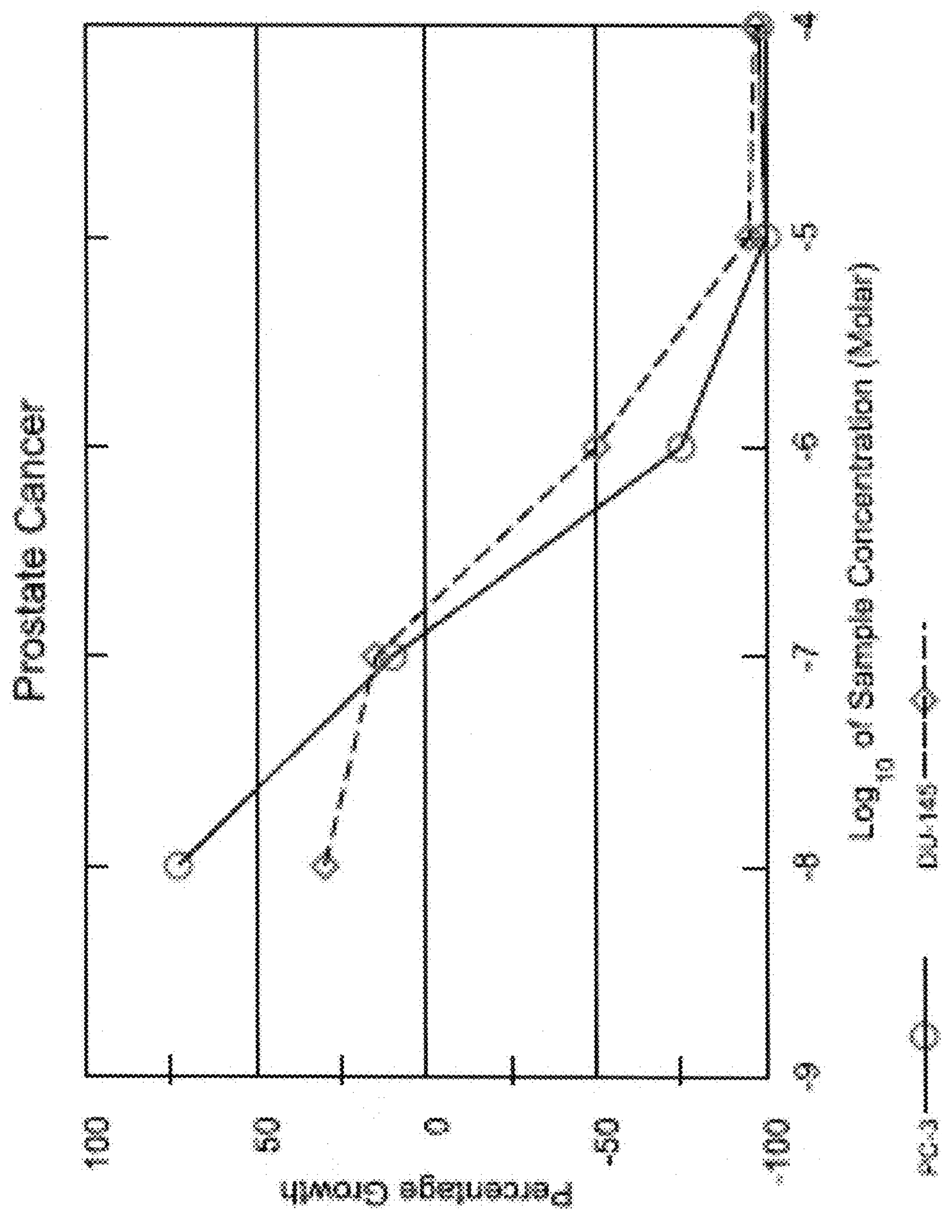
Figure 16 (con't)

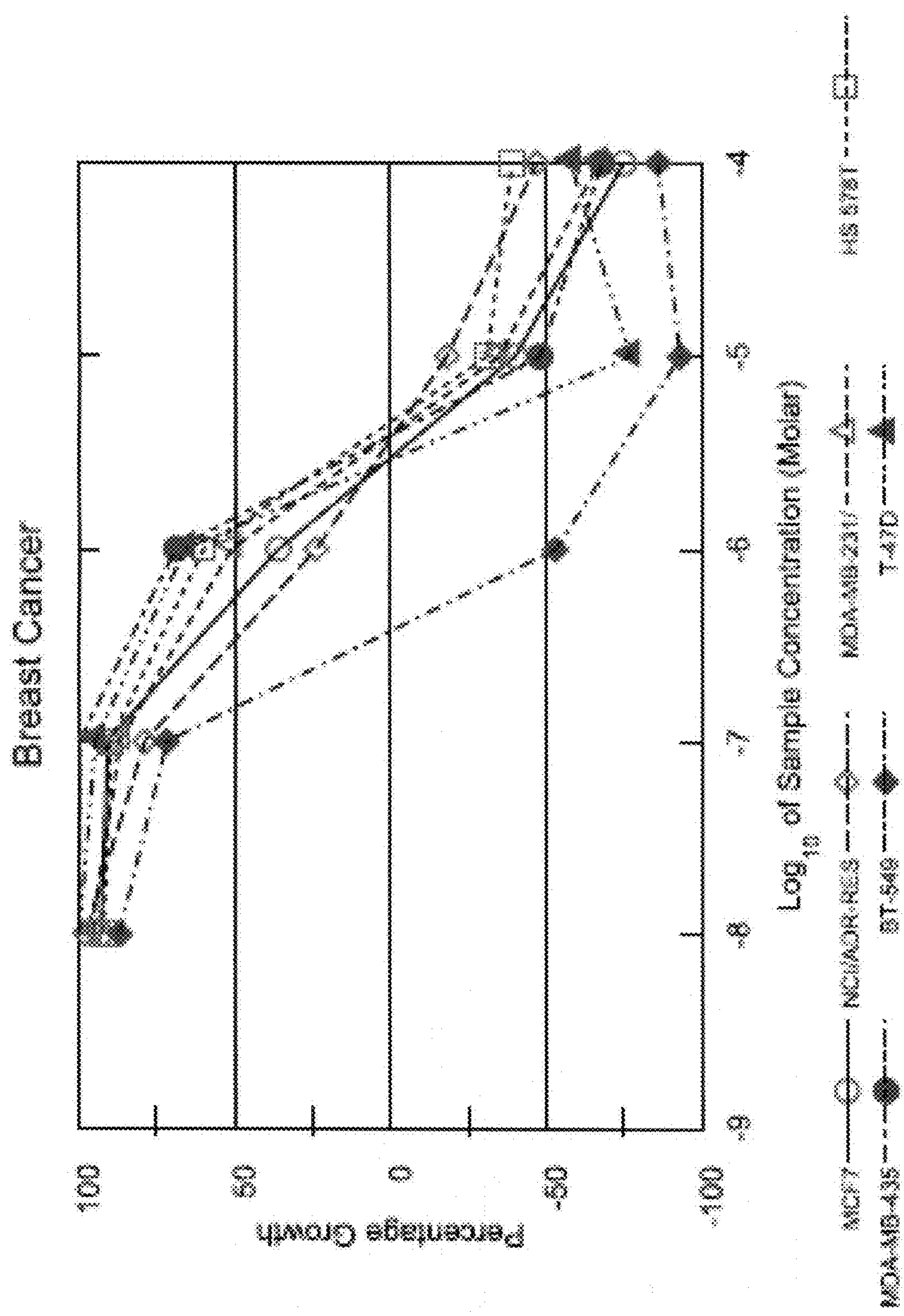
Figure 16 (con't)

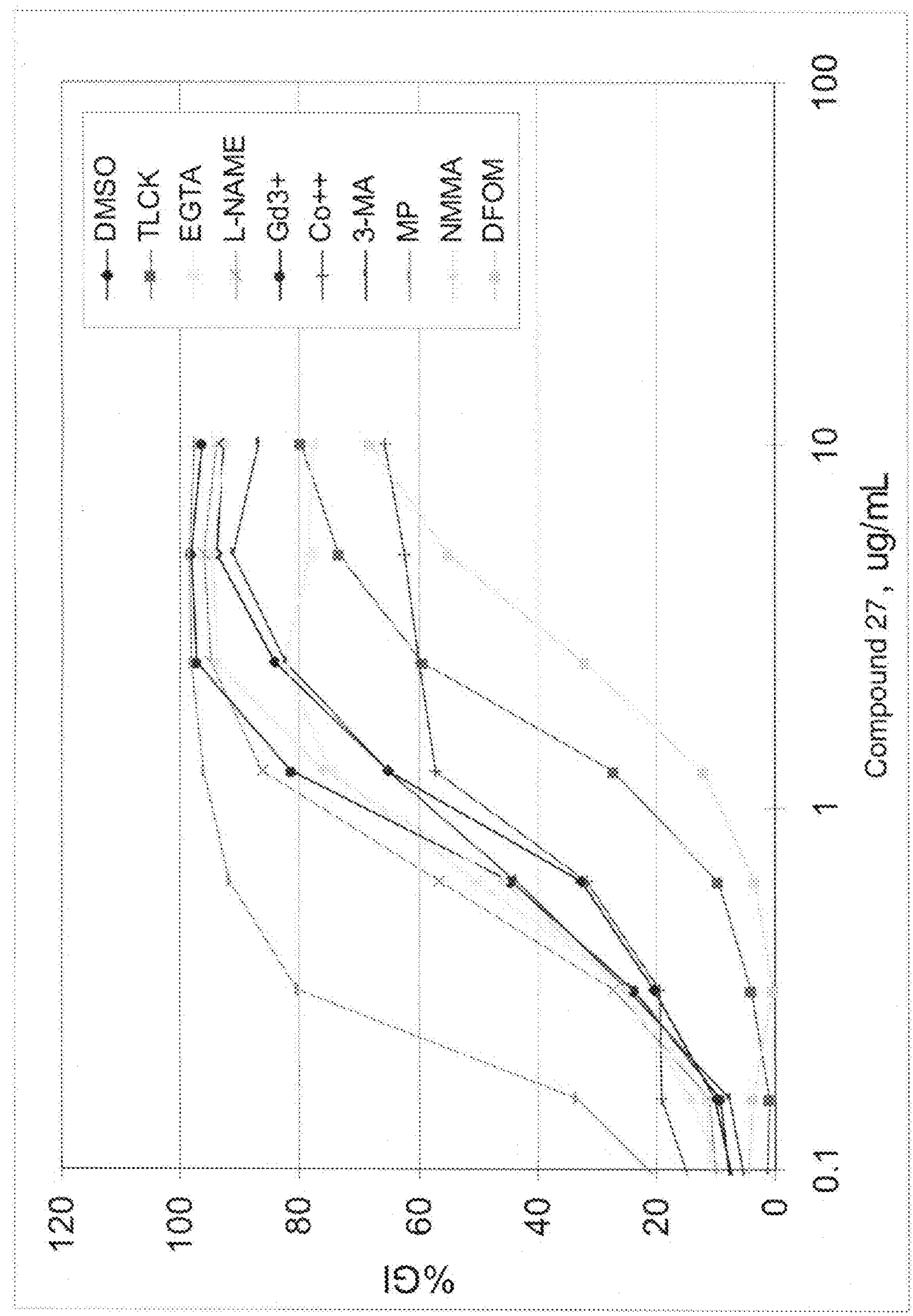
Figure 17 (con't)

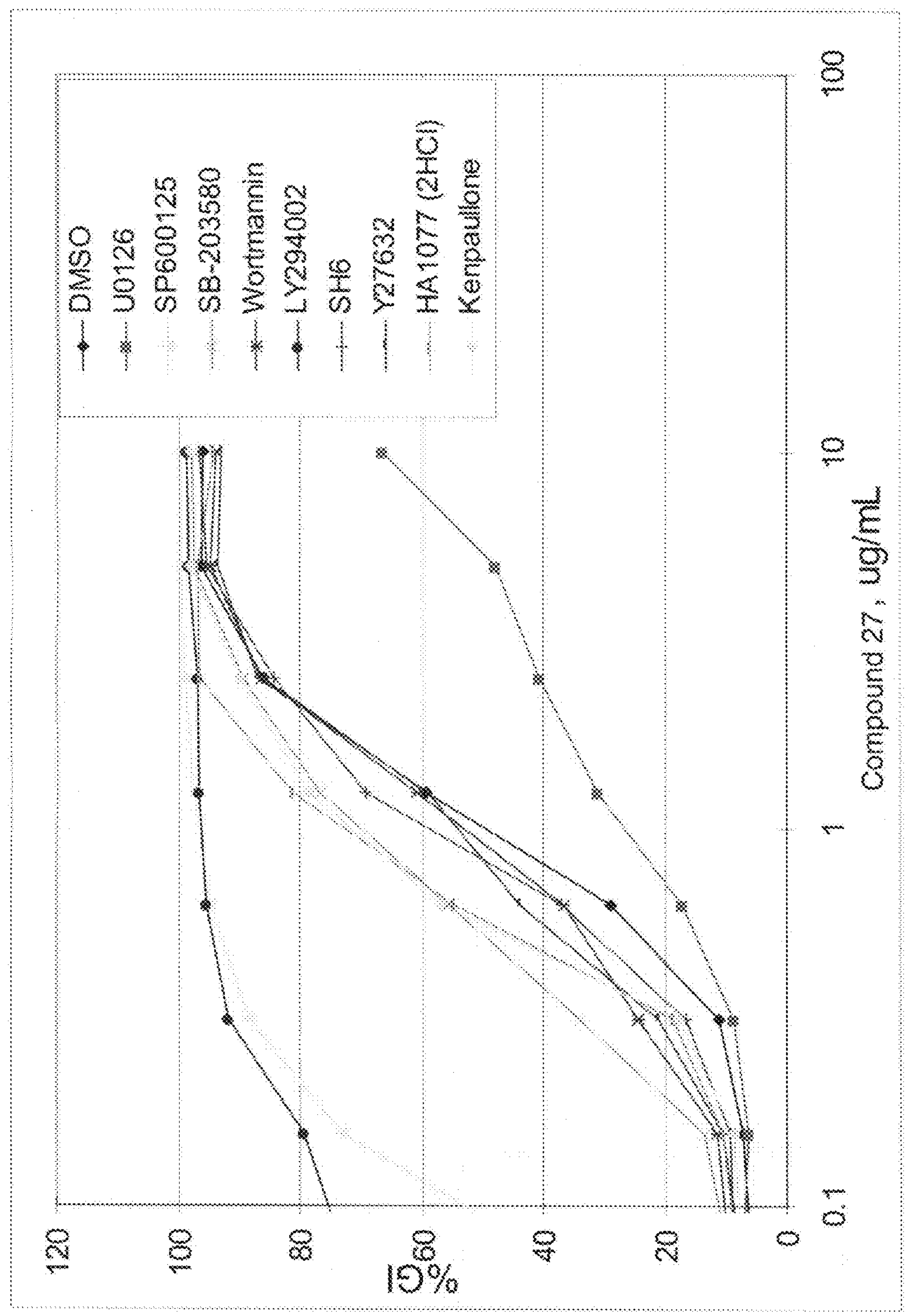
Figure 17 (con't)

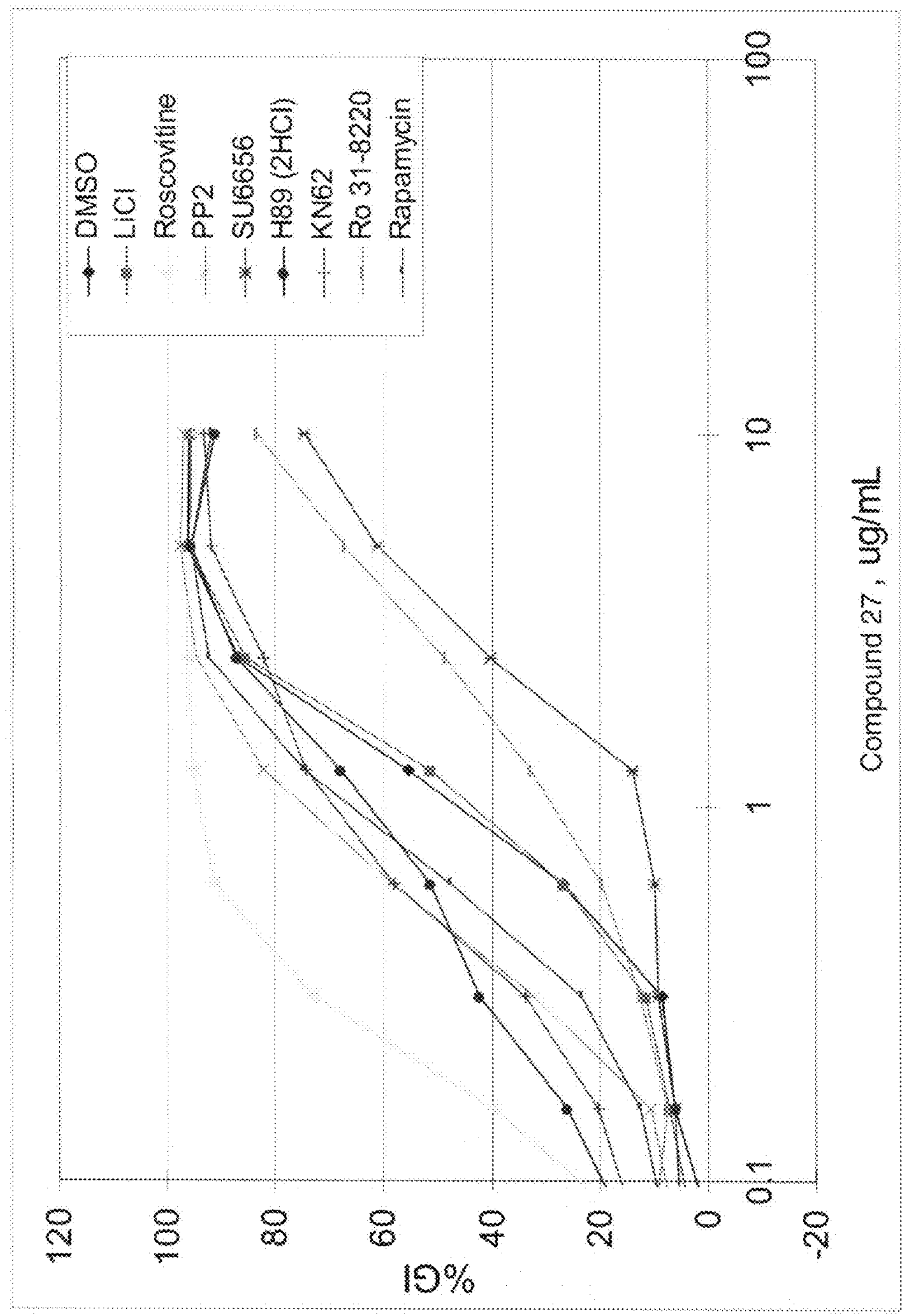
Figure 17 (con't)

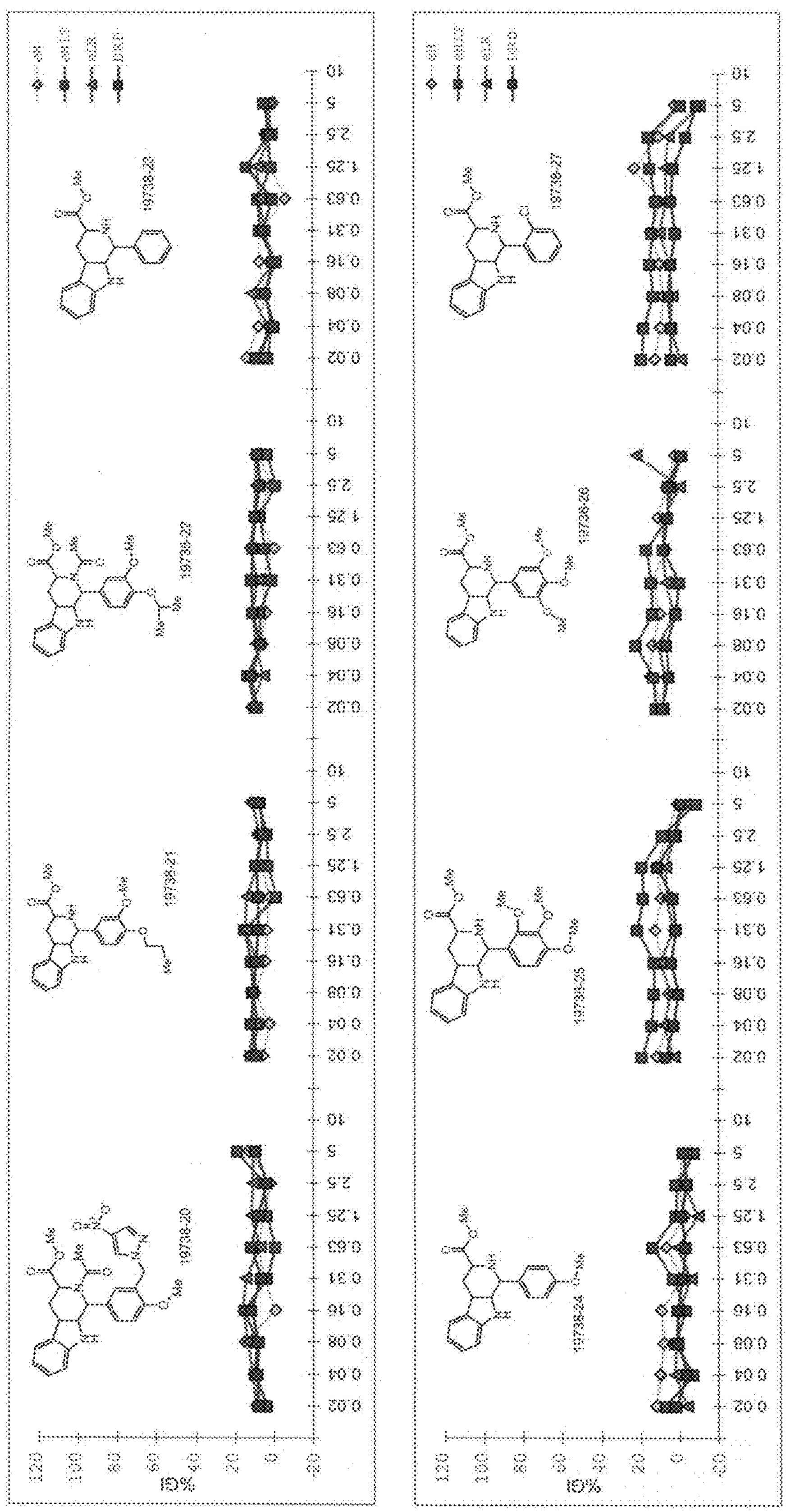
Figure 18 (con't)

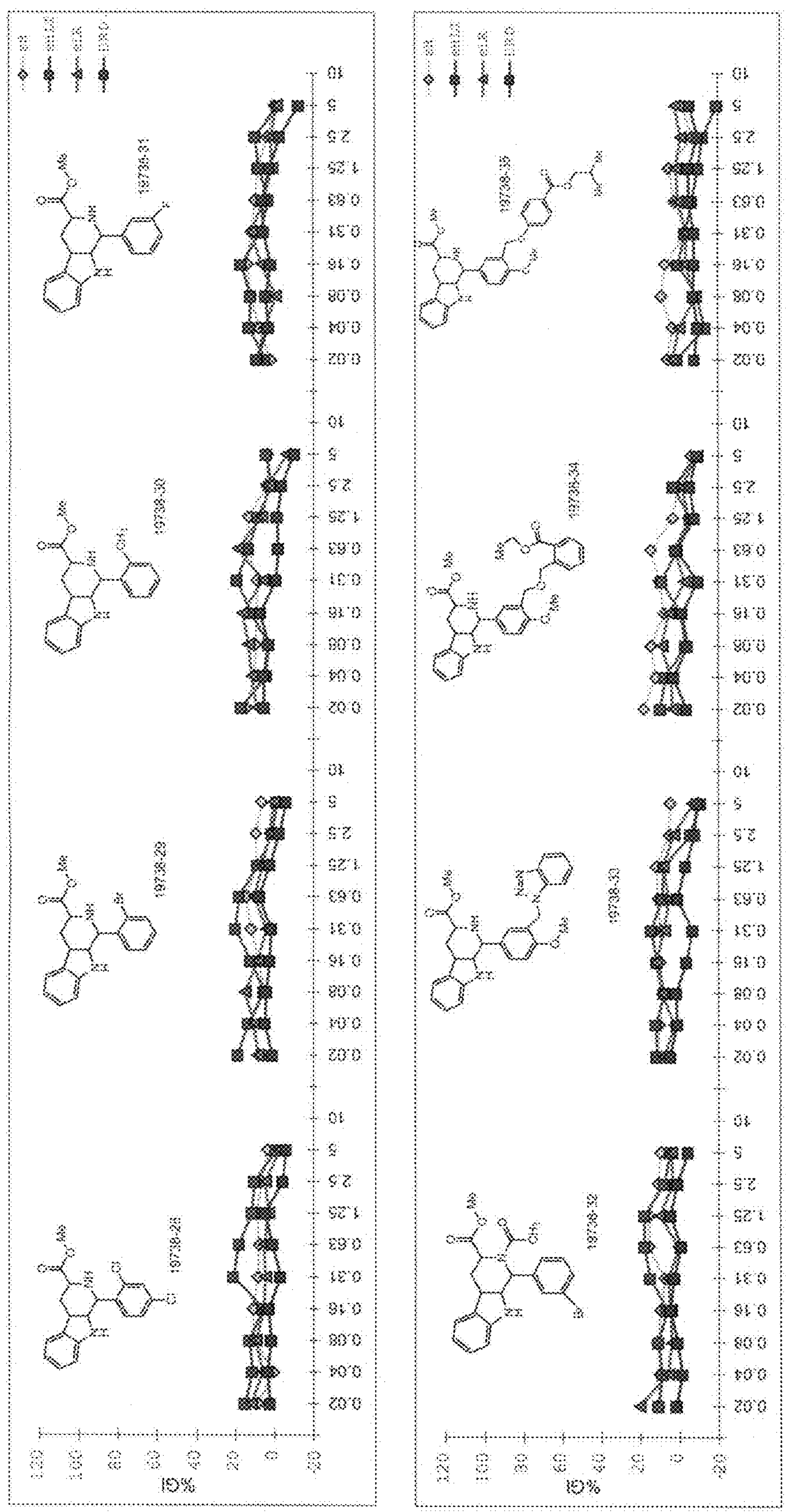
Figure 18 (con't)

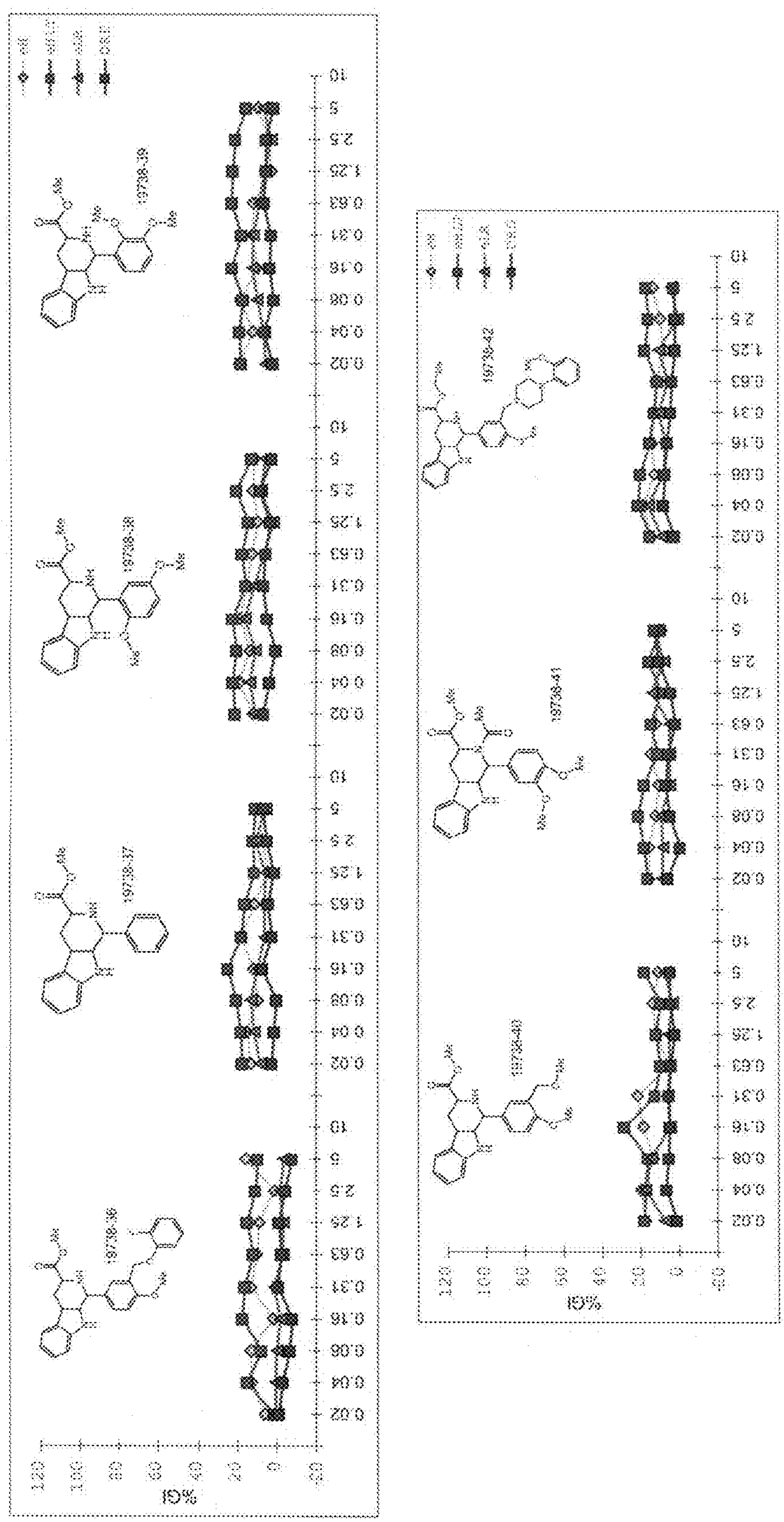
Figure 18 (con't)

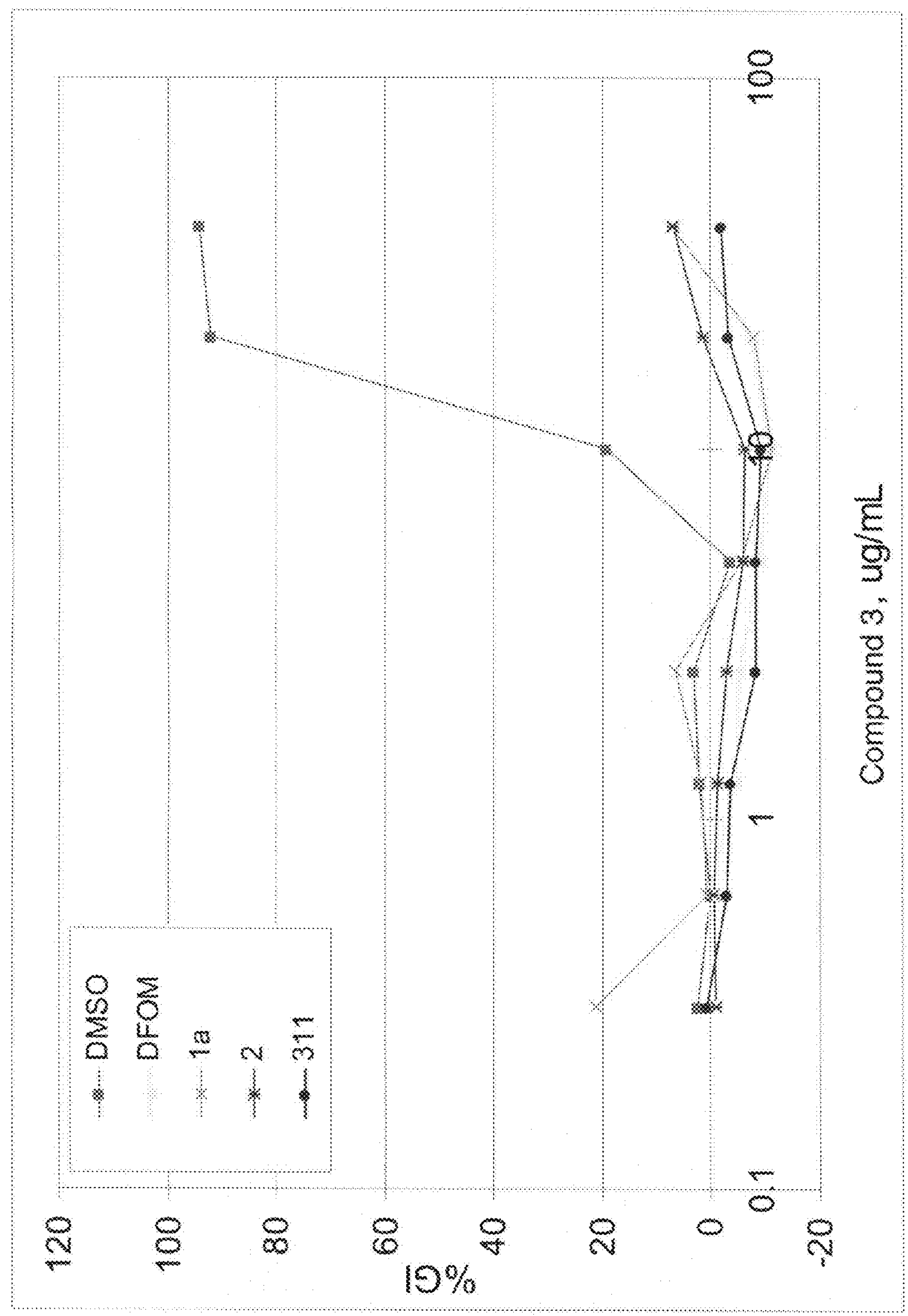
Figure 19 (con't)

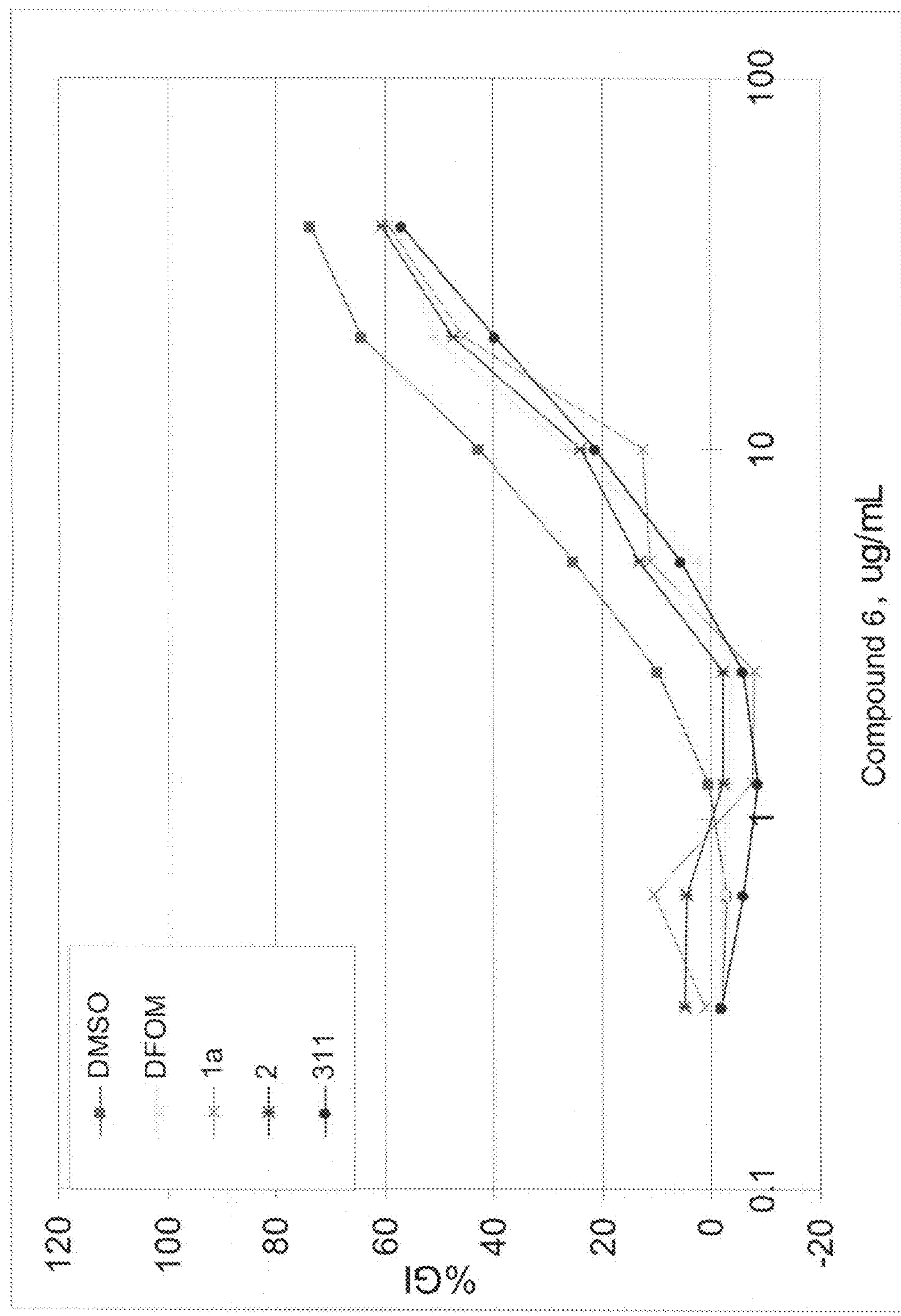
Figure 19 (con't)

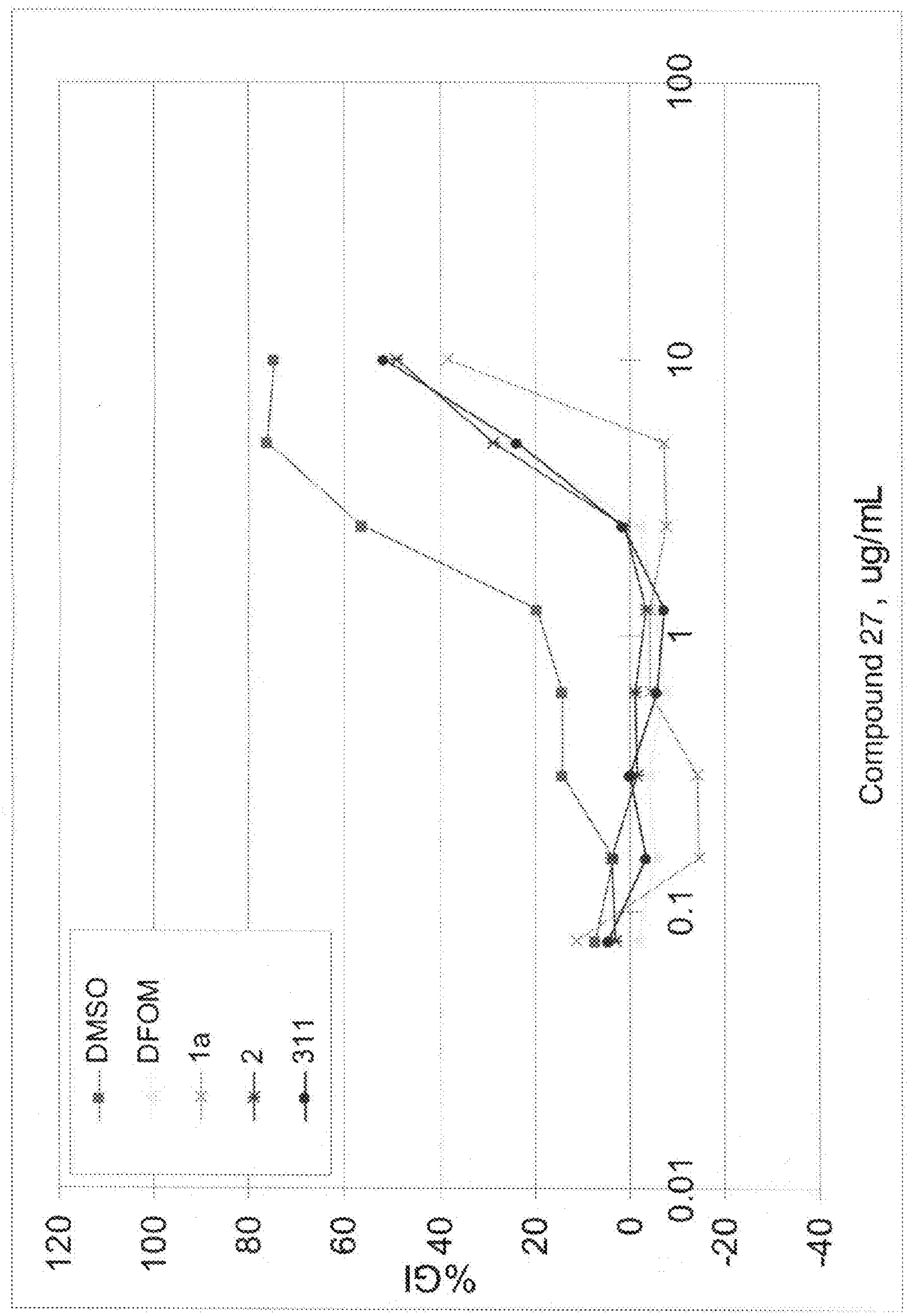
Figure 19 (con't)

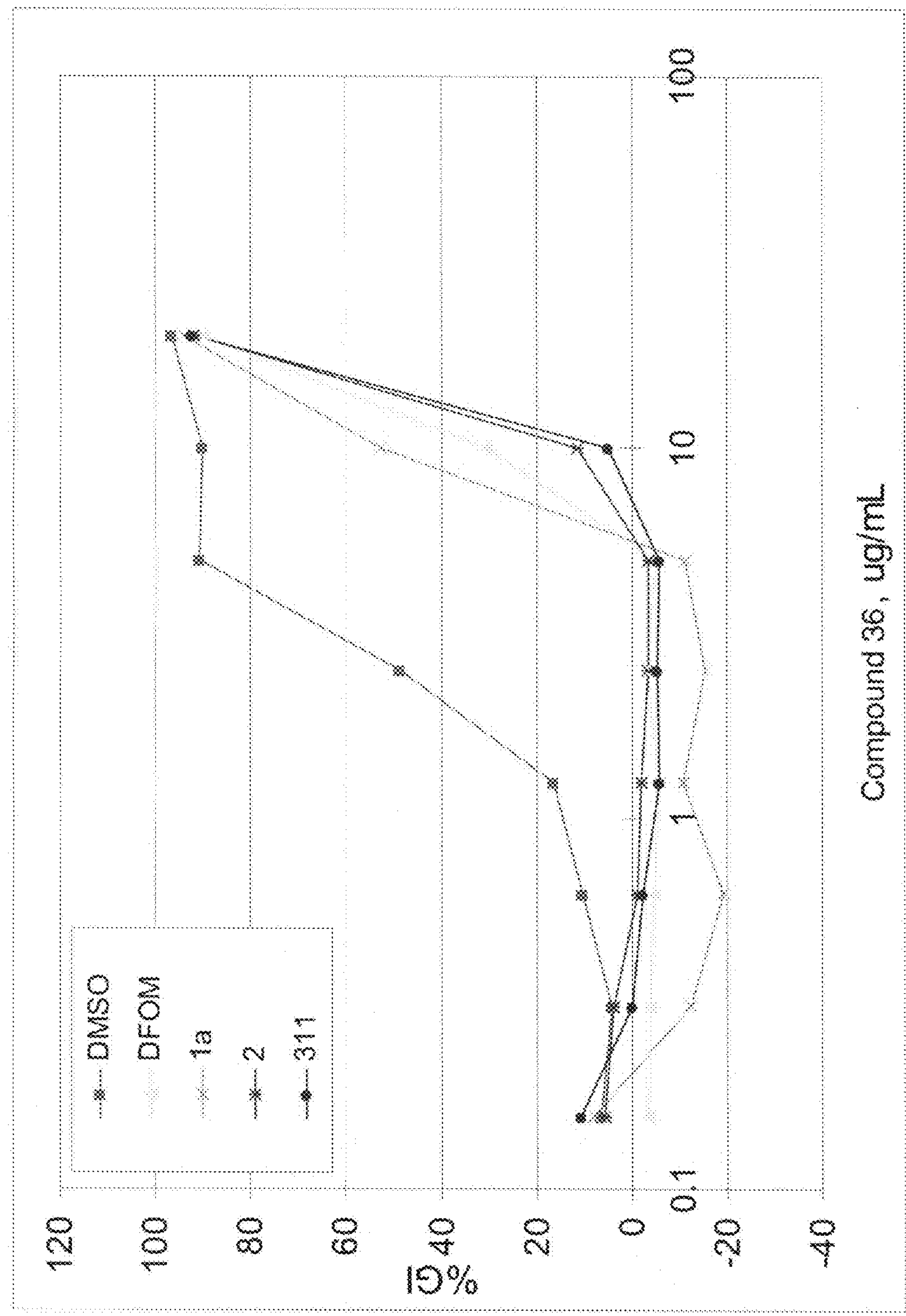
Figure 19 (con't)

E
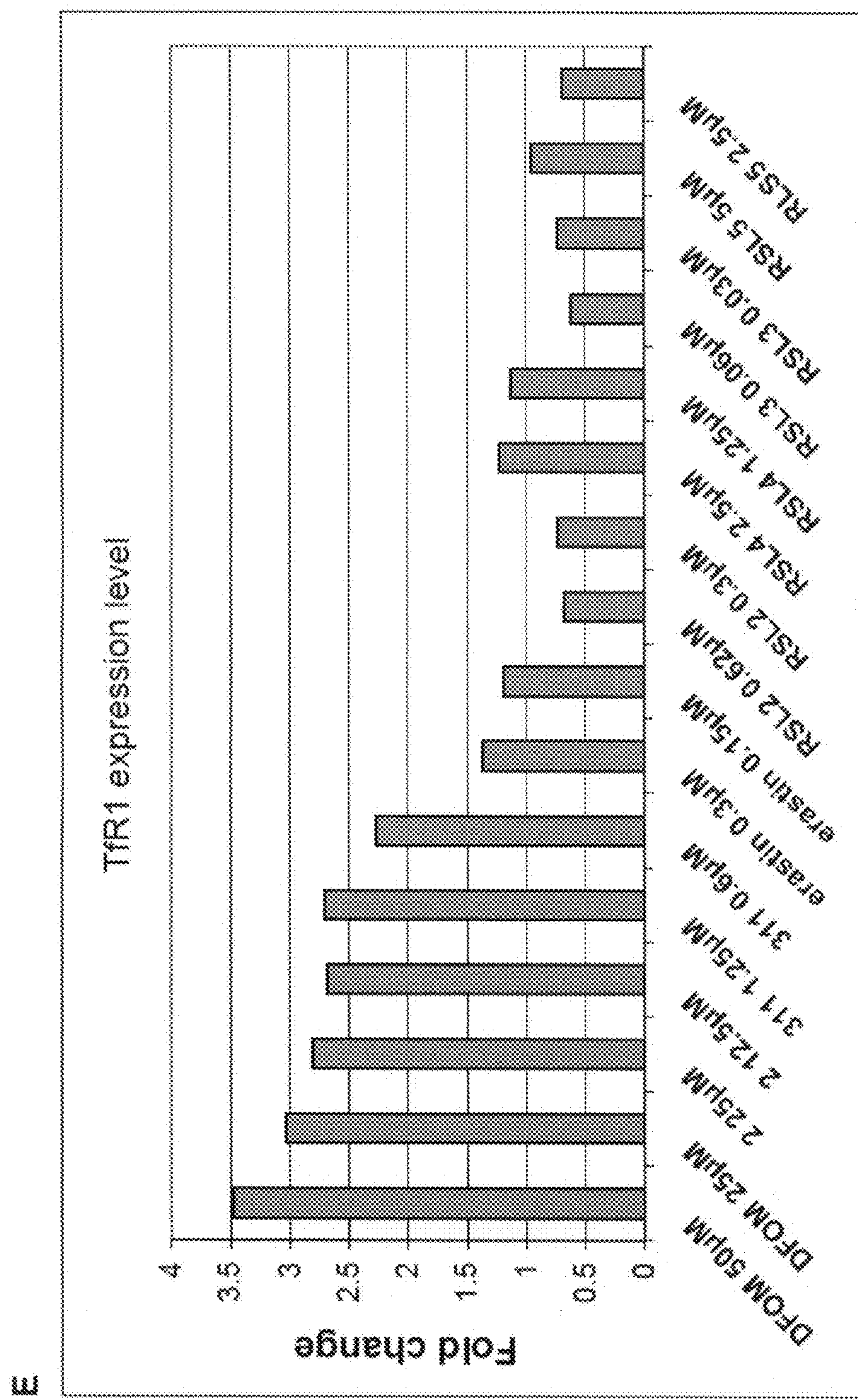
Figure 20 (con't)

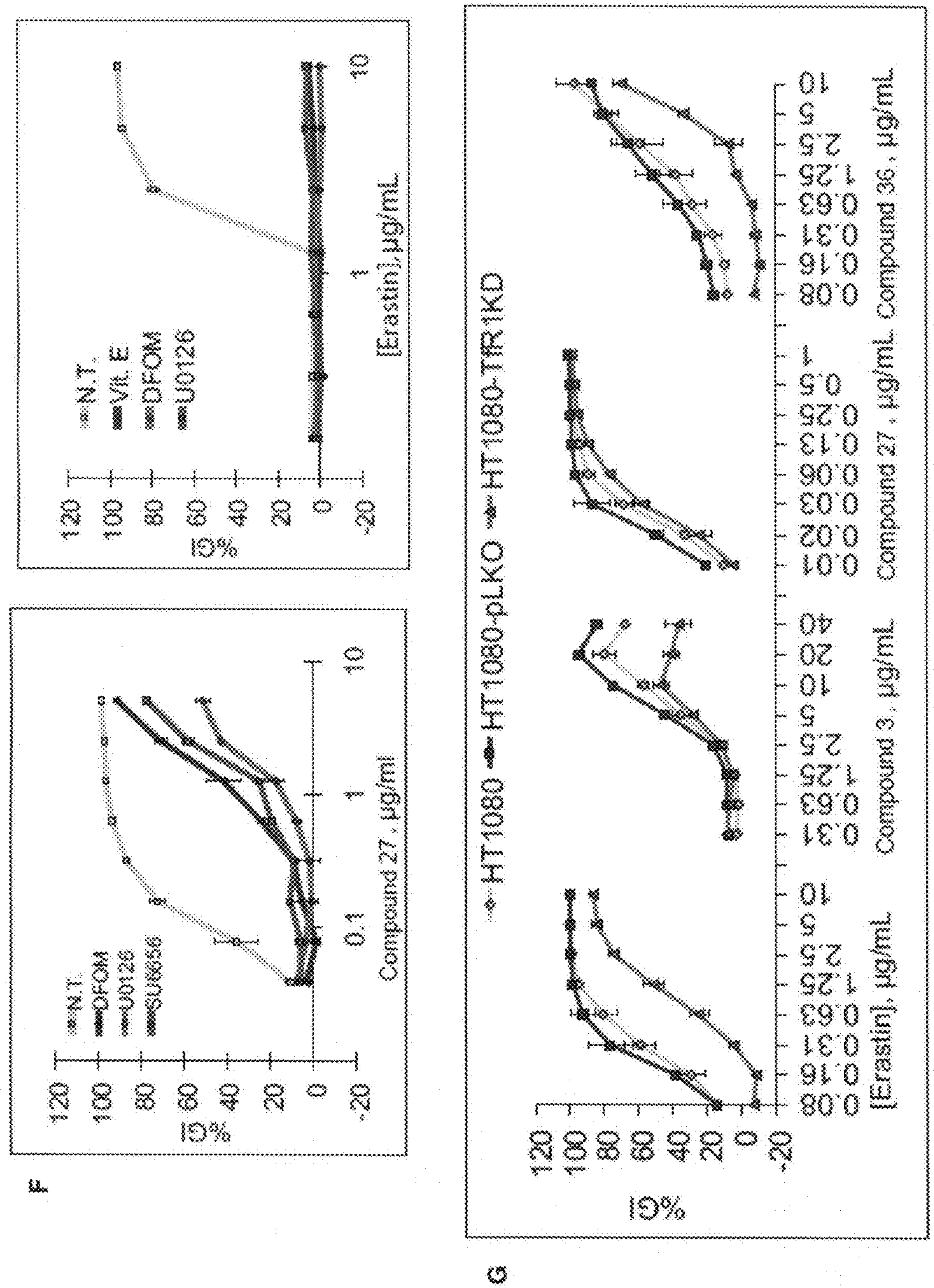
Figure 20 (con't)

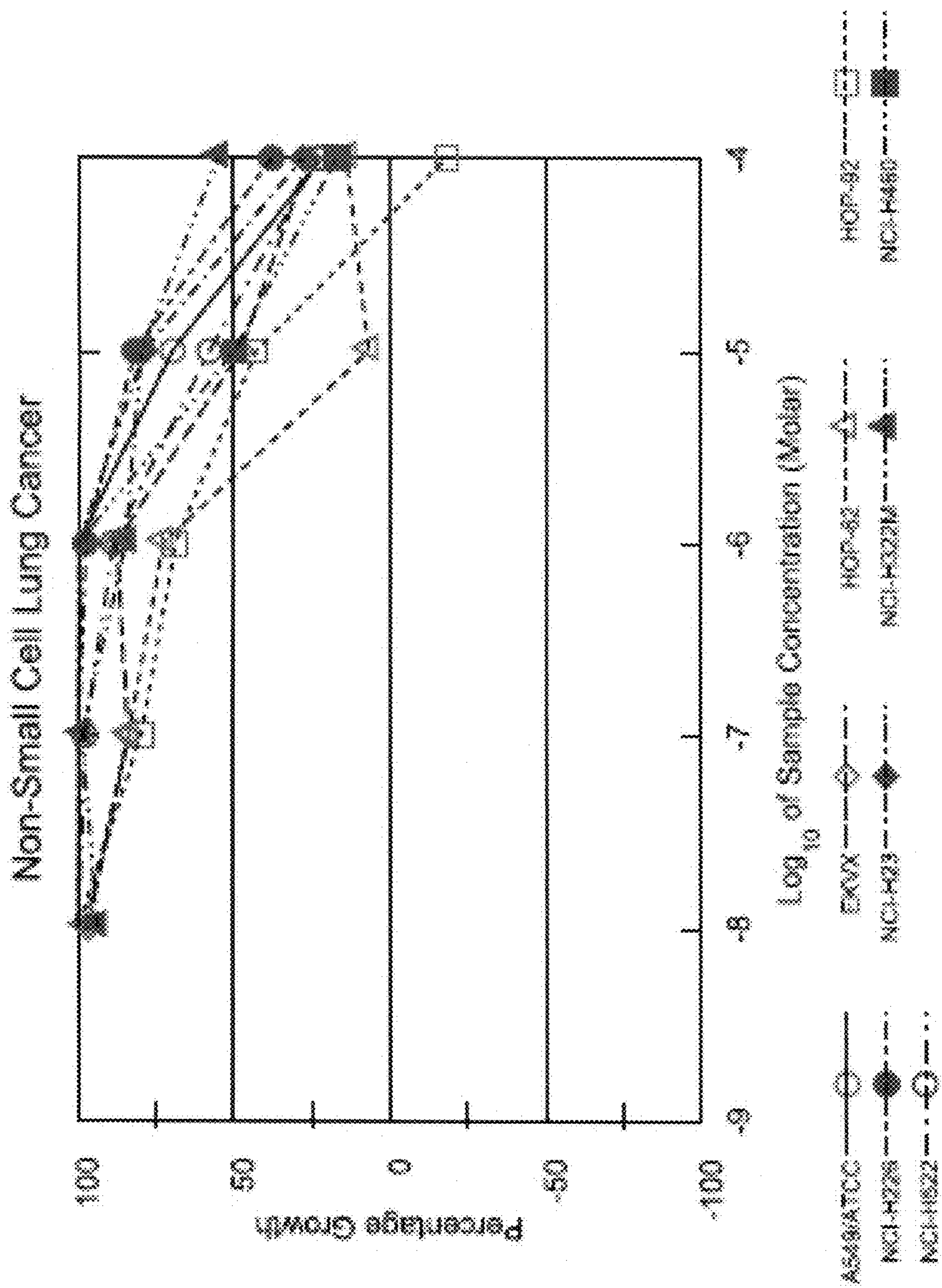
Figure 22 (con't)

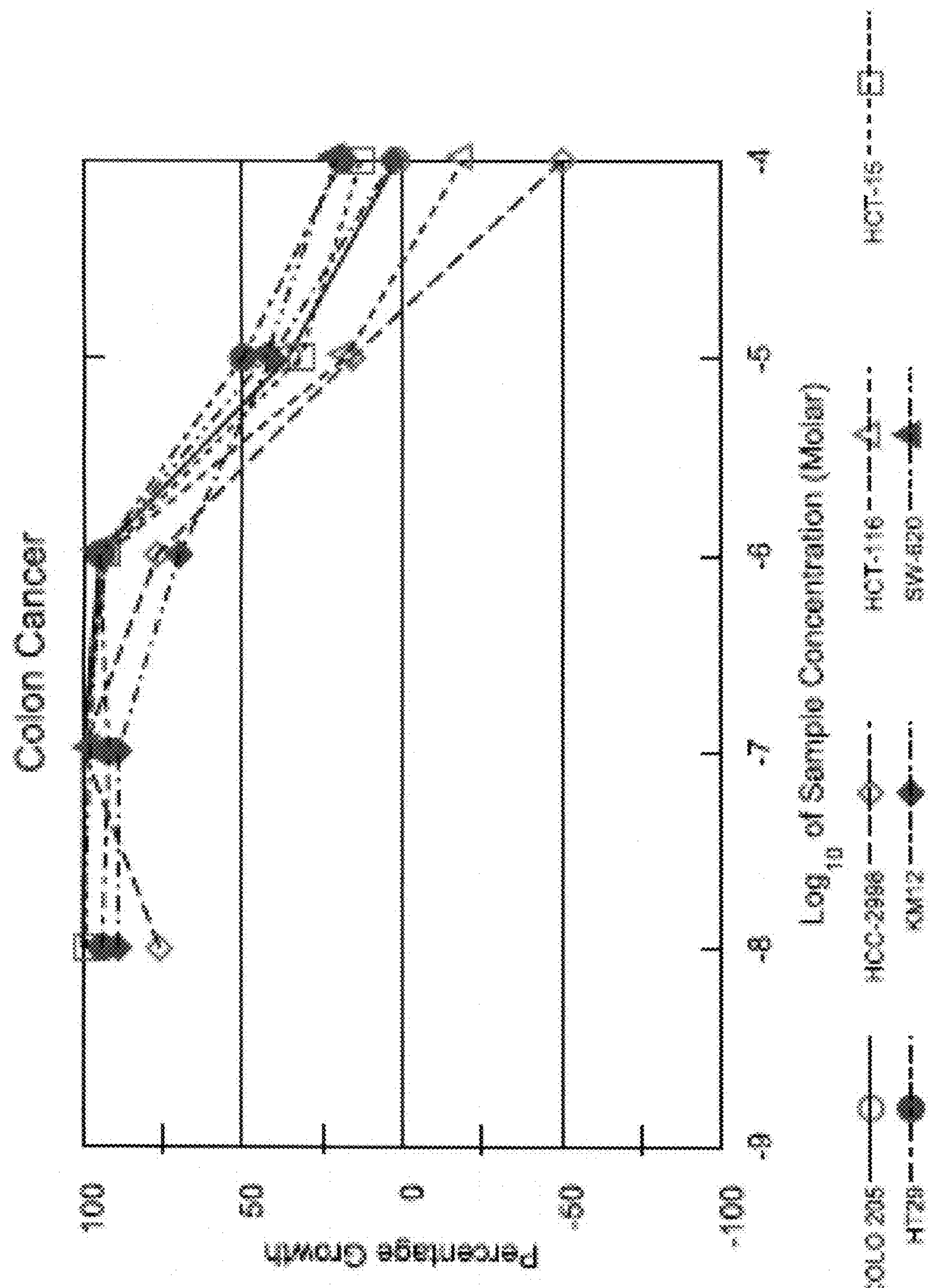
Figure 22 (con't)

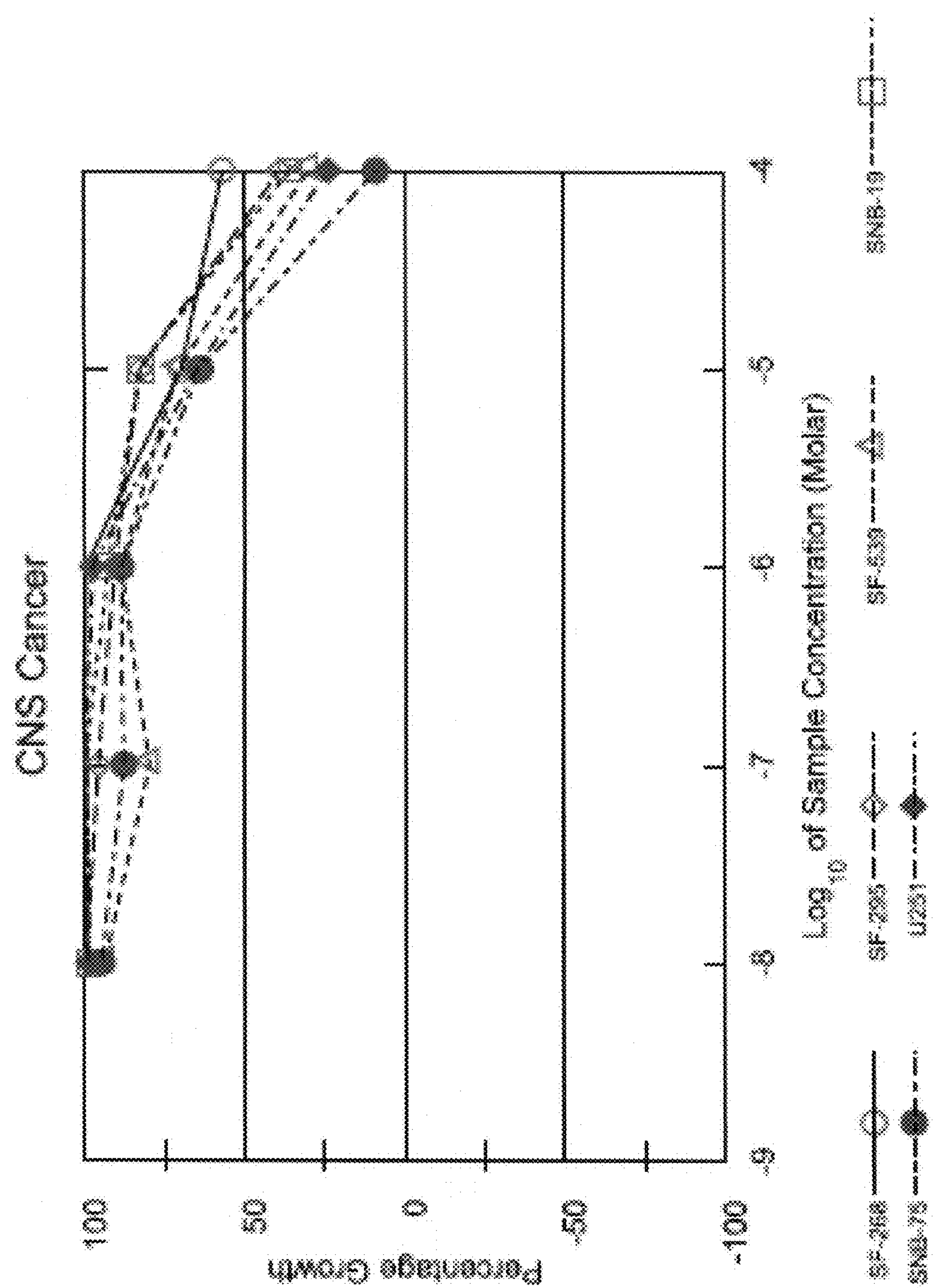
Figure 22 (con't)

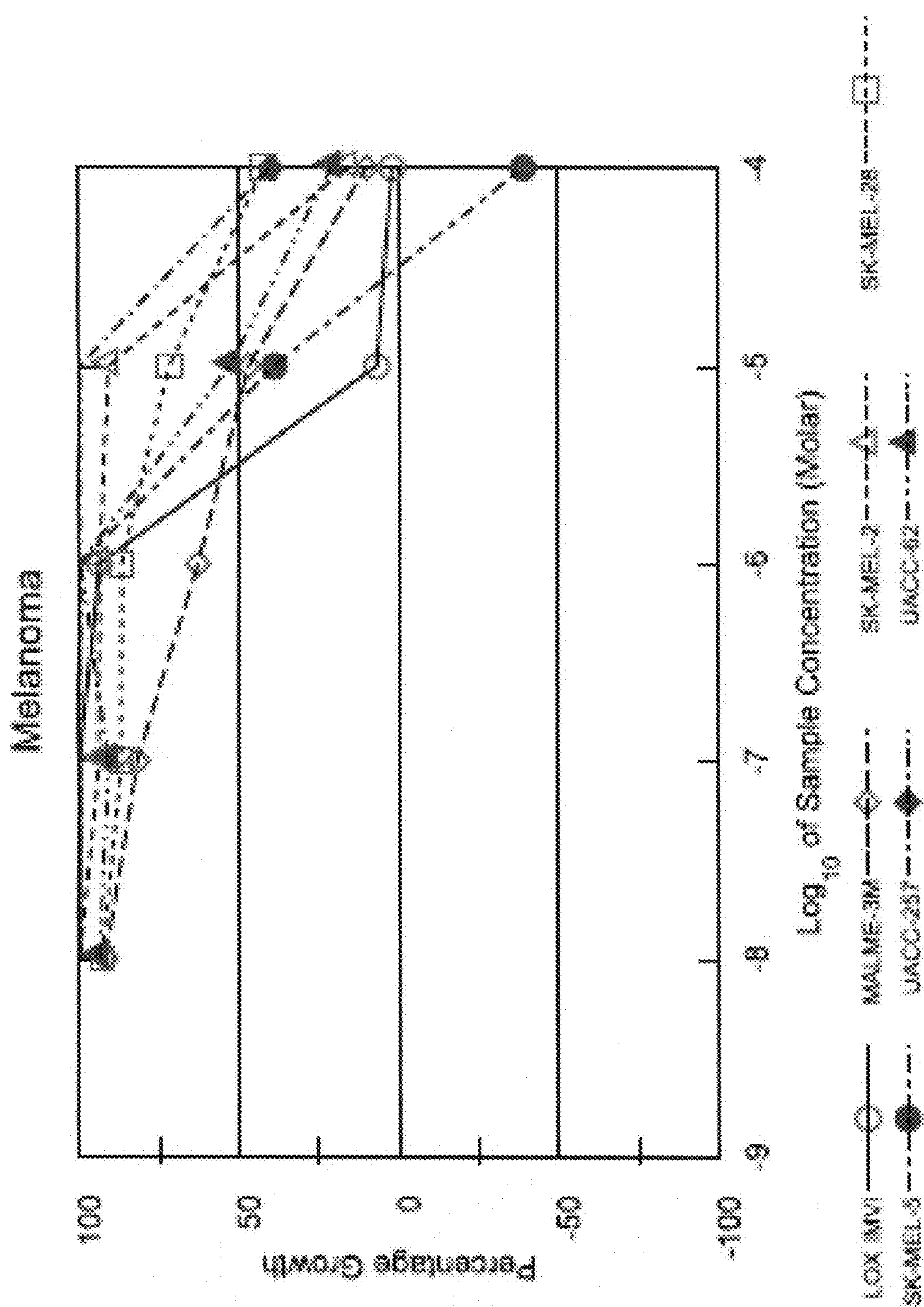
Figure 22 (con't)

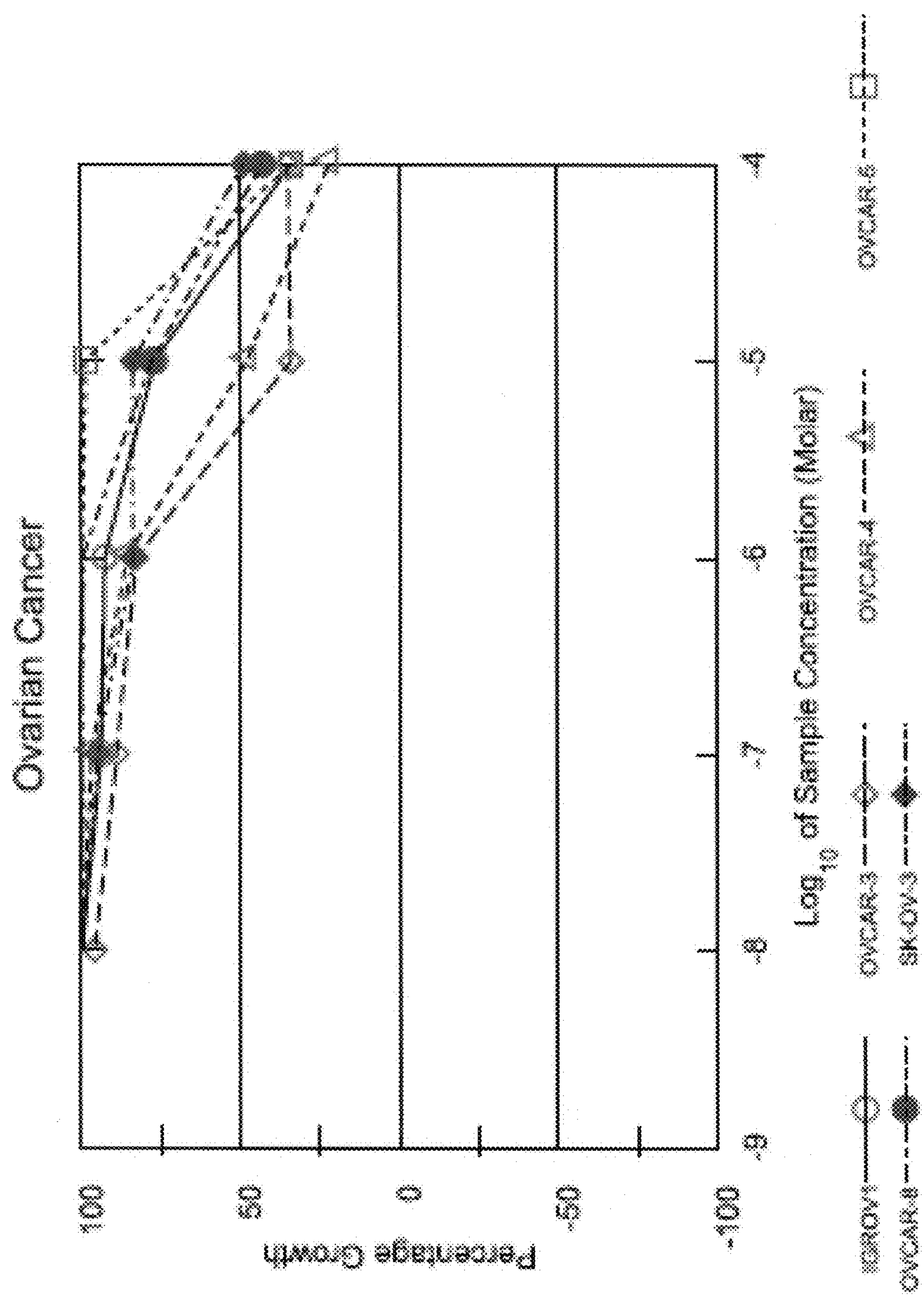
Figure 22 (con't)

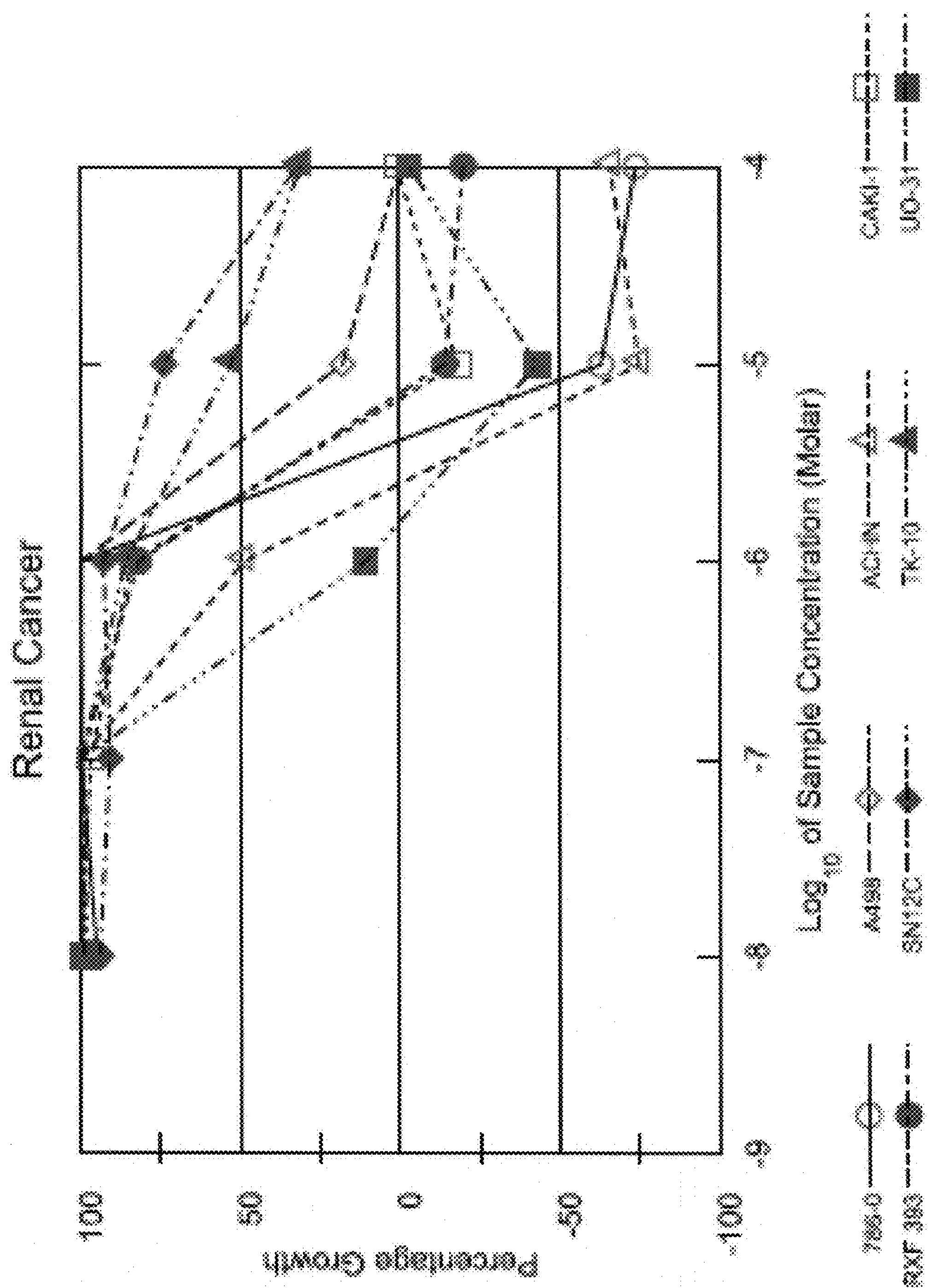
Figure 22 (con't)

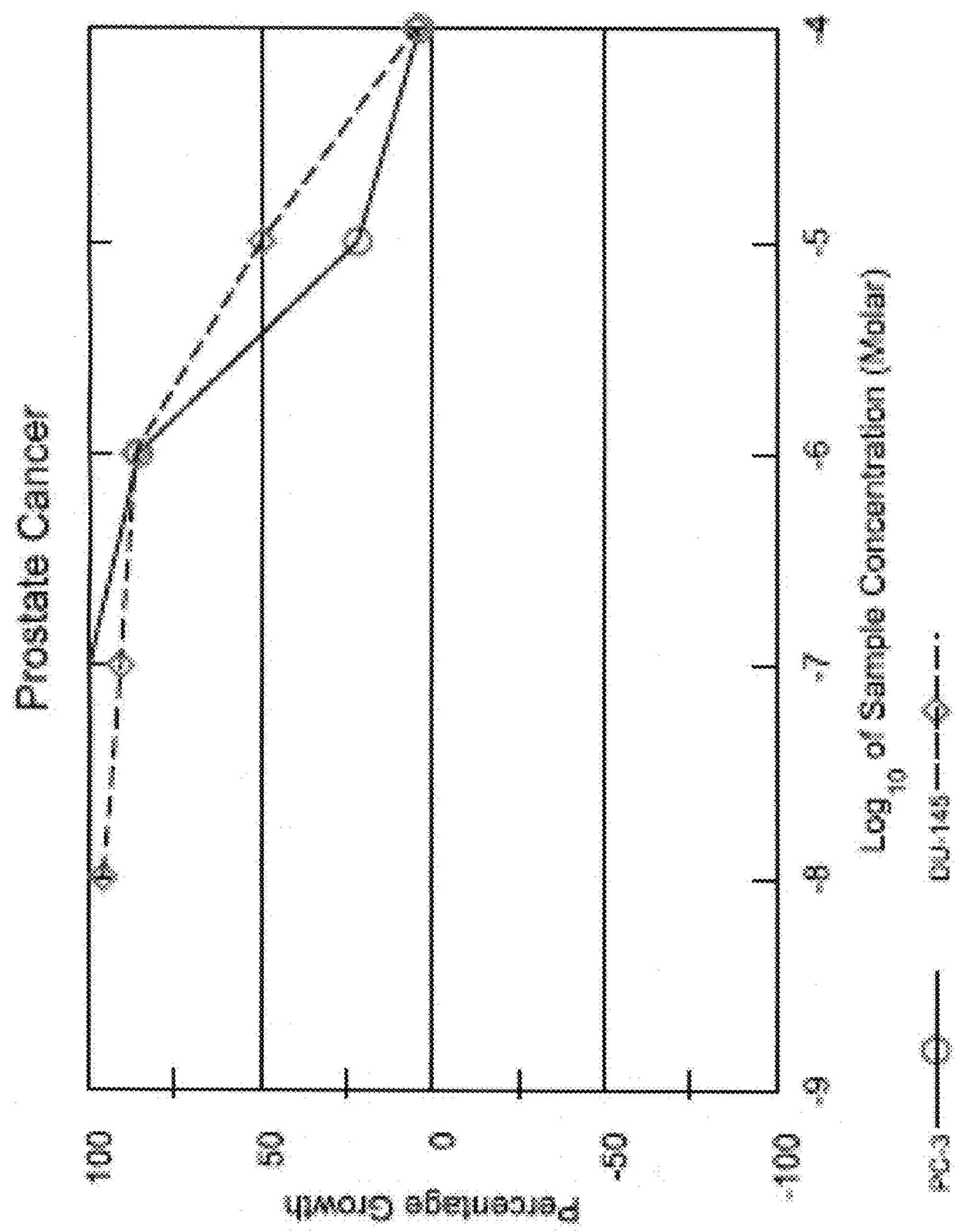
Figure 22 (con't)

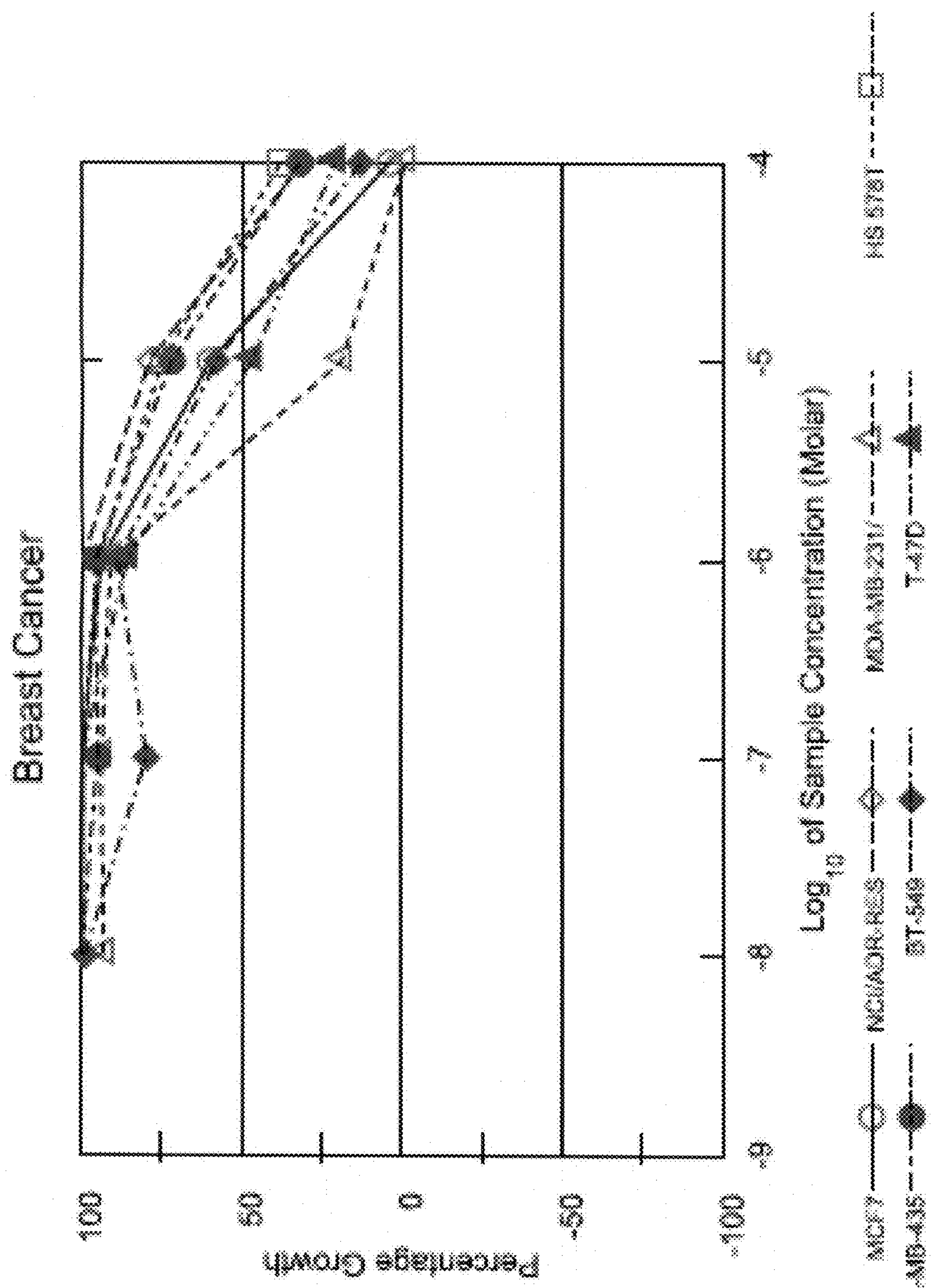
Figure 22 (con't)

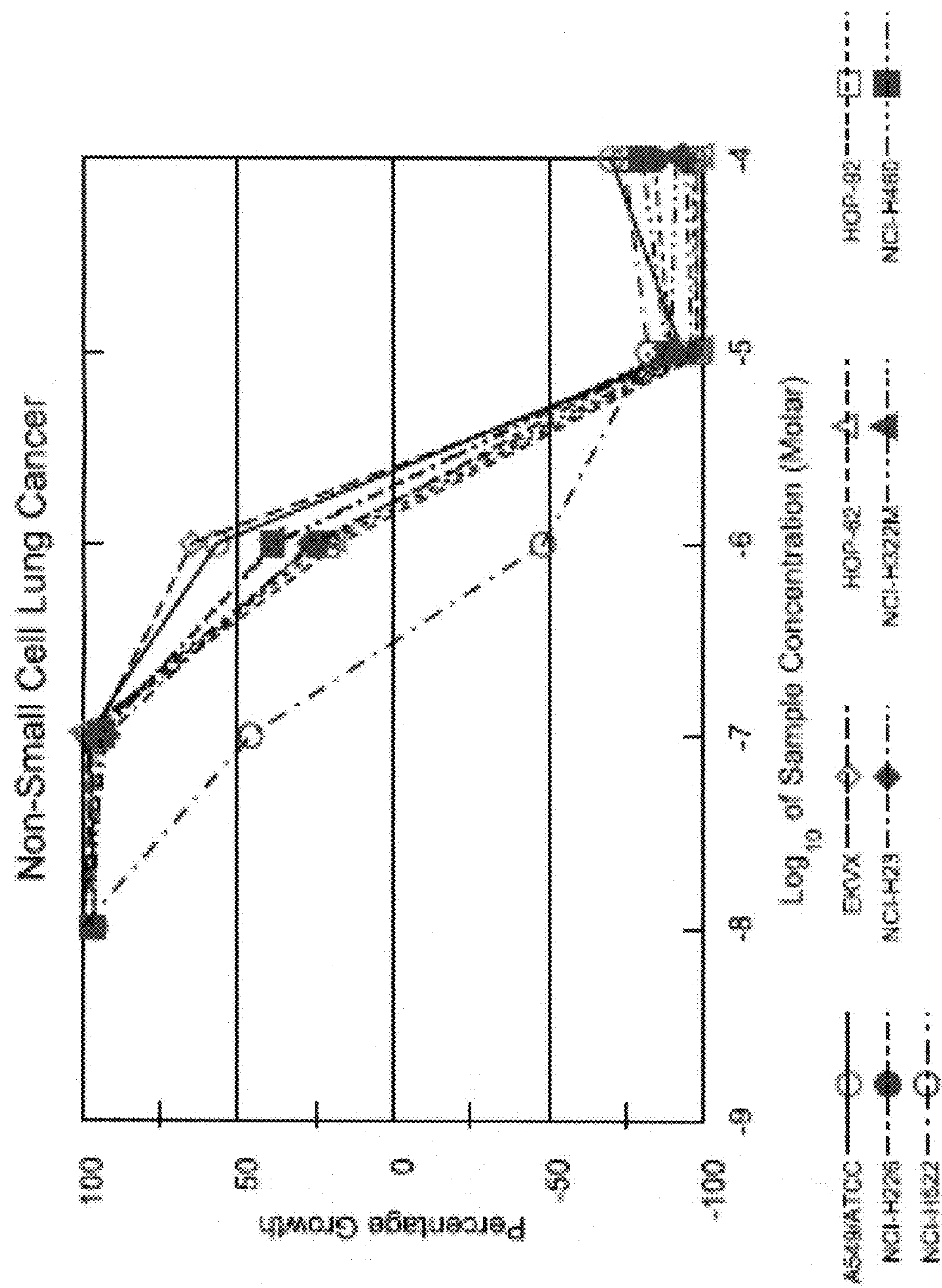
Figure 23 (con't)

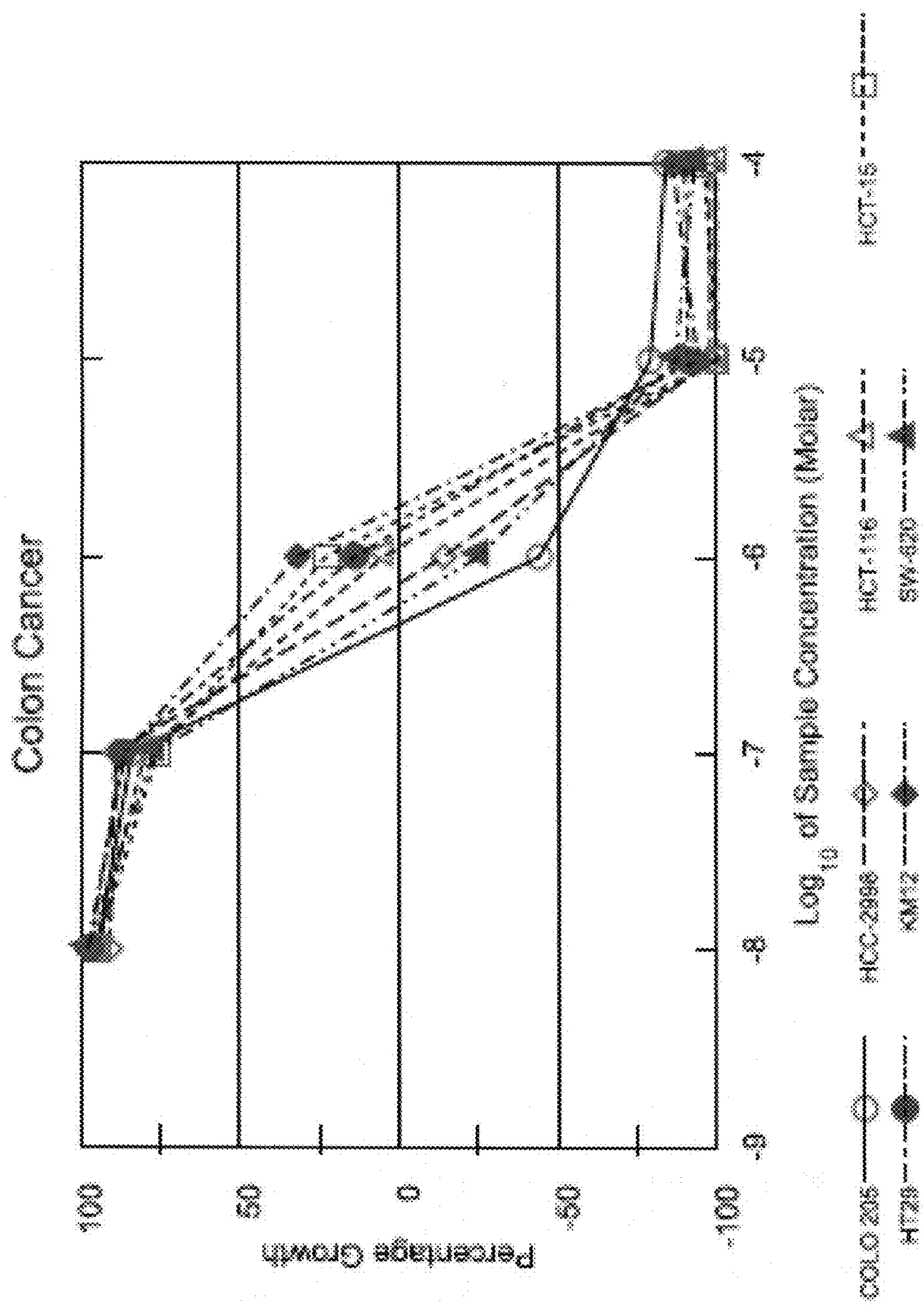
Figure 23 (con't)

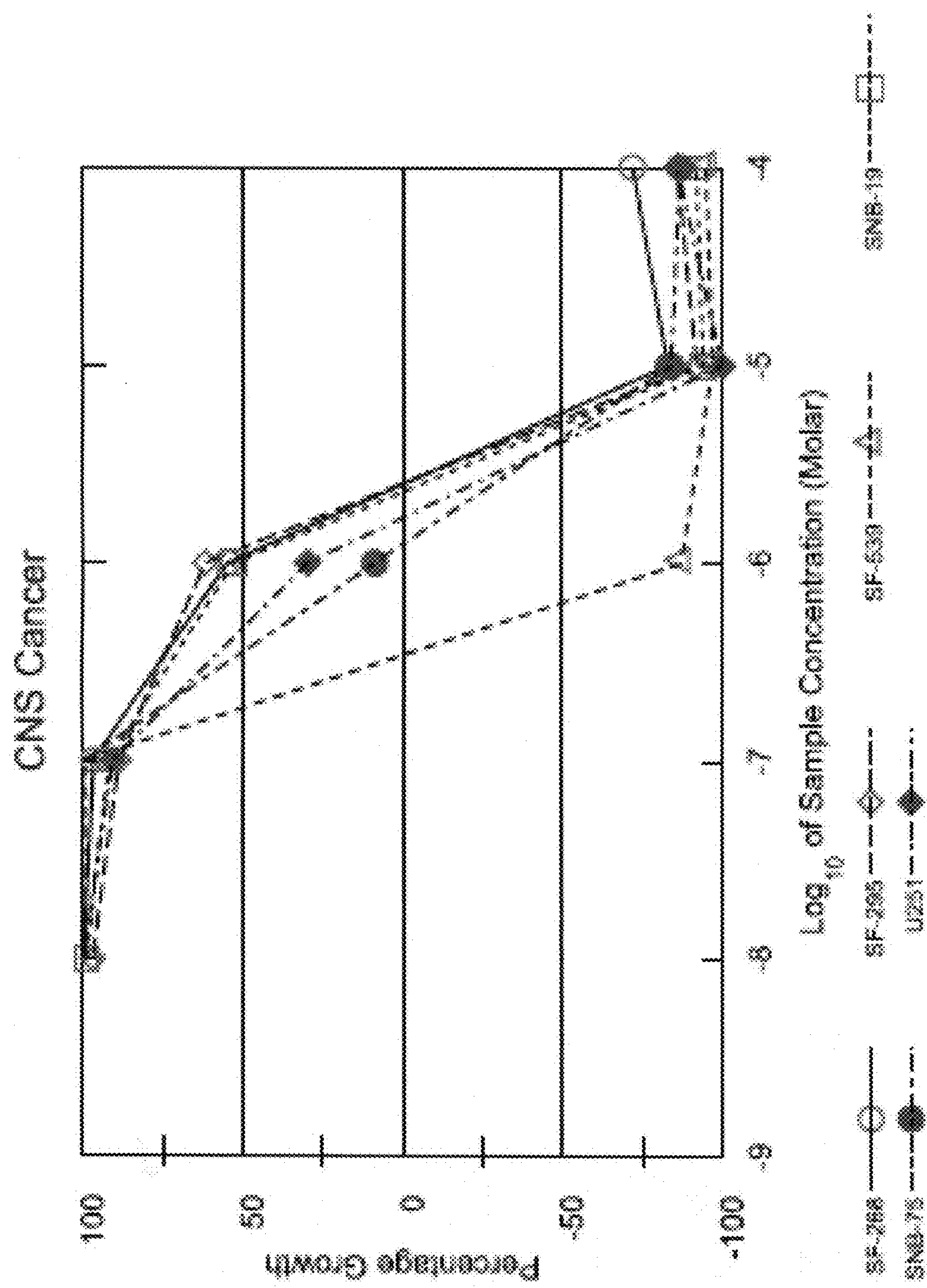
Figure 23 (con't)

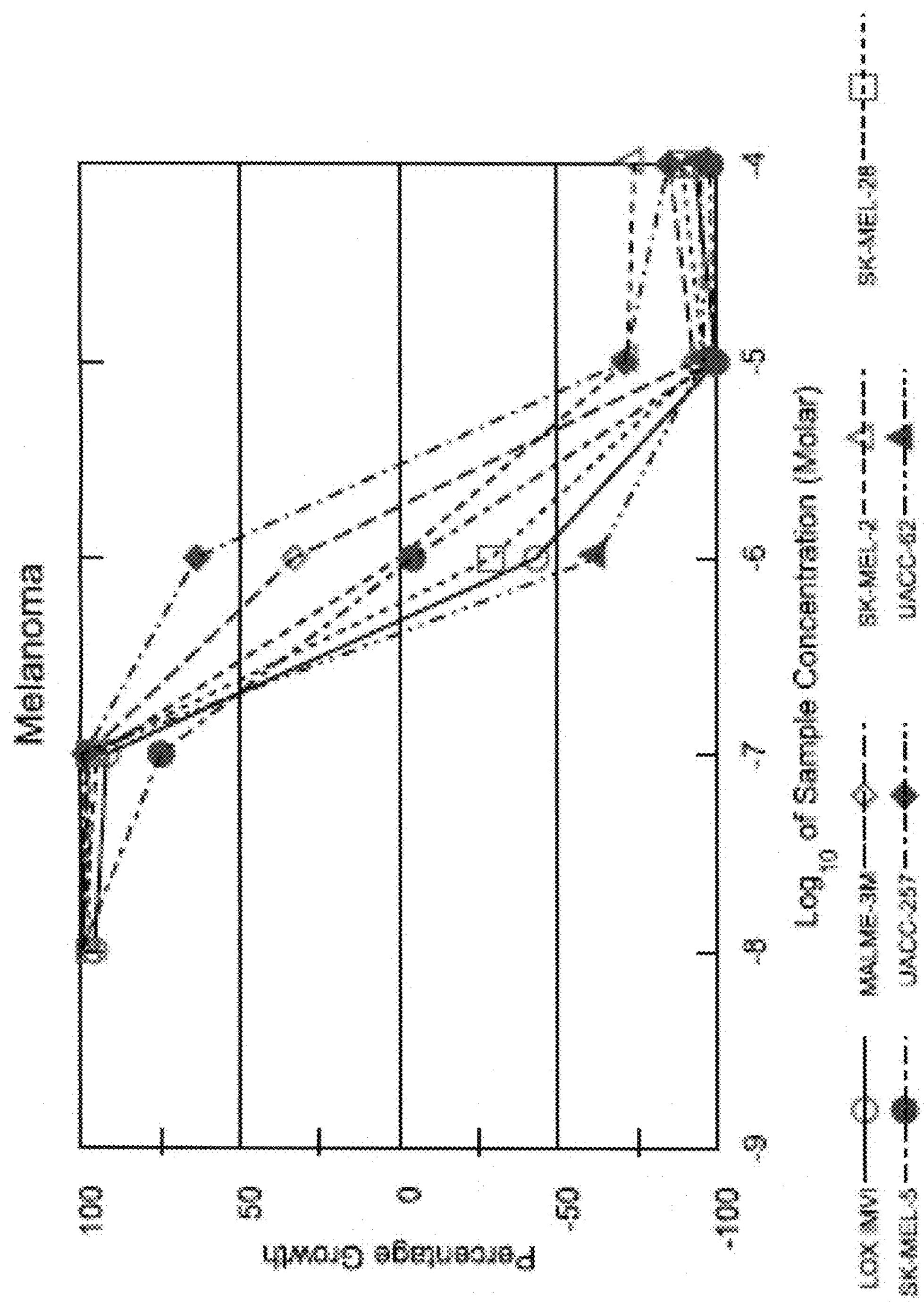
Figure 23 (con't)

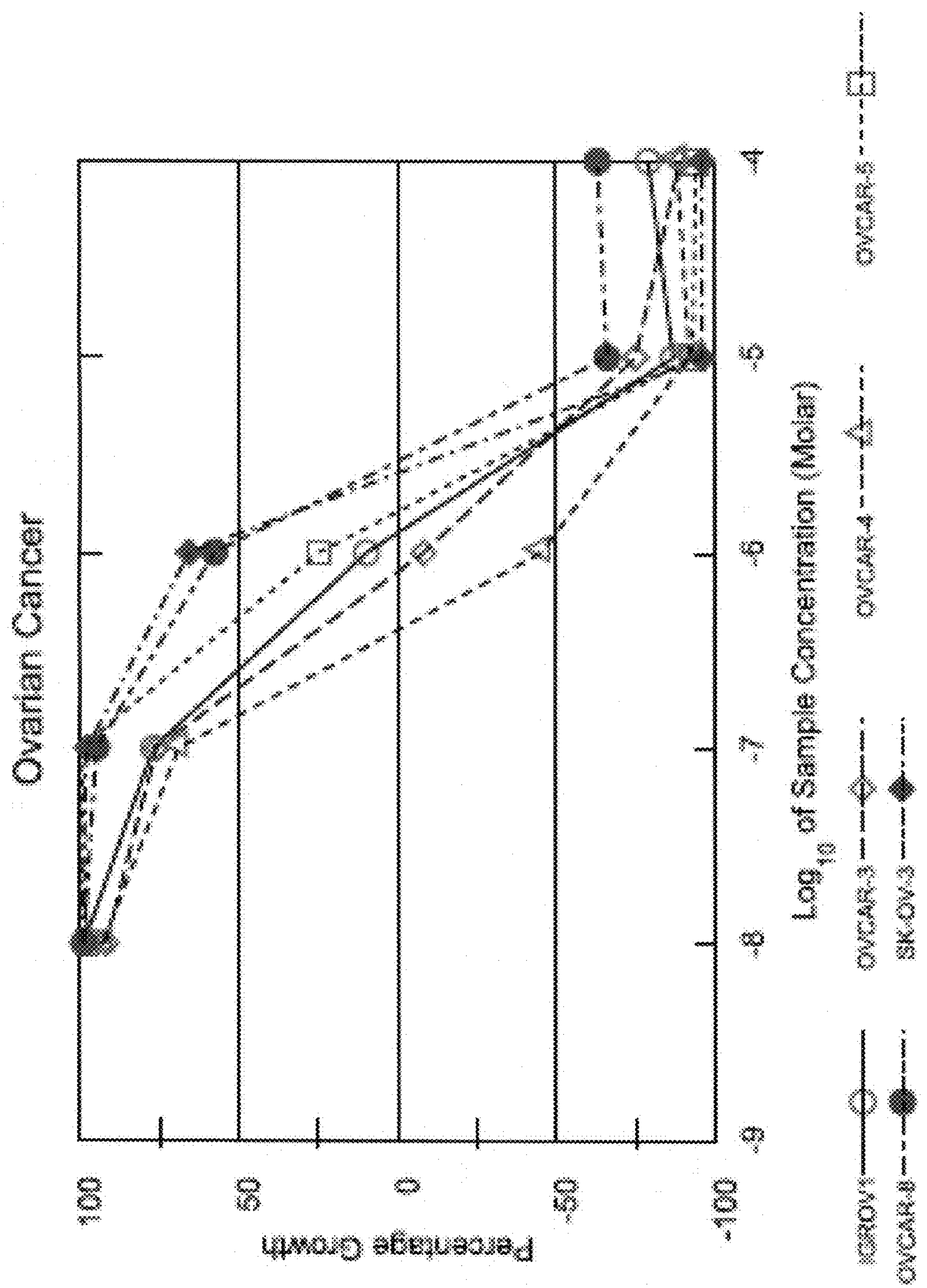
Figure 23 (con't)

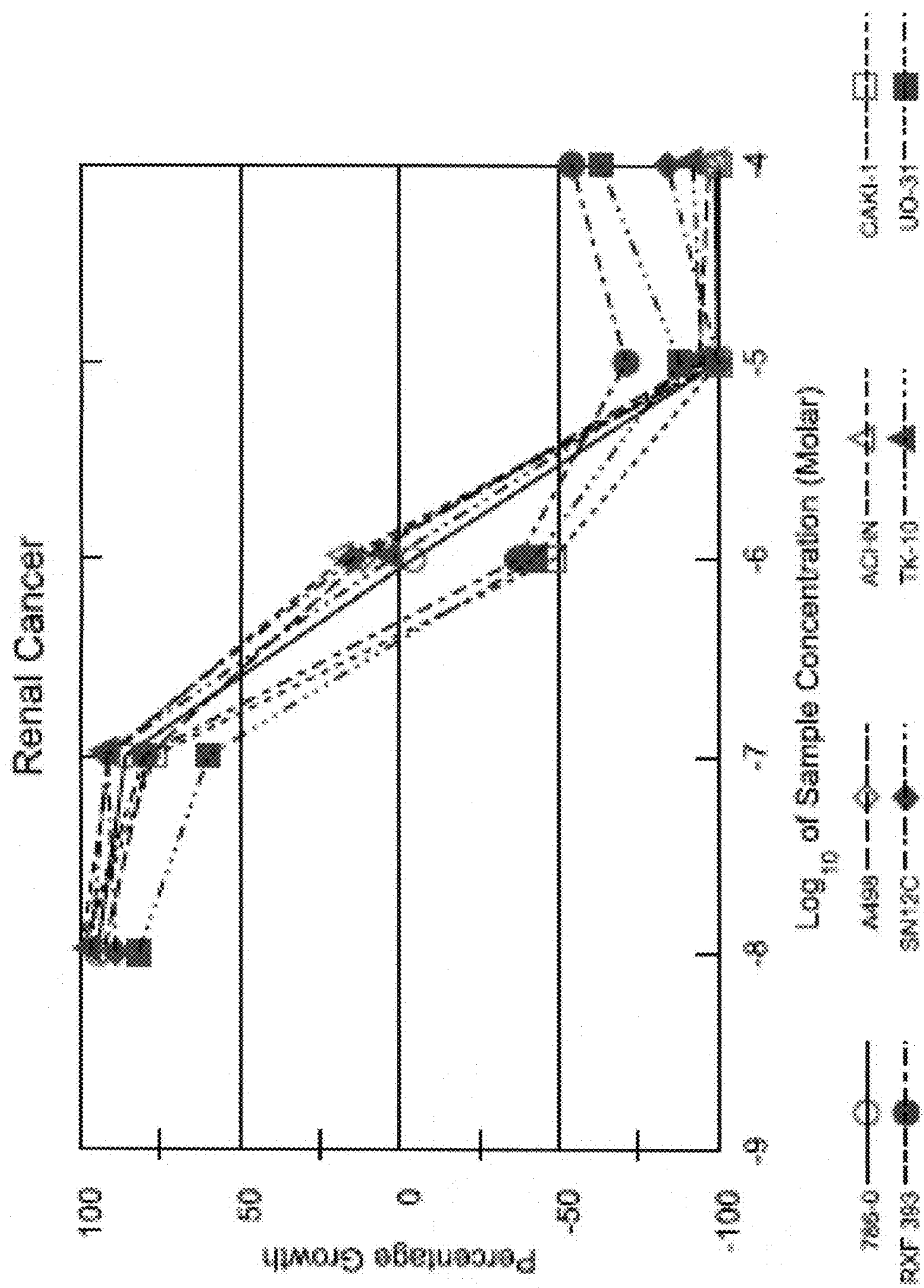
Figure 23 (con't)

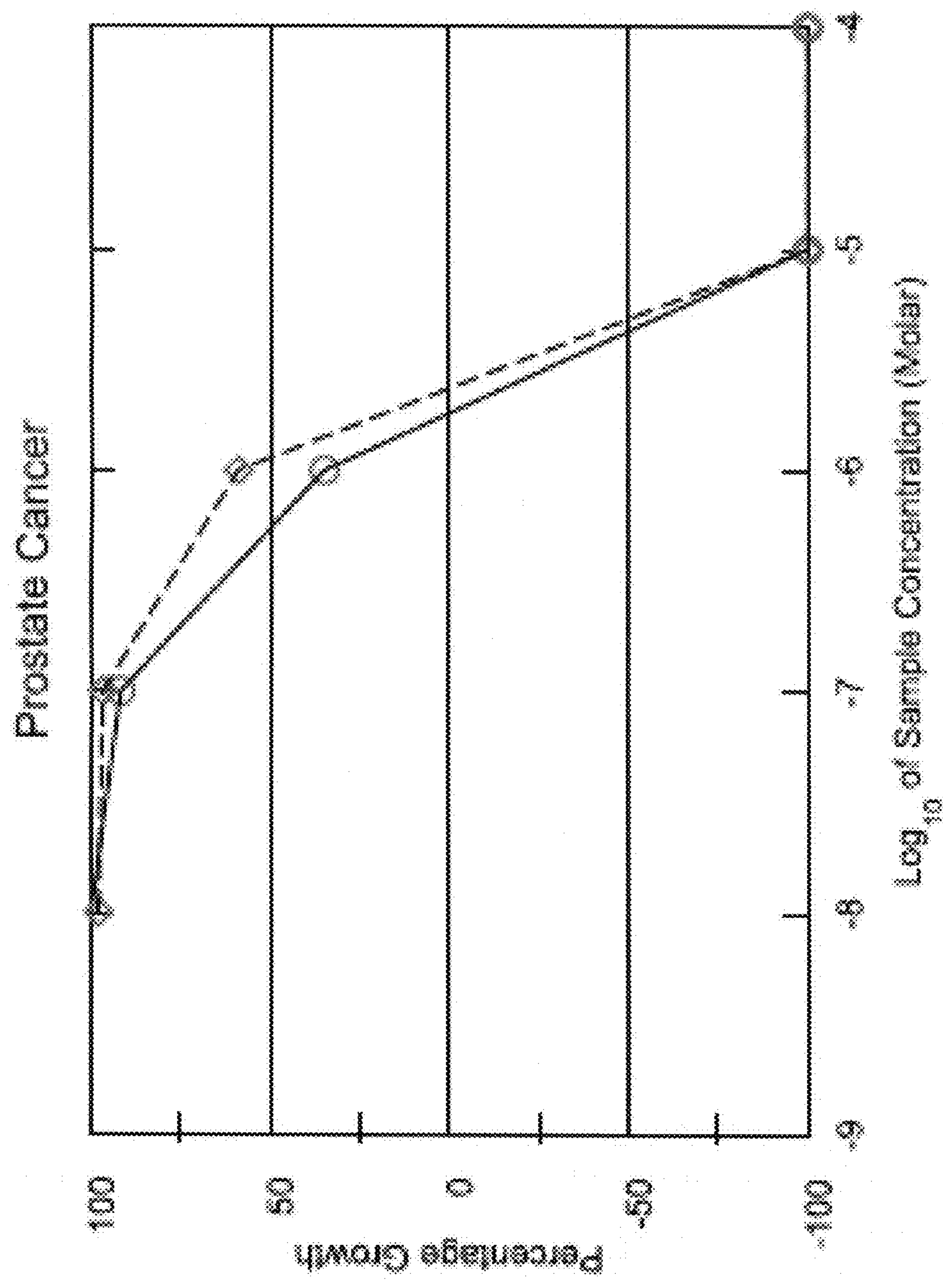
Figure 23 (con't)

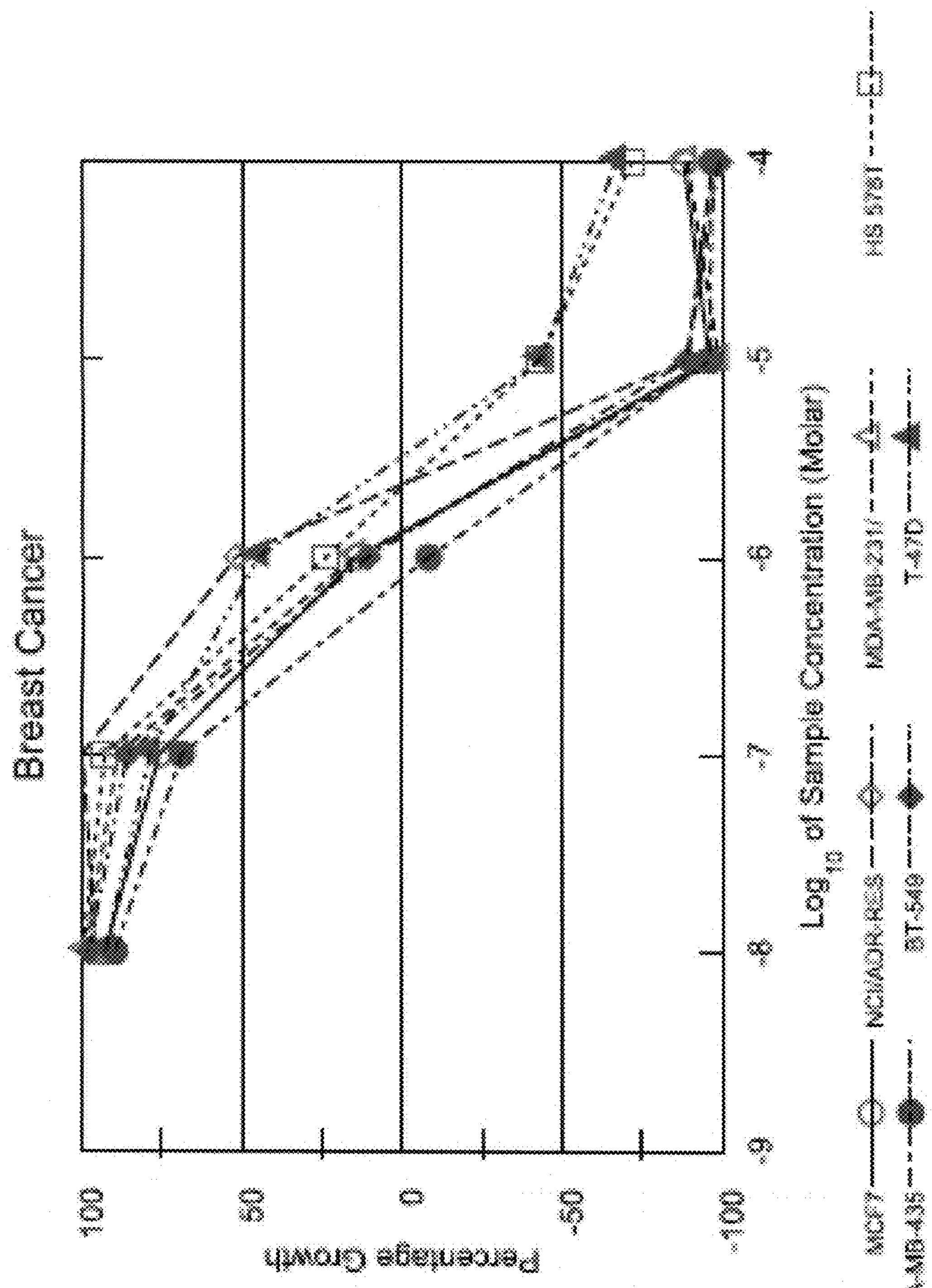
Figure 23 (con't)

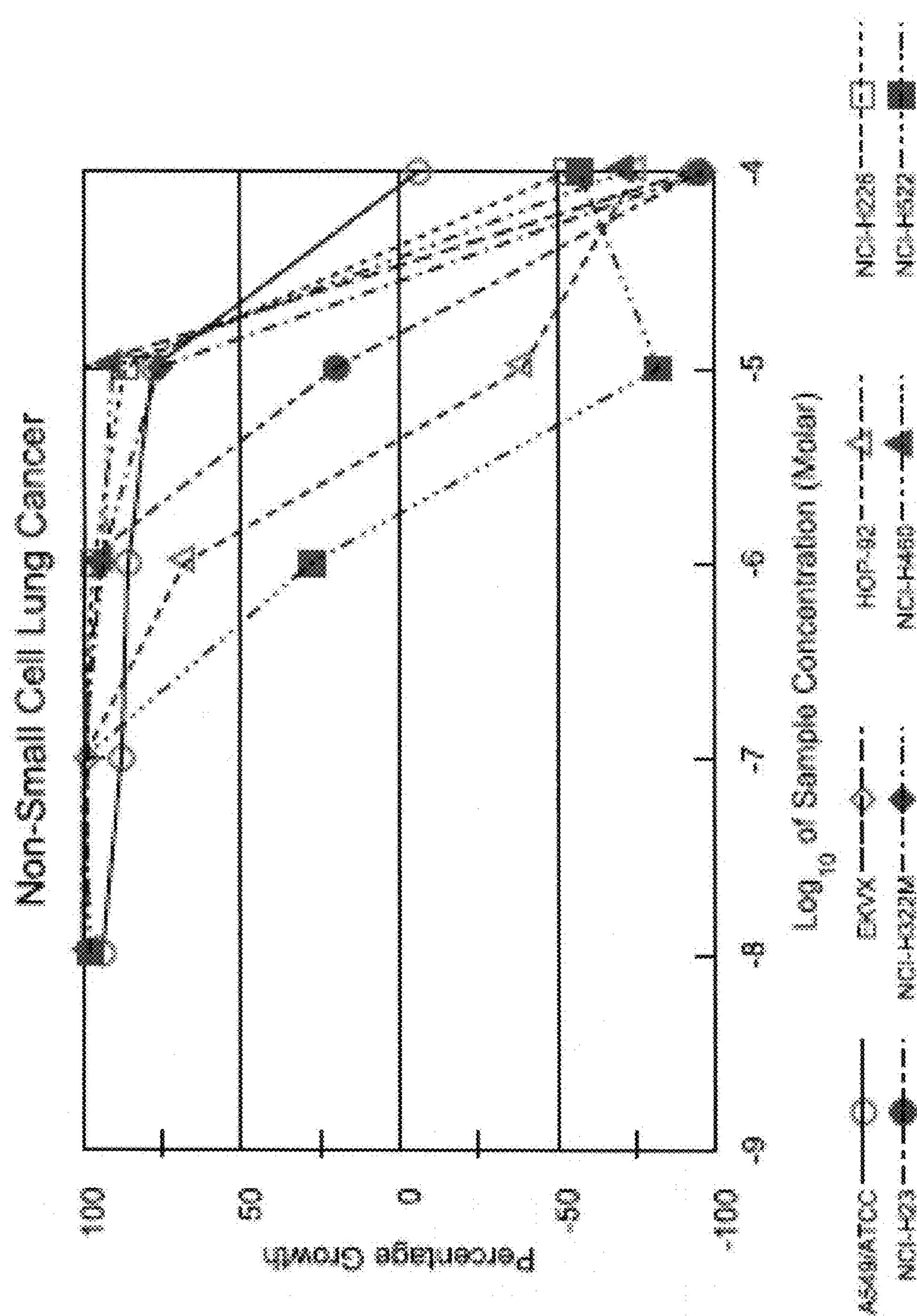
Figure 24 (con't)

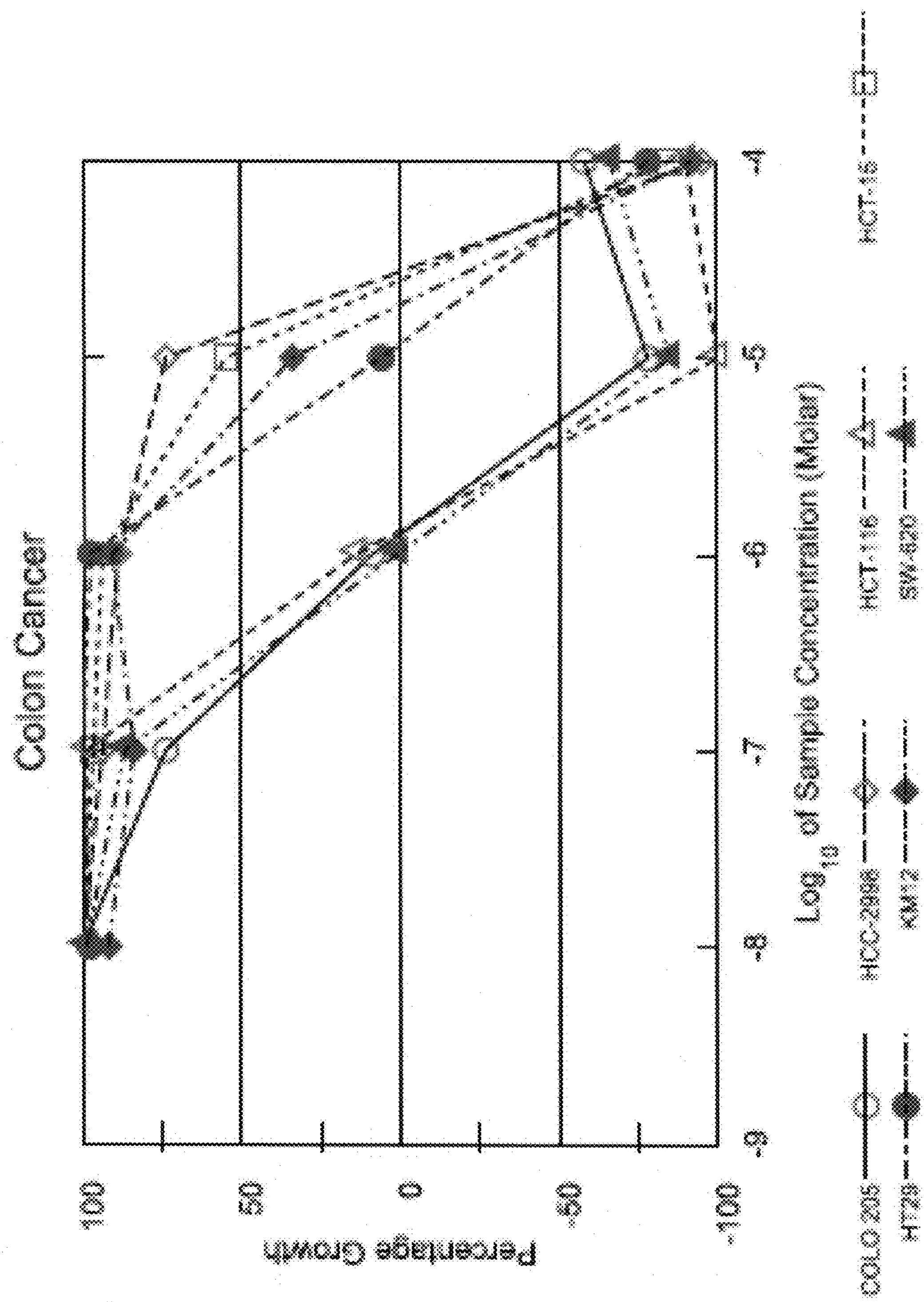
Figure 24 (con't)

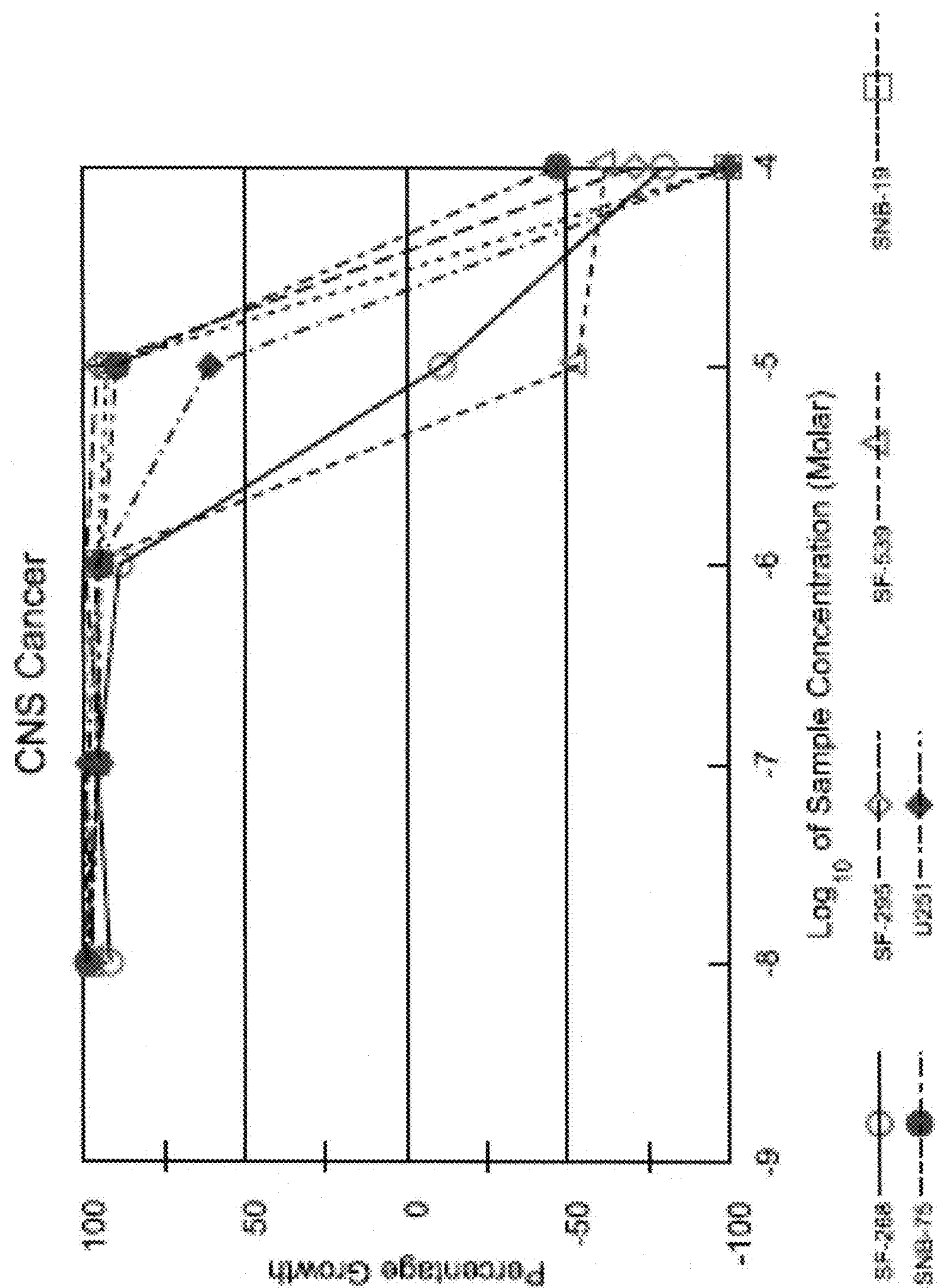
Figure 24 (con't)

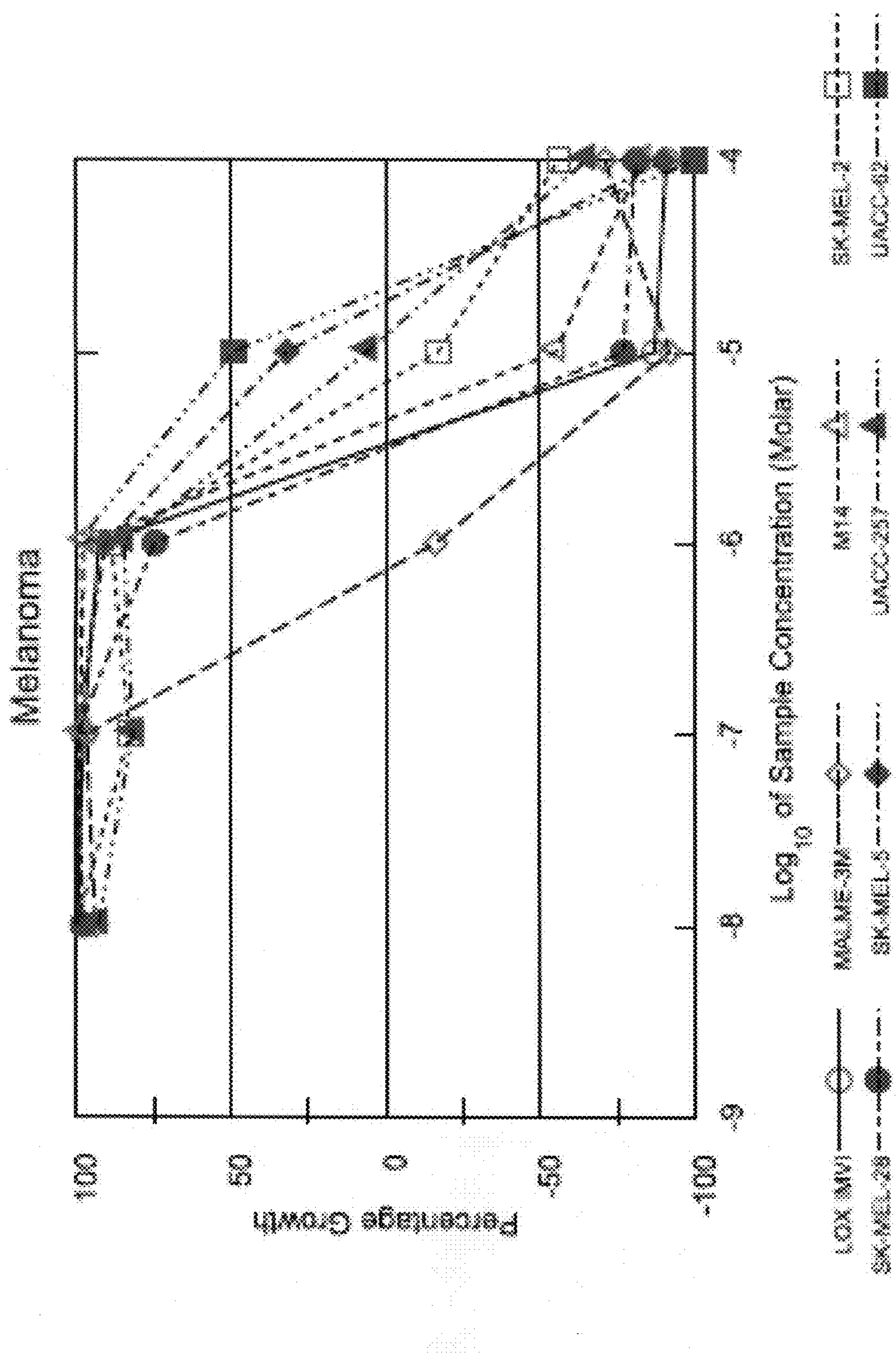
Figure 24 (con't)

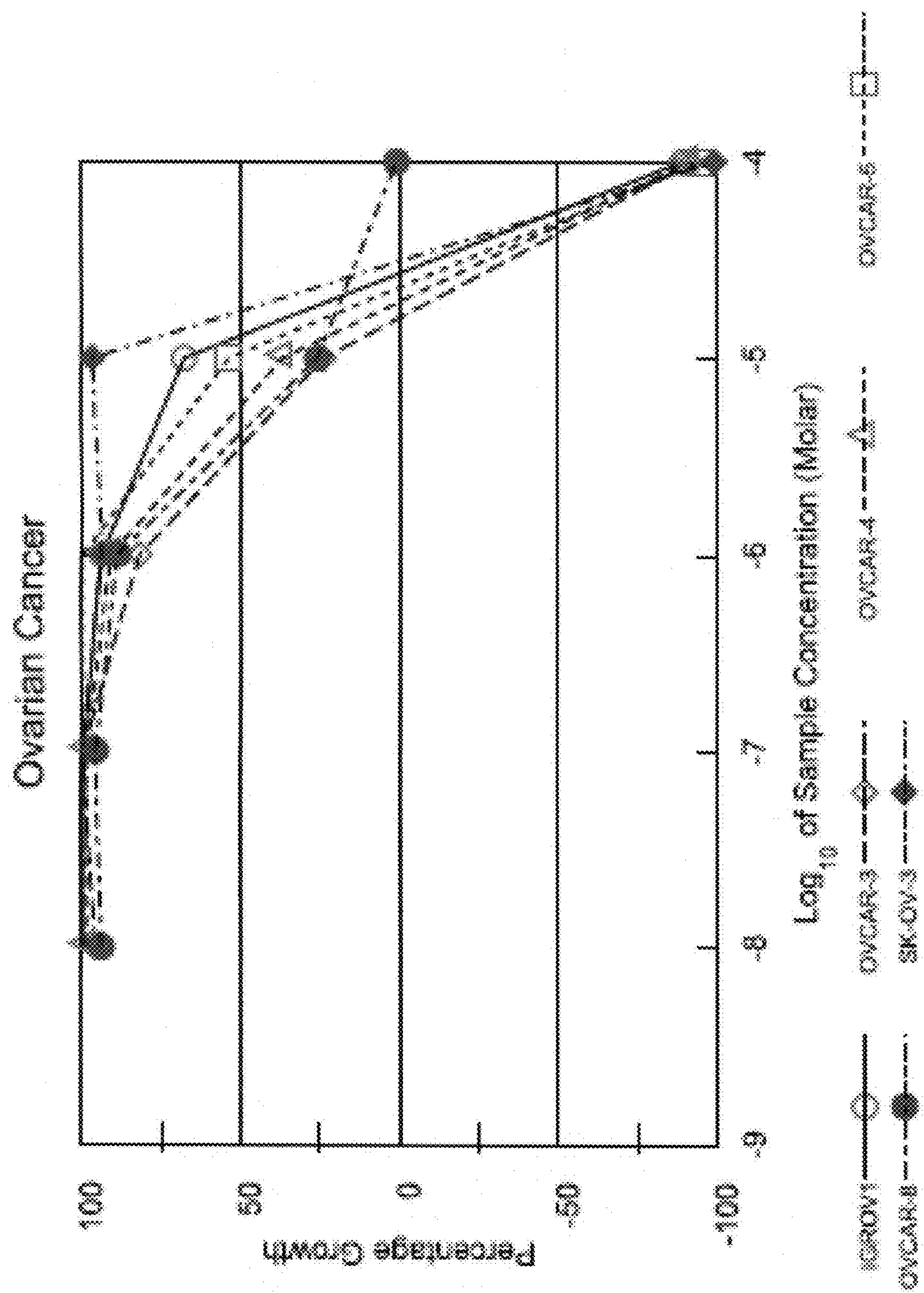
Figure 24 (con't)

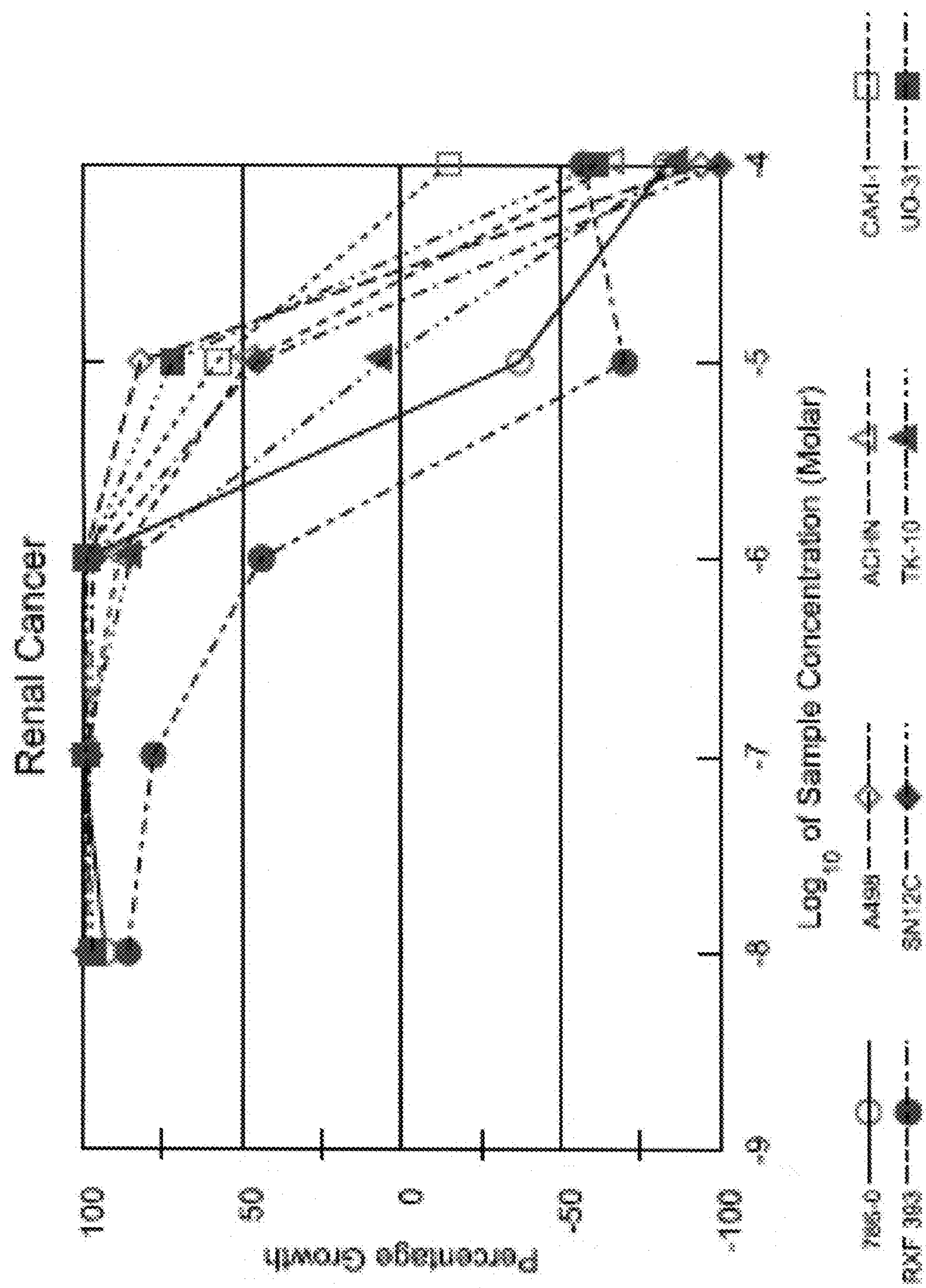
Figure 24 (con't)

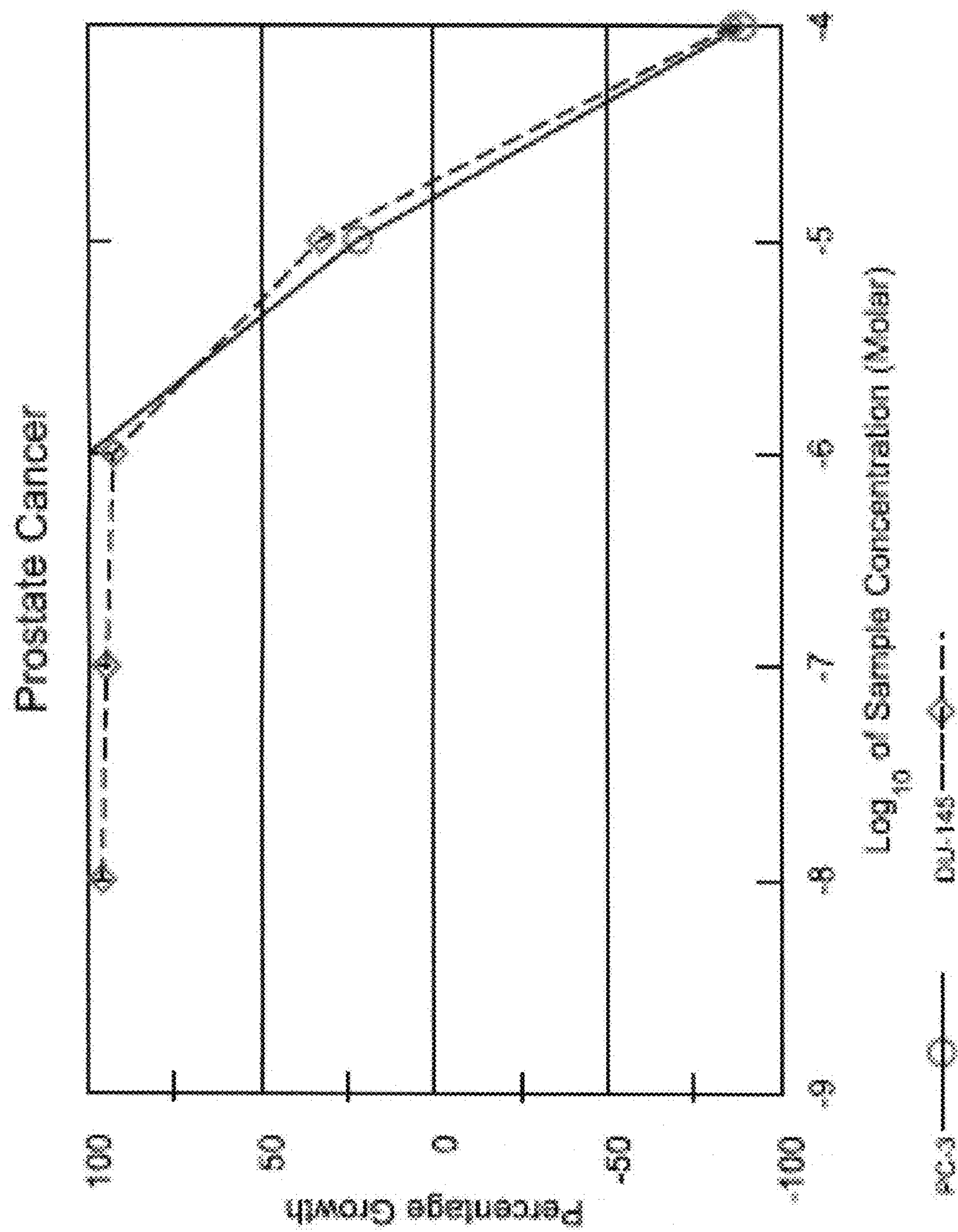
Figure 24 (con't)

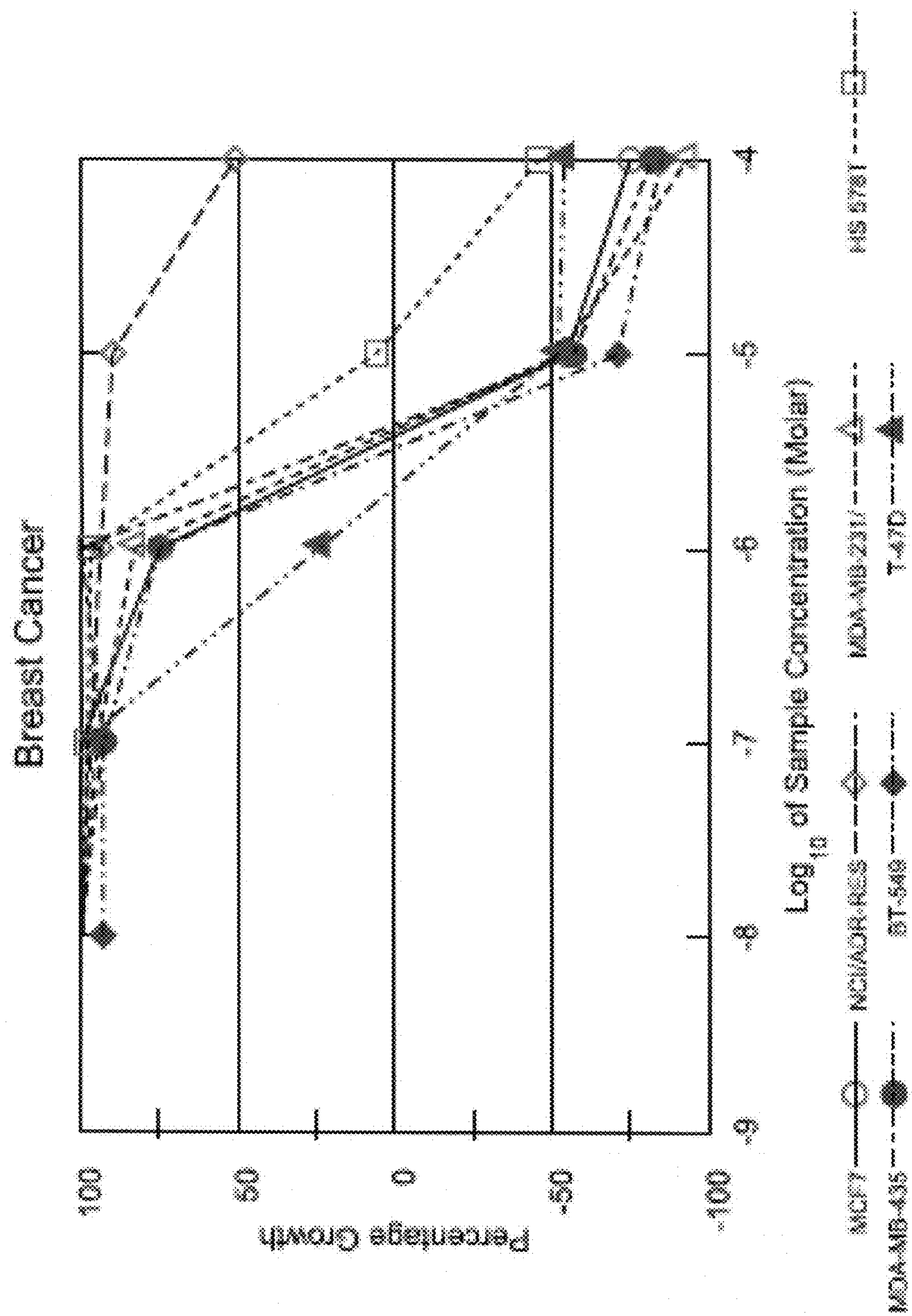
Figure 24 (con't)

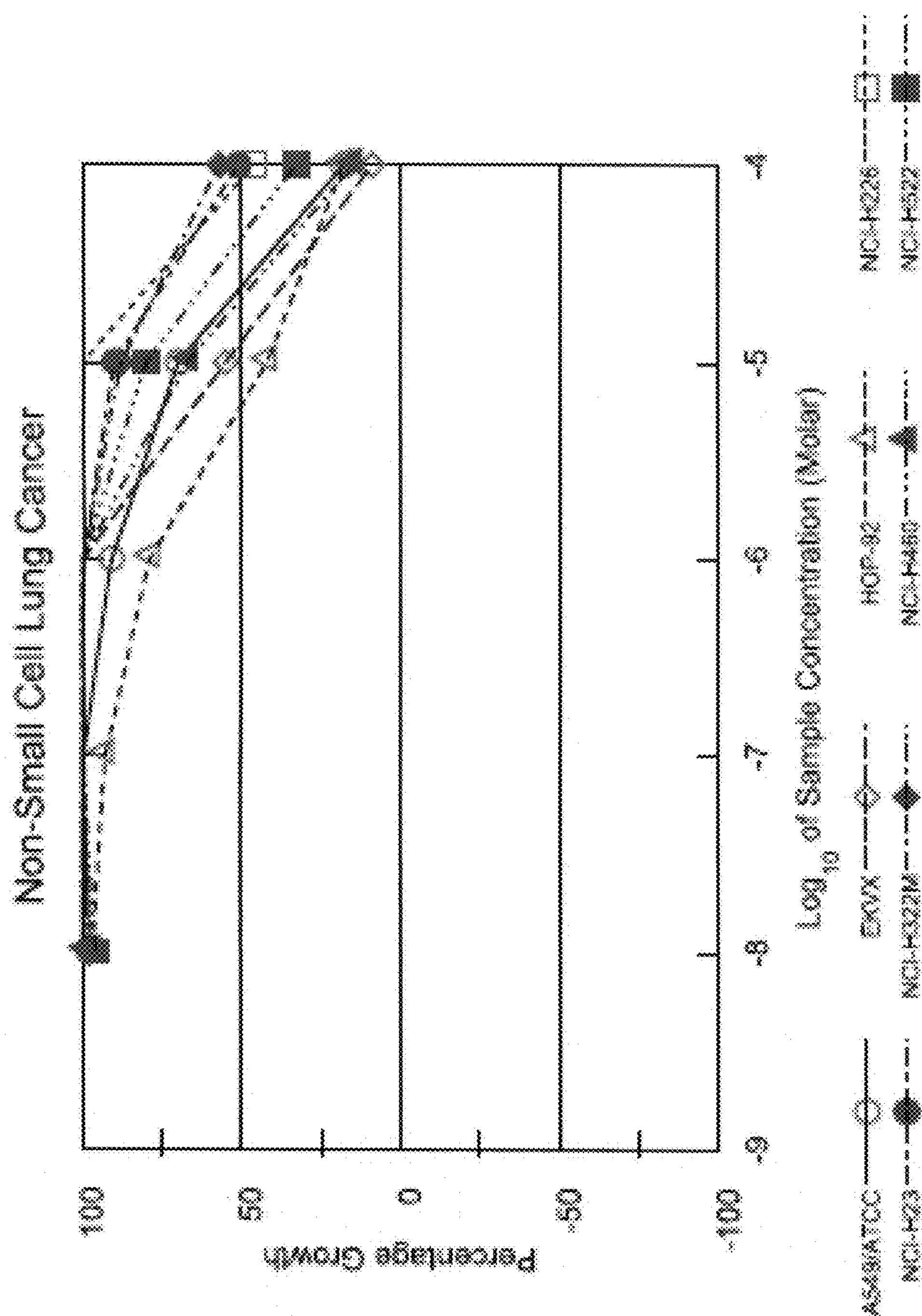
Figure 25 (con't)

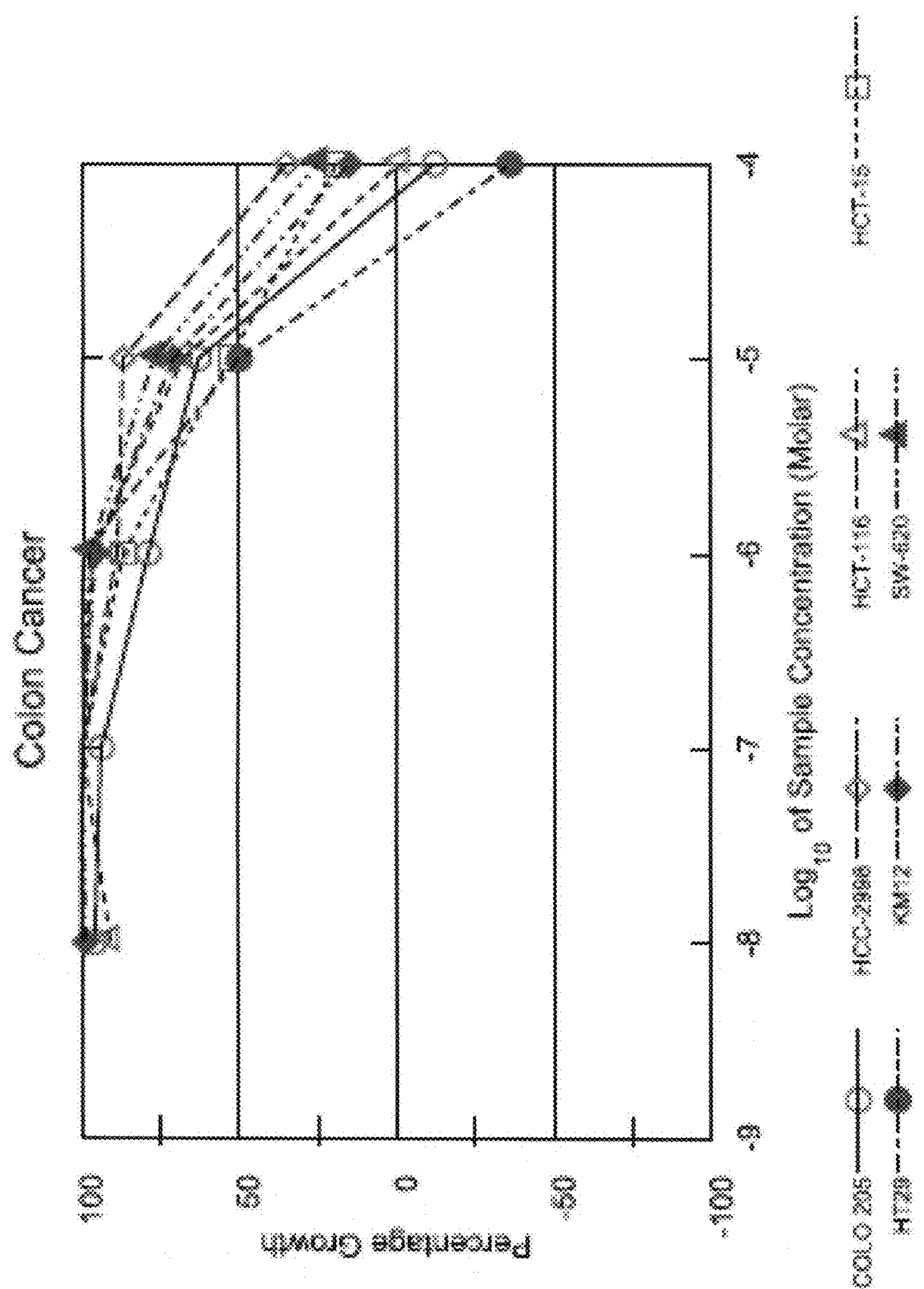
Figure 25 (con't)

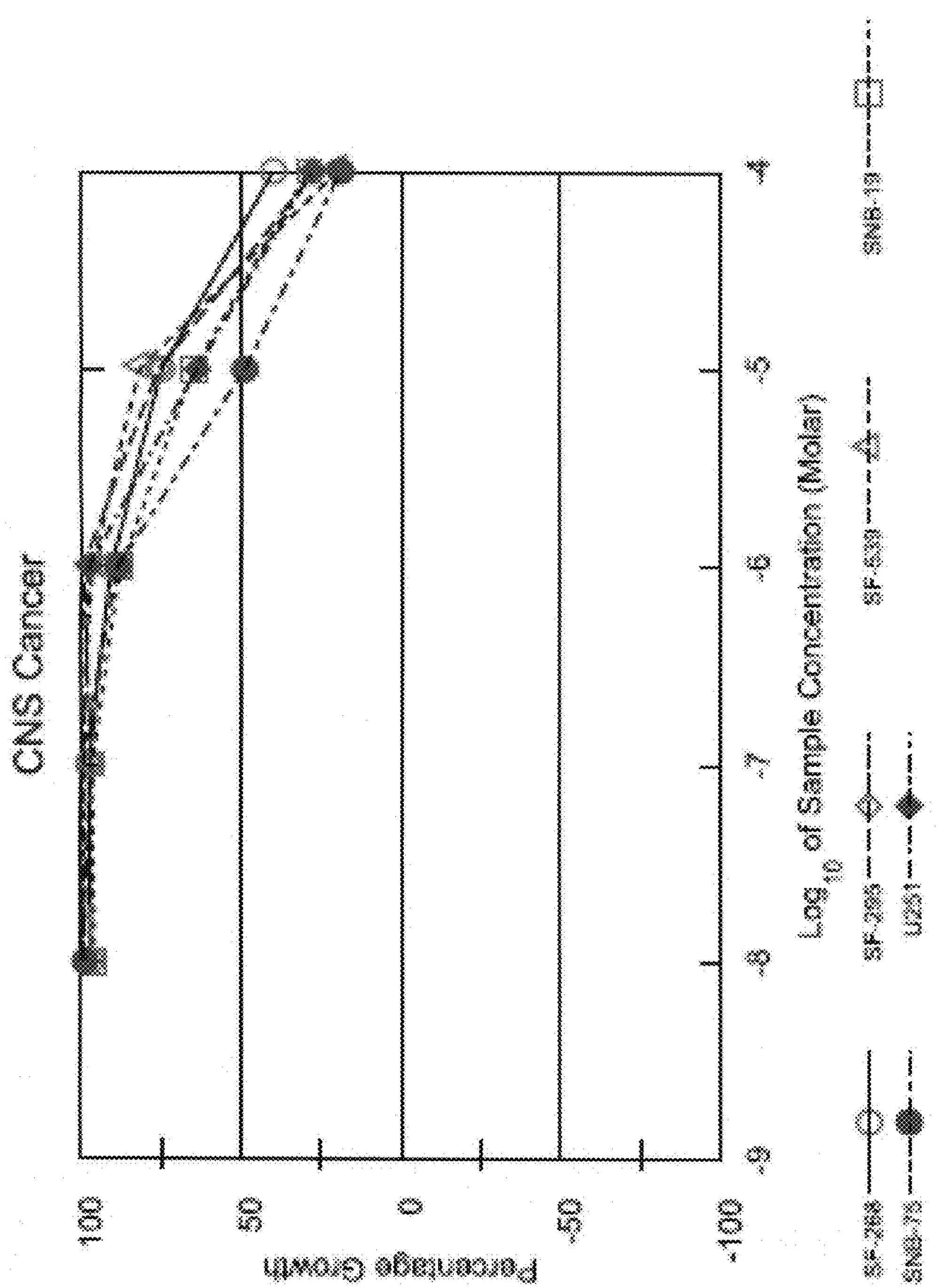
Figure 25 (con't)

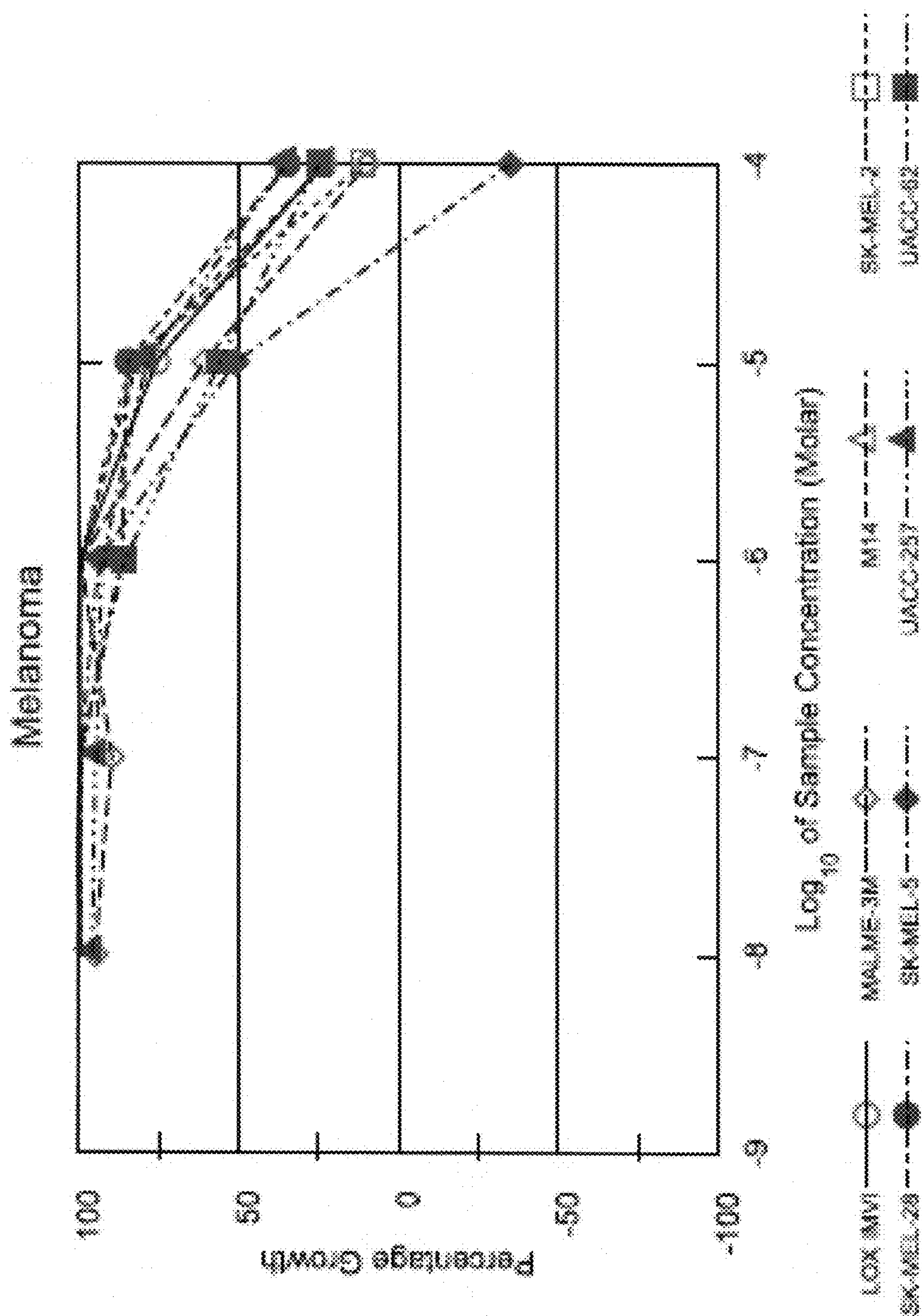
Figure 25 (con't)

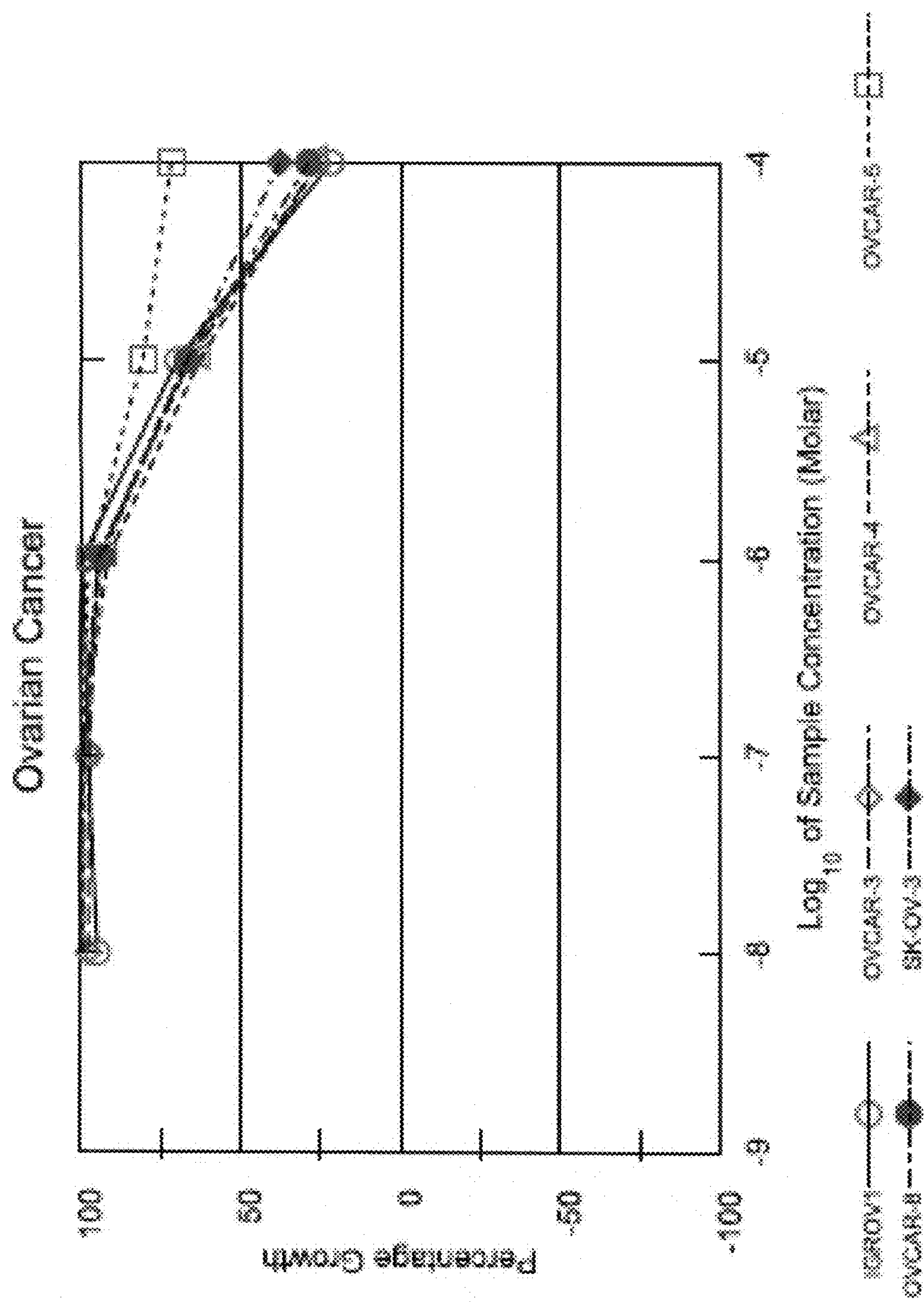
Figure 25 (con't)

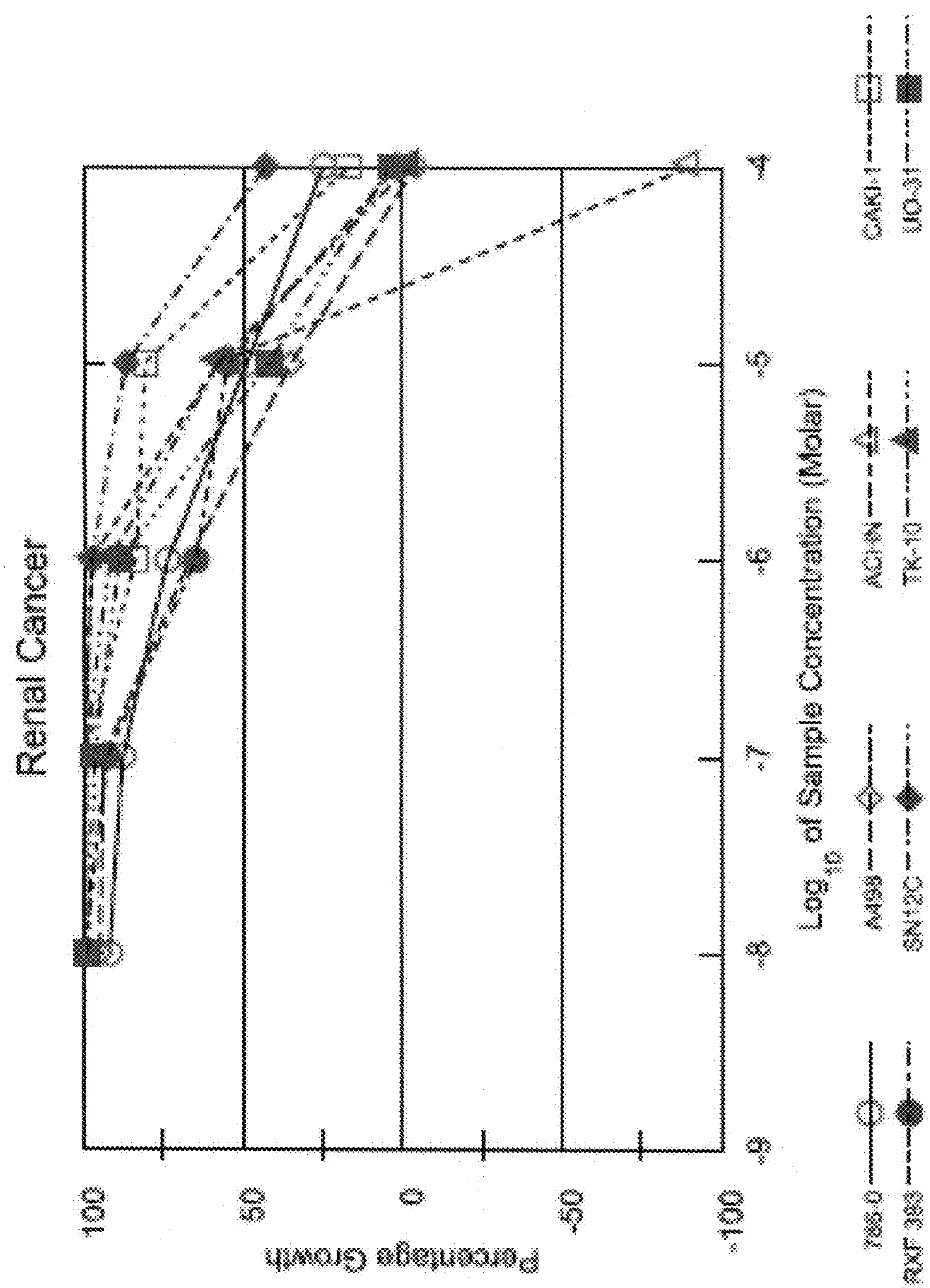
Figure 25 (con't)

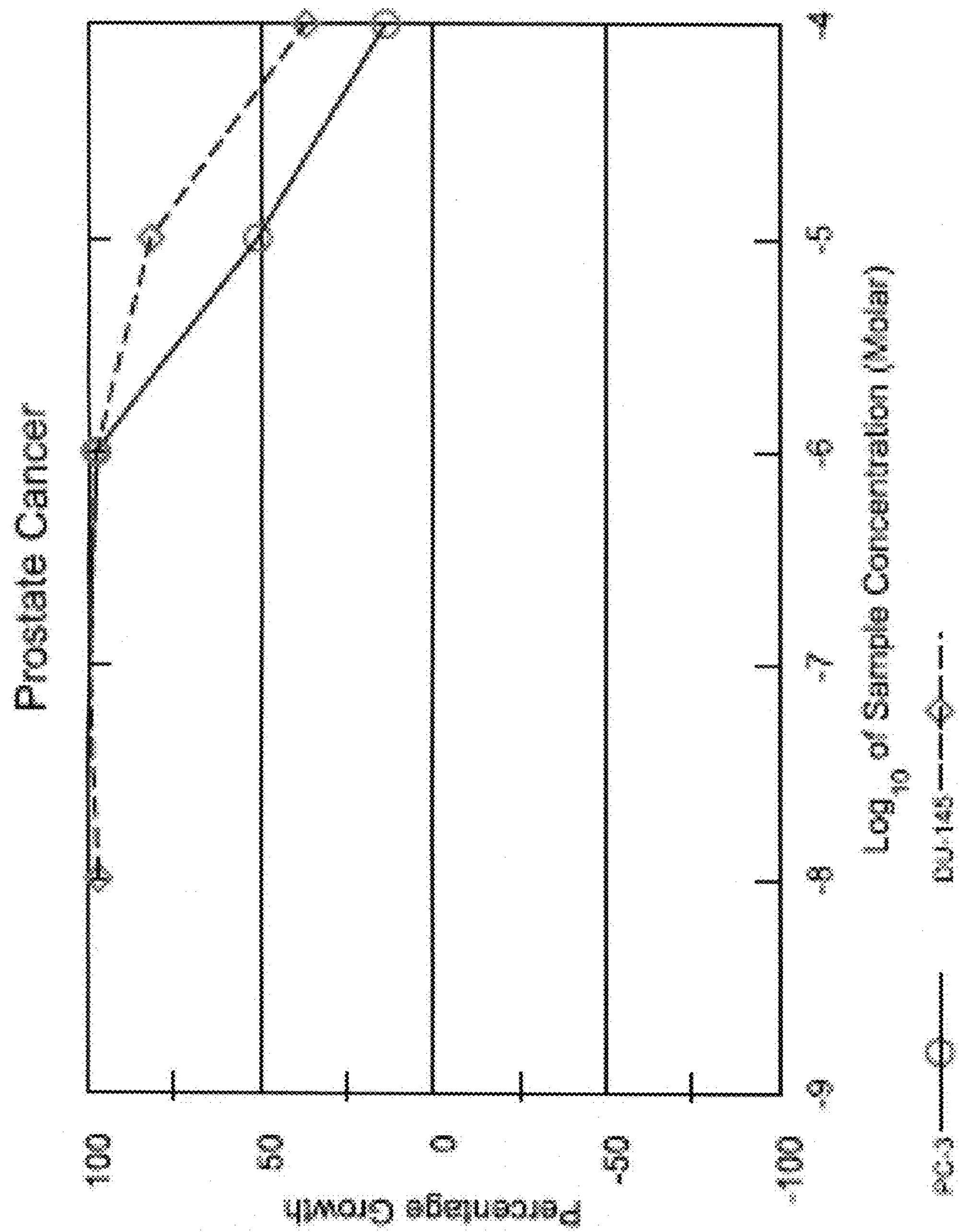
Figure 25 (con't)

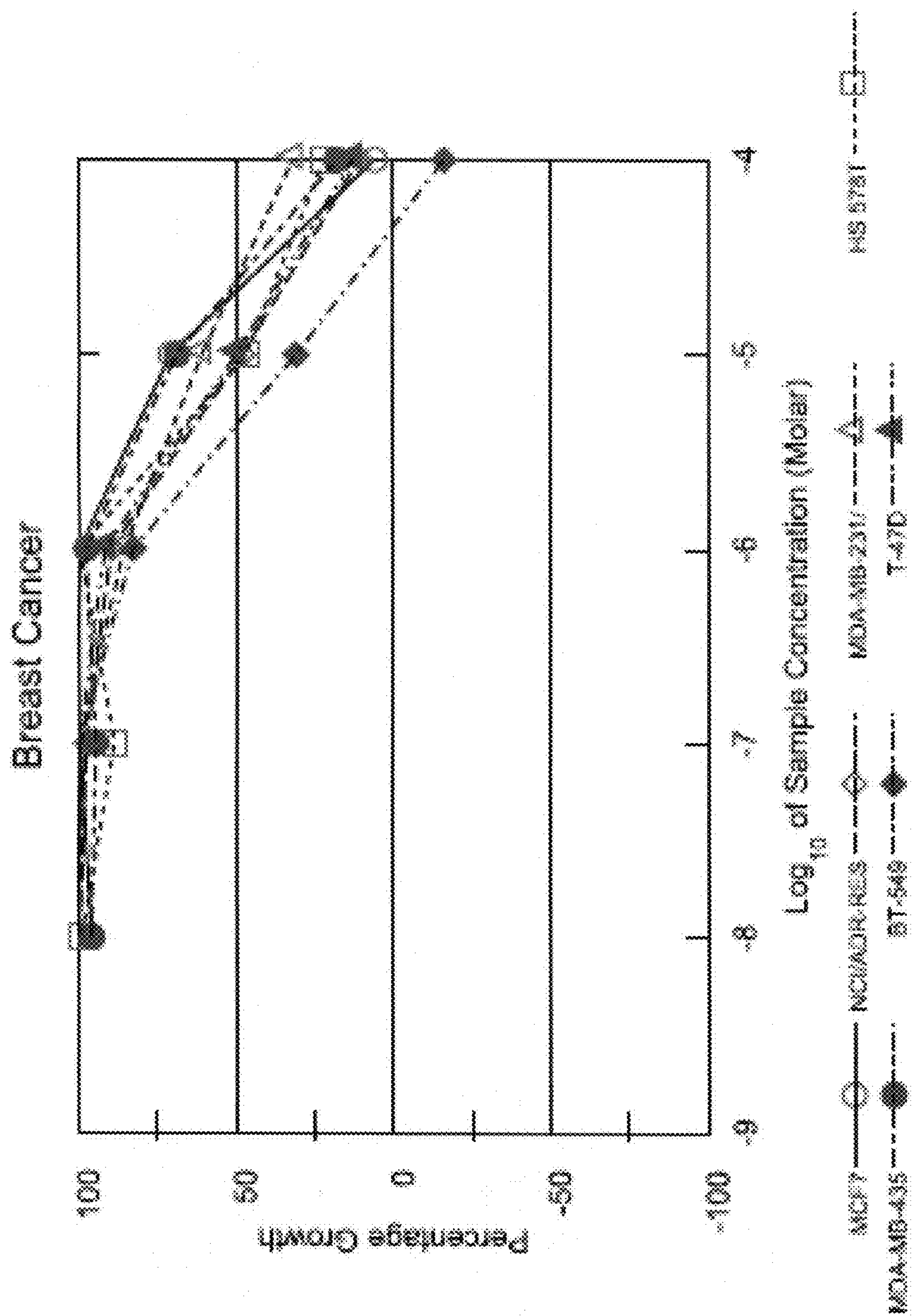
Figure 25 (con't)

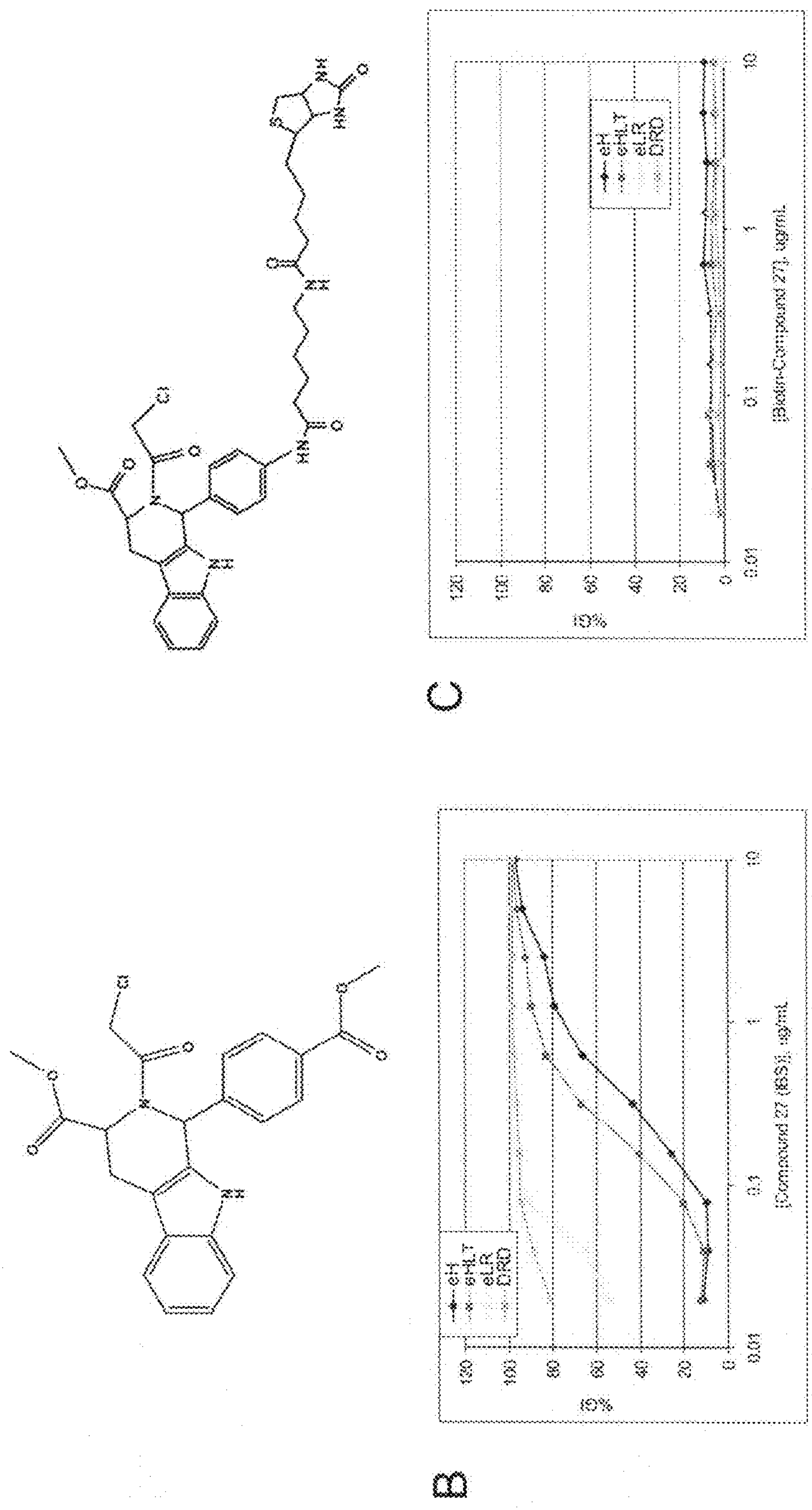
Figure 26 (con't)

B
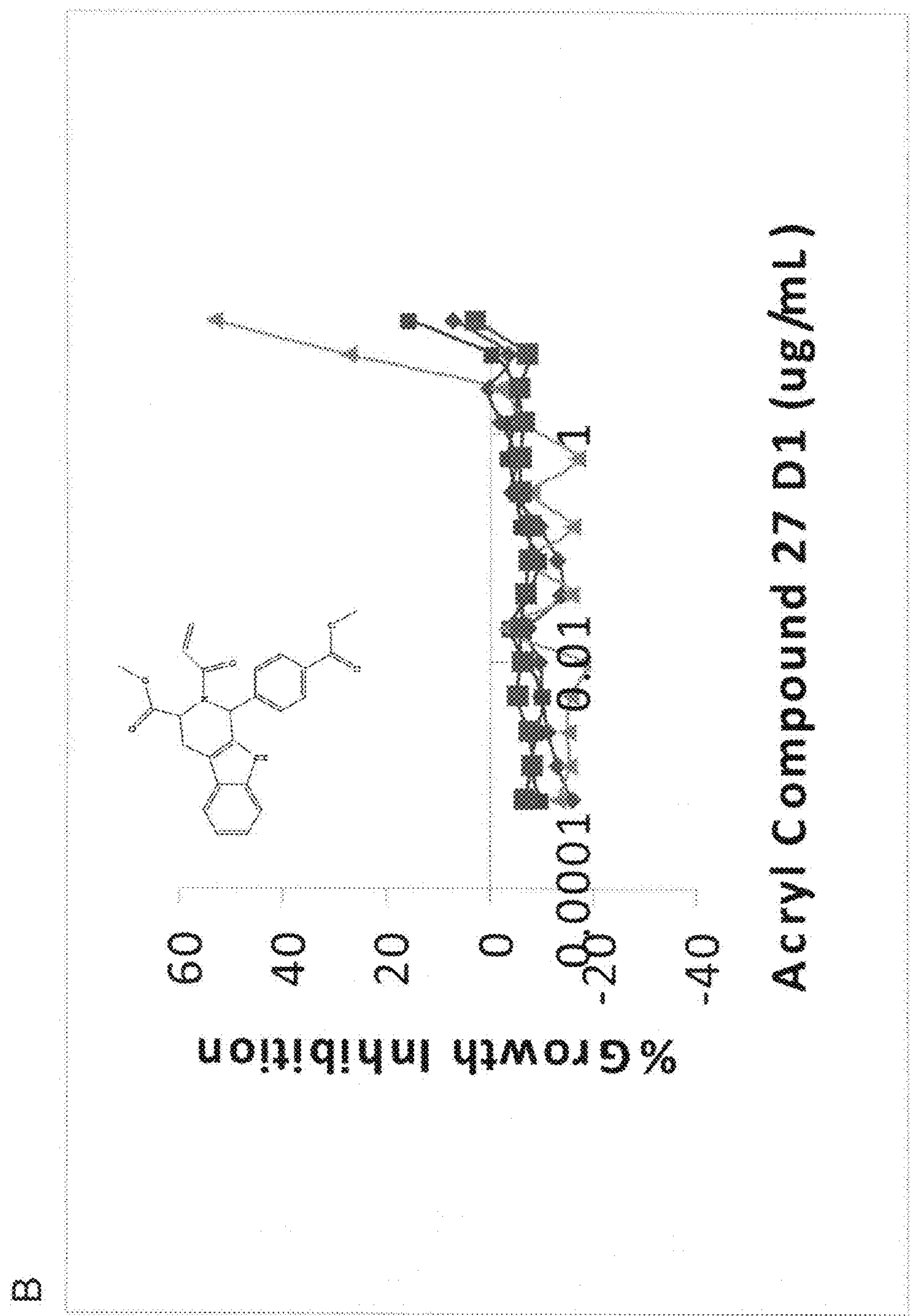
Figure 30 (con't)

1.2 eq EDC, 0.5 eq DMAP

S: dry $CH_2Cl_2$, 50 C

A

B

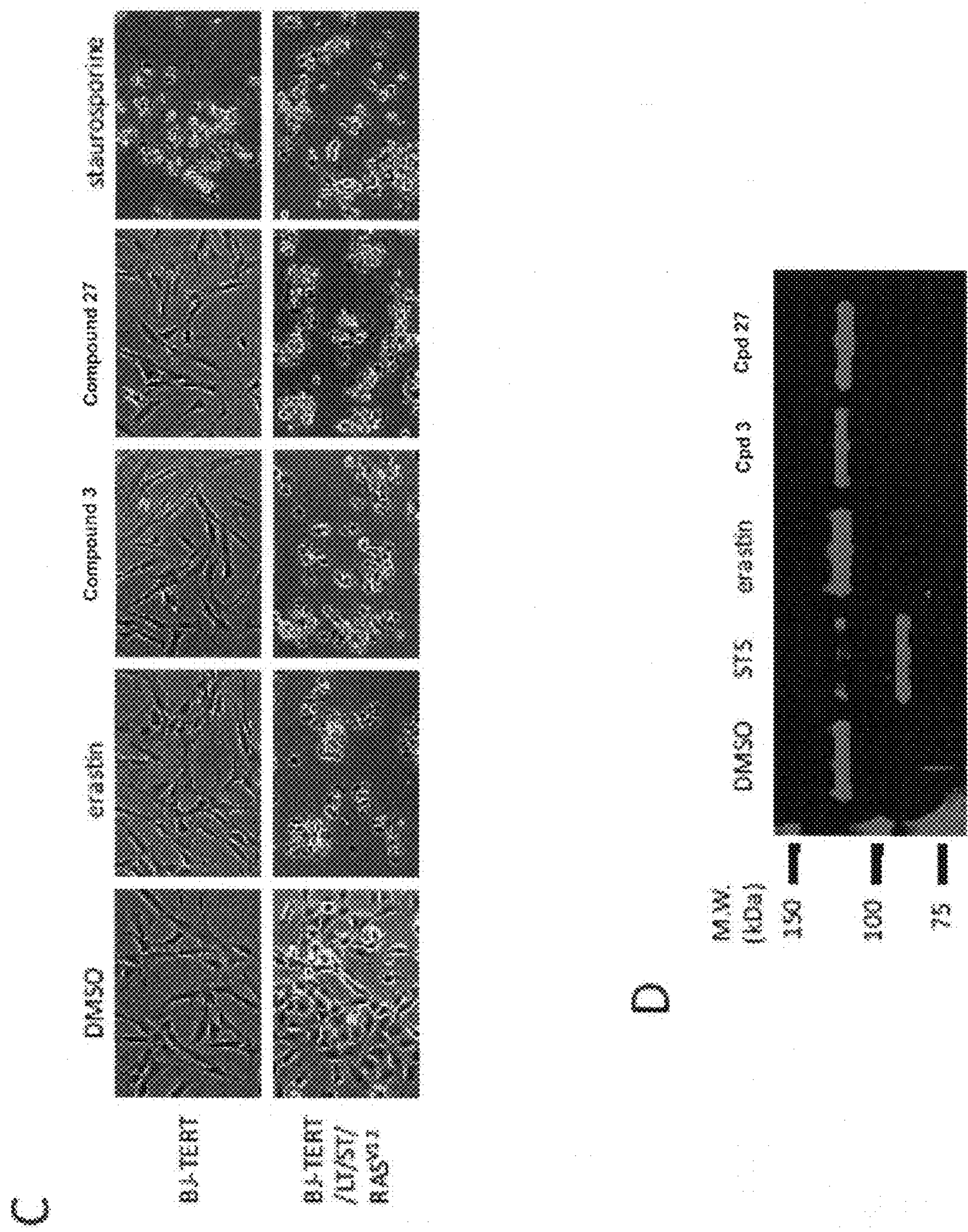
Figure 45 (con't)

| Input | Output | PCC* |
|---|---|---|
| Paclitaxel | Vinblastine | 0.857 |
| | Maytansine | 0.81 |
| | Rhizoxin | 0.759 |
| RSL3 | 6-methoxyguanine | 0.503 |

* Pairwise Co-relation Coefficient

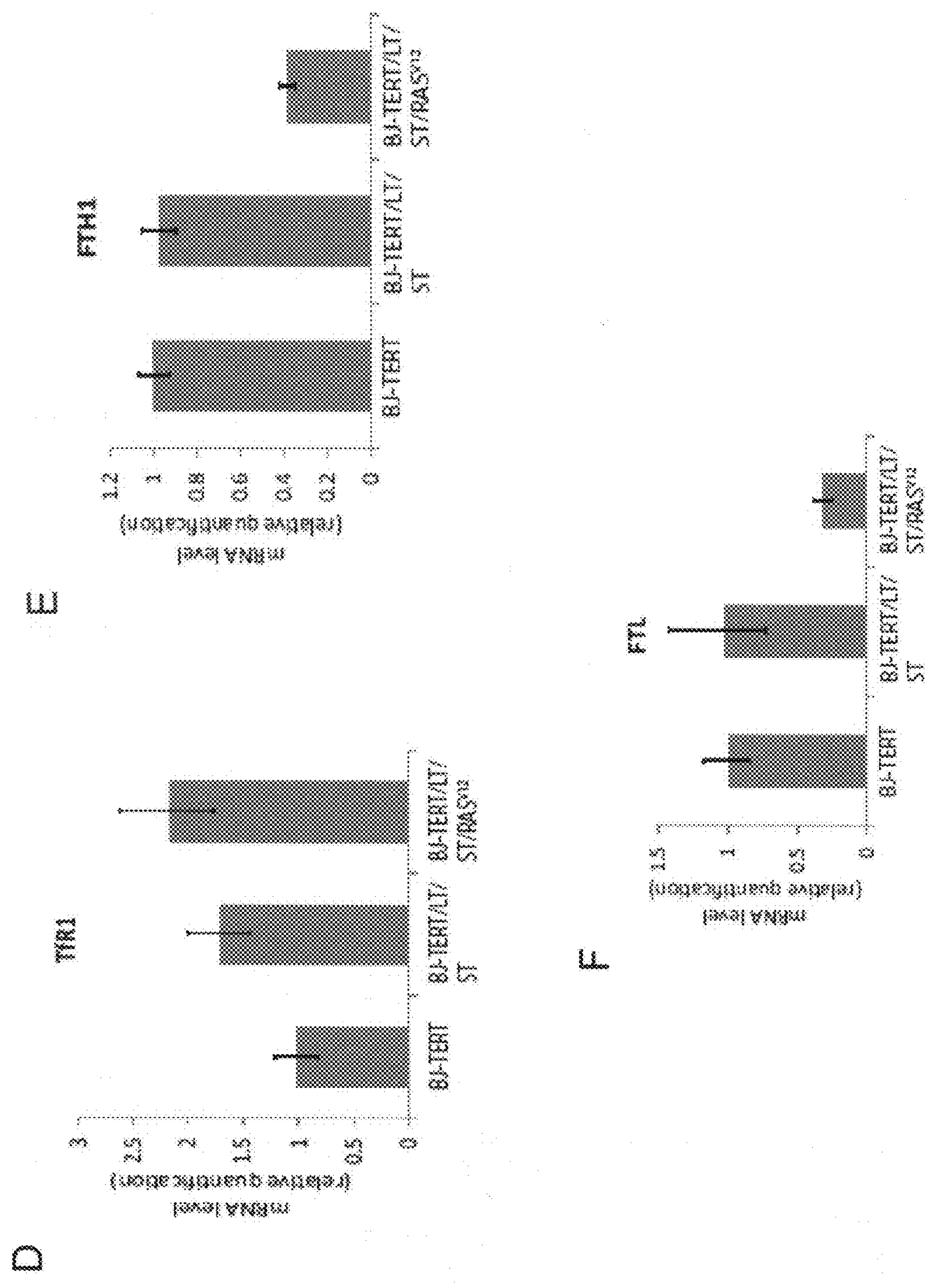
Figure 48 (con't)

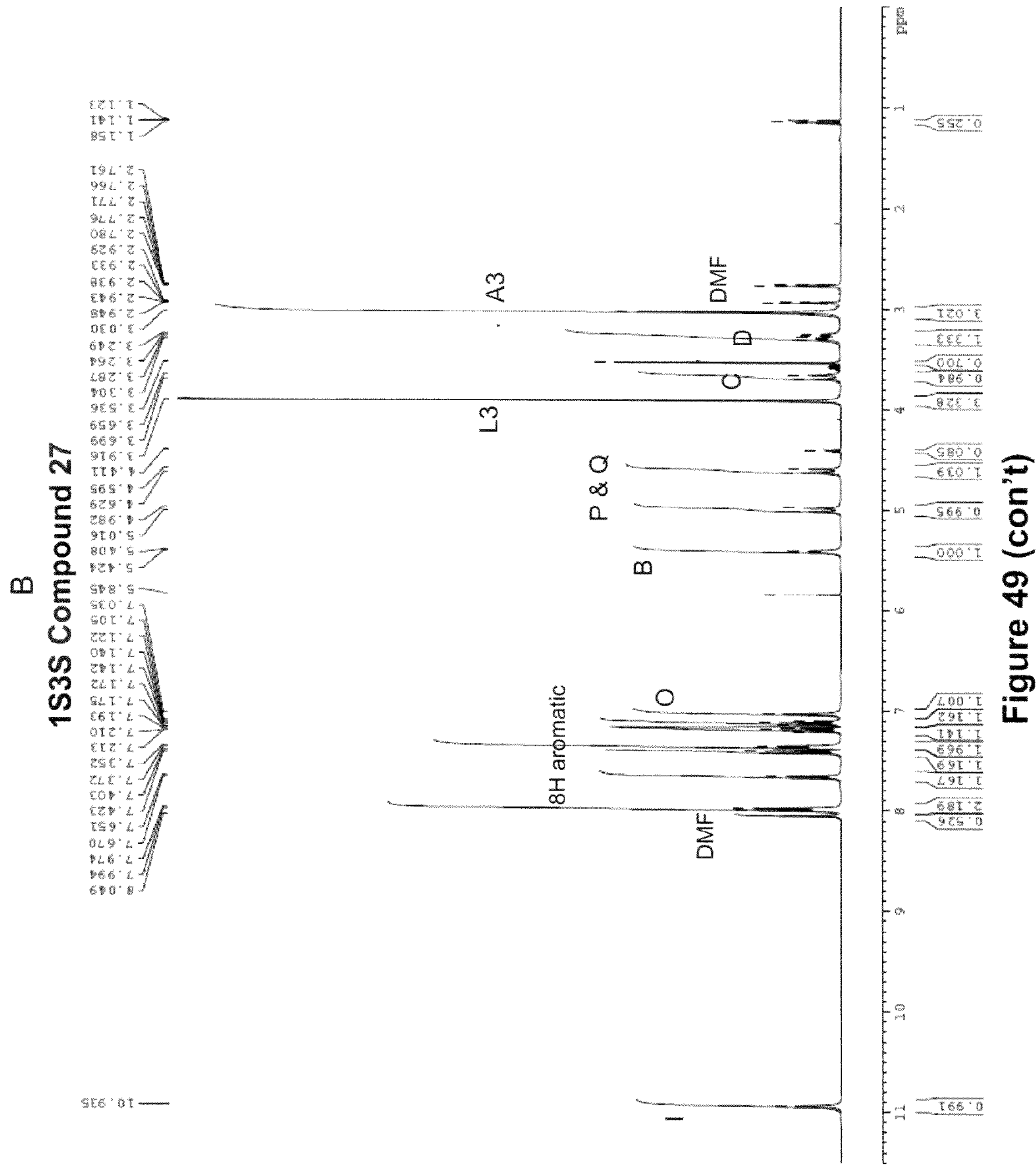
Figure 49 (con't)

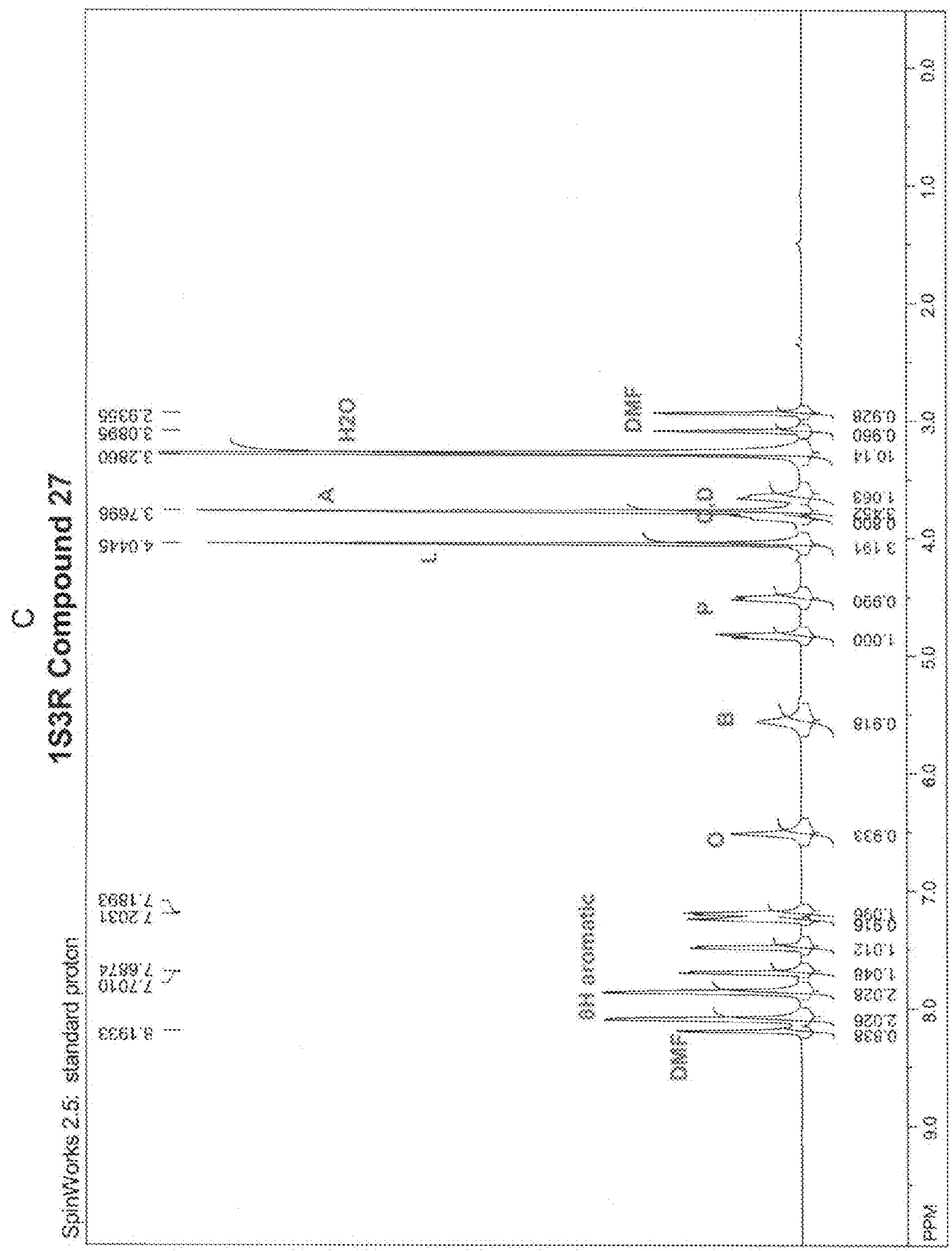
Figure 49 (con't)

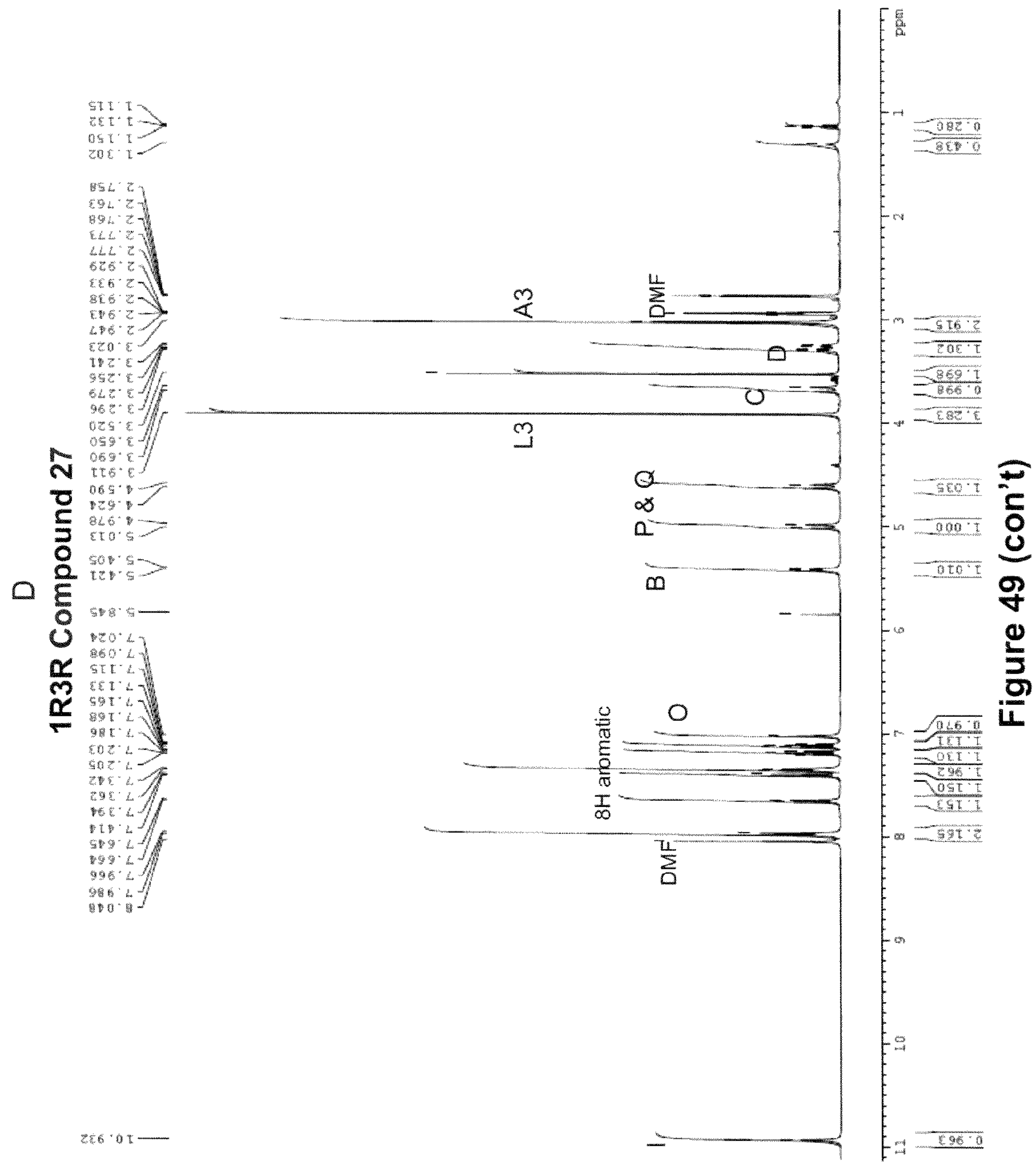
Figure 49 (con't)

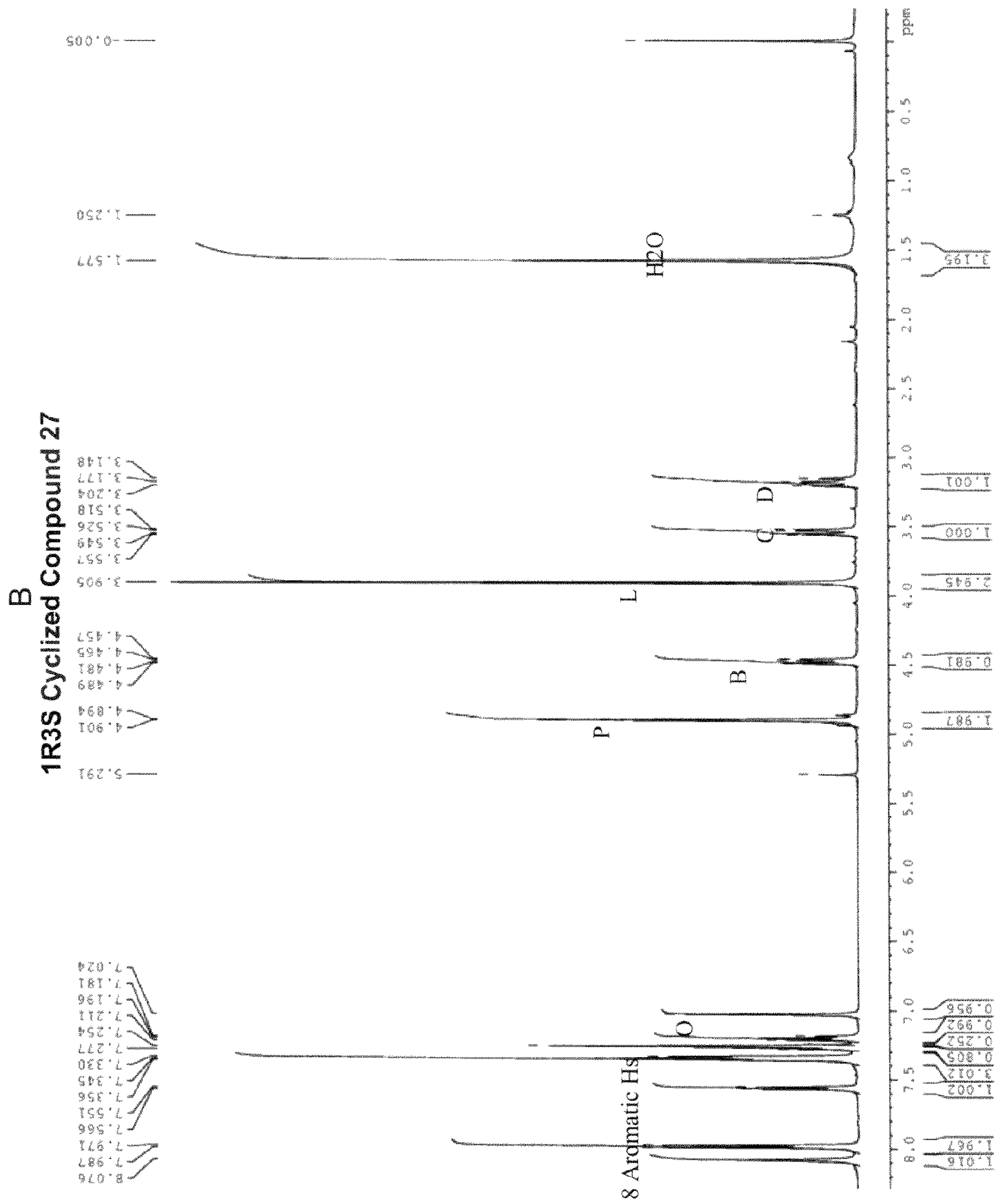
Figure 50 (con't)

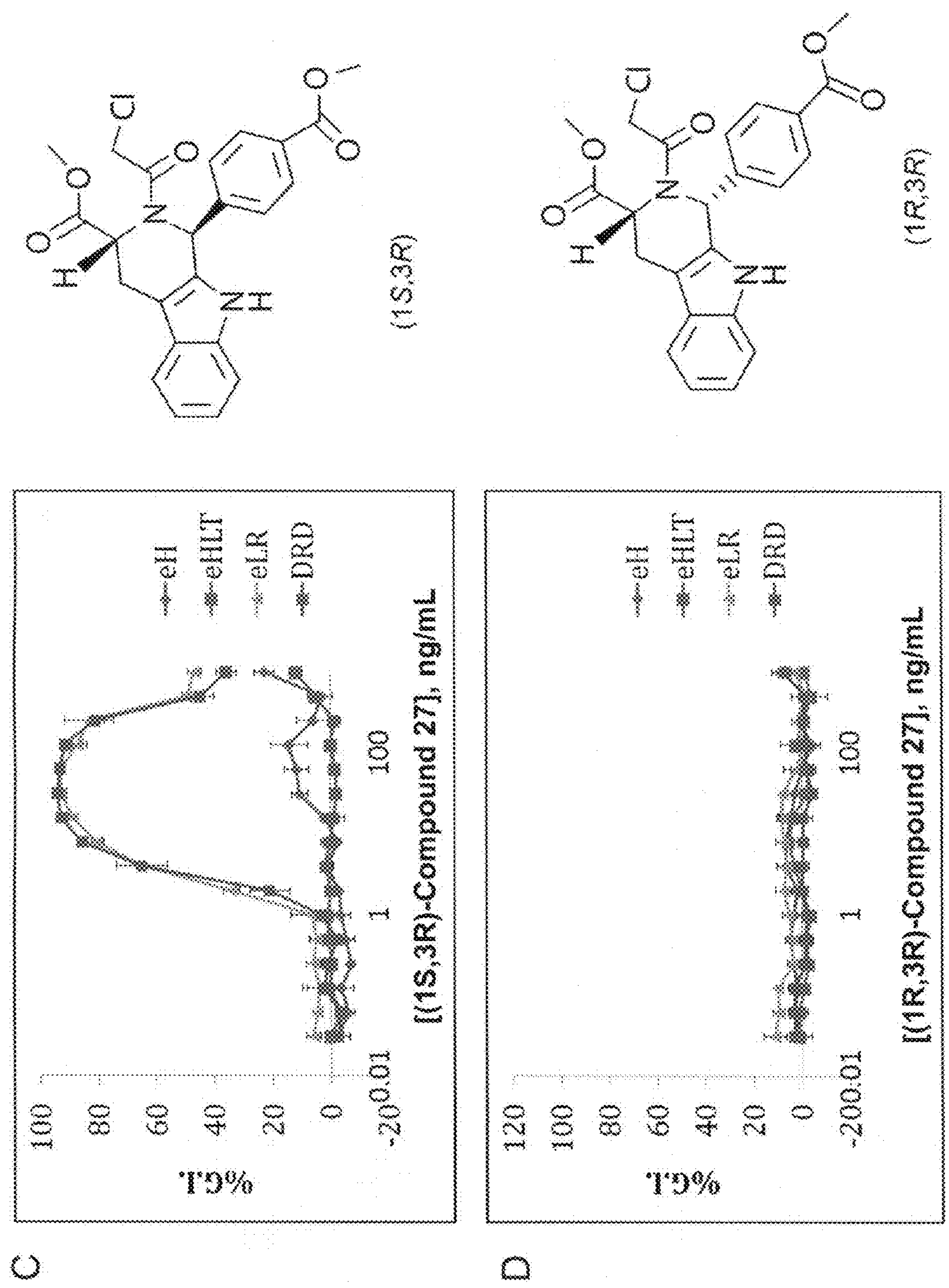
Figure 51 (con't)

ONCOGENIC-RAS-SIGNAL DEPENDENT LETHAL COMPOUNDS

RELATED APPLICATIONS

The present application claims the benefit of International Application No. PCT/US2008/002390, which was filed on Feb. 21, 2008, which claims the benefit of U.S. Provisional Application No. 60/902,575, which was filed on Feb. 21, 2007, both of which are incorporated herein in their entireties.

GOVERNMENT FUNDING

This invention was made with government support under grant no. 1 R01 CA097061-01 awarded by the National Institutes of Health/National Cancer Institute. The government has certain rights in the invention.

FIELD OF THE INVENTION

The present invention relates to compounds with cancer cell specific lethality. In particular, the present invention relates to RAS-selective lethal compounds and compositions. The present invention also relates to methods of screening for such compounds and methods of treating a condition in a mammal, e.g., by administering to the mammal a therapeutically effective amount of such compounds or compositions.

BACKGROUND OF THE INVENTION

Cancer can be effectively treated using targeted therapy. There are increasing efforts to fulfill the promise of targeted therapy using antibodies, peptides, and small molecules that selectively affect cancer cells. The key to successful targeted therapy is to identify target molecules that play a unique role in tumor cells. Tumor cells have a broad spectrum of mutations and chromosomal rearrangements affecting gene products that play critical roles in the genesis and maintenance of tumors (Hanahan and Weinberg, 2000; Vogelstein and Kinzler, 2004). Some of these mutated gene products are shared among cancer cells from different origins and may be good targets for developing anti-cancer drugs with a high therapeutic index.

Leads for new cancer therapeutics often emerge from target-based in vitro screening. For example, compounds that interfere with post-translational modifications of RAS, such as Farensyl Transferase Inhibitors (FTIs) are in clinical trials. In addition, targeted kinase inhibitors, such as Gleevec (Capdeville et al., 2002) and Sorafenib (Wilhelm et al., 2006) have been effective in treating tumors using a targeted therapy approach.

Many proteins cannot be targeted with enzymatic, active-site inhibitors. However, in some cases, the oncogenic functions of these targets can be inhibited by small molecules that disrupt their interaction with other necessary protein partners or other aspects of the protein's function. Small molecules that disrupt the interaction between the tumor suppressor p53 and the oncoprotein MDM2, or between pro-apoptotic and anti-apoptotic bcl-2 family proteins, induce selective death in a subset of tumor cells (Fry and Vassilev, 2005). In a more challenging approach to restore a mutant protein's function, others have reported the identification of pharmacological chaperones that convert the conformation of mutant p53 into wild type (Foster et al., 1999).

A complementary approach to such target-based discovery strategies is synthetic lethal screening. Activation of multiple downstream signaling molecules is crucial to RAS-mediated tumorigenesis and tumor maintenance. Synthetic lethal screening is a strategy for revealing critical RAS-linked targets. (Hartwell et al., 1997). For a given mutation "A", if there exists a second mutation "B" that is particularly lethal to the organism in the presence of A, mutation B is synthetic lethal with mutation A because the lethality requires the synthesis, or bringing together, of the two mutations. In synthetic lethal screening with oncogenic RAS, the second perturbation can be created by using a small molecule to alter the function of a target protein, rather than by introducing a mutation in the gene encoding the protein. (Stockwell, 2000). The existence of striking synthetic lethal interactions in genome-wide studies has been demonstrated in the work of Tong et al. with yeast deletion strains (Tong et al., 2001).

Classic yeast synthetic lethal screening involves cDNA library transformation, genome wide mutagenesis and colony-color assays in order to identify clones that are necessary for the survival of yeast cells with a given mutation (Barbour and Xiao, 2006); alternatively, use of gene deletion panels has been successful (Tong et al., 2001). Although these classic methods have been useful in elucidating functional genetic connectivity in model organisms, they are not as applicable to mammalian systems. Small molecules, and additionally RNAi libraries using siRNAs or shRNAs (Moffat and Sabatini, 2006), are more tractable than mutagenesis for carrying out synthetic lethal screening in cell culture systems.

Unlike synthetic lethal screening with mutations, synthetic lethal screening with small organic molecules does not provide direct information about the nature of the two mutations that cause synthetic lethality. The relevant target of each compound must ultimately be identified.

However, the use of small molecules in place of gene deletions offers a number of advantages that can overcome the lack of direct information about the target protein. First, compound addition can be varied in time and concentration, providing finer control of the perturbation to the target cell. Second, small molecules can induce a gain-of-function or affect just one domain of a protein, unlike deletion mutations or RNA interference (RNAi). Third, it is more straightforward to develop a chemotherapeutic reagent from a small molecule lead than from a gene deletion or RNAi reagent. For these reasons, the concept of synthetic lethal screening with small molecules is complementary to such studies with gene deletions or RNAi. Indeed, several groups have reported the discovery of small-molecules that are synthetic lethal to mutations such as p53 (Stockwell et al., 1999), ERBB2 (Fantin et al., 2002), p21 (Torrance et al., 2001), and DPC4 (Wang et al., 2006). Further optimization of such hit compounds may yield anti-cancer leads with high therapeutic indices.

Synthetic lethal screening using RAS oncogenes has been studied (Dolma et al., 2003). Considering its critical role in cancer development, mutant RAS has been the focus of much research (Barbacid, 1987; Malumbres and Barbacid, 2003; Shaw and Cantley, 2006). Because restoring GTPase activity to mutant RAS is a challenging task for small molecules, efforts have focused on the more feasible approach of inhibiting post-translational processing of the RAS proteins to inactivate their oncogenic signaling. The C-terminal four amino acids of RAS proteins, i.e. the CAAX motif, are conjugated to a fifteen carbon isoprenoid by farensyltransferase (FTase) in the endoplasmic reticulum. This allows RAS proteins to be anchored in the plasma membrane, which is essential for activity (Schafer et al., 1989; Schafer et al., 1990). Several 'CAAX peptide mimetic' compounds have been developed as FTIs and have shown promising results in pre-clinical mouse studies (Kohl et al., 1995; Nagasu et al., 1995).

However, these compounds showed mixed results in clinical trials, possibly because KRAS and NRAS, whose mutations are more prevalent than HRAS in human cancer, can be conjugated to a twenty carbon isoprenoid modification by geranylgeranyltransferase upon inhibition of FTase activity (Rowell et al., 1997; Whyte et al., 1997).

An alternative approach using 'S-farensyl cystein mimetic' compounds, such as FTS, has been reported to work on all three RAS proteins and to be less cytotoxic than FTIs (Marom et al., 1995). These compounds were identified as inhibitors of isoprenylcysteine carboxyl methyltransferase (ICMT), another enzyme involved in RAS protein maturation. However, these compounds are reported to have the 'off-target' effect of dislodging membrane-bound RAS proteins, which leads to inhibition of RAS signal activation (Marciano et al., 1995; Marom et al., 1995). The anti-tumor effect of FTIs and FTSs is significant in pre-clinical experiments and research is on-going to improve the efficacy of these reagents in clinical settings. However, there has been debate as to whether inhibition of RAS post-translational processing will result in cancer-cell selective inhibition, given that other proteins are also subject to the same lipid modifications.

The compound erastin was found to display synthetic lethality with oncogenic RAS. As expected, the target of erastin is not RAS itself: erastin binds to voltage-dependant anion channels, a novel target for anti-cancer drugs to induce RAS-RAF-MEK-dependent oxidative, non-apoptotic cell death. (Yagoda et al., 2007).

Accordingly, there exists a significant need to screen, identify, and/or develop compounds and compositions that selectively target tumor cells, especially RAS-selective lethal compounds and compositions.

SUMMARY OF THE INVENTION

To circumvent concerns with the target-based approach in the RAS field, the complementary approach of synthetic lethal screening with small molecules was used to identify those compounds that display synthetic lethality with oncogenic RAS. Novel small-molecules that have synthetic lethal interactions with mutant RAS have been identified and characterized. Moreover, their mechanisms of action have also been characterized.

Accordingly, one embodiment of the present invention is a compound having the formula I:

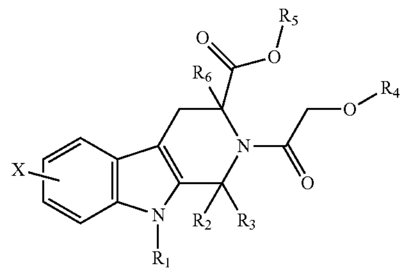

wherein $R_1$, $R_2$, $R_3$, and $R_6$ are independently selected from H, $C_{1-8}$alkyl, $C_{1-8}$alkoxy, $C_{1-8}$aralkyl, 3- to 8-membered carbocyclic, 3- to 8-membered heterocyclic, 3- to 8-membered aryl, or 3- to 8-membered heteroaryl, acyl, alkylsulfonyl, and arylsulfonyl, wherein each alkyl, alkoxy, aralkyl, carbocyclic, heterocyclic, aryl, heteroaryl, acyl, alkylsulfonyl, and arylsulfonyl is optionally substituted with at least one substituent;

$R_4$ and $R_5$ are independently selected from H, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

$R^7$ is selected from H, $C_{1-8}$alkyl, carbocycle, aryl, heteroaryl, heterocycle, alkylaryl, alkylheteroaryl, and alkylheterocycle, wherein each alkyl, carbocycle, aryl, heteroaryl, heterocycle, alkylaryl, alkylheteroaryl, and alkylheterocycle may be optionally substituted with at least one substituent;

$R^8$ is selected from H, $C_{1-8}$alkyl, $C_{1-8}$alkenyl, $C_{1-8}$alkynyl, aryl, carbocycle, heteroaryl, heterocycle, alkylaryl, alkylheteroaryl, alkylheterocycle, and heteroaromatic, wherein each alkyl, alkenyl, alkynyl, aryl, carbocycle, heteroaryl, heterocycle, alkylaryl, alkylheteroaryl, alkylheterocycle, and heteroaromatic may be optionally substituted with at least one substituent; and X is 0-4 substituents on the ring to which it is attached, or an enantiomer, optical isomer, diastereomer, N-oxide, crystalline form, hydrate, or pharmaceutically acceptable salt thereof.

An additional embodiment of the present invention is a compound of the formula:

(1)

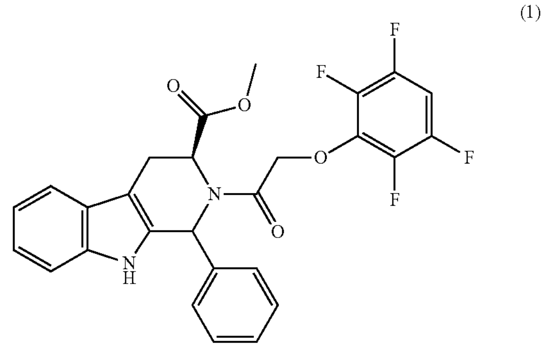 [SMILES: COC(=O)[C@@H]1Cc2c([nH]c3ccccc23)C(c2ccccc2)N1C(=O)COc1c(F)c(F)cc(F)c1F]

or an enantiomer, optical isomer, diastereomer, N-oxide, crystalline form, hydrate, or pharmaceutically acceptable salt thereof.

Another embodiment of the present invention is a compound of the formula:

(2)

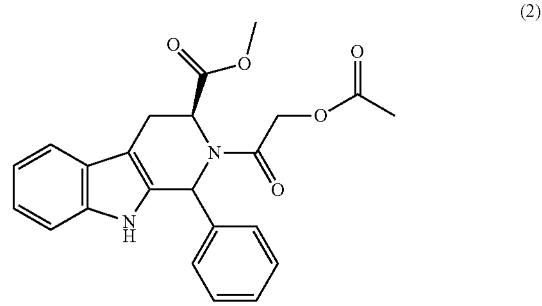 [SMILES: COC(=O)[C@@H]1Cc2c([nH]c3ccccc23)C(c2ccccc2)N1C(=O)COC(C)=O]

or an enantiomer, optical isomer; diastereomer, N-oxide, crystalline form, hydrate, or pharmaceutically acceptable salt thereof.

Another embodiment of the present invention is a pharmaceutical composition that includes a pharmaceutically acceptable carrier and one or more compounds of the present invention, including for example compounds of formula I, Ia, and Ib, as well as, compounds 1 and 2.

A further embodiment of the present invention is a composition containing a pharmaceutically acceptable carrier and a RAS-selective lethal compound of formula II:

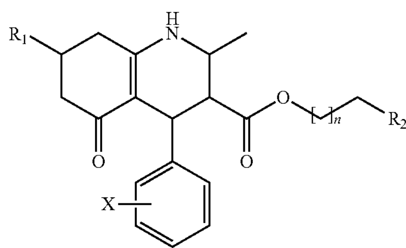

wherein $R_1$ and $R_2$ are independently selected from H, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^3R^4$, $OC(R^3)_2COOH$, $SC(R^3)_2COOH$, $NHCHR^3COOH$, $COR^4$, $CO_2R^4$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^3R^4$, $OC(R^3)_2COOH$, $SC(R^3)_2COOH$, $NHCHR^3COOH$, $COR^4$, $CO_2R^4$, sulfate, sulfonamide, sulfoxide, sulfonate, sulfone, thioalkyl, thioester, and thioether is optionally substituted with at least one substituent;

$R^3$ is selected from H, $C_{1-8}$alkyl, carbocycle, aryl, heteroaryl, heterocycle, alkylaryl, alkylheteroaryl, and alkylheterocycle, wherein each alkyl, carbocycle, aryl, heteroaryl, heterocycle, alkylaryl, alkylheteroaryl, and alkylheterocycle may be optionally substituted with at least one substituent;

$R^4$ is selected from H, $C_{1-8}$alkyl, $C_{1-8}$alkynyl, aryl, carbocycle, heteroaryl, heterocycle, alkylaryl, alkylheteroaryl, alkylheterocycle, and heteroaromatic, wherein each alkyl, alkenyl, alkynyl, aryl, carbocycle, heteroaryl, heterocycle, alkylaryl, alkylheteroaryl, alkylheterocycle, and heteroaromatic may be optionally substituted with at least one substituent;

X is selected from halo and $C_{1-8}$ alkyl; and n is 0-8, or an enantiomer, optical isomer, diastereomer, N-oxide, crystalline form, hydrate, or pharmaceutically acceptable salt thereof.

An additional embodiment of the present invention is a composition containing a pharmaceutically acceptable carrier and a RAS-selective lethal compound of formula III:

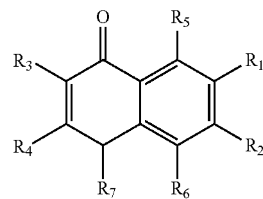

wherein $R_1$ is selected from H, halo, $C_{1-8}$ alkyl, $C_{1-8}$alkylene, 1-hydroxyl-β-D-glucose optionally substituted with from 1-4 acetates and/or 1-hydroxyl-β-D-glucose tetraacetate, and 1-thionyl-β-D-glucose optionally substituted with from 1-4 acetates, O, and/or $C_{1-8}$ alkoxy;

$R_2$ is selected from H, halo, $C_{1-8}$ alkyl, and 1-thionyl-β-D-glucose substituted with from 1-4 acetates, O, or $C_{1-8}$ alkoxy;

$R_3$ and $R_4$ are independently selected from H, halo, $C_{1-8}$ alkyl, $C_{1-8}$ alkoxy, 1-hydroxyl-β-D-glucose optionally substituted with from 1-4 acetates and/or 1-hydroxyl-β-D-glucose tetraacetate, and 1-thionyl-β-D-glucose optionally substituted with from 1-4 acetates;

$R_5$ and $R_6$ are independently selected from H, OH, and acetate esters; and $R_7$ is selected from H or carbonyl, or an enantiomer, optical isomer, diastereomer, N-oxide, crystalline form, hydrate, or pharmaceutically acceptable salt thereof.

Another embodiment of the present invention is a composition containing a pharmaceutically acceptable carrier and a RAS-selective lethal compound according to formula IV:

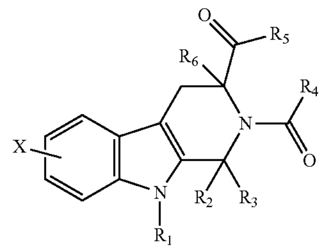

wherein $R_1$, $R_2$, $R_3$, $R_4$, $R_5$, and $R_6$ are independently selected from H, Halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^S$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

$R^7$ is selected from H, $C_{1-8}$alkyl, carbocycle, aryl, heteroaryl, heterocycle, alkylaryl, alkylheteroaryl, and alkylheterocycle, wherein each alkyl, carbocycle, aryl, heteroaryl, heterocycle, alkylaryl, alkylheteroaryl, and alkylheterocycle may be optionally substituted with at least one substituent;

$R^8$ is selected from H, $C_{1-8}$alkyl, $C_{1-8}$alkenyl, $C_{1-8}$alkynyl, aryl, carbocycle, heteroaryl, heterocycle, alkylaryl, alkylheteroaryl, alkylheterocycle, and heteroaromatic, wherein each alkyl, alkenyl, alkynyl, aryl, carbocycle, heteroaryl, heterocycle, alkylaryl, alkylheteroaryl, alkylheterocycle, and heteroaromatic may be optionally substituted with at least one substituent; and X is 0-4 substituents on the ring to which it is attached, or an enantiomer, optical isomer, diastereomer, N-oxide, crystalline form, hydrate, or pharmaceutically acceptable salt thereof.

A further embodiment of the present invention is a composition containing a pharmaceutically acceptable carrier and a RAS-selective lethal compound according to formula V:

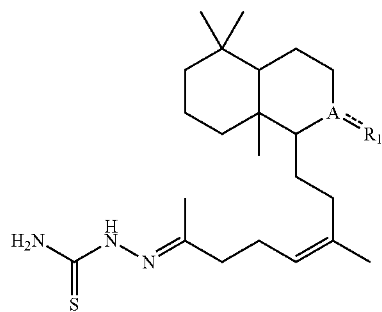

wherein $R_1$ is independently selected from H, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^2R^3$, $OC(R^2)_2COOH$, $SC(R^2)_2COOH$, $NHCHR^2COOH$, $COR^3$, $CO_2R^3$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^2R^3$, $OC(R^2)_2COOH$, $SC(R^2)_2COOH$, $NHCHR^2COOH$, $COR^3$, $CO_2R^3$, sulfate, sulfonamide, sulfoxide, sulfonate, sulfone, thioalkyl, thioester, and thioether is optionally substituted with at least one substituent;

$R^2$ is selected from H, $C_{1-8}$alkyl, carbocycle, aryl, heteroaryl, heterocycle, alkylaryl, alkylheteroaryl, and alkylheterocycle, wherein each alkyl, carbocycle, aryl, heteroaryl, heterocycle, alkylaryl, alkylheteroaryl, and alkylheterocycle may be optionally substituted with at least one substituent;

$R^3$ is selected from H, $C_{1-8}$alkyl, $C_{1-8}$alkenyl, $C_{1-8}$alkynyl, aryl, carbocycle, heteroaryl, heterocycle, alkylaryl, alkylheteroaryl, alkylheterocycle, and heteroaromatic, wherein each alkyl, alkenyl, alkynyl, aryl, carbocycle, heteroaryl, heterocycle, alkylaryl, alkylheteroaryl, alkylheterocycle, and heteroaromatic may be optionally substituted with at least one substituent; and A is C, N, or S, or an enantiomer, optical isomer, diastereomer, N-oxide, crystalline form, hydrate, or pharmaceutically acceptable salt thereof.

An embodiment of the present invention is a compound having the formula VI:

(VI)

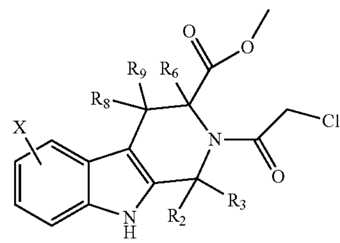

wherein $R_2$ and $R_3$ are independently selected from H, methyl, methyl benzoate, propargyl, and phenyl, wherein at least one of $R_2$ and $R_3$ is other than H;

$R_6$, $R_8$, and $R_9$ are independently selected from H, halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent; and X is 0-4 substituents on the ring to which it is attached; or an enantiomer, optical isomer, diastereomer, N-oxide, crystalline form, hydrate, or pharmaceutically acceptable salt thereof.

In another embodiment of the present invention, a compound is provided having the formula VII:

(VII)

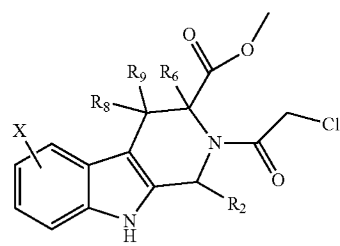

wherein $R_2$ is selected from halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, thioether, wherein each alkyl, alkoxy, carbocyclic, heterocyclic, aryl, heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

$R_6$, $R_8$, and $R_9$ are independently selected from H, halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent; and X is 0-4 substituents on the ring to which it is attached, or an enantiomer, optical isomer, diastereomer, N-oxide, crystalline form, hydrate, or pharmaceutically acceptable salt thereof.

A further embodiment of the present invention is a compound having the formula VIII:

(VIII)

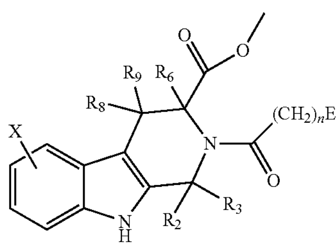

wherein $R_2$ and $R_3$ are independently selected from H, halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, thioether, wherein each alkyl, alkoxy, carbocyclic, heterocyclic, aryl, heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, thioether and is optionally substituted with at least one substituent, and wherein at least one of $R_2$ and $R_3$ is other than H;

$R_6$, $R_8$, and $R_9$ are independently selected from H, halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

X is 0-4 substituents on the ring to which it is attached;

n is 0 or 1;

E is an electrophilic group that has a lower electrophilicity index value than does Cl; or an enantiomer, optical isomer, diastereomer, N-oxide, crystalline form, hydrate, or pharmaceutically acceptable salt thereof.

In a further embodiment of the present invention is a compound according to formula IX:

(IX)

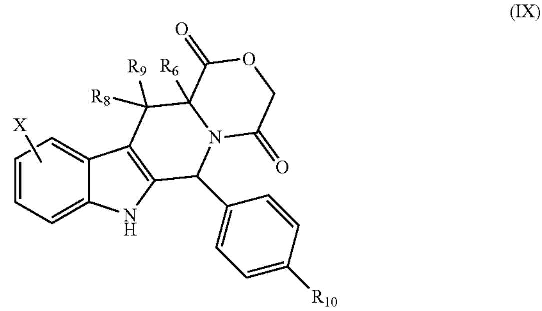

wherein $R_6$, $R_8$, and $R_9$ are independently selected from H, halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

X is 0-4 substituents on the ring to which it is attached; and $R_{10}$ is selected from the group consisting of a $C_{1-8}$ ester and an acid, which ester or acid is hydrolyzable in vivo; or an enantiomer, optical isomer, diastereomer, N-oxide, crystalline form, hydrate, or pharmaceutically acceptable salt thereof.

Compositions are provided comprising a pharmaceutical carrier and a compound selected from the group consisting of compounds of formula VI, compounds of formula VII, compounds of formula VIII, and compounds of formula IX.

Methods of treating a condition in a mammal are provided, comprising administering to the mammal a therapeutically effective amount of a compound selected from the group consisting of compounds of formula VI, compounds of formula VII, compounds of formula VIII, and compounds of formula IX.

Surprisingly, it has been found that only specific stereoisomers of certain of the compounds of the present invention are biologically active, e.g., exhibit selective lethality toward tumor cells. Accordingly, as set forth in more detail below, such stereoisomers are also part of the present invention.

For example, another embodiment of the present invention is a compound having the formula X:

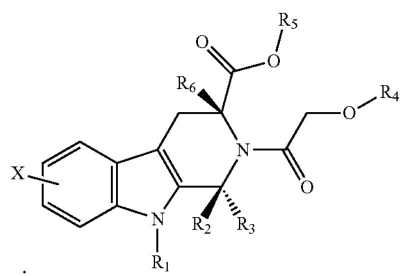

wherein $R_1$, $R_2$, $R_3$, and $R_6$ are independently selected from H, $C_{1-8}$alkyl, $C_{1-8}$alkoxy, $C_{1-8}$aralkyl, 3- to 8-membered carbocyclic, 3- to 8-membered heterocyclic, 3- to 8-membered aryl, or 3- to 8-membered heteroaryl, acyl, alkylsulfonyl, and arylsulfonyl, wherein each alkyl, alkoxy, aralkyl, carbocyclic, heterocyclic, aryl, heteroaryl, acyl, alkylsulfonyl, and arylsulfonyl is optionally substituted with at least one substituent;

$R_4$ and $R_5$ are independently selected from H, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^S$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

$R^7$ is selected from H, $C_{1-8}$alkyl, carbocycle, aryl, heteroaryl, heterocycle, alkylaryl, alkylheteroaryl, and alkylheterocycle, wherein each alkyl, carbocycle, aryl, heteroaryl, heterocycle, alkylaryl, alkylheteroaryl, and alkylheterocycle may be optionally substituted with at least one substituent;

$R^8$ is selected from H, $C_{1-8}$alkyl, $C_{1-8}$alkenyl, $C_{1-8}$alkynyl, aryl, carbocycle, heteroaryl, heterocycle, alkylaryl, alkylheteroaryl, alkylheterocycle, and heteroaromatic, wherein each alkyl, alkenyl, alkynyl, aryl, carbocycle, heteroaryl, heterocycle, alkylaryl, alkylheteroaryl, alkylheterocycle, and heteroaromatic may be optionally substituted with at least one substituent; and X is 0-4 substituents on the ring to which it is attached, wherein $R_2$ and $R_3$ are not the same group, or a N-oxide, crystalline form, hydrate, or pharmaceutically acceptable salt thereof.

In a further embodiment of the invention, a compound is selected from the group consisting of:

A

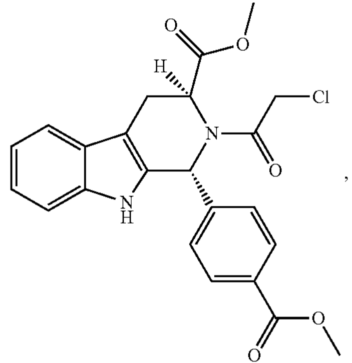

, (1R,3S) - Compound 27

-continued

B

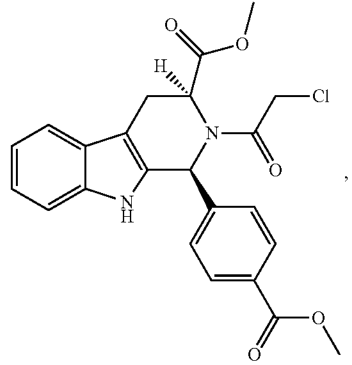

, (1S,3S) - Compound 27

C

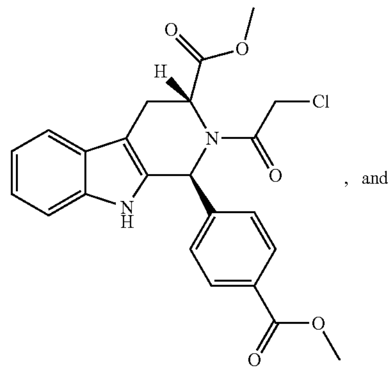

, and (1S,3R) - Compound 27

D

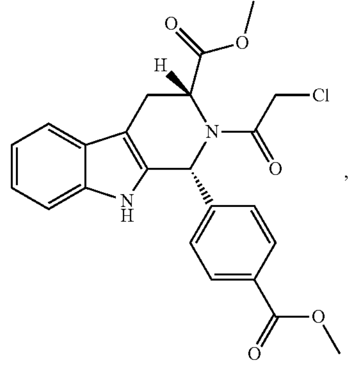

, (1R,3R) - Compound 27 and mixtures thereof, or a N-oxide, crystalline form, hydrate, or pharmaceutically acceptable salt thereof.

A preferable embodiment of the present invention is an enantiomerically pure compound having the structure:

C

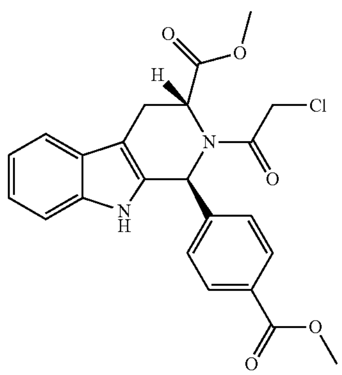

(1S,3R) - Compound 27 or a N-oxide, crystalline form, hydrate, or pharmaceutically acceptable salt thereof.

One preferred compound of formula X is:

(X1)

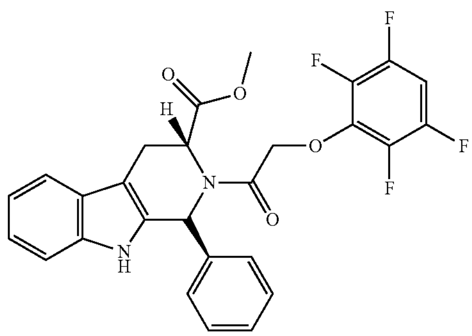

or a N-oxide, crystalline form, hydrate, or pharmaceutically acceptable salt thereof.

Another preferred compound of formula X is:

(X2)

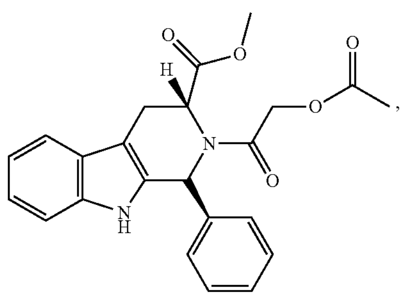

wherein the phenyl ring is optionally substituted with methoxycarbonyl, or a N-oxide, crystalline form, hydrate, or pharmaceutically acceptable salt thereof.

Another embodiment of the present invention is a composition comprising a pharmaceutically acceptable carrier and a RAS-selective lethal compound according to formula XI:

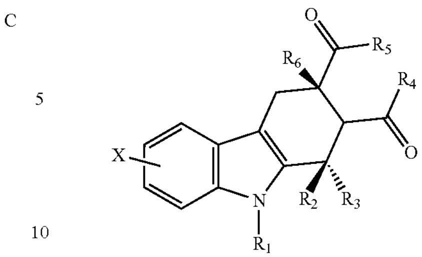

wherein $R_1$, $R_2$, $R_3$, $R_4$, $R_5$, and $R_6$ are independently selected from H, Halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

$R^7$ is selected from H, $C_{1-8}$alkyl, carbocycle, aryl, heteroaryl, heterocycle, alkylaryl, alkylheteroaryl, and alkylheterocycle, wherein each alkyl, carbocycle, aryl, heteroaryl, heterocycle, alkylaryl, alkylheteroaryl, and alkylheterocycle may be optionally substituted with at least one substituent;

$R^8$ is selected from H, $C_{1-8}$alkyl, $C_{1-8}$alkenyl, $C_{1-8}$alkynyl, aryl, carbocycle, heteroaryl, heterocycle, alkylaryl, alkylheteroaryl, alkylheterocycle, and heteroaromatic, wherein each alkyl, alkenyl, alkynyl, aryl, carbocycle, heteroaryl, heterocycle, alkylaryl, alkylheteroaryl, alkylheterocycle, and heteroaromatic may be optionally substituted with at least one substituent; and X is 0-4 substituents on the ring to which it is attached, wherein $R_2$ and $R_3$ are not the same group, or a N-oxide, crystalline form, hydrate, or pharmaceutically acceptable salt thereof.

Another embodiment of the present invention is a compound having the formula XII:

(XII)

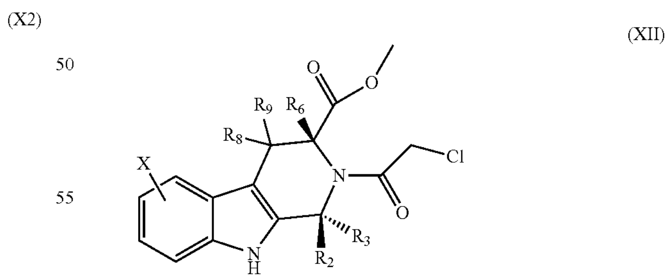

wherein $R_2$ and $R_3$ are independently selected from H, methyl, methyl benzoate, propargyl, and phenyl, wherein at least one of $R_2$ and $R_3$ is other than H;

$R_6$, $R_8$, and $R_9$ are independently selected from H, halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent; and X is 0-4 substituents on the ring to which it is attached;

wherein $R_2$ and $R_3$ are not the same group, or a N-oxide, crystalline form, hydrate, or pharmaceutically acceptable salt thereof.

In another embodiment of the present invention, a compound is provided having the formula XIII:

(XIII)

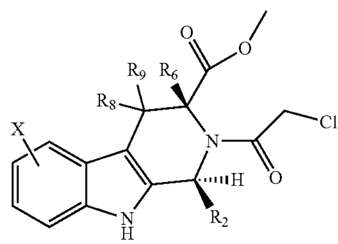

wherein $R_2$ is selected from halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, thioether, wherein each alkyl, alkoxy, carbocyclic, heterocyclic, aryl, heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

$R_6$, $R_8$, and $R_9$ are independently selected from H, halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent; and X is 0-4 substituents on the ring to which it is attached, or a N-oxide, crystalline form, hydrate, or pharmaceutically acceptable salt thereof.

A further embodiment of the present invention is a compound having the formula XIV:

(XIV)

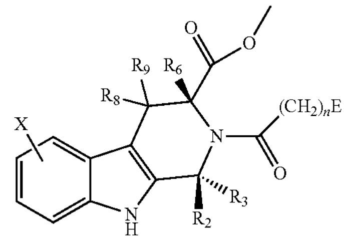

wherein $R_2$ and $R_3$ are independently selected from H, halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, thioether, wherein each alkyl, alkoxy, carbocyclic, heterocyclic, aryl, heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, thioether and is optionally substituted with at least one substituent, and wherein at least one of $R_2$ and $R_3$ is other than H;

$R_6$, $R_8$, and $R_9$ are independently selected from H, halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

X is 0-4 substituents on the ring to which it is attached;

n is 0 or 1;

E is an electrophilic group that has a lower electrophilicity index value than does Cl;

wherein $R_2$ and $R_3$ are not the same group, or a N-oxide, crystalline form, hydrate, or pharmaceutically acceptable salt thereof.

A further embodiment of the present invention is a compound according to formula XV:

(XV)

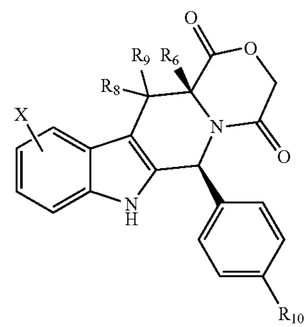

wherein $R_6$, $R_8$, and $R_9$ are independently selected from H, halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

X is 0-4 substituents on the ring to which it is attached; and $R_{10}$ is selected from the group consisting of a $C_{1-8}$ ester and an acid, which ester or acid is hydrolyzable in vivo; or a N-oxide, crystalline form, hydrate, or pharmaceutically acceptable salt thereof.

In another aspect of the present invention, a compound is provided which is selected from the group consisting of:

E

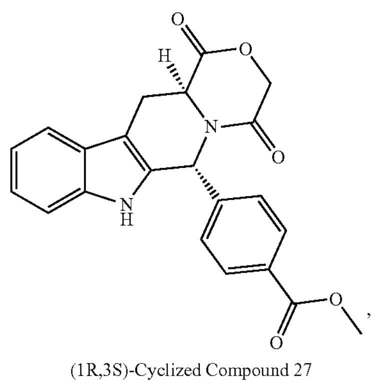

(1R,3S)-Cyclized Compound 27

F

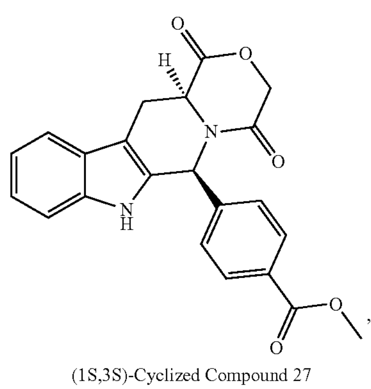

(1S,3S)-Cyclized Compound 27

-continued

G

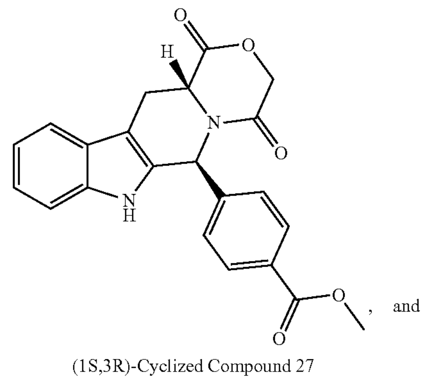

(1S,3R)-Cyclized Compound 27 and

H

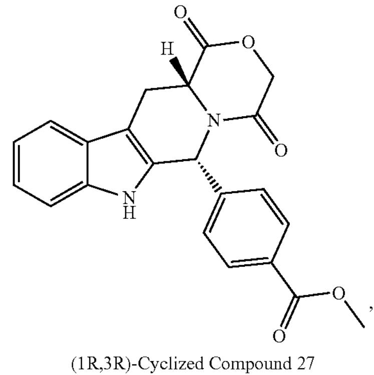

(1R,3R)-Cyclized Compound 27 and mixtures thereof, or a N-oxide, crystalline form, hydrate, or pharmaceutically acceptable salt thereof.

A further preferred embodiment is an enantiomerically pure compound having the structure:

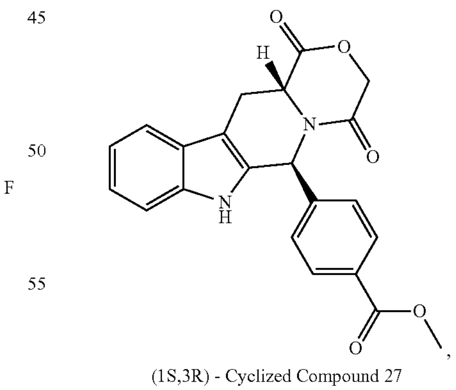

(1S,3R) - Cyclized Compound 27 or a N-oxide, crystalline form, hydrate, or pharmaceutically acceptable salt thereof.

A preferred embodiment of the present invention is a pharmaceutical composition comprising a pharmaceutically acceptable carrier and an enantiomerically pure RAS-selective lethal compound having the structure:

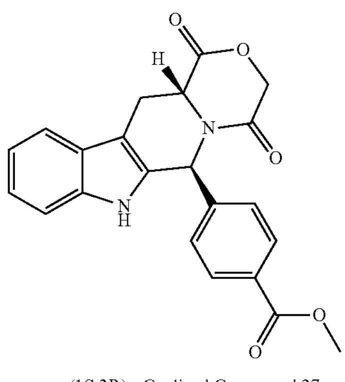

(1S,3R) - Cyclized Compound 27 or a N-oxide, crystalline form, hydrate, or pharmaceutically acceptable salt thereof.

In one aspect of this embodiment, the compound according to formula XV has an optional substituent, which is independently selected from the group consisting of cyano, oxo, nitro, acyl, acylamino, halogen, hydroxy, amino acid, amine, amide, carbamate, ester, ether, carboxylic acid, thio, thioalkyl, thioester, thioether, $C_{1-8}$alkyl, $C_{1-8}$alkene, $C_{1-8}$alkyne, $C_{1-8}$alkoxy, $C_{1-8}$aralkyl, 3- to 8-membered carbocyclic, 3- to 8-membered heterocyclic, 3- to 8-membered aryl, or 3- to 8-membered heteroaryl, sulfate, sulfonamide, sulfoxide, sulfonate, sulfone, alkylsulfonyl, arylsulfonyl, $C_{1-8}$alkoxy alkyne, $C_{1-8}$ alkyl alkyne, and $C_{1-8}$ alkyne acetate.

Other embodiments of the present invention include methods of treating a condition in a mammal. These methods include the step of administering to the mammal a therapeutically effective amount of a compound or composition as described above. In one preferred embodiment, the condition is cancer. In another preferred embodiment, the condition is characterized by cells with enhanced RAS signaling activity.

An additional embodiment of the present invention is a method for identifying RAS-selectively lethal compounds. This method includes the steps of:

(a) determining a % GI of candidate compounds in a BJ cell system comprising a plurality of isogenic cell lines at least one of which is non-tumorigenic and at least one of which is tumorigenic, wherein a % GI of at least 90% at a concentration of about 10 μM or less in at least one tumorigenic BJ cell line is considered to be a lethal compound, (b) determining a potency profile, in the BJ cell system, of the candidate compounds from (a) determined to be lethal, wherein those candidate compounds having at least a 4-fold differential potency between non-tumorigenic and tumorigenic cell lines in the BJ cell system are considered to be selective, and (c) identifying the selective candidate compounds from (b), which have a similar potency profile for each of the tumorigenic cell lines in the BJ cell system, wherein those candidate compounds having a similar potency profile are considered to be RAS-selectively lethal compounds.

BRIEF DESCRIPTION OF THE DRAWINGS

The file of this patent or patent application contains at least one drawing executed in color. Copies of this patent or patent application with color drawing(s) will be provided by the United States Patent and Trademark Office upon request and payment of the necessary fee.

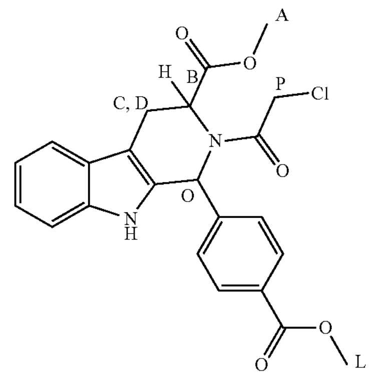

Figure 50:
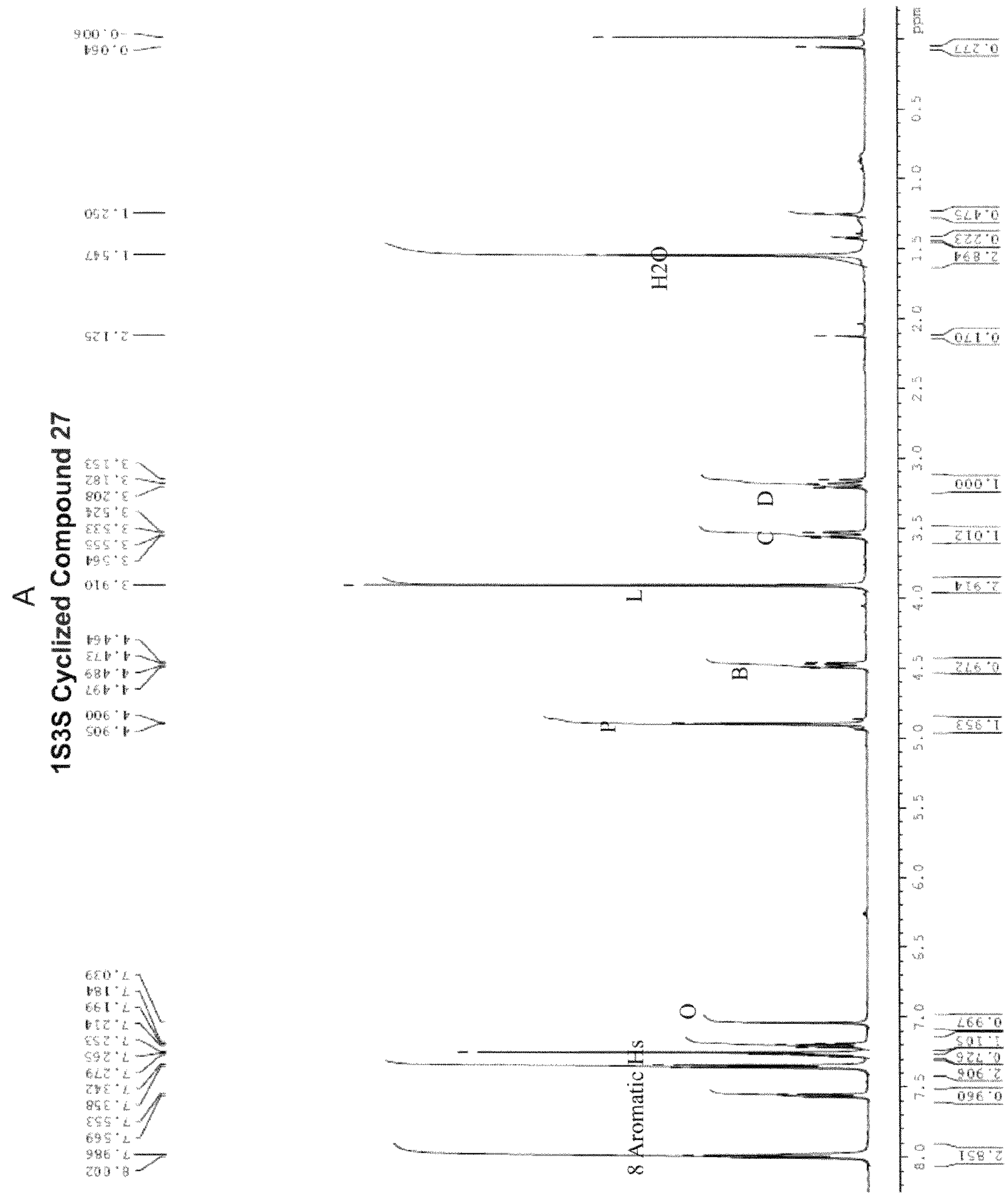

FIG. 50 shows NMR data for two of the stereoisomeric conformations of Cyclized Compound 27. NMR data is shown for 1S,3S Cyclized Compound 27 (panel A) and for 1R,3S Cyclized Compound 27 (panel B). The NMR data shows that these stereoisomers of Cyclized Compound 27 were each enantiomerically pure. The legend for the NMR data is as follows, stereochemistry not shown.

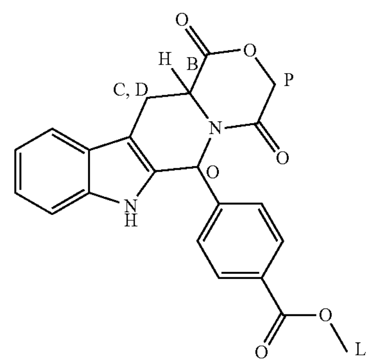

Figure 51:
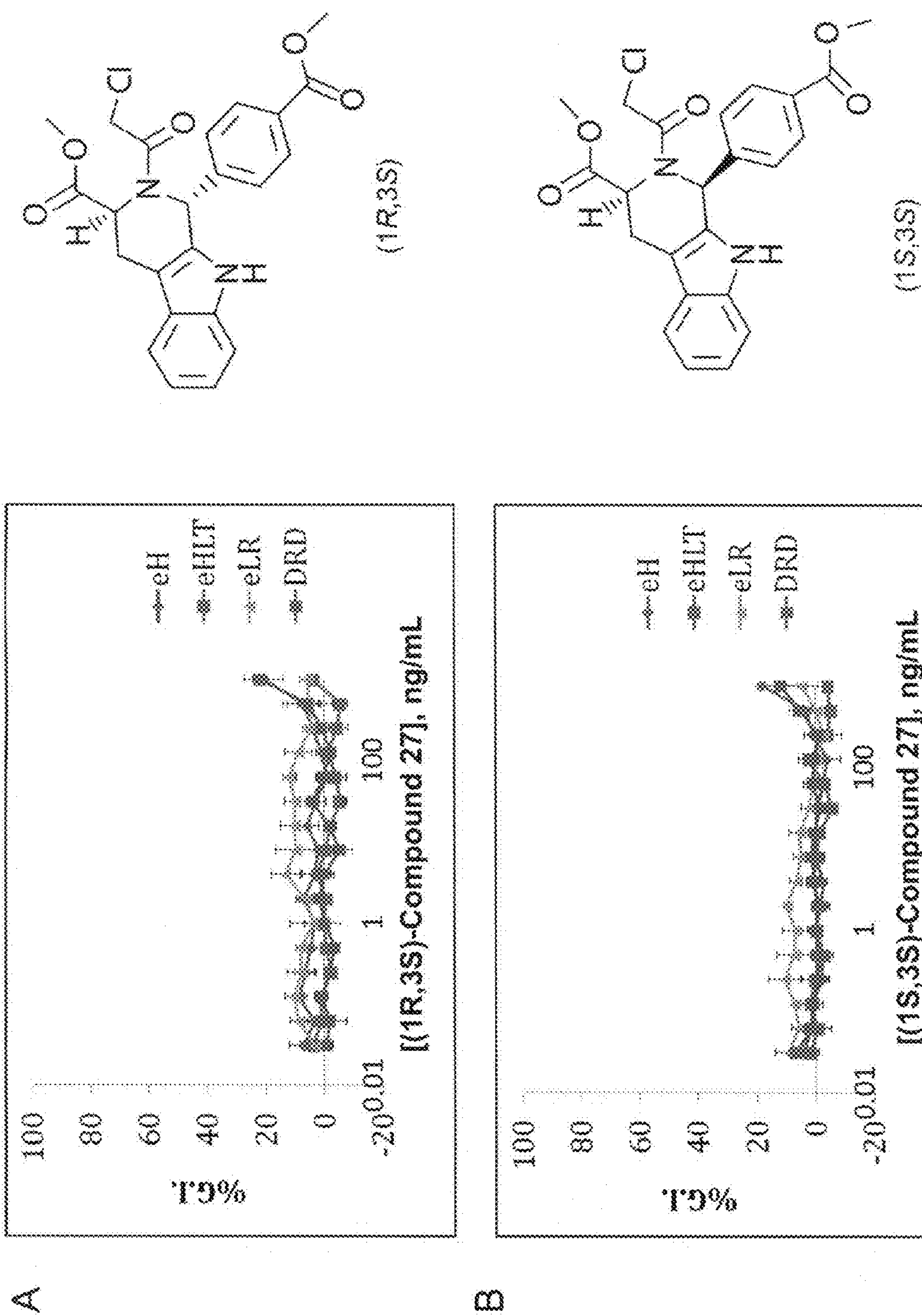

FIG. 51 shows percent cell growth inhibition for the four stereoisomeric conformations of Compound 27, namely (1R,3S) Compound 27 (panel A), (1S,3S) Compound 27 (panel B), 1S,3R Compound 27 (panel C), and 1R,3R Compound 27 (panel D), in BJeH-hTERT (eH), BJeHLT-hTERT/LT/ST (eHLT), BJeLR-hTERT/LT/ST/HRASG12V (eLR), and BJDRD-hTERT/p53DD/CDK4/cyclinD1/ST/HRASG12V (DRD) cells. Only the 1S,3R Compound 27 stereoisomer demonstrates selective lethality towards BJ tumor cell lines containing mutant HRAS versus isogenic cell lines lacking oncogenic HRAS.

DETAILED DESCRIPTION OF THE INVENTION

Target-based, in-vitro screening has been successful for developing cancer drugs as exemplified by Gleevec or Sorafenib. Synthetic lethal screening using small molecules is a complementary approach that involves testing compounds for selective lethality in tumor cells harboring a specific oncogene. Synthetic lethal screening using small molecules can identify cancer drug leads with a potentially high therapeutic index. Oncogenic RAS ($HRAS^{G12V}$) is used as a specific mutation in synthetic lethal screening and identified four compounds whose activity depends on oncogenic-RAS-signaling. Mechanistic studies on these compounds suggest that oncogenic-RAS-signaling in tumor cells enriches their pool of iron, which is an important factor for enabling their selective lethality. Further optimization of these compounds may allow for the development of anticancer therapeutic agents with a degree of genotype selectivity.

To circumvent concerns with the target-based approach in the RAS field, the complementary approach of synthetic lethal screening with small molecules was employed to identify those small molecules that display synthetic lethality with oncogenic RAS. 47,725 small molecules were tested in a series of isogenic cell lines. This yielded four compounds with synthetic lethal interactions with oncogenic RAS ($HRAS^{G12V}$). Testing these four hit compounds in multiple cell lines revealed proliferation-rate independent activity, but increased lethality towards tumor cells with oncogenic RAS. Counter-screening with chemical inhibitors to identify suppressors of hit-compound-induced cell death revealed some insights into their mechanism of action, such as MAPK/ERK kinase (MEK) dependency and iron dependency. Cells transformed with $HRAS^{G12V}$ have increased iron content relative to their normal cell counterparts through up-regulation of the transferrin receptor 1.

The four hit compounds have synthetic lethal interactions with oncogenic RAS ($HRAS^{G12V}$), which suggests that the activity of those compounds depends on $HRAS^{G12V}$ signaling. Traditional chemotherapeutic reagents have shown high potency in cancer cell killing, but they frequently target proteins directly involved with DNA replication or metabolism, which makes them proliferation-rate dependent, with a modest therapeutic index. Considering this, lethal compounds with oncogenic-signal-dependent activity have drawn interest as alternative chemotherapeutic reagents.

Such iron-proliferation-dependent compounds were identified by incorporating the DRD cell line into the counter-screening process. Only hit compounds showing more potency in DRD cells than that in BJ-TERT/LT/ST cells were chosen for further study. Hit compounds that have almost the same growth inhibitory potency between BJ-TERT/LT/ST/$RAS^{V12}$ cells and DRD cells (Erastin, Compound 3, and Compound 27) were shown to require activation of MEK, a critical downstream effector of oncogenic RAS. Hit compounds that have somewhat lower potency in DRD cells than in BJ-TERT/LT/ST/$RAS^{V12}$ cells (Compound 6 and Compound 3) showed no dependency on MEK activation. Even with MEK-independent lethal compounds, the contribution of $HRAS^{G12V}$ in increasing sensitivity was observed suggesting that RAS downstream signals other than the RAF-MEK-MAPK or the PI3K pathway are responsible for the observed increase in sensitivity.

One interesting property of these compounds is their iron-dependent mechanism of action. The iron dependency of these compounds is evident because different iron chelators are able to suppress the lethality induced by these compounds. Many cancer cells are reported to have an enriched iron pool (Shterman et al., 1991). Cancer patients have higher levels of iron than normal individuals (Stevens et al., 1988). The BJ cell system recaptured this relationship between iron and cancer, as BJ-TERT/LT/ST/$RAS^{V12}$ cells have more iron than their isogenic, non-tumorigenic counterparts. The greater iron content in BJ-TERT/LT/ST/$RAS^{V12}$ cells, together with the iron-dependent action of these hit compounds, suggests that the increased iron pool within cancer cells might be a target for inducing cancer-cell-specific lethality. Indeed, this possibility has been explored by testing iron chelators for anticancer properties (Kalinowski and Richardson, 2005). A number of iron chelators are reported to have good potency in inhibiting cancer cell growth. For example, bleomycin, a key component of standard chemotherapeutic regimens for treating patient with germ-cell tumors (Kondagunta and Motzer, 2006), is known to oxidatively damage DNA through its complex with iron (Dorr, 1992). Another iron chelator, Triapine, entered Phase II clinical trials in a combination therapy with cisplatin to treat ovarian cancer (Low and Schoenfeldt, 2005).

There are two suggested mechanisms of lethality caused by such iron chelators. One is that the iron chelators deplete iron from critical biomolecules mediating the mitochondrial respiratory chain (iron-sulfur proteins) and DNA synthesis (ribonucleotide reductase), which leads to loss of cell viability (Cazzola et al., 1990; Green et al., 2001). The other is that the iron chelators generate reactive oxygen species by facilitating Fenton chemistry, which damages biological molecules, such as nucleic acids, lipids, and proteins (Halliwell and Gutteridge, 1990).

The compounds of the present invention do not deplete the cellular iron pool. Therefore, it is unlikely that their lethality stems from a similar mechanism of action of known iron chelators. Instead, binding to target proteins may elicit iron-mediated toxic responses involving either reactive oxygen species generation (in case of Erastin and Compound 3) or not (in case of Compound 36 and Compound 27). For example, the lethality of Erastin and Compound 3 was inhibited by both antioxidants and iron chelators. It is possible that binding to target proteins causes a change in cellular redox potential or a local redistribution of the iron pool to initiate Fenton chemistry. Such an indirect role of iron in anticancer drug-induced toxicity was suggested in a report explaining iron-dependent lethality of anthracyclines (Kwok and Richardson, 2003). Alternatively, binding to a target can hyper-activate an oxidase complex, such as NADPH oxidase, to induce a so-called "respiratory burst." The NADPH oxidase complex is found to be up-regulated upon PDGF treatment exerting multiple effects on carcinogenic processes (Arbiser et al., 2002). The NADPH oxidase complex is also reported to be activated by some anticancer drugs, such as paclitaxel (Alexandre et al., 2006) or arsenic acid (Chou et al., 2004). The NADPH oxidase complex is essentially an electron transport chain having iron-containing heme molecules (Cross and Segal, 2004). Therefore, treatment with iron chelators removes iron from the hemes, preventing the onset of a "respiratory burst" by a compound.

The increased iron concentration in BJ-TERT/LT/ST/$RAS^{V12}$ cells compared to their isogenic counter parts raises the possibility that oncogenic RAS signaling alters iron metabolism to augment the cellular labile iron pool. Oncogene-induced upregulation of cellular iron has been reported for c-myc and E1A (Tsuji et al., 1995; Wu et al., 1999). Oncogenic signals from c-myc or E1A downregulate expression of the heavy subunit of ferritin (H-ferritin), which stores labile iron. Because ferritin functions as an iron buffer, downregulation of ferritin by oncogenic signals results in an increased intracellular iron pool. Consequently, proliferation-driving enzymes, such as ribonucleotide reductase, are replenished with sufficient iron.

In contrast, there are few established connections between oncogenic RAS and iron metabolism. The existence of a mitogen-responsive element in the 5' untranslated region (UTR) of TfR1 mRNA has been reported, suggesting that RAS-RAF-MEK-MAPK signaling may upregulate TfR1 level (Casey et al., 1988; Ouyang et al., 1993). However, the data herein suggests that oncogenic-RAS-signaling increases the cellular iron pool through both TfR1-dependent and—independent pathways. First, the expression level of TfR1 in BJ-TERT, BJ-TERT/LT/ST, and BJ-TERT/LT/ST/$RAS^{V12}$ was gradually increased, while the total amount of cellular iron abruptly increased in BJ-TERT/LT/ST/RAS$^{V12}$ cells, implying that the status of iron-regulatory factors other than TfR1 was changed to accommodate more iron. Second, diminishing TfR1 protein levels by shRNAs resulted in only partial recovery of HT1080 cell death compared to the result with iron chelators, which suggests that a TfR1-independent labile iron pool that is regulated by oncogenic-RAS-signaling contributed to the increase in cellular iron and compound sensitivity. Efforts to identify target proteins of these compounds may ultimately reveal novel proteins in iron metabolism regulation; some such proteins are likely to be connected to the RAS signaling pathway.

In summary, four novel lethal classes of compounds with cancer-cell specificity have been identified using isogonics-engineered cell lines and high-throughput cell-based screening. While many currently used chemotherapeutic reagents are cytostatic and proliferation-dependent in vitro, the compounds of the present invention are cytotoxic and not proliferation-dependent. Preliminary mechanism of action studies with these compounds revealed that they have interesting features, such as oncogenic-RAS-signal-dependent action and iron-dependent activity. These results suggest a connection between oncogenic RAS and iron metabolism, and support the notion that the cellular iron pool is enriched by oncogenic signals and can be a target for developing anti-cancer drugs with a favorable therapeutic index.

In view of the foregoing, one embodiment of the present invention is a compound having the formula I:

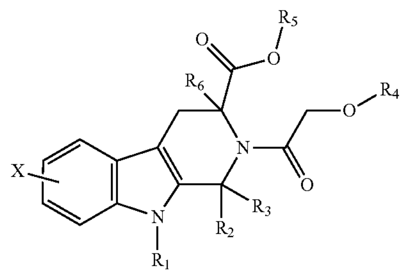

wherein $R_1$, $R_2$, $R_3$, and $R_6$ are independently selected from H, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, acyl, alkylsulfonyl, and arylsulfonyl, wherein each alkyl, alkoxy, aralkyl, carbocyclic, heterocyclic, aryl, heteroaryl, acyl, alkylsulfonyl, and arylsulfonyl is optionally substituted with at least one substituent;

$R_4$ and $R_5$ are independently selected from H, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

$R^7$ is selected from H, $C_{1-8}$alkyl, carbocycle, aryl, heteroaryl, heterocycle, alkylaryl, alkylheteroaryl, and alkylheterocycle, wherein each alkyl, carbocycle, aryl, heteroaryl, heterocycle, alkylaryl, alkylheteroaryl, and alkylheterocycle may be optionally substituted with at least one substituent;

$R^8$ is selected from H, $C_{1-8}$alkyl, $C_{1-8}$alkynyl, aryl, carbocycle, heteroaryl, heterocycle, alkylaryl, alkylheteroaryl, alkylheterocycle, and heteroaromatic, wherein each alkyl, alkenyl, alkynyl, aryl, carbocycle, heteroaryl, heterocycle, alkylaryl, alkylheteroaryl, alkylheterocycle, and heteroaromatic may be optionally substituted with at least one substituent; and X is 0-4 substituents on the ring to which it is attached, or an enantiomer, optical isomer, diastereomer, N-oxide, crystalline form, hydrate, or pharmaceutically acceptable salt thereof.

All possible enantiomers, optical isomers, and diastomers of each formula and compound recited herein are part of the invention, whether they are explicitly shown or not. In the present invention, the isomeric forms of the compounds may be synthesized de novo. Alternatively, the specific desired isomeric form may be separated from, e.g., a racemic solution using conventional techniques, such as for example, gas chromatography. Moreover, the present application includes every possible combination of each R group, whether explicitly identified or not.

Preferably, in this embodiment, $R_2$ is a substituted aryl, a halo-substituted aryl, a tetra-substituted aryl, a tetra-fluoro substituted aryl, or a $C_{1-8}$ alkyl substituted with carbonyl.

In certain embodiments, X represents 0-4 substituents. As used herein, the term "substituent" means H, cyano, oxo, nitro, acyl, acylamino, halogen, hydroxy, amino acid, amine, amide, carbamate, ester, ether, carboxylic acid, thio, thioalkyl, thioester, thioether, $C_{1-8}$ alkyl, $C_{1-8}$alkoxy, $C_{1-8}$alkenyl, $C_{1-8}$aralkyl, 3- to 8-membered carbocyclic, 3- to 8-membered heterocyclic, 3- to 8-membered aryl, or 3- to 8-membered heteroaryl, sulfate, sulfonamide, sulfoxide, sulfonate, sulfone, alkylsulfonyl, and arylsulfonyl. In certain embodiments X represents one substituent, such as halogen or nitro, especially chloro. In other embodiments, X represents no substituents on the ring (i.e., all substituents are hydrogen atoms).

Preferred classes of compounds of formula I are defined by:

(Ia)

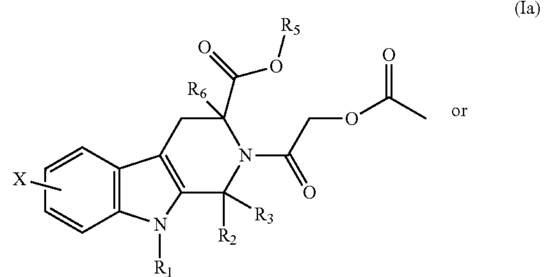

-continued (Ib)

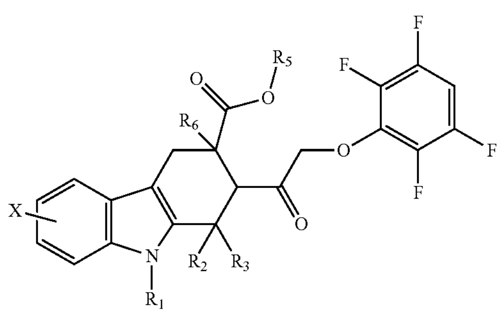

or an enantiomer, optical isomer, diastereomer, N-oxide, crystalline form, hydrate, or pharmaceutically acceptable salt thereof.

One preferred compound of formula I is:

(1)

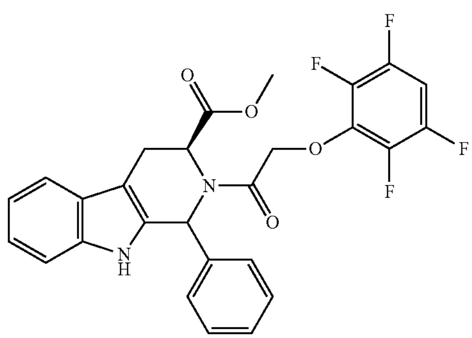

or an enantiomer, optical isomer, diastereomer, N-oxide, crystalline form, hydrate, or pharmaceutically acceptable salt thereof.

Another preferred compound of formula I is:

(2)

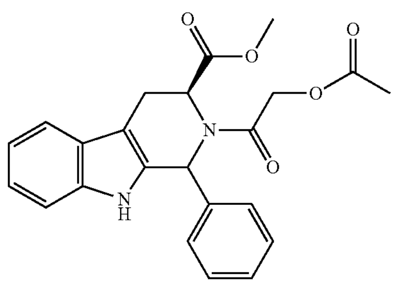

or an enantiomer, optical isomer, diastereomer, N-oxide, crystalline form, hydrate, or pharmaceutically acceptable salt thereof.

A further embodiment of the present invention is a composition containing a pharmaceutically acceptable carrier and a RAS-selective lethal compound of formula II:

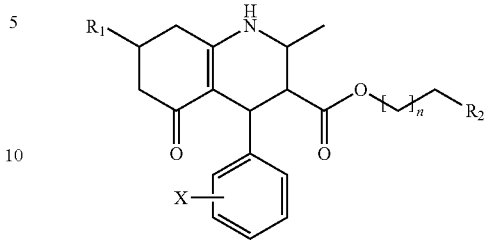

wherein $R_1$ and $R_2$ are independently selected from H, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^3R^4$, $OC(R^3)_2COOH$, $SC(R^3)_2COOH$, $NHCHR^3COOH$, $COR^4$, $CO_2R^4$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^3R^4$, $OC(R^3)_2COOH$, $SC(R^3)_2COOH$, $NHCHR^3COOH$, $COR^4$, $CO_2R^4$, sulfate, sulfonamide, sulfoxide, sulfonate, sulfone, thioalkyl, thioester, and thioether is optionally substituted with at least one substituent;

$R^3$ is selected from H, $C_{1-8}$alkyl, carbocycle, aryl, heteroaryl, heterocycle, alkylaryl, alkylheteroaryl, and alkylheterocycle, wherein each alkyl, carbocycle, aryl, heteroaryl, heterocycle, alkylaryl, alkylheteroaryl, and alkylheterocycle may be optionally substituted with at least one substituent;

$R^4$ is selected from H, $C_{1-8}$alkyl, $C_{1-8}$alkenyl, $C_{1-8}$alkynyl, aryl, carbocycle, heteroaryl, heterocycle, alkylaryl, alkylheteroaryl, alkylheterocycle, and heteroaromatic, wherein each alkyl, alkenyl, alkynyl, aryl, carbocycle, heteroaryl, heterocycle, alkylaryl, alkylheteroaryl, alkylheterocycle, and heteroaromatic may be optionally substituted with at least one substituent;

X is selected from halo and $C_{1-8}$ alkyl; and n is 0-8, or an enantiomer, optical isomer, diastereomer, N-oxide, crystalline form, hydrate, or pharmaceutically acceptable salt thereof.

Preferably, each optional substituent is independently selected from the group consisting of H, cyano, oxo, nitro, acyl, acylamino, halogen, hydroxy, amino acid, amine, amide, carbamate, ester, ether, carboxilic acid, thio, thioalkyl, thioester, thioether, $C_{1-8}$ alkyl, $C_{1-8}$alkoxy, $C_{1-8}$alkenyl, $C_{1-8}$aralkyl, 3- to 8-membered carbocyclic, 3- to 8-membered heterocyclic, 3- to 8-membered aryl, or 3- to 8-membered heteroaryl, sulfate, sulfonamide, sulfoxide, sulfonate, sulfone, alkylsulfonyl, and arylsulfonyl.

In one preferred composition, the RAS-selective lethal compound is a compound of formula IIa:

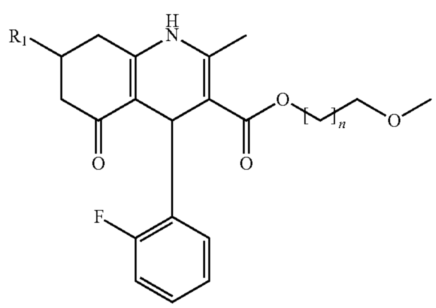

or a compound of formula IIb:

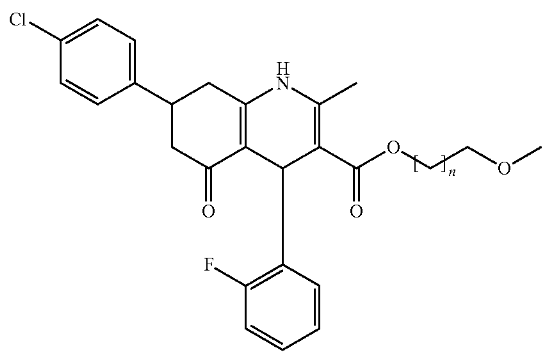 [SMILES: COCCOC(=O)C1=C(C)NC2=C(C(=O)CC(c3ccc(Cl)cc3)C2)C1c1ccccc1F]

or enantiomers, optical isomers, diastereomers, N-oxides, crystalline forms, hydrates, or pharmaceutically acceptable salts of either formula IIa or IIb.

Representative, non-limiting examples of compounds of formula II according to the present invention are compounds 3, 4, and 5:

(3)

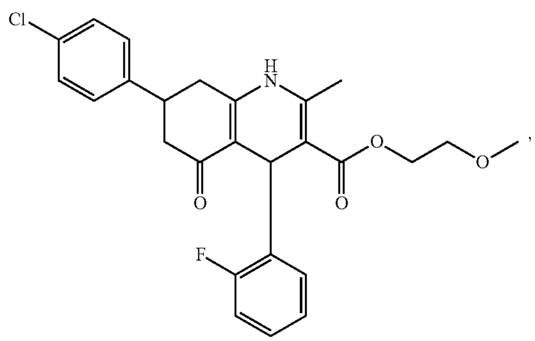

-continued (4)

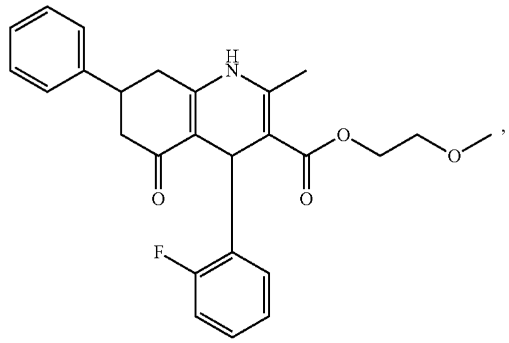

and (5)

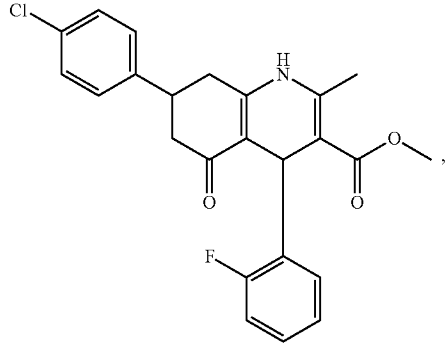

or an enantiomer, optical isomer, diastereomer, N-oxide, crystalline form, hydrate, or pharmaceutically acceptable salt thereof.

An additional embodiment of the present invention is a composition containing a pharmaceutically acceptable carrier and a RAS-selective lethal compound of formula III:

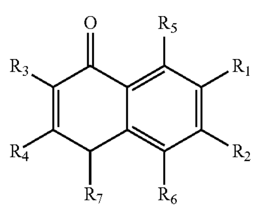

wherein $R_1$ is selected from H, halo, $C_{1-8}$ alkyl, $C_{1-8}$alkylene, 1-hydroxyl-β-D-glucose optionally substituted with from 1-4 acetates and/or 1-hydroxyl-β-D-glucose tetraacetate, and 1-thionyl-β-D-glucose optionally substituted with from 1-4 acetates, 0, and/or $C_{1-8}$ alkoxy;

$R_2$ is selected from H, halo, $C_{1-8}$ alkyl, and 1-thionyl-β-D-glucose substituted with from 1-4 acetates, O, or $C_{1-8}$ alkoxy;

$R_3$ and $R_4$ are independently selected from H, halo, $C_{1-8}$ alkyl, $C_{1-8}$ alkoxy, 1-hydroxyl-β-D-glucose optionally substituted with from 1-4 acetates and/or 1-hydroxyl-β-D-glucose tetraacetate, and 1-thionyl-β-D-glucose optionally substituted with from 1-4 acetates;

$R_5$ and $R_6$ are independently selected from H, OH, and acetate esters; and $R_7$ is selected from H or carbonyl, or an enantiomer, optical isomer, diastereomer, N-oxide, crystalline form, hydrate, or pharmaceutically acceptable salt thereof.

Preferably, the RAS-selective lethal compound is a compound of formula IIIa:

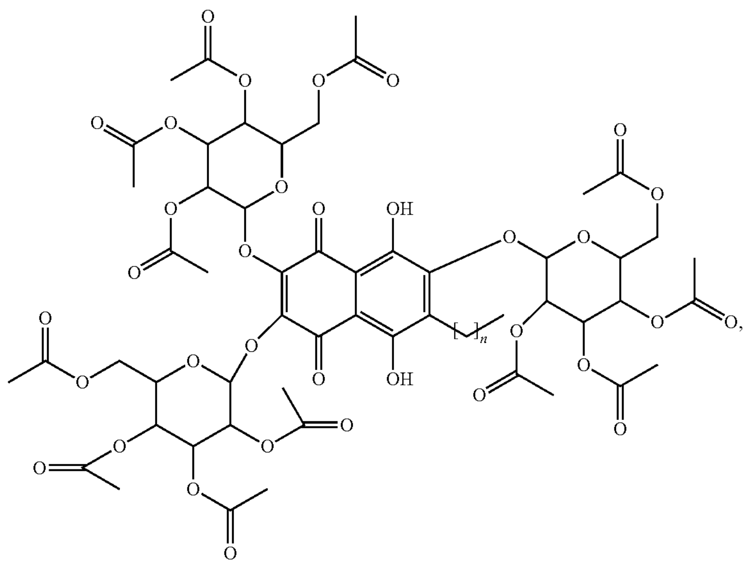

wherein n is 0-8, or an enantiomer, optical isomer, diastereomer, N-oxide, crystalline form, hydrate, or pharmaceutically acceptable salt thereof. Preferably, n is 1-8. In the present invention, where a numerical range is described, all integers within the range, including the end points are intended to be included.

Representative, non-limiting examples of compounds for formula III according to the present invention include compounds 6-26:

(6)

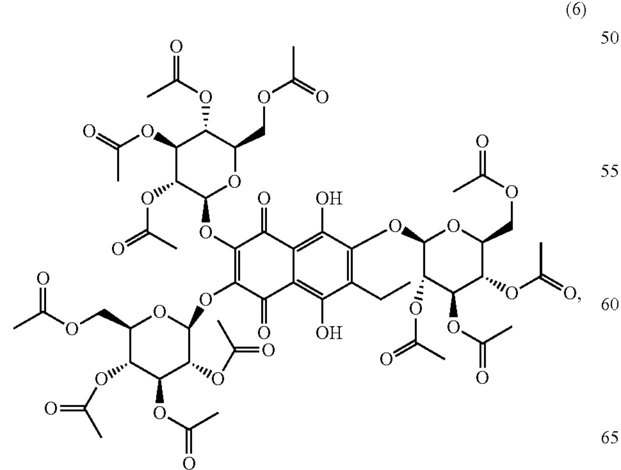

-continued (7)

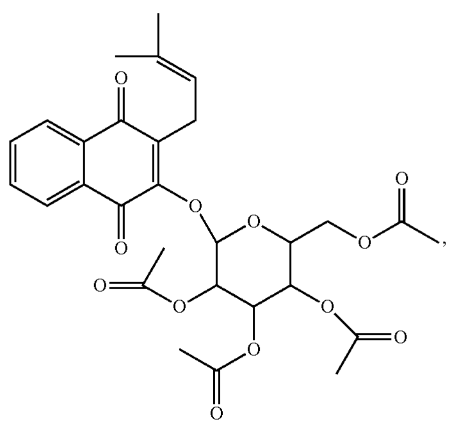

(8)

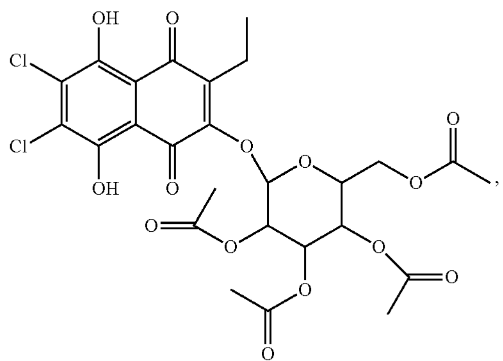

-continued
(9)
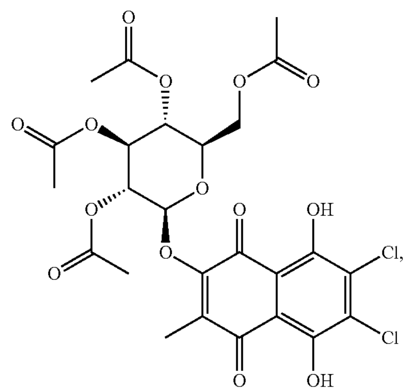
(10)
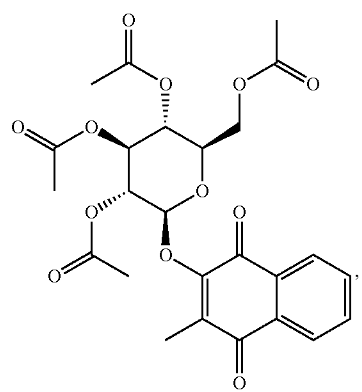
(11)
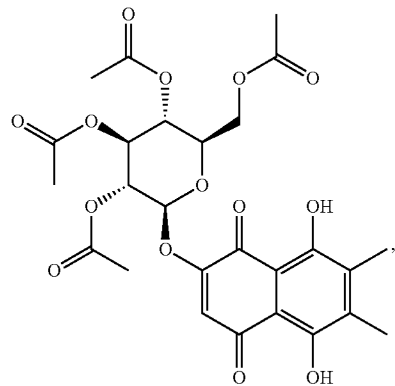
(12)
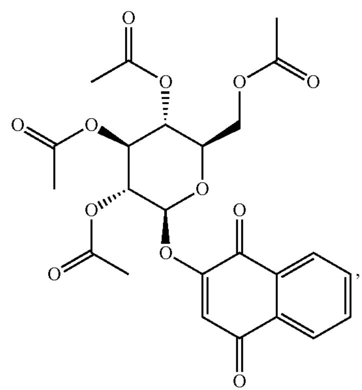
-continued
(13)
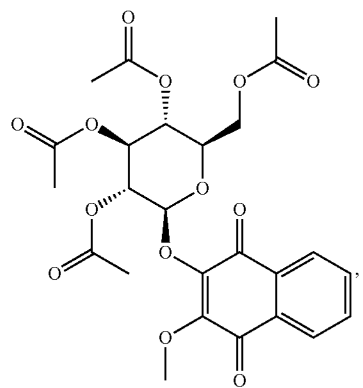
(14)
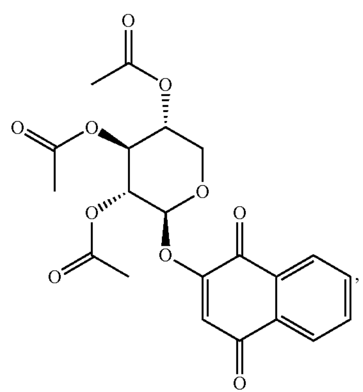
(15)
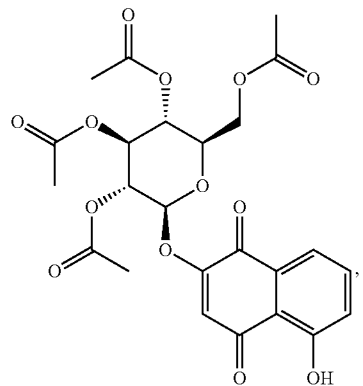
(16)
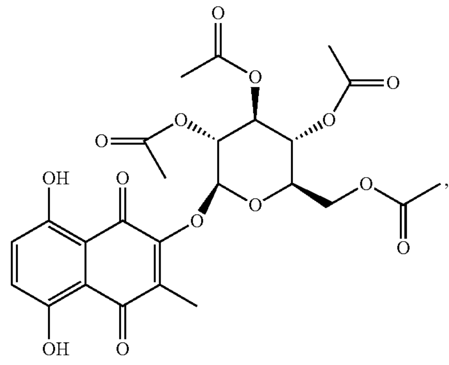

-continued
(17)
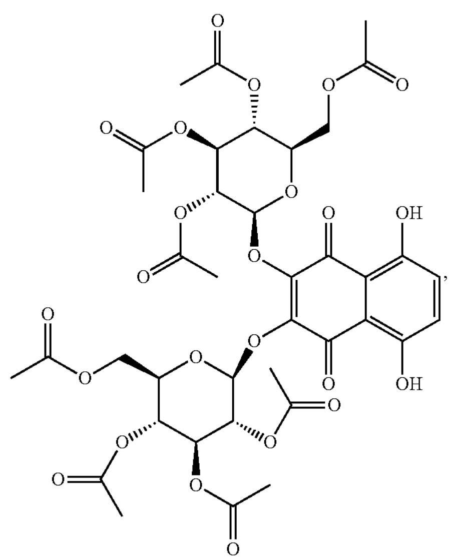
(18)
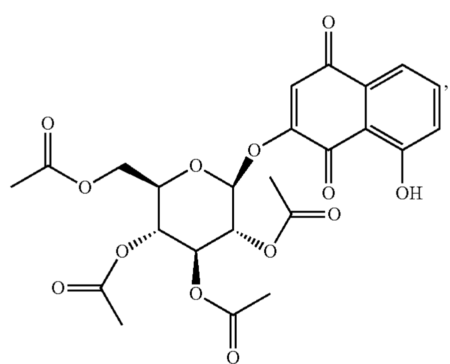
(19)
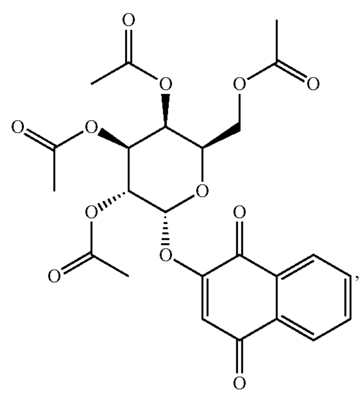
-continued
(20)
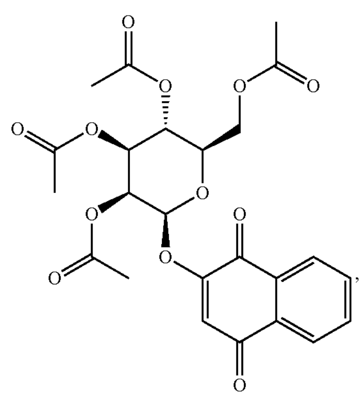
(21)
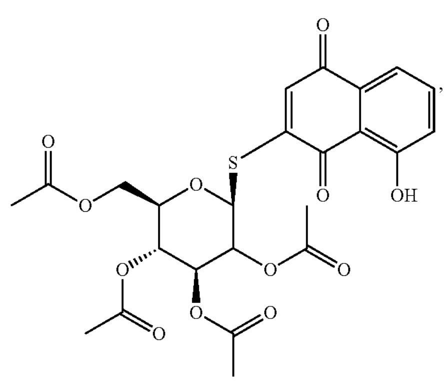
(22)
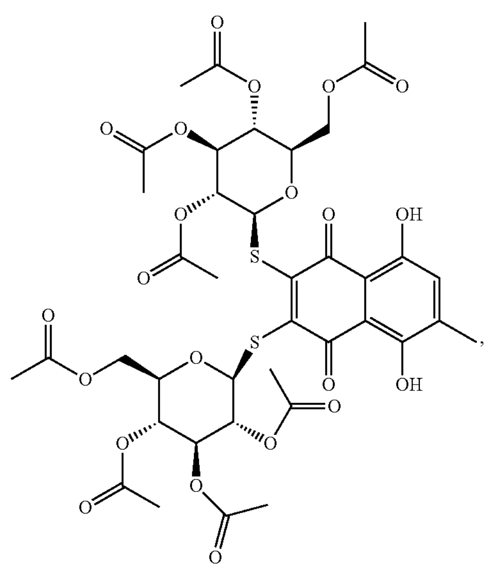

-continued (23)

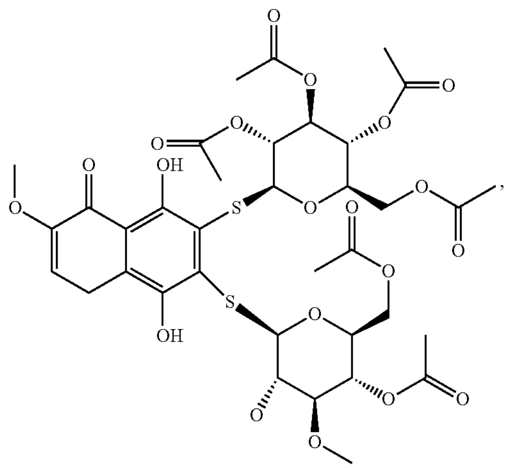

(24)

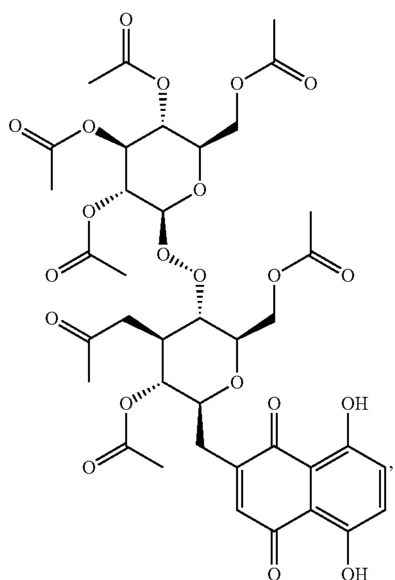

(25)

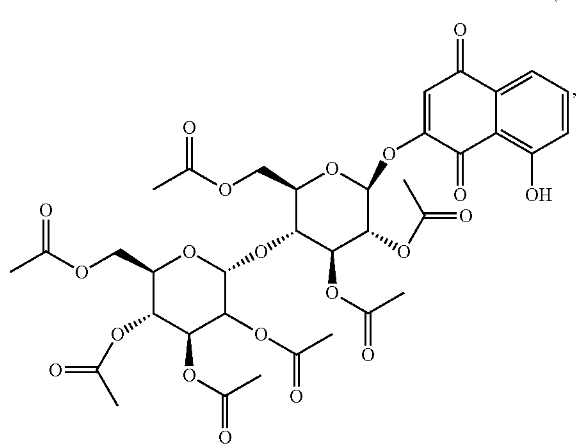

-continued and (26)

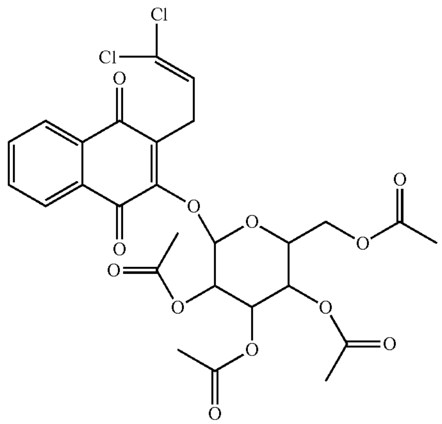

or an enantiomer, optical isomer, diastereomer, N-oxide, crystalline form, hydrate, or pharmaceutically acceptable salt thereof.

Another embodiment of the present invention is a composition containing a pharmaceutically acceptable carrier and a RAS-selective lethal compound according to formula IV:

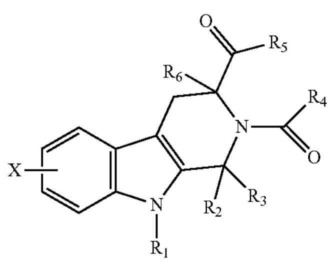

wherein $R_1$, $R_2$, $R_3$, $R_4$, $R_5$, and $R_6$ are independently selected from H, Halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

$R^7$ is selected from H, $C_{1-8}$alkyl, carbocycle, aryl, heteroaryl, heterocycle, alkylaryl, alkylheteroaryl, and alkylheterocycle, wherein each alkyl, carbocycle, aryl, heteroaryl, heterocycle, alkylaryl, alkylheteroaryl, and alkylheterocycle may be optionally substituted with at least one substituent;

$R^8$ is selected from H, $C_{1-8}$alkyl, $C_{1-8}$alkynyl, aryl, carbocycle, heteroaryl, heterocycle, alkylaryl, alkylheteroaryl, alkylheterocycle, and heteroaromatic, wherein each alkyl, alkenyl, alkynyl, aryl, carbocycle, heteroaryl, heterocycle, alkylaryl, alkylheteroaryl, alkylheterocycle, and heteroaromatic may be optionally substituted with at least one substituent; and X is 0-4 substituents on the ring to which it is attached, or an enantiomer, optical isomer, diastereomer, N-oxide, crystalline form, hydrate, or pharmaceutically acceptable salt thereof.

Preferably, each optional substituent is independently selected from the group consisting of H, cyano, oxo, nitro, acyl, acylamino, halogen, hydroxy, amino acid, amine, amide, carbamate, ester, ether, carboxilic acid, thio, thioalkyl, thioester, thioether, $C_{1-8}$ alkyl, $C_{1-8}$alkoxy, $C_{1-8}$alkenyl, $C_{1-8}$aralkyl, 3- to 8-membered carbocyclic, 3- to 8-membered heterocyclic, 3- to 8-membered aryl, or 3- to 8-membered heteroaryl, sulfate, sulfonamide, sulfoxide, sulfonate, sulfone, alkylsulfonyl, and arylsulfonyl.

Preferably, the RAS-selective lethal compound is a compound of formula IVa, IVb, IVc, or IVd:

(IVa)

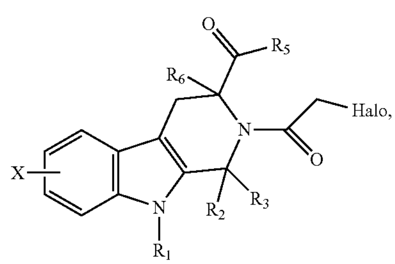

(IVb)

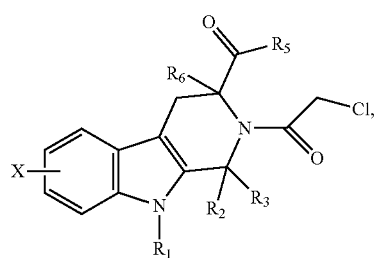

(IVc)

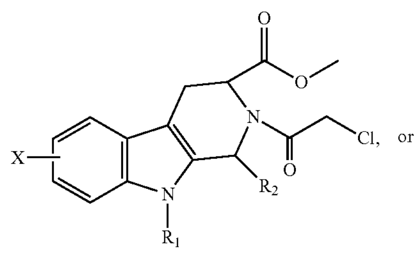

(IVd)

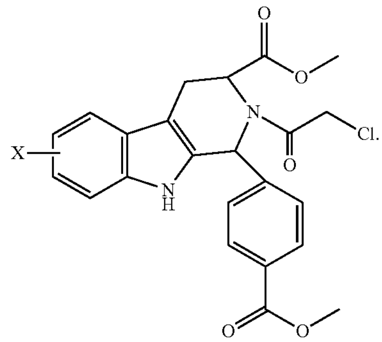

Representative, non-limiting examples of compounds of formula IV according to the present invention include compounds 27-35:

(27)

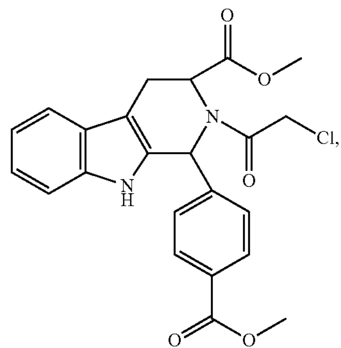

(28)

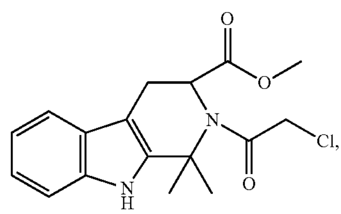

(29)

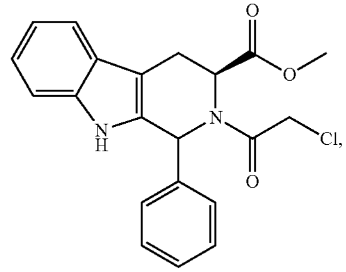

(30)

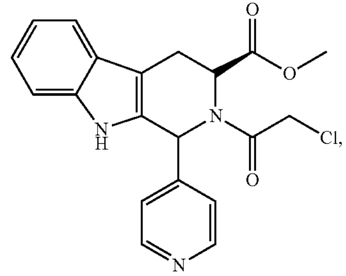

(31)

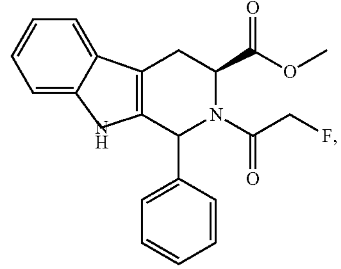

-continued (1)

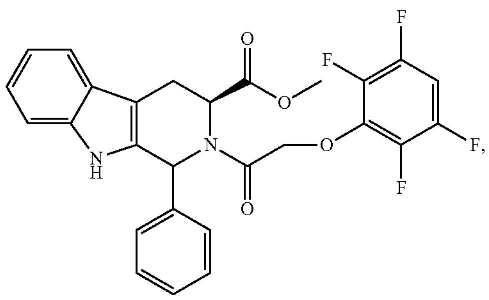

(2)

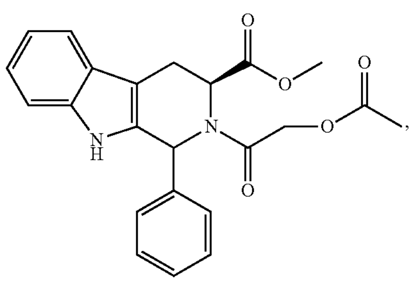

(32)

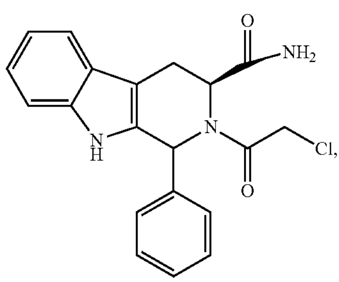

(33)

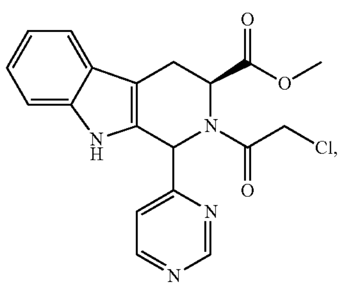

(34)

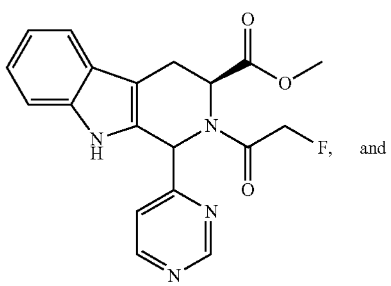

-continued (35)

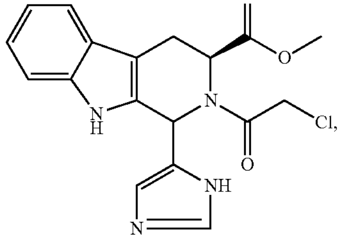

or an enantiomer, optical isomer, diastereomer, N-oxide, crystalline form, hydrate, or pharmaceutically acceptable salt thereof.

A further embodiment of the present invention is a composition containing a pharmaceutically acceptable carrier and a RAS-selective lethal compound according to formula V:

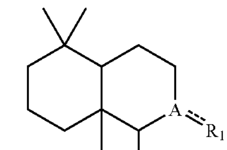

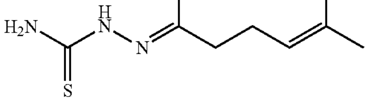

wherein $R_1$ is independently selected from H, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^2R^3$, $OC(R^2)_2COOH$, $SC(R^2)_2COOH$, $NHCHR^2COOH$, $COR^3$, $CO_2R^3$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^2R^3$, $OC(R^2)_2COOH$, $SC(R^2)_2COOH$, $NHCHR^2COOH$, $COR^3$, $CO_2R^3$, sulfate, sulfonamide, sulfoxide, sulfonate, sulfone, thioalkyl, thioester, and thioether is optionally substituted with at least one substituent;

$R^2$ is selected from H, $C_{1-8}$alkyl, carbocycle, aryl, heteroaryl, heterocycle, alkylaryl, alkylheteroaryl, and alkylheterocycle, wherein each alkyl, carbocycle, aryl, heteroaryl, heterocycle, alkylaryl, alkylheteroaryl, and alkylheterocycle may be optionally substituted with at least one substituent;

$R^3$ is selected from H, $C_{1-8}$alkyl, $C_{1-8}$alkenyl, $C_{1-8}$alkynyl, aryl, carbocycle, heteroaryl, heterocycle, alkylaryl, alkylheteroaryl, alkylheterocycle, and heteroaromatic, wherein each alkyl, alkenyl, alkynyl, aryl, carbocycle, heteroaryl, heterocycle, alkylaryl, alkylheteroaryl, alkylheterocycle, and heteroaromatic may be optionally substituted with at least one substituent; and A is C, N, or S, or an enantiomer, optical isomer, diastereomer, N-oxide, crystalline form, hydrate, or pharmaceutically acceptable salt thereof.

Preferably, each optional substituent is independently selected from the group consisting of H, cyano, oxo, nitro, acyl, acylamino, halogen, hydroxy, amino acid, amine, amide, carbamate, ester, ether, carboxilic acid, thio, thioalkyl, thioester, thioether, $C_{1-8}$ alkyl, $C_{1-8}$alkoxy, $C_{1-8}$alkenyl, $C_{1-8}$aralkyl, 3- to 8-membered carbocyclic, 3- to 8-membered heterocyclic, 3- to 8-membered aryl, or 3- to 8-membered heteroaryl, sulfate, sulfonamide, sulfoxide, sulfonate, sulfone, alkylsulfonyl, and arylsulfonyl.

Representative, non-limiting examples of compounds of formula V according to the present invention include compounds 36 and 37:

(36)

(37)

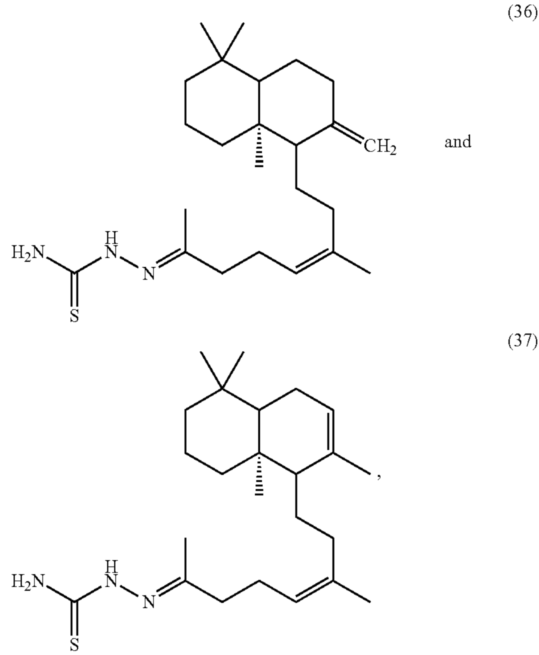

or an enantiomer, optical isomer, diastereomer, N-oxide, crystalline form, hydrate, or pharmaceutically acceptable salt thereof.

Another embodiment of the present invention is a compound having the formula VI:

(VI)

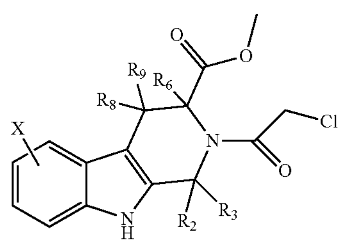

wherein $R_2$ and $R_3$ are independently selected from H, methyl, methyl benzoate, propargyl, and phenyl, wherein at least one of $R_2$ and $R_3$ is other than H;

$R_6$, $R_8$, and $R_9$ are independently selected from H, halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent; and X is 0-4 substituents on the ring to which it is attached; or an enantiomer, optical isomer, diastereomer, N-oxide, crystalline form, hydrate, or pharmaceutically acceptable salt thereof.

In one aspect of this embodiment, the compound of formula VI has an optional substituent, which is independently selected from the group consisting of H, cyano, oxo, nitro, acyl, acylamino, halogen, hydroxy, amino acid, amine, amide, carbamate, ester, ether, carboxylic acid, thio, thioalkyl, thioester, thioether, $C_{1-8}$alkyl, $C_{1-8}$alkoxy, $C_{1-8}$alkene, $C_{1-8}$alkyne, $C_{1-8}$aralkyl, 3- to 8-membered carbocyclic, 3- to 8-membered heterocyclic, 3- to 8-membered aryl, or 3- to 8-membered heteroaryl, sulfate, sulfonamide, sulfoxide, sulfonate, sulfone, alkylsulfonyl, arylsulfonyl, $C_{1-8}$alkoxy alkyne, $C_{1-8}$ alkyl alkyne, and $C_{1-8}$ alkyne acetate.

A preferable embodiment is a compound of formula VI in which $R_2$ is phenyl and $R_3$ is H.

Another preferable embodiment is a compound of formula VI, wherein $R_2$ is methyl benzoate and $R_3$ is H.

Another preferable embodiment is a compound of formula VI, wherein $R_2$ and $R_3$ are each methyl.

In another embodiment of the present invention, a compound is provided having the formula VII:

(VII)

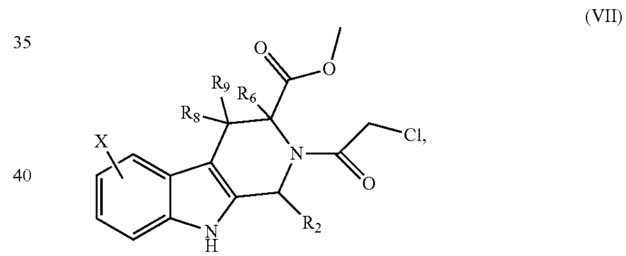

wherein $R_2$ is selected from halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, thioether, wherein each alkyl, alkoxy, carbocyclic, heterocyclic, aryl, heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

$R_6$, $R_8$, and $R_9$ are independently selected from H, halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent; and X is 0-4 substituents on the ring to which it is attached, or an enantiomer, optical isomer, diastereomer, N-oxide, crystalline form, hydrate, or pharmaceutically acceptable salt thereof.

In one aspect of this embodiment, the compound of formula VII has an optional substituent, which is independently selected from the group consisting of cyano, oxo, nitro, acyl, acylamino, halogen, hydroxy, amino acid, amine, amide, carbamate, ester, ether, carboxylic acid, thio, thioalkyl, thioester, thioether, $C_{1-8}$ alkyl, $C_{1-8}$alkene, $C_{1-8}$alkyne, $C_{1-8}$alkoxy, $C_{1-8}$aralkyl, 3- to 8-membered carbocyclic, 3- to 8-membered heterocyclic, 3- to 8-membered aryl, or 3- to 8-membered heteroaryl, sulfate, sulfonamide, sulfoxide, sulfonate, sulfone, alkylsulfonyl, arylsulfonyl, $C_{1-8}$alkoxy alkyne, $C_{1-8}$ alkyl alkyne and $C_{1-8}$ alkyne acetate.

A preferred embodiment of a compound according to formula VII, is wherein $R_6$, $R_8$, and $R_9$ are each H.

A preferred embodiment of a compound according to formula VII is wherein $R_2$ is —$(CH_2)_{1-8}C{\equiv}CH$.

A preferred embodiment of a compound according to formula VII is wherein $R_2$ is —$(CH_2)C{\equiv}CH$ and X is zero.

Another preferred embodiment of a compound according to formula VII is wherein X is 1-4 substituents, and at least one substituent for X is —$O(CH_2)_{1-8}$—$C{\equiv}CH$.

Another preferred embodiment of a compound according to formula VII is wherein X is 1 substituent and the substituent for X is —$O(CH_2)$—$C{\equiv}CH$ at the 5-indole position, and $R_3$ is methyl benzoate.

A further embodiment of the present invention is a compound having the formula VIII:

(VIII)

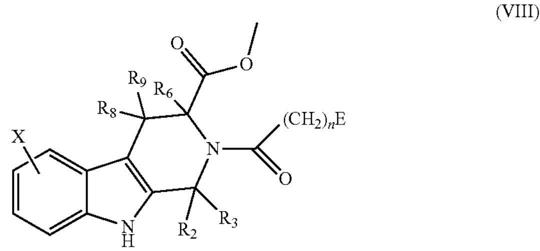

wherein $R_2$ and $R_3$ are independently selected from H, halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, thioether, wherein each alkyl, alkoxy, carbocyclic, heterocyclic, aryl, heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, thioether and is optionally substituted with at least one substituent, and wherein at least one of $R_2$ and $R_3$ is other than H;

$R_6$, $R_8$, and $R_9$ are independently selected from H, halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

X is 0-4 substituents on the ring to which it is attached;

n is 0 or 1;

E is an electrophilic group that has a lower electrophilicity index value than does Cl; or an enantiomer, optical isomer, diastereomer, N-oxide, crystalline form, hydrate, or pharmaceutically acceptable salt thereof.

In one aspect of this embodiment, the compound according to formula VIII has an optional substituent, which is independently selected from the group consisting of cyano, oxo, nitro, acyl, acylamino, halogen, hydroxy, amino acid, amine, amide, carbamate, ester, ether, carboxylic acid, thio, thioalkyl, thioester, thioether, $C_{1-8}$alkyl, $C_{1-8}$alkene, $C_{1-8}$alkyne, $C_{1-8}$alkoxy, $C_{1-8}$aralkyl, 3- to 8-membered carbocyclic, 3- to 8-membered heterocyclic, 3- to 8-membered aryl, or 3- to 8-membered heteroaryl, sulfate, sulfonamide, sulfoxide, sulfonate, sulfone, alkylsulfonyl, arylsulfonyl, $C_{1-8}$alkoxy alkyne, $C_{1-8}$ alkyl alkyne, and $C_{1-8}$ alkyne acetate.

A preferred embodiment of the compound according to formula VIII, is wherein $R_6$, $R_8$, and $R_9$ are each H.

A preferred embodiment of the compound according to formula VIII, is wherein n is zero.

Another preferred embodiment of the compound according to formula VIII, is wherein E is selected from the group consisting of cyclopropoxyl; —C(=O)H; $N_3$; —OC(=O)$CH_3$; and —O-tetrafluorophenyl.

A further embodiment of the compound according to formula VIII, is wherein n is zero.

Another embodiment of the compound according to formula VIII, is wherein E is an electrophilic group selected from the group consisting of Br, I, hypochlorite, sulfur dioxide, carbon disulfide, benzene, and sodium.

A preferred embodiment of the compound according to formula VIII, is wherein $R_2$ is —$(CH_2)_{1-8}$—$C{\equiv}CH$.

A preferred embodiment of the compound according to formula VIII, is wherein X is 1-4 substituents, and at least one substituent for X is —$O(CH_2)_{1-8}$—$C{\equiv}CH$.

A further embodiment of the present invention is a compound according to formula IX:

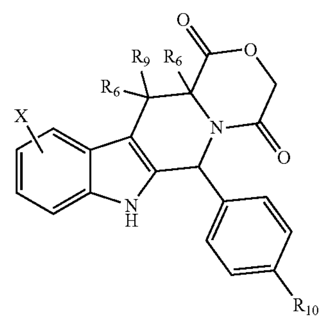

wherein $R_6$, $R_8$, and $R_9$ are independently selected from H, halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

X is 0-4 substituents on the ring to which it is attached; and $R_{10}$ is selected from the group consisting of a $C_{1-8}$ ester and an acid, which ester or acid is hydrolyzable in vivo; or an enantiomer, optical isomer, diastereomer, N-oxide, crystalline form, hydrate, or pharmaceutically acceptable salt thereof.

In one aspect of this embodiment, the compound according to formula IX, has an optional substituent, which is independently selected from the group consisting of cyano, oxo, nitro, acyl, acylamino, halogen, hydroxy, amino acid, amine, amide, carbamate, ester, ether, carboxylic acid, thio, thioalkyl, thioester, thioether, $C_{1-8}$alkyl, $C_{1-8}$alkene, $C_{1-8}$alkyne, $C_{1-8}$alkoxy, $C_{1-8}$aralkyl, 3- to 8-membered carbocyclic, 3- to 8-membered heterocyclic, 3- to 8-membered aryl, or 3- to 8-membered heteroaryl, sulfate, sulfonamide, sulfoxide, sulfonate, sulfone, alkylsulfonyl, arylsulfonyl, $C_{1-8}$alkoxy alkyne, $C_{1-8}$ alkyl alkyne, and $C_{1-8}$ alkyne acetate.

A preferred embodiment of a compound according to formula IX, is wherein $R_6$, $R_8$, and $R_9$ are each H.

A preferred embodiment of a compound according to formula IX, is wherein $R_{10}$ is —COOH or —C(=O)OCH$_3$.

As noted previously, it has been found that some of the compounds exhibit stereoisomeric selectivity in in vitro biological assays. Indeed, as shown in more detail below, surprisingly, in certain cases only one of, e.g., four stereoisomers of a particular compound are active in the in vitro activity experiments disclosed herein. Such stereoisomeric selectivity in this area is highly unusual and could not have been predicted.

In view of the foregoing, another embodiment of the present invention is a compound having the formula X:

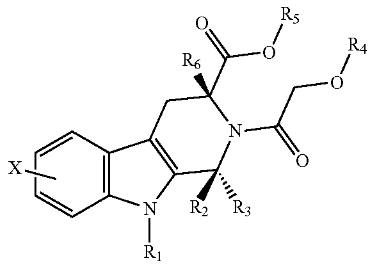

wherein $R_1$, $R_2$, $R_3$, and $R_6$ are independently selected from H, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, acyl, alkylsulfonyl, and arylsulfonyl, wherein each alkyl, alkoxy, aralkyl, carbocyclic, heterocyclic, aryl, heteroaryl, acyl, alkylsulfonyl, and arylsulfonyl is optionally substituted with at least one substituent;

$R_4$ and $R_5$ are independently selected from H, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

$R^7$ is selected from H, $C_{1-8}$alkyl, carbocycle, aryl, heteroaryl, heterocycle, alkylaryl, alkylheteroaryl, and alkylheterocycle, wherein each alkyl, carbocycle, aryl, heteroaryl, heterocycle, alkylaryl, alkylheteroaryl, and alkylheterocycle may be optionally substituted with at least one substituent;

$R^8$ is selected from H, $C_{1-8}$alkyl, $C_{1-8}$alkenyl, $C_{1-8}$alkynyl, aryl, carbocycle, heteroaryl, heterocycle, alkylaryl, alkylheteroaryl, alkylheterocycle, and heteroaromatic, wherein each alkyl, alkenyl, alkynyl, aryl, carbocycle, heteroaryl, heterocycle, alkylaryl, alkylheteroaryl, alkylheterocycle, and heteroaromatic may be optionally substituted with at least one substituent; and X is 0-4 substituents on the ring to which it is attached, wherein $R_2$ and $R_3$ are not the same group, or a N-oxide, crystalline form, hydrate, or pharmaceutically acceptable salt thereof.

In a preferred embodiment, $R_2$ is a larger and/or bulkier group than is $R_3$. A preferable $R_3$ is H.

Preferable embodiments are compounds of formula X in which $R_2$ is a substituted aryl, a halo-substituted aryl, a tetra-substituted aryl, a tetra-fluoro substituted aryl, or a $C_{1-8}$ alkyl substituted with carbonyl.

In certain embodiments, substituent X represents 0-4 substituents. As used in such embodiments, the term "substituent" means H, cyano, oxo, nitro, acyl, acylamino, halogen, hydroxy, amino acid, amine, amide, carbamate, ester, ether, carboxylic acid, thio, thioalkyl, thioester, thioether, $C_{1-8}$ alkyl, $C_{1-8}$alkoxy, $C_{1-8}$alkenyl, $C_{1-8}$aralkyl, 3- to 8-membered carbocyclic, 3- to 8-membered heterocyclic, 3- to 8-membered aryl, or 3- to 8-membered heteroaryl, sulfate, sulfonamide, sulfoxide, sulfonate, sulfone, alkylsulfonyl, and arylsulfonyl. In certain embodiments, substituent X represents one substituent, such as halogen or nitro, especially chloro. In other embodiments, substituent X represents no substituents on the ring (i.e., all substituents are hydrogen atoms).

In certain embodiments, substituents of Formula X have an optional substituent. Preferably, each optional substituent is independently selected from the group consisting of H, cyano, oxo, nitro, acyl, acylamino, halogen, hydroxy, amino acid, amine, amide, carbamate, ester, ether, carboxilic acid, thio, thioalkyl, thioester, thioether, $C_{1-8}$ alkyl, $C_{1-8}$alkoxy, $C_{1-8}$alkenyl, $C_{1-8}$aralkyl, 3- to 8-membered carbocyclic, 3- to 8-membered heterocyclic, 3- to 8-membered aryl, or 3- to 8-membered heteroaryl, sulfate, sulfonamide, sulfoxide, sulfonate, sulfone, alkylsulfonyl, and arylsulfonyl.

Preferred classes of compounds of formula X are defined by:

Xa

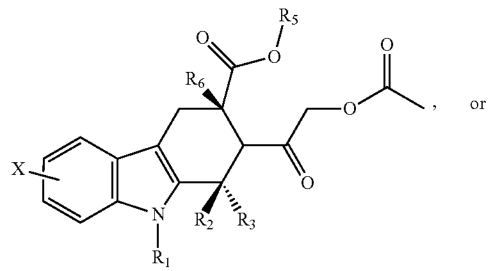

Xb

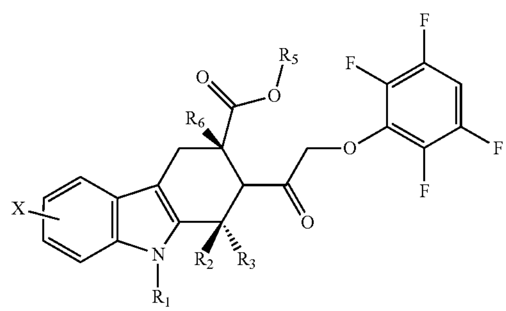

or a N-oxide, crystalline form, hydrate, or pharmaceutically acceptable salt thereof.

A further embodiment of the invention is a compound selected from the group consisting of:

A

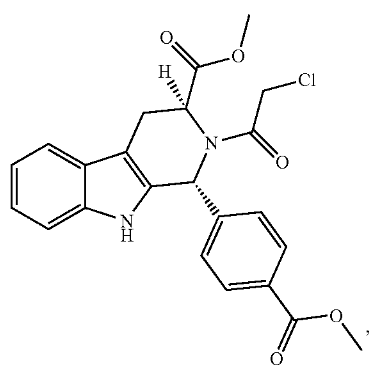

(1R,3S)-Compound 27

B

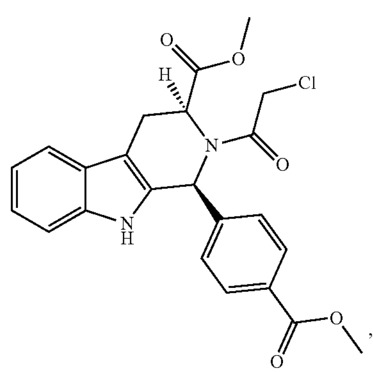

(1S,3S)-Compound 27

-continued

C

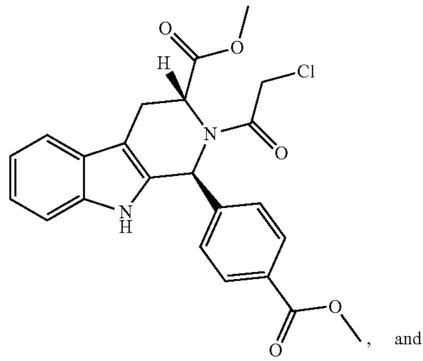

(1S,3R)-Compound 27

D

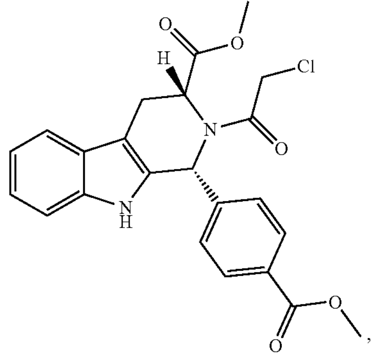

(1R,3R)-Compound 27 and mixtures thereof, or a N-oxide, crystalline form, hydrate, or pharmaceutically acceptable salt thereof.

Preferably, the compound of this embodiment is (1S,3R) Compound 27 (shown as formula C above), or a N-oxide, crystalline form, hydrate, or pharmaceutically acceptable salt thereof. More preferably, (1S,3R) Compound 27 is enantiomerically pure.

A preferable embodiment of the present invention is an enantiomerically pure compound having the structure:

C

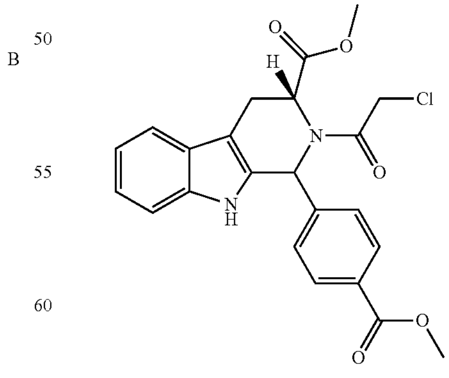

(1S,3R) - Compound 27 or a N-oxide, crystalline form, hydrate, or pharmaceutically acceptable salt thereof.

One preferred compound of the present invention is:

(X1)

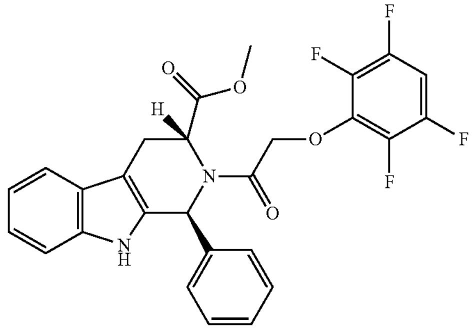

or a N-oxide, crystalline form, hydrate, or pharmaceutically acceptable salt thereof.

Another preferred compound of the present invention is:

(X2)

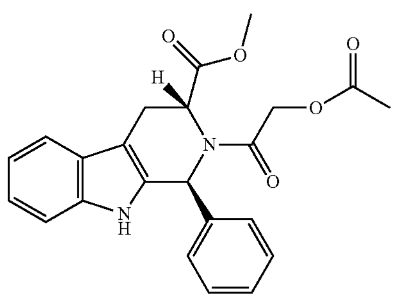

wherein the phenyl ring is optionally substituted with methoxycarbonyl,
or a N-oxide, crystalline form, hydrate, or pharmaceutically acceptable salt thereof.

Another embodiment of the present invention is a pharmaceutical composition comprising a pharmaceutically acceptable carrier and a RAS-selective lethal compound according to any one of formulas X, Xa, Xb, X1 and X2 and stereoisomers of Compound 27 of formulas A, B, C, and D, or a N-oxide, crystalline form, hydrate, or pharmaceutically acceptable salt thereof. When the pharmaceutical composition comprises a stereoisomer of Compound 27, preferably a stereoisomer of formula C is present.

A preferred embodiment is a pharmaceutical composition comprising a pharmaceutically acceptable carrier and an enantiomerically pure RAS-selective lethal compound having the structure:

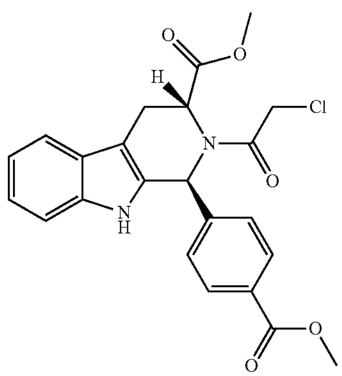

(1S,3R) - Compound 27 or a N-oxide, crystalline form, hydrate, or pharmaceutically acceptable salt thereof.

Another embodiment of the present invention is a composition comprising a pharmaceutically acceptable carrier and a RAS-selective lethal compound according to formula XI:

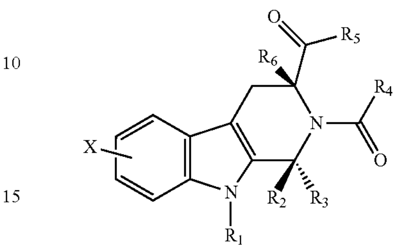

wherein $R_1$, $R_2$, $R_3$, $R_4$, $R_5$, and $R_6$ are independently selected from H, Halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

$R^7$ is selected from H, $C_{1-8}$alkyl, carbocycle, aryl, heteroaryl, heterocycle, alkylaryl, alkylheteroaryl, and alkylheterocycle, wherein each alkyl, carbocycle, aryl, heteroaryl, heterocycle, alkylaryl, alkylheteroaryl, and alkylheterocycle may be optionally substituted with at least one substituent;

$R^8$ is selected from H, $C_{1-8}$alkyl, $C_{1-8}$alkenyl, $C_{1-8}$alkynyl, aryl, carbocycle, heteroaryl, heterocycle, alkylaryl, alkylheteroaryl, alkylheterocycle, and heteroaromatic, wherein each alkyl, alkenyl, alkynyl, aryl, carbocycle, heteroaryl, heterocycle, alkylaryl, alkylheteroaryl, alkylheterocycle, and heteroaromatic may be optionally substituted with at least one substituent; and X is 0-4 substituents on the ring to which it is attached, wherein $R_2$ and $R_3$ are not the same group, or a N-oxide, crystalline form, hydrate, or pharmaceutically acceptable salt thereof.

In a preferred embodiment, $R_2$ is a larger and/or bulkier group than is $R_3$. A preferable $R_3$ is H.

In one aspect of this embodiment, the compound of formula XI has an optional substituent, which is independently selected from the group consisting of H, cyano, oxo, nitro, acyl, acylamino, halogen, hydroxy, amino acid, amine, amide, carbamate, ester, ether, carboxilic acid, thio, thioalkyl, thioester, thioether, $C_{1-8}$ alkyl, $C_{1-8}$alkoxy, $C_{1-8}$aralkyl, 3- to 8-membered carbocyclic, 3- to 8-membered heterocyclic, 3- to 8-membered aryl, or 3- to 8-membered heteroaryl, sulfate, sulfonamide, sulfoxide, sulfonate, sulfone, alkylsulfonyl, and arylsulfonyl.

In this embodiment, the RAS-selective lethal compound of the composition is a compound of formula XIa:

(XIa)
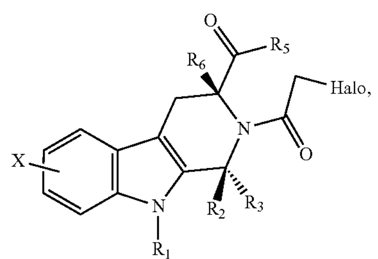
(XIb)
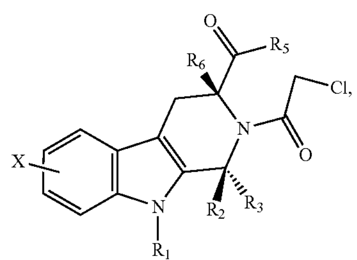
(XIc)
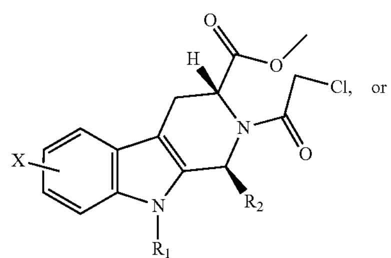
(XId)
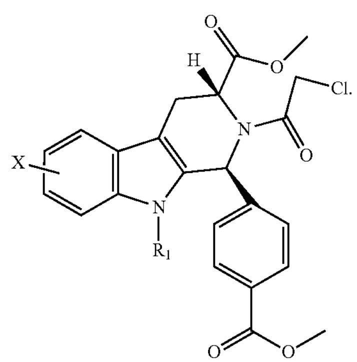
Representative, non-limiting examples of compounds of formula XI present in the composition include the following:
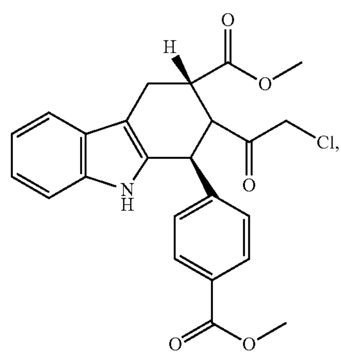
(1S, 3R) - Compound 27
-continued
(XI-29)
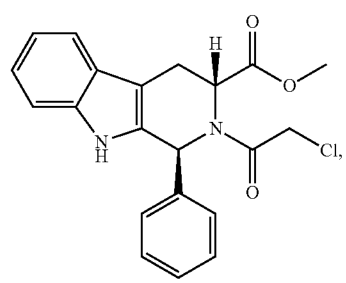
(XI-30)
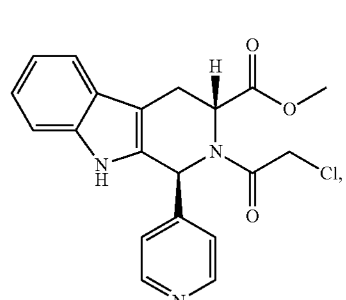
(XI-31)
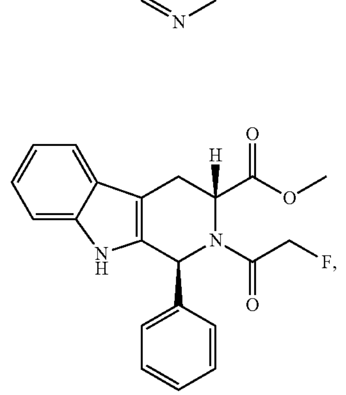
(XI-1)
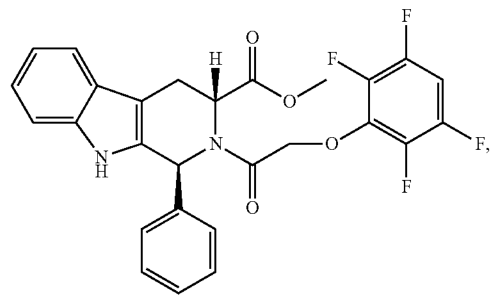
(XI-2)
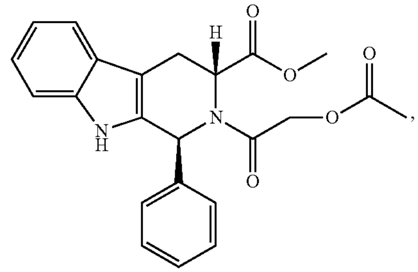

-continued (XI-32)

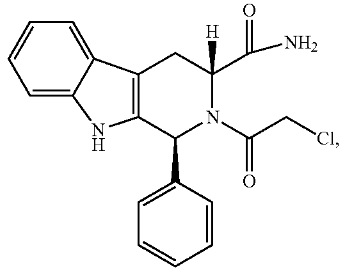

(XI-33)

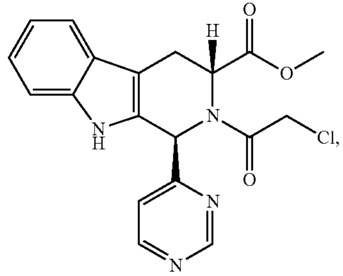

(XI-34)

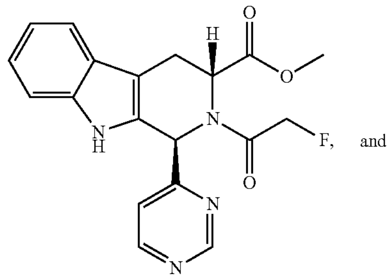

(XI-35)

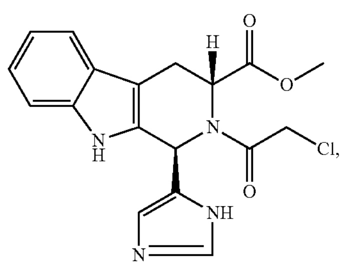

and mixtures thereof, or a N-oxide, crystalline form, hydrate, or pharmaceutically acceptable salt thereof.

Another embodiment of the present invention is a compound having the formula XII:

(XII)

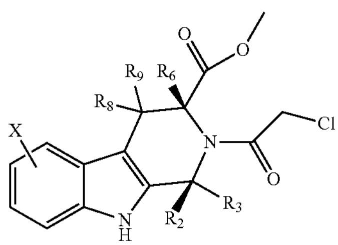

wherein $R_2$ and $R_3$ are independently selected from H, methyl, methyl benzoate, propargyl, and phenyl, wherein at least one of $R_2$ and $R_3$ is other than H;

$R_6$, $R_8$, and $R_9$ are independently selected from H, halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent; and X is 0-4 substituents on the ring to which it is attached;

wherein $R_2$ and $R_3$ are not the same group, or a N-oxide, crystalline form, hydrate, or pharmaceutically acceptable salt thereof.

A preferred embodiment is a compound of formula XII in which $R_2$ is a larger and/or bulkier group than is $R_3$. A preferable $R_3$ is H. And, substituent X is as previously defined.

In one aspect of this embodiment, the compound of formula XII has an optional substituent, which is independently selected from the group consisting of H, cyano, oxo, nitro, acyl, acylamino, halogen, hydroxy, amino acid, amine, amide, carbamate, ester, ether, carboxylic acid, thio, thioalkyl, thioester, thioether, $C_{1-8}$alkyl, $C_{1-8}$alkoxy, $C_{1-8}$alkene, $C_{1-8}$alkyne, $C_{1-8}$aralkyl, 3- to 8-membered carbocyclic, 3- to 8-membered heterocyclic, 3- to 8-membered aryl, or 3- to 8-membered heteroaryl, sulfate, sulfonamide, sulfoxide, sulfonate, sulfone, alkylsulfonyl, arylsulfonyl, $C_{1-8}$alkoxy alkyne, $C_{1-8}$ alkyl alkyne, and $C_{1-8}$ alkyne acetate.

A preferable embodiment is a compound of formula XII in which $R_2$ is phenyl and $R_3$ is H.

Another preferable embodiment is a compound of formula XII, wherein $R_2$ is methyl benzoate and $R_3$ is H.

Another embodiment of the present invention is a compound having the formula XIII:

(XIII)

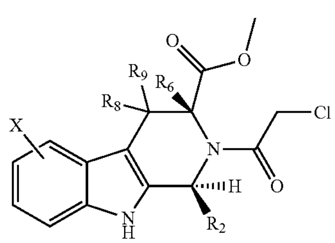

wherein $R_2$ is selected from halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, thioether, wherein each alkyl, alkoxy, carbocyclic, heterocyclic, aryl, heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

$R_6$, $R_8$, and $R_9$ are independently selected from H, halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent; and X is 0-4 substituents on the ring to which it is attached, or a N-oxide, crystalline form, hydrate, or pharmaceutically acceptable salt thereof.

In one aspect of this embodiment, the compound according to formula XIII has an optional substituent, which is independently selected from the group consisting of cyano, oxo, nitro, acyl, acylamino, halogen, hydroxy, amino acid, amine, amide, carbamate, ester, ether, carboxylic acid, thio, thioalkyl, thioester, thioether, $C_{1-8}$ alkyl, $C_{1-8}$alkene, $C_{1-8}$alkyne, $C_{1-8}$alkoxy, $C_{1-8}$aralkyl, 3- to 8-membered carbocyclic, 3- to 8-membered heterocyclic, 3- to 8-membered aryl, or 3- to 8-membered heteroaryl, sulfate, sulfonamide, sulfoxide, sulfonate, sulfone, alkylsulfonyl, arylsulfonyl, $C_{1-8}$alkoxy alkyne, $C_{1-8}$ alkyl alkyne and $C_{1-8}$ alkyne acetate. And, substituent X is as previously defined.

A preferred embodiment of a compound according to formula XIII, is wherein $R_6$, $R_8$, and $R_9$ are each H.

Another preferred embodiment of a compound according to formula XIII, is wherein $R_2$ is —$(CH_2)_{1-8}C{\equiv}CH$.

A further preferred embodiment of a compound according to formula XIII, is wherein $R_2$ is —$(CH_2)C{\equiv}CH$ and X is zero.

Another preferred embodiment of a compound according to formula XIII, is wherein X is 1-4 substituents, and at least one substituent for X is —$O(CH_2)_{1-8}$—$C{\equiv}CH$.

Another preferred embodiment of a compound according to formula XIII, is wherein X is 1 substituent and the substituent for X is —$O(CH_2)$—$C{\equiv}CH$ at the 5-indole position, and $R_2$ is methyl benzoate.

A further embodiment of the present invention is a compound having the formula XIV:

(XIV)

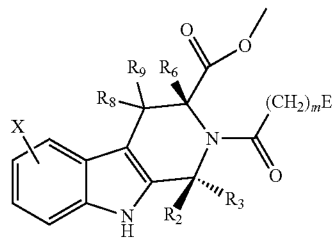

wherein $R_2$ and $R_3$ are independently selected from H, halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, thioether, wherein each alkyl, alkoxy, carbocyclic, heterocyclic, aryl, heteroaryl, carboxylate, ester, ether, amide, carbohydrate, amino acid, acyl; alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, thioether and is optionally substituted with at least one substituent, and wherein at least one of $R_2$ and $R_3$ is other than H;

$R_6$, $R_8$, and $R_9$ are independently selected from H, halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

X is 0-4 substituents on the ring to which it is attached;

n is 0 or 1;

E is an electrophilic group that has a lower electrophilicity index value than does Cl;

wherein $R_2$ and $R_3$ are not the same group, or a N-oxide, crystalline form, hydrate, or pharmaceutically acceptable salt thereof.

A preferred embodiment is a compound of formula XIV in which $R_2$ is a larger and/or bulkier group than is $R_3$. A preferable $R_3$ is H. And, substituent X is as previously defined.

In one aspect of this embodiment, the compound according to formula XIV has an optional substituent, which is independently selected from the group consisting of cyano, oxo, nitro, acyl, acylamino, halogen, hydroxy, amino acid, amine, amide, carbamate, ester, ether, carboxylic acid, thio, thioalkyl, thioester, thioether, $C_{1-8}$alkyl, $C_{1-8}$alkene, $C_{1-8}$alkyne, $C_{1-8}$alkoxy, $C_{1-8}$aralkyl, 3- to 8-membered carbocyclic, 3- to 8-membered heterocyclic, 3- to 8-membered aryl, or 3- to 8-membered heteroaryl, sulfate, sulfonamide, sulfoxide, sulfonate, sulfone, alkylsulfonyl, arylsulfonyl, $C_{1-8}$alkoxy alkyne, $C_{1-8}$ alkyl alkyne, and $C_{1-8}$ alkyne acetate.

A preferred embodiment of the compound according to formula XIV, is wherein $R_6$, $R_8$, and $R_9$ are each H.

Another preferred embodiment of the compound according to formula XIV, is wherein n is zero.

Another preferred embodiment of the compound according to formula XIV, is wherein E is selected from the group consisting of cyclopropoxyl; —C(=O)H; $N_3$; —OC(=O)$CH_3$; and —O-tetrafluorophenyl.

A further preferred embodiment of the compound according to formula XIV, is wherein n is zero.

Another preferred embodiment of the compound according to formula XIV, is wherein E is an electrophilic group selected from the group consisting of Br, I, hypochlorite, sulfur dioxide, carbon disulfide, benzene, and sodium.

Another preferred embodiment of the compound according to formula XIV, is wherein $R_2$ is —$(CH_2)_{1-8}$—$C{\equiv}CH$.

Another preferred embodiment of the compound according to formula XIV, is wherein X is 1-4 substituents, and at least one substituent for X is —$O(CH_2)_{1-8}$—$C{\equiv}CH$.

A further embodiment of the present invention is a compound according to formula XV:

(XV)

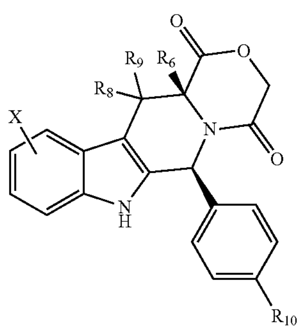

wherein $R_6$, $R_8$, and $R_9$ are independently selected from H, halo, $C_{1-8}$alkyl, $C_{1-8}$alkoxy, 3- to 8-membered carbocyclic, 3- to 8-membered heterocyclic, 3- to 8-membered aryl, or 3- to 8-membered heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, ether, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent;

X is 0-4 substituents on the ring to which it is attached; and $R_{10}$ is selected from the group consisting of a $C_{1-8}$ ester and an acid, which ester or acid is hydrolyzable in vivo; or a N-oxide, crystalline form, hydrate, or pharmaceutically acceptable salt thereof.

In one aspect of this embodiment, the compound according to formula XV has an optional substituent, which is independently selected from the group consisting of cyano, oxo, nitro, acyl, acylamino, halogen, hydroxy, amino acid, amine, amide, carbamate, ester, ether, carboxylic acid, thio, thioalkyl, thioester, thioether, $C_{1-8}$alkyl, $C_{1-8}$alkene, $C_{1-8}$alkoxy, $C_{1-8}$aralkyl, 3- to 8-membered carbocyclic, 3- to 8-membered heterocyclic, 3- to 8-membered aryl, or 3- to 8-membered heteroaryl, sulfate, sulfonamide, sulfoxide, sulfonate, sulfone, alkylsulfonyl, arylsulfonyl, $C_{1-8}$alkoxy alkyne, $C_{1-8}$ alkyl alkyne, and $C_{1-8}$ alkyne acetate. And, substituent X is as previously defined.

A preferred embodiment of a compound according to formula XV, is wherein $R_6$, $R_8$, and $R_9$ are each H.

Another preferred embodiment of a compound according to formula XV, is wherein $R_{10}$ is —COOH or —C(═O)$OCH_3$.

In another aspect of the present invention, a compound is provided which is selected from the group consisting of:

E

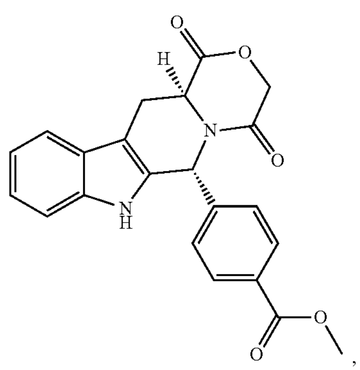

(1R,3S) - Cyclized Compound 27

F

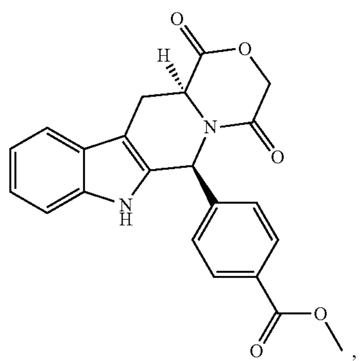

(1S,3S) - Cyclized Compound 27

G

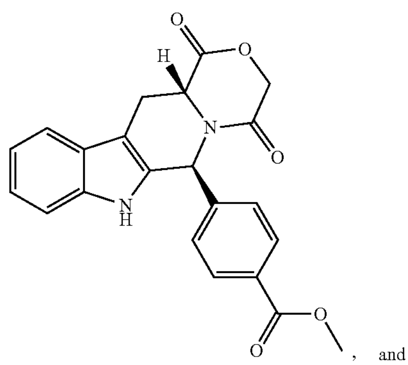

(1S,3R) - Cyclized Compound 27

H

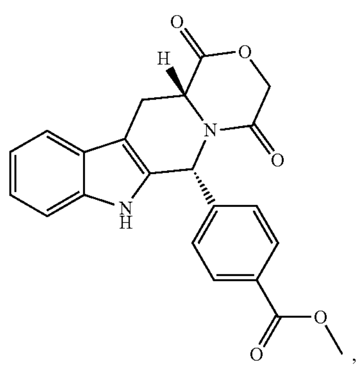

(1R,3R) - Cyclized Compound 27 and mixtures thereof, or a N-oxide, crystalline form, hydrate, or pharmaceutically acceptable salt thereof.

In this embodiment, preferably the compound is:

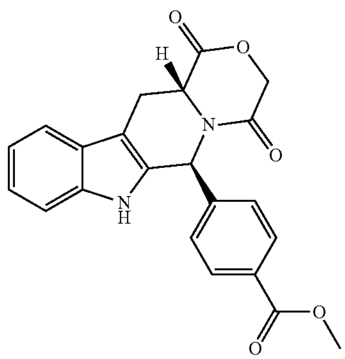

(1S,3R) - Cyclized Compound 27 or a N-oxide, crystalline form, hydrate, or pharmaceutically acceptable salt thereof.

A more preferred embodiment is wherein the compound is enantiomerically pure.

A further preferred embodiment is an enantiomerically pure compound having the structure:

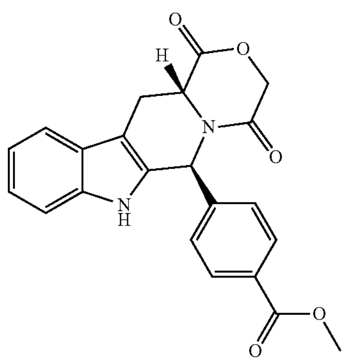

(1S,3R) - Cyclized Compound 27 or a N-oxide, crystalline form, hydrate, or pharmaceutically acceptable salt thereof.

Compositions, including pharmaceutical compositions are provided comprising a pharmaceutically acceptable carrier and a RAS-selective lethal compound according to any one of formulas XV and stereoisomers of cyclic compound 27 of formulas E, F, G, and H, or a N-oxide, crystalline form, hydrate, or pharmaceutically acceptable salt thereof. When the pharmaceutical composition comprises a stereoisomer of Cyclized Compound 27, preferably a stereoisomer of formula G is present.

A preferred embodiment of the present invention is a pharmaceutical composition comprising a pharmaceutically acceptable carrier and an enantiomerically pure RAS-selective lethal compound having the structure:

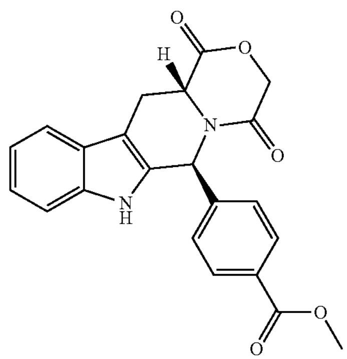

(1S,3R) - Cyclized Compound 27 or a N-oxide, crystalline form, hydrate, or pharmaceutically acceptable salt thereof.

It is contemplated that all embodiments of the invention can be combined with one or more other embodiments, even those described under different aspects of the invention.

Compositions, including pharmaceutical compositions are provided comprising, optionally a pharmaceutical carrier, and a compound selected from the group consisting of compounds of formula VI, compounds of formula VII, compounds of formula VIII, and compounds of formula IX, which compounds are RAS-selective lethal compounds.

Compositions, including pharmaceutical compositions are provided comprising a RAS-selective lethal compound according to any one of formulas X, Xa, Xb, X1, X2, XII, XIII, XIV, XV, stereoisomers of Compound 27 of formulas A, B, C, and D, stereoisomers of Cyclized Compound 27 of formulas E, F, G, and H, or a N-oxide, crystalline form, hydrate, or pharmaceutically acceptable salt thereof.

As used herein, the term "acyl" has its art-recognized meaning and refers to a group represented by the general formula hydrocarbylC(O)—, preferably alkylC(O)—.

As used herein, the term "acylamino" has its art-recognized meaning and refers to an amino group substituted with an acyl group and may be represented, for example, by the formula hydrocarbylC(O)NH—.

As used herein, the term "acyloxy" has its art-recognized meaning and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like. Other alkoxy groups within the scope of the invention include, for example, the following:

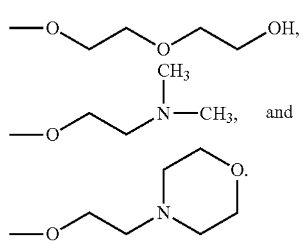

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer, such as from 1 to 8. Likewise, preferred cycloalkyls have from 3-10 carbon atoms in their ring structure, and more preferably have 5, 6 or 7 carbons in the ring structure.

Moreover, unless otherwise indicated, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

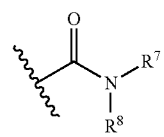

wherein $R^7$ and $R^8$ each independently represent a hydrogen or hydrocarbyl group, or $R^7$ and $R^8$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

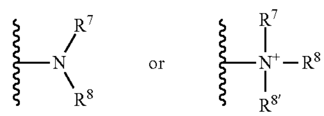

wherein $R^7$, $R^8$, and $R^{8'}$ each independently represent a hydrogen or a hydrocarbyl group, or $R^7$ and $R^8$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 3- to 8-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

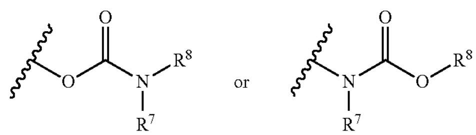

wherein $R^7$ and $R^8$ independently represent hydrogen or a hydrocarbyl group.

The terms “carbocycle”, “carbocyclyl”, and “carbocyclic”, as used herein, refers to a non-aromatic saturated or unsaturated ring in which each atom of the ring is carbon. Preferably a carbocycle ring contains from 3 to 10 atoms, more preferably from 3 to 8 atoms, including 5 to 7 atoms, such as for example, 6 atoms.

The term “carbocyclylalkyl”, as used herein, refers to an alkyl group substituted with a carbocycle group.

The term “carbonate” is art-recognized and refers to a group —$OCO_2$—$R^7$, wherein $R^7$ represents a hydrocarbyl group.

The term “carboxy”, as used herein, refers to a group represented by the formula —$CO_2H$.

The term “ester”, as used herein, refers to a group —C(O)$OR^7$ wherein $R^7$ represents a hydrocarbyl group.

The term “ether”, as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include “alkoxyalkyl” groups, which may be represented by the general formula alkyl-O-alkyl.

The terms “halo” and “halogen” are used interchangeably herein and mean halogen and include chloro, fluoro, bromo, and iodo.

The terms “hetaralkyl” and “heteroaralkyl”, as used herein, refers to an alkyl group substituted with a hetaryl group.

The terms “heteroaryl” and “hetaryl” include substituted or unsubstituted aromatic single ring structures, preferably 3- to 8-membered rings, more preferably 5- to 7-membered rings, even more preferably 5- to 6-membered rings, whose ring structures include at least one heteroatom, preferably one to four heteroatoms, more preferably one or two heteroatoms. The terms “heteroaryl” and “hetaryl” also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term “heteroatom” as used herein means an atom of any element other than carbon or hydrogen. Preferred heteroatoms are nitrogen, oxygen, and sulfur.

The terms “heterocyclyl”, “heterocycle”, and “heterocyclic” refer to substituted or unsubstituted non-aromatic ring structures, preferably 3- to 10-membered rings, more preferably 3- to 8-membered rings, whose ring structures include at least one heteroatom, preferably one to four heteroatoms, more preferably one or two heteroatoms. The terms “heterocyclyl” and “heterocyclic” also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term “heterocyclylalkyl”, as used herein, refers to an alkyl group substituted with a heterocycle group.

The term “hydrocarbyl”, as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term “hydroxyalkyl”, as used herein, refers to an alkyl group substituted with a hydroxy group.

The term “lower” when used in conjunction with a chemical moiety, such as, acyl, acyloxy, alkyl, alkenyl, alkynyl, or alkoxy is meant to include groups where there are ten or fewer non-hydrogen atoms in the substituent, preferably eight or fewer, such as for example, from about 3 to 8 carbon atoms, more preferably less than 6 carbon atoms. A “lower alkyl”, for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms “polycyclyl”, “polycycle”, and “polycyclic” refer to two or more rings (e.g., cycloalkyls, cycloalkenyls, cycloalkynyls, aryls, heteroaryls, and/or heterocyclyls) in which two or more atoms are common to two adjoining rings, e.g., the rings are “fused rings”. Each of the rings of the polycycle can be substituted or unsubstituted. In certain embodiments, each ring of the polycycle contains from 3 to 10 atoms in the ring, preferably from 3 to 8, such as for example, 5 to 7.

The term “substituted” refers to moieties having substituents replacing a hydrogen on one or more carbons of the backbone. It will be understood that “substitution” or “substituted with” includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term “substituted” is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —$OSO_3H$, or a pharmaceutically acceptable salt thereof.

The term "sulfonamide" is art-recognized and refers to the group represented by the general formulae

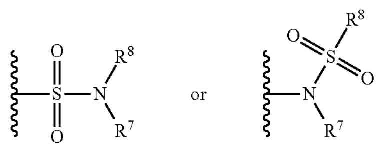

wherein $R^7$ and $R^8$ independently represents hydrogen or hydrocarbyl.

The term "sulfoxide" is art-recognized and refers to the group —S(O)—$R^7$, wherein $R^7$ represents a hydrocarbyl.

The term "sulfonate" is art-recognized and refers to the group $SO_3H$, or a pharmaceutically acceptable salt thereof.

The term "sulfone" is art-recognized and refers to the group —$S(O)_2$—$R^7$, wherein $R^7$ represents a hydrocarbyl.

The term "thioalkyl", as used herein, refers to an alkyl group substituted with a thiol group.

The term "thioester", as used herein, refers to a group —C(O)S$R^7$ or —SC(O)$R^7$ wherein $R^7$ represents a hydrocarbyl.

The term "thioether", as used herein, is equivalent to an ether, wherein the oxygen is replaced with a sulfur.

The term "urea" is art-recognized and may be represented by the general formula

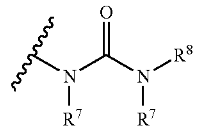

wherein $R^7$ and $R^8$ independently represent hydrogen or a hydrocarbyl.

The term "substantially optically pure" or "enantiomerically pure" means having at least about 95% of the described enantiomer with no single impurity greater than about 1% and preferably, at least about 97.5% enantiomeric excess.

The pharmaceutically acceptable salts of the compounds of the present invention include the acid addition and the base salts thereof. A pharmaceutically acceptable salt of a compound of the present invention may be readily prepared by mixing together solutions of a compound of the present invention and the desired acid or base, as appropriate. The salt may precipitate from solution and be collected by filtration or may be recovered by evaporation of the solvent. Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts. Suitable base salts are formed from bases which form non-toxic salts and examples are the sodium, potassium, aluminium, calcium, magnesium, zinc and diethanolamine salts. For a review on suitable salts see Berge et al, J. Pharm. Sci., 66, 1-19, 1977.

Esters of the compounds of the formulas of the present invention that are hydrolyzable in vivo include carboxy group(s) which is/are present in the form of readily hydrolyzable ester groups. As used herein, esters that are hydrolyzable in vivo include the lower alkanoyloxy-alkyl esters (e.g., the acetoxymethyl, pivaloyloxymethyl, 1-acetoxyethyl and 1-pivaloyloxyethyl ester); the lower alkoxycarbonyloxyalkyl esters (e.g., the methoxycarbonyloxymethyl, 1-ethoxycarbonyloxyethyl and 1-isopropoxycarbonyloxyethyl ester); the lactonyl esters (e.g., the phthalidyl and thiophthalidyl ester); the lower alkoxymethyl esters (e.g., the methoxymethyl ester); the lower alkanoylaminomethyl esters (e.g., the acetamidomethyl ester); the benzyl and cyanomethyl esters; 2,2-dimethyl-1-oxopropoxy)methyl ester; 2-[(2-methylpropoxy) carbonyl]-2-pentenyl ester; 1-[[(1-methylethoxy)-carbonyl] oxy]ethyl ester; 1-(acetyloxy)ethyl ester; (5-methyl-2-oxo-1, 3-dioxol-4-yl)methyl ester; 1-[[(cyclohexyloxy)carbonyl] oxy]ethyl ester; and 3,3-dimethyl-2-oxobutyl ester. It will be appreciated by those of ordinary skill in the art that the readily hydrolyzable esters of the compounds of the present invention can be formed at a free carboxy group.

In another embodiment, the present invention is a pharmaceutical composition that includes a pharmaceutically acceptable carrier and a RAS-selective lethal compound according to the present invention, including compounds of formula I, Ia, and/or Ib, such as for example, compounds 1 and/or 2.

Another embodiment of the present invention is a method of treating a condition in a mammal. This method includes the step of administering to the mammal a therapeutically effective amount of a RAS-selective lethal compound according to the present invention, including compounds of formula I, Ia, and/or Ib, such as for example, compounds 1 and/or 2.

In the present invention, a "therapeutically effective amount" is an amount sufficient to effect beneficial or desired results. In terms of treatment of a mammal, a "therapeutically effective amount" of a compound is an amount sufficient to treat, manage, palliate, ameliorate, or stabilize a condition, such as cancer, in the mammal. A therapeutically effective amount can be administered in one or more doses.

The therapeutically effective amount is generally determined by a physician on a case-by-case basis and is within the skill of one in the art. Several factors are typically taken into account when determining an appropriate dosage. These factors include age, sex and weight of the patient, the condition being treated, the severity of the condition and the form of the drug being administered.

Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of animal, and like factors well known in the arts of medicine and veterinary medicine. In general, a suitable dose of a compound according to the invention will be that amount of the compound, which is the lowest dose effective to produce the desired effect. The effective dose of a compound maybe administered as two, three, four, five, six or more sub-doses, administered separately at appropriate intervals throughout the day.

A compound of the present invention may be administered in any desired and effective manner: as pharmaceutical compositions for oral ingestion, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a compound of the present invention may be administered in conjunction with other treatments. A compound or composition of the present invention maybe encapsulated or otherwise protected against gastric or other secretions, if desired.

While it is possible for a compound of the invention to be administered alone, it is preferable to administer the compound as a pharmaceutical formulation (composition). The pharmaceutically acceptable compositions of the invention comprise one or more compounds as an active ingredient in admixture with one or more pharmaceutically-acceptable carriers and, optionally, one or more other compounds, drugs, ingredients and/or materials. Regardless of the route of administration selected, the compounds of the present invention are formulated into pharmaceutically-acceptable dosage forms by conventional methods known to those of skill in the art. See, e.g., Remington's Pharmaceutical Sciences (Mack Publishing Co., Easton, Pa.).

In one aspect of this embodiment, one or more compounds or compositions of the present invention may be conjointly administered to the mammal with an agent that kills cells through an apoptotic mechanism. In this aspect, the agent is, e.g., a chemotherapeutic agent—including combinations of chemotherapeutic agents. Agents useful in the present invention include, e.g., an EGF-receptor antagonist, arsenic sulfide, adriamycin, cisplatin, carboplatin, cimetidine, caminomycin, mechlorethamine hydrochloride, pentamethylmelamine, thiotepa, teniposide, cyclophosphamide, chlorambucil, demethoxyhypocrellin A, melphalan, ifosfamide, trofosfamide, Treosulfan, podophyllotoxin or podophyllotoxin derivatives, etoposide phosphate, teniposide, etoposide, leurosidine, leurosine, vindesine, 9-aminocamptothecin, camptoirinotecan, crisnatol, megestrol, methopterin, mitomycin C, ecteinascidin 743, busulfan, carmustine (BCNU), lomustine (CCNU), lovastatin, 1-methyl-4-phenylpyridinium ion, semustine, staurosporine, streptozocin, phthalocyanine, dacarbazine, aminopterin, methotrexate, trimetrexate, thioguanine, mercaptopurine, fludarabine, pentastatin, cladribin, cytarabine (ara C), porfiromycin, 5-fluorouracil, 6-mercaptopurine, doxorubicin hydrochloride, leucovorin, mycophenolic acid, daunorubicin, deferoxamine, floxuridine, doxifluridine, raltitrexed, idarubicin, epirubican, pirarubican, zorubicin, mitoxantrone, bleomycin sulfate, actinomycin D, safracins, saframycins, quinocarcins, discodermolides, vincristine, vinblastine, vinorelbine tartrate, vertoporfin, paclitaxel, tamoxifen, raloxifene, tiazofuran, thioguanine, ribavirin, EICAR, estramustine, estramustine phosphate sodium, flutamide, bicalutamide, buserelin, leuprolide, pteridines, enediynes, levamisole, aflacon, interferon, interleukins, aldesleukin, filgrastim, sargramostim, rituximab, BCG, tretinoin, betamethosone, gemcitabine hydrochloride, verapamil, VP-16, altretamine, thapsigargin, oxaliplatin, iproplatin, tetraplatin, lobaplatin, DCP, PLD-147, JM118, JM216, JM335, satraplatin, docetaxel, deoxygenated paclitaxel, TL-139, 5'-nor-anhydrovinblastine (hereinafter: 5'-nor-vinblastine), camptothecin, irinotecan (Camptosar, CPT-11), topotecan (Hycamptin), BAY 38-3441, 9-nitrocamptothecin (Orethecin, rubitecan), exatecan (DX-8951), lurtotecan (GI-147211C), gimatecan, homocamptothecins diflomotecan (BN-80915) and 9-aminocamptothecin (IDEC-13'), SN-38, ST1481, karanitecin (BNP1350), indolocarbazoles (e.g., NB-506), protoberberines, intoplicines, idenoisoquinolones, benzo-phenazines, NB-506, and combinations thereof.

Pharmaceutically acceptable carriers are well known in the art (see, e.g., Remington's Pharmaceutical Sciences (Mack Publishing Co., Easton, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier used in a pharmaceutical composition of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

The pharmaceutical compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monosterate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be “acceptable” in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Pharmaceutical compositions suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type maybe employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Pharmaceutical compositions for rectal or vaginal administration may be presented as a suppository, which maybe prepared by mixing one or more active ingredient(s) with one or more suitable nonirritating carriers which are solid at room temperature, but liquid at body temperature and, therefore, will melt in the rectum or vaginal cavity and release the active compound. Pharmaceutical compositions which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active compound may be mixed under sterile conditions with a suitable pharmaceutically-acceptable carrier. The ointments, pastes, creams and gels may contain excipients. Powders and sprays may contain excipients and propellants.

Pharmaceutical compositions suitable for parenteral administrations comprise one or more compound in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug, it is desirable to slow its absorption from subcutaneous or intramuscular injection. This may be accomplished by the use of a liquid suspension of crystalline or amorphous material having poor water solubility.

The rate of absorption of the drug then depends upon its rate of dissolution which, in turn, may depend upon crystal size and crystalline form. Alternatively, delayed absorption of a parenterally-administered drug may be accomplished by dissolving or suspending the drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

Preferably, the mammal is a human. Preferably, the condition is characterized by cells with enhanced RAS signaling activity. In another preferred embodiment, the condition is cancer. Preferably, the cancer is selected from the group consisting of leukemia, non-small cell lung carcinoma, colon cancer, CNS cancer, melanoma, ovarian cancer, renal cancer, prostate cancer, breast cancer, and pancreatic cancer.

In another embodiment, the present invention is a method of treating a condition in a mammal, as defined above. This method includes administering to the mammal a therapeutically effective amount of a composition or pharmaceutical composition that contains a pharmaceutically acceptable carrier and a compound according to formula I, Ia, Ib, II, IIa, IIb, III, IIIa, IV, IVa, IVb, IVc, IVd, and/or V, including compounds 1-37.

Additional methods of treating a condition in a mammal are provided, comprising administering to the mammal a therapeutically effective amount of a compound selected from the group consisting of compounds of formula VI, compounds of formula VII, compounds of formula VIII, compounds of formula IX, and combinations thereof.

Further methods of treating a condition in a mammal are also provided. These methods comprise administering to the mammal a therapeutically effective amount of a pharmaceutical composition comprising a pharmaceutically acceptable carrier and a therapeutically effective amount of a compound selected from the group consisting of compounds of formula VI, compounds of formula VII, compounds of formula VIII, compounds of formula IX, and combinations thereof.

Other methods of treating a condition in a mammal are provided. These methods comprise administering to the mammal a therapeutically effective amount of a compound according to any one of formulas X, Xa, Xb, X1, X2, XII, XIII, XIV, XV, stereoisomers of Compound 27 of formulas A, B, C, and D, stereoisomers of Cyclized Compound 27 of formulas E, F, G, and H, or a N-oxide, crystalline form, hydrate, or pharmaceutically acceptable salt thereof.

Further methods of treating a condition in a mammal are also provided. These methods comprise administering to the mammal a therapeutically effective amount of a compound according to any one of formulas X, Xa, Xb, X1, X2, XII, XIII, XIV, XV, stereoisomers of Compound 27 of formulas A, B, C, and D, stereoisomers of Cyclized Compound 27 of formulas E, F, G, and H, or a N-oxide, crystalline form, hydrate, or pharmaceutically acceptable salt thereof.

In these embodiments, preferably, the mammal is a human. Preferably, the condition is characterized by cells with enhanced RAS signaling activity. In another preferred embodiment, the condition is cancer. Preferably, the cancer is selected from the group consisting of leukemia, non-small cell lung carcinoma, colon cancer, CNS cancer, melanoma, ovarian cancer, renal cancer, prostate cancer, breast cancer, and pancreatic cancer.

An additional embodiment of the present invention is a method for identifying RAS-selectively lethal compounds. This method includes the steps of:

(a) determining a percent growth inhibition ("% GI") of candidate compounds in a BJ cell system comprising a plurality of isogenic cell lines at least one of which is non-tumorigenic and at least one of which is tumorigenic, wherein a % GI of at least 90% at a concentration of about 1 μM or less in the candidate compound in at least one tumorigenic BJ cell line is considered to be a lethal compound, (b) determining a potency profile, in the BJ cell system, of the candidate compounds from (a) determined to be lethal, wherein those candidate compounds having at least a 4-fold differential potency between non-tumorigenic and tumorigenic cell lines in the BJ cell system are considered to be selective, and (c) identifying the selective candidate compounds from (b), which have a similar potency profile for each of the tumorigenic cell lines in the BJ cell system, wherein those candidate compounds having a similar potency profile are considered to be RAS-selectively lethal compounds.

Preferably, in this method, the BJ cell system comprises isogenic cell lines, which are derived from BJ cells. The BJ cell lines are selected from the group consisting of BJ-TERT, BJ-TERT/LT/ST, BJ-TERT/LT/ST/RAS$^{V12}$, BJ-TERT/LT/RAS$^{V12}$/ST, and BJ-TERT/p53DD/CDK4/cyclinD1/ST/RAS$^{V12}$. The construction of an exemplary BJ cell system is described in more detail below and in, e.g., Dolma et al., Cancer Cell, 3:285-296 (2003), which is incorporated by reference as if recited in full herein and in, e.g., Hahn et al., 1999. In the isogenic cell lines used, oncogenic elements were sequentially introduced to convert human primary fibroblast cells into tumorigenic cells. Briefly, BJ cells were engineered successively to express the catalytic subunit of human telomerase (hTERT), the SV40 large T and small T antigens (LT and ST), and an oncogenic allele of HRAS (HRAS$^{G12V}$). These cells lines are identified as BJ-TERT, BJ-TERT/LT/ST, and BJ-TERT/LT/ST/RAS$^{V12}$. Only the BJ-TERT/LT/ST/RAS$^{V12}$ cells form tumors in nude mice. Also, phenotypic changes associated with expression of each genetic element are indicated along with cell doubling time. Both RAS$^{V12}$ harboring cells (BJ-TERT/LT/ST/RAS$^{V12}$ and BJ-TERT/p53DD/CDK4/cyclinD1/ST/RAS$^{V12}$ cells) can form tumors in nude mice but differ in cell doubling time, which allows filtering out proliferation-rate dependent lethal compounds. Preferably, in the method for identifying RAS-selectively lethal compounds, step (a) is carried out using BJ-TERT/LT/ST/RAS$^{V12}$ cells.

Preferably, in this method, the tumorigenic cell lines in the BJ cell system are selected from BJ-TERT/LT/ST/RAS$^{V12}$, BJ-TERT/LT/RAS$^{V12}$/ST, and BJ-TERT/p53DD/CDK4/cyclinD1/ST/RAS$^{V12}$.

In another embodiment of the present invention, a method for characterizing the mechanism of action of a RAS-selectively lethal candidate compound is provided. In this method, a compound already determined to be RAS-selectively lethal using the procedures described above is used in a death kinetics assay with a tumorigenic BJ cell line using a plasma membrane integrity assay. Preferably, in the death kinetics assay the tumorigenic BJ cell line is BJ-TERT/LT/ST/RAS$^{V12}$. Preferably, the plasma membrane integrity assay is a trypan blue assay, which is described in detail in the Examples. The cell killing effects of hit compounds are confirmed using the trypan blue assay.

In this method, if the plasma membrane of the tumorigenic cell line becomes permeable within about 8-hours of treatment with a candidate compound, the candidate compound is considered to have a mechanism of action similar to the compounds of Formula IV. More particularly, if the plasma membrane of the tumorigenic cell line becomes permeable within about 8-hours of treatment with a candidate compound, the candidate compound is considered to have a mechanism of action similar to compound 27.

If, however, the plasma membrane of the tumorigenic cell line becomes permeable within about 12-hours of treatment with a candidate compound, the candidate compound is considered to have a mechanism of action similar to the compounds of Formula II. More particularly, if the plasma membrane of the tumorigenic cell line becomes permeable within about 12-hours of treatment with a candidate compound, the candidate compound is considered to have a mechanism of action similar to compound 3.

In another embodiment of the present invention, a further method for characterizing the mechanism of action of a RAS-selectively lethal compound is provided. In this method, compound(s) already determined to be RAS-selectively lethal candidate compound(s) using the procedures described above is/are used in a counter-screen with a tumorigenic BJ cell line and a panel of biologically active compounds with known function. Next, those biologically active compounds that reverse the lethality of each candidate compound are determined, wherein the specific pattern of reversed lethality defines a perturbation profile. If the perturbation profile of a RAS-selectively lethal compound is the same as, or similar to, a compound having a previously defined perturbation profile, the two compounds are considered to have the same or similar mechanisms of action. A flow chart showing the screening strategy for identifying genetically selective compounds and ruling out proliferation-dependent compounds is provided in FIG. 34.

In this method, it is preferred that the panel of biologically active compounds includes the following: GSH (Reduced glutathione), L-Mimosine, Actinomycin D, Cyclohexamide, z-VAD(OMe)-fmk, Boc-D(OMe)-fmk, DPQ, BHT, alpha-tocopherol (Vit. E), ALLN (Calpain inhibitor 1), TLCK, EGTA, L-NAME (HCl), Gd3+(6H2O), Co++ (6H2O), 3-methladenine, methyl pyruvate, NMMA, Desferrioxamine Mesylate, U0126, SP600125, SB-203580, Wortmannin, LY294002, SH6, Y27632, HA1077 (2HCl), Kenpaullone, LiCl, (R)-Roscovitine, PP2, SU6656, H89 (2HCl), KN62, Ro 31-8220, and Rapamycin.

More particularly, the panel of biologically active compounds, their respective functions, and the concentration of each biologically active compound used in the counter screen are shown in Table 1:

TABLE 1

Biologically active compounds used for screening.

| Compound | Function | Final Concentration |
|---|---|---|
| GSH (Reduced glutathione) | inactivate cisplatin, antioxidant | 5 mM |
| L-Mimosine | cell cycle blocker, G1 arrest | 350 uM |
| Actinomycin D | transcription blocker | 16 nM |
| Cyclohexamide | translation blocker | 1.5 uM |
| z-VAD(OMe)-fmk | pan-caspase inhibitor | 50 uM |
| Boc-D(OMe)-fmk | pan-caspase inhibitor | 50 uM |
| DPQ | PARP inhibitor | 10 uM |
| BHT | anti-oxidant | 400 uM |
| alpha-tocopherol (Vit. E) | anti-oxidant | 100 uM |
| ALLN (Calpain inhibitor 1) | cysteine protease inhibitor | 45 uM |
| TLCK | serine protease inhibitor | 100 uM |
| EGTA | calcium chelator | 2 mM |
| L-NAME (HCI) | anti-oxidant | 300 uM |
| Gd3+ (6H2O) | direct blocker of I(OGD) current and Ca2+ | 656 uM |
| Co++ (6H2O) | calcium channel blocker | 656 uM |
| 3-methladenine | macroautophagy inhibitor | 5 mM |
| methylpyruvate | cell-permeant bioenergetic substrate | 5 mM |
| NMMA | inhibits NO formation from Arg | 250 uM |
| Desferrioxamine Mesylate | Fe mobilizer (inhibits fenton chemistry) | 150 uM |
| U0126 | MEK1/2 inhibitor | 10 uM |
| SP600125 | JNK inhibitor | 10 uM |
| SB-203580 | SAPK inhibitor | 10 uM |
| Wortmannin | PI3K inhibitor | 1 uM |
| LY294002 | PI3K inhibitor | 50 uM |
| SH6 | inhibit phosphorylation of Akt | 20 uM |
| Y27632 | ROCK, PRK2 inhibitor | 20 uM |
| HA1077 (2HCl) | ROCK, PRK2 inhibitor | 50 uM |
| Kenpaullone | GSK-3, CDKs inhibitor | 10 uM |
| LiCl | GSK-3 inhibitor | 10 uM |
| (R)-Roscovitine | CDKs inhibitor | 50 uM |
| PP2 | Src, Fyn, Lck inhibitor | 5 uM |

TABLE 1-continued

Biologically active compounds used for screening.

| Compound | Function | Final Concentration |
|---|---|---|
| SU6656 | Src, Fyn, Lck inhibitor | 50 uM |
| H89 (2HCl) | inhibit PKA, MSKs, but not RSKs | 25 uM |
| KN62 | CaM-Ks inhibitor | 10 uM |
| Ro 31-8220 | inhibit conventional PKCs | 5 uM |
| Rapamycin | mTOR inhibitor | 0.1 uM |

In the present invention, those RAS-selectively lethal compound(s) that have perturbation profiles in which drug candidate-induced cell death is inhibited by a protein synthesis inhibitor, a MEK inhibitor, a general Src-kinase inhibitor, an iron chelator, and an antioxidant are considered to have the same or similar mechanism of action as a compound of Formula II, such as for example, compound 3.

In the present invention, those RAS-selectively lethal compound(s) that have perturbation profiles in which drug candidate-induced cell death is inhibited by reduced glutathione only are considered to have the same or similar mechanism of action as a compound of Formula III, such as for example, compound 6.

In the present invention, those RAS-selectively lethal compound(s) that have perturbation profiles in which drug candidate-induced cell death is inhibited by a protein synthesis inhibitor and an iron chelator are considered to have the same or similar mechanism of action as a compound of Formula V, such as for example, compound 36.

In the present invention, those RAS-selectively lethal compound(s) that have perturbation profiles in which drug candidate-induced cell death is inhibited by a MEK inhibitor, an iron chelator, and a general Src-kinase inhibitor are considered to have the same or similar mechanism of action as a compound of Formula IV, such as for example, compound 27, or for example, 1S,3R Compound 27 or 1S,3R Cyclized Compound 27.

In another embodiment of the present invention, a further method for characterizing the mechanism of action of a RAS-selectively lethal compound is provided. In this method, an NCI60 test is used to determine a sensitivity profile for each compound already determined to be a RAS-selectively lethal candidate compound using the methods described above. A candidate compound having the same or similar sensitivity profile in the NCI60 test as a compound according to Formulae I-V is considered to have the same mechanism of action as such a compound of Formulae I-V. The NCI60 test is described in more detail in the Examples.

Preferably, the methods described above for identifying RAS-selectively lethal compounds are high-throughput screening methods. In the present invention, the RAS-selectively lethal compounds may be selected from any entity capable of functioning as such. Thus, in the present invention "RAS-selectively lethal compounds" are those entities that selectively kill cells that encode or express a mutant RAS protein as described in detail herein. For example, the RAS-selectively lethal compounds may be selected from antibodies, RNAi, siRNA, shRNA, antisense sequences, and small molecules. Preferably, the RAS-selectively lethal compounds are small molecules.

The following examples are provided to further illustrate the compositions and methods of the present invention. These examples are illustrative only and are not intended to limit the scope of the invention in any way.

EXAMPLES

Example 1

Materials and Methods

Cell Lines

BJ-fibroblast-derived cell lines were grown in a 4:1 mixture of DMEM to M199 supplemented with penicillin and streptomycin (pen/strep), and 15% heat-inactivated fetal bovine serum (BJ medium). TRE-fibroblast-derived cell lines and the human lung carcinoma cell line A549 were grown in DMEM supplemented with pen/strep and 10% calf serum. MS1 and SVR cells were grown in DMEM supplemented with pen/strep and 5% calf serum. The human lung carcinoma cell line Calu-1 and colon carcinoma cell line HCT116 were grown in McCoy's 5A medium supplemented with pen/strep and 10% calf serum. The human pancreas carcinoma cell line MIA PaCa-2 was maintained in DMEM supplemented with pen/strep, 10% calf serum, and 2.5% horse serum. The human fibrosarcoma cell line HT1080 was maintained in DMEM supplemented with non-essential amino acids, pen/strep, and 10% calf serum.

The BJ cell system consists of 5 isogenic cell lines that are derived from common human fibroblast cells. It contains two non-tumorigenic versions, BJ-TERT and BJ-TERT/LT/ST, and three tumorigenic versions, BJ-TERT/LT/ST/RAS$^{V12}$, BJ-TERT/LT/RAS$^{V12}$/ST, and BJ-TERT/p53DD/CDK4/cyclinD1/ST/RAS$^{V12}$. The true oncogenic-RAS-signal dependent lethal compound should have the same potency in the three tumorigenic cell lines because the three have oncogenic version of HRAS (RAS$^{G12V}$) in common and they have the same cell-signal context despite being engineered in a different manner.

An aim of screening was to identify compounds lethal to BJ-TERT/LT/ST/RAS$^{v12}$ cells, while having minimal effects on their isogenic cell precursors.

A549, Calu-1, HCT116 and MIA PaCa-2 cell lines have an oncogenic mutation in the KRAS gene. Compounds which tested positive in the oncogenic HRAS primary screen were also tested for their selectivity against oncogenic KRAS which is more commonly mutated in human cancers.

Compound Libraries

Compound libraries were composed of a combination of synthetic and natural product-like compounds. A number of filters were applied in choosing these compounds. The TIC library was selected in part for natural product-like features, including a number of chiral centers, number of unsaturated rings, and lack of steroids, which are abundant in natural-product collections. The BBB library was filtered to eliminate reactive or toxic groups that are unlikely to make effective drug molecules. The filters included the presence of chiral centers, the presence of unsaturated rings, the lack of steroids, and the lack of reactive or toxic groups. In total, 47,725 small molecules were obtained from different providers: 2,056 from TimTec; 8,669 from IBS; 17,520 from Chembridge; 12,240 from Asinex; 5,240 from Life Chemicals; and 2,000 from MicroSource Discovery. All compounds were prepared as 4 mg/mL solutions in DMSO in 384-well polypropylene plates (Greiner, cat.#781280) and stored at −80° C. These plates are designated as mother plates. Wells in the outer two rows and columns were left empty to minimize edge effects from affecting the screening data.

Identification of Small Molecules that are Synthetic Lethal to Oncogenic RAS: Primary Screening Daughter plates were prepared by diluting mother plates 75-fold in DMEM to obtain a compound concentration of 53.3 μg/mL with 1.33% DMSO in 384-deep-well polypropylene plates (Greiner, cat.#781270). Assay plates were prepared by seeding 1,000 BJ-TERT/LT/ST/RAS$^{V12}$ cells per well in 36 μL of growth media in black, clear-bottom, 384-well plates (Corning Inc., cat. #3712). Columns 3-22 and rows C through N were treated with compounds from a daughter library plate by transferring 4 μL from the daughter library plate to the assay plates. The final compound concentration in the assay plates was 5 μg/mL with 0.1% DMSO. All liquid handling was carried out using a Biomek FX AP384 module (Beckman Coulter). The assay plates were incubated for 48 hours at 37° C. in a humidified incubator containing 5% $CO_2$. Cell viability was measured using alamar blue (Invitrogen, cat.# DAL1100), which detects changes in cellular reductive potential (Nociari et al., 1998). Subsequently, percent growth inhibition was calculated. All experiments were performed in triplicate and median percent growth inhibition was determined. Compounds that inhibited alamar blue metabolism in BJ-TERT/LT/ST/RAS$^{v12}$ cells more than 50% were considered initial hits.

Retesting Compounds in Dilution Series in Three BJ Cell Lines

Empty "step-daughter plates" were filled with 50 μL DMEM, except for columns 3 and 13, where 100 μL of hit compound solution were cherry-picked from daughter plates. After compound transfer, 2-fold dilution series across columns 3 through 12 and columns 13 through 22 was made by transferring 50 μL of compound solution to the next column successively (10-point dilution series), with extensive mixing. Hit-picking and 2-fold dilution series were carried out using Biomek FX Span-8 module (Beckman Coulter). Assay plates were prepared by seeding 1,000 BJ-TERT, BJ-TERT/LT/ST, and BJ-TERT/LT/ST/RAS$^{V12}$ cells per well in 36 μL growth medium. Cells in assay plates were treated with compounds from step-daughter plates by transferring 4 μL. The final concentration of the compound was 5.33 μg/mL to 0.01 μg/mL in this 10-point, 2-fold dilution series. Assay plates were returned to the culture incubator and maintained for 48 hours before adding alamar blue.

Retesting Compounds in Dilution Series in Four BJ Cell Lines

Fresh daughter plates were made from the mother plate and cherry-picked hits from the first round, 2-fold dilution series experiment as described above. Assay plates were prepared by seeding 1,000 BJ-TERT, BJ-TERT/LT/ST, BJ-TERT/LT/ST/RAS$^{V12}$ or BJ-TERT/p53DD/CDK4/cyclinD1/ST/RAS$^{V12}$ (DRD) cells per well in 32 μL growth media. Cells in the assay plates were treated with compounds from the step-daughter plate by transferring 8 μL solution. The final concentration of the compound was 10.66 μg/mL to 0.02 μg/mL in a 10-point, 2-fold dilution series manner. Assay plates were returned to the culture incubator and maintained for 48 hours before adding alamar blue.

Alamar Blue Assay

Cells were seeded in 384-well assay plates, treated with candidate compounds, and incubated in the culture incubator in 40 μL culture volume per well. After 24 or 48 hours of compound treatment, 10 μL of 50% alamar blue solution in growth medium was transferred to the assay plates, which resulted in 10% final concentration alamar blue. Plates were incubated further for 16 hours to allow reduction of alamar blue, which results in the generation of red fluorescence. The fluorescence intensity was determined using a Victor 3 plate reader (Perkin Elmer) with a 535 nm excitation filter and a 590 nm emission filter.

Vi-Cell Analysis (Trypan Blue Assay)

200,000 cells were seeded in 6-well plates and treated with the indicated amount of 2-fold dilution series concentration of a candidate compound in 2 mL BJ growth medium. After 24 hours, cells were released with trypsin/EDTA, harvested in 1.1 mL growth medium, and transferred to a Vi-Cell (Beckman Coulter) disposable cup. After, trypan blue staining, 100 images of sample were taken and analysis of the images was carried out automatically by a Vi-Cell cell viability analyzer (Beckman Coulter).

Counter Screening with Biologically Active Compounds

Biologically active compounds listed in Table 1 were dissolved in BJ medium at 10× final concentration and aliquoted into eppendorf tubes. 100 μL of each 10× solution was transferred to column 1 to column 12 or column 13 to column 24 of a single row in a 384-well daughter plate. This plate was designated as ‘10× biologically active plate’. In order to prepare lethal compound solution, Erastin and compounds 3, 6, 27, and 36 were dissolved in BJ medium at a concentration of 100 μg/mL, 400 μg/mL, 400 μg/mL, 100 μg/mL, and 200 μg/mL, respectively. Empty daughter plates were filled with 50 μL BJ media except for columns 5 and 13 where 100 μL of each lethal solution was transferred. After lethal solution transfer, 2-fold dilution series across columns 5 to 12 and columns 13 to 20 was made by transferring 50 μL compound solution to the next column successively (8-point dilution series), with mixing. These five plates were each designated ‘10× lethal plate’. Five assay plates were prepared by seeding 4,000 BJ-TERT/LT/ST/RAS$^{V12}$ cells per well in 32 μL of growth media in black, clear bottom 384-well plates. Cells in assay plates were first treated with biologically active compounds by transferring 4 μL from the 10× inhibitor plate. Cells were then treated with each lethal compound in a 2-fold dilution series by transferring 4 μL solution from each 10× lethal plate. Assay plates were returned to the culture incubator and maintained for 24 hours before adding alamar blue. Percent growth inhibition (% GI) was calculated by the following formula using fluorescence intensity values:

$$\% GI=100*(1-(X-N)/(-N))$$

wherein

X is the fluorescent intensity value measured at 590 nm for cells treated with biologically active compound and lethal compound;

N is the fluorescent intensity value measured at 590 nm for a control containing no cells (i.e. biologically active compound in growth media); and P is the fluorescent intensity value measured at 590 nm for a control containing no lethal compound (i.e., cells treated with biologically active compound).

Counter Screening with Iron Chelators

BJ-TERT/LT/ST/RAS$^{V12}$ cells were seeded in 384-well assay plates at a concentration of 4,000 cells per well in 32 μL volume. Cells were treated with iron chelators by transferring 4 μL of 1 mM deferoxamine mesylate (Calbiochem, cat.#252750), 500 μM compound 1a (Chembridge, cat.#5175092), 1 mM compound 2 (Ryan Scientific, cat.#LT01784723), or 100 μM compound 311 (Chembridge, cat.#5135701) in growth media to the assay plate. Then, 4 μL was transferred from the ‘10× lethal plate’ (described in ‘counter screening with biologically active compounds’) to the assay plate in order to induce cell death. Assay plates were incubated for 24 hours and alamar blue was added to the plates at a final concentration of 10%.

Effect of Cell Cycle Inhibitors on Compound 36-Induced Cell Death

BJ-TERT/LT/ST/RAS$^{V12}$ cells were seeded in a 384-well assay plate at a concentration of 4,000 cells per well in 32 μL culture volume. Cells were treated with cell cycle inhibitors by transferring 4 μL of 500 μM apigenin (Sigma, cat.#A3145), 1.5 mM monastrol (Sigma, cat.#M8515), 1 mM olomoucine (Sigma, cat.#00886), 2 μM Nocodazole (Sigma, cat.#M1404), 6 mM Hydroxy-urea (Sigma, cat.#H8627), 0.1 μM colchicine (Sigma, cat.#D6165), or 50 μM Rapamycine (Sigma, cat.#RO395) in growth media to the assay plate. Then, 4 μL was transferred from a daughter plate that had an 8-point, 2-fold dilution series of Compound 36 (starting at column 5, 200 μg/mL and ending at column 12, 1.5625 μg/mL in growth media) to the assay plate. The assay plate was incubated for 24 hours and alamar blue was added to the assay plate at a final concentration of 10%.

Monitoring Cellular Iron Level Using Flow Cytometry

Cells were seeded in 6-well plates (200,000 cells per well) in BJ medium. The next day, the cell monolayer was washed with phosphate buffered saline (“PBS”) twice and stained with 5 μM of Phen Green SK, diacetate (Molecular Probe, cat.#P14313) in PBS by incubating the plate for 15 minutes in a culture incubator. Cells were released with trypsin/EDTA, harvested in 2 mL PBS, and centrifuged at 1,000 rpm for 5 min. The cell pellet was re-suspended in 1 mL of PBS, the cell suspension was transferred to disposable FACS tubes, and the fluorescence profile of the sample was monitored using a FACSCalibur system (BD Biosciences).

Western Blot

Monitoring Cleavage of PARP and Caspase-3 Upon Compound Treatment

2×10$^{6}$ BJ-TERT/LT/ST/RAS$^{V12}$ cells were seeded in 10 cm dishes and treated with 1 μM staurosporine, 10 μg/mL erastin, 20 μg/mL Compound 3, and 1 μg/mL Compound 27 for 16 h. Both dying cells and live cells in each 10 cm dish were harvested and collected in the same 15 mL tubes by centrifuging cell suspension at 1,000 rpm for 5 min. Cell pellets were washed three times with PBS and cells were lysed in 200 μL of denaturing lysis buffer (50 mM HEPES KOH [pH 7.4], 40 mM NaCl, 2 mM EDTA, 1.5 mM $Na_3VO_4$, 50 mM NaF, 10 mM sodium pyrophosphate, 10 mM sodium β-glycerophosphate, 0.5% Triton X-100, and protease inhibitor tablet [Roche, cat.#11836170001]). Protein content was quantified using a Bio-Rad protein assay reagent (Bio-Rad, cat.#500-00006). Equal amounts of protein were resolved on SDS-polyacrylamide gels. The electrophoresed proteins were transblotted onto a PVDF membrane, blocked with 5% milk, and incubated with rabbit primary antibodies specific to: PARP (Santa Cruz, cat.#sc-7150), cleaved caspase-3 (Cell Signaling Technology, cat.#9661) overnight at 4° C. The membrane was then incubated in IRDye 800 goat anti-rabbit antibody (Li-cor Bioscience cat.#926-32211) at 1:3,000 dilutions for 45 min at room temperature. After washing off the unbound antibodies, membranes were scanned using the Odyssey™ Imaging System (Li-cor Bioscience).

Basal Expression Level of TfR1

BJ-TERT, BJ-TERT/LT/ST, and BJ-TERT/LT/ST/RAS$^{V12}$ cells were seeded prior to the experiment in 10-cm dishes and allowed to grow to 80% confluence. The cell monolayer was washed three times with PBS and cells were lysed in 200 μL of denaturing lysis buffer (50 mM HEPES KOH (pH 7.4), 40 mM NaCl, 2 mM EDTA, 1.5 nN $Na_3VO_4$, 50 mM NaF, 10 mM sodium pyrophosphate, 10 mM sodium β-glycerophosphate, 0.5% Triton X-100, and protease inhibitor tablet (Roche, cat.#11836170001)). Protein content was quantified using a Bio-Rad protein assay reagent (Bio-Rad, cat.#500-

00006) according to the manufacturer's instructions. Equal amounts of protein were resolved on SDS-polyacrylamide gels. The electrophoresed proteins were transblotted onto a PVDF membrane, blocked with 5% milk, and incubated with goat primary antibodies specific to transferrin receptor 1 (Santa Cruz, cat.#sc-7087) overnight at 4° C. The membrane was then incubated in IRDye 800 rabbit anti-goat antibody (Rockland Immunochemicals cat.#605-432-013) at 1:3,000 dilution for 45 minutes at room temperature. After washing off the unbound antibodies, membranes were scanned using the Licor Odyssey™ Imaging System.

TfR1 Expression Level Upon Compound Treatment $2\times10^6$ BJ-TERT/LT/ST/RAS$^{V12}$ cells were seeded in 10 cm dishes and treated with the iron chelators deferoxamine mesylate, 2, or 311, or Erastin, Compound 3, Compound 6, Compound 27, or Compound 36 at the indicated concentrations for 24 hours. Both dying cells and live cells in each 10 cm dish were then harvested and collected in the same 15 mL tubes by the centrifuging cell suspension at 1,000 rpm for 5 minutes. Cell pellets were washed three times with PBS and cells were lysed in 200 μL of denaturing lysis buffer. Proteins in the cell lysate were quantified and resolved on SDS-polyacrylamide gels as described above. The membrane was incubated with anti-transferrin-receptor-1 (Santa Cruz, cat.#sc-7087) and then with IRDye 800 rabbit anti-goat antibody (Rockland Immunochemicals, cat.#605-432-013).

shRNA Knock Down Experiments

Virus Production

Lentiviral plasmids encoding shRNA targeting VDAC2 (cat.#SHGLY-NM_003375), VDAC3 (cat.#SHGLY-NM_005662), HRAS (cat.#SHGLY-NM_005343), NRAS (cat.#SHGLY-NM_002524), KRAS (cat.#SHGLY-NM_004985 and SHGLY-NM_033360), or TfR1 (Sigma, cat.#SHGLY-NM_003234). All shRNA clones were purchased from Sigma's MISSION® shRNA collection. Plasmid DNA was purified using a HiSpeed Plasmid Midi kit (Qiagen, cat.#12643) according to the manufacturer's instructions. On day 1, $2\times10^6$ 293T cells were seeded in 10 cm tissue culture dishes. On day 2, 2.8 μg of the shRNA-plasmid construct and 2.5 μg of pDelta8.9 and 0.28 μg of pVSV-G helper plasmids were co-transfected into the 293T cells using FuGENE® 6 Transfection Reagent (Roche, cat.#11-814-443-001). On day 3, the medium was replaced with 7.5 mL of VCM (Viral Collection Media) that consisted of DMEM supplemented with penicillin and streptomycin (pen/strep), and 30% Hyclone iFCS (Hyclone, cat.#83007-198). On day 4, in the morning, the supernatant containing virus was harvested to empty 50 mL conical tubes and 7.5 mL of fresh VCM was added back to the virus producing 293T cell monolayer. The VCM was harvested and replaced again in the evening. On day 5, in the morning, the supernatant was harvested and the 293T cell culture was bleached. The collected virus supernatant was filtered through 0.45 μm syringe filter (Nalgene, cat.#190-9945), aliquoted in 2 mL to the cryovials, and stored at −80° C. freezer until the time of use.

Generation of Stable Cell Lines

On day one, $3\times10^5$ Calu-1 cells or $2\times10^5$ HT1080 cells were seeded in 10-cm dishes; on day 2, frozen virus stock was thawed at 37° C., hexadimethrine bromide (polybrene) (Sigma, cat.#H9268) was added to the virus solution at a final concentration of 8 μg/mL and growth media from cell culture was replaced with the virus/polybrene mixture. The culture was returned to the tissue culture incubator for 2 hours, with rocking of the dishes every 30 min in order to prevent drying. After 2 h, 10 mL growth medium was added, the culture was incubated for 2 days, and cells stably expressing shRNA were selected by adding puromycin (Sigma, cat.#P9620) at a final concentration of 1.5 μg/mL.

Monitoring Drug Sensitivity

On the day of experiment, assay plates were prepared by seeding 3,000 HT1080, HT1080-pLKO, HT1080-TfR1 KD, Calu-1, Calu-1-pLKO, or Calu-1-509 cells per well in 36 μL of growth media to black, clear bottom 384-well plates. Also, assay plates were prepared by seeding 1,500 shRNA infected HT1080 or Calu-1 cells per well. Cells in assay plates were treated with each lethal compound in a 2-fold dilution series by transferring 4 μL solution from a 10× lethal plate of Erastin, Compound 3, Compound 27, or Compound 36. Assay plates were returned to the culture incubator and maintained for 24 hours before adding alamar blue. Percent growth inhibition (% GI) was calculated using fluorescence intensity values.

Real-Time RT-PCR

Total RNA was extracted using RNeasy kit (Qiagen, cat.#74104) as described in the manufacturer's handbook. One microgram of RNA sample was subject to reverse transcription reaction using TaqMan® Reverse Transcription Reagents (Applied Biosystems, cat.# N8080234) according to the manufacturer's instruction. Then, Q-PCR was carried out using Power SYBR® Green PCR Master Mix (Applied Biosystems, cat.#4367659) and 7300 Real-Time PCR System (Applied Biosystems). The sequence of primers for Q-PCR is shown in Table 11. The mRNA level of human acidic ribosomal phosphoprotein P0 was measured using the SEQ ID NOs. 17 and 18 primers and used as a reference for quantification.

Results

Compounds that inhibited alamar blue metabolism in BJ-TERT/LT/ST/RAS$^{V12}$ cells more than 50% were considered initial hits and tested in an extensive two-fold dilution series in BJ-TERT, BJ-TERT/LT/ST and BJ-TERT/LT/ST/RAS$^{V12}$ cells. The TIC library had a large number of hits (897 compounds). In this case, another round of primary screening was carried out using BJ-TERT/LT/ST cells and calculated delta percent growth inhibition (Δ% GI), as percent growth inhibition (% GI) in BJ-TERT/LT/ST/RAS$^{V12}$ cells minus % GI in BJ-TERT/LT/ST cells. 66 compounds showed up as hits with >50 Δ% GI. Also of interest were the 224 compounds in the TIC library that showed more than 90% growth inhibition in BJ-TERT/LT/ST/RAS$^{V12}$ cells, because of their strong growth inhibition activity. In total, 533 compounds (66 TIC Δ% GI hits, 224 TIC>90% GI hits, 197 BBB>50% GI hits, and 46 MS>50% GI hits) were selected from the primary screening and tested further.

In the subsequent two-fold dilution series testing, selectivity was calculated as the ratio of $GI_{50}$ values in BJ-TERT/LT/ST and BJ-TERT/LT/ST/RAS$^{V12}$ cells. Hit compounds showing at least 4-fold selectivity for HRAS$^{G12V}$ were further tested in BJ-TERT/p53DD/CDK4/cyclinD1/ST/RAS$^{V12}$ (DRD) cells that were engineered to express hTERT, oncogenic HRAS (HRAS$^{G12V}$), dominant negative p53, and constitutively active CDK4/cyclinD, which inactivates the RB protein. The p53DD/CDK4/cyclinD1 combinations substitute for the SV40 large T oncoprotein (Dolma et al., 2003; Hahn et al., 2002). DRD cells are also derived from BJ primary cells and the effects of mutations in both lines should be similar. Accordingly, ideal synthetic lethal compounds should have similar growth inhibitory potency in both cell lines. The use of DRD cells as a counter-screen enabled the elimination of compounds that (i) have idiosyncratic activity in BJ-TERT/LT/ST/RAS$^{V12}$ cells, (ii) are simply more potent in rapidly dividing cells (DRD cells divide more slowly than BJ-TERT/LT/ST/RAS$^{V12}$ cells), and (iii) target the SV40 viral protein rather than an endogenous oncogenic signaling pathway.

Seventy compounds from the two-fold dilution series experiments were used as 'inputs' for the DRD cell line test (i.e. testing whether these compounds were equally active in DRD and BJ-TERT/LT/ST/RAS$^{V12}$ cells). These 70 compounds included well-known anti-neoplastic compounds, such as camptothecins, artemisins, prostaglandins, teniposide, vinblastine, and taxol. None of these known anti-neoplastic compounds was successful in the DRD cell test (i.e. they were not equally active in DRD cells and BJ-TERT/LT/ST/RAS$^{V12}$ cells).

Figure 1:
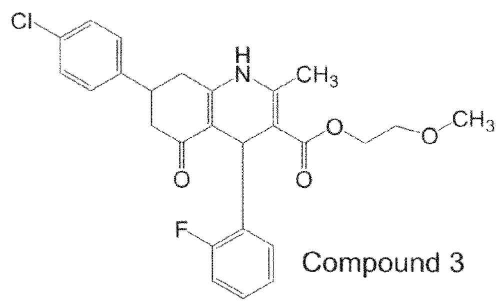
FIG. 1 shows seven compounds that were equally active in BJ-TERT/p53DD/CDK4/cyclinD1/ST/$RAS^{V12}$ (DRD) cells and BJ-TERT/LT/ST/$RAS^{V12}$ cells in an Alamar blue assay DRD counter screen. These compounds are divided into 4 groups based on their structures.
Figure 1:
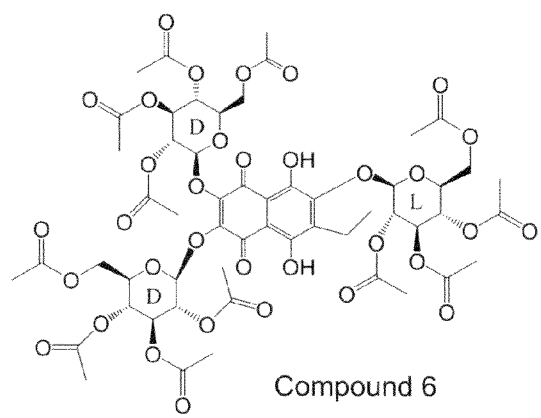
Figure 1:
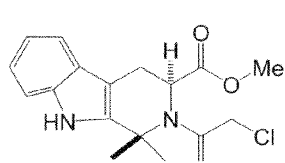
Figure 1:
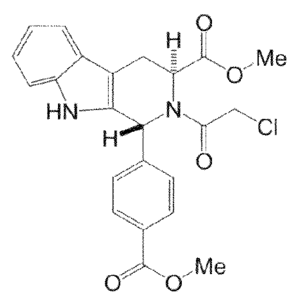
Figure 1:
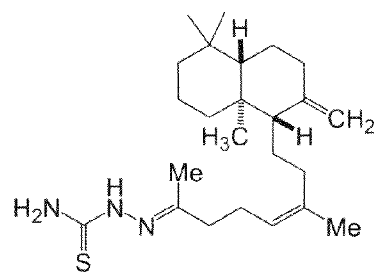
Figure 1:
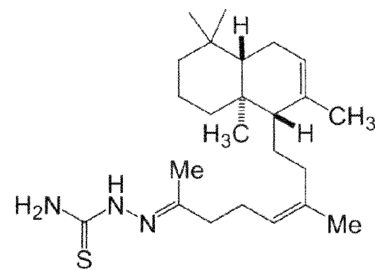

However, seven compounds with unknown functions or activities were identified (FIG. 1) that passed the DRD cell line test. These seven compounds were divided into four groups based on their structures. The most potent, selective, and active hits from each group were identified. These compounds included both synthetic compounds and natural product derivatives with four different scaffolds (FIG. 1). The most potent compound inhibited the growth of cancer cells at a concentration of a few nanomolar. The most selective compound showed 16-fold selectivity towards HRAS$^{G12V}$ harboring cells. Below, the biological activities of these four hit compounds and their structural analogs are summarized.

Compound 3

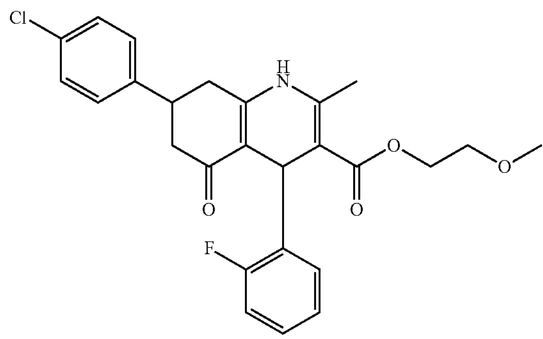

Figure 2:
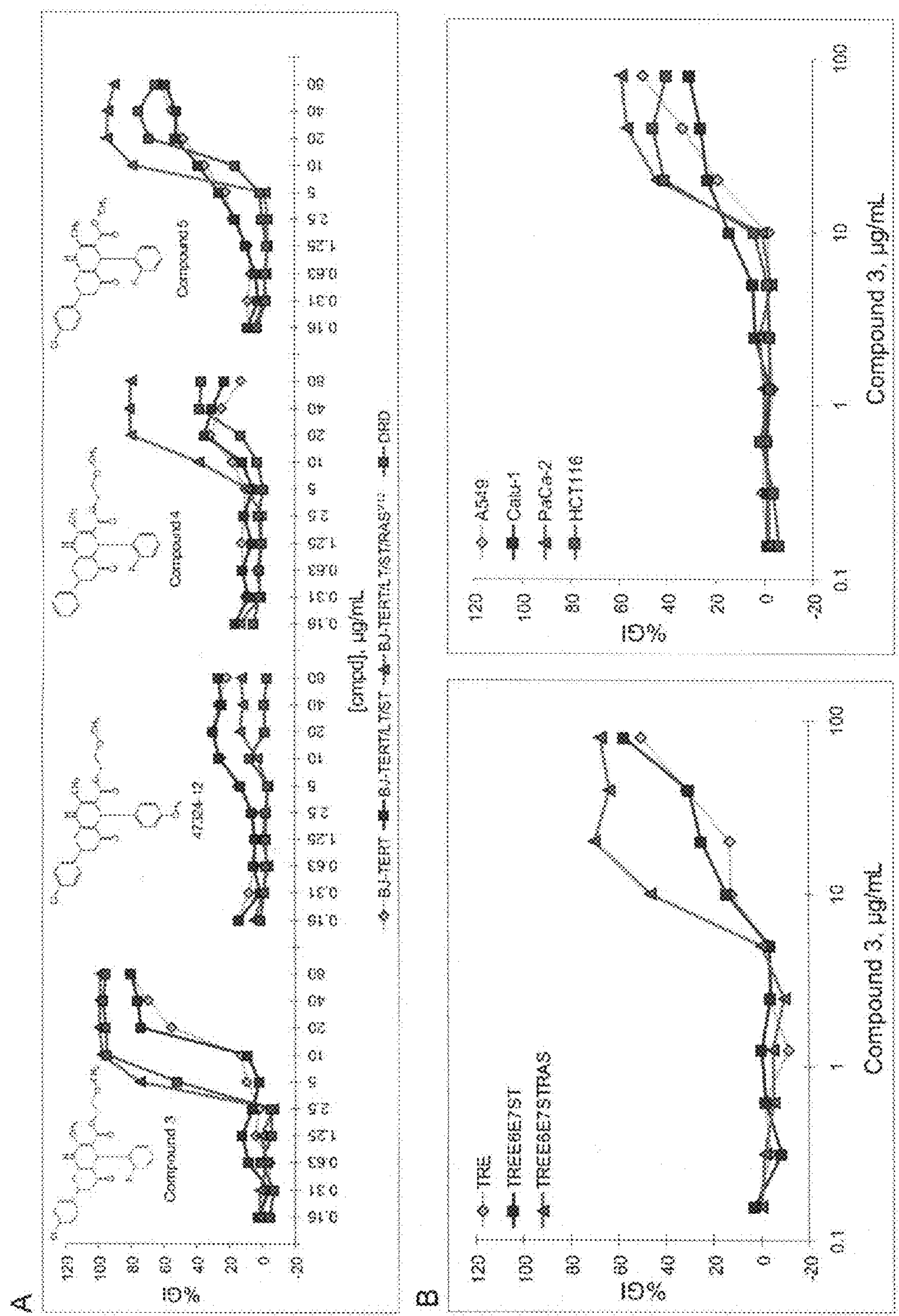
FIG. 2A shows the selectivity and potency of compounds of Formula II and other structurally related analogs (including Compounds 3, 4, 5, and 47324-12) using an Alamar blue assay in BJ-TERT (eH), BJ-TERT/LT/ST (eHLT), BJ-TERT/LT/ST/$RAS^{V12}$ (eLR), and DRD cells.
FIG. 2B shows the selectivity and potency of Compound 3 using an Alamar blue assay in TRE, TRE/E6/E7/ST, and TRE/E6/E7/ST/$RAS^{v12}$ cells (left panel) and in A549, Calu-1, PaCa, and HCT116 cells (right panel).
Figure 3:
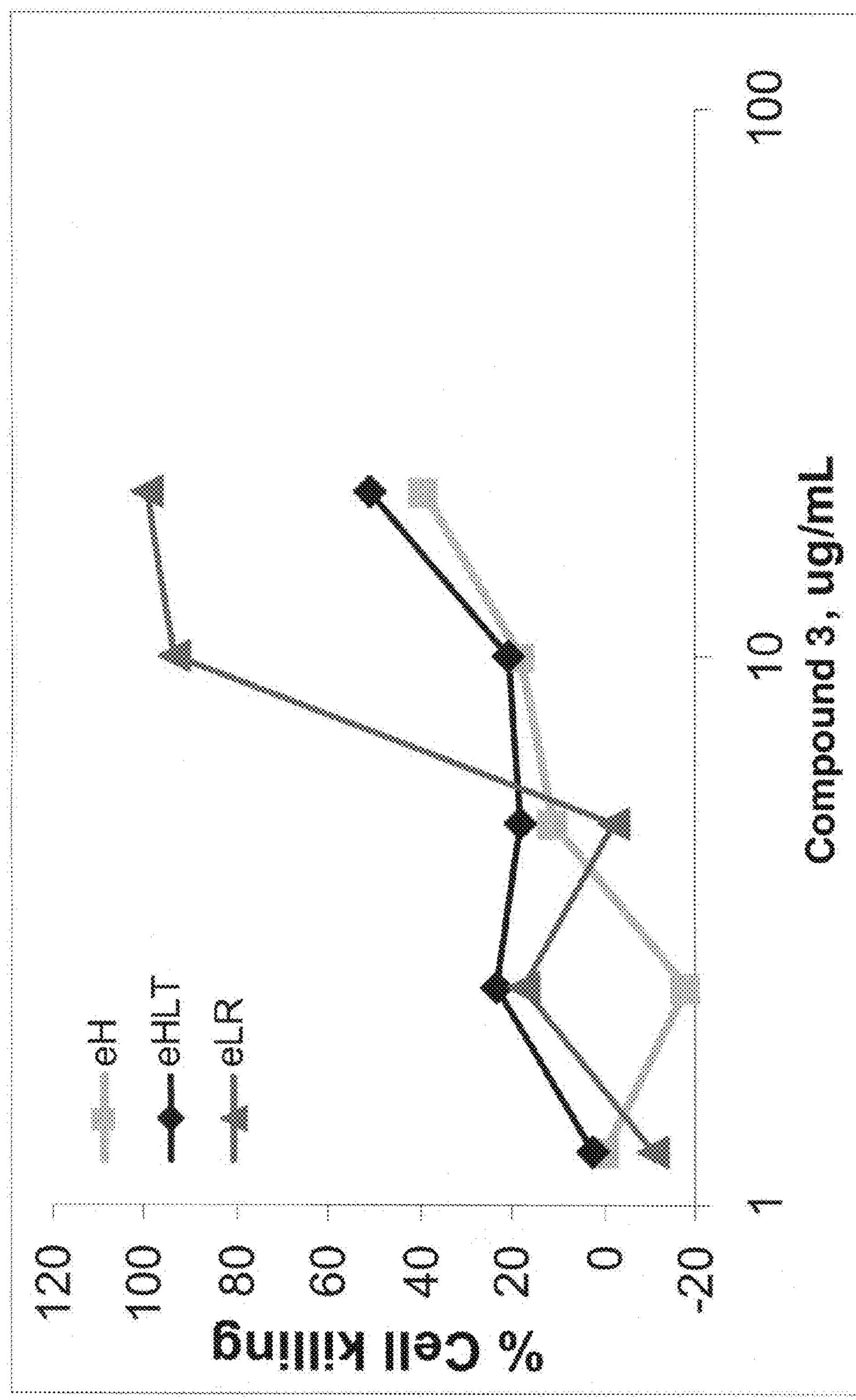
FIG. 3 shows the selectivity and potency of Compound 3 using a ViCell (Trypan blue exclusion) assay.

Compound 3 is a synthetic compound derived from 3-quinolinecarboxylic acid (FIG. 2A). This compound showed moderate potency ($IC_{90}$=10 μg/mL). The degree of selectivity against HRAS$^{G12V}$ was 4-8 folds, as measured by alamar blue reduction (FIG. 2A). The $IC_{90}$ value for Compound 3 in BJ-TERT/LT/ST/RAS$^{V12}$ cells was almost the same as in DRD cells, which indicates that its activity depends on oncogenic RAS signaling rather than proliferation rate (FIG. 2A). A trypan blue exclusion assay was performed to confirm the growth inhibitory effect and the HRAS$^{v12}$ selectivity. This was performed in a Vi-Cell (Beckman Coulter), which stains cells with trypan blue, takes 100 images, and analyzes the images to calculate the number of viable cells (i.e. cells excluding trypan blue). This assay eliminates false positives caused by auto-fluorescence or redox activity from a compound in the alamar blue assay. Trypan blue exclusion assays with Compound 3 revealed a similar level of potency and selectivity as the alamar blue assay (FIG. 3).

Figure 4:
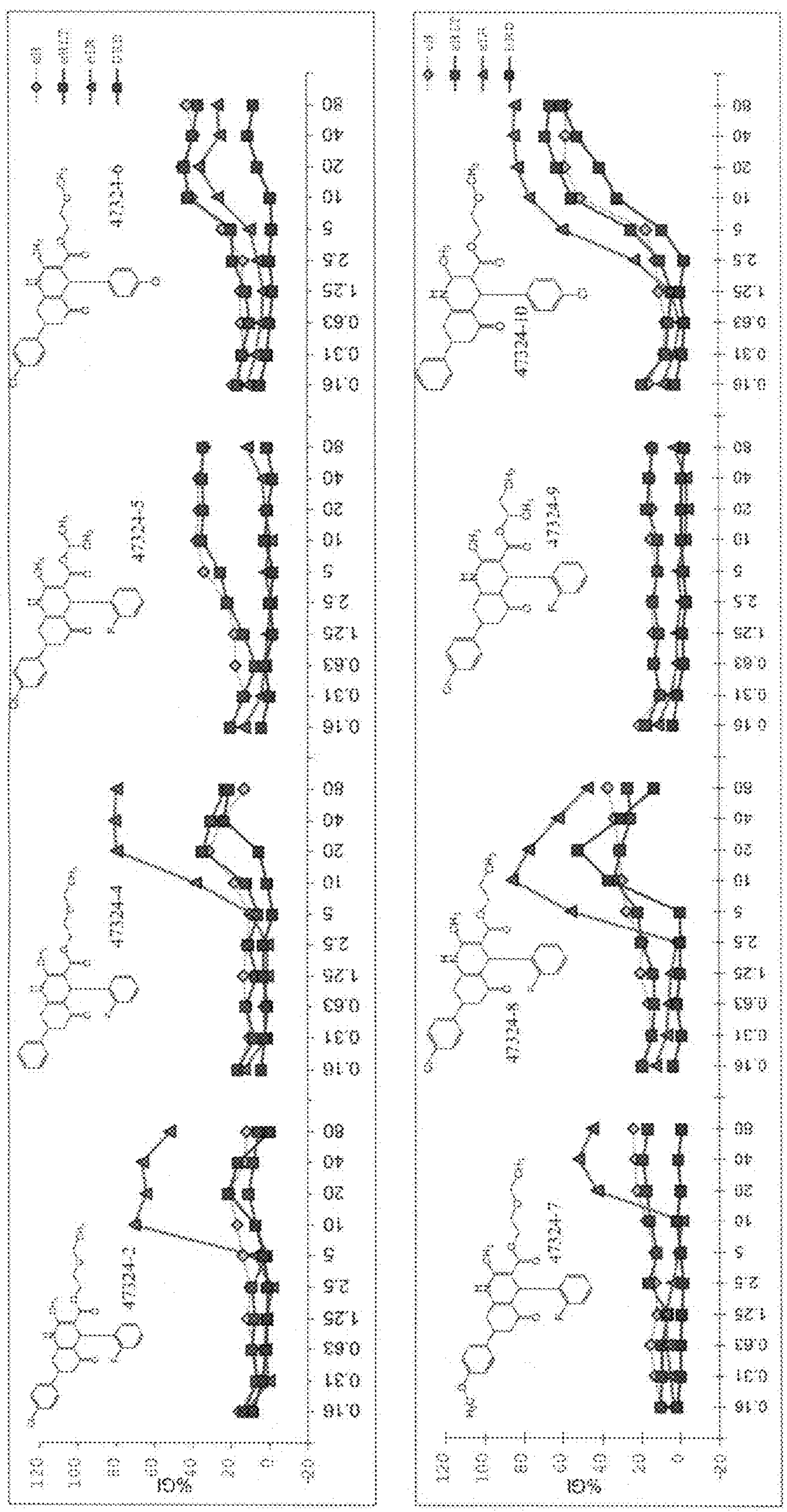
FIG. 4 shows the selectivity and potency of additional Formula II compounds and/or other structurally related analogs using an Alamar blue assay in the BJ-TERT (eH), BJ-TERT/LT/ST (eHLT), BJ-TERT/LT/ST/$RAS^{V12}$ (eLR), and BJ-TERT/p53DD/CDK4/cyclinD1/ST/$RAS^{V12}$ (DRD) cells.

Structural analogs of Compound 3 with more than 90% similarity, as assessed by the Tanimoto coefficient, were obtained. These analogs were tested in the engineered BJ cell system to define their structure-activity relationship (FIG. 2A and FIG. 4). Six analogs that have substituents on the bottom phenyl ring other than fluoro lost growth inhibitory activity, suggesting a critical role for this fluorophenyl functionality in selective growth inhibition (FIG. 2A—47324-12 and FIG. 4—47324-6, -13, -17, -21, and -32). Two analogs lacking a chloro substituent on the upper phenyl ring had a similar level of potency in BJ-TERT/LT/ST/RAS$^{V12}$ cells as the original hit, but were inactive in the DRD cell line, implying that the presence of the chlorophenyl increases the compound's genuine selectivity for oncogenic RAS signaling (FIG. 2A—Compound 4 and FIG. 4—47324-4). Three analogs differing only in the length of carboxylic acid alkyl chain showed varied potency and selectivity, which opens the possibility of modifying this region to obtain better analogs, especially in terms of solubility, and to create affinity reagents (FIG. 2A—Compound 5 and FIG. 4—47324-2 and -8).

Figure 5:
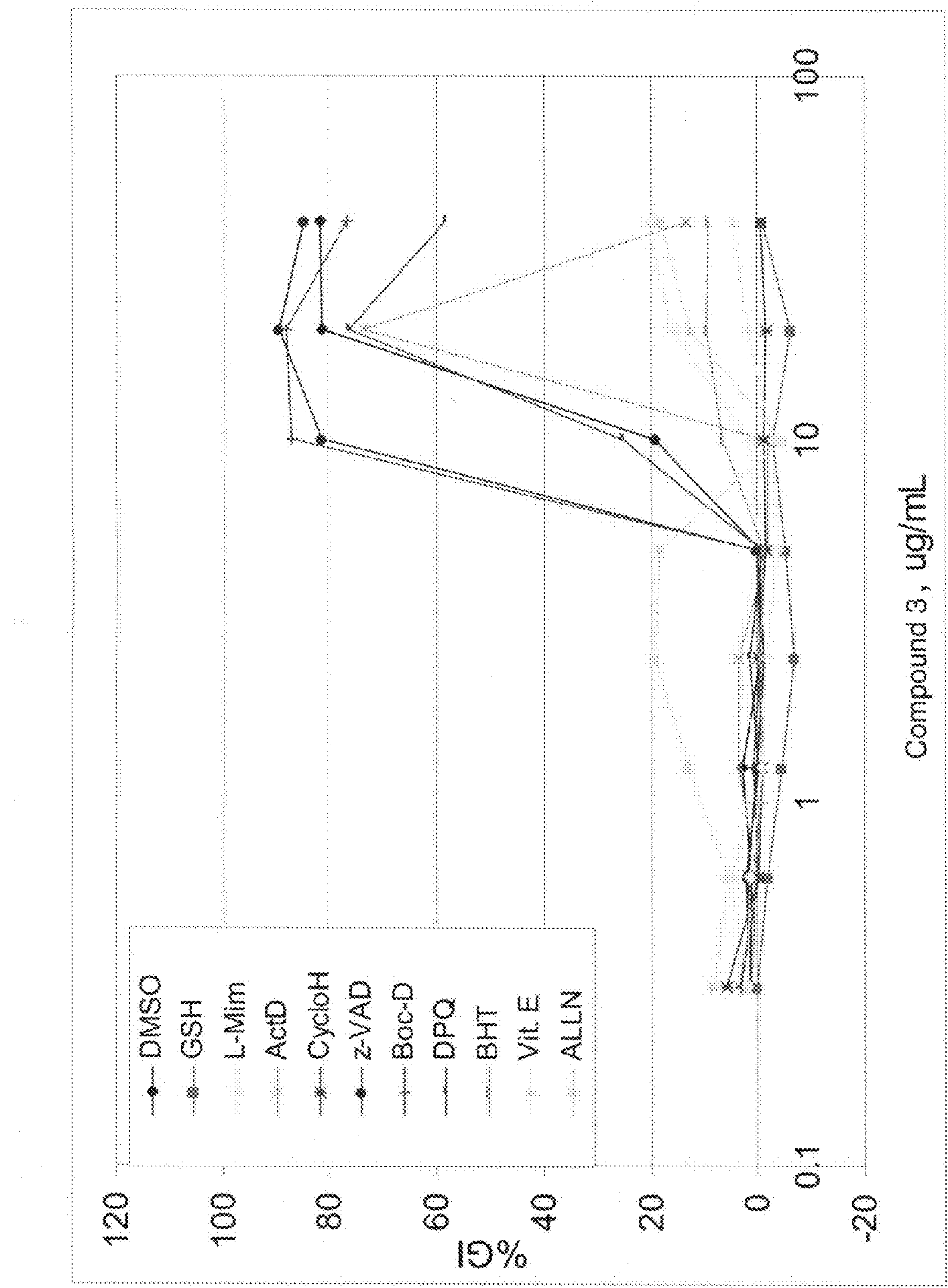
FIG. 5 shows the results of counter screening Compound 3 with 36 biologically active compounds, including antioxidants, iron chelators, and protein synthesis inhibitors in BJ-TERT/LT/ST/$RAS^{V12}$ cells.
Figure 6:
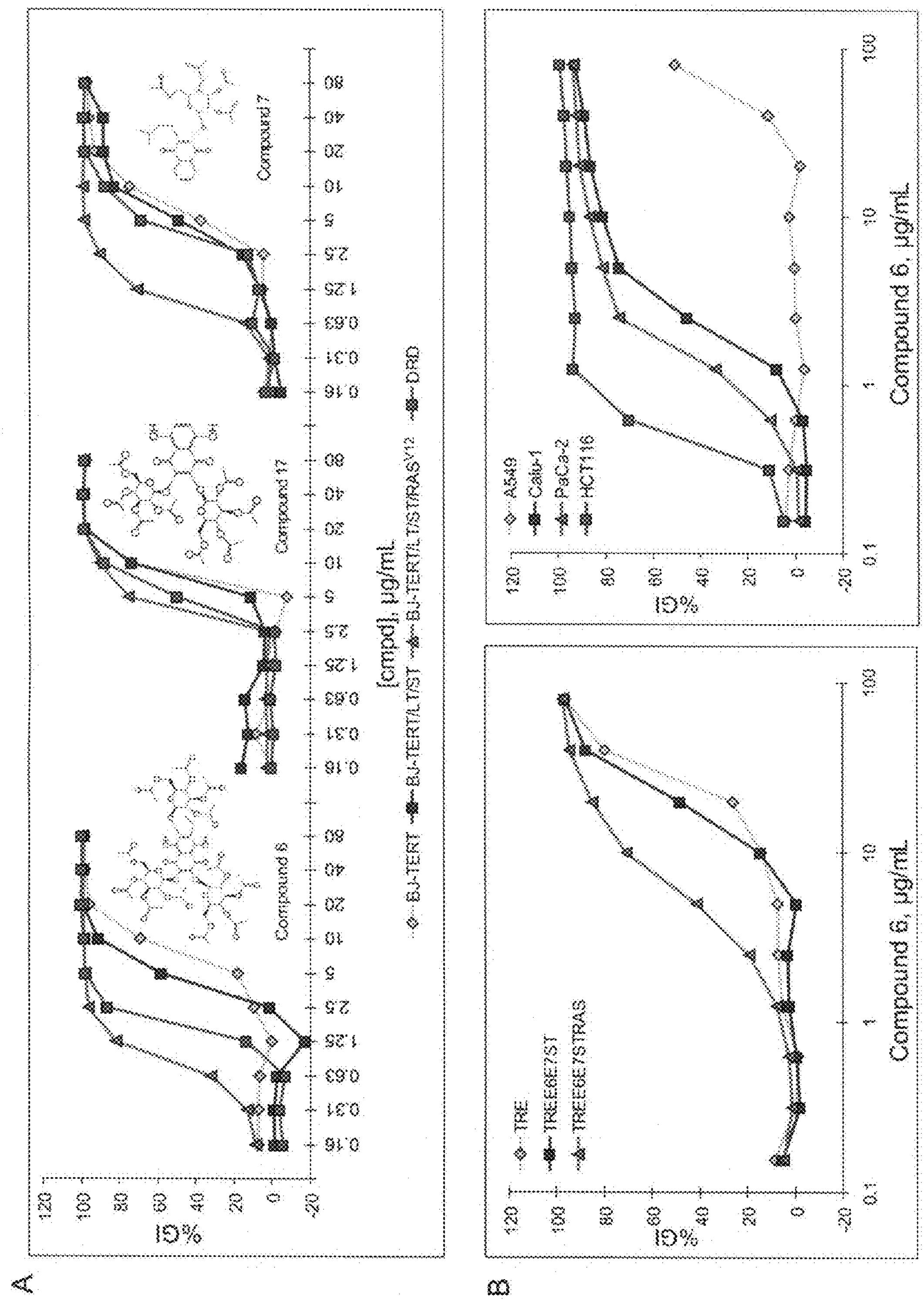
FIG. 6A shows the selectivity and potency of Compounds of Formula III (including Compounds 6, 17, and 7) using an Alamar blue assay in BJ-TERT (eH), BJ-TERT/LT/ST (eHLT), BJ-TERT/LT/ST/$RAS^{V12}$ (eLR), and BJ-TERT/p53DD/CDK4/cyclinD1/ST/$RAS^{V12}$ (DRD) cells.
FIG. 6B shows the selectivity and potency of Compound 6 using an Alamar blue assay in TRE, TRE/E6/E7/ST, and TRE/E6/E7/ST/$RAS^{v12}$ cells (left) and in A549, Calu-1, PaCa, and HCT116 cells (right).

To assess potential mechanisms of action underlying Compound 3-induced cell death, counter screening with 36 compounds having known biological functions was conducted (FIG. 5). These 36 compounds were selected based on their known property of inhibiting aspects of cell death signaling or kinase-signaling pathways related to RAS (FIG. 5). Multiple compounds were able to inhibit Compound 3-induced cell death, including anti-oxidants (GSH, BHT, Vit. E), iron chelators (L-mim, DFOM), and a protein synthesis inhibitor (cycloheximide) (FIG. 5). It is likely that Compound 3 generates iron-mediated reactive oxygen species (ROS) to kill these tumor cells. In addition, this process requires new protein synthesis.

Several kinase inhibitors suppressed Compound 3-induced cell death, but most importantly, U0126, a MEK1/2 inhibitor, completely blocked Compound 3-induced cell death, demonstrating that it is specifically the RAS-RAF-MEK pathway that causes Compound 3 sensitivity, as opposed to other aspects of RAS signaling (FIG. 5).

To ensure that the oncogenic-RAS-selective-lethal nature of these compounds was relevant beyond the BJ cell system, Compound 3 was tested in another pair of human fibroblast cell lines, with or without oncogenic RAS, known as the TRE cell system (Dolma et al., 2003; Lessnick et al., 2002). TRE cells were derived from primary human fibroblasts of another patient and were engineered to express the catalytic subunit of human telomerase (hTERT). The cells were further engineered to sequentially express human papilloma virus E6, E7 antigen, SV40 virus ST antigen, and oncogenic HRAS (HRAS$^{G12V}$). Two of the cell lines were named TRE/E6/E7/ST and TRE/E6/E7/ST/RAS$^{V12}$. When tested in TRE, TRE/E6/E7/ST and TRE/E6/E7/ST/RAS$^{V12}$ cells, the selectivity of Compound 3 against oncogenic RAS was manifest, although its growth inhibition potency was less than in the BJ cell system (FIG. 2B).

Among the three RAS genes (HRAS, KRAS, NRAS), the BJ cell system employed HRAS mutations to initiate oncogenic signals. All three RAS proteins can activate common down stream effectors but, for unknown reasons, human cancer cells have biased mutation rates among the three RAS genes; more than 70% contain KRAS mutations, 25% NRAS mutations, and less than 5% HRAS mutations (Rodenhuis, 1992). Since KRAS mutations are most prevalent in human cancers, the activity of Compound 3 in KRAS-mutation-harboring cancer cells was tested (FIG. 2B). Compound 3 showed less activity in KRAS-mutation-harboring cancer cells, raising the possibility that this compound preferentially targets HRAS signaling. This makes Compound 3 less attractive as a therapeutic agent for a broad array of cancers, but potentially useful as a research tool to define differences in downstream signaling pathways activated by HRAS and KRAS.

Overall, Compound 3 has selective lethality toward oncogenic HRAS signaling, but tends to be cytostatic and less potent in cells other than BJ-derived cell lines. One advantage of this compound is that it is relatively easy to modify the original hit compound, because it is a simple synthetic compound. Synthesis of additional structural analogs based on this preliminary SAR study may yield more selective and potent compounds that can be used as research tools.

Compound 6

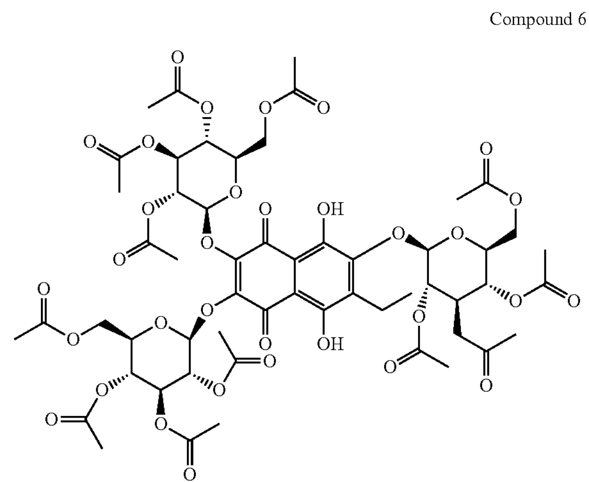 [SMILES: CCc1c(O)c2c(c(O)c1O[C@H]1O[C@@H](COC(C)=O)[C@H](OC(C)=O)[C@@H](CC(C)=O)[C@@H]1OC(C)=O)C(=O)C(O[C@@H]1O[C@H](COC(C)=O)[C@@H](OC(C)=O)[C@H](OC(C)=O)[C@H]1OC(C)=O)=C(O[C@@H]1O[C@H](COC(C)=O)[C@@H](OC(C)=O)[C@H](OC(C)=O)[C@H]1OC(C)=O)C2=O]

Compound 6 is a glycosylated echinochrome, a pigment of sea urchin which has a red color (Nishibori, 1961). Echinochromes are known to have biological activities, such as free radical scavenging and iron chelation, but anti-cancer effects have not been addressed (Lebedev et al., 2005). The 5,8-dihydroxy-1,4-naphthoquinone backbone is also found in anthracyclines (doxorubicin, daunorubicin) and anthracenediones (e.g., mitoxantrone). However, none of these traditional chemotherapeutic agents were active in counter-screening using the DRD cell line, suggesting some unique properties of Compound 6.

Figure 7:
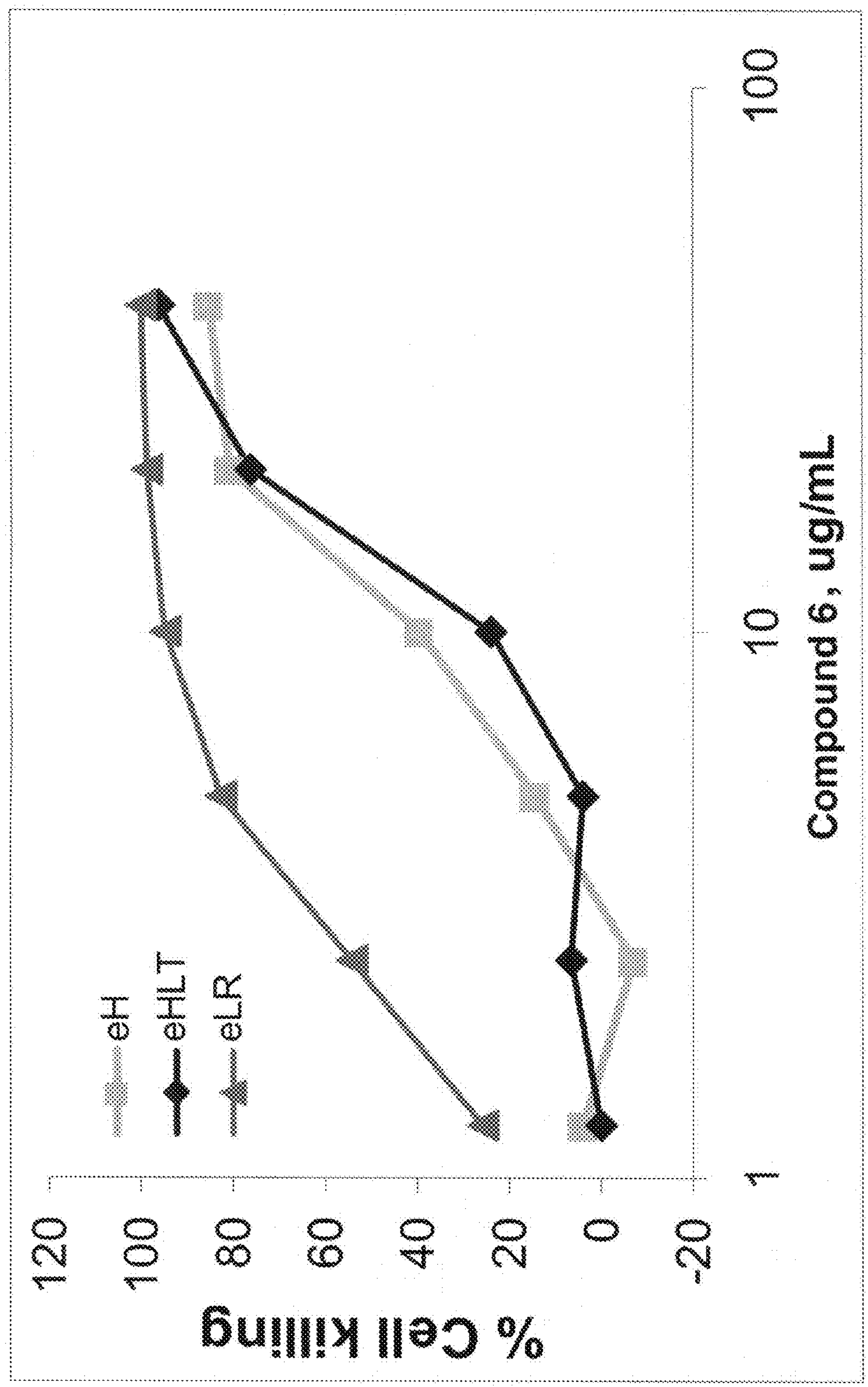
FIG. 7 shows the selectivity and potency of Compound 6 using a ViCell (Trypan blue exclusion) assay.

Compound 6 had reasonable potency in BJ-TERT/LT/ST/RAS$^{V12}$ cells ($IC_{90}$=2.5 μg/mL) and the degree of selectivity towards oncogenic HRAS was 4-8 fold in the BJ cell system (FIG. 6A). The growth inhibitory potential in DRD cells was slightly less than that in BJ-TERT/LT/ST/RAS$^{V12}$ cells, but still greater than that in BJ-TERT/LT/ST cells. This suggests that Compound 6 is an oncogenic-RAS-selective lethal compound and that the presence of idiosyncratic factors in BJ-TERT/LT/ST/RAS$^{V12}$ cells increases their sensitivity further (FIG. 6A). Vi-Cell analysis of trypan blue exclusion confirmed the potency and selectivity of Compound 6 (FIG. 7). When this compound was tested in the TRE cell model, it showed consistent selectivity towards oncogenic HRAS (FIG. 6B). It also showed reasonable potency in inhibiting growth of three other mutant-KRAS-harboring cancer cell lines (FIG. 6B).

Figure 8:
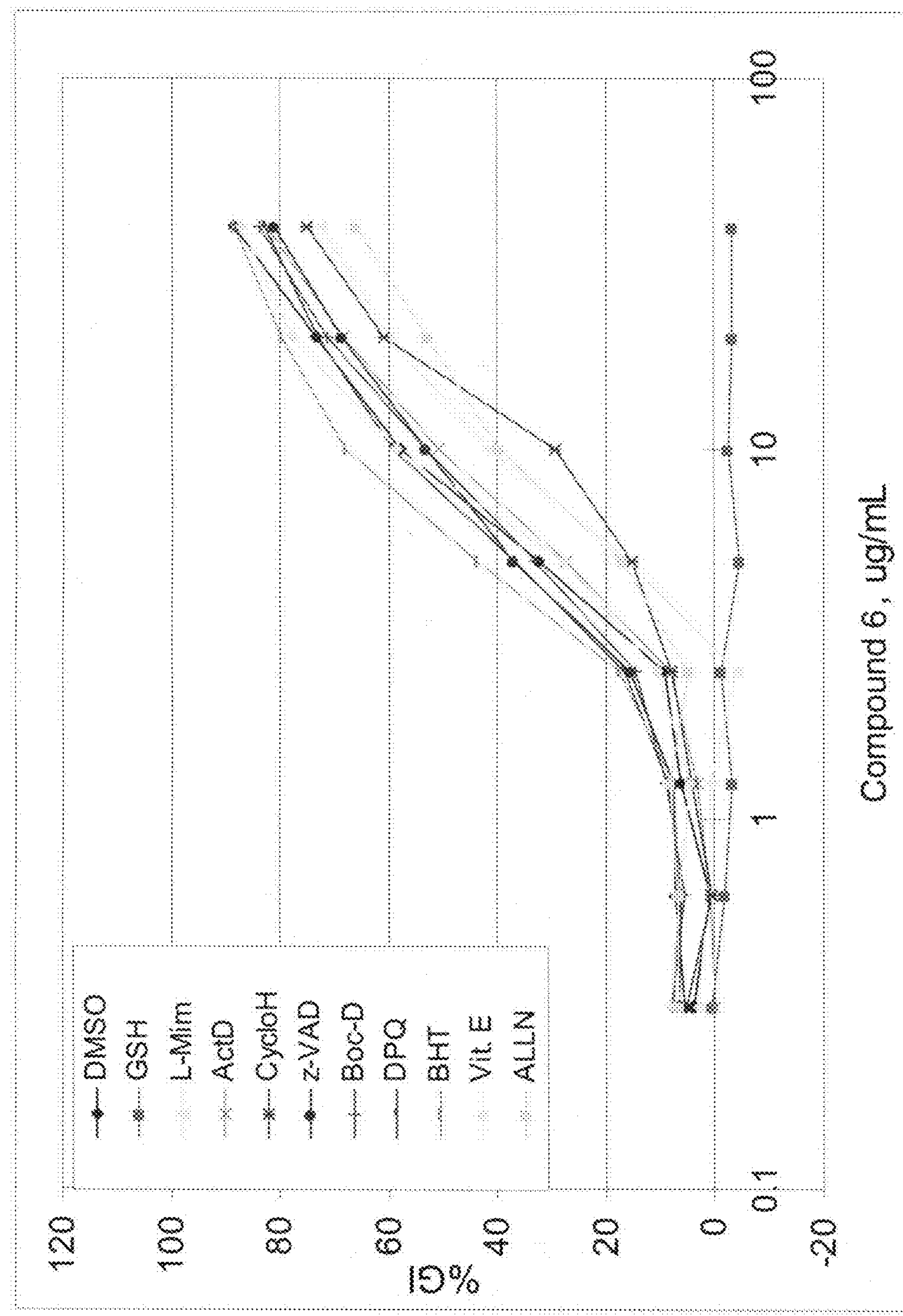
FIG. 8 shows the results of counter screening Compound 6 with 36 biologically active compounds, including antioxidants, iron chelators, and protein synthesis inhibitors in BJ-TERT/LT/ST/$RAS^{V12}$ cells.

Based on previous reports about echinochrome, it was expected that reactive oxygen species scavengers or iron chelators might suppress Compound 6-induced cell death. However, the counter screening revealed that only reduced glutathione (GSH) was able to inhibit Compound 6-induced cell death, implying that the mechanism of action for this compound is different from that of the parental echinochrome (FIG. 8). GSH can deplete reactive oxygen species (ROS), but two other ROS scavenger molecules, vitamin E (vit. E) and butylated hydroxytoluene (BHT), didn't suppress Compound 6-induced cell death. These results imply that ROS do not play a major role in Compound 6 lethality. It is possible that Compound 6 is conjugated to GSH, which results in the inactivation of the compound or excretion of the Compound 6-GSH conjugate from the intracellular environment. This mechanism has been seen with other anti-cancer drugs (Borst et al., 2000; Kartalou and Essigmann, 2001). A calcium/calmodulin protein kinase inhibitor (CaM-Ks inhibitor), KN62, also protected BJ-TERT/LT/ST/RAS$^{V12}$ cells from Compound 6-induced death. However, the role of CaM-Ks in the activity of Compound 6 is not straightforward, because EGTA, a calcium chelator, slightly increased sensitivity of BJ-TERT/LT/ST/RAS$^{V12}$ cells to Compound 6 (FIG. 8).

Figure 9:
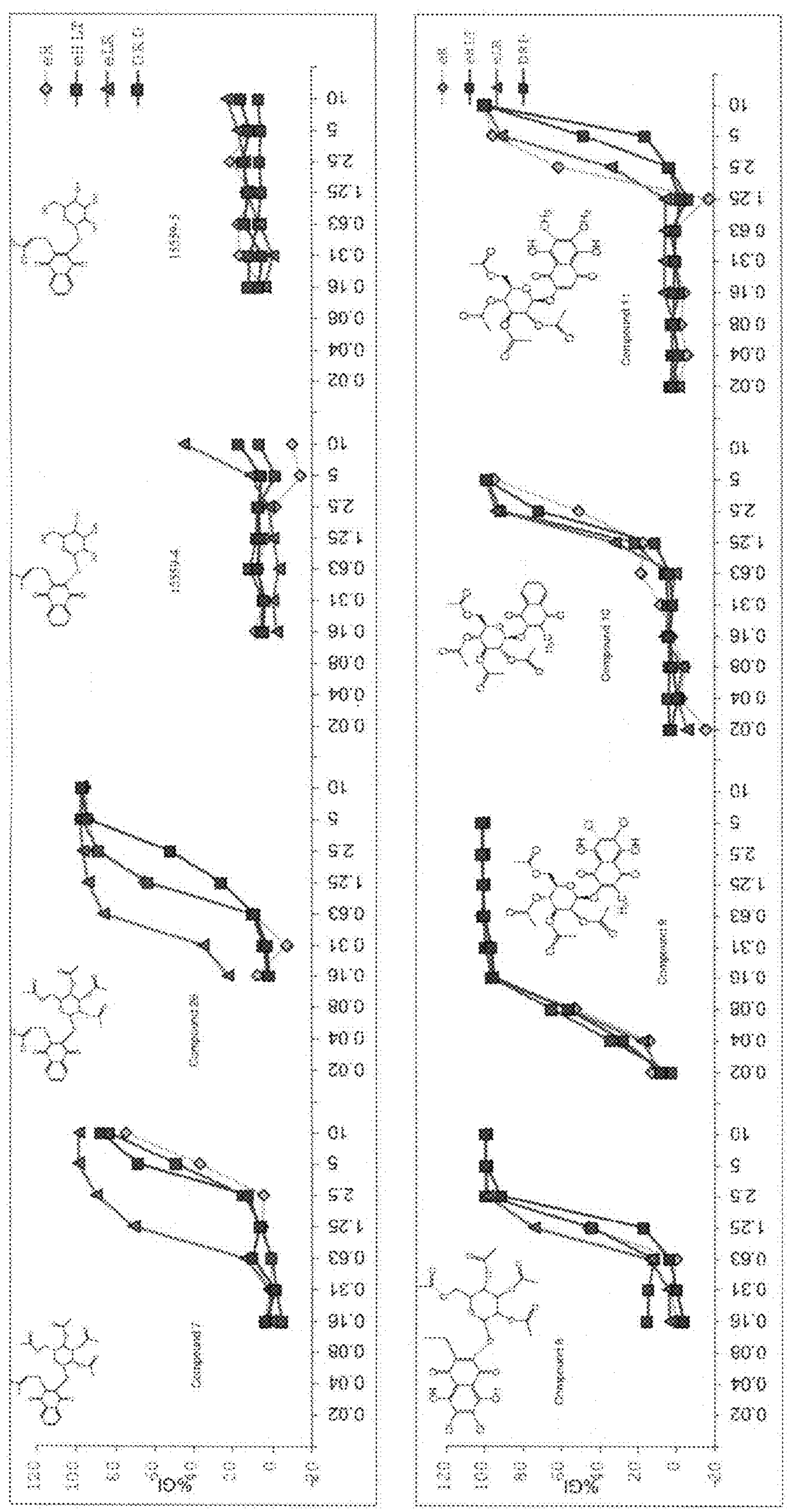
FIG. 9 shows the selectivity and potency of additional Formula III compounds and other structurally related analogs using an Alamar blue assay in the BJ-TERT (eH), BJ-TERT/LT/ST (eHLT), BJ-TERT/LT/ST/$RAS^{V12}$ (eLR), and BJ-TERT/p53DD/CDK4/cyclinD1/ST/$RAS^{V12}$ (DRD) cells.

Structural analog searching identified 22 available compounds that have a 1,4-napthoquinone backbone with various carbohydrate appendages (FIG. 9). Active analogs typically have one O-linked carbohydrate and slightly different modifications in the core 1,4-napthoquinone ring. However, none of them were as selective as Compound 6, implying the existence of near-optimal features in this parent compound. The ethyl substituent on the hydroxyl-containing ring is a unique feature in Compound 6. A search for structural analogs that have the 1,4-napthoquinone backbone with a carbon chain of more than 2 carbons in length resulted in the identification of lapachol, a known compound with anticancer activity.

Lapachol is a biologically active constituent of *Tabebuia impetiginosa* tree bark that has been used for diminishing fever and pain in patients in South America. Early in the 20$^{th}$ century, lapachol and related analogs were synthesized, and some compounds, including lapachol and beta-lapachone, showed anti-cancer activity in vitro and in vivo (da Consolacao et al., 1975; Pardee et al., 2002). Glycosylated lapachol was tested in the BJ cell model, a similar degree of potency and selectivity was observed, although the potency in DRD cells was less than that of Compound 6. (FIG. 9). The National Cancer Institute has tested lapachol in their in vitro and in vivo cancer models and concluded that although it is active in tumor growth inhibition, the background cytotoxicity is too high to warrant clinical use (Block et al., 1974). However, its cancer-cell-specific action, as well as broad spectrum range of anticancer activity, attracted many researchers; development of anti-cancer drugs from lapachol or beta-lapachone is ongoing (Pardee et al., 2002). Based on the structural analysis, it would be interesting to synthesize and test analogs of lapachol with a short aliphatic chain, as is found in Compound 6.

Compound 36

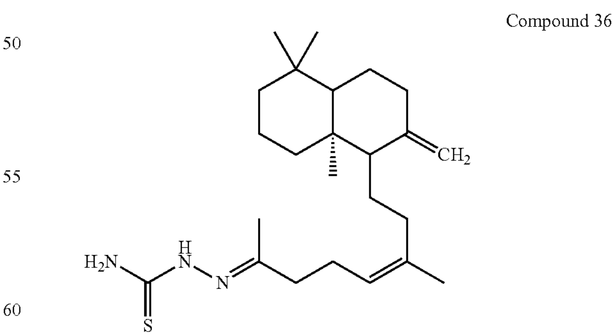

Figure 10:
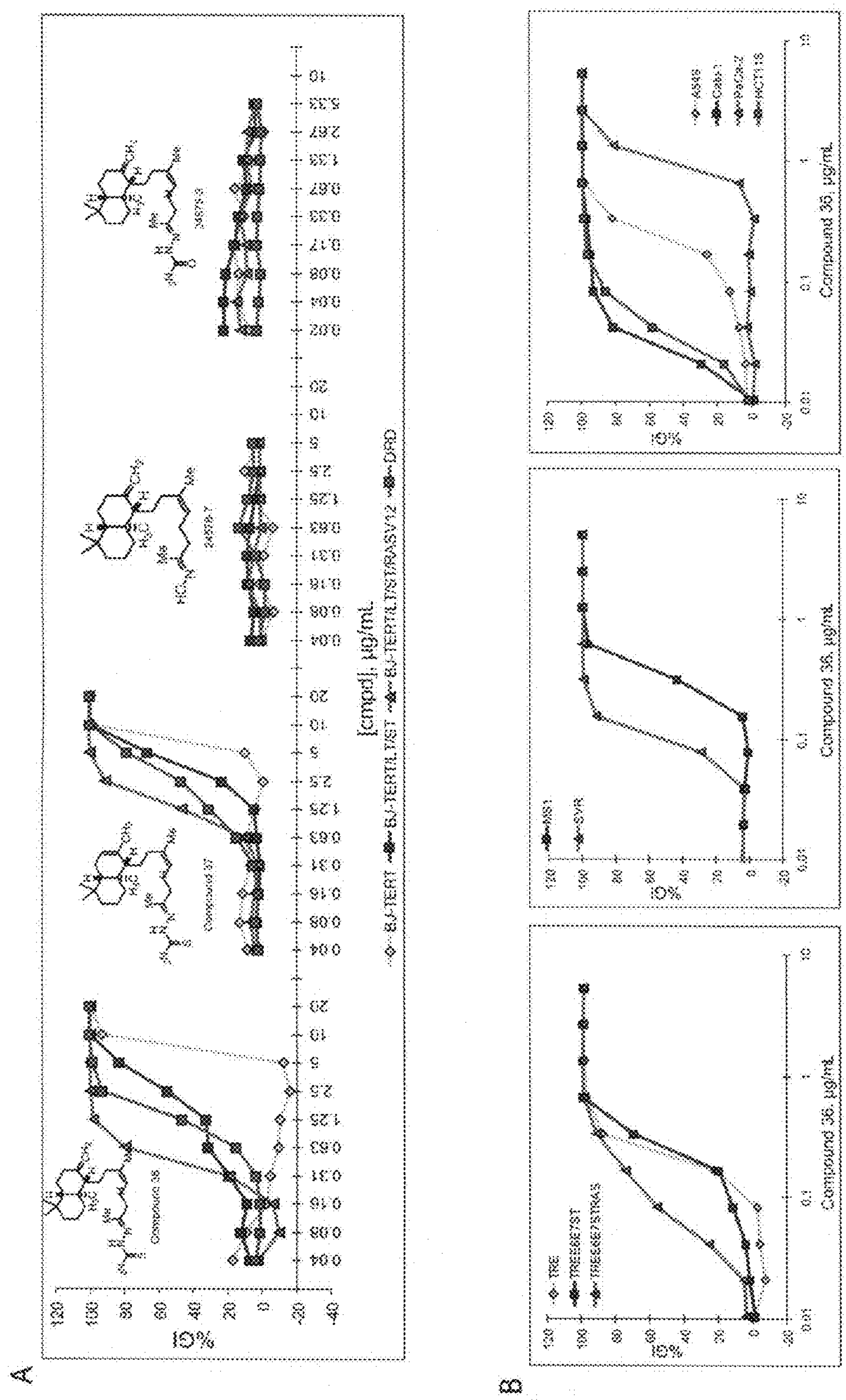
FIG. 10A shows the selectivity and potency of compounds of Formula V (including Compounds 36 and 37, as well as 24578-7 and 24578-3) using an Alamar blue assay in BJ-TERT (eH), BJ-TERT/LT/ST (eHLT), BJ-TERT/LT/ST/$RAS^{V12}$ (eLR), and BJ-TERT/p53DD/CDK4/cyclinD1/ST/$RAS^{V12}$ (DRD) cells.
FIG. 10B shows the selectivity and potency of Compound 36 using an Alamar blue assay in TRE, TRE/E6/E7/ST, and TRE/E6/E7/ST/$RAS^{v12}$ cells (left panel), in MS1 and SVR cells (center panel), and in A549, Calu-1, PaCa, and HCT116 cells (right panel).
FIG. 10C shows the inability of cell cycle blockers (apigenin, monastrol, olomoucine, nocodazole, hydroxyurea, colchicine, and rapamycin) to suppress Compound 36-induced cell death in BJ-TERT/LT/ST/$RAS^{V12}$ cells using an Alamar blue assay.
Figure 11:
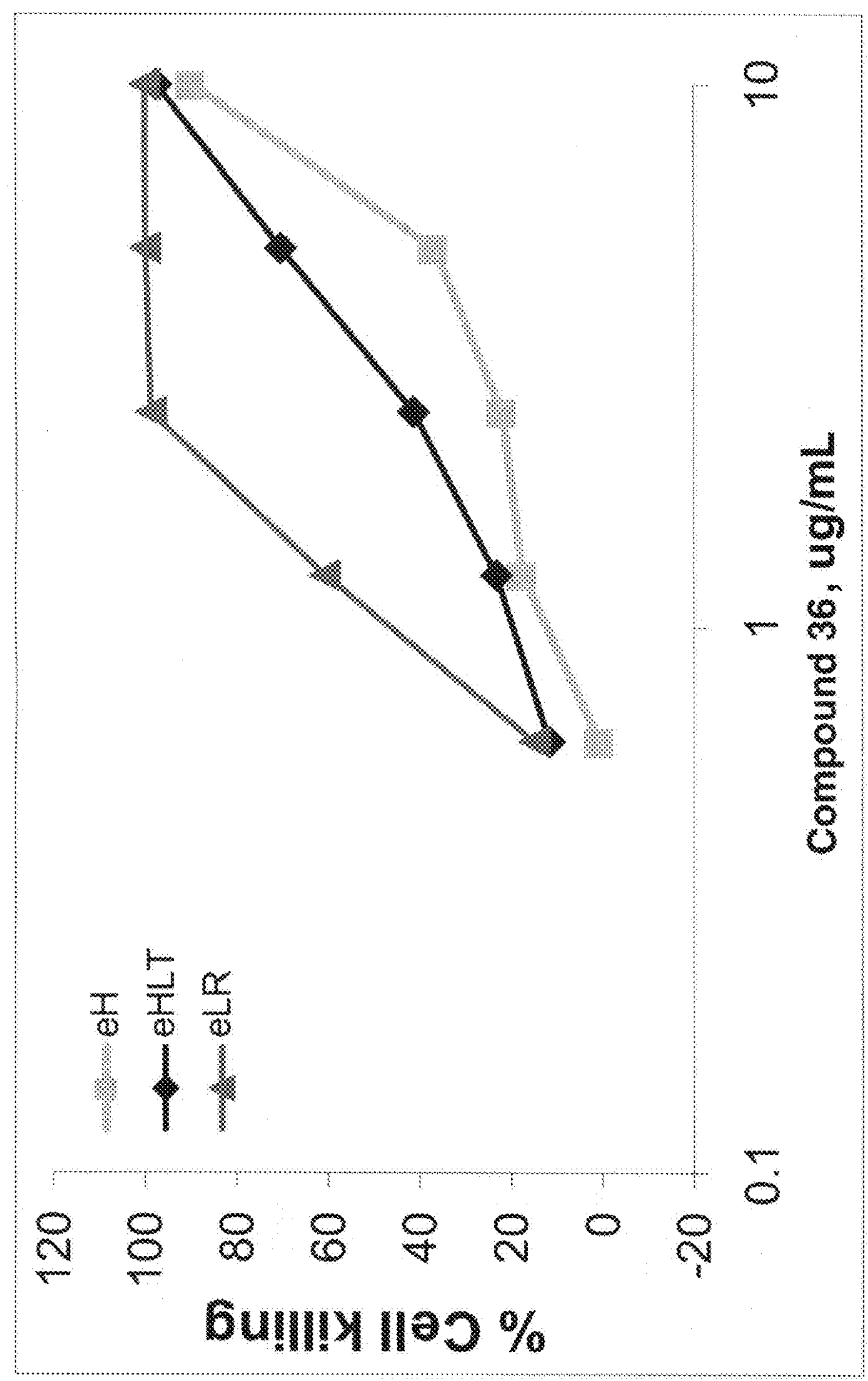
FIG. 11 shows the selectivity and potency of Compound 36 using a ViCell (Trypan blue exclusion) assay.

Compound 36 is a natural product derivative containing the labdane diterpene skeleton found in compounds from plant and marine sources. A number of labdane diterpene derivatives have been reported to have a wide range of biological activities, including antibiotic, anti-inflammatory, cardiotonic, and cytotoxic effects (Singh et al., 1999). However, a cancer-cell-selective growth inhibitory effect has not been described for this group of compounds. Compound 36 showed reasonable potency for growth inhibition of BJ-TERT/LT/ST/RAS$^{V12}$ cells. The $IC_{90}$ value was 1 μg/mL (FIG. 10A). The degree of selectivity between BJ-TERT/LT/ST/RAS$^{V12}$ and BJ-TERT was up to 16-fold (FIG. 10A). BJ-TERT/LT/ST cells showed intermediate sensitivity, implying that the activity of the compound depends on altered signaling by LT/ST, while oncogenic RAS signaling further augments sensitivity. Vi-Cell analysis confirmed the growth inhibitory potency and selectivity (FIG. 11).

The sensitivity of DRD cells was close to that of BJ-TERT/LT/ST cells. However, the increase in sensitivity upon activation of oncogenic RAS signaling was seen in two additional pairs of isogenic cell lines with or without oncogenic RAS (TRE cell lines and MS1/SVR. MS1 and SVR cells are mouse pancreatic endothelial cells that were engineered to express SV40 LT protein with (SVR cells) or without HRAS$^{G12V}$ (MS1 cells) (Arbiser et al., 1997) (FIG. 10B)). Compound 36 was active in other KRAS-mutation-harboring cancer cell lines with varying degrees of sensitivity (FIG. 10B).

Figure 12:
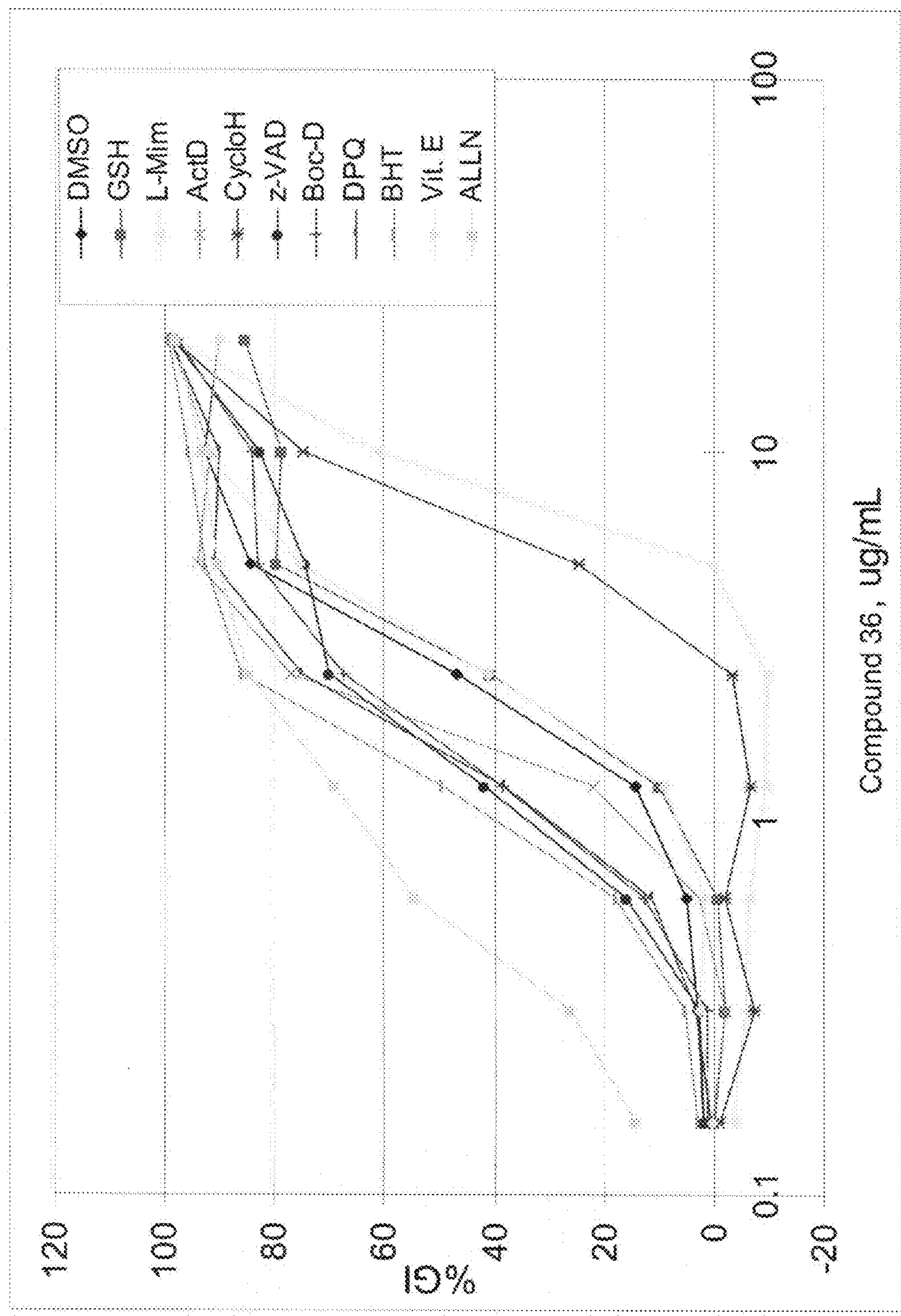
FIG. 12 shows the results of counter screening Compound 36 with 36 biologically active compounds, including antioxidants, iron chelators, and protein synthesis inhibitors in BJ-TERT/LT/ST/$RAS^{V12}$ cells.

Counter screening with bioactive compounds revealed that iron chelators (L-Mim and DFOM) and a protein synthesis inhibitor (cycloheximide) were effective in suppressing Compound 36-induced cell death (FIG. 12). Since L-mimosine is know to have the activity of both iron chelation and cell cycle blocking, other cell cycle blockers were tested in order to dissect the function needed for suppressing Compound 36-induced cell death. None of cell cycle blockers were effective in cell death suppression, but other iron chelators were effective suppressors, indicating that iron chelation is likely the cause of the protective effect of L-minosine (FIG. 10C). Compound 36-induced cell death requires new protein synthesis, based on the effect of cycloheximide. Selectivity towards HRAS$^{G12V}$ is mediated by RAS downstream signaling other than RAS-RAF-MEK pathway, based on the inability of MEK1/2 inhibitors to suppress Compound 36.

Figure 13:
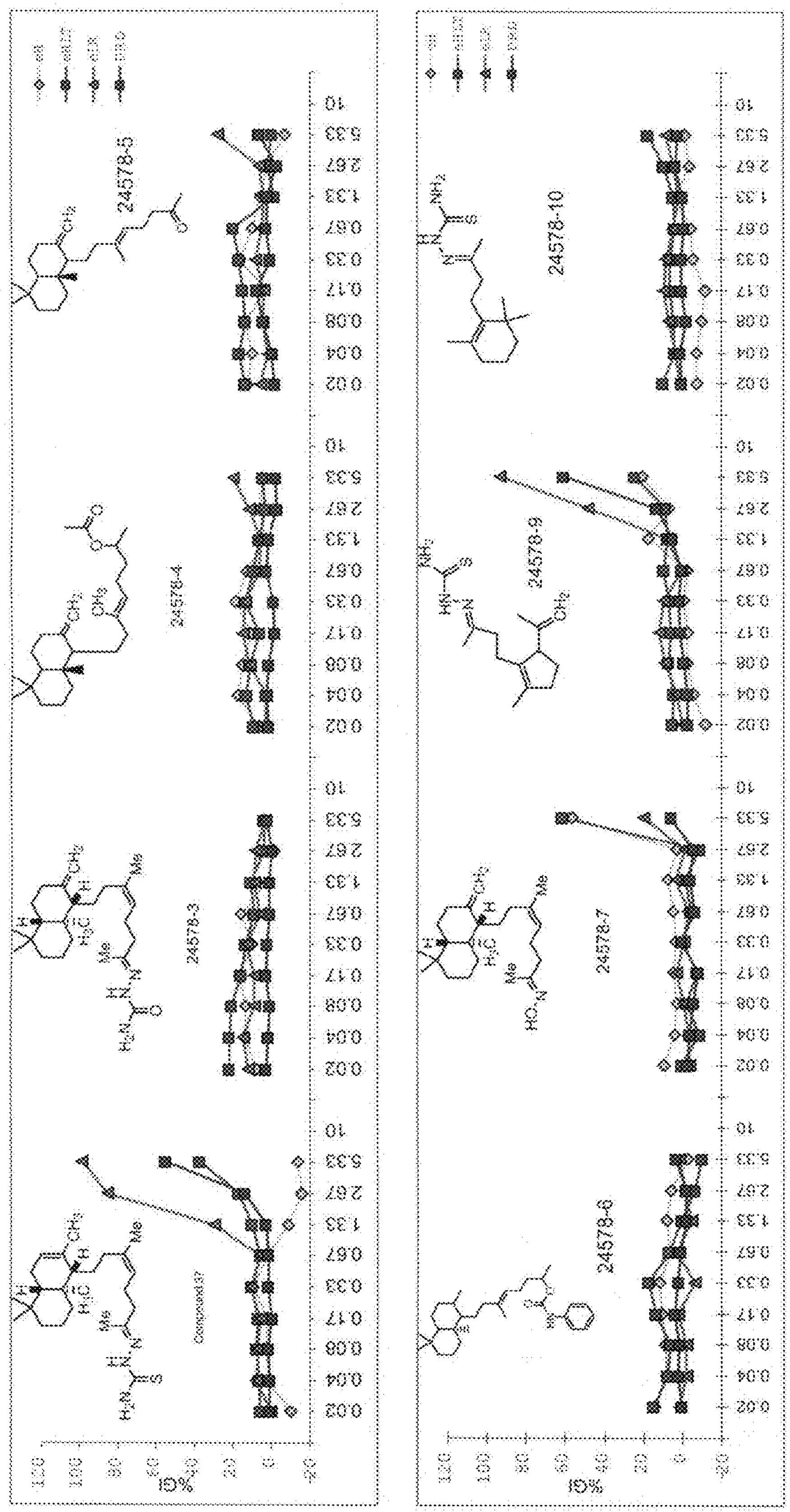
FIG. 13 shows the selectivity and potency of additional Formula V analogs and other structurally related compounds using an Alamar blue assay in the BJ-TERT (eH), BJ-TERT/LT/ST (eHLT), BJ-TERT/LT/ST/RAS$^{V12}$ (eLR), and BJ-TERT/p53DD/CDK4/cyclinD1/ST/RAS$^{V12}$ (DRD) cells.

Structural analog searching resulted in identification of 15 analogs (FIG. 13). One analog differed only in the location of double bond in the transdecalin ring; this analog had slightly lower potency and selectivity than the original hit (FIG. 10A—Compound 36). An analog that does not have the thiourea functionality in the thiosemicarbazone moiety was not active in inhibiting cell growth in the BJ cell system, implying that this moiety is critical for activity (FIG. 10A—24578-7). Indeed, an analog was found that differs only in an oxygen atom substitution for nitrogen. This analog was not active in the BJ cell system, confirming the importance of the thiosemicarbazone group (FIG. 10A—24578-3).

Thiosemicarbazones are known to have multiple functions in biological systems. One particular class, called heterocyclic thiosemicarbazones (HCTs), binds iron and induces cytotoxicity in various cancer cells (Liu et al., 1995). Some HCTs, like Triapine, are reported to have cancer cell specific lethal effects (Finch et al., 2000). It is believed that these HCTs deplete iron from key enzymes such as ribonucleotide reductase or decrease the protein levels of cell cycle modulators, which results in inhibition of tumor cell growth (Le and Richardson, 2002). Based on the structural requirement of an intact thiosemicarbazone moiety and the iron-dependent mechanism, Compound 36 may have a similar mechanism of action to the HCTs in inducing tumor-cell-specific lethality. To test this hypothesis, 9 HCTs that were reported to be active in NCI's in vivo test were collected and tested in the BJ cell lines (FIG. 13). Some HCTs showed good selectivity between BJ-TERT and BJ-TERT/LT/ST/RAS$^{V12}$ cells. However, none was as effective and selective as Compound 36. Moreover, the sensitivity of the DRD cell line was never greater than in BJ-TERT cells, implying that the activity of HCTs are generally unrelated to oncogenic RAS signaling. This suggests some novel features of Compound 36 unrelated to HCTs that remain to be elucidated.

Compound 27

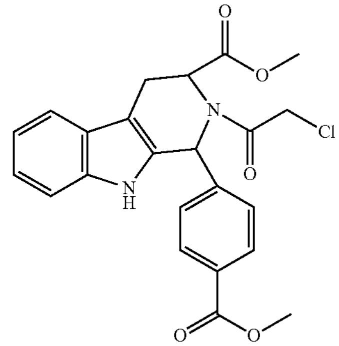 [SMILES: CCOC(=O)C1Cc2c([nH]c3ccccc23)C(c2ccc(C(=O)OC)cc2)N1C(=O)CCl]

Figure 14:
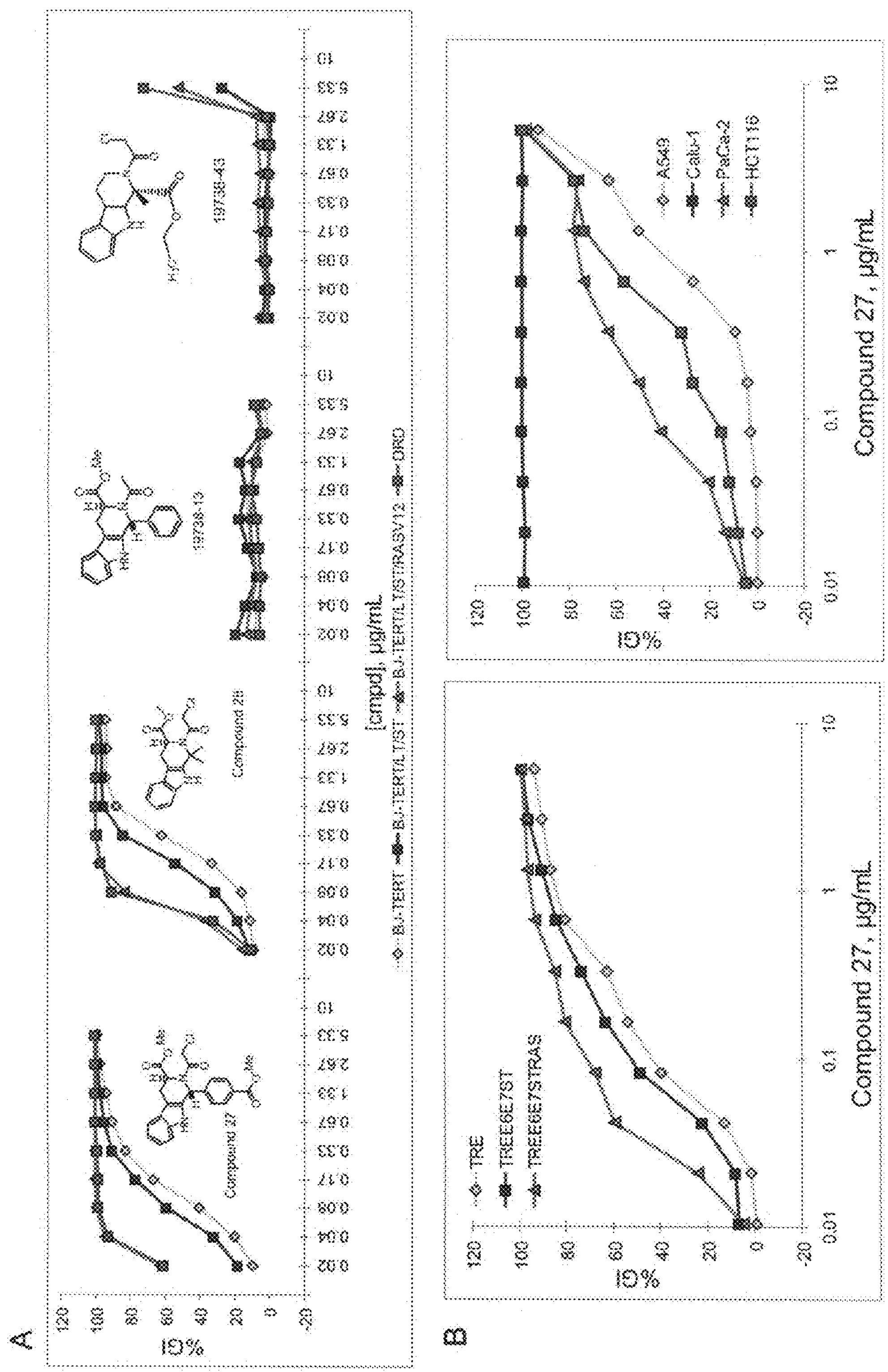
FIG. 14A shows the selectivity and potency of compounds of Formula IV (including Compounds 27, 28, and 19738-13) and other structurally related compounds using an Alamar blue assay in BJ-TERT (eH), BJ-TERT/LT/ST (eHLT), BJ-TERT/LT/ST/RAS$^{V12}$ (eLR), and BJ-TERT/p53DD/CDK4/cyclinD1/ST/RAS$^{v12}$ (DRD) cells.
FIG. 14B shows the selectivity and potency of Compound 27 using an Alamar blue assay in TRE, TRE/E6/E7/ST, and TRE/E6/E7/ST/RAS$^{V12}$ cells (left panel) and in A549, Calu-1, PaCa, and HCT116 cells (right panel).
FIG. 14C shows the results of NCI60 screening of Compound 27. 18 of the 60 human cell lines tested are shown. These 18 cell lines include a representative sensitive group and a resistant group.
FIG. 14D shows the time-dependent effect of Erastin, Compound 36, Compound 27, Compound 6, and Compound 3 on cell viability using a ViCell (Trypan blue exclusion) assay.
FIG. 14E shows cell growth inhibition of Compound 27 using an Alamar blue assay in Calu-1, Calu-1pLKO, and Calu-1-509 cells.
Figure 15:
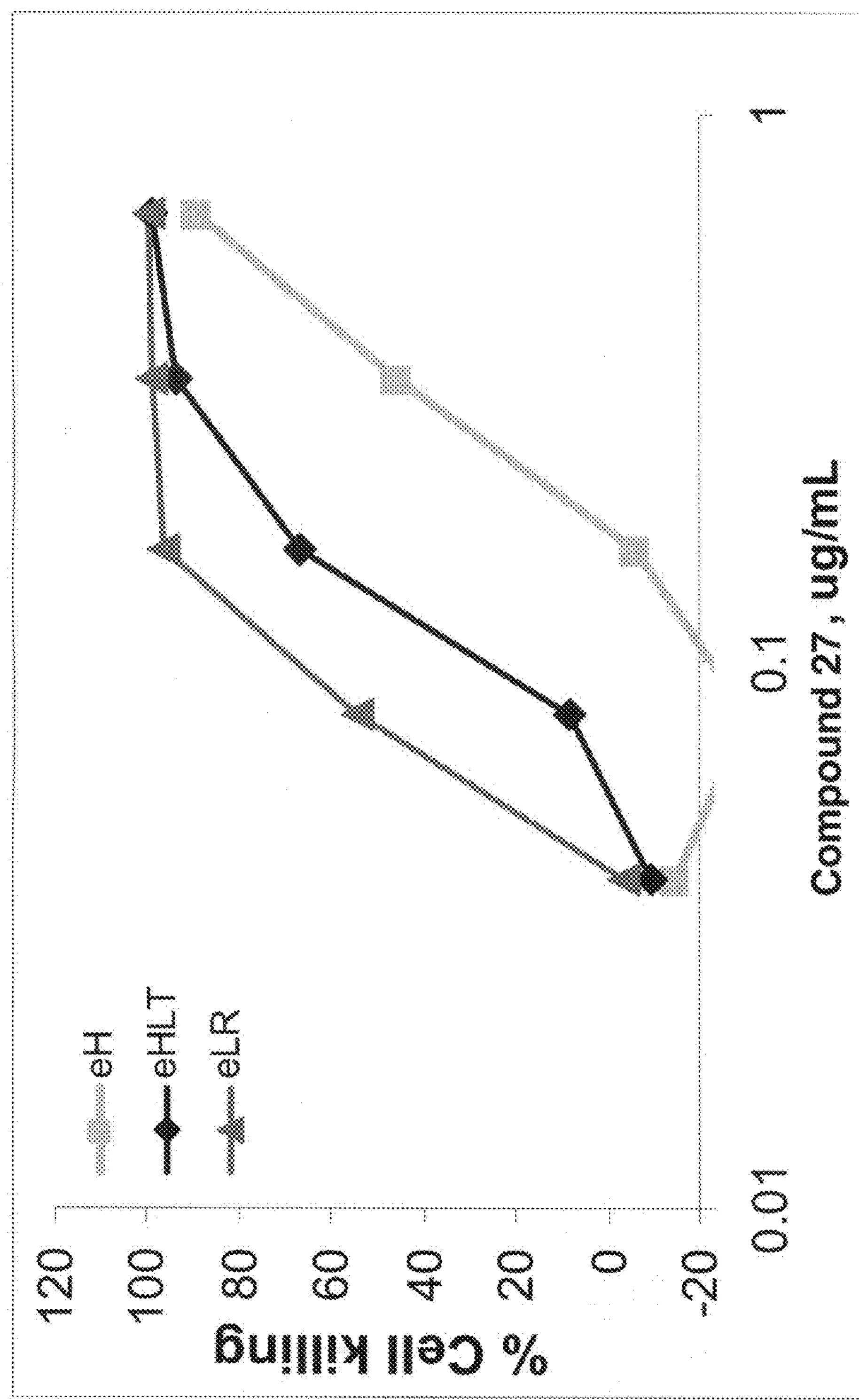
FIG. 15 shows the selectivity and potency of Compound 27 using a ViCell (Trypan blue exclusion) assay.

Compound 27 is a natural product derivative having an indole backbone. This compound inhibited the growth of BJ-TERT/LT/ST/RAS$^{V12}$ cells at concentrations as low as 0.01 μg/mL. The selectivity of Compound 27 was four-fold between oncogenic-RAS-expressing BJ cells and non-oncogenic-RAS-expressing BJ cells (FIG. 14A). The potency in DRD cells was the same as in BJ-TERT/LT/ST/RAS$^{V12}$ cells, indicating that Compound 27 activity depends on oncogenic RAS signaling rather than the proliferation rate (FIG. 14A). Vi-Cell analysis confirmed Compound 27 cell growth inhibition activity and selectivity with trypan blue exclusion (FIG. 15).

When this compound was tested in the TRE cell system, HRAS$^{G12V}$-expressing cells were slightly more sensitive than their isogenic counterparts (FIG. 14B). This compound was active in all oncogenic-KRAS-harboring cancer cell lines tested (FIG. 14B). Among them, Calu-1 cells, which were derived from human lung carcinoma, were particularly sensitive to Compound 27 (FIG. 14B). The $IC_{90}$ in Calu-1 cells was in the single-digit nanomolar range.

Figure 16:
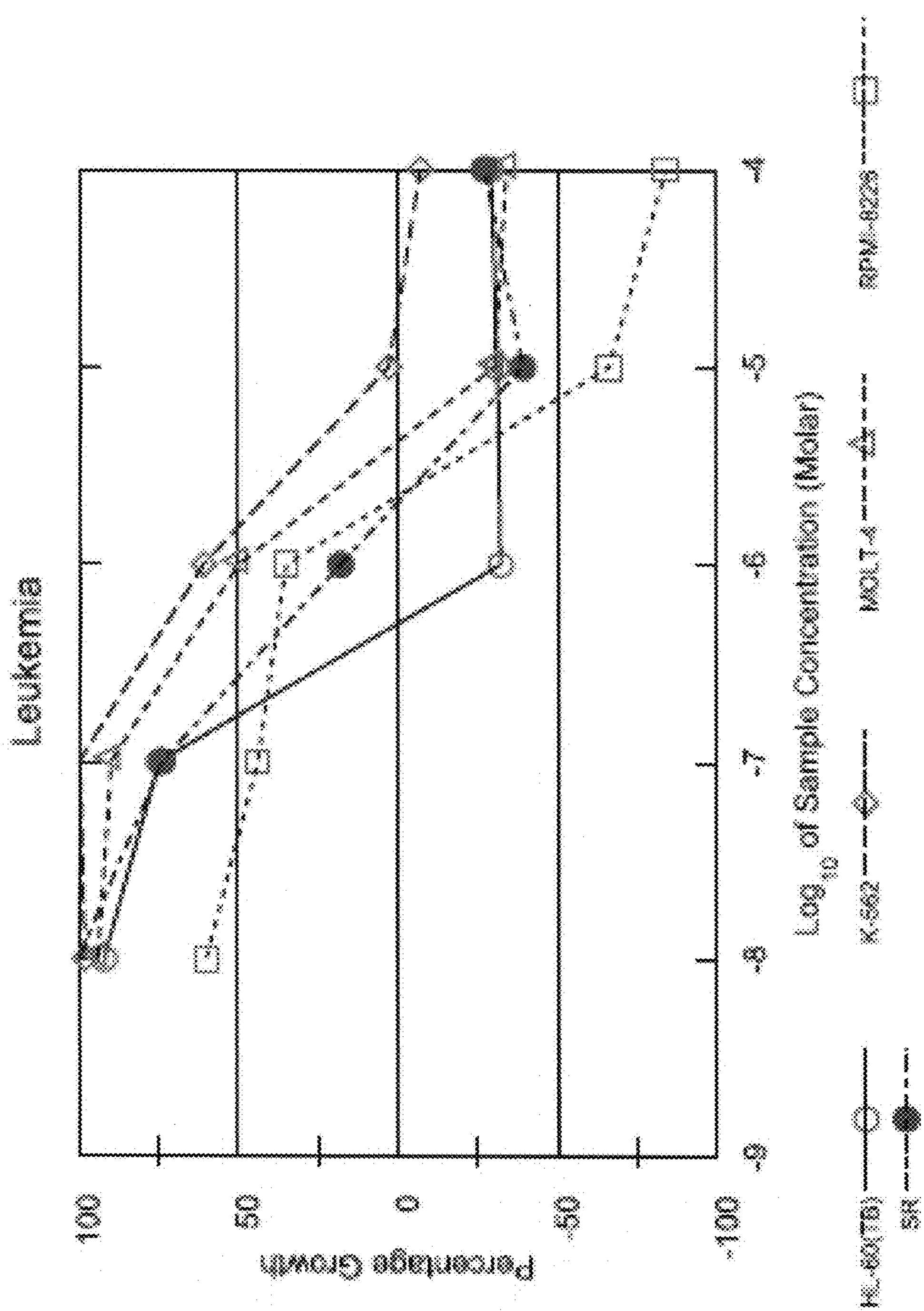
FIG. 16 shows the results of NCI60 screening of Compound 27.

Compound 27 was submitted to the Developmental Therapeutics Program (DTP) at the National Cancer Institute (NCI) in order to determine if there were additional cell lines, like Calu-1, that are particularly sensitive to the compound. Compound 27 was tested in 60 different human cancer cell lines (the NCI60 panel, see below) and the growth inhibitory potency of Compound 27 was determined across these cell lines. A number of cell lines were particularly sensitive to Compound 27 treatment. These compounds were sensitive to nanomolar concentrations and up to $10^4$-fold more sensitive than the resistant cell lines (FIG. 14C and FIG. 16). Moreover, the sensitivity profiling of Compound 27 across the 60 cancer cell lines was distinct from those of known compounds in the NCI database, as assessed by the COMPARE algorithm (Paull et al., 1989). This suggested that the mechanism of action for Compound 27 is unique. The kinetics of cell death induced by Compound 27 was also uniquely rapid compared to other hit compounds. The plasma membrane of BJ-TERT/LT/ST/RAS$^{V12}$ cells becomes permeable to trypan blue upon 8 hours of Compound 27 treatment (FIG. 14D).

To confirm that the unique properties of Compound 27 are relevant to oncogenic-RAS-signaling pathways by knocking down KRAS expression in oncogenic-KRAS-harboring cancer cells using RNAi, Compound 27 was tested. Previously, Calu-1-derived cell lines were developed: Calu-1-509 cells stably express an shRNA targeting KRAS and Calu-1 cells are lung carcinoma cells harboring mutant KRAS (G12C). When Compound 27 was tested in Calu-1-509 cells, they were more resistant to Compound 27 than parental Calu-1 or Calu-1-pLKO expressing the puromycin resistance gene without any shRNA (FIG. 14E), which confirms the involvement of oncogenic-RAS-signaling in Compound 27-induced cell death.

Figure 17:
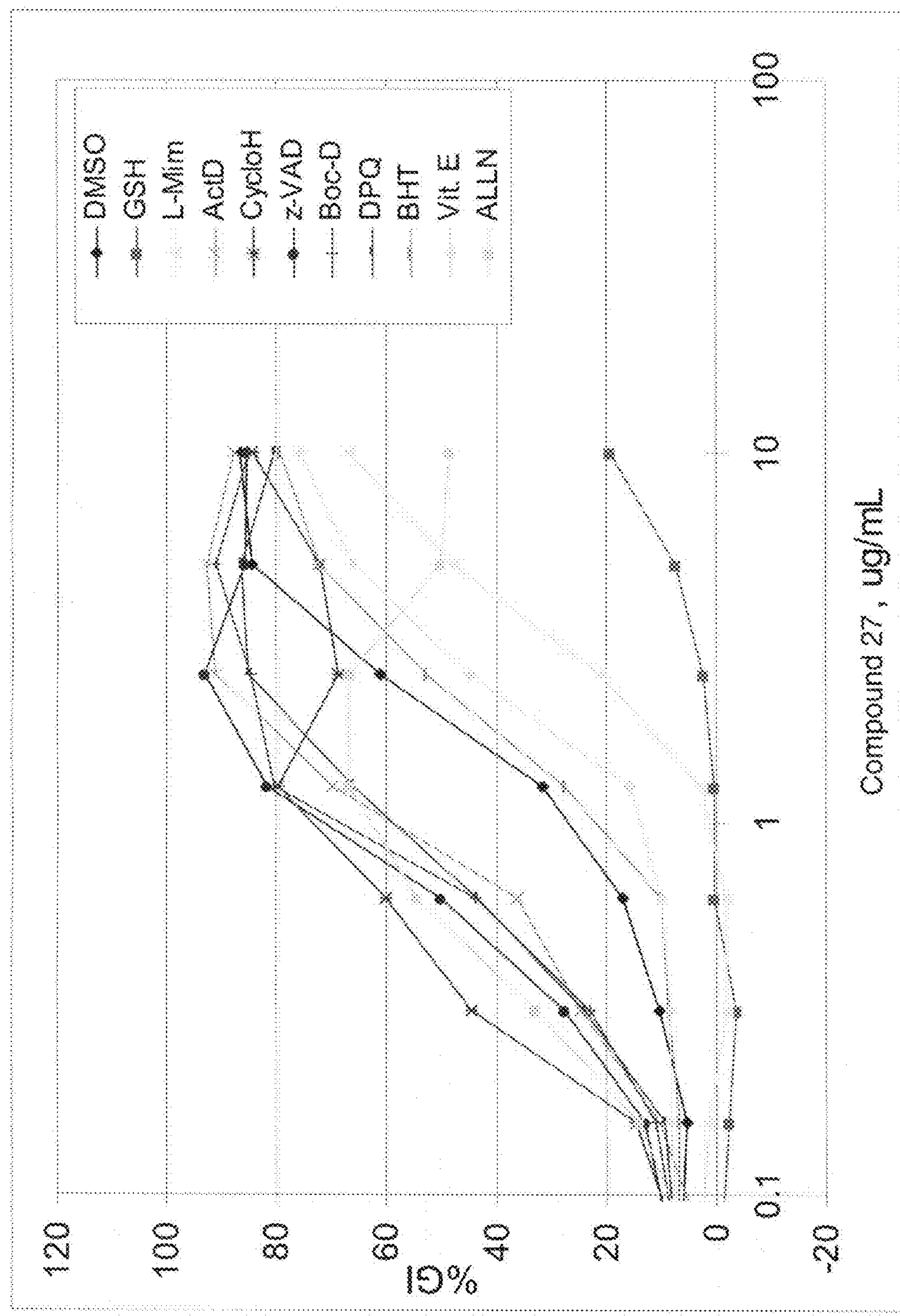
FIG. 17 shows the results of counter screening Compound 27 with 36 biologically active compounds, including antioxidants, iron chelators, and protein synthesis inhibitors in BJ-TERT/LT/ST/RAS$^{V12}$ cells.

Counter-screening using chemical inhibitors revealed that GSH, L-Mim, TLCK, DFOM, SU6656, Ro31-8220, and U0126 were effective in suppressing Compound 27-induced cell death (FIG. 17). Because other ROS scavengers included in the list of chemical inhibitors were not as effective as GSH, Compound 27 is likely to act as a substrate of GSH modification that is then inactivated or excreted. Cell death suppression by iron chelators (L-Mim and DFOM) reveals an iron-dependent activity of Compound 27. Compound 36 also showed iron-dependent lethality. However, the nature of iron-mediated toxicity induced by Compound 36 and Compound 27 may be different, because Compound 36 generates ROS and Compound 27 does not.

U0126 counter screening revealed that oncogenic RAS-RAF-MEK signaling is important for sensitivity in Compound 27. The non-receptor tyrosine kinase inhibitor SU6656 and the protein kinase C inhibitor Ro31-8220 partially suppressed Compound 27-induced cell death, which reflects other aspects of RAS signaling that contribute to sensitivity against this compound.

Figure 42:
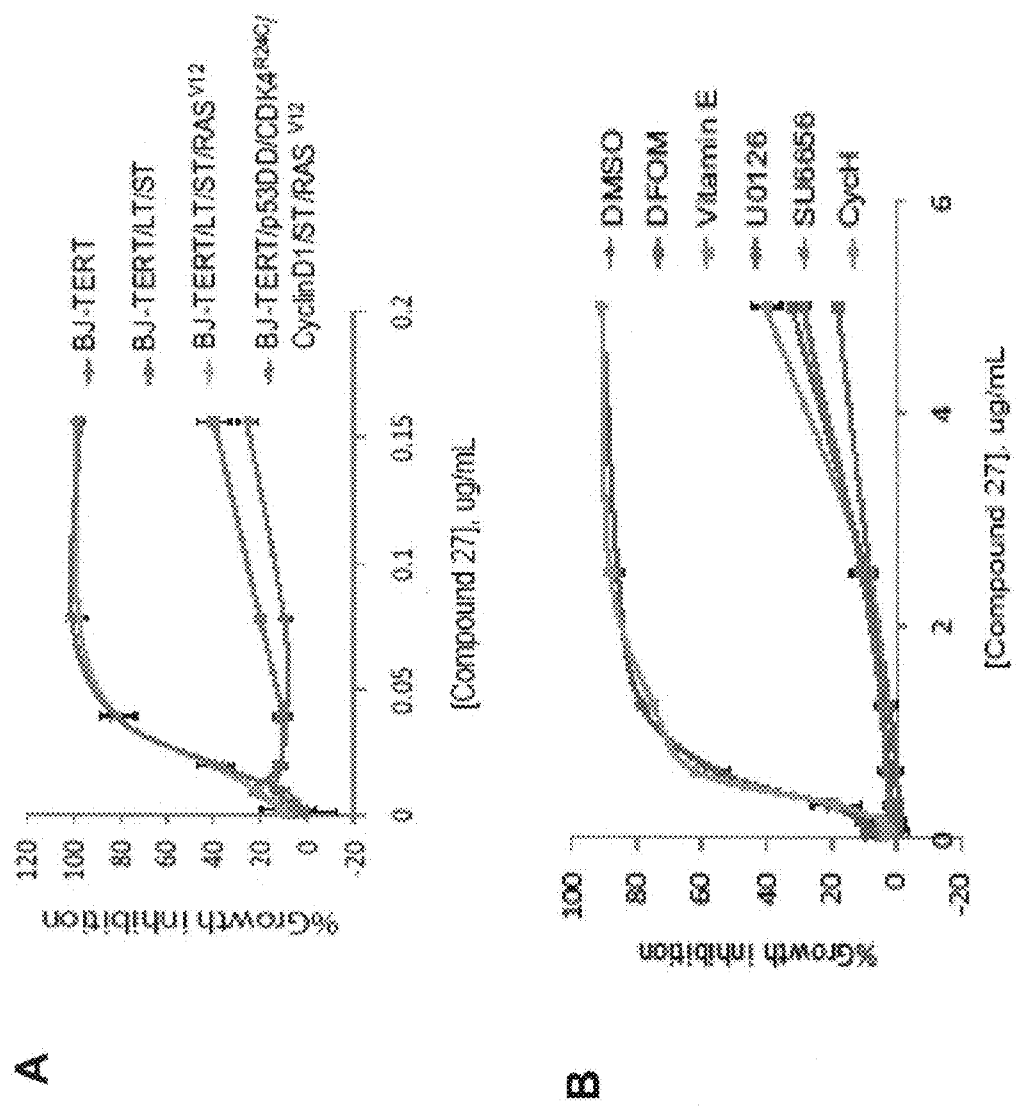
FIG. 42 shows in panel A the effect of Compound 27 on percent growth inhibition in four BJ-derived cell lines, and in panel B the percent growth inhibition using alamar blue in a HT1080 cell line treated with Compound 27 in the presence of each indicated bioactive compound.

For Compounds 27 and 3, the $IC_{50}$ value in BJ-TERT/LT/ST/$RAS^{V12}$ cells was similar to that in DRD cells, which indicates that the synthetic lethal interaction is relevant beyond a single cell line as shown in FIG. 42 for Compound 27, for example. BJ-TERT, BJ-TERT/LT/ST, BJ-TERT/LT/ST/$RAS^{V12}$, and DRD cells were treated with COMPOUND 27 in 384-well plates for 48 hours. The data represents the mean±SD of triplicate samples. The results also indicate that the compounds are not proliferation-dependent in their activity. Thus, the screening cascade yielded two compounds, Compound 27 and Compound 3, that have a degree of synthetic lethality with oncogenic RAS.

Figure 38:
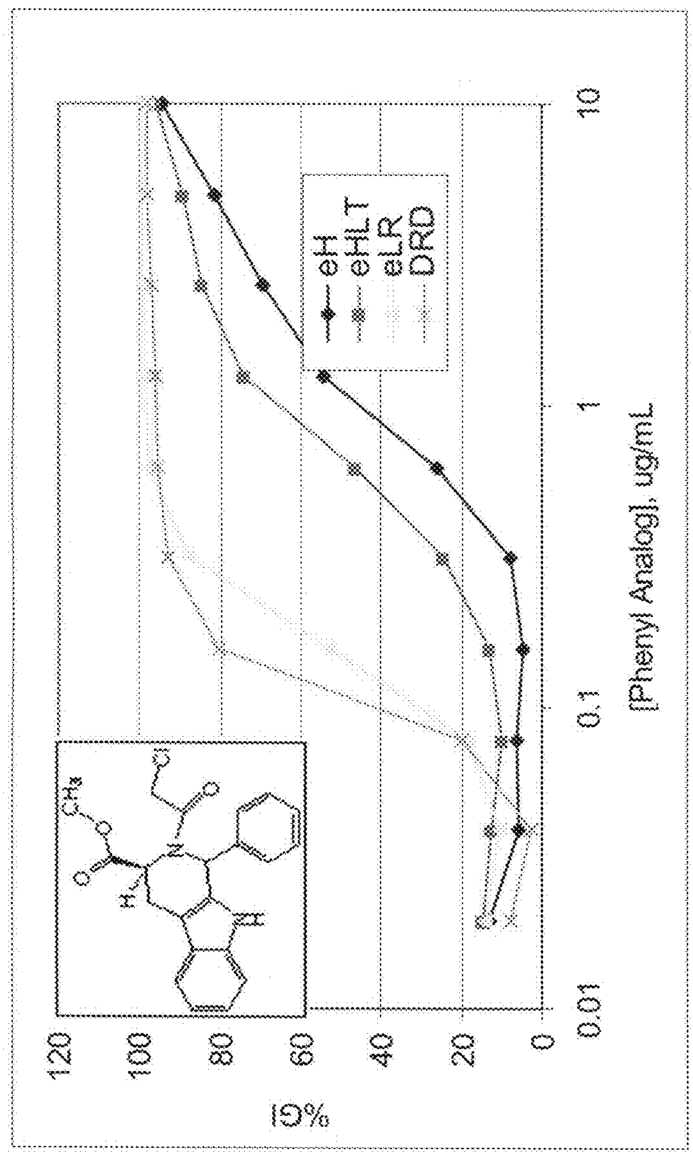
FIG. 38 shows the percent growth inhibition of an analog of Compound 27 in which methyl benzoate is replaced with phenyl.

Regarding structure activity relationships (SAR), an analog of Compound 27 having an unsubstituted phenyl in place of the methyl benzoate was shown to be active. See FIG. 38. Structural analog searching identified a compound lacking the phenyl substituent on the backbone, but containing all other moieties (FIG. 14A—Compound 28). This analog showed virtually the same activity and selectivity in the BJ cell system, suggesting this phenyl substituent is not needed. Although phenyl ring deletion may be tolerated, some additions onto the phenyl ring and some groups in place of the phenyl group result in loss of activity. For example, each of the following groups in place of the methyl benzoate of Compound 27 result in analogs having insufficient activity:

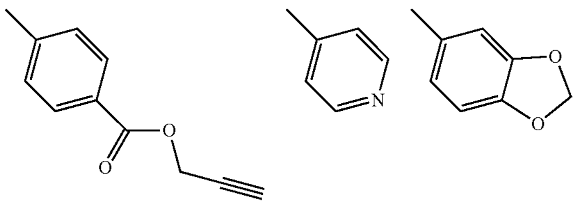

-continued

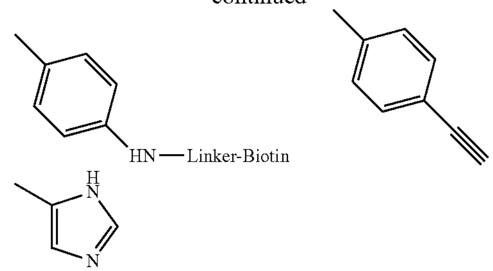

Figure 35:
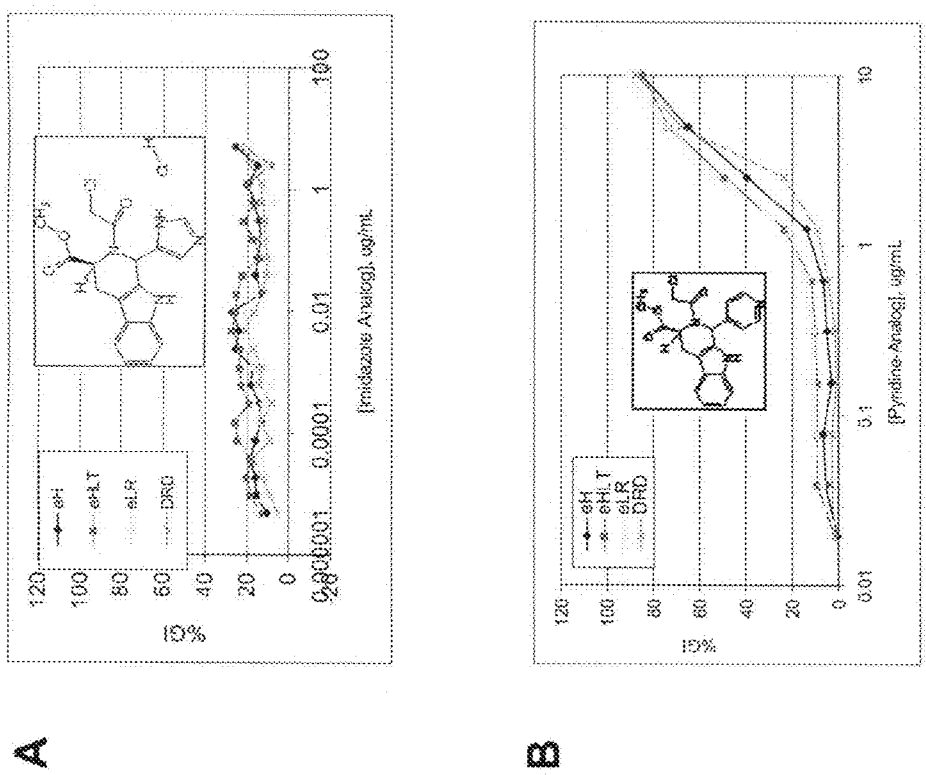
FIG. 35 shows the percent growth inhibition of an analog of Compound 27 in which the methyl benzoate is replaced with imidazole (A) and pyridine (B).

The percent growth inhibition of the imidazolyl and the pyridinyl analogs is shown in FIG. 35, for example.

Figure 26:
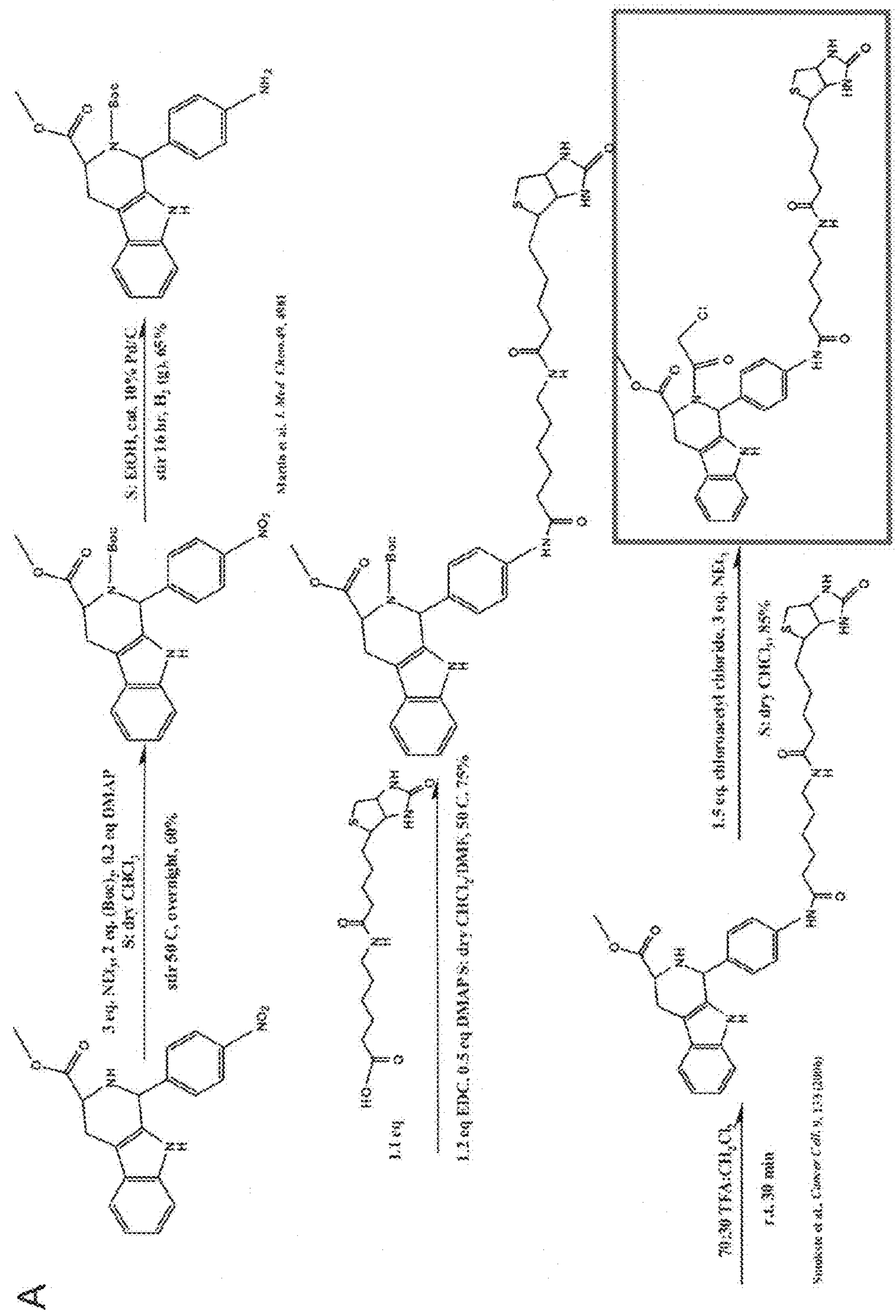
FIG. 26 shows a schematic method of making a biotinylated analog of Compound 27 (A) and the percent growth inhibition of Compound 27 (B) and the biotinylated analog of Compound 27 (C).

The method of preparing the biotinylated analog of Compound 27 is shown in FIG. 26 and provided in Example 5. The biotinylated product shown, which includes the chloroacetyl group, was not sufficiently active. This is shown in the second sheet of FIG. 26 comparing the calculated percent growth inhibition of Compound 27 to that of the bioninyated analog in a cell viability assay.

Figure 27:
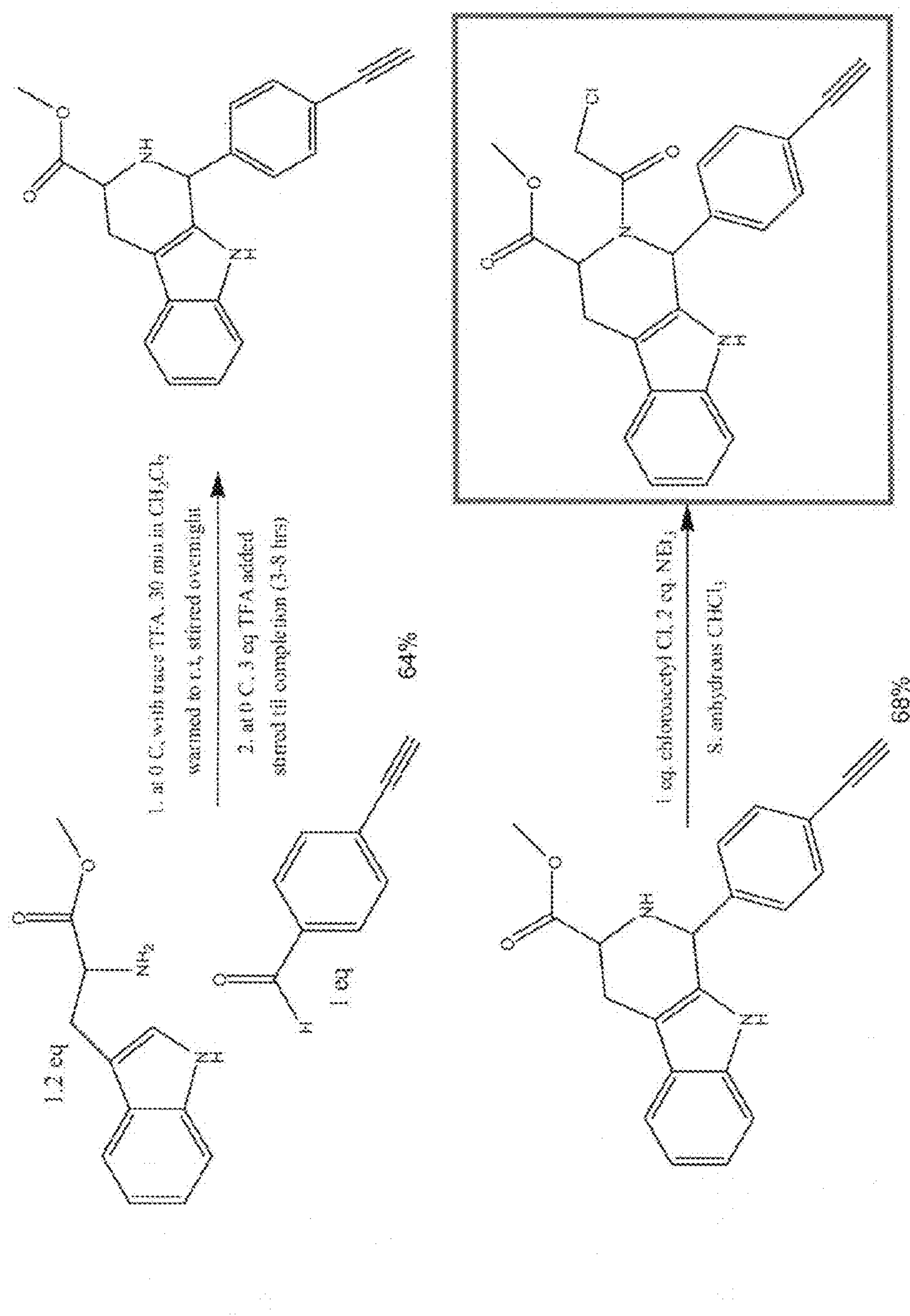
FIG. 27 shows a schematic method of making a Compound 27 analog in which the phenyl ring is para substituted with an ethynyl group.

The method of making the analog having an ethynyl group at the para position on the phenyl ring is shown in FIG. 27 and provided in Example 5. The racemic compound had insufficient activity. Diastereomers formed at the chiral carbon on the indole ring attaching the para ethynyl-phenyl showed activity but lacked selectivity, however.

Figure 39:
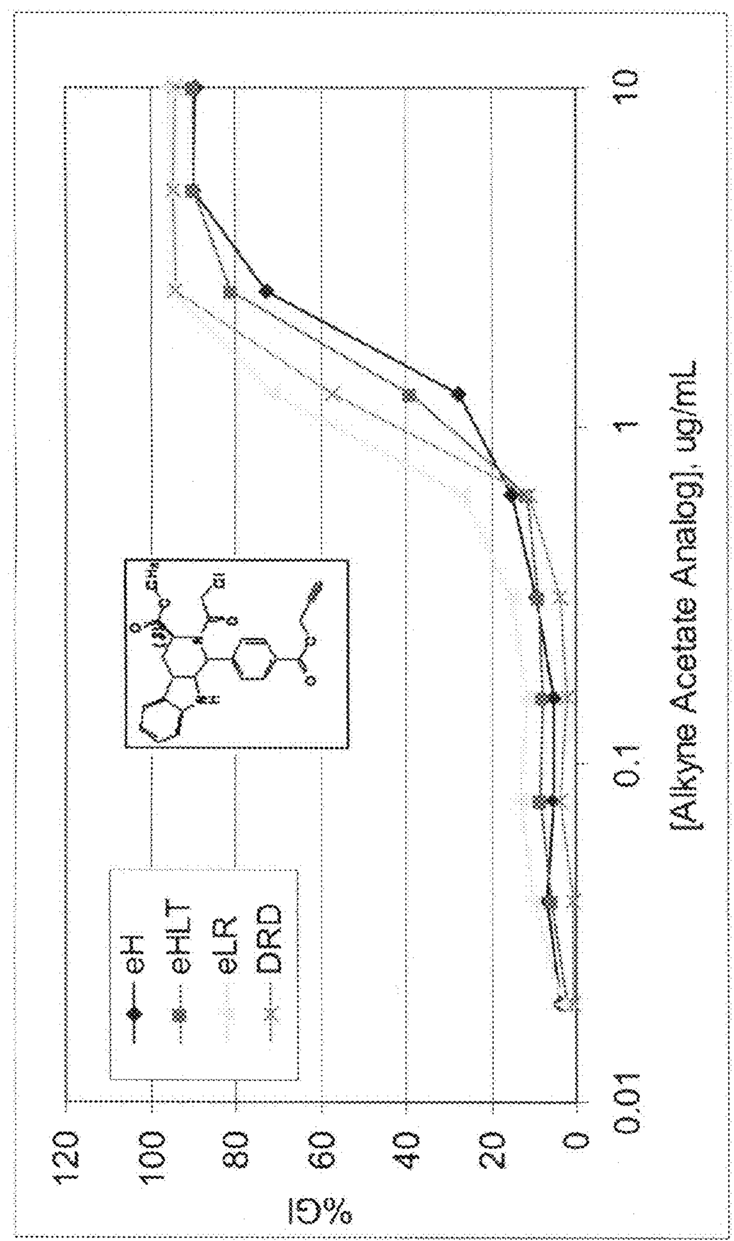
FIG. 39 shows percent growth inhibition of an analog of Compound 27 in which an alkyne acetate is substituted on the phenyl ring.

Data regarding an analog having an alkyne acetate on the phenyl ring is shown in FIG. 39, and the process for making it is shown in Example 5.

Figure 28:
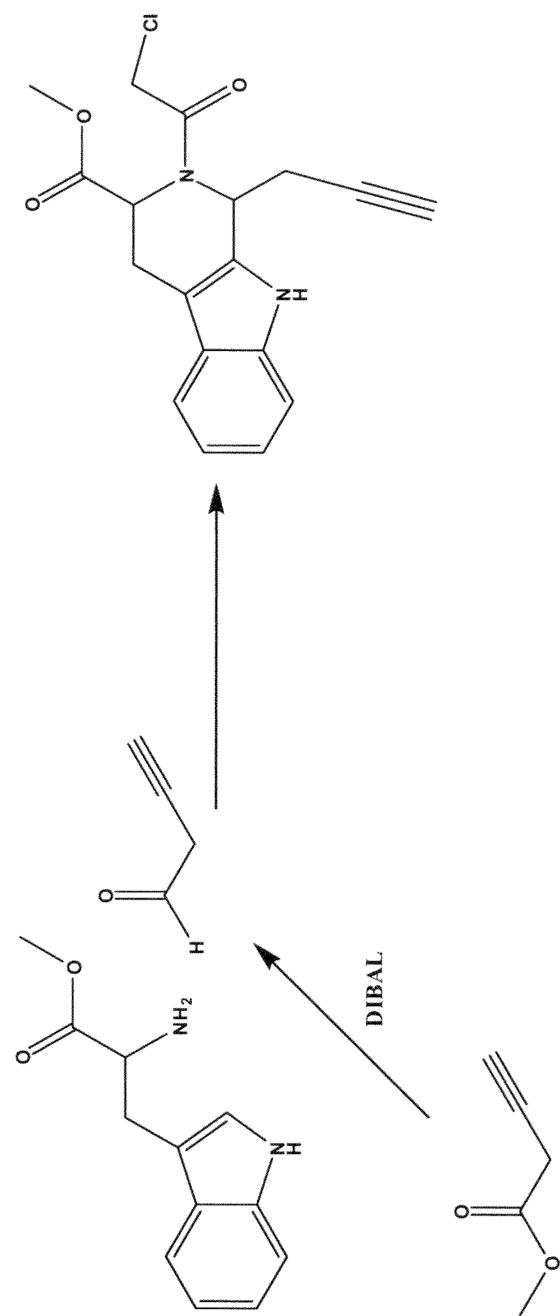
FIG. 28 schematically shows a method of making a Compound 27 analog in which —$CH_2C{\equiv}CH$ is attached to the indole in place of the phenyl ring.

Another analog involving the replacement of the methyl benzoate is a compound having a $-CH_2C\equiv CH$ attached to the indole. The method of making this compound is shown in FIG. 28. The $CH_3O(C{=}O)CH_2C\equiv CH$ starting material is commercially available. DIBAL refers to diisobutyl aluminum hydride, a reducing agent. Pictet-Spengler cyclization proceeds.

Figure 29:
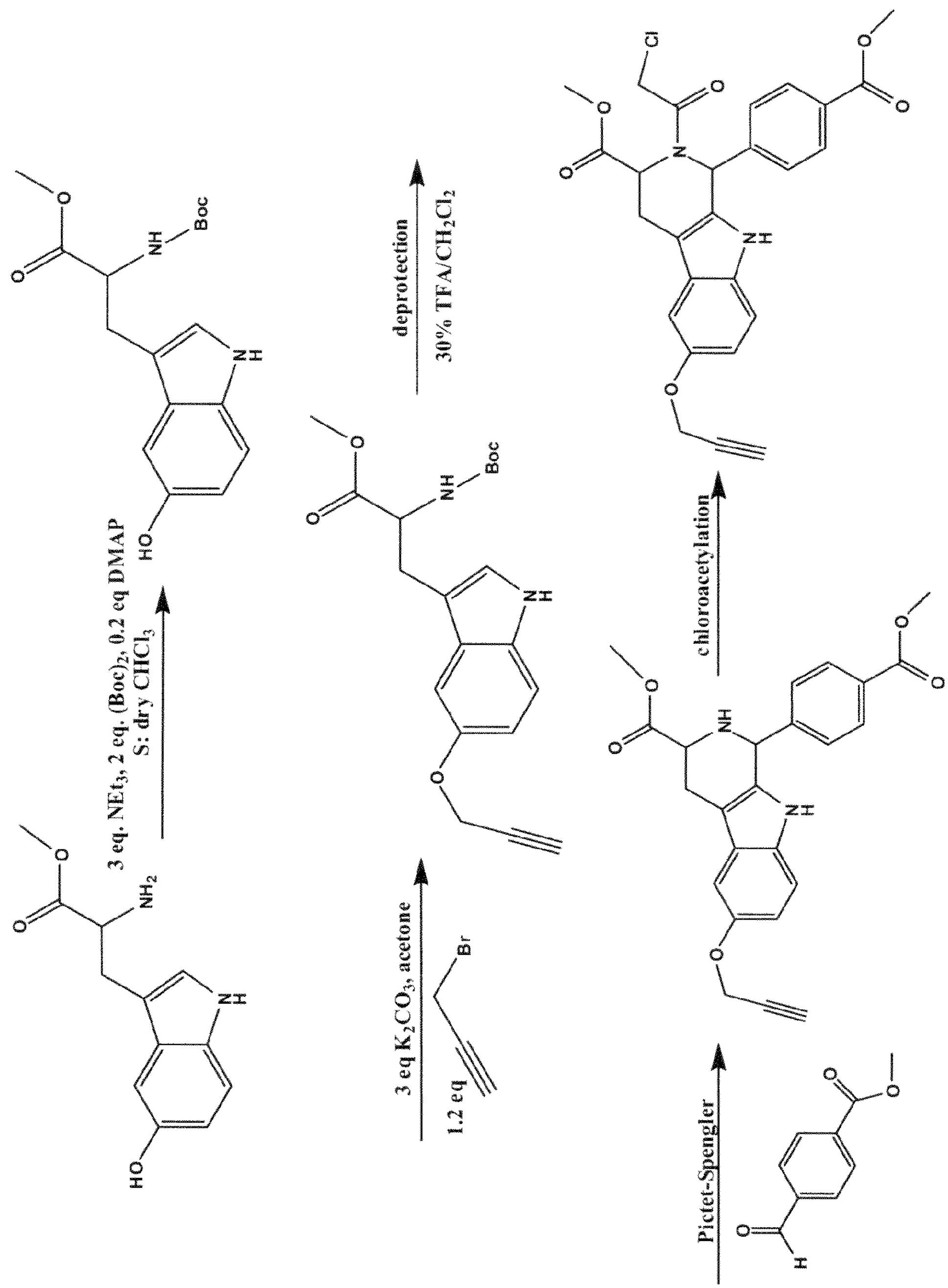
FIG. 29 schematically shows a method of making a Compound 27 analog in which X is one and the substituent is —O—$CH_2{\equiv}CH$ at the 5-indole position.

Optional substitution on the 6-membered ring of the indole is permissible. As noted, X is 0-4 substituent(s). When X is 1-4 substituent(s), the substituent can be independably selected from any substituent as defined herein. FIG. 29 shows the method of making an analog in which X is 1 and the substituent is $-OCH_2C\equiv CH$ at the 5-indole position.

Figure 18:
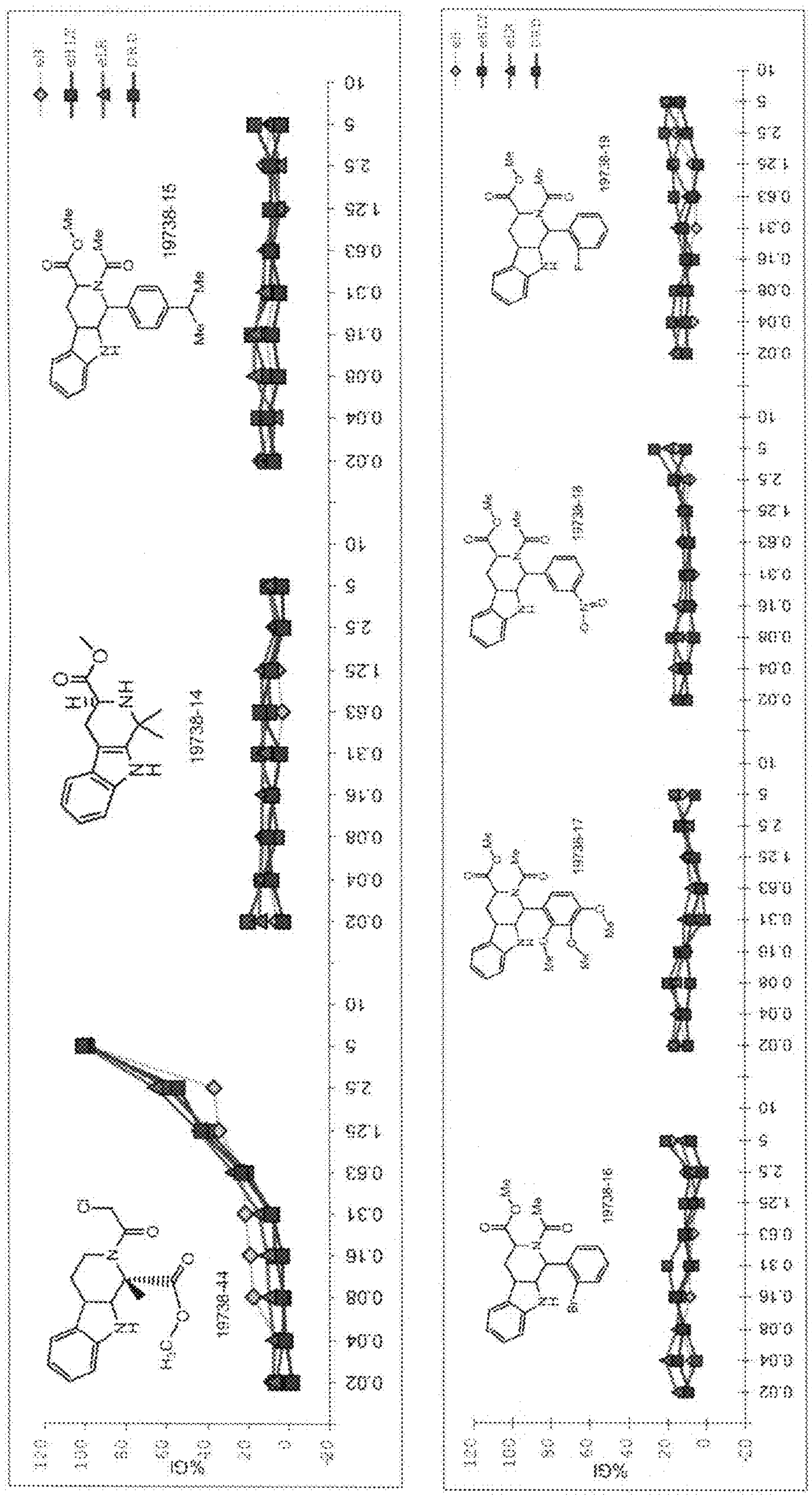
FIG. 18 shows the selectivity and potency of additional compounds of Formula V and other structurally related compounds using an Alamar blue assay in BJ-TERT (eH), BJ-TERT/LT/ST (eHLT), BJ-TERT/LT/ST/RAS$^{V12}$ (eLR), and BJ-TERT/p53DD/CDK4/cyclinD1/ST/RAS$^{V12}$ (DRD) cells.

On the other hand, analogs without the chloromethyl group or the chloro substituent alone did not inhibit cell growth at all, emphasizing a critical role for this group (FIG. 14A—19738-13 and FIG. 18—19738-14). An additional 28 analogs were identified without this chloromethyl group and they were all inactive in all cell lines in the BJ cell system (FIG. 18).

Figure 34:
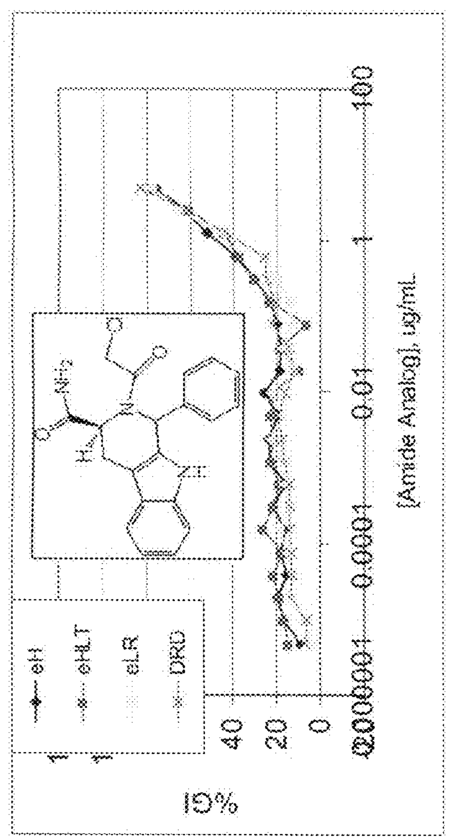
FIG. 34 shows the percent growth inhibition of an analog of Compound 27 in which an amide group and ethyl ester (diastereomer data shown) replace the methyl ester.
Figure 34:
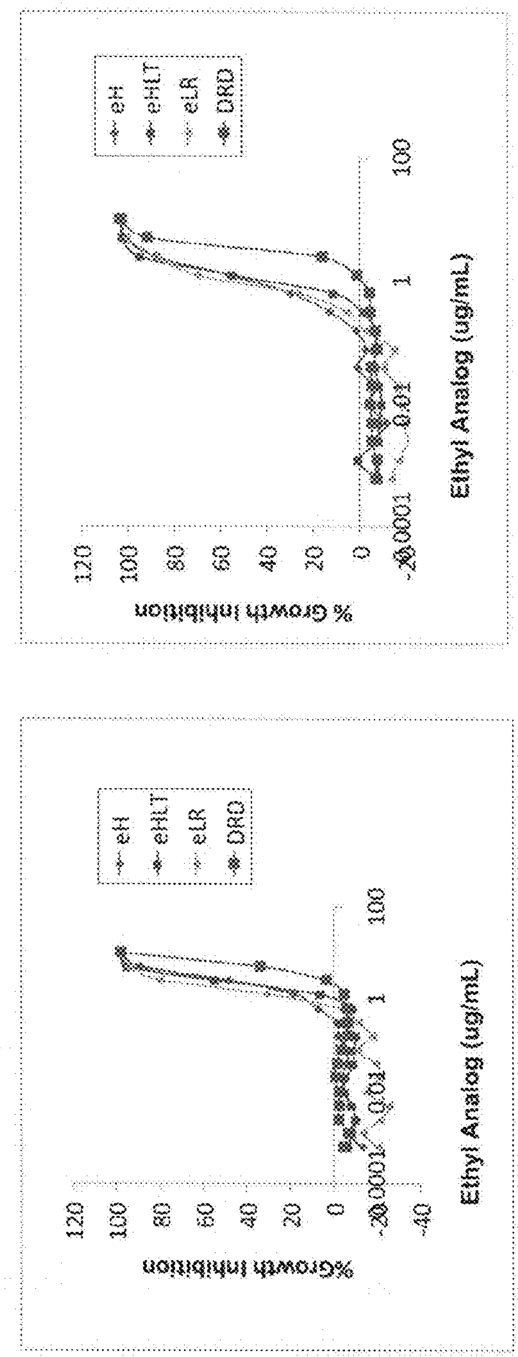
Figure 37:
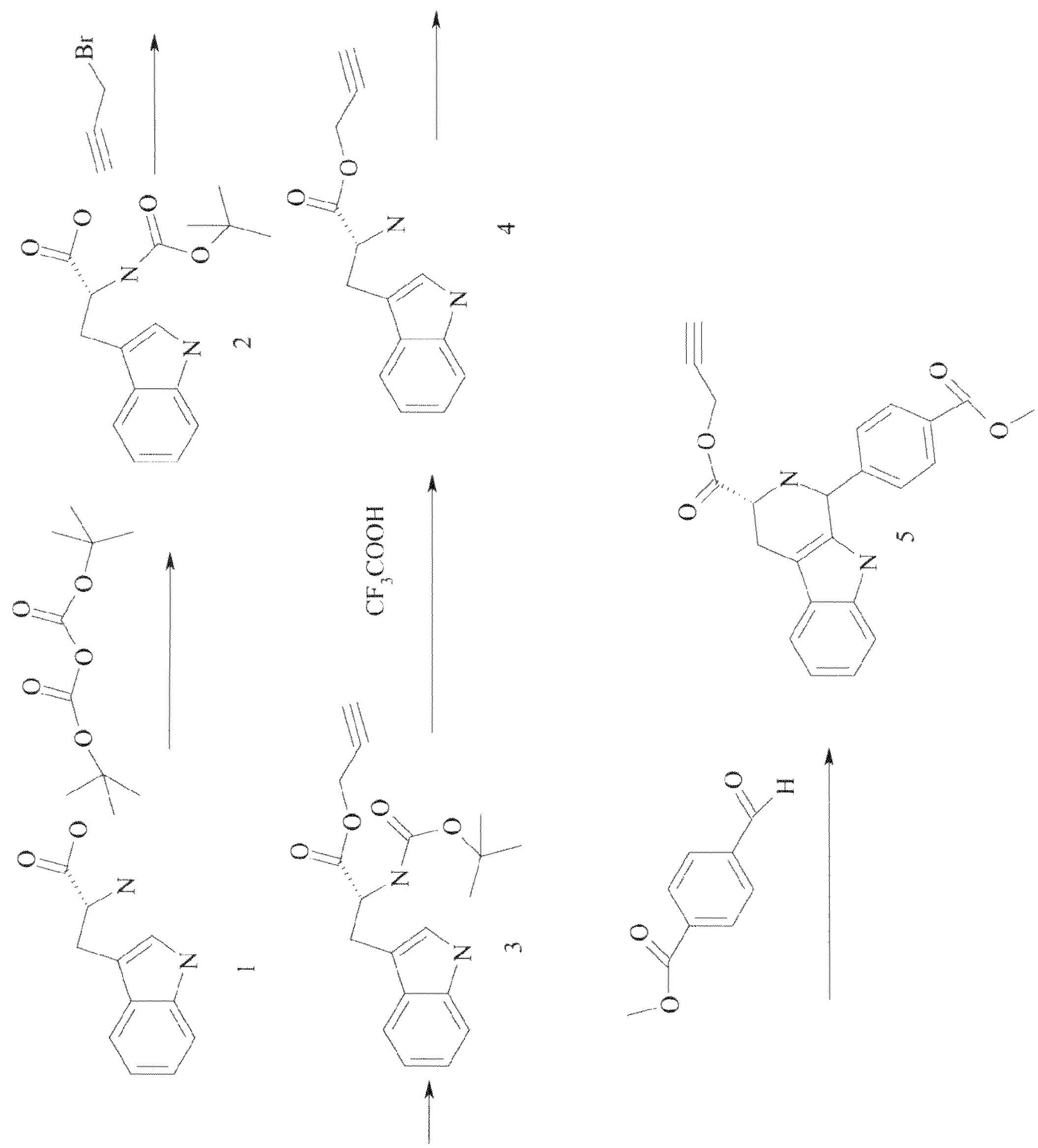
FIG. 37 shows a method of making an analog of Compound 27 in which the methyl ester is replaced with propargyl.

Analogs without the methyl ester were identified. See, for example, FIG. 14A—19738-43. The analogs showed weak activity compared to Compound 27, indicating that the methyl ester group is important. Analogs of Compound 27 were also tested in which the methyl ester group was replaced with each of the following: $-C({=}O)OCH_2CH_3$; $-C({=}O)NH_2$; and $-C({=}O)OCH_2C\equiv CH$. The percent growth inhibition for the amide analog and the diastereomers of the ethyl analog are shown in FIG. 34. The method of making the propargyl analog is shown in FIG. 37, in which alkylation of Compound 5 shown therein is the last step. Each of these analogs was found to be insufficiently active. Extending the methyl ester by replacement with propargyl or ethyl or converting the methyl ester to an amide is therefore not favorable for activity.

Returning to discussion of the chloromethyl groups, the essentiality of the chloromethyl electrophile suggests that Compound 27 covalently labels its target protein. This should make target identification easier, but suggests caution in translating this compound to in vivo studies as there may be some non-specific reactivity of this electrophilic side chain. Development candidates would ideally have attenuated reactivity at this site. In addition, in vivo toxicology studies may reveal whether this compound and its analogs possess a therapeutic index. The Cl substituent is a very good leaving group with high reactivity, although it could result in off-target effects in vivo.

Figure 30:
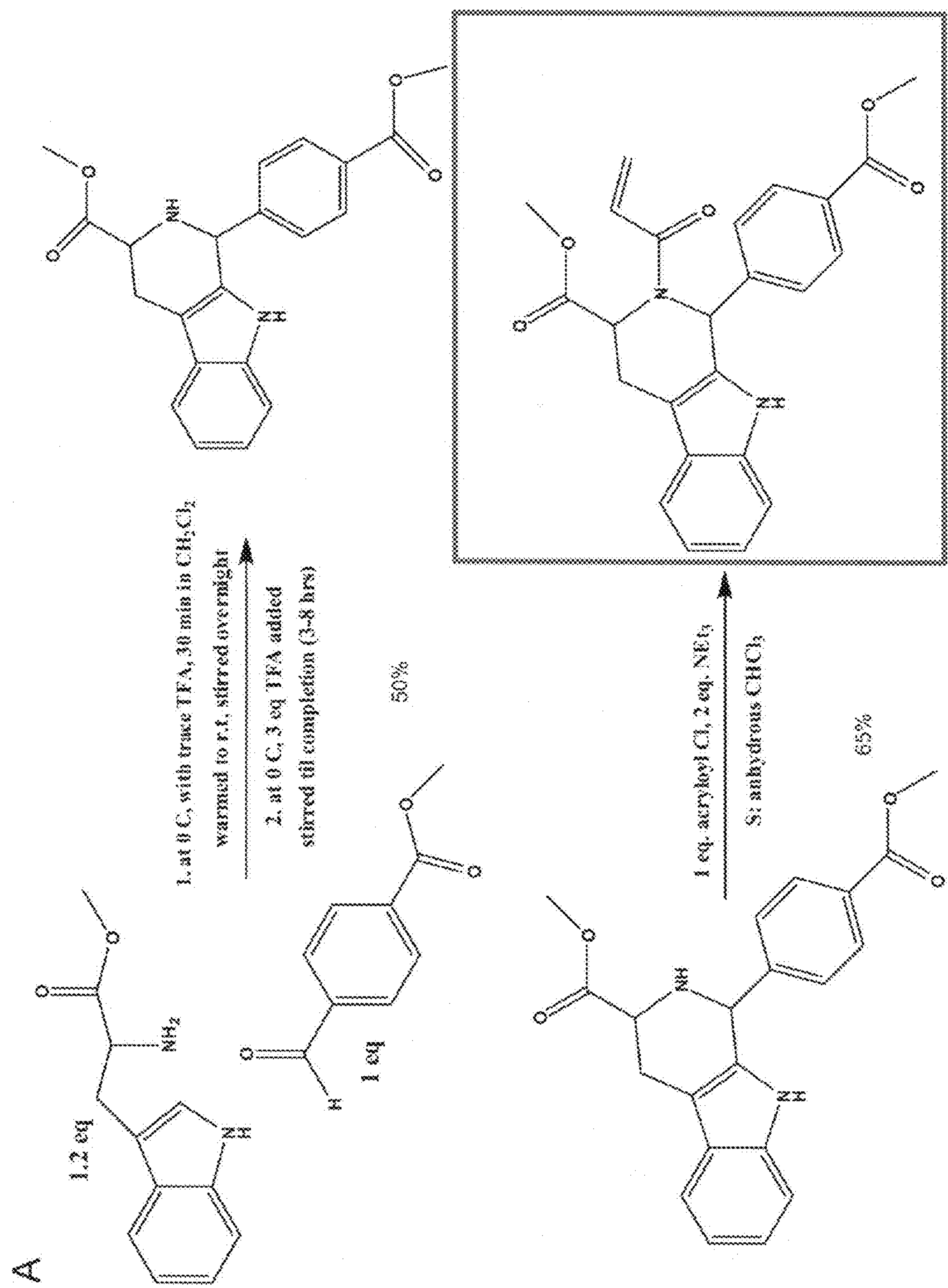
FIG. 30 schematically shows a method of making an acryl Compound 27 analog in which —$CH_2Cl$ of the chloromethyl group is replaced with an ethenyl group (A), and the percent growth inhibition for the acryl analog (B).
Figure 31:
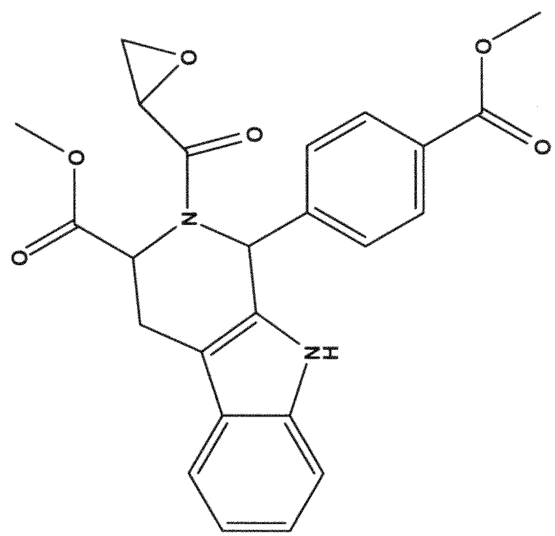
FIG. 31 schematically shows a method of making a Compound 27 analog in which —$CH_2Cl$ of the chloromethyl group is replaced with cyclopropoxyl.
Figure 31:
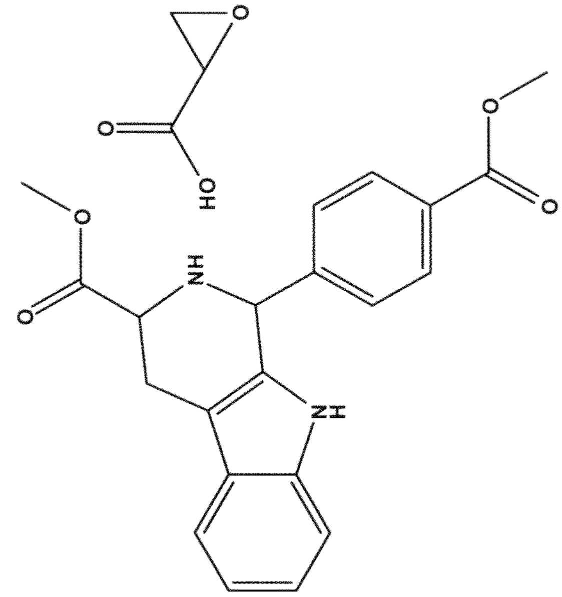
Figure 32:
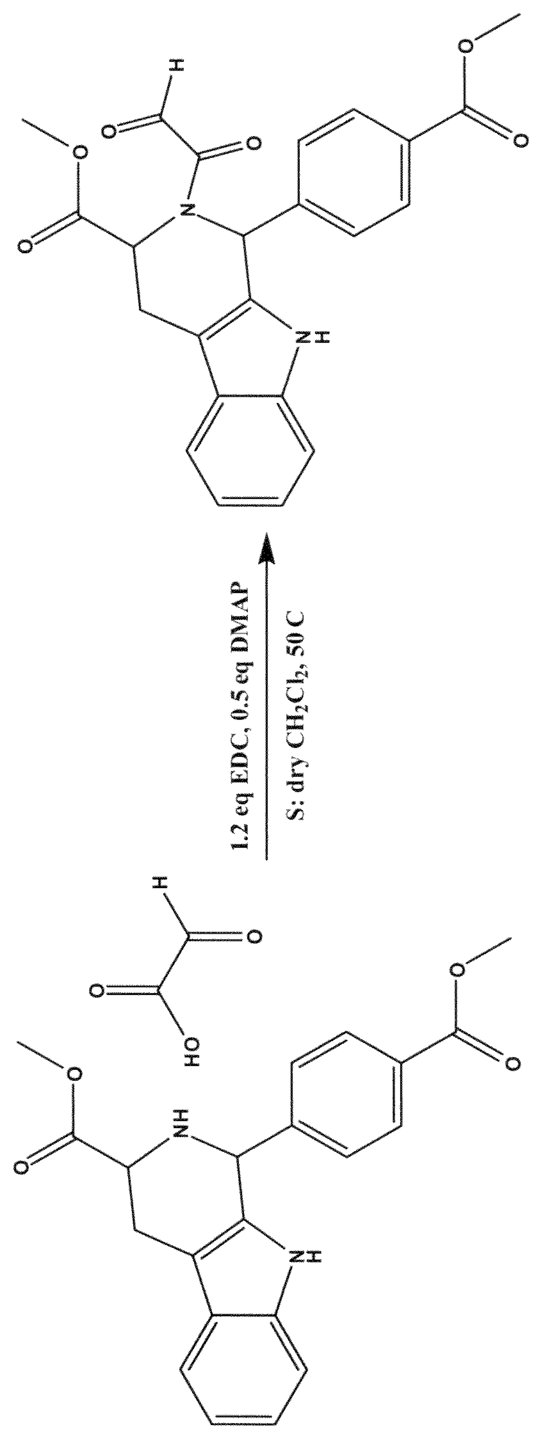
FIG. 32 schematically shows a method of making a Compound 27 analog in which chloromethyl group is replaced with an oxoacetamide group.
Figure 36:
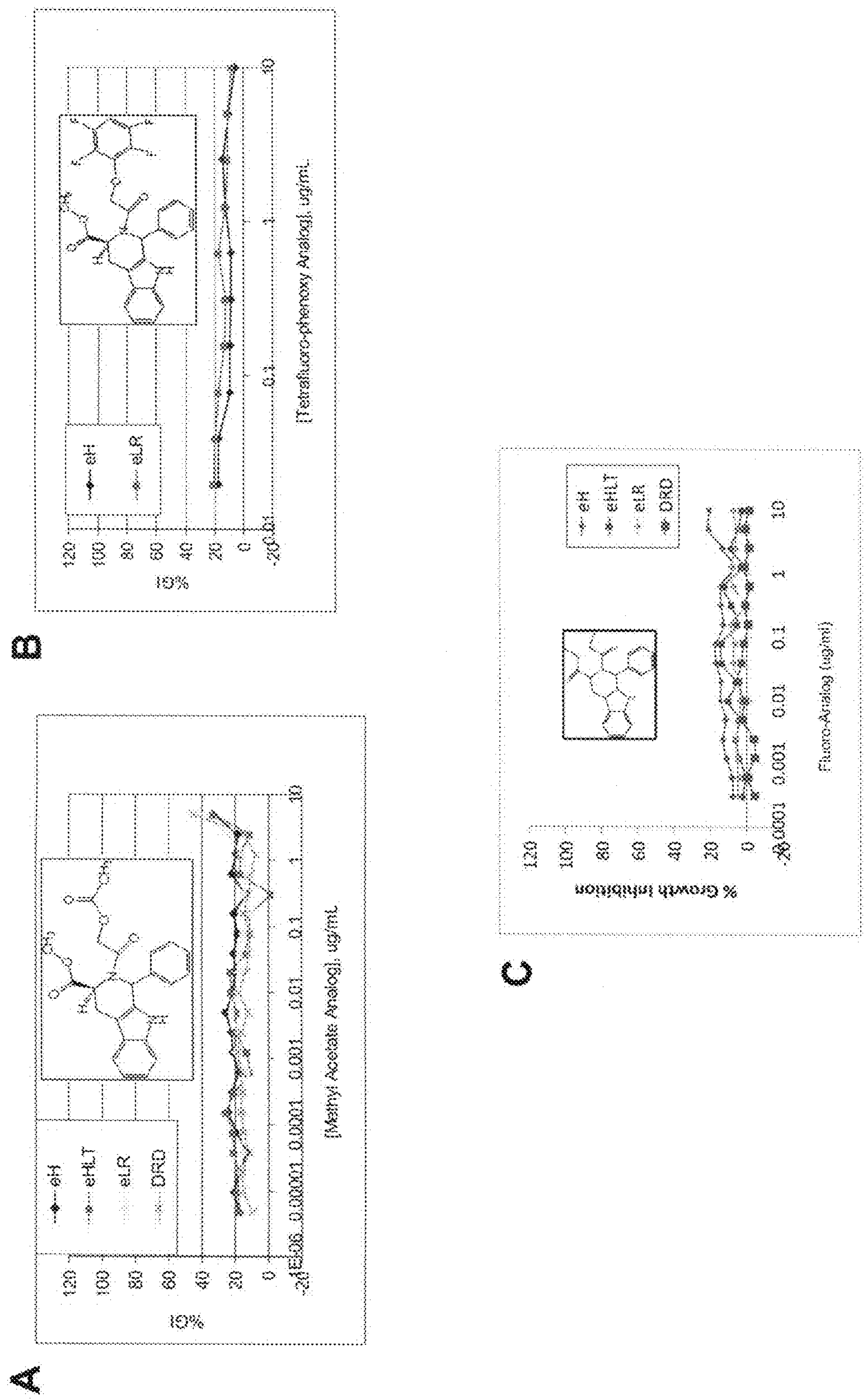
FIG. 36 shows the percent growth inhibition of analogs of Compound 27 in which the chloromethyl is replaced with —O-tetrafluoromethyl (B), —$OC({=}O)CH_3$ (A) and —F (C).

Analogs of Compound 27 were tested in which the Cl of the chloromethyl group was replaced. The following groups in place of Cl were found to confer insufficient activity to the analogs: —OC(═O)$CH_3$ which has a pKa (conjugated acid) of 4.76; —O-tetrafluorophenyl which has a pKa (conjugated acid of <10); and —F which has a pKa (conjugated acid) of 3.15. The percent growth inhibition of the —O-tetrafluorophenyl, —OC(═O)$CH_3$, and —F analogs is shown in FIG. 36. It is noted that F has a higher electrophilicity index value than does Cl. An acryl analog was also tested, replacing the —$CH_2$Cl group with an ethenyl group to form an α,β-unsaturated amide. The process of making the acryl analog is shown in FIG. 30. The acryl analog was found to be insufficiently active, as shown in the second sheet of FIG. 30B. In view of these results, the nucleophile may preferably attack at the alpha carbon. The strength of the nucleophile also appears to be limited, as the fluoro and acetate leaving groups were not eliminated. Further analogs include, in place of the chloromethyl group, cycloproxyl or aldehyde, i.e., —C(═O)H, or in place of the Cl, $N_3$. Regarding the cyclopropoxyl analog, the epoxy amide (which encompasses the ring N), could be attacked by the nucleophile at the alpha or beta position. A process of making the cyclopropoxyl analog is shown in FIG. 31. Regarding the aldehyde analog, this group may allow for nucleophilic attack at the alpha position. A process of making the aldehyde analog which is an oxacetamide including the ring carbon, is shown in FIG. 32. A dicarbonyl electrophile is used to prepare the oxoacetamide. The α-azido compound incorporates a small group which is mild acid having a pKa of 4.6. Replacing the Cl electrophile or the —$CH_2$Cl group with a group having a lower electrophilicity index value than that of Cl (which is 3.67) is a targeted approach concerning the SAR of the chloromethyl.

Figure 33:
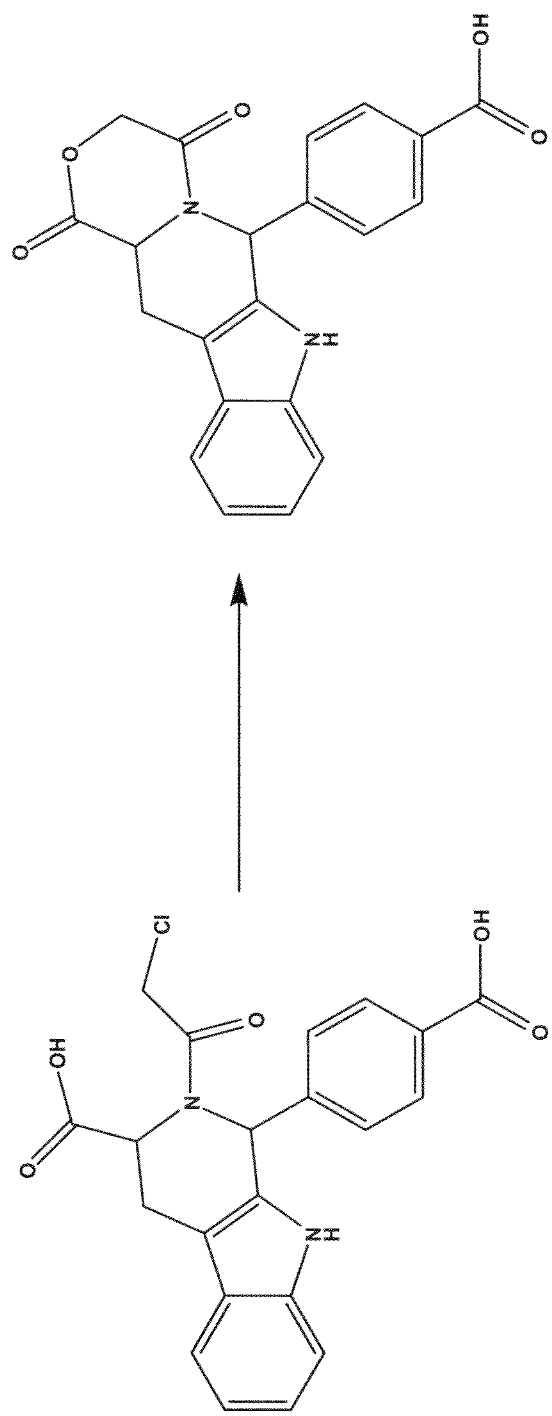
FIG. 33 schematically shows the cyclization of Compound 27 to produce the lactone.

Cyclization of the —($C_6H_4$)—C(═O)OH analog of Compound 27 may proceed by treating with mild base. The resulting lactone is shown in FIG. 33. The electrophile is not present in the cyclized compound.

Based on its strong potency against numerous cancer cell lines, and its unique patterns of selectivity, Compound 27 is the most interesting candidate out of these four scaffolds. From the SAR studies, possible sites where affinity tags can be attached without eliminating the activity of the compound may be inferred. Moreover, the essentiality of the chloromethyl group suggests that the target is covalently labeled by this compound.

Iron-Dependent Activity of Hit Compounds

Figure 19:
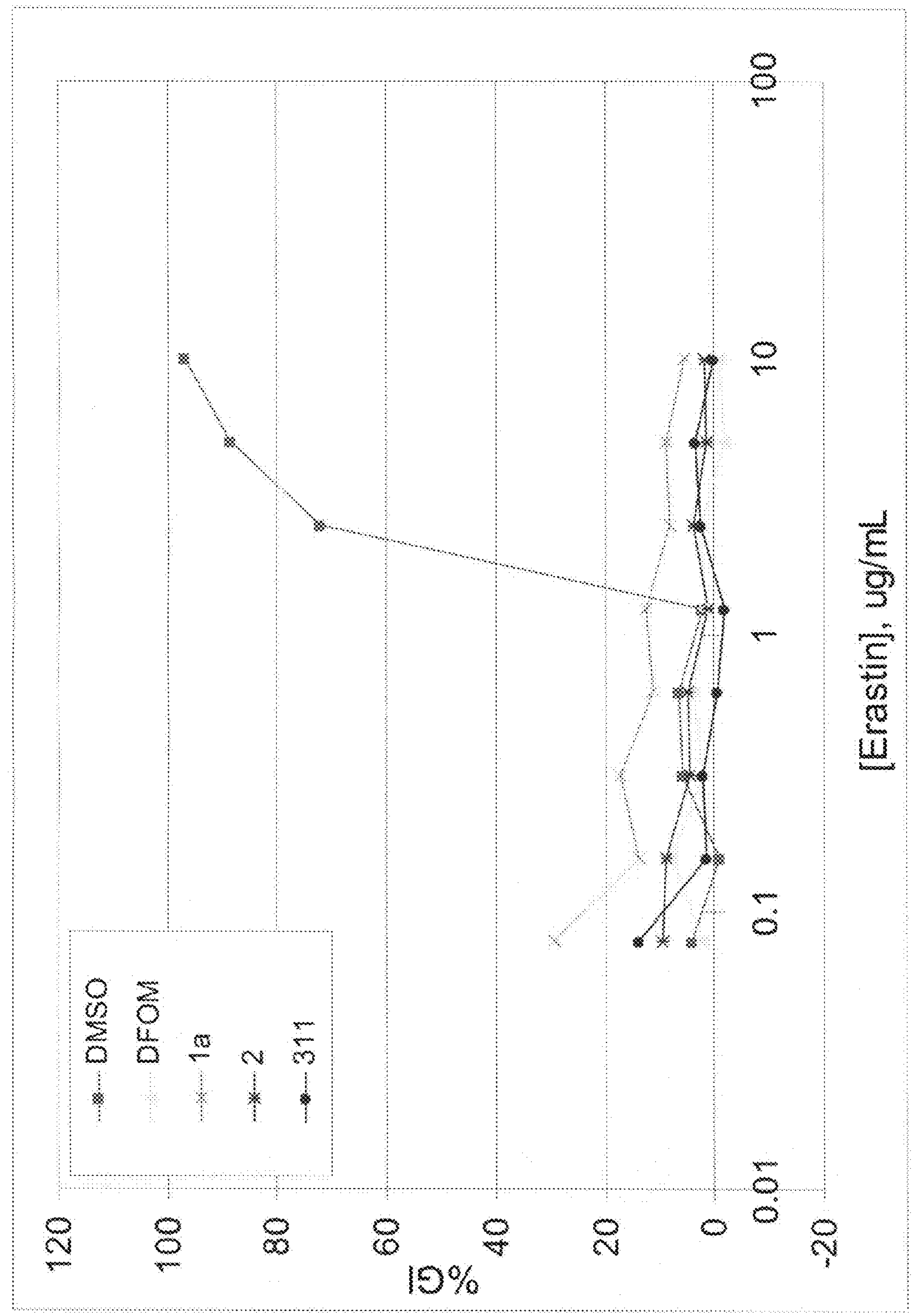
FIG. 19 shows the results of counter screening of Erastin, Compound 3, Compound 6, Compound 27, and Compound 36 with known iron chelators in BJ-TERT/LT/ST/RAS$^{V12}$ cells.

Interestingly, all of these compounds, except Compound 6, were inhibited by iron chelators, such as DFOM. Three additional iron-binding compounds were tested for their protective effect in order to test whether the protective effect of DFOM comes from its ability to deplete iron or from other factors that may be specific to DFOM. Also included in these analyses was Erastin, a previously identified cancer-cell-specific lethal compound (Dolma et al., 2003). The activities of Erastin, Compound 3, and Compound 36 were significantly inhibited by all of these iron chelators (FIG. 19). Compound 27-induced cell death was also suppressed by all of these iron chelators moderately, indicating that its activity also depends on iron (FIG. 19).

Figure 20:
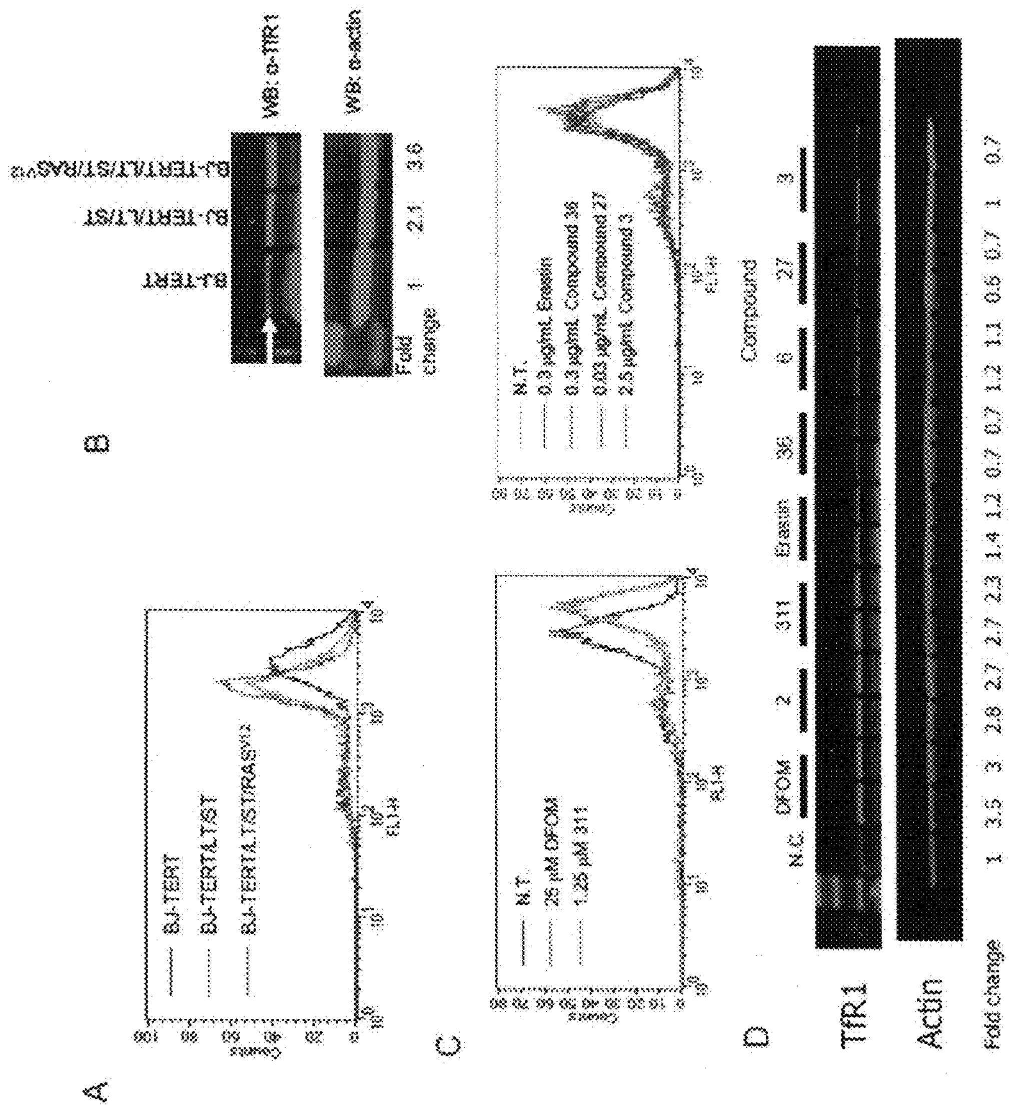
FIG. 20A shows the cellular iron levels in BJ-TERT, BJ-TERT/LT/ST, and BJ-TERT/LT/ST/RAS$^{V12}$ cells using the fluorescent iron sensor, Phen Green SK.
FIG. 20B shows the expression level of transferrin receptor 1 (TfR1) in BJ-TERT, BJ-TERT/LT/ST, BJ-TERT/LT/ST/RAS$^{V12}$ cells by Western blot. An antibody against actin was included as a control for assessing protein loading.
FIG. 20C shows the cellular iron levels in BJ-TERT/LT/ST/RAS$^{V12}$ cells, treated with indicated compounds for 24 hours, using the fluorescent iron sensor, Phen Green SK.
FIG. 20D shows the expression level of transferrin receptor 1 (TfR1) in BJ-TERT/LT/ST/RAS$^{V12}$ cells treated with DFOM, 2, 311, Erastin, Compound 36, Compound 6, Compound 27, and Compound 3 by Western blot. An antibody against actin was included as a control for assessing protein loading.
FIG. 20E shows a quantitative representation of the expression level of transferrin receptor 1 (TfR1) in BJ-TERT/LT/ST/RAS$^{V12}$ cells treated with DFOM, 2, 311, Erastin, Compound 36, Compound 6, Compound 27, and Compound 3 by Western blot (see FIG. 20D).
FIG. 20F shows cell growth inhibition in HT1080, HT1080-vector, and HT1080-TfR1KD cells by Compound 27 (left panel) or Erastin (right panel) in the presence of 150 μM DFOM, 10 μM U0126, 50 μM SU6656, or 100 μM Vitamin E, as indicated, using an Alamar blue assay.
FIG. 20G shows cell growth inhibition of Erastin, Compound 3, Compound 27, and Compound 36 (from left to right) in HT1080, HT1080-vector, and HT1080-TfR1KD cells using an Alamar blue assay.
Figure 21:
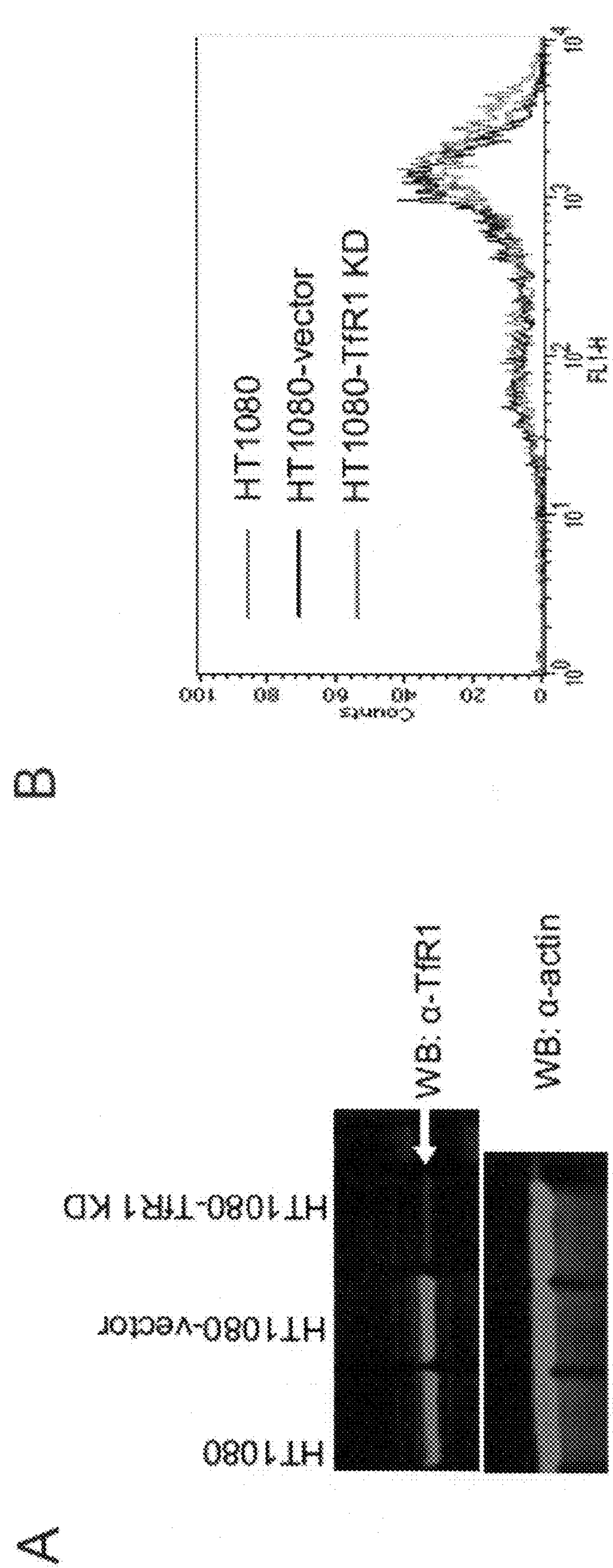
FIG. 21A shows the expression level of TfR1 in HT1080, HT1080-vector, and HT1080-TfR1 KD cells by Western blot analysis with an antibody directed against TfR1. An antibody against actin was included as a control for assessing protein loading.
FIG. 21B shows the level of the basal iron pool in HT1080, HT1080-vector, and HT1080-TfR1 KD cells.
Figure 48:
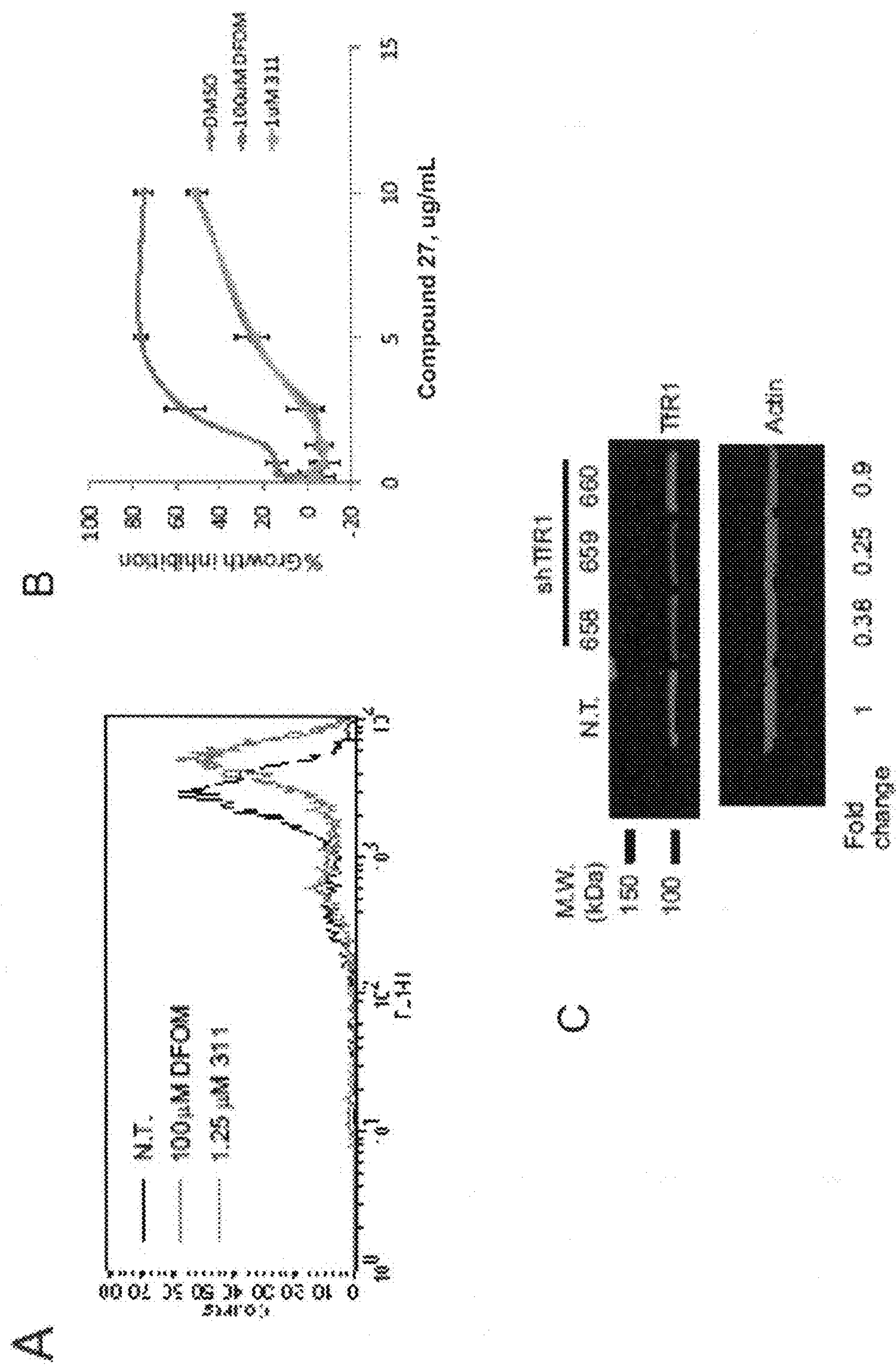
FIG. 48 shows the results of flow cytometry to confirm iron depletion of the iron chelators in BJ-TERT/LT/ST/$RAS^{V12}$ cells treated with the indicated iron chelators in panel A; percent growth inhibition in BJ-TERT/LT/ST/$RAS^{V12}$ cells treated with Compound 27 in the presence or absence of iron chelators in panel B; the level of TfR1 in each cell line was determined by Western blot using an antibody against TfR1 using whole cell lysates from BJ-TERT/LT/ST/$RAS^{V12}$ cells infected with either non-targeting shRNA (N.T.) or three different TfR1-targeting shRNAs (658, 659, 660) that were prepared, in panel C; the relative expression level of a gene among the three cell lines was expressed as a ratio of transcripts in a cell line to those in BJ-TERT where cellular RNAs were prepared from each cell line, real-time PCR was performed with each gene-specific primer set, and the expression levels of TfR1 (panel D), FTH1 (panel E) and FTL (panel F) were first normalized to the level of endogenous control (RPLPO).

However, these engineered BJ tumor cells might have altered iron content compared to their non-tumorigenic counterparts, shifting selection pressure in the screening to identify iron-dependent lethal compounds. To test this hypothesis, cellular iron levels were monitored using a fluorescent iron sensor, Phen Green SK (PGSK) (FIG. 20A; FIG. 48A). This cell-permeable molecule has green auto-fluorescence, which diminishes upon binding to cellular iron (Petrat et al., 2000). When the intensity of fluorescence from PGSK-treated BJ cells was detected using flow cytometry, BJ-TERT and BJ-TERT/LT/ST cells showed a similar profile, whereas BJ-TERT/LT/ST/$RAS^{V12}$ cells showed decreased fluorescence. This indicated that BJ-TERT/LT/ST/$RAS^{V12}$ cells have a greater basal level of iron than its isogenic precursors (FIG. 20A). Increased fluorescence intensity was seen in iron-chelator-treated BJ-TERT/LT/ST/$RAS^{V12}$ cells. When these cells were treated with Compounds 3 and 27 in the presence of iron chelators, the activities of the compounds were significantly inhibited, highlighting the importance of iron levels for inducing lethality (FIG. 48B).

It was hypothesized that iron-metabolism-related proteins in BJ-TERT/LT/ST/$RAS^{V12}$ cells might be adapted to allow increased iron uptake and maintenance. Transferrin receptor 1 (TfR1) is a membrane protein that binds to the transferrin-iron complex and is internalized to release iron within the cytoplasm (Cheng et al., 2004). The expression level of TfR1 was monitored by Western blot and showed an increased amount of TfR1 expression in BJ-TERT/LT/ST/$RAS^{V12}$ cells (FIG. 20B). Thus, BJ-TERT/LT/ST/$RAS^{V12}$ cells may have greater levels of iron because they have a greater abundance of TfR1 protein, which leads to increased iron uptake.

A simple hypothesis as to how these hit compounds exploit increased iron content to induce oncogenic-RAS-signal-dependent lethality is (a) that they bind to iron to deplete the cellular iron pool and (b) that cancer cells have higher dependency on iron, which results in differential sensitivity to iron chelators. To test this hypothesis, BJ-TERT/LT/ST/$RAS^{V12}$ cells were treated with these hit compounds and changes in cellular iron level were monitored using PGSK (FIG. 20C). Treatment with control iron chelators, DFOM and 311, induced a peak shift in the fluorescence profile, indicating dequenching of PGSK, caused by iron depletion (FIG. 20C (left panel)). In contrast, none of the iron-dependent lethal compounds induced dequenching of PGSK (FIG. 20C (right panel)).

Another indirect approach to monitor changes in iron level upon compound treatment was used. TfR1 is important in iron homeostasis, and it is known that the level of TfR1 protein is tightly regulated in relation to changes in iron concentration. Cells actively upregulate TfR1 under iron-depleted conditions (Templeton, 2002). Treatment with control iron chelators in BJ-TERT/LT/ST/$RAS^{V12}$ cells induced an increase in TfR1 protein level, indicating the iron regulatory machinery in BJ-TERT/LT/ST/$RAS^{V12}$ cells is normal. However, none of these hit compounds induced TfR1 (FIGS. 20D & E). Thus, it is unlikely that these compounds bind to and deplete cellular iron.

BJ-TERT/LT/ST/$RAS^{V12}$ cells are already engineered with a number of antibiotic resistance genes. Accordingly, an alternative cell line, HT1080, was used to generate TfR1 knock-down cells using shRNAs targeted against TfR1. These TfR1 knock-down cells were used to validate the importance of iron in hit-compound-induced cell death by reducing iron levels using a genetic manipulation and to compare the drug sensitivity between the modified cell line and the parental cell line. HT1080 cells showed good sensitivity against Compound 27 and Erastin treatment, and shared a similar mechanistic profile: treatment with iron chelators, MEK inhibitors or non-receptor tyrosine kinase inhibitors effectively inhibited Compound 27-induced cell death, while treatment with iron chelators, MEK inhibitors or antioxidants inhibited Erastin-induced cell death, in HT1080 cells (FIG. 20F). Erastin, Compound 3 and Compound 27 all were found to induce a similar phenotype, RAS-RAF-MEK-dependent oxidative, iron-dependent cell death. The bioactive compounds used suppressed cell death in all three compounds. See data for bioactives tested for Compound 27 (FIG. 42).

shRNA expression plasmids were delivered to HT1080 cells using a lentiviral system (Moffat et al., 2006) and puromycin was used to generate an HT1080-derived cell line, HT1080-TfR1KD, which stably expresses an shRNA targeting TfR1. These HT1080-TfR1KD cells have a lower level of TfR1, determined by western blotting (FIG. 21A), and have a slightly decreased basal level of cellular iron, determined by PGSK staining (FIG. 21B). When these iron-dependent lethal compounds were tested in HT1080-TfR1KD cells, they showed decreased sensitivity to Erastin, Compound 3, and Compound 36, while parental HT1080 cells and vector-infected HT1080 cells showed similar sensitivity to all compounds (FIG. 20G). These results indicate that the TfR1-regulated iron pool is one of the factors determining sensitivity of these tumor cells to oncogenic-RAS-signal-dependent lethal compounds.

To validate the importance of iron in lethal compound-induced cell death, iron levels were reduced using a genetic method, and then drug sensitivity was compared between the modified cell line and the parental cell line. Three different shRNAs targeting TfR1 were delivered to BJ-TERT/LT/ST/RAS$^{V12}$ cells using a lentiviral system (Moffat et al., 2006). Two shRNA clones displayed moderate level of knock down efficiency (clone 658 and 659) whereas one shRNA clone was not effective, as assessed by western blot analysis (clone 660) (FIG. 48C). When erastin was tested in these cells, erastin became less effective in clone-658-expressing and clone-659-expressing cells, compared to clone-660-expressing and non-targeting-shRNA-expressing cells. However, the level of cell death suppression was not comparable to that of iron-chelator-treated cells. This partial rescuing activity of shRNAs targeting TfR1 may reflect insufficient level of knock down or the existence of other mechanisms for enriching the iron content of RAS-transformed cells.

To explore other aspects of oncogenic-RAS-signaling relevant to iron enrichment, the expression level of other genes whose functions are known to modulate cellular iron content was compared. The TfR1-mediated pathway is one route of iron uptake, but the cellular iron pool is also controlled by an iron storage protein complex, consisting of ferritin heavy chain 1 (FTH1) and ferritin light chain (FTL). (Harrison and Arosio, 1996). Real-time RT-PCR analysis showed a gradual increase in TfR1 mRNA levels across the BJ-TERT, BJ-TERT/LT/ST and BJ-TERT/LT/ST/RAS$^{V12}$ cells, in agreement with western blot analysis (FIG. 48D and FIG. 20B). Interestingly, the expression level of both FTH1 and FTL was specifically decreased in BJ-TERT/LT/ST/RAS$^{V12}$ cells (FIGS. 48E and 48F), indicating that oncogenic-RAS-signaling has a dual mechanism to augment the cellular labile iron pool: one is to increase iron uptake via up-regulation of TfR1, the other is to reduce the capacity of iron storage via down-regulation of FTH1 and FTL.

Involvement of VDAC3 in Erastin-Induced and Compound 3-Induced Cell Death

As erastin, Compound 3, and Compound 27 emerged from a similar screening setting, and share a common genetic selectivity and induced phenotype, whether Compound 3 and Compound 5 act through the same mechanism as erastin, by engaging mitochondrial VDACs was replaced. Using affinity purification and mass spectrometry, mitochondrial voltage-dependent anion channels (VDACs) were identified as specific targets of erastin (Yagoda et al., 2007).

Mammalian cells have three VDAC isoforms, VDAC1, VDAC2 and VDAC3. An erastin affinity analog specifically purifies VDAC2 and VDAC3 only in lysates of BJ-TERT/LT/ST/RAS$^{V12}$ cells, not of BJ-TERT cells. RNA interference experiments targeting VDAC2 and VDAC3 demonstrated that erastin binding to VDAC2 and VDAC3 induces a gain-of-function lethality: knocking down VDAC3 makes cells resistant to erastin, and knocking down VDAC2 reduces their sensitivity to erastin (Yagoda et al., 2007).

Figure 43:
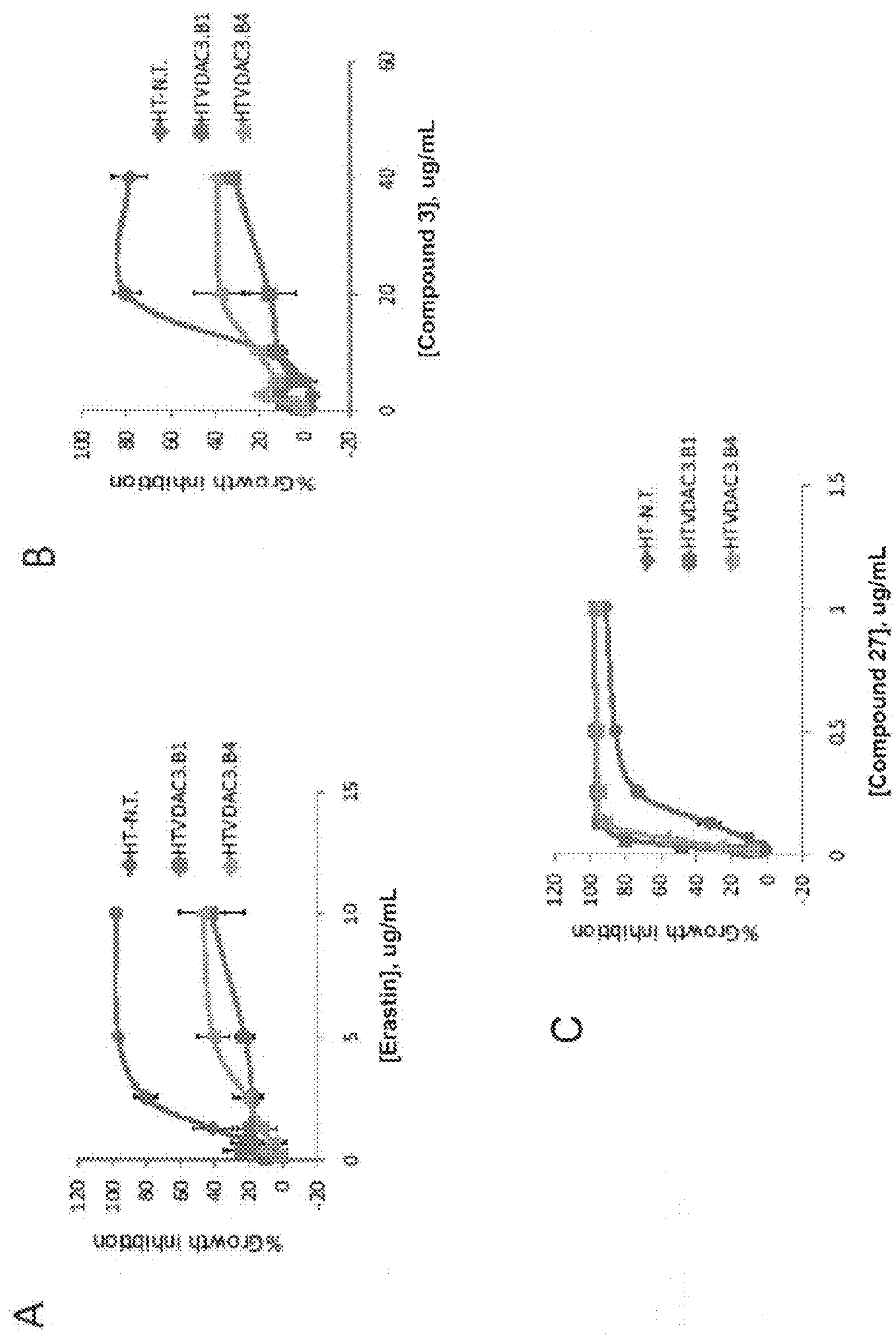
FIG. 43 shows the percent growth inhibition using alamar blue in HT1080 cells infected with lentivirus encoding shRNAs targeting VDAC3 and treated with erastin in panel A, Compound 3 in panel B, and Compound 27 in panel C.
Figure 44:
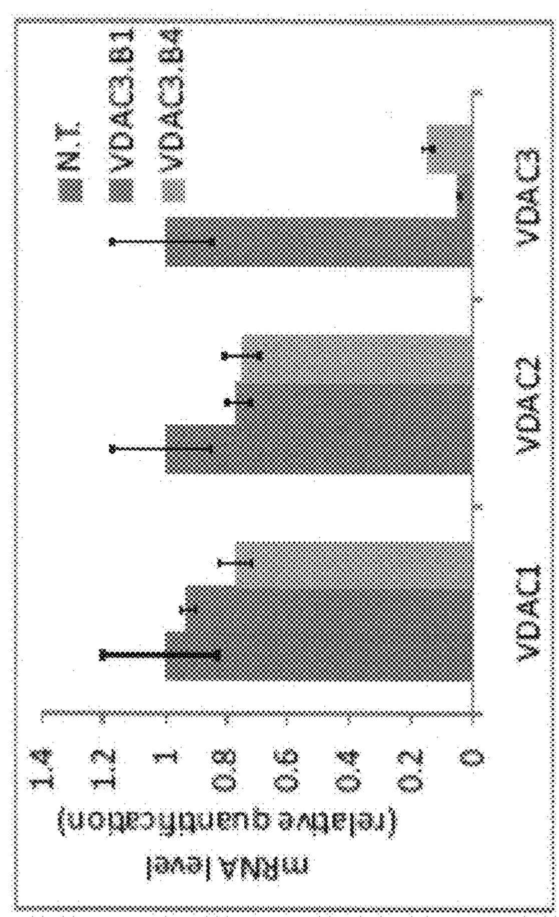
FIG. 44 shows the mRNA levels (relative quantification) of VDAC1, VDAC2, and VDAC3 to determine the specificity of shRNAs targeting VDAC3 using Q-PCR.

To test the possibility of VDAC involvement in the synthetic lethal action of Compound 3 and Compound 27, VDAC3 in HT1080 cells were knocked down, using short hairpin RNAs (shRNAs) specifically targeting VDAC3. Knockdown of VDAC3 protein suppressed erastin-induced and Compound 3-induced cell death, whereas Compound 27 lethality was not affected (FIG. 43). Introduction of shRNAs targeting VDAC3 did not change the level of other VDAC isoforms (VDAC1 and VDAC2), as assessed by quantitative PCR (Q-PCR) (FIG. 44). Thus, Compound 3 acts through at least VDAC3, as does erastin. However, Compound 27 appears to act in a VDAC3-independent manner.

This is of interest, because it demonstrates that the oxidative, non-apoptotic cell death pathway targeted by these compounds is not restricted to VDAC involvement, but can be activated under other conditions and may be more generally important.

Figure 45:
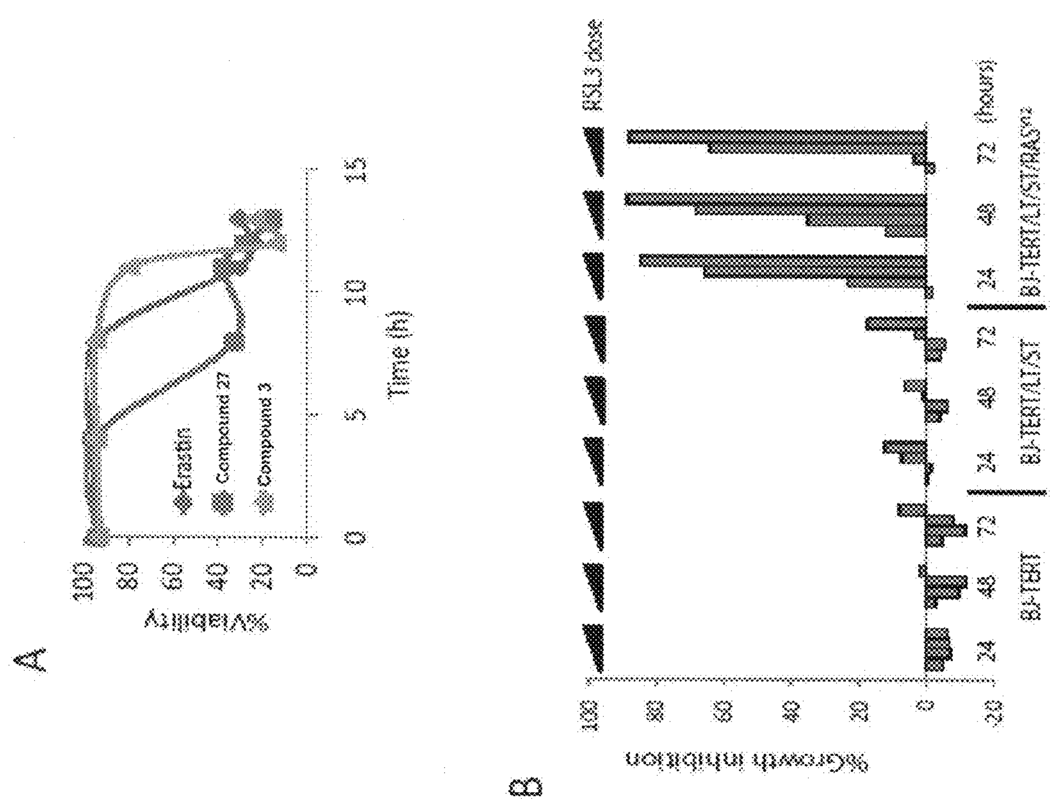
FIG. 45 shows cell viability over time after treatment determined from kinetic analysis of cell death induced by 5 ug/ml erastin, 20 ug/ml Compound 3 and 0.5 ug/ml Compound 5 in panel A, the time dependent effect of Compound 27 on three BJ cell lines on growth inhibition in panel B, a photograph of the two BJ cell lines treated with 5 ug/ml erastin, 20 ug/ml Compound 3, 0.5 μ/mL of Compound 27, or 1 μM of staurosporine for 24 h. in panel C, and lysates of staurosporine-treated but not erastin-treated, Compound 3-treated or Compound 27-treated BJ-TERT/LT/ST/$RAS^{V12}$ cells that contain the PARP-1 fragment produced by caspase-3/7 cleavage, analyzed by Western blot with an antibody directed against human PARP-1 in panel D.

Compound 27 has Oncogenic-RAS-Signal Dependent Lethality with a Unique Sensitivity Profile Compound 27's ability to induce synthetic lethality with oncogenic RAS was rapid and quite potent. This compound inhibited the growth of BJ-TERT/LT/ST/RAS$^{V12}$ and DRD cells as low as 10 ng/mL (FIG. 42 panel A) and started to kill sensitive cells as early as 8 hours after treatment (FIG. 45 panels A and C). A trypan blue exclusion assay was carried out to confirm the growth inhibitory effect and the selectivity of Compound 27. This was performed in a Vi-Cell (Beckman Coulter), which stains cells with trypan blue, takes 100 images, and analyzes the images to calculate the number of viable cells (i.e. cells excluding trypan blue). This assay eliminates false positives caused by auto-fluorescence or redox activity from a compound in the alamar blue assay. The trypan blue exclusion assays with Compound 27 revealed a similar level of potency and selectivity as the alamar blue assay (FIG. 45 panel B). Moreover, longer treatment had little effect on the viability of cells lacking oncogenic RAS, confirming the qualitative nature of Compound 27's selectivity (FIG. 45 panel B).

Cell death induced by Compound 27 treatment was not blocked by pan-caspase inhibitors (z-VAD-fmk, Boc-D-fmk), suggesting that a caspase-independent death pathway is involved in Compound 27-induced cell death. Because the survival effect of caspase inhibitors can be masked by activation of alternative cell death pathways upon drug treatment, we employed a more sensitive measurement of caspase activation to examine the possible involvement of caspases in Compound 27-induced cell death. Poly(ADP-ribose) polymerase-1 (PARP-1) is an abundant nuclear enzyme that is subject to cleavage by activated caspase 3/7. Staurosporine, erastin, Compound 3 and Compound 5 treatments of BJ-TERT/LT/ST/RAS$^{V12}$ cells were compared, cell lysates were prepared, PARP-1 cleavage was analyzed by western blot with an anti-PARP-1 antibody (FIG. 45 panelD). Only staurosporine-treated sample showed PARP-1 cleavage, indicating that staurosporine induces classical apoptotic cell death involving caspases, whereas erastin, Compound 3, and Compound 27 activate a non-apoptotic pathway (FIG. 45 panelD).

Figure 46:
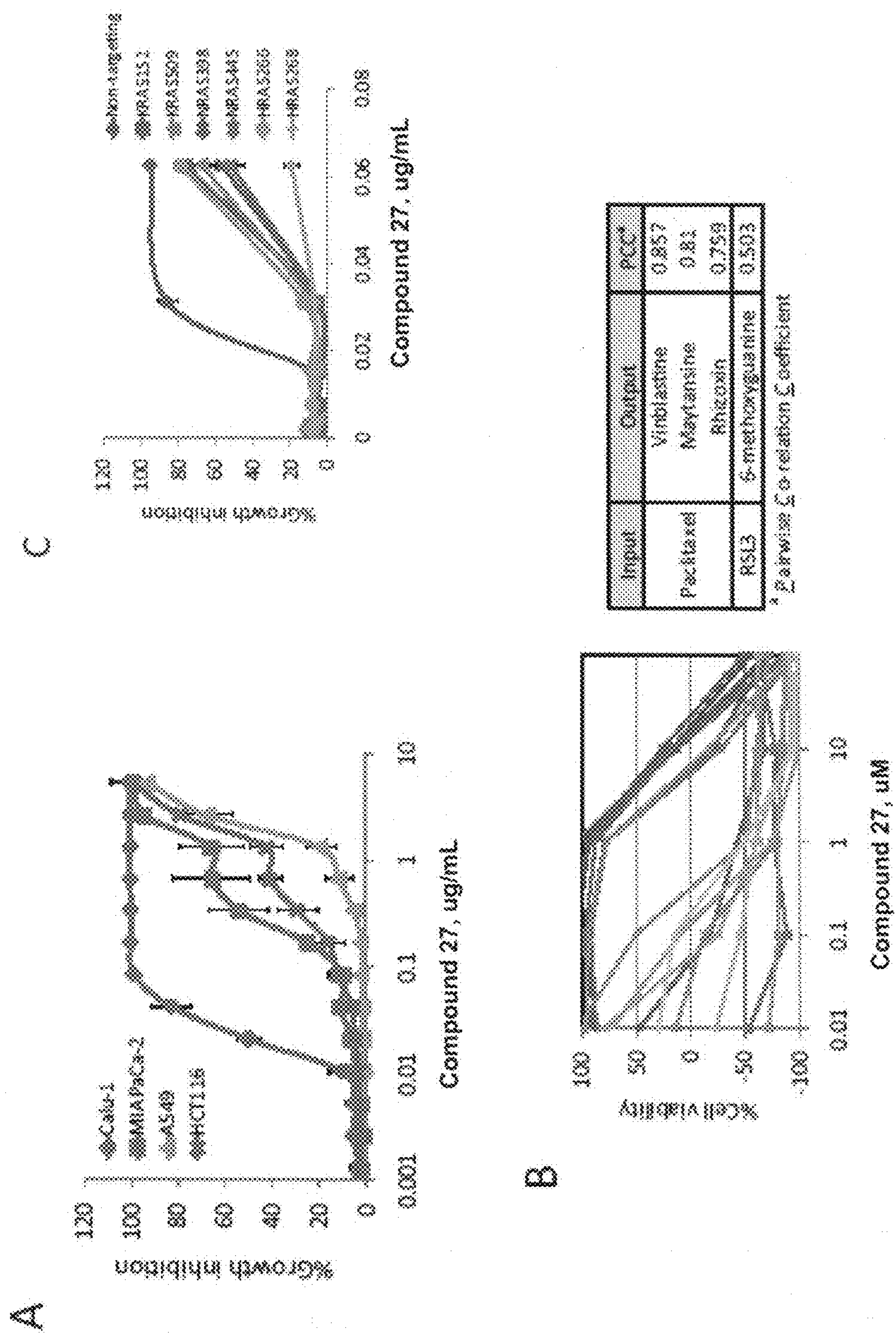
FIG. 46 shows percent growth inhibition using alamar blue indicating that Compound 27 was active in killing four KRAS mutation harboring cancer cells, A549, Calu-1, PaCa-2 and HCT116 cells, treated for 24 hour in panel A; the activity of Compound 27 tested in 60 different human cancer cell lines where the left chart shows the result of 18 cell lines that are representative of sensitive and resistant groups (zero viability meaning a cytostatic effect, and negative viability meaning a cytotoxic effect) and the right table shows results of the COMPARE analysis for paclitaxel and Compound 27 in panel B; percent growth inhibition using alamar blue showing attenuation of RAS signaling in Calu-1 cells by infecting with lentivirus containing shRNAs targeting H, N, or KRAS confers resistance to Compound 27-induced lethality in panel C.

Among the three RAS genes (HRAS, KRAS, NRAS), the BJ cell system employed HRAS mutations to initiate oncogenic signals. All three RAS protein can activate common downstream effectors but, for elusive reasons, human cancer cells have biased mutation rates among the three RAS genes; more than 70% contain KRAS mutations, 25% NRAS mutations and less than 5% HRAS mutations (Rodenhuis, 1992). Since KRAS mutations are the most prevalent in human cancers, the activity of Compound 27 in KRAS-mutation-harboring cancer cells (FIG. 46 panel A). This compound was active in all oncogenic-KRAS-harboring cancer cell lines tested (FIG. 46 panel A). Among them, Calu-1 cells were the most sensitive to Compound 27 (FIG. 46 panel A); the $IC_{50}$ in Calu-1 cells was 20 ng/mL.

Considering Compound 27's high potency, the compound was tested in a broader range of cancer cell lines to see if additional cell lines, like Calu-1, are particularly sensitive. Compound 27 was tested in 60 different human cancer cell lines (the NCI60 panel) and the growth inhibitory potency of Compound 27 was determined across these cell lines. A number of cell lines were particularly sensitive to Compound 27 treatment; nanomolar concentrations of Compound 27 were often sufficient to induce growth arrest or cell killing, and there was up to $10^4$-fold differences in sensitivity between resistant and sensitive cell lines (FIG. 46 panel B). Moreover, the sensitivity profile of Compound 27 across the 60 cancer cell lines was distinct from those of known compounds in the NCI database, as assessed by the COMPARE algorithm (Paull et al., 1989), which suggests the mechanism of action for Compound 27 is unique (FIG. 46B). The COMPARE algorithm compares sensitivity profiles of an input compound to those of all other compounds in the database, and returns a similarity score in terms of Pairwise Correlation Coefficient (PCC). In control tests, the sensitivity profile of paclitaxel grouped with vinblastine, maytansine and rhizoxin, with high PCC values (FIG. 46B). All of these compounds are known to perturb microtubule integrity, which demonstrates the usefulness of the COMPARE algorithm to understand the mechanism of compound action. In contrast, the COMPARE analysis of Compound 3 returned only compounds with low PCC values (FIG. 46B). In other words, no compounds in the NCI database had a similar pattern of cell killing as Compound 27.

Figure 47:
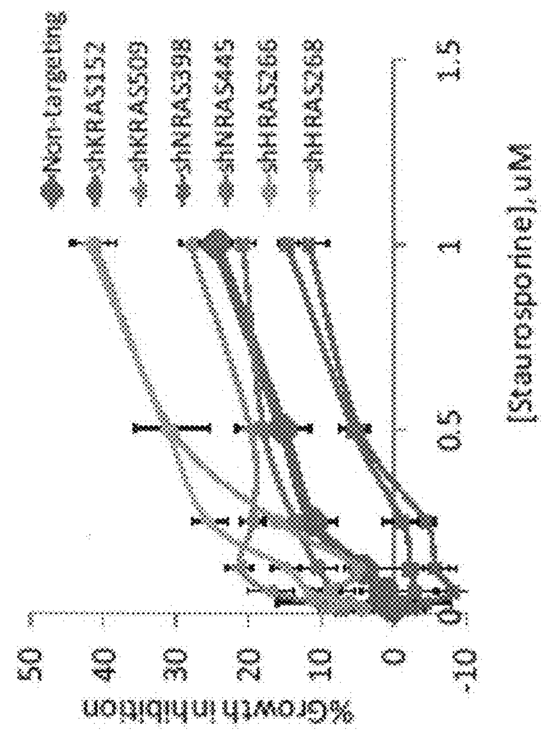
FIG. 47 shows percent growth inhibition in staurosporine-treated cells to examine changes in drug sensitivity.

It was inferred that the oncogenic RAS-signal-dependent lethality of Compound 27 should persist in cancer cell lines other than HRAS-transformed fibroblasts, because the protein target of Compound 27 is not HRAS itself, but is a protein associated with the oncogenic RAS network whose status changes upon activation of oncogenic RAS signaling, regardless of subtype of RAS (H-, N-, or K-RAS) or tissue origin (sarcomas or carcinomas). To test this hypothesis, Calu-1 cells were cultured which were derived from a human lung carcinoma, and attenuated oncogenic RAS signaling using shRNAs targeting HRAS, NRAS or KRAS. Compound 27 was less effective in Calu-1 cells expressing shRNAs targeting each RAS isoform, regardless of subtype (FIG. 46C). Treatment with shRNAs targeting RAS isoforms did not lead to a general survival effect, since loss of sensitivity to staurosporine was not observed. (FIG. 47).

Example 2

Lack of potency and non-specific toxicity are the major hurdles in anti-cancer drug development. Traditionally, these features were not examined until the very late phase of drug development. Ideally, efforts to address the two properties should be made in early stage of drug discovery and only drug candidates that show consistent and robust activity should be put forward to improve overall efficiency.

NCI60 anti-cancer screening ("NCI60 test") is a system that provides an opportunity to assess a drug candidate's potency and selectivity at a relatively early stage of drug discovery. The primary purpose of NCI60 anti-cancer screening is to identify lethal compounds that have significantly increased potency against some selective cancer cell lines. Such compounds would be expected to kill sensitive cancer cells while having minimal effect on healthy cells in a predetermined concentration range. NCI60 anti-cancer screening makes use of 60 cancer cell lines from different human tissue origins. Cells are seeded on a 96-well plate, treated with lethal compounds in 5-point, 10-fold dilution series pattern starting at 100 μM (i.e. 10 nM, 100 nM, 1 μM, 10 μM, 100 μM) for 2 days, and measured for cell viability using sulforhodamine B dye. The optical densities of treated samples are determined using a plate reader and percent growth value is calculated by processing the optical density value.

Three parameters are used in determining potency and selectivity of a given test agent from the NCI60 anti-cancer screening data: $GI_{50}$, TGI, and $LC_{50}$. $GI_{50}$ is the concentration of test agent which inhibits cell growth by 50%, calculated as follows:

$$100\times(T-T_0)/(C-T_0)=50$$

wherein

T is the optical density of test well after 2-days of treatment, $T_0$ is the optical density at time 0, and C is the optical density of a control well without a test agent.

Thus, $GI_{50}$ measures the growth inhibitory power of a test agent.

TGI is the concentration of a test agent which completely inhibits cell growth, calculated as follows:

$$100\times(T-T_0)/(C-T_0)=0$$

wherein

T is the optical density of test well after 2-days of treatment, $T_0$ is the optical density at time 0, and C is the optical density of a control well without a test agent.

Thus, TGI measures the cytostatic effect of a test agent.

The $LC_{50}$ is the concentration of a test agent that causes the death of 50% of the cells, calculated as follows:

$$100\times(T-T_0)/T_0=-50$$

wherein

T is the optical density of test well after 2-days of treatment, and $T_0$ is the optical density at time 0.

Thus, $LC_{50}$ measures the lethal effect of a test agent.

The entire NCI60 test is replicated at least twice to ensure consistency of the data and to determine accurate $GI_{50}$, TGI and $LC_{50}$ values. The panel of results for each candidate compound in the NCI60 test is known as the "sensitivity profile."

Based on our past experience, test agents (i.e., candidate compounds) with nanomolar (nM) range TGI or $LC_{50}$ values are considered to have enough potency for in vivo testing. If the sensitivity of some cancer cell lines is greater than average of all 60 cell lines, then, the test agent can be expected to be able to induce selective cell killing. Moreover, if the sensitivity profile of a test agent across the 60 cell lines is distinct from that of known anti-cancer reagents, the test agent can be considered a novel class of anti-cancer agent.

In comparing sensitivity profiling, the COMPARE analysis was conducted, which was developed from NCI. The NCI provides a COMPARE server for users to input the $GI_{50}$, TGI, or $LC_{50}$ values of their test compound as a 'seed' for COMPARE analysis. The server then compares the sensitivity pattern of the 'seed' to those in their database consisting of sensitivity profiling data from >100,000 compounds and sends out the result of COMPARE analysis by displaying rank-ordered lists of compounds. To derive COMPARE rankings, an index of similarity called "pair-wise correlation coefficient" (PCC) was used. In general, a PCC value greater than 0.7 indicates the same mechanism of action or the same target of the two compounds.

Figure 22:
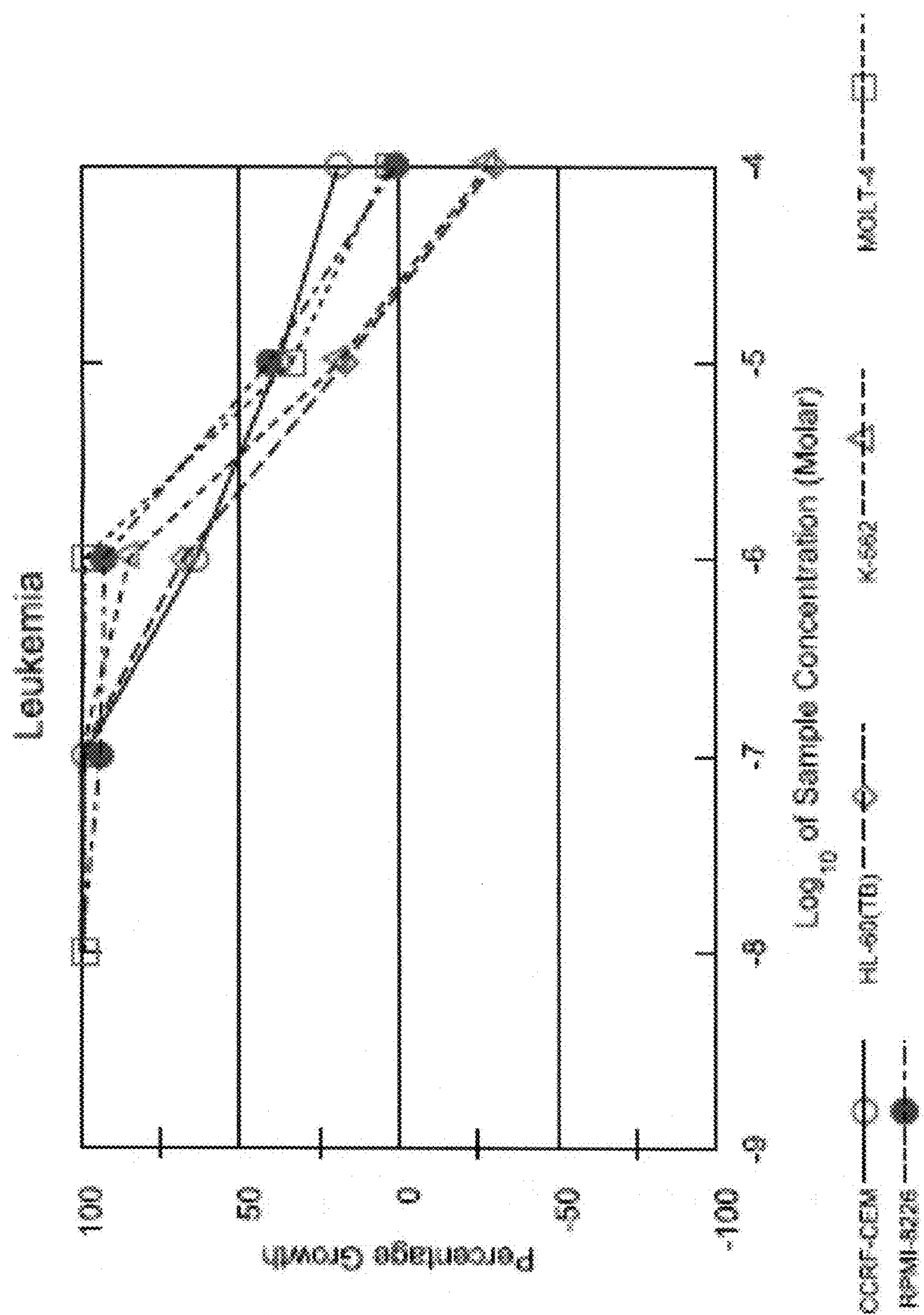
FIG. 22 shows the results of NCI60 screening of Erastin.
Figure 23:
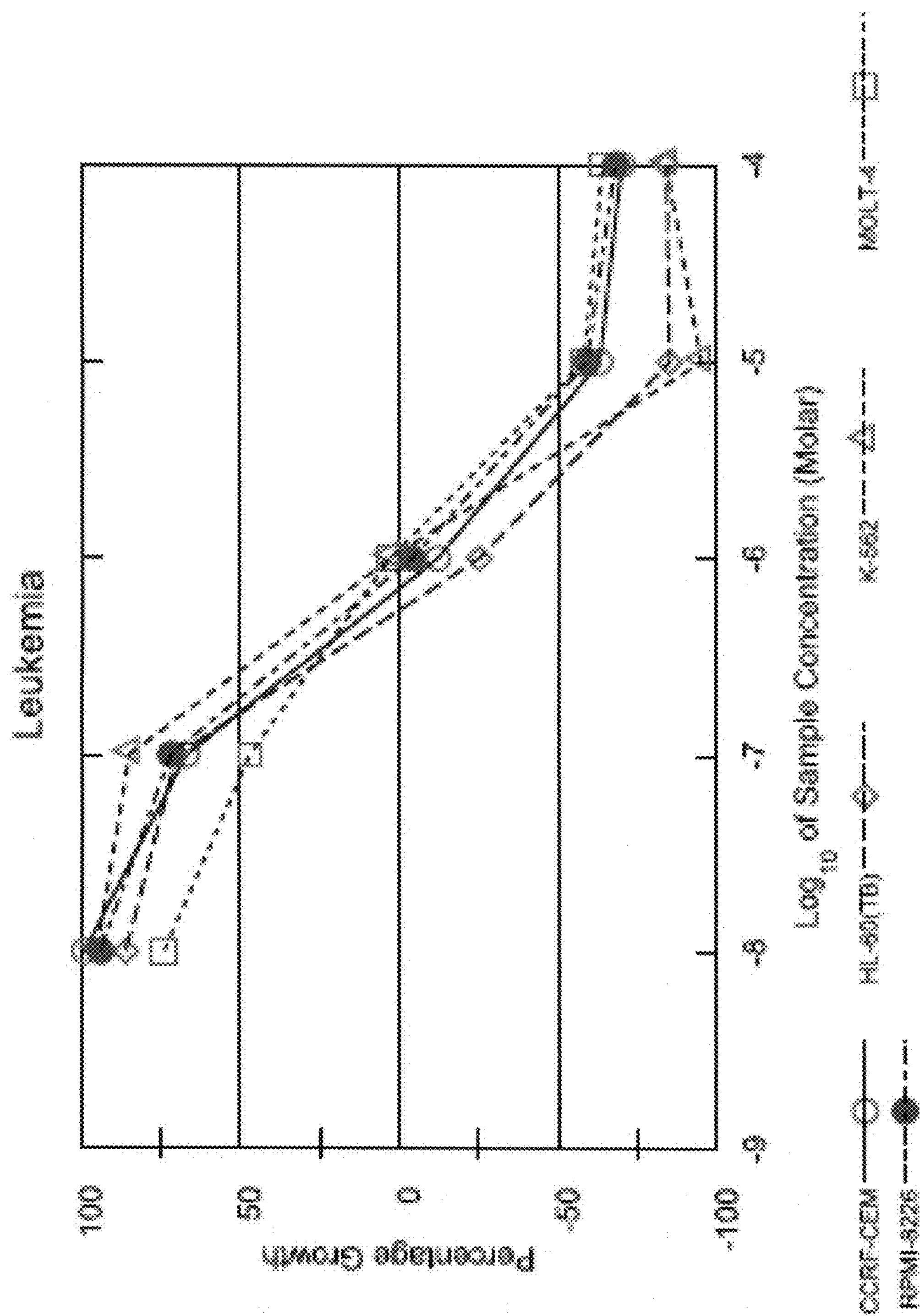
FIG. 23 shows the results of NCI60 screening of Compound 36.
Figure 24:
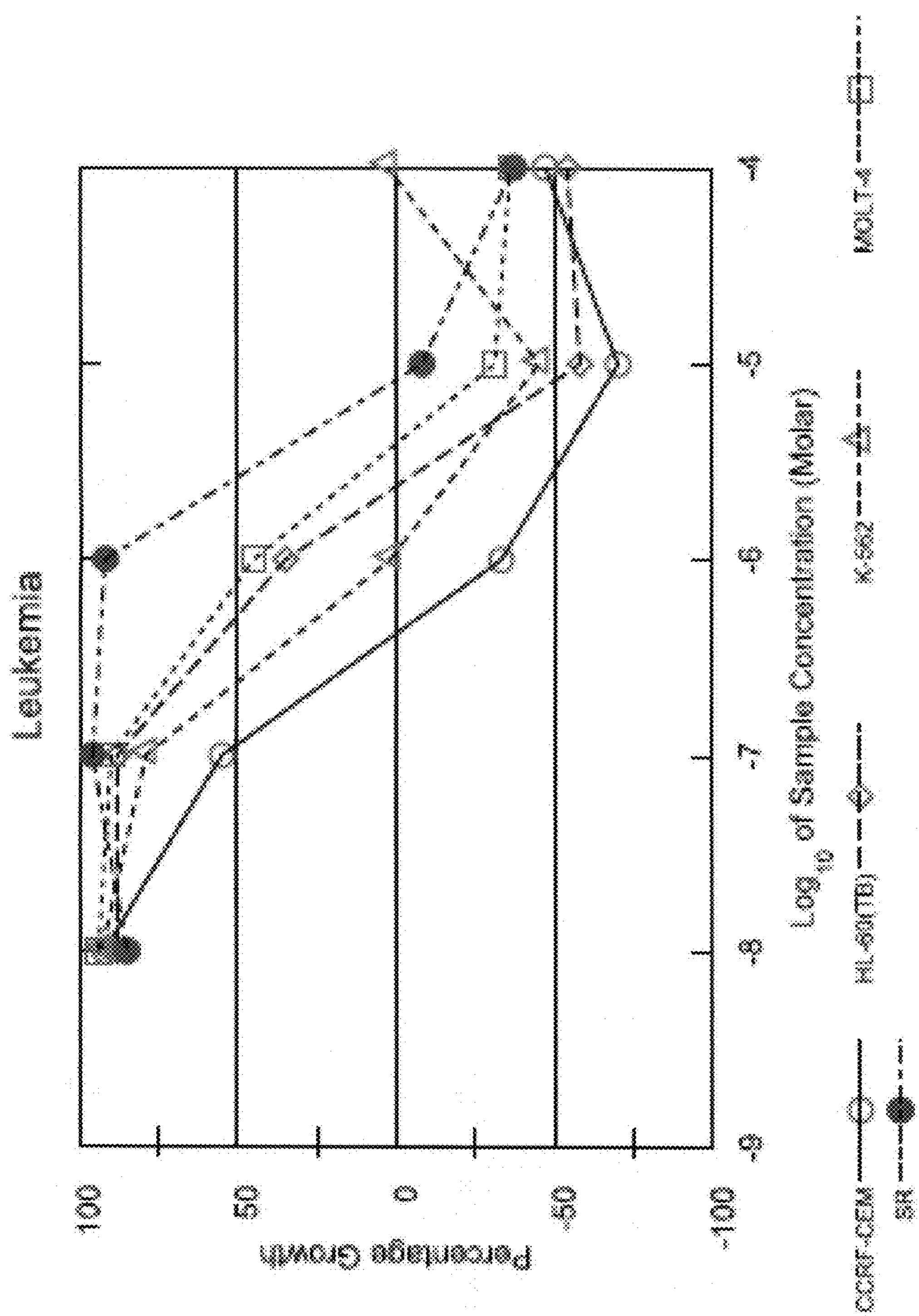
FIG. 24 shows the results of NCI60 screening of Compound 6.
Figure 25:
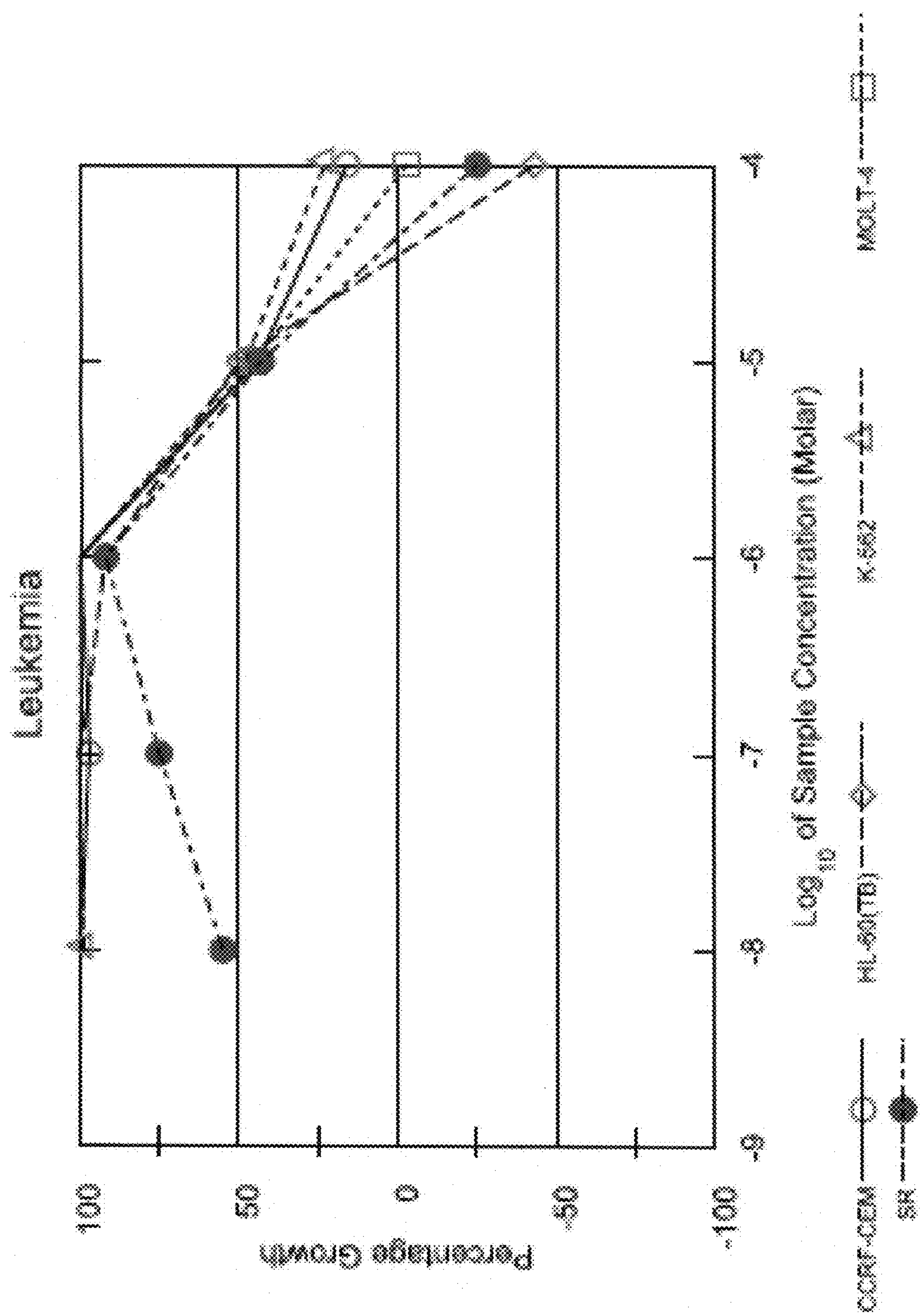
FIG. 25 shows the results of NCI60 screening of Compound 3.

Erastin (Table 2; FIG. 22), and Compounds 3 (Table 3; FIG. 25), 6 (Table 4; FIG. 24), 27 (Table 6; FIG. 16), and 36 (Table 5; FIG. 23) were submitted for NCI60 testing. The results of the NCI60 screening of Erastin and Compounds 3, 6, 27, and 36 are summarized in Tables 2-6. A $GI_{50}$ concentration below 10 μM was reported as sensitive. The tumor type, cell line, $GI_{50}$, TGI, and $LC_{50}$, and RAS mutation (if any) are also summarized.

TABLE 2

Cancer cell lines sensitive to Erastin identified by NCI60.
ERASTIN - NCI60

| Tumor Type | Cell Line | GI 50% (μM) | GI 100% (μM) | LC 50% (μM) | RAS Mutation |
|---|---|---|---|---|---|
| Renal Cancer | 786-0 | 2.03 | 4.12 | 8.36 | |
| | ACHN | 0.979 | 2.5 | 6.3 | |
| | CAKI-1 | 2.15 | n.d. | >10 | |
| | RXF 393 | 2.16 | 7.2 | >10 | |
| | UO-31 | 0.373 | 1.63 | >10 | |
| Leukemia | HL-60 | 2.26 | >10 | >10 | NRAS Q61L |
| | K-562 | 3.39 | >10 | >10 | |

TABLE 3

Cancer cell lines sensitive to Compound 3 identified by NCI60.
Compound 3 - NCI60

| Tumor Type | Cell Line | GI 50% (μM) | GI 100% (μM) | LC 50% (μM) | RAS Mutation |
|---|---|---|---|---|---|
| Leukemia | CCRF-CEM | 7.95 | >10 | >10 | KRAS G12D |
| | HL-60(TB) | 9.8 | >10 | >10 | NRAS Q61L |
| | K-562 | 9.16 | >10 | >10 | |
| | MOLT-4 | 8.39 | >10 | >10 | NRAS Q61L |
| | SR | 7.15 | >10 | >10 | |
| Non-small lung carcinoma | HOP-92 | 6.18 | >10 | >10 | |
| Colon Cancer | HT29 | 9.82 | >10 | >10 | |
| CNS Cancer | SNB-75 | 9.61 | >10 | >10 | |
| Renal Cancer | 786-0 | 9.27 | >10 | >10 | |
| | A498 | 3.39 | >10 | >10 | |
| | UO-31 | 6.82 | >10 | >10 | |
| Breast Cancer | NCI/ADR-RES | 8.93 | >10 | >10 | |
| | Hs578T | 9.31 | >10 | >10 | HRAS G12D |
| | BT-549 | 4.28 | >10 | >10 | |

TABLE 4

Cancer cell lines sensitive to Compound 6 identified by NCI60.
Compound 6 - NCI60

| Tumor Type | Cell Line | GI 50% (μM) | GI 100% (μM) | LC 50% (μM) | RAS Mutation |
|---|---|---|---|---|---|
| Leukemia | CCRF-CEM | 0.115 | 0.422 | n.d. | KRAS G12D |
| | HL-60(TB) | 0.516 | 2.38 | 8.25 | NRAS Q61L |
| | K-562 | 0.238 | | >10 | |
| | MOLT-4 | 0.783 | 3.91 | >10 | NRAS Q61L |
| | RPMI-8226 | 2.37 | 6.77 | >10 | KRAS G12A |
| | SR | 2.65 | 8.4 | >10 | |
| Non-small cell lung carcinoma | HOP-92 | 1.48 | 4.31 | >10 | |
| | NCI-H23 | 4.17 | >10 | >10 | KRAS G12C |
| | NCI-H522 | 0.49 | 1.79 | 5.12 | |
| Colon Cancer | COLO 205 | 0.232 | 1.26 | 4.78 | |
| | HCT-116 | 0.376 | 1.32 | 3.64 | KRAS G13D |
| | HT29 | 3.32 | >10 | >10 | |
| | KM12 | 5.2 | >10 | >10 | |
| | SW-620 | 0.271 | 1.03 | 3.9 | KRAS G12V |
| CNS Cancer | SF-268 | 2.46 | 7.71 | >10 | |
| | SF-539 | 2.32 | 4.71 | 9.59 | |
| Melanoma | LOX IMVI | 1.73 | 3.29 | 6.25 | |
| | MALME-3M | 0.261 | 0.723 | 2.8 | |
| | M14 | 2.07 | 4.38 | 9.28 | |
| | SK-MEL-2 | 2.32 | 6.87 | >10 | NRAS Q16R |
| | SK-MEL-28 | 1.46 | 3.11 | 6.63 | |
| | SK-MEL-5 | 5 | >10 | >10 | |
| | UACC-257 | 2.78 | >10 | >10 | |
| | UACC-62 | 9.78 | >10 | >10 | |
| Ovarian Cancer | OVCAR-3 | 3.52 | >10 | >10 | |
| | OVCAR-4 | 5.71 | >10 | >10 | |
| | OVCAR-8 | 4.22 | >10 | >10 | |
| Renal Cancer | 786-0 | 2.51 | 5.54 | >10 | |
| | ACHN | 8.76 | >10 | >10 | |
| | RXF393 | 0.652 | 2.41 | 6.6 | |
| | SN12C | 8.1 | >10 | >10 | |
| | TK-10 | 2.76 | >10 | >10 | |
| Prostate Cancer | PC-3 | 5.07 | >10 | >10 | |
| | DU-145 | 5.28 | >10 | >10 | |
| Breast Cancer | MCF-7 | 1.55 | 3.78 | 9.18 | |
| | MDA-MB-231/ATCC | 1.75 | 4.09 | 9.52 | KRAS G13D |
| | HS 578T | 3.31 | >10 | >10 | HRAS G12D |
| | MDA-MB-435 | 2.21 | 4.38 | 9.07 | |
| | BT-549 | 1.49 | 3.27 | 7.21 | |
| | T-47D | 4.53 | 2.06 | 9.35 | |

TABLE 5

Cancer cell lines sensitive to Compound 36 identified by NCI60.
Compound 36 - NC160

| Tumor Type | Cell Line | GI 50% (μM) | GI 100% (μM) | LC 50% (μM) | RAS Mutation |
|---|---|---|---|---|---|
| Leukemia | CCRF-CEM | 0.165 | 0.705 | 5.57 | KRAS G12D |
| | HL-60(TB) | 0.163 | 0.545 | 2.62 | NRAS Q61L |
| | K-562 | 0.267 | 1.08 | 3.51 | |
| | MOLT-4 | 0.0773 | 1.1 | 7.39 | NRAS Q61L |
| | RPMI-8226 | 0.194 | 0.889 | 6.98 | KRAS G12A |
| | SR | 1.32 | 3.4 | 8.78 | |
| Non-small cell lung | A549/ATCC | 1.11 | 2.4 | 5.15 | KRAS G12S |

TABLE 5-continued

Cancer cell lines sensitive to Compound 36 identified by NCI60. Compound 36 - NC160

| Tumor Type | Cell Line | GI 50% (μM) | GI 100% (μM) | LC 50% (μM) | RAS Mutation |
|---|---|---|---|---|---|
| carcinoma | EKVX | 1.24 | 2.51 | 5.09 | |
| | HOP-62 | 0.405 | 1.42 | 3.77 | KRAS G12C |
| | HOP-92 | 0.479 | 1.52 | 3.96 | |
| | NCI-H226 | 0.48 | 1.66 | 4.55 | |
| | NCI-H23 | 0.44 | 1.65 | 4.23 | KRAS G12C |
| | NCI-H322M | 0.606 | 1.99 | 4.93 | |
| | NCI-H460 | 0.626 | 2.02 | 5.02 | KRAS Q61H |
| | NCI-H522 | 0.0829 | 0.309 | 1.18 | |
| Colon Cancer | COLO 205 | 0.184 | 0.451 | 1.46 | |
| | HCC-2998 | 0.24 | 0.733 | 2.68 | KRAS A146T |
| | HCT-116 | 0.252 | 1.11 | 3.32 | KRAS G13D |
| | HCT-15 | 0.305 | 1.53 | 3.93 | KRAS G13D |
| | HT29 | 0.322 | 1.37 | 4.1 | |
| | KM12 | 0.469 | 1.8 | 4.47 | |
| | SW-620 | 0.184 | 0.569 | 2.54 | KRAS G12V |
| CNS Cancer | SF-268 | 1.09 | 2.5 | 5.74 | |
| | SF-295 | 1.19 | 2.52 | 5.33 | |
| | SF-539 | 0.191 | 0.349 | 0.638 | |
| | SNB-19 | 1.05 | 2.29 | 5 | |
| | SNB-75 | 0.372 | 1.26 | 4.3 | |
| | U251 | 0.47 | 1.7 | 4.12 | |
| Melanoma | LOX IMVI | 0.203 | 0.478 | 1.32 | |
| | MALME-3M | 0.55 | 1.83 | 4.57 | |
| | M14 | 0.384 | 1.59 | 4.8 | |
| | SK-MEL-2 | 0.297 | 1.01 | 4.93 | NRAS Q16R |
| | SK-MEL-28 | 0.239 | 0.592 | 2.07 | |
| | SK-MEL-5 | 0.209 | 0.898 | 3.05 | |
| | UACC-257 | 1.26 | 2.97 | 6.99 | |
| | UACC-62 | 0.214 | 0.427 | 0.853 | |
| Ovarian Cancer | IGROV1 | 0.254 | 1.28 | 4.17 | |
| | OVCAR-3 | 0.204 | 0.804 | 4.2 | |
| | OVCAR-4 | 0.147 | 0.405 | 1.31 | |
| | OVCAR-5 | 0.492 | 1.62 | 4.33 | KRAS G12V |
| | OVCAR-8 | 1.16 | 2.94 | 7.48 | |
| | SK-OV-3 | 1.26 | 2.56 | 5.2 | |
| Renal Cancer | 786-0 | 0.252 | 0.907 | 3.02 | |
| | A498 | 0.268 | 1.29 | 3.85 | |
| | ACHN | 0.366 | 1.43 | 3.78 | |
| | CAKI-1 | 0.165 | 0.413 | 1.08 | |
| | RXF393 | 0.181 | 0.485 | 2.49 | |
| | SN12C | 0.351 | 1.35 | 3.67 | |
| | TK-10 | 0.296 | 1.08 | 3.47 | |
| | UO-31 | 0.125 | 0.385 | 1.47 | |
| Prostate Cancer | PC-3 | 0.548 | 1.82 | 4.26 | |
| | DU-145 | 1.14 | 2.35 | 4.84 | |
| Breast Cancer | MCF-7 | 0.265 | 1.34 | 3.83 | |
| | NCI/ADR-RES | 1.04 | 2.34 | 5.27 | |
| | MDA-MB-231/ATCC | 0.341 | 1.36 | 3.27 | KRAS G13D |
| | HS 578T | 0.42 | 2.27 | >10 | HRAS G12D |
| | MDA-MB-435 | 0.175 | 0.781 | 3 | |
| | BT-549 | 0.302 | 1.3 | 4.07 | |
| | T-47D | 0.701 | 3.21 | >10 | |

TABLE 6

Cancer cell lines sensitive to Compound 27 identified by NCI60. Compound 27 - NCI60

| Tumor Type | Cell Line | GI 50% (μM) | GI 100% (μM) | LC 50% (μM) | RAS Mutation |
|---|---|---|---|---|---|
| Leukemia | CCRF-CEM | 0.0195 | 0.0431 | 0.0953 | KRAS G12D |
| | HL-60(TB) | 0.28 | 0.537 | 1.2 | NRAS Q61L |
| | MOLT-4 | 1.02 | 2.74 | 7.39 | NRAS Q61L |
| | RPMI-8226 | 0.0431 | 2.22 | 6.99 | KRAS G12A |
| | SR | 0.4 | 1.6 | 6.58 | |
| Non-small cell lung carcinoma | A549/ATCC | 2.51 | >10 | >10 | KRAS G12S |
| | EKVX | 2.31 | 5.63 | >10 | |
| | HOP-92 | 0.0991 | 1.07 | 5.85 | |
| | NCI-H226 | 0.688 | 2.79 | >10 | |
| | NCI-H23 | 1.15 | 2.95 | 7.59 | KRAS G12C |
| | NCI-H322M | 3.6 | >10 | >10 | |
| | NCI-H460 | 1.43 | 3.11 | 6.74 | KRAS Q61H |
| | NCI-H522 | 1.63 | 3.74 | 8.58 | |
| Colon Cancer | COLO 205 | 1.67 | 3.44 | 7.07 | |
| | HCC-2998 | 2.01 | 5.1 | >10 | KRAS A146T |
| | HCT-116 | 0.364 | 1.48 | 3.84 | KRAS G13D |
| | HCT-15 | 1.45 | 2.83 | 5.54 | KRAS G13D |
| | HT29 | 0.415 | 1.46 | 4.06 | |
| | KM12 | 0.188 | 1.19 | 4.15 | |
| | SW-620 | 0.681 | 2.09 | 5.25 | KRAS G12V |
| CNS Cancer | SF-268 | 0.0692 | 0.218 | 0.577 | |
| | SF-295 | 1.1 | 2.97 | 8.06 | |
| | SF-539 | 0.118 | 0.241 | 0.492 | |
| | SNB-19 | 2.35 | 7.41 | >10 | |
| | SNB-75 | 0.745 | 3.06 | >10 | |
| | U251 | 1.1 | 2.3 | 4.79 | |
| Melanoma | LOX IMVI | 0.182 | 0.387 | 0.826 | |
| | MALME-3M | 0.406 | 1.53 | 4.6 | |
| | M14 | 1.07 | 2.25 | 4.75 | |
| | SK-MEL-2 | 1.74 | 4.13 | 9.82 | NRAS Q16R |
| | SK-MEL-28 | 1.62 | 3.31 | 6.76 | |
| | SK-MEL-5 | 1.38 | 2.67 | 5.16 | |
| | UACC-257 | 1.37 | 7.46 | >10 | |
| | UACC-62 | 1.21 | 2.47 | 5.04 | |
| Ovarian Cancer | IGROV1 | 0.0209 | 0.0571 | 0.27 | |
| | OVCAR-3 | 0.353 | 1.57 | 6.59 | |
| | OVCAR-4 | 4.3 | >10 | >10 | |
| | OVCAR-5 | 2.24 | 5.71 | >10 | KRAS G12V |
| | OVCAR-8 | 2.32 | >10 | >10 | |
| | SK-OV-3 | 1.68 | 3.34 | 6.67 | |
| Renal Cancer | 786-0 | 0.0603 | 0.473 | 2.52 | |
| | A498 | 1.83 | 4.52 | >10 | |
| | ACHN | 0.187 | 1.05 | 3.25 | |
| | CAKI-1 | 0.0211 | 0.0381 | 0.0687 | |
| | RXF393 | 1.3 | 3 | 6.93 | |
| | SN12C | 1.25 | 2.77 | 6.12 | |
| | TK-10 | 1.9 | 3.96 | 8.25 | |
| | UO-31 | 0.02 | 0.0385 | 0.0743 | |
| Prostate Cancer | PC-3 | 0.231 | 1.08 | 3.29 | |
| | DU-145 | 0.308 | 1.4 | 4.01 | |
| Breast Cancer | MCF-7 | 0.782 | 3.98 | >10 | |
| | NCI/ADR-RES | 2.56 | >10 | >10 | |
| | MDA-MB-231/ATCC | 1.2 | 3.32 | 9.18 | KRAS G13D |
| | HS 578T | 0.403 | 2.85 | >10 | HRAS G12D |
| | MDA-MB-435 | 1.71 | 3.74 | 8.19 | |

TABLE 6-continued

| Cancer cell lines sensitive to Compound 27 identified by NCI60. Compound 27 - NCI60 | | | | | |
|---|---|---|---|---|---|
| Tumor Type | Cell Line | GI 50% (μM) | GI 100% (μM) | LC 50% (μM) | RAS Mutation |
| | BT-549 | 0.131 | 0.316 | 0.765 | |
| | T-47D | 1.64 | 5.16 | >10 | |

When considering the potency of the NCI60-tested compounds, Compound 27 was the only one that showed a nanomolar (nM) concentration range of cell killing activity. Both Erastin (Table 2; FIG. 22) and Compound 27 (Table 6; FIG. 16) showed interesting selectivity against some specific cancer cell lines. Indeed, Erastin showed selectivity against tissue origin—renal cancer cells are more sensitive to Erastin treatment (FIG. 22). The COMPARE analysis was conducted to determine whether Erastin or Compound 27 have overlapping sensitivity profiling with any of the compounds in the database. However, the highest PCC scores of Erastin or Compound 27 were 0.4 and 0.5 respectively using TGI value as an input, which implies that the mechanism of action or target protein of these two compounds are novel ones.

The sensitivity profile data from NCI60 anti-cancer screening can also be used for biomarker identification when it is combined with expression profile data of the 60 cancer cell lines cDNA microarray data of NCI60 cancer cell lines are available from public resources. The expression profile of 9,706 genes in the 60 NCI cell lines was downloaded and a search was carried out for genes that are over-expressed only in sensitive cell lines upon Erastin or Compound 27 treatment. The cut-off value was set at 10-fold greater than the average amount of mRNA. Several genes were identified that are specifically up-regulated in Erastin sensitive cell lines (Table 6B). The top hit gene was PDGF-B polypeptide, which recaptured the oncogenic-RAS-signal dependent lethality of Erastin because RAS is one of the major downstream mediators of PDGF/PDGFR signaling. Human protein tyrosine phosphatase 1E (PTP1E) and phospholipase C beta 4 are among the top hit genes and they are involved in the PDGF/PDGFR signaling directly or indirectly suggesting that status of PDGF/PDGFR signaling can be an important biomarker for Erastin sensitivity.

TABLE 6B

| Results of biomarker identification using sensitivity profile data from NCI60 anti-cancer screening in combination with expression profile data of the 60 cancer cell lines. | | |
|---|---|---|
| % Sensitive | % Resistant | Gene Name |
| 100 | 5 | Platelet-derived growth factor beta polypeptide (simian sarcoma viral (v-sis) oncogene homolog) |
| 100 | 7 | Aldehyde reductase 1 (low Km aldose reductase) |
| 100 | 7 | ESTs, Weakly similar to KIAA0108 |
| 100 | 7 | Human protein tyrosine phosphatase 1E (PTP1E) |
| 100 | 9 | Crystallin zeta (quinone reductase) |
| 100 | 11 | Phospholipase C, beta 4 |
| 100 | 11 | Unknown |
| 100 | 11 | Unknown |
| 100 | 11 | Aldehyde reductase 1 (low Km aldose reductase) |
| 67 | 22 | SID 272525, ESTs [5':, 3':N35886] |
| 56 | 16 | AXL AXL receptor tyrosine ki0se Chr.19 [112500, (DW), 5':T85905, 3':T91043] |
| 56 | 18 | SID 42787, ESTs 5':R59827, 3':R59717] |

TABLE 6B-continued

| Results of biomarker identification using sensitivity profile data from NCI60 anti-cancer screening in combination with expression profile data of the 60 cancer cell lines. | | |
|---|---|---|
| % Sensitive | % Resistant | Gene Name |
| 56 | 24 | ESTs Chr.6 [154211, (DI), 5':R51950, 3':R53619] |
| 56 | 39 | SID 49722, ESTs [5':H29102, 3':H28999] |
| 56 | 24 | SID 236277, ESTs [5':H61273, 3':H61274] |
| 56 | 20 | SID 486215, Uroki0se-type plasminogen activator [5':, 3':AA040727] |
| 56 | 33 | SID W 486055, Ctyochome P450 IB1 (dioxin-inducible) [5':AA043141, 3':AA040872] |
| 56 | 20 | Human LOT1 mR0, complete cds Chr.6 [486715, (I), 5':, 3':AA043116] |
| 56 | 51 | SID W 510056, *Homo sapiens* (clone zap128) mR0, 3' end of cds [5':AA053065, 3':AA053409] |

Figure 40:
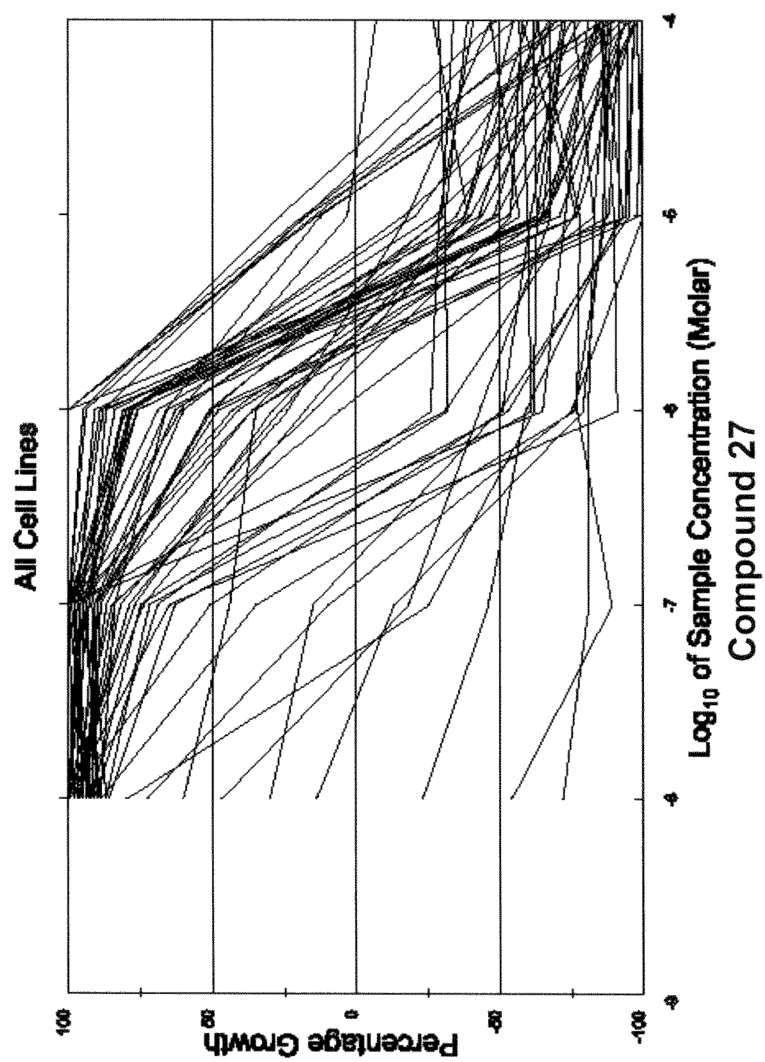
FIG. 40 shows the percent growth vs. log concentration for Compound 27 in the NCI60 test in all cell lines.
Figure 41:
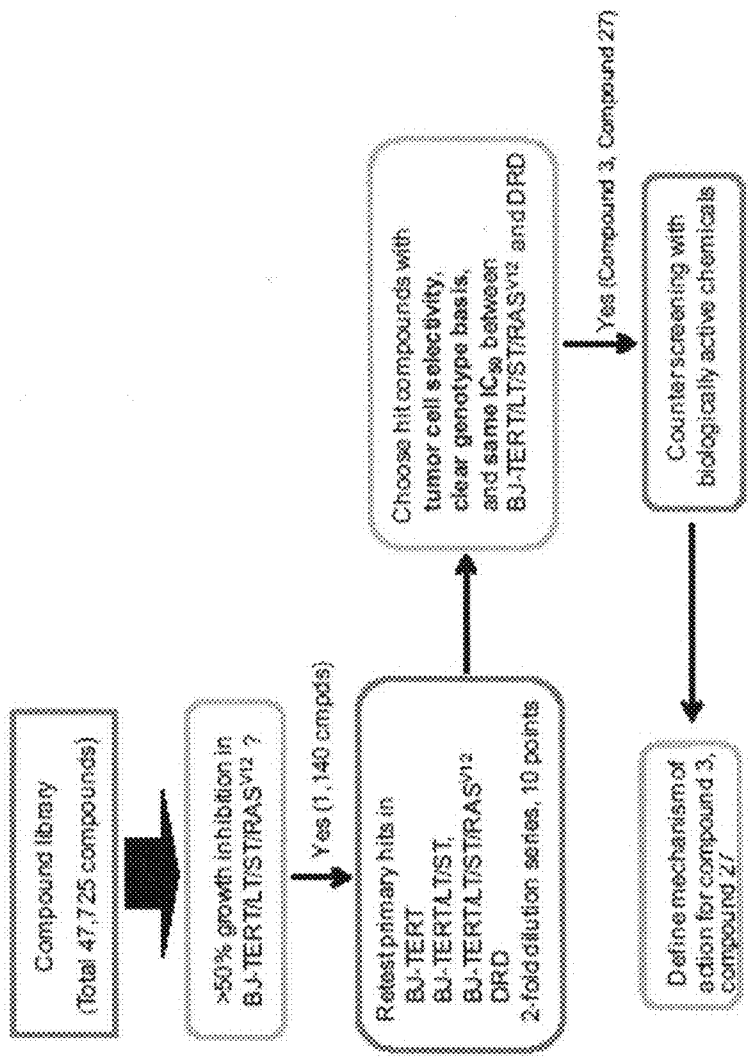
FIG. 41 shows a flow chart of the screening strategy for identifying genetically selective compounds and ruling out proliferation-dependent compounds.

The results of the NCI60 test demonstrates that Compound 27 has a unique sensitivity profile across the 60 human cancer cell line panel and a very potent lethality for some selective cancer cell lines. The sensitive cell lines are: SF-539, LOX, IGROV1, CAKI-1, UO-31, BT-549, CCRF-CEM, 786-0, HOP-92, PC-3, DU-145, NCI-H522, SF-268, SF-295, and SNB-75. Any lethal compound that shows a similar sensitivity profile in the NCI60 test can be considered to have a similar mechanism of action. A plot of the percent growth vs. log concentration for Compound 27 in the NCI60 test in all cell lines of Table 6 is shown in FIG. 40.

In addition, Erastin and Compounds 3, 6, 27, and 36 were tested to determine their potency and selectivity for additional cell lines using the Alamar Blue assay (see above). The results of this additional testing are summarized in Tables 7-10 (no additional cell lines were identified as sensitive for Compound 3). If a concentration of below 10 μg/ml of the compound inhibited the cancer cell line's growth by 50 percent, the cell line was reported as sensitive. The tumor type, cell line, maximum percentage inhibition, the concentration of compound required to inhibit cell growth by 50%, and RAS mutation (if any) are also summarized.

TABLE 7

| Additional cancer cell lines sensitive to Erastin identified by Alamar Blue assay. ERASTIN - ALAMAR BLUE ASSAY | | | | |
|---|---|---|---|---|
| Tumor Type | Cell Line | Maximum Inhibition % | GI 50% (μM) | RAS Mutation |
| Foreskin fibroblasts w/ TERT, LT, ST, RAS | BJELR | 100 | 6 | HRAS G12V |
| Leimyosarcoma, vulva | SK-LMS-1 | 100 | 6 | |
| Uterine sarcoma | MES-CA | 100 | 3 | |
| Fibrosarcoma | HT1080 | 98 | 2 | NRAS Q16K |
| Ewing sarcoma, anaplastic osteosarcoma | SK-ES-1 | 98 | 7 | |
| Osteosarcoma | U-2 OS | 96 | 6 | |
| Cervical carcinoma | HeLa | 94 | 0.6 | |
| Ewing sarcoma | TC71 | 92 | 10 | |
| Peripheral neuroepithelioma | TC32 | 88 | 8 | |
| Acute myelogenous leukemia | U973 | 73 | 10 | |
| Uterine, mixed mesodermal tumor | SK-UT | 73 | 4 | |
| Non-small cell lung carcinoma | Calu-1 | 100 | 6 | KRAS G12C |

TABLE 8

| Additional cancer cell lines sensitive to Compound 6 identified by Alamar Blue assay. Compound 6 - ALAMAR BLUE ASSAY | | | | |
|---|---|---|---|---|
| Tumor Type | Cell Line | Maximum Inhibition % | GI 50% (μM) | RAS Mutation |
| Pancreatic Cancer | PaCa-2 | 100 | 0.6 | HRAS G12C |
| Non-small cell lung carcinoma | Calu-1 | 100 | 2.5 | KRAS G12C |

TABLE 9

| Additional cancer cell lines sensitive to Compound 36 identified by Alamar Blue assay. Compound 36 - ALAMAR BLUE ASSAY | | | | |
|---|---|---|---|---|
| Tumor Type | Cell Line | Maximum Inhibition % | GI 50% (μM) | RAS Mutation |
| Pancreatic Cancer | PaCa-2 | 100 | 1.5 | HRAS G12C |

TABLE 9-continued

| Additional cancer cell lines sensitive to Compound 36 identified by Alamar Blue assay. Compound 36 - ALAMAR BLUE ASSAY | | | | |
|---|---|---|---|---|
| Tumor Type | Cell Line | Maximum Inhibition % | GI 50% (μM) | RAS Mutation |
| Non-small cell lung carcinoma | Calu-1 | 100 | 0.3 | KRAS G12C |

TABLE 10

| Additional cancer cell lines sensitive to Compound 27 identified by Alamar Blue assay. Compound 27 - ALAMAR BLUE ASSAY | | | | |
|---|---|---|---|---|
| Tumor Type | Cell Line | Maximum Inhibition % | GI 50% (μM) | RAS Mutation |
| Pancreatic Cancer | PaCa-2 | 100 | 0.125 | HRAS G12C |
| Non-small cell lung carcinoma | Calu-1 | 100 | 0.001 | KRAS G12C |

TABLE 11

| Sequence of Primers for Q-PCR. | | |
|---|---|---|
| Description | Sequence | Identification |
| Sequence of primers used in real-time quantitative PCR | | |
| VDAC1 F: | 5'-CCTGGACAGCAGGAAACAGTAAC-3' | SEQ ID NO.: 1 |
| VDAC1 R: | 5'-AGGCGTCAGGGTCAATCTGA-3' | SEQ ID NO.: 2 |
| VDAC2 F: | 5'-TGATTTTGCTGGACCTGCAA-3' | SEQ ID NO.: 3 |
| VDAC2 R: | 5'-CAGCAAGCCAGCCCTCAT-3' | SEQ ID NO.: 4 |
| VDAC3 F: | 5'-AATTTCGCCCTGGGTTACAA-3' | SEQ ID NO.: 5 |
| VDAC3 R: | 5'-TCAGTGCCATCGTTCACATGT-3' | SEQ ID NO.: 6 |
| TfR1 F: | 5'-GAAAACAGACAGATTTGTCATG-3' | SEQ ID NO.: 7 |
| TfR1 R: | 5'-CTCTTTTGGAGATACGTAGGG-3' | SEQ ID NO.: 8 |
| DMT1 F: | 5'-CATCACTATTATGGCCCTCAC-3' | SEQ ID NO.: 9 |
| DMT1 R: | 5'-GAACATGCCCTTGAGTACCTG-3' | SEQ ID NO.: 10 |
| HCP1 F: | 5'-GGTCTTTGCCTTTGCCACTATC-3' | SEQ ID NO.: 11 |
| Sequence of primers used in real-time quantitative PCR | | |
| HCP1 R: | 5'-CAGGTGTGATGACTAATGACAGG-3' | SEQ ID NO.: 12 |
| FTH1 F: | 5'-CAGATCAACCTGGAGCTCTAC-3' | SEQ ID NO.: 13 |
| FTH1 R: | 5'-CTTCAAAGCCACATCATCGC-3' | SEQ ID NO.: 14 |
| FTL F: | 5'-GGCCCTGGAGAAAAAGC-3' | SEQ ID NO.: 15 |
| FTL R: | 5'-GAAGTGAGTCTCCAGGAAG-3' | SEQ ID NO.: 16 |
| RPLP0 F: | 5'-ACGGGTACAAACGAGTCCTG-3' | SEQ ID NO.: 17 |
| RPLP0 R: | 5'-GCCTTGACCTTTTCAGCAAG-3' | SEQ ID NO.: 18 |

Example 3

Below is a representative synthesis for compounds of formula IV. In particular, the synthesis of compound 27 is set forth below:

Synthesis of Methyl Esters of L- and D-Tryptophanes Chlorohydrates

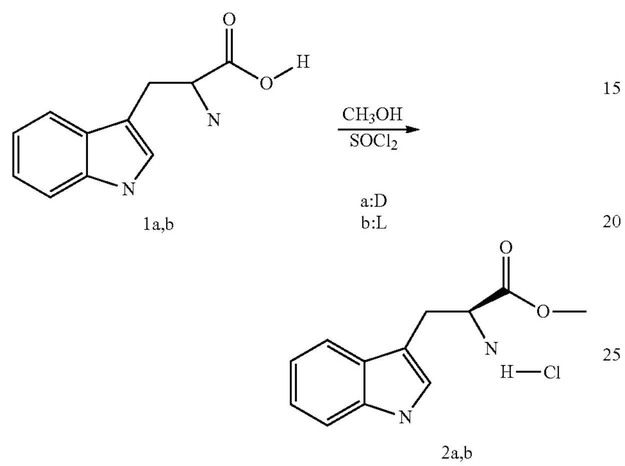

Thionylchloride (0.064 mol) was slowly added to a cooled (0° C.) suspension of tryptophane (0.049 mol) in methanol (150 mL). The reaction mixture was warmed up to 40° C. and stirred at this temperature for six hours. All solvents were removed and the solid residue was triturated with ether. The solid was filtered off to give the required product.

D-tryptophane (2a): yield 98%, M.p. 232-233° C. NMR$^1$H (δ, ppm, DMSO-d6, 300 MHz): 3.39 (2H, m, $CH_2$); 3.63 (3H, s, $CH_3O$); 4.20 (1H, t, CH, $J_{HH}$=5.5 Hz); 7.07 (2H, dt, Ar, $J_{HH}$=21 Hz, 6 Hz); 7.26 (1H, d, $H_2$, $J_{HH}$=3 Hz); 7.39 (1H, d, Ar, $J_{HH}$=7.8 Hz); 7.53 (1H, d, Ar, $J_{HH}$=7.8 Hz). NMR$^{13}$C (δ, ppm, DMSO-d6, 125.76 MHz): 26.01 (s), 52.61 (d), 106.26 (s), 111.45 (s), 117.84 (s), 118.50 (s), 121.05 (s), 124.80 (s), 126.79 (s), 136.13 (s), 169.57 (s). m/z 218 ($M^+$).

L-tryptophane (2b): yield 98%, M.p. 225-226° C. NMR$^1$H (δ, ppm, DMSO-d6, 300 MHz): 3.29 (2H, m, $CH_2$); 3.62 (3H, s, $CH_3O$); 4.18 (1H, t, CH, $J_{HH}$=5.5 Hz); 6.99 (1H, t, Ar, $J_{HH}$=4,5 Hz); 7.07 (1H, t, Ar, $J_{HH}$=4.5 Hz); 7.25 (1H, d, $H_2$, $J_{HH}$=3 Hz); 7.37 (1H, d, Ar, $J_{HH}$=4.8 Hz); 7.51 (1H, d, Ar, $J_{HH}$=4.8 Hz). NMR$^{13}$C (δ, ppm, DMSO-d6, 125.76 MHz): 25.94 (s), 52.85 (d), 106.33 (s), 111.08 (s), 117.86 (s), 118.44 (s), 120.97 (s), 124.78 (s), 126.81 (s), 136.12 (s), 169.42 (s). m/z 218 ($M^+$).

Free-Base of Compounds 2a and 2b:

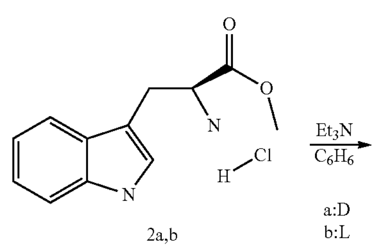

-continued

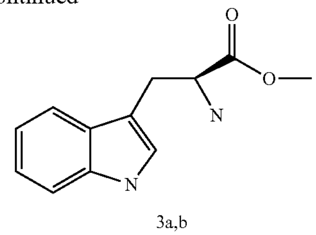

Triethylamine (0.055 mol) was added to a suspension of the corresponding hydrochloride 2a or 2b (0.05 mol) in benzene (100 mL) at room temperature. The mixture was stirred for one hour and then filtered. The filtrate was concentrated to give the product as a clear oil, which was dried under a high vacuum for ten minutes. The product was immediately used for the following reaction:

Synthesis of (3S)- and (3R)-methyl-1-(p-carbmethoxyphenyl)-1,2,3,4-tetrahydro-9H-pyrido[3,4-b]-indole-3-carboxylates

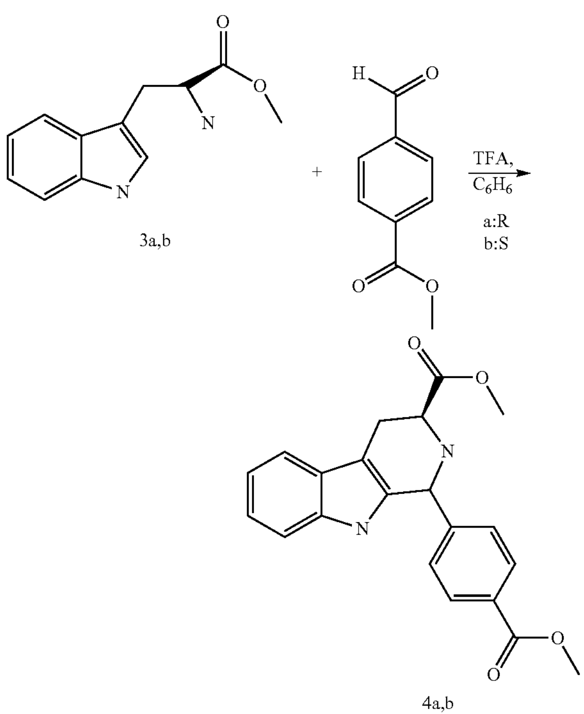

4 Å molecular sieves (2 g) and trifluoroacetic acid (0.5 mL) were added to a solution of 3a or 3b (0.06 mol) and methyl benzaldehyde-4-carboxylate (0.05 mol) in benzene (150 mL). The reaction mixture was stirred at reflux for one hour and additional trifluoroacetic acid (0.138 mol) was added. The reaction mixture was refluxed for three more hours and then cooled to room temperature. Water (50 mL) was added and the resulting mixture was basified to a pH of 8 with 30% NaOH in water. The layers were separated. The organic layer was dried with $MgSO_4$, concentrated to about one quarter of its original volume, and poured into hexane (300 mL). The precipitated solid was filtered off, washed with hexane, and dried under a vacuum to yield the product.

Cis-, trans-(3R)-methyl-1-(p-carbmethoxyphenyl)-1,2,3,4-tetrahydro-9H-pyrido[3,4-b]-indole-3-carboxylate: yield 80%, M.p. 124-125° C. NMR$^1$H (δ, ppm, $CDCl_3$, 300 MHz): 2.47 (1H, br.s, NH); 3.05-3.24 (2H, m, Ar—$CH_2$); 3.68 (3H, s, $CO_2CH_3$); 3.79 (3H, s, $OCH_3$); 3.94 (1H, dd, $ArCH_2CH$, $J_{HH}$=10.5; 2.8 Hz); 5.27 (0.45H, s, Ar—CH); 5.39 (0.55H, s, Ar—CH) and 7.12-8.18 (9H, m, ArH and indol NH). NMR$^{13}$C (δ, ppm, $CDCl_3$, 125.76 MHz): 25.68 (d), 52.84 (dd), 54.80 (s), 56.76 (s), 58.61 (s), 109.16 (d), 111.01 (d), 118.44 (d), 119.76 (d), 122.17 (s), 127.08 (d), 128.62 (d), 130.00 (d), 130.46 (s), 133.60 (d), 136.40 (d), 147.21 (d), 166.66 (d), 173.99 (d). m/z 364 ($M^+$).

Cis-, trans-(3S)-methyl-1-(p-carbmethoxyphenyl)-1,2,3,4-tetrahydro-9H-pyrido[3,4-b]-indole-3-carboxylate: yield 60%, M.p. 115-116° C. NMR$^1$H (δ, ppm, $CDCl_3$, 300 MHz): 2.47 (1H, br.s, NH); 3.04-3.26 (2H, m, Ar—$CH_2$); 3.71 (3H, s, $CO_2CH_3$); 3.82 (3H, s, $OCH_3$); 3.96 (1H, dd, $ArCH_2CH$, $J_{HH}$=10.5; 2.8 Hz); 5.28, 5.39 (1H, twu s, Ar—CH); 7.14-7.94 (9H, m, ArH and indol NH). NMR$^{13}$C (δ, ppm, $CDCl_3$, 125.76 MHz): 25.70 (d), 52.62 (dd), 54.61 (s), 56.75 (s), 58.41 (s), 109.02 (d), 111.01 (s), 118.32 (d), 119.32 (d), 122.14 (s), 127.03 (d), 128.41 (d), 129.74 (d), 130.23 (d), 133.94 (d), 136.39 (d), 147.24 (d), 166.83 (d), 174.05 (d). m/z 364 ($M^+$).

Synthesis of cis-, trans-(3S)- and (3R)-methyl-1-(1,3-benzodioxol-5-yl)-2-(chloroacetyl)-2,3,4,9-tetrahydro-1H-β-carboline-3-carboxilates

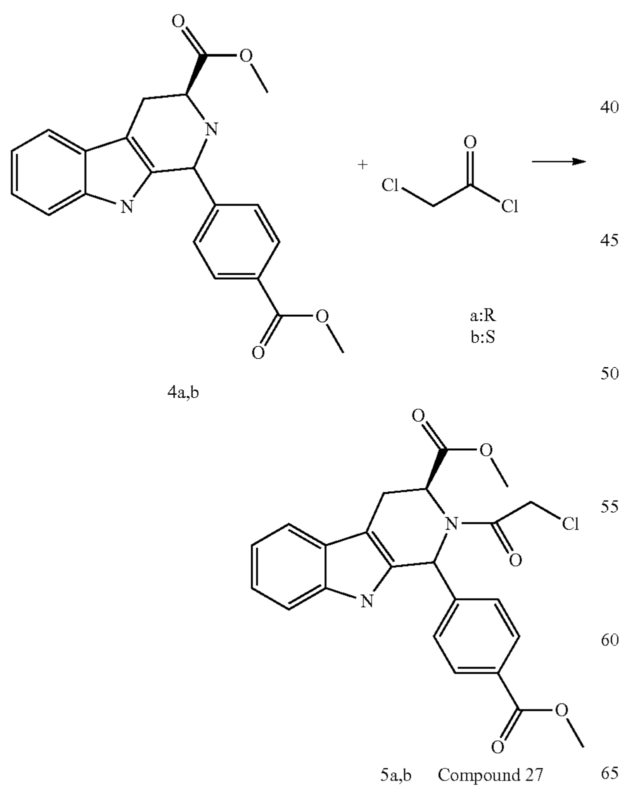

Chloroacetyl chloride (0.096 mol) was slowly added to a cooled-on-ice, stirred solution of 4a or 4b (0.04 mol) and $NaHCO_3$ (0.048 mol) in dry chloroform (200 mL). The reaction mixture was allowed to warm to room temperature and stirred for four hours. Dichloromethane (200 mL) was added to the reaction mixture. The resulting solution was washed with $NaHCO_3$, washed with a saturated solution of NaCl, dried with $MgSO_4$, and concentrated. The solid residue was triturated with ether, filtered off, and washed with small amount of methanol to yield the product.

Cis-, trans-(3R)-methyl-1-(1,3-benzodioxol-5-yl)-2-(chloroacetyl)-2,3,4,9-tetrahydro-1H-β-carboline-3-carboxilate: yield 60%, M.p. 273-275° C. NMR$^1$H (δ, ppm, DMSO-d6, 500 MHz): 2.86 (3H, s, $OCH_3$); 3.11-3.50 (2H, m, $CH_2Cl$); 3.83 (3H, s, $OCH_3$); 4.38 (1H, d, $ArCH_2$, $J_{HH}$=14 Hz); 4.77 (1H, d, $ArCH_2$, $J_{HH}$=14 Hz); 5.19 (1H, d, ArCH, $J_{HH}$=2.5 Hz); 6.91 (1H, s, Ar); 7.01-7.08 (2H, dt, Ar, $J_{HH}$=25 Hz, 3 Hz); 7.23-7.53 (3H, m, Ar); 7.85 (2H, d, Ar, $J_{HH}$=4 Hz); 10.82 (1H, s, NH). NMR$^{13}$C (δ, ppm, DMSO-d6, 125.76 MHz): 21.01 (s), 42.78 (s), 51.09 (s), 51.39 (s), 51.99 (s), 52.48 (s), 106.34 (s), 111.10 (s), 118.02 (s), 118.67 (s), 121.56 (s), 125.79 (s), 128.72 (d), 128.90 (s), 136.36 (s), 144.50 (s), 165.82 (s), 166.87 (s), 169.97 (s). m/z 440 ($M^+$).

Cis-, trans-(3S)-methyl-1-(1,3-benzodioxol-5-yl)-2-(chloroacetyl)-2,3,4,9-tetrahydro-1H-β-carboline-3-carboxilate: yield 45%, M.p. 272-273° C. NMR$^1$H (δ, ppm, DMSO-d6, 500 MHz): 2.84 (1H, s, $OCH_3$); 3.12-3.49 (2H, m, $CH_2Cl$); 3.82 (3H, s, $OCH_3$); 4.48 (1H, d, $ArCH_2$, $J_{HH}$=14 Hz); 4.86 (1H, d, $ArCH_2$, $J_{HH}$=14 Hz); 5.23 (1H, d, ArCH, $J_{HH}$=2.5 Hz); 6.91 (1H, s, Ar); 7.03-7.10 (2H, dt, Ar, $J_{HH}$=25 Hz, 3 Hz); 7.21-7.54 (3H, m, Ar); 7.84 (2H, d, Ar, $J_{HH}$=4 Hz); 10.92 (1H, s, NH). NMR$^{13}$C (δ, ppm, DMSO-d6, 125.76 MHz): 21.07 (s), 43.08 (s), 51.15 (s), 51.50 (s), 52.13 (s), 52.53 (s), 106.50 (s), 111.25 (s), 118.10 (s), 118.69 (s), 121.62 (s), 125.87 (s), 128.77 (d), 128.95 (s), 136.43 (s), 144.69 (s), 165.92 (s), 166.97 (s), 170.09 (s). m/z 440 ($M^+$).

As will be appreciated by one skilled in the art, other formula IV compounds (e.g., Compounds 1, 2, and 28-35) may be synthesized using the above scheme, but starting with a different aldehyde.

Example 4

The maximum tolerated dose of Compound 27 was tested in mice.

Each mouse in the study was administered a single intraperitoneal injection of Compound 27 dissolved in sterile PBS at 100 mg/kg, 200 mg/kg, or 400 mg/kg.

None of the mice died. Accordingly, the maximum tolerated dose of Compound 27 was determined to be greater than 400 mg/kg.

Example 5
Analogs of Compound 27
Synthesis of Biotinylated Compound 27
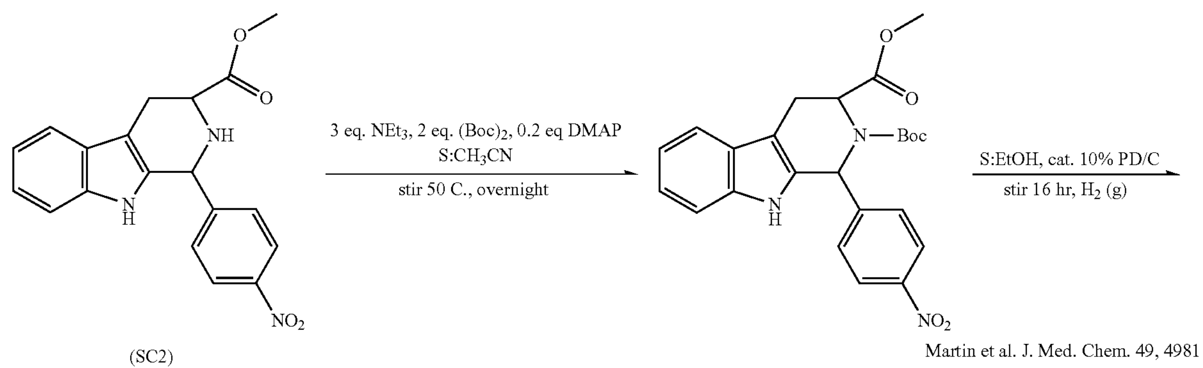
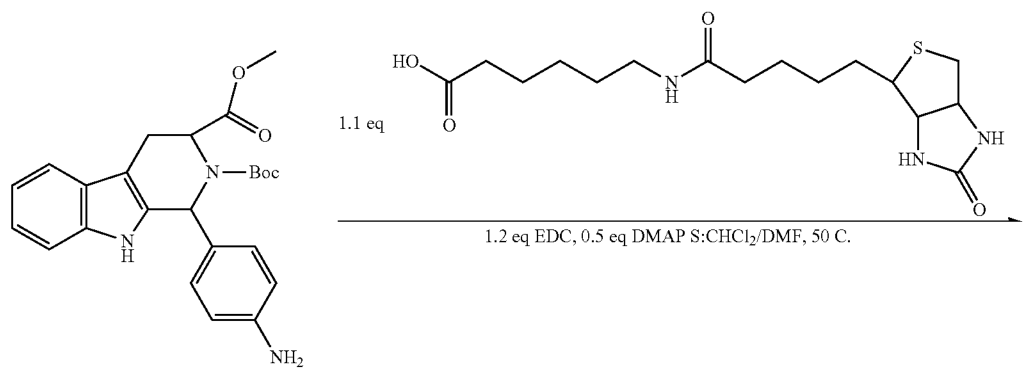
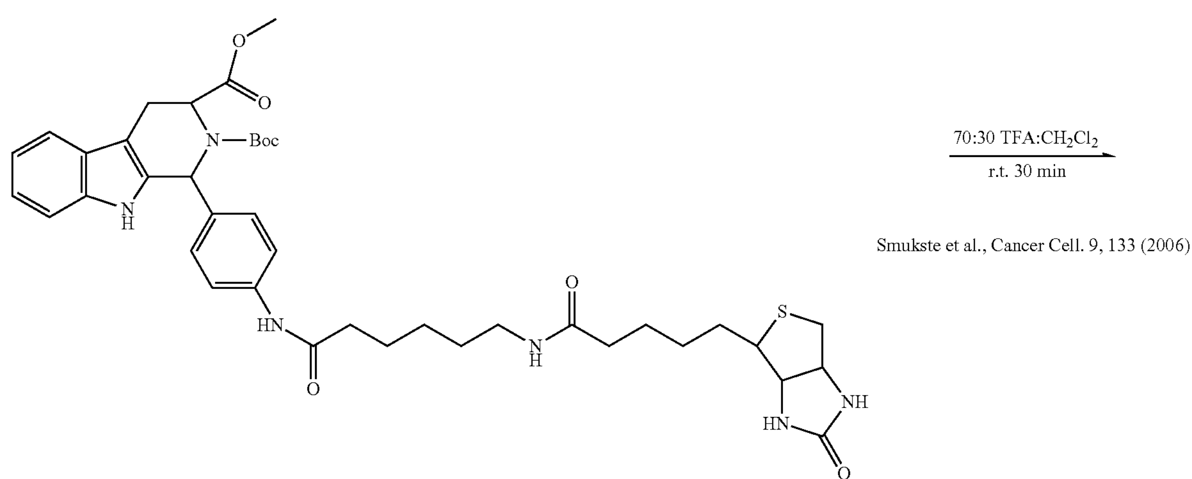

-continued

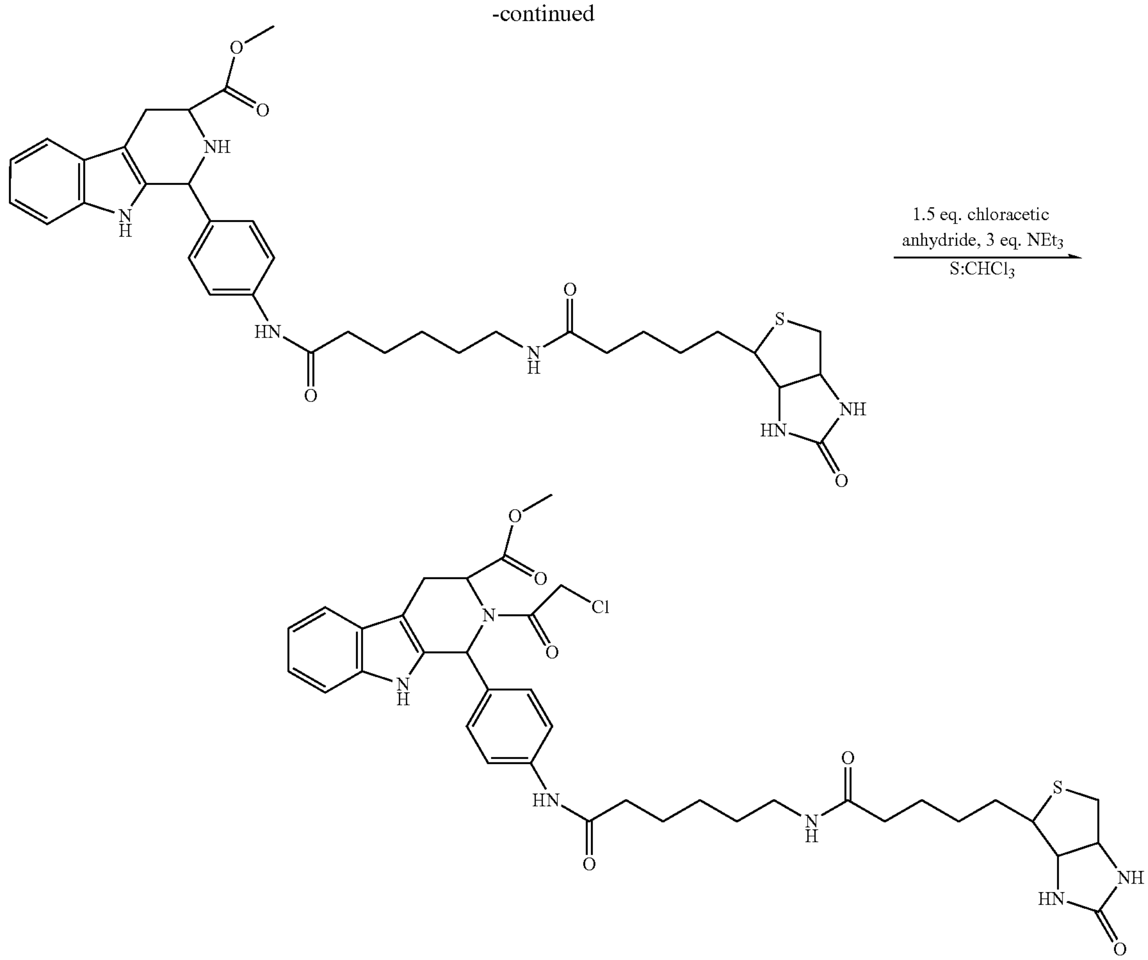

Boc Protection

Scaffold 2 (SC2) was dissolved in dry $CH_3CN$ (~2 mL) along with 3 eq. of triethylamine and stirred under $N_2$. Boc anhydride (2+ eq) and DMAP (0.2 eq) were dissolved in 200 uL of $CH_3CN$ and then added dropwise to the reaction mixture which changes from yellow to dark brown in color upon addition. The reaction was heated to 50° C. and left to stir overnight. An additional 1-3 equivalents of Boc anhydride were added as needed. Upon reaction completion, $CH_3CN$ was removed under reduced pressure and the mixture was redissolved in $CH_2Cl_2$. The reaction was quenched by addition of 2N $NH_4Cl$, the organic layer was removed, washed with brine and dried with $Na_2SO_4$. The resulting crude product was purified by silica chromatography using 2% MeOH in $CH_2Cl_2$.

Reduction

Boc-protected product dissolved in a small amount of $CH_2Cl_2$ was added to 20-30 mL EtOH. The reaction vessel was first evacuated and then refilled with Ar several times to replace the air in the vessel, then a catalytic amount of 10% Pd/C catalyst was added. The reaction vessel was again evacuated and then refilled with $H_2$. The reaction was left to stir overnight. Product had Rf value 0.21-0.25 in 25% A (A=10% MeOH in EtOAc) in $CH_2Cl_2$. Purified crude product by silica gel chromatography, eluting with a gradient between 10-25% A in $CH_2Cl_2$.

Peptide Coupling

The amine product was dissolved in dry $CHCl_3$ (~1 mL) and stirred under $N_2$ in a dry conical vial. Biotin-linked 6-aminohexanoic acid (1.1 eq) was dissolved along with EDC (1.2 eq) and DMAP (0.5 eq) in dry DMF (~1 mL). This solution was then added dropwise to the amine solution and left to stir at 50° C. overnight. Upon reaction completion, $CH_2Cl_2$ was added and then the combined organic layer was washed successively with 1N HCl, $H_2O$, saturated aqueous $NaHCO_3$ and brine, and then dried with $Na_2SO_4$. Aqueous layers were also back-extracted to recover coupled product dissolved in them. The compound was purified by silica chromatography using 7% MeOH in $CH_2Cl_2$.

Deprotection

The coupled product was dissolved in a solution of 30% TFA/$CH_2Cl_2$ and stirred for an hour at room temperature. The solution turned a reddish pink color. Solvents and TFA were removed in vacuo, redissolved in $CH_2Cl_2$ and crude product was extracted with 5% aqueous $K_2CO_3$ solution. The organic phase was washed twice with dd$H_2O$, dried with $Na_2SO_4$ and the organic phase concentrated.

Chloroacetylation

The deprotected product was dissolved in anhydrous $CHCl_3$ and 2-3 equivalents of triethylamine were added. To this was added 0.5 equivalents of chloroacetyl chloride diluted in a solution of dry $CHCl_3$. Consecutive half equivalents were added and the reaction was followed by MS until all the deprotected product was chloroacetylated.

Synthesis of Para Compound 27 Analog

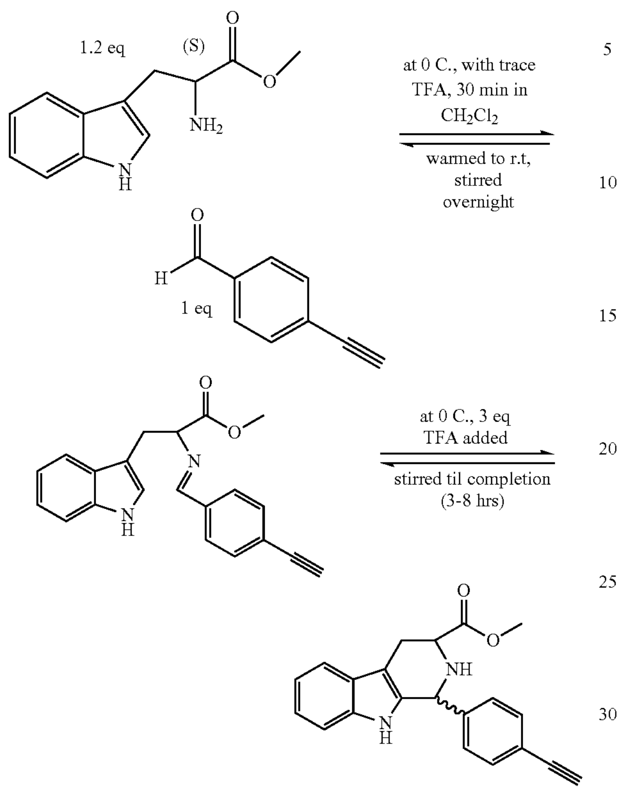

Pictet Spengler Reaction

The hydrochloride salt of L-tryptophan methyl ester was "free-based" by dissolving it in $CH_2Cl_2$ and then adding 5% aqueous $K_2CO_3$. The organic layer was extracted, dried with $Na_2SO_4$, and concentrated in vacuo. To a dry vial was added L-tryptophan methyl ester along with molecular sieves dissolved in dry $CH_2Cl_2$. 4-ethynylbenzaldehyde and 0.1 eq of TFA were added to the reaction mixture at 0° C. and the solution was then allowed to return to room temperature and stirred overnight. The following day, 3 equivalents of TFA were added to the solution and the reaction was allowed to stir for an additional 3-8 hours. Work-up was done by quenching the reaction with saturated aqueous $NaHCO_3$, the organic phase was separated, washed with brine and dried with $Na_2SO_4$ and then concentrated to give the crude product. The compound was purified by dry-loaded silica gel chromatography in 20:80 EtOAc:Hexane with 1% $NEt_3$ to give the two diastereomers ('cis' Rf=0.29, 'trans' Rf=0.13)

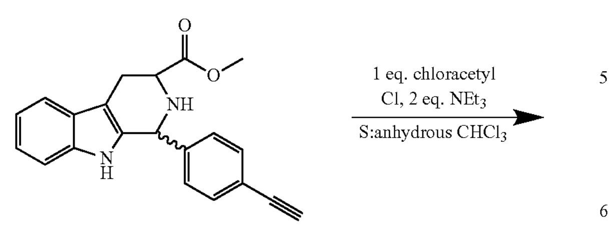

Chemical Formula: $C_{21}H_{18}N_2O_2$
Exact Mass: 330.14
Molecular Weight: 330.38
m/z: 330.14 (100.0%). 331.14 (23.0%), 332.14 (3.1%)
Elemental Analysis: C, 76.34; H, 5.49; N, 8.48; O, 9.69

-continued

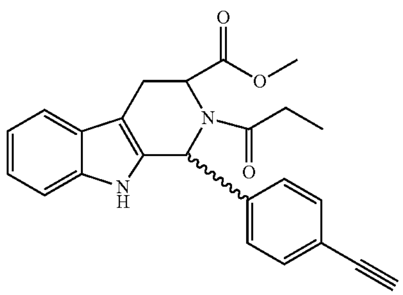

Chemical Formula: $C_{23}H_{19}ClN_2O_3$
Exact Mass: 406.11
Molecular Weight: 406.86
m/z: 406.11 (100.0%), 408.11 (32.8%), 407.11 (25.9%), 409.11 (8.1%), 408.12 (3.0%), 410.11 (1.2%)
Elemental Analysis: C, 67.90; H, 4.71; Cl, 8.71; N, 6.89; O, 11.80

Chloroacetylation

The intermediate (one of the diastereomers) was dissolved in anhydrous $CH_2Cl_2$ and 2-3 equivalents of triethylamine added. To this was added 0.5 equivalents of chloroacetyl chloride diluted in a solution of dry $CH_2Cl_2$ dropwise at 0° C. Consecutive half equivalents were added and the reaction was followed by MS and TLC until all the starting material was chloroacetylated. Reaction was quenched by addition of saturated $NaHCO_3$ and the organic layer was extracted, washed with brine and dried with $Na_2SO_4$ and then concentrated. Purification was done by silica gel chromatography in 20:80 EtOAc:Hexane.

Synthesis of Acrylyl Compound 27 Analog

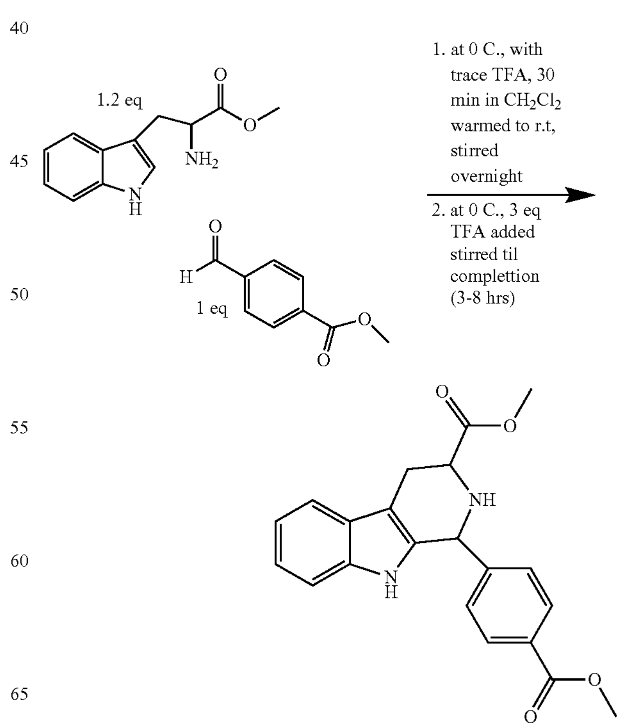

-continued

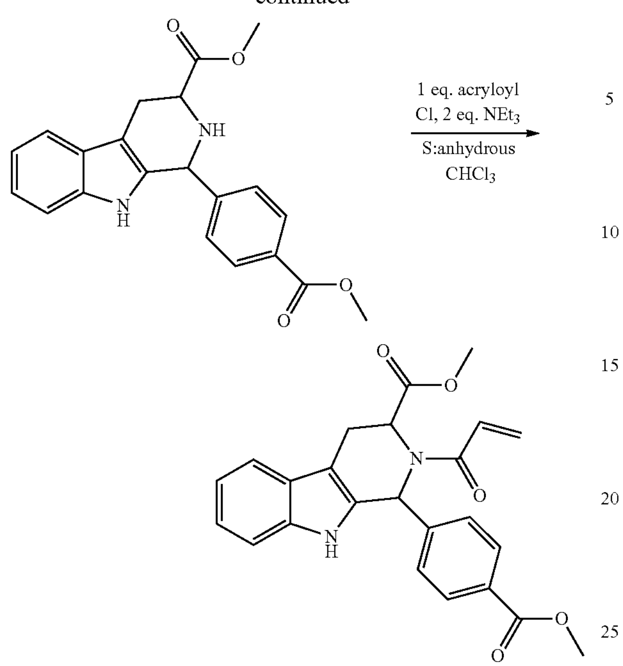

Synthesis was analogous to that of para Compound 27 analog, except methyl 4-formyl-benzoate was used in place 4-ethynyl benzaldehyde. Purified by silica gel chromatography in EtOAc/Hex (dry-loading), using gradient from 100% Hexane to 40:60 EtOAc/Hex. Cis diastereomer has Rf 0.35, trans diastereomer has Rf 0.17 in 40:60 EtOAc:Hexane. Instead of chloroacetylation, acryloyl chloride was used to acryloylate the intermediate in an identical procedure used for chloroacetylation to give the acrylamide version of Compound 27.

Synthesis of Ethyl Compound 27 Analog

An analogous procedure to that of the para Compound 27 analog was used, except an L-tryptophan ethyl ester was used and methyl 4-formyl-benzoate in the pictet-spengler reaction. The two diastereomers were separated by silica gel chromatography using EtOAc/Hexane and eluted with a gradient from 100% Hexane to 40:60 EtOAc/Hex. The first diastereomer, D1 has an Rf value of 0.14 and D2 an Rf value of 0.06 in EtOAc:Hexane. Chloroacetylation was carried out as described above and the ethyl analog is shown as follows:

Synthesis of methyl (3S)-1-phenyl-2,3,4,9-tetrahydro-1H-β-carboline-3-carboxylate (C)

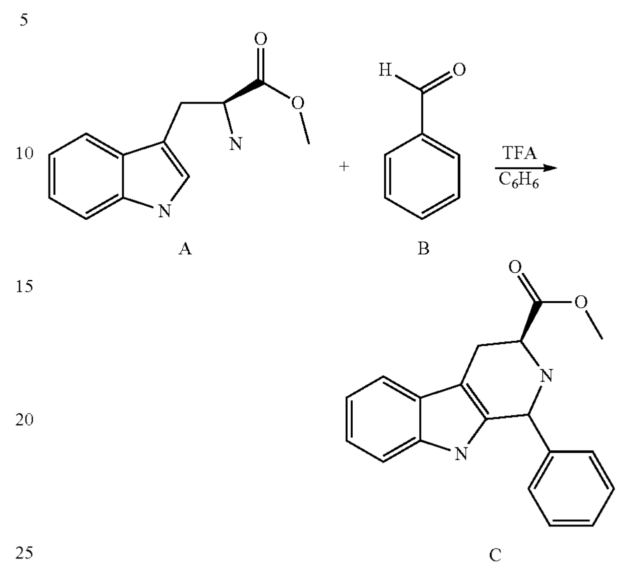

To the solution of 0.06 mol of L-tryptophan methyl ester and 0.05 mol of benzaldehyde in 150 ml of benzene, 0.5 ml of trifluoroacetic acid and 2 g of molecular sieves (4 Å) were added. The reaction mixture was refluxed for 1 hour, and then 0.138 mol (3 equiv.) of trifluoroacetic acid was added and the mixture was further refluxed for 3 hours. The reaction mixture was cooled down to room temperature and diluted with water and basified with 30% solution of NaOH. The organic layer was separated, dried over $MgSO_4$ and the solvent was removed in vacuo. The residue was washed with diethyl ether, and the precipitate thus formed was filtered off to give the required product (80% yield).

Melting point: 217-218° C. NMR$^1$H (δ, ppm, $CDCl_3$, 500 MHz): 2.46 (1H, br.s, NH); 3.04-3.27 (2H, m, Ar—$CH_2$); 3.79 (3H, s, $OCH_3$); 3.97 (1H, dd, $ArCH_2CH$, $J_{HH}$=10.5; 2.8 Hz); 5.23 (0.75H, s, Ar—CH); 5.39 (0.25H, s, Ar—CH) and 7.15-7.68 (10H, m, ArH and indol NH).

NMR$^{13}$C (δ, ppm, $CDCl_3$, 125.76 MHz): 25.46 (d), 51.73 (d), 54.05 (s), 56.23 (s), 57.77 (s), 106.95 (d), 111.20 (d), 117.60 (d), 118.39 (d), 120.79 (d), 126.52 (s), 127.21 (s), 127.70 (s), 128.13 (s), 135.34 (d), 136.37 (d), 143.02 (d), 173.78 (d). m/z 306 ($M^+$).

Synthesis of methyl(3s)-2-(chloroacetyl)-1-phenyl-2,3,4,9-tetrahydro-1H-β-carboline-3-carboxilates (D)

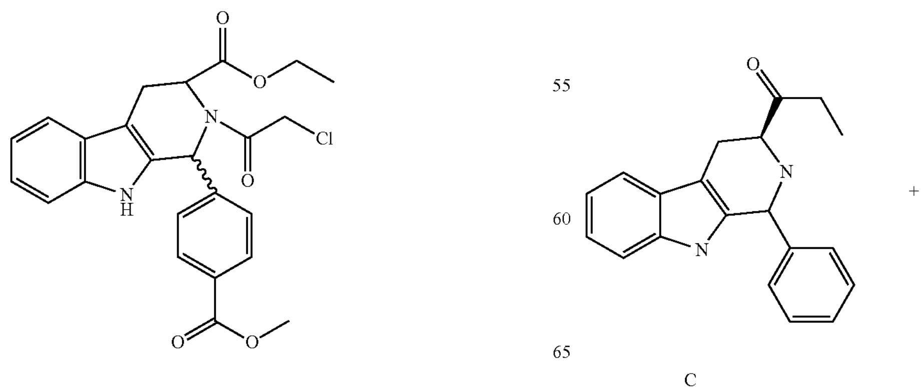

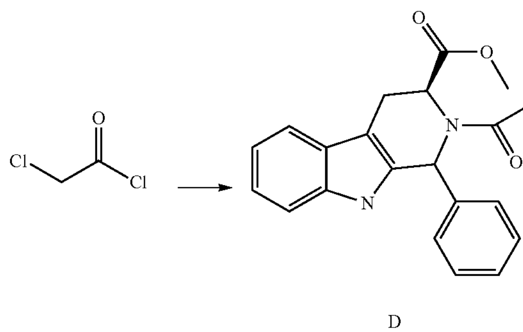

To a stirred, cooled on ice/water mixture containing a solution of 0.04 mol of compound C and 0.048 mol of $NaHCO_3$ in 200 ml of dry chloroform, 0.096 mol of chloroacetylchloride was added drop wise. The reaction mixture was stirred for 4 hours at room temperature, diluted with dichloromethane and consecutively washed with a saturated aqueous solution of $NaHCO_3$ and brine. The organic layer was separated and dried over $MgSO_4$. The solvent was removed on rotary evaporator and the residue was washed with diethyl ether. The precipitate was filtered off and washed with a small quantity of methanol to yield the desired product (60% yield).

m.p. 173-175° C. NMR$^1$H (δ, ppm, $CDCl_3$, 500 MHz): 3.00 (2H, br.s, $CH_2$); 3.22 (1H, m, CH); 3.69 (3H, s, $OCH_3$); 4.22-4.34 (2H, m, $CH_2$); 4.93 (1H, br.s, CH); 6.99 (1H, br.s, Ar); 7.75 (7H, m, Ar); 7.60 (1H, br.s, Ar); 7.89 (1H, s, NH).

NMR$^{13}$C (δ, ppm, $CDCl_3$, 125.76 MHz): 21.62 (s), 42.66 (s), 52.16 (s), 52.22 (s), 53.54 (s), 107.46 (s), 111.31 (s), 118.57 (d), 119.85 (d), 122.52 (d), 126.37 (d), 128.26 (s), 129.48 (s), 136.80 (d), 138.96 (d), 167.14 (s), 170.04 (s). m/z 383.5 ($M^+$).

Synthesis of (3S)-1-phenyl-2,3,4,9-tetrahydro-1H-β-carboline-3-carboxamide (E)

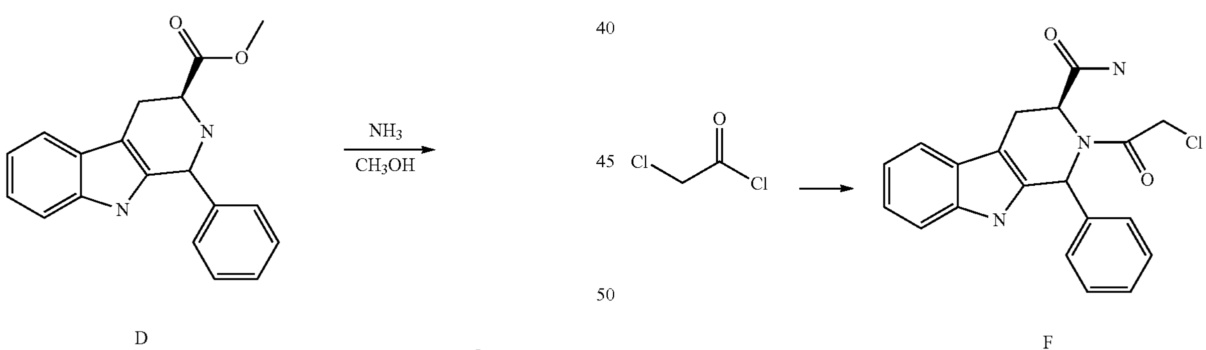

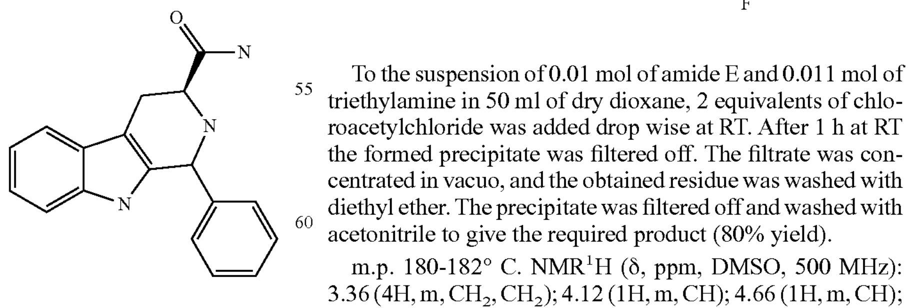

Ammonia gas was bubbled through the solution of 0.01 mol of compound D in 50 ml of methanol for 2 h at RT, and the reaction mixture was left for 24 h. The precipitate formed was filtered off (50% yield) and used in subsequent reactions without further purification.

m.p. 153° C. NMR$^1$H (δ, ppm, DMSO, 500 MHz): 2.73 (1H, m, $CH_2$); 2.97 (1H, m, $CH_2$); 3.20 (1H, NH); 3.38 (1H, s, CH); 5.22 (1H, s, CH); 7.01 (2H, m, Ar); 7.30 (6H, m, Ar); 7.42 (1H, br.s, Ar); 10.65 (1H, s, NH).

NMR$^{13}$C (δ, ppm, DMSO, 125.76 MHz): 24.89 (s), 51.65 (s), 54.04 (s), 108.01 (s), 110.96 (s), 117.44 (s), 118.16 (s), 120.61 (s), 126.68 (s), 126.87 (s), 127.88 (s), 128.24 (s), 134.21 (s), 136.08 (s), 142.95 (s), 174.91 (s). m/z 291 ($M^+$).

Synthesis of (3S)-2-(chloroacetyl)-1-phenyl-2,3,4,9-tetrahydro-1H-β-carboline-3-carboxamide (F)

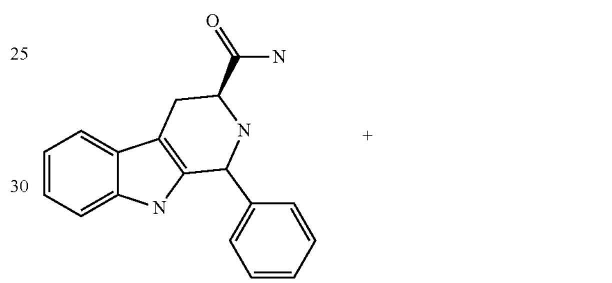

To the suspension of 0.01 mol of amide E and 0.011 mol of triethylamine in 50 ml of dry dioxane, 2 equivalents of chloroacetylchloride was added drop wise at RT. After 1 h at RT the formed precipitate was filtered off. The filtrate was concentrated in vacuo, and the obtained residue was washed with diethyl ether. The precipitate was filtered off and washed with acetonitrile to give the required product (80% yield).

m.p. 180-182° C. NMR$^1$H (δ, ppm, DMSO, 500 MHz): 3.36 (4H, m, $CH_2$, $CH_2$); 4.12 (1H, m, CH); 4.66 (1H, m, CH); 5.08 (1H, m, $NH_2$); 6.12 (1H, m, $NH_2$); 7.25 (9H, m, Ar); 10.98 (1H, br.s, NH).

NMR$^{13}$C (δ, ppm, DMSO, 125.76 MHz): 24.07 (s), 43.01 (s), 56.41 (s), 56.99 (s), 102.85 (s), 111.21 (s), 117.73 (s), 118.63 (s), 120.88 (s), 125.82 (s), 126.39 (s), 128.12 (s), 128.98 (s), 134.12 (s), 135.15 (s), 143.95 (s), 167.42 (s), 172.42 (s). m/z 367.5 ($M^+$).

Synthesis of 2-[(3S)-3-(aminocarbonyl)-1-phenyl-1,3,4,9-tetrahydro-2H-β-carbolin-2-yl]-2-oxoethyl acetate (G)

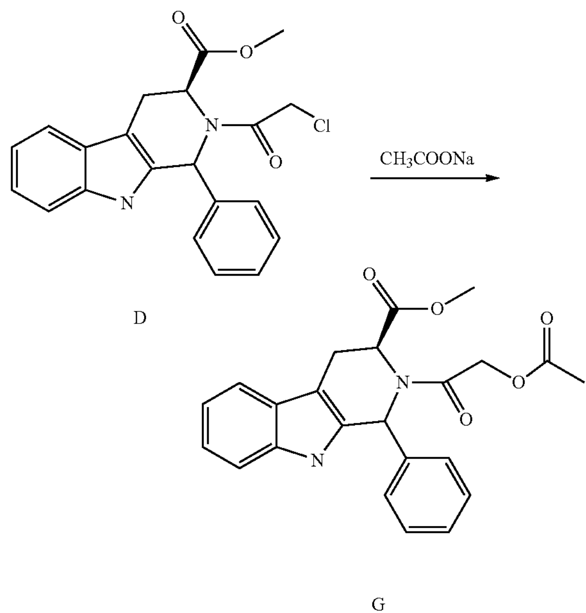

To the suspension of 0.01 mol of compound D in 20 ml of DMSO, 2 equivalents of anhydrous sodium acetate was added. The reaction mixture was stirred for 48 h at RT and diluted with water. The precipitate was filtered off, dried and washed with diethyl ether to give the required product (50% yield).

m.p. 195-197° C. NMR$^1$H (δ, ppm, DMSO, 500 MHz): 2.13 (3H, s, $CH_3$); 2.85 (2H, s, $CH_2$); 3.36 (5H, m, $CH_2$ and $OCH_3$); 4.85 (1H, br. s, CH); 5.12 (1H, br.s, CH); 6.88-7.55 (9H, m, Ar); 10.94 (1H, s, NH).

NMR$^{13}$C (δ, ppm, DMSO, 125.76 MHz): 21.05 (d), 40.41 (s), 50.95 (d), 51.47 (s), 61.71 (s), 106.16 (s), 111.19 (s), 118.02 (s), 118.62 (s), 121.47 (s), 125.93 (s), 127.86 (d), 128.69 (s), 129.72 (s), 136.31 (s); 139.53 (s), 166.90 (s), 169.81 (s); 170.25 (s). m/z 406 ($M^+$).

Synthesis of methyl (3S)-1-phenyl-2-[(2,3,5,6-tetrafluorophenoxy)acetyl]-2,3,4,9-tetrahydro-1H-β-carboline-3-carboxylate (H)

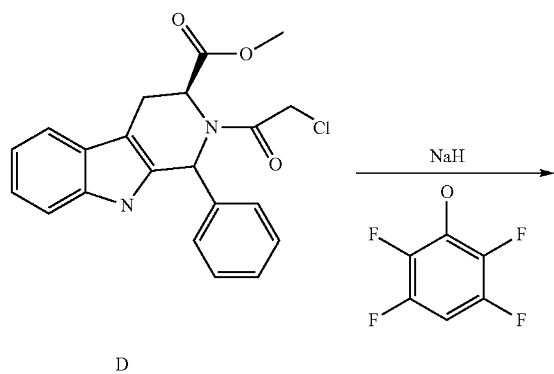

-continued

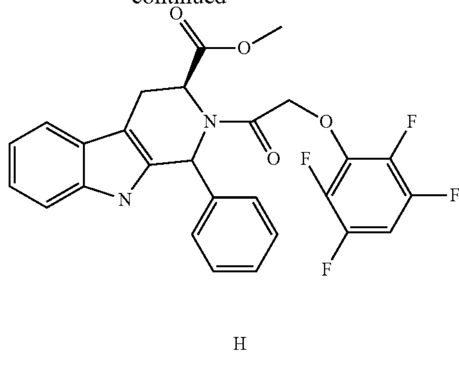

Method A. To the solution of 0.01 mol of tetrafluorophenol in 50 ml of DMFA, 0.013 mol of sodium hydride was added and the mixture was stirred at RT during 12 h. Then to the reaction mixture were added 0.01 mol of compound D and 0.01 mol of KI. The resulting mixture was stirred for 48 h at RT. The reaction mixture was diluted with water and the precipitate was filtered off. According to LCMS spectral data, the resulting product had a purity of 76% and subsequent purification was unsuccessful most likely due to instability of the final product.

Method B. Similar to Method A, the reaction mixture was stirred for 5 days. LC-MS spectrum showed 4% of the product. Probably decomposition of the product took place as result of prolonged exposure to alkaline medium.

Method C. Similar to Method A, but the reaction mixture was refluxed. LCMS spectrum showed 24% of the product. Attempts to further purify were unsuccessful. A number of other standard methods were tried, but they did not lead to a positive result.

Synthesis of methyl (3S)-1-(1H-imidazol-5-yl)-2,3,4,9-tetrahydro-1H-β-carboline-3-carboxylate (I)

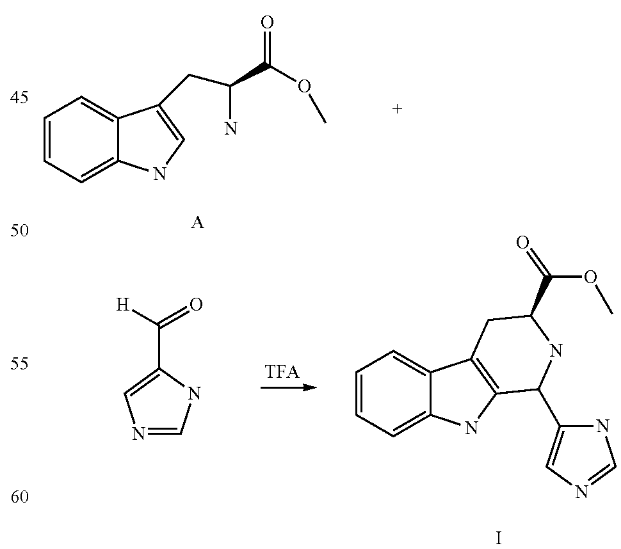

To the solution of 0.01 mol of ester A in 50 ml of trifluoroacetic acid, a solution of 0.011 mol of aldehyde in 10 ml of methanol was added. The mixture was refluxed for 1 h, cooled down to RT, and basified to pH 8-9 using a 30% aqueous solution of NaOH. The precipitate was filtered off and washed with diethyl ether to give the required product (33% yield).

m.p. 225-226 (во3[)° C. NMR[1]H (δ, ppm, DMSO, 500 MHz): 2.77 (1H, m, $CH_2$); 3.00 (1H, m, $CH_2$); 3.66; 3.71 (3H, s, s, $OCH_3$); 3.88 (1H, m, CH); 5.27 (1H, s, CH); 6.95 (3H, m, ArH); 7.28 (1H, br.s., Ar); 7.42 (1H, br.s., Ar); 7.66 (1H, br.s., Ar); 10.40; 10.74 (1H s, s, indol NH).

NMR[13]C (δ, ppm, DMSO, 125.76 MHz): 24.45 (d), 50.61 (s), 51.54 (s), 56.79 (s), 106.08 (s), 111.23 (d), 117.35 (d), 118.28 (d), 120.53 (d), 126.61 (d), 134.91 (s), 135.11 (s), 136.02 (s), 173.04 (d). m/z 296 ($M^+$).

Synthesis of methyl (3S)-2-(chloroacetyl)-1-(1H-imidazol-5-yl)-2,3,4,9-tetrahydro-H-β-carboline-3-carboxylate (J)

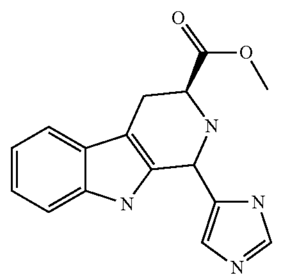

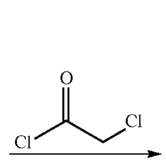

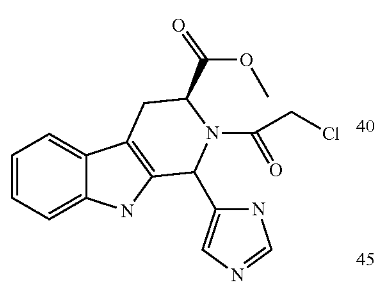

To the suspension of 0.01 mol of compound I, 0.024 mol of chloroacetylchloride was added drop wise with stirring at RT. The reaction mixture was refluxed during 2 h, cooled down, the precipitated product was filtered off and washed with acetonitrile. The required product was isolated as HCl salt (60% yield).

m.p. 250 (decomposition)° C. NMR[1]H (δ, ppm, dmso, 500 MHz): 3.16 (1H, m, $CH_2$); 3.30 (3H, s, $OCH_3$); 3.55 (3H, m, $CH_2$ and CH); 4.54 (1H, d, $CH_2$, J=14 Hz); 4.90 (1H, d, $CH_2$, J=14 Hz); 5.13 (1H, br.s, CH); 6.56 (1H, s, Im); 7.03 (1H, br.s, Ar); 7.12 (1H, br.s, Ar); 7.21 (1H, s, Im); 7.33 (1H, br. s, Ar); 7.57, (1H, br. s, Ar); 11.12 (1H, br.s., NH).

NMR[13]C (δ, ppm, DMSO, 125.76 MHz): 21.88 (s), 43.08 (s), 44.31 (s); 52.23 (s), 53.36 (s), 106.53 (s), 111.39 (s), 118.17 (s), 118.70 (s), 118.80 (s); 121.71 (s), 125.63 (s), 126.81 (s), 131.17 (s), 133.69 (s), 136.61 (s), 167.48 (s), 170.27 (s). m/z 372.5 ($M^+$).

Synthesis of methyl (3S)-1-pyridin-4-yl-2,3,4,9-tetrahydro-1H-β-carboline-3-carboxylate (K)

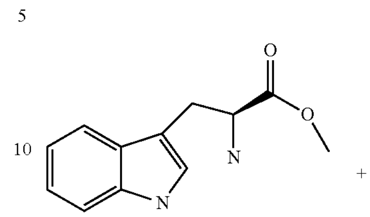

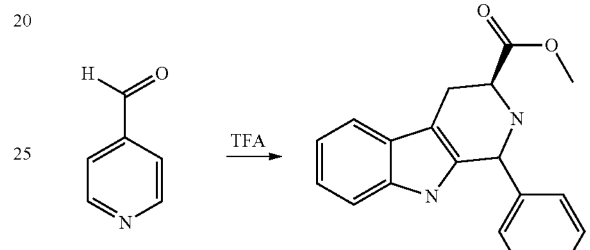

Compound K was synthesized (25% yield) using the same procedure as for compound I.

m.p. 220-225 (sublimation)° C. NMR[1]H (δ, ppm, DMSO, 500 MHz): 3.17 (2H, m, $CH_2$); 3.63; (3H, s, $OCH_3$); 3.77 (1H, br.s, CH); 5.34 (1H, s, CH); 7.04 (2H, br.s, PyH); 7.30 (4H, m., Ar); 8.05 (2H, br.s., PyH); 10.71 (1H, s, indol NH).

NMR[13]C (δ, ppm, DMSO, 125.76 MHz): 24.73 (s), 51.67 (s), 51.95 (s), 53.07 (s), 106.89 (s), 111.13 (s), 117.74 (s), 118.50 (s), 121.08 (s), 123.33 (s), 126.41 (s), 132.92 (s), 136.17s), 149.53 (s), 151.43 (s), 173.65 (s). m/z 307 ($M^+$).

Synthesis of methyl (3S)-2-(chloroacetyl)-1-pyridin-4-yl-2,3,4,9-tetrahydro-1H-β-carboline-3-carboxylate (L)

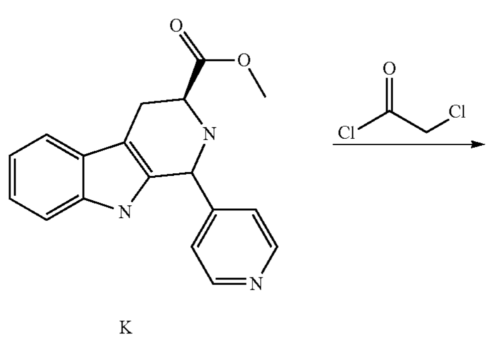

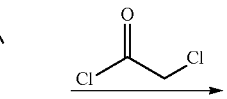

-continued

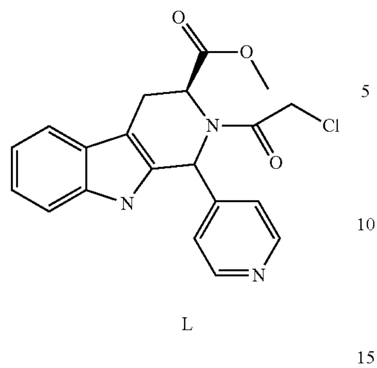

L

Synthesis was carried out using the same procedure as for compound J. The product was obtained as a hydrochloride salt with 86% purity (see LCMS spectrum of 90 mg crude sample). During the purification in polar solvent ($CH_3OH$, $CH_3CN$), the compound decomposed and oxidized into compound M.

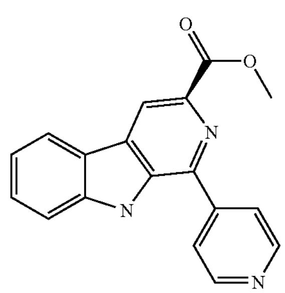

M

Methyl (3S)-1-[4-(prop-2-ynyloxy)phenyl]-2,3,4,9-tetrahydro-1H-β-carboline-3-carboxylate (O)

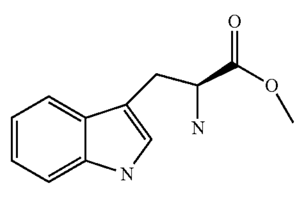

N

+

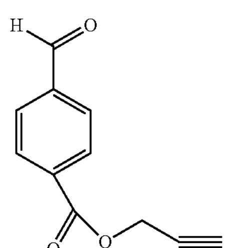

M

TFA →

-continued

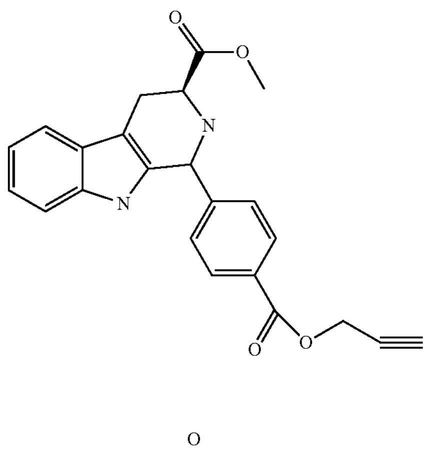

O

To a solution of 0.01 mol of ester N in 50 ml of trifluoroacetic acid a solution of 0.011 mol of aldehyde M in 10 ml of methanol was added. The reaction mixture was stirred at reflux for 1 h. 30% aqueous solution of NaOH was added to the cooled to RT reaction mixture until pH 8-9. The aqueous layer was decanted and the residue was treated with hexane. The precipitate formed was filtered off.

Yield 35%, purity 78% according to LCMS data, m/z 388 ($M^+$).

Methyl (3S)-2-(chloroacetyl)-1-[4-(prop-2-ynyloxy)phenyl]-2,3,4,9-tetrahydro-1H-β-carboline-3-carboxylate (Q)

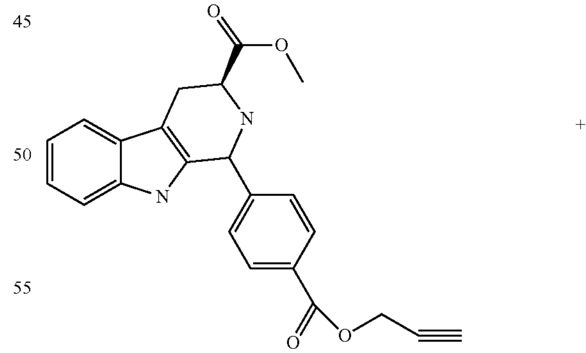

P

+

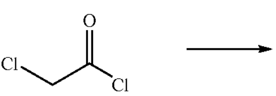

→

-continued

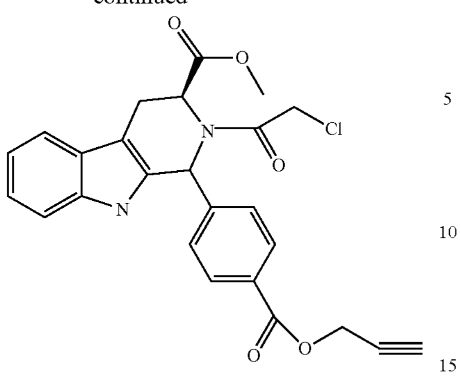

Q

-continued

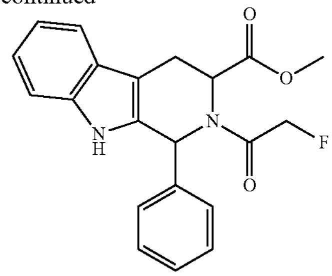

R
Mol. Wt.: 366.39

To a solution of 0.01 mol of compound P in dry dioxane, 0.024 mol of chloroacetylchloride was added with stirring at RT. The reaction mixture was refluxed for 1 h, cooled down and the solvent was removed in vacuo. To the residue, diethyl ether was added, and the precipitate was filtered off and washed with methanol. Yield 60%, m.p. 218° C. NMR$^1$H (δ, ppm, dmso, 500 MHz): 2.89 (2H, s, $CH_2$), 3.21 (5H, m, CH, CH, $OCH_3$); 4.36 (1H, d, $CH_2$, J=12 Hz); 4.77 (1H, d, $CH_2$, J=12 Hz); 4.90 (1H, s, CH); 5.22 (1H, br.s, CH); 6.90 (1H, s, Ar); 7.00 (2H, m, Ar); 7.25 (3H, m, Ar); 7.54 (1H, d, Ar, J=7 Hz); 7.88 (1H, d Ar, J=9 Hz); 10.82 (1H, br.s., NH). NMR$^{13}$C (δ, ppm, DMSO, 125.76 MHz): 21.10 (s) 44.31 (s); 52.21 (d), 52.49 (d), 77.92 (d), 106.52 (s), 111.32 (s), 118.16 (s), 118.77 (s), 125.87 (s), 128.34 (s), 129.06 (s), 136.44 (s), 145.08 (s), 164.70 (s), 166.98 (s), 170.08 (s). m/z 463 ($M^+$).

Methyl(3S)-1-phenyl-2-fluoroacetyl-2,3,4,9-tetrahydro-1H-β-carboline-3-carboxylate (R)

Typical Procedure (the same reaction was performed several times on different scale):

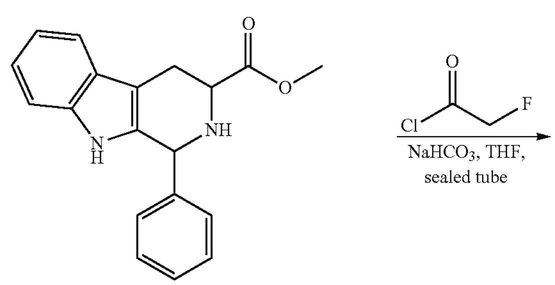

K
Mol. Wt.: 306.36

Starting material K was prepared according to the previously described procedure.

In an oven dried tube, a mixture of K (100 mg, 1 eq.) and $NaHCO_3$ (250 mg, 10 eq.) was taken and dry THF (3 mL) was added under an inert atmosphere. To this mixture was carefully added fluoroacetyl chloride (0.08 mL, 2 eq., caution: highly toxic and volatile) and the reaction tube was sealed. The mixture was then heated at 60° C. overnight. Next day after cooling to RT, the mixture was quenched with water and diluted with ethyl acetate. The organic layer was separated, washed with brine solution and dried ($MgSO_4$). TLC (60:40, ethyl acetate/hexanes) indicated slightly higher moving spots (mixture of distereomers) and no starting material left. There were some low moving impurities. After concentrating the solution, the resulting solid was dissolved in methylene chloride and the desired product was obtained after silica gel column purification using 20 to 40% ethyl acetate/hexane mixture as eluent. Yield 70 mg (58%, mixture of distereomers).

MS (367.08, M+H).

NMR$^1$H (δ, ppm, DMSO, 400 MHz): 2.83 (1H, s); 3.01-3.69 (5H, m); 4.76-6.19 (3H, m); 6.83-7.74 (9H, m); 10.91 (1H, br.s, NH).

NMR$^{19}$F (δ, ppm, DMSO, 376.33 MHz): −90.90 (s, first diastereomer), −93.76 (s, second diastereomer).

HPLC (acetonitrile/water, 20-90% gradient): single peak at 13.4 min

Example 6
Synthesis of the Four Stereoisomers of Compound 27
Synthesis of (1R,3S) Compound 27 and (1S,3S) Compound 27
-continued
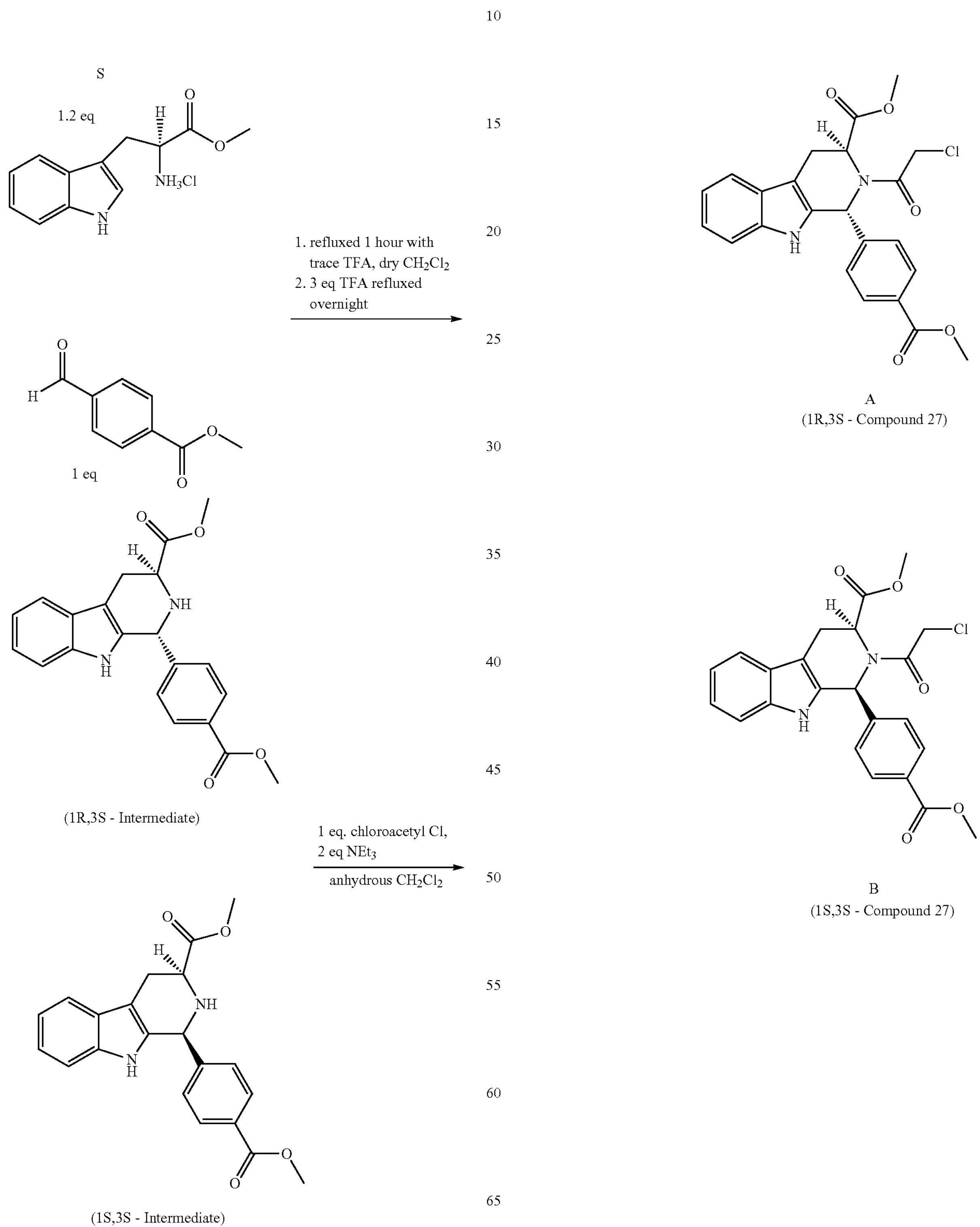

Synthesis of (1R,3R) Compound 27 and (1S,3R) Compound 27

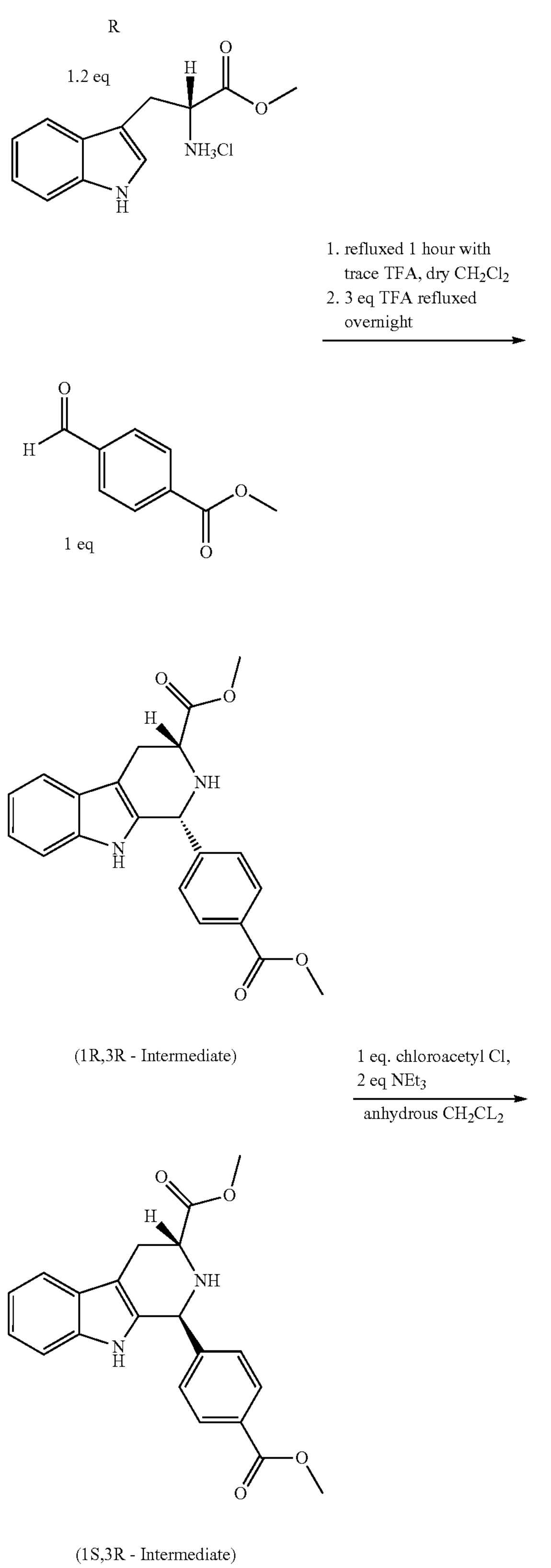

-continued

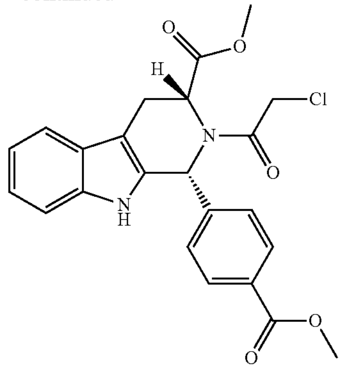

D (1R,3R - Compound 27)

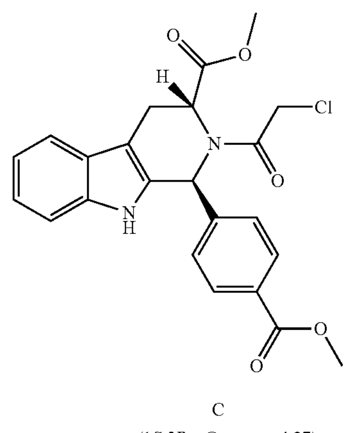

C (1S,3R - Compound 27)

Pictet Spengler Reaction

To a suspension of 1.2 eq of the corresponding S or R (1 eq.) tryptophan methyl ester hydrochloride (Sigma) in dichloromethane at room temperature was added 1.3 eq. of triethylamine (Sigma). The mixture was stirred for 1 hour and then filtered. The filtrate was concentrated to give the required product as a clear oil, which was dried under high vacuum for 10 minutes to give the S or R tryptophan methyl ester. Immediately afterwards, the S or R tryptophan methyl ester along with molecular sieves were dissolved in dry anhydrous dichloromethane, 1 eq of methyl 4-formylbenzoate (Sigma) and 0.1 eq of TFA (Sigma) were added to the reaction mixture and the solution was refluxed for an hour. After an hour, 3 equivalents of TFA were added to the solution and the reaction was allowed to stir under reflux overnight. After cooling to room temperature, a work-up was done by addition of water, quenching the reaction with 30% NaOH, separating the organic phase, washing with brine, drying with $Na_2SO_4$, and then concentrating to give the crude product. Each crude product was purified by dry-loaded silica gel chromatography in a gradient elution from 100% hexane with 1% $NEt_3$ to 20:80 EtOAc:Hexane with 1% $NEt_3$ to give the two separate diastereomers which are intermediates in the preparation of Compound 27. Mixed fractions were repurified again with the same protocol. Yield: 1R,3S Compound 27 Intermediate 18% and 1S,3S Compound 27 Intermediate 34%; 1R,3R Compound 27 Intermediate 41% and 1S,3R Compound 27 Intermediate 16%.

Chloroacetylation

Each of the four intermediates produced above was dissolved in anhydrous $CH_2Cl_2$ and 1.1 equivalents of sodium bicarbonate were added. To this was added 0.5 equivalents of chloroacetyl chloride dropwise at 0° C. Consecutive half equivalents were added and the reaction was followed by MS and TLC until all the starting material was chloroacetylated. The respective products were filtered and each filtrate was extracted, washed with brine, dried with $Na_2SO_4$, and then concentrated. Each compound was purified by silica gel chromatography in 20:80 EtOAc:Hexane. Yield: 1R,3S Compound 27 (49%), 1S,3S Compound 27 (5%), 1R,3R Compound 27 (2%), and 1S,3R Compound 27 (79%).

NMR

Figure 49:
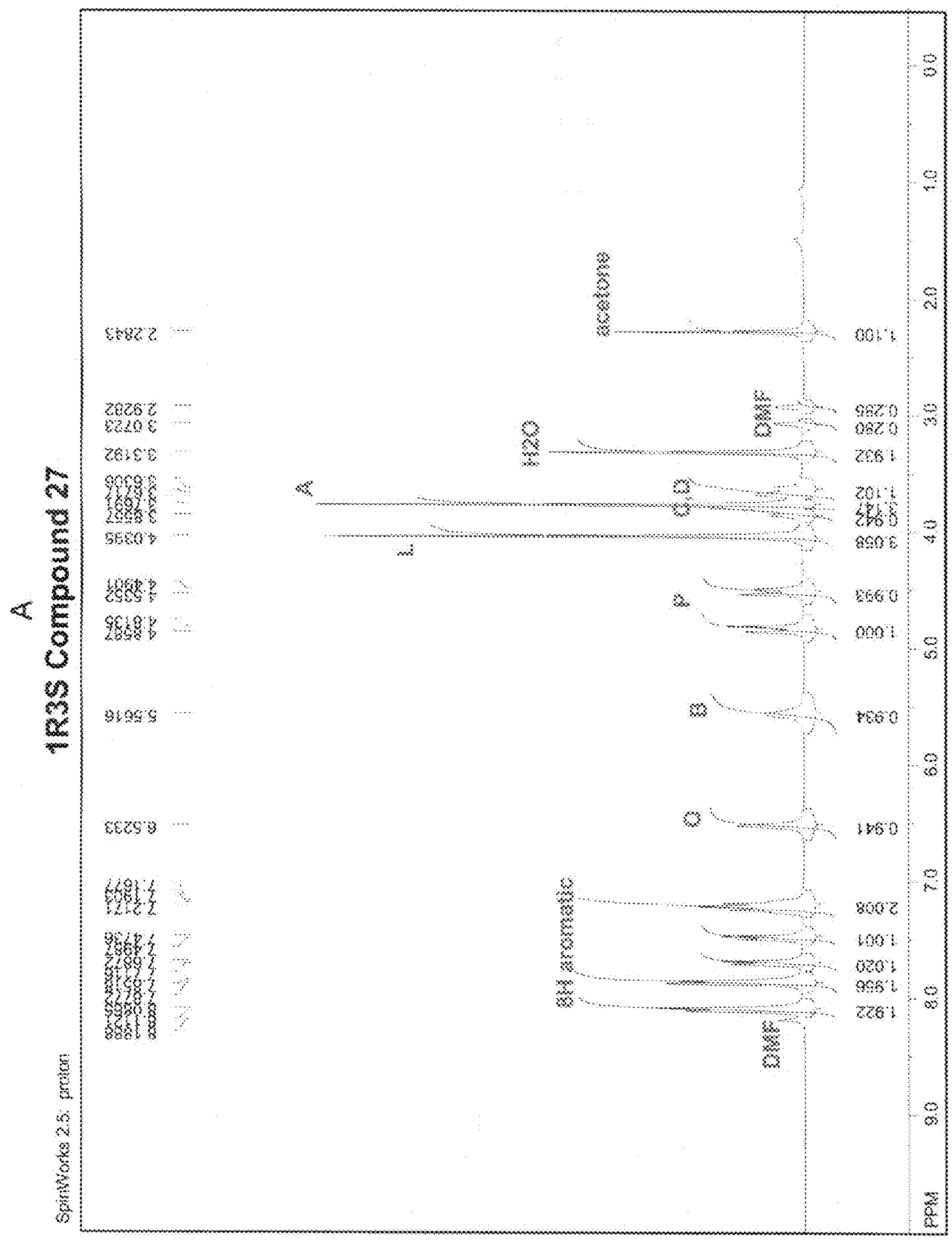
FIG. 49 shows NMR data for the four stereoisomeric conformations of Compound 27. Panel A shows NMR data for (1R,3S) Compound 27. Panel B shows NMR data for (1S,3S) Compound 27. Panel C shows NMR data for (1S,3R) Compound 27. Panel D shows NMR data for (1R,3R) Compound 27. The NMR data indicate that the four stereoisomers of Compound 27 were each enantiomerically pure. The legend for the NMR data is as follows, stereochemistry not shown.

Each of the four stereoisomers of Compound 27 were evaluated by NMR. FIG. 49 shows that each stereoisomer, 1R,3S Compound 27 (panel A), 1S,3S Compound 27 (panel B), 1S,3R Compound 27 (panel C), and 1R,3R Compound 27 (panel D) is enantiomerically pure.

Example 7

Synthesis of Stereoisomers of Cyclized Compound 27

Representative Example

Synthesis of 1S,3S Cyclized Compound 27

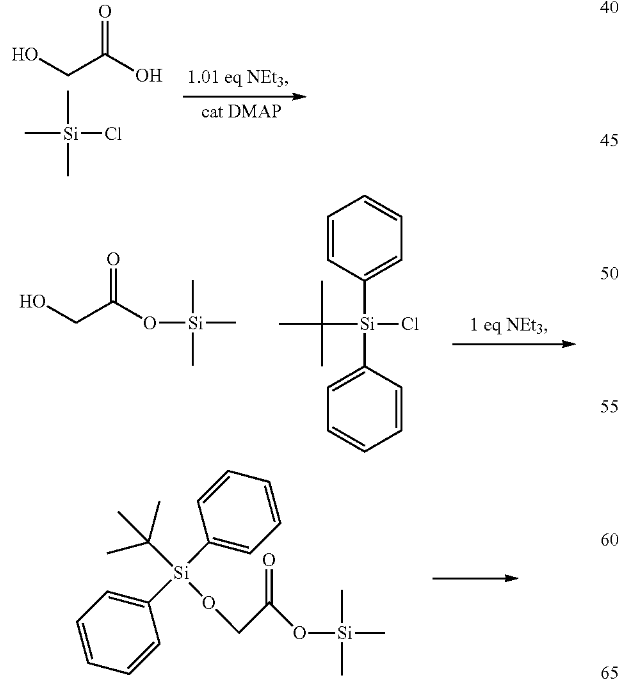

-continued

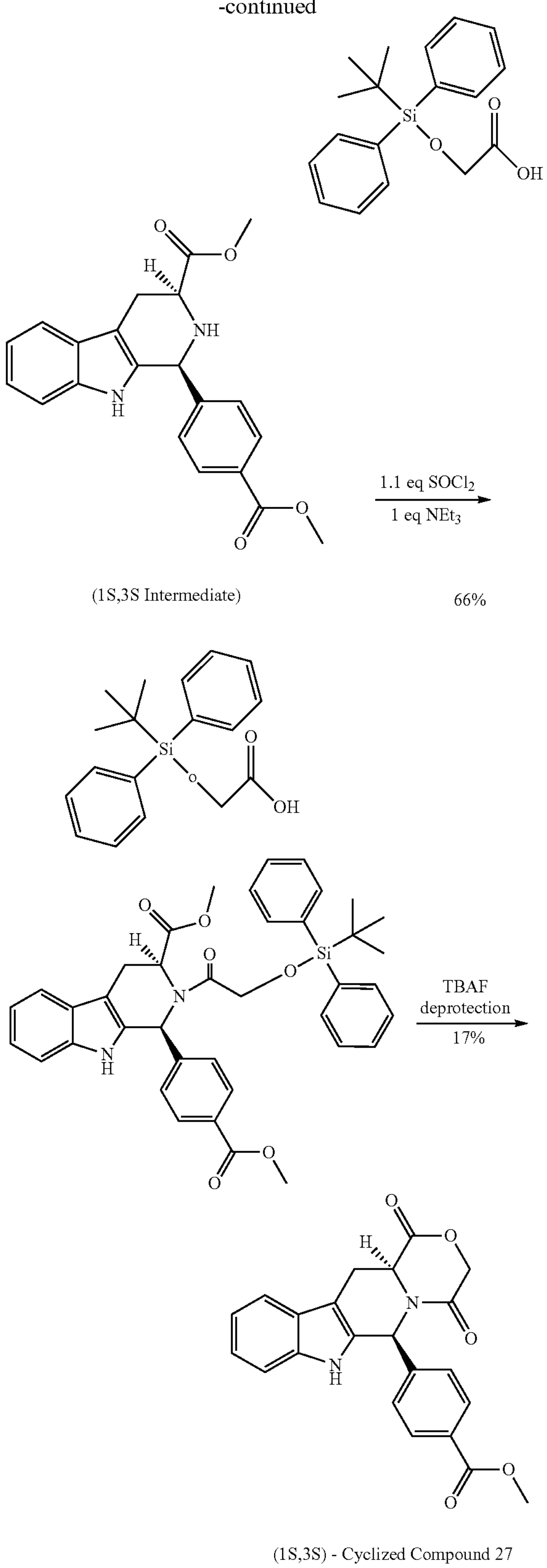

Protection of Glycolic Acid

The protocol according to Nicolaou, K. C., et. al., Studies toward Diazonamide A: Initial Synthetic Forays Directed toward the Originally Proposed Structure, 126 (32) JACS 2004, 10162-10173, was followed. Briefly, 1 eq. of glycolic acid (Sigma) was added to an oven-dried flask and dried on a vacuum pump for 1 hour, and then dissolved in anhydrous THF under $N_2$. To this solution at 0° C. was added a catalytic amount of 4-DMAP (Sigma) and 1.01 eq. $NEt_3$. Following five minutes of stirring at 0° C., 1.05 eq. TMSCI (Sigma) was added dropwise, yielding a white slurry. This suspension was stirred for an additional hour at 0° C., and then mixed for a second hour at room temperature (RT). A second equivalent (1 eq.) of $NEt_3$ was added at RT followed by 1.05 eq. of tert-butyldiphenylsilyl chloride (TBDPSCI) (Sigma), and this was stirred for 8 hours at 25° C. (or overnight). Upon completion, the reaction was quenched by the addition of an aqueous solution of HOAc (about 30% w/v) and stirred for 1 hour at RT. Water was added, and this solution was extracted with $Et_2O$ three times. The combined organic layers were then washed with water twice, dried with $Na_2SO_4$ and concentrated in vacuo. The resultant light yellow oil was purified by flash column chromatography (silica gel, $Et_2O$/hexanes, 1:1 Rf=0.18). Yield: 78%.

Preparation of Acyl Chloride and Acylation 1 eq. of siloprotected glycolic acid from the previous step was transferred to a reaction flask, concentrated, and dried on a vacuum pump for one hour. Protected glycolic acid was dissolved in anhydrous $CH_2Cl_2$ and 1 eq. of thionyl chloride (Sigma) was added along with a catalytic amount of anhydrous DMF. Stirring was allowed for 2 hours under nitrogen. The reaction mixture was concentrated, redissolved in anhydrous $CH_2Cl_2$, and reconcentrated. This process was repeated twice more to remove as much $SOCl_2$ as possible. Siloprotected glycolic acid oil was redissolved in dry dichloromethane, 1 eq. of $NEt_3$ and 1 eq. of 1S,3S Intermediate (synthesized as described in Example 6) were added and allowed to stir overnight under nitrogen. The mixture was dry loaded and purified by flash column chromatography (silica gel, 100% hexane→20:80 ether:hexane, 50:50 ether:hexane→20:80 EtOAc:hexane→100% EtOAc→100% $CHCl_3$→5% EtOH/$CHCl_3$). Yield: 66%.

Deprotection and Cyclization 1 eq. of siloprotected 1S,3S Compound 27 was dissolved in anhydrous dichloromethane in an oven-dried flask under $N_2$. TBAF was added in THF (1.0M, Sigma) in an appropriate volume to give 1.1 eq. of TBAF. Stirring was allowed for five hours. The reaction was quenched with the addition of saturated $NH_4Cl$. The organic layer was extracted three times with dichloromethane. The organic layers were combined, washed with brine, dried with $Na_2SO_4$, filtered and concentrated. 1S,3S Cyclized Compound 27 was purified by flash column chromatography (silica gel 0→100% EtOAc in hexane). Rf=0.43 in 80:20 EtOAc:Hex. Yield=17%.

NMR

The 1S,3S Cyclized Compound 27 obtained according to the synthesis above and the 1R,3S Cyclized Compound 27 obtained according to the analogous synthesis as above were each evaluated by NMR. FIG. 50 shows that 1S,3S Cyclized Compound 27 (panel A) and 1R,3S Cyclized Compound 27 (panel B) are each enantiomerically pure.

The synthesis of 1S,3R Cyclized Compound 27 and 1R,3R Cyclized Compound 27 is analogous to that of 1S,3S Cyclized Compound 27 and 1R,3S Cyclized Compound 27 as above. It is considered that 1S,3R Cyclized Compound 27 and 1R,3R Cyclized Compound 27 obtained from the analogous method to that above are enantiomerically pure.

Example 8

Biological Testing of the Stereoisomers of Compound 27

Each of the four stereoisomers of Compound 27 (Example 6) was tested in four engineered cell lines derived from primary human fibroblasts. BJ cells were engineered successively to express the catalytic subunit of human telomerase (hTERT); the SV40 large T and small T antigens (LT and ST), and an oncogenic allele of HRAS ($HRAS^{G12V}$). These cell lines are identified as BJeH, BJeHLT, and BJeLR. DRD cells were engineered to express hTERT, oncogenic HRAS ($HRAS^{G12V}$), dominant negative p53, and constitutively active CDK4/cyclinD, which inactivates the RB protein; the p53DD/CDK4/cyclinD1 combinations substitute for the SV40 large T oncoprotein. Of the four cell types, only BJeLR and DRD cells form tumors in nude mice.

Cell growth inhibition was determined for the four stereoisomers of Compound 27, and percent growth inhibition is plotted in FIG. 51. (1R,3S) Compound 27 (panel A), (1S,3S) Compound 27 (panel B), and 1R,3R Compound 27 (panel D) each show no appreciable growth inhibition. One of the four synthetic stereoisomers, 1S,3R Compound 27 (panel C), however, showed strong cell growth inhibition in two cell lines. Moreover, the results indicate that of the four synthetic stereoisomers, only 1S,3R Compound 27 has selective lethality towards BJ tumor cell lines containing mutant HRAS versus isogenic cell lines lacking oncogenic HRAS.

The $EC_{50}$ of the active stereoisomer, 1S,3R Compound 27, is about 5 ng/mL (~10 nM), whereas the synthesis according to Example 3 above produces a compound having an $EC_{50}$ of about 50 ng/mL (~100 nM). It is considered that some racemization occurred regarding the bond linking the methyl benzoate to the pyrido-indole group in the synthesis of Example 3. Although a mixture of diastereomers are produced each having apparent activity, it has now been discovered that enantiomeric purity does not result from the Example 3 synthesis. Upon resolving each stereoisomer, surprisingly it was found that only one of the four synthetic diastereomers (1S,3R Compound 27) was active in vitro. In this field, the identification of one out of four stereoisomers having essentially all of the biological activity was unexpected and could not have been predicted.

INCORPORATION BY REFERENCE

All publications and patents referred to herein or listed below are hereby incorporated by reference in their entirely as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

DOCUMENTS

1. Alexandre, J., Batteux, F., Nicco, C., Chereau, C., Laurent, A., Guillevin, L., Weill, B., and Goldwasser, F. (2006). Accumulation of hydrogen peroxide is an early and crucial step for paclitaxel-induced cancer cell death both in vitro and in vivo. International journal of cancer 119, 41-48.
2. Arbiser, J. L., Moses, M. A., Fernandez, C. A., Ghiso, N., Cao, Y., Klauber, N., Frank, D., Brownlee, M., Flynn, E., Parangi, S., et al. (1997). Oncogenic H-ras stimulates tumor angiogenesis by two distinct pathways. Proc Natl Acad Sci USA 94, 861-866.

3. Arbiser, J. L., Petros, J., Klafter, R., Govindajaran, B., McLaughlin, E. R., Brown, L. F., Cohen, C., Moses, M., Kilroy, S., Arnold, R. S., and Lambeth, J. D. (2002). Reactive oxygen generated by Nox1 triggers the angiogenic switch. Proceedings of the National Academy of Sciences of the United States of America 99, 715-720.
4. Banerjee, D., Schnieders, B., Fu, J. Z., Adhikari, D., Zhao, S. C., and Bertino, J. R. (1998). Role of E2F-1 in chemosensitivity. Cancer Res. 58, 4292-4296.
5. Barbacid, M. (1987). ras genes. Annu Rev Biochem 56, 779-827.
6. Barbour, L., and Xiao, W. (2006). Synthetic lethal screen. Methods Mol Biol 313, 161-169.
7. Bernards, A. (2005). Ras superfamily and interacting proteins database. Methods Enzymol. 407, 1-9.
8. Block, J. B., Serpick, A. A., Miller, W., and Wiernik, P. H. (1974). Early clinical studies with lapachol (NSC-11905). Cancer Chemother Rep 2 4, 27-28.
9. Bryant, H. E., Schultz, N., Thomas, H. D., Parker, K. M., Flower, D., Lopez, E., Kyle, S., Meuth, M., Curtin, N. J., and Helleday, T. (2005). Specific killing of BRCA2-deficient tumours with inhibitors of poly(ADP-ribose) polymerase. Nature 434, 913-917.
10. Borst, P., Evers, R., Kool, M., and Wijnholds, J. (2000). A family of drug transporters: the multidrug resistance-associated proteins. J Natl Cancer Inst 92, 1295-1302.
11. Capdeville, R., Buchdunger, E., Zimmermann, J., and Matter, A. (2002). Glivec (STI571, imatinib), a rationally developed, targeted anticancer drug. Nat Rev Drug Discov 1, 493-502.
12. Casey, J. L., Di Jeso, B., Rao, K., Rouault, T. A., Klausner, R. D., and Harford, J. B. (1988). The promoter region of the human transferrin receptor gene. Ann NY Acad Sci 526, 54-64.
13. Cazzola, M., Bergamaschi, G., Dezza, L., and Arosio, P. (1990). Manipulations of cellular iron metabolism for modulating normal and malignant cell proliferation: achievements and prospects. Blood 75, 1903-1919.
14. Cheng, Y., Zak, O., Aisen, P., Harrison, S. C., and Walz, T. (2004). Structure of the human transferrin receptor-transferrin complex. Cell 116, 565-576.
15. Chou, W. C., Jie, C., Kenedy, A. A., Jones, R. J., Trush, M. A., and Dang, C. V. (2004). Role of NADPH oxidase in arsenic-induced reactive oxygen species formation and cytotoxicity in myeloid leukemia cells. Proc Natl Acad Sci USA 101, 4578-4583.
16. Cross, A. R., and Segal, A. W. (2004). The NADPH oxidase of professional phagocytes—prototype of the NOX electron transport chain systems. Biochimica et biophysica acta 1657, 1-22.
17. da Consolacao, M., Linardi, F., de Oliveira, M. M., and Sampaio, M. R. (1975). A lapachol derivative active against mouse lymphocytic leukemia P-388. J Med Chem 18, 1159-1161.
18. Dolma, S., Lessnick, S. L., Hahn, W. C., and Stockwell, B. R. (2003). Identification of genotype-selective antitumor agents using synthetic lethal chemical screening in engineered human tumor cells. Cancer Cell 3, 285-296.
19. Dorr, R. T. (1992). Bleomycin pharmacology: mechanism of action and resistance, and clinical pharmacokinetics. Seminars in oncology 19, 3-8.
20. Fantin, V. R., Berardi, M. J., Scorrano, L., Korsmeyer, S. J., and Leder, P. (2002). A novel mitochondriotoxic small molecule that selectively inhibits tumor cell growth. Cancer Cell 2, 29-42.
21. Finch, R. A., Liu, M., Grill, S. P., Rose, W. C., Loomis, R., Vasquez, K. M., Cheng, Y., and Sartorelli, A. C. (2000). Triapine (3-aminopyridine-2-carboxaldehyde-thiosemicarbazone): A potent inhibitor of ribonucleotide reductase activity with broad spectrum antitumor activity. Biochem Pharmacol 59, 983-991.
22. Foster, B. A., Coffey, H. A., Morin, M. J., and Rastinejad, F. (1999). Pharmacological rescue of mutant p53 conformation and function. Science 286, 2507-2510.
23. Fry, D. C., and Vassilev, L. T. (2005). Targeting protein-protein interactions for cancer therapy. Journal of molecular medicine (Berlin, Germany) 83, 955-963.
24. Green, D. A., Antholine, W. E., Wong, S. J., Richardson, D. R., and Chitambar, C. R. (2001). Inhibition of malignant cell growth by 311, a novel iron chelator of the pyridoxal isonicotinoyl hydrazone class: effect on the R2 subunit of ribonucleotide reductase. Clin Cancer Res 7, 3574-3579.
25. Hahn, W. C., Counter, C. M., Lundberg, A. S., Beijersbergen, R. L., Brooks, M. W., and Weinberg, R. A. (1999). Creation of human tumour cells with defined genetic elements. Nature 400, 464-468.
26. Hahn, W. C., Dessain, S. K., Brooks, M. W., King, J. E., Elenbaas, B., Sabatini, D. M., DeCaprio, J. A., and Weinberg, R. A. (2002). Enumeration of the simian virus 40 early region elements necessary for human cell transformation. Mol Cell Biol 22, 2111-2123.
27. Halliwell, B., and Gutteridge, J. M. (1990). Role of free radicals and catalytic metal ions in human disease: an overview. Methods Enzymol 186, 1-85.
28. Hanahan, D., and Weinberg, R. A. (2000). The hallmarks of cancer. Cell 100, 57-70.
29. Harrison, P. M., and Arosio, P. (1996). The ferritins: molecular properties, iron storage function and cellular regulation. Biochim. Biophys. Acta. 1275, 161-203.
30. Hartwell, L. H., Szankasi, P., Roberts, C. J., Murray, A. W., and Friend, S. H. (1997). Integrating genetic approaches into the discovery of anticancer drugs. Science 278, 1064-1068.
31. Kalinowski, D. S., and Richardson, D. R. (2005). The evolution of iron chelators for the treatment of iron overload disease and cancer. Pharmacol Rev 57, 547-583.
32. Kartalou, M., and Essigmann, J. M. (2001). Mechanisms of resistance to cisplatin. Mutat Res 478, 23-43.
33. Kohl, N. E., Omer, C. A., Conner, M. W., Anthony, N. J., Davide, J. P., deSolms, S. J., Giuliani, E. A., Gomez, R. P., Graham, S. L., Hamilton, K., and et al. (1995). Inhibition of farnesyltransferase induces regression of mammary and salivary carcinomas in ras transgenic mice. Nat Med 1, 792-797.
34. Kondagunta, G. V., and Motzer, R. J. (2006). Chemotherapy for advanced germ cell tumors. J Clin Oncol 24, 5493-5502.
35. Kwok, J. C., and Richardson, D. R. (2003). Anthracyclines induce accumulation of iron in ferritin in myocardial and neoplastic cells: inhibition of the ferritin iron mobilization pathway. Molecular pharmacology 63, 849-861.
36. Le, N. T., and Richardson, D. R. (2002). The role of iron in cell cycle progression and the proliferation of neoplastic cells. Biochim Biophys Acta 1603, 31-46.
37. Lebedev, A. V., Ivanova, M. V., and Levitsky, D. O. (2005). Echinochrome, a naturally occurring iron chelator and free radical scavenger in artificial and natural membrane systems. Life Sci 76, 863-875.

38. Lemasters, J. J., and Holmuhamedov, E. (2006). Voltage-dependent anion channel (VDAC) as mitochondrial governator—thinking outside the box. Biochim. Biophys. Acta. 1762, 181-190.

39. Lessnick, S. L., Dacwag, C. S., and Golub, T. R. (2002). The Ewing's sarcoma oncoprotein EWS/FLI induces a p53-dependent growth arrest in primary human fibroblasts. Cancer Cell 1, 393-401.

40. Liu, M. C., Lin, T. S., and Sartorelli, A. C. (1995). Chemical and biological properties of cytotoxic alpha-(N)-heterocyclic carboxaldehyde thiosemicarbazones. Prog Med Chem 32, 1-35.

41. Low, J. A., and Schoenfeldt, M. (2005). Clinical trials referral resource. Current clinical trials investigating 3-AP. Oncology (Williston Park) 19, 354, 357-358.

42. Malumbres, M., and Barbacid, M. (2003). RAS oncogenes: the first 30 years. Nat Rev Cancer 3, 459-465.

43. Marciano, D., Ben-Baruch, G., Marom, M., Egozi, Y., Haklai, R., and Kloog, Y. (1995). Farnesyl derivatives of rigid carboxylic acids-inhibitors of ras-dependent cell growth. J Med Chem 38, 1267-1272.

44. Marom, M., Haklai, R., Ben-Baruch, G., Marciano, D., Egozi, Y., and Kloog, Y. (1995). Selective inhibition of Ras-dependent cell growth by farnesylthiosalisylic acid. J Biol Chem 270, 22263-22270.

45. Moffat, J., Grueneberg, D. A., Yang, X., Kim, S. Y., Kloepfer, A. M., Hinkle, G., Piqani, B., Eisenhaure, T. M., Luo, B., Grenier, J. K., et al. (2006). A lentiviral RNAi library for human and mouse genes applied to an arrayed viral high-content screen. Cell 124, 1283-1298.

46. Moffat, J., and Sabatini, D. M. (2006). Building mammalian signalling pathways with RNAi screens. Nat Rev Mol Cell Biol 7, 177-187.

47. Nagasu, T., Yoshimatsu, K., Rowell, C., Lewis, M. D., and Garcia, A. M. (1995). Inhibition of human tumor xenograft growth by treatment with the farnesyl transferase inhibitor B956. Cancer Res 55, 5310-5314.

48. Neshat, M. S., Mellinghoff, I. K., Tran, C., Stiles, B., Thomas, G., Petersen, R., Frost, P., Gibbons, J. J., Wu, H., and Sawyers, C. L. (2001). Enhanced sensitivity of PTEN-deficient tumors to inhibition of FRAP/mTOR. Proc. Natl. Acad. Sci. USA 98, 10314-10319.

49. Nishibori, K. (1961). Isolation of echinochrome A from the spines of the sea urchin, Stomopneustes variolaris (Lamarck). Nature 192, 1293-1294.

50. Nociari, M. M., Shalev, A., Benias, P., and Russo, C. (1998). A novel one-step, highly sensitive fluorometric assay to evaluate cell-mediated cytotoxicity. Journal of immunological methods 213, 157-167.

51. Ouyang, Q., Bommakanti, M., and Miskimins, W. K. (1993). A mitogen-responsive promoter region that is synergistically activated through multiple signalling pathways. Mol Cell Biol 13, 1796-1804.

52. Pardee, A. B., Li, Y. Z., and Li, C. J. (2002). Cancer therapy with beta-lapachone. Curr Cancer Drug Targets 2, 227-242.

53. Paull, K. D., Shoemaker, R. H., Hodes, L., Monks, A., Scudiero, D. A., Rubinstein, L., Plowman, J., and Boyd, M. R. (1989). Display and analysis of patterns of differential activity of drugs against human tumor cell lines: development of mean graph and COMPARE algorithm. J Natl Cancer Inst 81, 1088-1092.

54. Petrat, F., de Groot, H., and Rauen, U. (2000). Determination of the chelatable iron pool of single intact cells by laser scanning microscopy. Arch Biochem Biophys 376, 74-81.

55. Rodenhuis, S. (1992) ras and human tumors. Semin Cancer Biol 3, 241-247.

56. Rowell, C. A., Kowalczyk, J. J., Lewis, M. D., and Garcia, A. M. (1997). Direct demonstration of geranylgeranylation and farnesylation of Ki-Ras in vivo. J Biol Chem 272, 14093-14097.

57. Schafer, W. R., Kim, R., Sterne, R., Thorner, J., Kim, S. H., and Rine, J. (1989). Genetic and pharmacological suppression of oncogenic mutations in ras genes of yeast and humans. Science 245, 379-385.

58. Schafer, W. R., Trueblood, C. E., Yang, C. C., Mayer, M. P., Rosenberg, S., Poulter, C. D., Kim, S. H., and Rine, J. (1990). Enzymatic coupling of cholesterol intermediates to a mating pheromone precursor and to the ras protein. Science 249, 1133-1139.

59. Shaw, R. J., and Cantley, L. C. (2006). Ras, PI(3)K and mTOR signalling controls tumour cell growth. Nature 441, 424-430.

60. Shterman, N., Kupfer, B., and Moroz, C. (1991). Comparison of transferrin receptors, iron content and isoferritin profile in normal and malignant human breast cell lines. Pathobiology 59, 19-25.

61. Singh, M., Pal, M., and Sharma, R. P. (1999). Biological activity of the labdane diterpenes. Planta Med 65, 2-8.

62. Smith, M. R., DeGudicibus, S. J., and Stacey, D. W. (1986). Requirement for c-ras proteins during viral oncogene transformation. Nature 320, 540-543.

63. Stevens, R. G., Jones, D. Y., Micozzi, M. S., and Taylor, P. R. (1988). Body iron stores and the risk of cancer. N Engl J Med 319, 1047-1052.

64. Stockwell, B. R., Haggarty, S. J., and Schreiber, S. L. (1999). High-throughput screening of small molecules in miniaturized mammalian cell-based assays involving post-translational modifications. Chem Biol 6, 71-83.

65. Stockwell, B. R. (2000). Chemical genetics: ligand-based discovery of gene function. Nat. Rev. Genet. 1, 116-125.

66. Templeton, D. M. (2002). Molecular and cellular iron transport, (New York: Marcel Dekker).

67. Tong, A. H., Evangelista, M., Parsons, A. B., Xu, H., Bader, G. D., Page, N., Robinson, M., Raghibizadeh, S., Hogue, C. W., Bussey, H., et al. (2001). Systematic genetic analysis with ordered arrays of yeast deletion mutants. Science 294, 2364-2368.

68. Torrance, C. J., Agrawal, V., Vogelstein, B., and Kinzler, K. W. (2001). Use of isogenic human cancer cells for high-throughput screening and drug discovery. Nature biotechnology 19, 940-945.

69. Tsuji, Y., Akebi, N., Lam, T. K., Nakabeppu, Y., Torti, S. V., and Torti, F. M. (1995). FER-1, an enhancer of the ferritin H gene and a target of E1A-mediated transcriptional repression. Mol Cell Biol 15, 5152-5164.

70. Varma, H., Voisine, C., DeMarco, C. T., Cattaneo, E., Lo, D. C., Hart, A. C., and Stockwell, B. R. (2007). Selective inhibitors of death in mutant huntingtin cells. Nature chemical biology 3, 99-100.

71. Vogelstein, B., and Kinzler, K. W. (2004). Cancer genes and the pathways they control. Nat Med 10, 789-799.

72. Wang, H., Han, H., and Von Hoff, D. D. (2006). Identification of an Agent Selectively Targeting DPC4 (Deleted in Pancreatic Cancer Locus 4)-Deficient Pancreatic Cancer Cells. Cancer Res 66, 9722-9730.

73. Whyte, D. B., Kirschmeier, P., Hockenberry, T. N., Nunez-Oliva, I., James, L., Catino, J. J., Bishop, W. R., and Pai, J. K. (1997). K- and N-Ras are geranylgeranylated in cells treated with farnesyl protein transferase inhibitors. J Biol Chem 272, 14459-14464.

74. Wilhelm, S., Carter, C., Lynch, M., Lowinger, T., Dumas, J., Smith, R. A., Schwartz, B., Simantov, R., and Kelley, S. (2006). Discovery and development of sorafenib: a multi-kinase inhibitor for treating cancer. Nat Rev Drug Discov 5, 835-844.

75. Wu, K. J., Polack, A., and Dalla-Favera, R. (1999). Coordinated regulation of iron-controlling genes, H-ferritin and IRP2, by c-MYC. Science 283, 676-679.

76. Yagoda, N., von Rechenberg, M., Zaganjor, E., Bauer, A. J., Yang, W. S., Fridman, D. J., Wolpaw, A. J., Smukste, I., Peltier, J. M., Boniface, J. J., et al. (2007) RAS-RAF-MEK-dependent oxidative cell death involving voltage-dependent anion channels. Nature 447, 864-868.

What is claimed is:

1. A compound selected from the group consisting of:

A

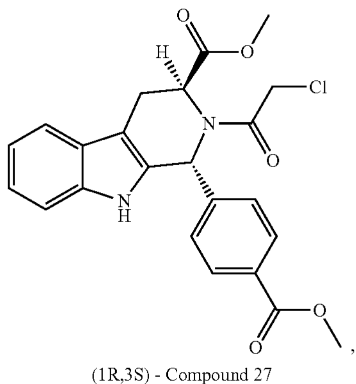

(1R,3S) - Compound 27

B

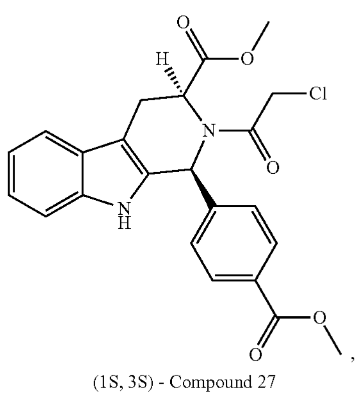

(1S, 3S) - Compound 27

C

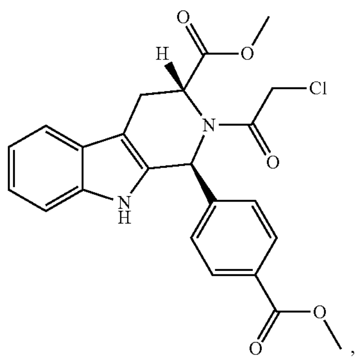

(1S, 3R) - Compound 27 and

-continued

D

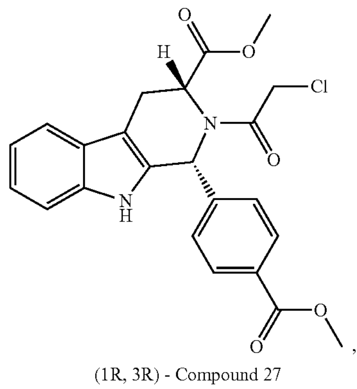

(1R, 3R) - Compound 27 and mixtures thereof, or a N-oxide, crystalline form, or pharmaceutically acceptable salt thereof.

2. The compound according to claim 1, which is:

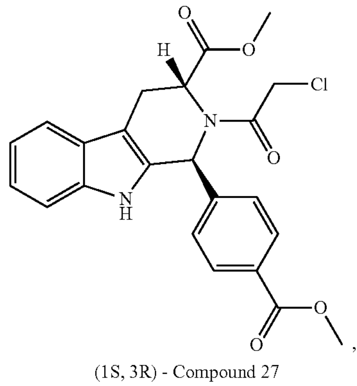 [SMILES: COC(=O)c1ccc([C@H]2c3[nH]c4ccccc4c3C[C@H](C(=O)OC)N2C(=O)CCl)cc1]

(1S, 3R) - Compound 27 or a N-oxide, crystalline form, or pharmaceutically acceptable salt thereof.

3. The compound according to claim 2, which is enantiomerically pure.

4. A pharmaceutical composition comprising a pharmaceutically acceptable carrier and an enantiomerically pure RAS-selective lethal compound having the structure:

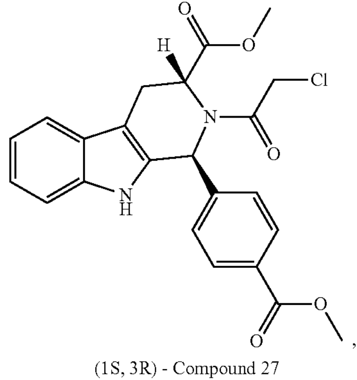 [SMILES: COC(=O)c1ccc([C@H]2c3[nH]c4ccccc4c3C[C@H](C(=O)OC)N2C(=O)CCl)cc1]

(1S, 3R) - Compound 27 or a N-oxide, crystalline form, or pharmaceutically acceptable salt thereof.

* * * * *

SEQUENCE LISTING

```
<160> NUMBER OF SEQ ID NOS: 18

<210> SEQ ID NO 1
<211> LENGTH: 23
<212> TYPE: DNA
<213> ORGANISM: Artificial
<220> FEATURE:
<223> OTHER INFORMATION: synthetic construct; VDAC1 F

<400> SEQUENCE: 1

cctggacagc aggaaacagt aac                                              23


<210> SEQ ID NO 2
<211> LENGTH: 20
<212> TYPE: DNA
<213> ORGANISM: Artificial
<220> FEATURE:
<223> OTHER INFORMATION: synthetic construct; VDAC1 R

<400> SEQUENCE: 2

aggcgtcagg gtcaatctga                                                  20


<210> SEQ ID NO 3
<211> LENGTH: 20
<212> TYPE: DNA
<213> ORGANISM: Artificial
<220> FEATURE:
<223> OTHER INFORMATION: synthetic construct; VDAC2 F

<400> SEQUENCE: 3

tgattttgct ggacctgcaa                                                  20


<210> SEQ ID NO 4
<211> LENGTH: 18
<212> TYPE: DNA
<213> ORGANISM: Artificial
<220> FEATURE:
<223> OTHER INFORMATION: synthetic construct; VDAC2 R

<400> SEQUENCE: 4

cagcaagcca gccctcat                                                    18


<210> SEQ ID NO 5
<211> LENGTH: 20
<212> TYPE: DNA
<213> ORGANISM: Artificial
<220> FEATURE:
<223> OTHER INFORMATION: synthetic construct; VDAC3 F

<400> SEQUENCE: 5

aatttcgccc tgggttacaa                                                  20


<210> SEQ ID NO 6
<211> LENGTH: 21
<212> TYPE: DNA
<213> ORGANISM: Artificial
```

<220> FEATURE:
<223> OTHER INFORMATION: synthetic construct; VDAC3 R

<400> SEQUENCE: 6
tcagtgccat cgttcacatg t 21

<210> SEQ ID NO 7
<211> LENGTH: 22
<212> TYPE: DNA
<213> ORGANISM: Artificial
<220> FEATURE:
<223> OTHER INFORMATION: synthetic construct; TfR1 F

<400> SEQUENCE: 7
gaaaacagac agatttgtca tg 22

<210> SEQ ID NO 8
<211> LENGTH: 21
<212> TYPE: DNA
<213> ORGANISM: Artificial
<220> FEATURE:
<223> OTHER INFORMATION: synthetic construct; TfR1 R

<400> SEQUENCE: 8
ctcttttgga gatacgtagg g 21

<210> SEQ ID NO 9
<211> LENGTH: 21
<212> TYPE: DNA
<213> ORGANISM: Artificial
<220> FEATURE:
<223> OTHER INFORMATION: synthetic construct; DMT1 F

<400> SEQUENCE: 9
catcactatt atggccctca c 21

<210> SEQ ID NO 10
<211> LENGTH: 21
<212> TYPE: DNA
<213> ORGANISM: Artificial
<220> FEATURE:
<223> OTHER INFORMATION: synthetic construct; DMT1 R

<400> SEQUENCE: 10
gaacatgccc ttgagtacct g 21

<210> SEQ ID NO 11
<211> LENGTH: 22
<212> TYPE: DNA
<213> ORGANISM: Artificial
<220> FEATURE:
<223> OTHER INFORMATION: synthetic construct; HCP1 F

<400> SEQUENCE: 11
ggtctttgcc tttgccacta tc 22

<210> SEQ ID NO 12
<211> LENGTH: 23
<212> TYPE: DNA
<213> ORGANISM: Artificial
<220> FEATURE:
<223> OTHER INFORMATION: synthetic construct; HCP1 R

<400> SEQUENCE: 12
caggtgtgat gactaatgac agg 23

<210> SEQ ID NO 13
<211> LENGTH: 21
<212> TYPE: DNA
<213> ORGANISM: Artificial
<220> FEATURE:
<223> OTHER INFORMATION: synthetic construct; FTH1 F

<400> SEQUENCE: 13
cagatcaacc tggagctcta c 21

<210> SEQ ID NO 14
<211> LENGTH: 20
<212> TYPE: DNA
<213> ORGANISM: Artificial
<220> FEATURE:
<223> OTHER INFORMATION: synthetic construct; FTH1 R

<400> SEQUENCE: 14
cttcaaagcc acatcatcgc 20

<210> SEQ ID NO 15
<211> LENGTH: 17
<212> TYPE: DNA
<213> ORGANISM: Artificial
<220> FEATURE:
<223> OTHER INFORMATION: synthetic construct; FTL F

<400> SEQUENCE: 15
ggccctggag aaaaagc 17

<210> SEQ ID NO 16
<211> LENGTH: 19
<212> TYPE: DNA
<213> ORGANISM: Artificial
<220> FEATURE:
<223> OTHER INFORMATION: synthetic construct; FTL R

<400> SEQUENCE: 16
gaagtgagtc tccaggaag 19

<210> SEQ ID NO 17
<211> LENGTH: 20
<212> TYPE: DNA
<213> ORGANISM: Artificial
<220> FEATURE:
<223> OTHER INFORMATION: synthetic construct; RPLP0 F

<400> SEQUENCE: 17
acgggtacaa acgagtcctg 20

<210> SEQ ID NO 18
<211> LENGTH: 20
<212> TYPE: DNA
<213> ORGANISM: Artificial
<220> FEATURE:
<223> OTHER INFORMATION: synthetic construct; RPLP0 R

<400> SEQUENCE: 18
gccttgacct tttcagcaag 20